United States Patent [19]

Taylor

[11] Patent Number: 5,032,166

[45] Date of Patent: Jul. 16, 1991

[54] HERBICIDAL PYRIDINE SULFONYLUREAS

[75] Inventor: Eric D. Taylor, Wilmington, Del.

[73] Assignee: E. I. du Pont de Nemours and Company, Wilmington, Del.

[21] Appl. No.: 477,739

[22] Filed: Feb. 9, 1990

Related U.S. Application Data

[60] Division of Ser. No. 243,865, Sep. 15, 1988, Pat. No. 4,946,494, which is a continuation-in-part of Ser. No. 115,502, Oct. 30, 1987, abandoned.

[51] Int. Cl.$^5$ .................. C07D 239/69; C07D 401/62; C07D 401/14; A01N 43/54

[52] U.S. Cl. .......................................... 71/92; 71/90; 544/122; 544/123; 544/320; 544/321; 544/324; 544/331

[58] Field of Search ...................... 71/92, 90; 544/122, 544/123, 320, 331

[56] References Cited

U.S. PATENT DOCUMENTS

| | | | |
|---|---|---|---|
| 4,518,776 | 5/1985 | Meyer et al. | 544/206 |
| 4,544,401 | 10/1985 | Levitt | 71/92 |
| 4,579,583 | 4/1986 | Föry et al. | 71/92 |
| 4,639,264 | 1/1987 | Töpfl | 71/87 |
| 4,690,707 | 9/1987 | Föry et al. | 71/93 |

FOREIGN PATENT DOCUMENTS

| | | |
|---|---|---|
| 101670 | 2/1984 | European Pat. Off. . |
| 232067 | 8/1987 | European Pat. Off. . |

*Primary Examiner*—John M. Ford

[57] ABSTRACT

The invention relates to certain 6-amino-substituted 2-pyridinesulfonylureas, intermediates thereof, and compositions and methods of their use.

14 Claims, No Drawings

HERBICIDAL PYRIDINE SULFONYLUREAS

RELATED APPLICATION

This is a division of application Ser. No. 07/243,865, filed Sept. 15, 1988, now U.S. Pat. No. 4,946,494, which is a continuation-in-part of Ser. No. 07/115,502 filed Oct. 30, 1987, now abandoned.

BACKGROUND OF THE INVENTION

This invention relates to novel pyridine sulfonylurea herbicidal compounds, agriculturally suitable compositions thereof and a method of using them to control the growth of undesired vegetation.

New compounds effective for controlling the growth of undesired vegetation are in constant demand. In the most common situation, such compounds are sought to selectively control the growth of weeds in useful crops such as cotton, rice, corn, wheat and soybeans, to name a few. Unchecked weed growth in such crops can cause significant losses, reducing profit to the farmer and increasing costs to the consumer. In other situations, herbicides are desired which will control all plant growth. Examples of areas in which complete control of all vegetation is desired are areas around railroad tracks and industrial storage areas. There are many products commercially available for these purposes, but the search continues for products which are more effective, less costly and environmentally safe.

The "sulfonylurea" herbicides are an extremely potent class of herbicides discovered within the last few years. A multitude of structural variations exist within this class of herbicides, but they generally consist of a sulfonylurea bridge, $-SO_2NHCONH-$, linking two aromatic or heteroaromatic rings.

U.S. Pat. Nos. 4,579,583 and 4,690,707 disclose herbicidal pyridinesulfonylureas of the formula

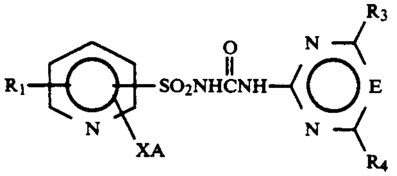

wherein
XA is $NR_6R_7$; and
$R_6$ and $R_7$ are independently H, $C_1$-$C_4$ alkyl, $C_3$-$C_6$ alkenyl, $C_3$-$C_6$ alkynyl, $C_3$-$C_6$ alkoxyalkyl, $C_1$-$C_4$ cyanoalkyl, or taken together form a 5- or 6-membered heterocyclic ring which may also contain O, S, SO or $NR_8$.

U.S. Pat. No. 4,544,401 discloses herbicidal pyridine sulfonylureas of the formula

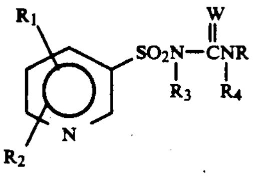

wherein
$R_1$ is $NR_6R_7$; and
$R_2$ is H, Cl, Br or $CH_3$.

EP-A-101,670 discloses a process for the preparation of herbicidal sulfonylureas of the formula

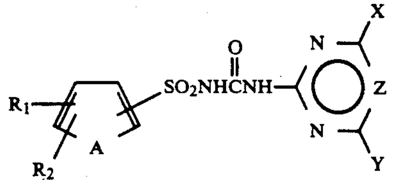

wherein
A is —C═N—; and
$R_1$ is $NH(C_1C_4)$alkyl or $N(C_1$-$C_4$ alkyl$)_2$.

U.S. Pat. No. 4,518,776 discloses a process for the preparation of herbicidal sulfonylureas of the formula

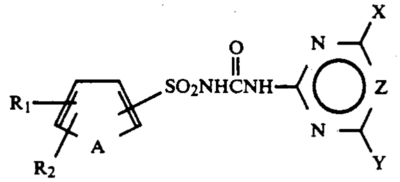

wherein
A is —C═N—; and
$R_1$ is $NH_2$, $NH(C_1$-$C_4)$alkyl or $N(C_1$-$C_4$ alkyl$)_2$.

SUMMARY OF THE INVENTION

This invention relates to novel agriculturally suitable herbicidal compounds of the Formula

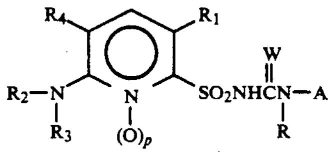

I wherein
W is O or S;
R is H or $CH_3$;
$R_1$ is H, F, Cl, Br, I, CN, $C_1$-$C_2$ alkyl, $C_1$-$C_2$ haloalkyl, $OCH_3$, $OCH_2CH_3$, $OCH_2CF_3$, $OCF_2H$, $SCH_3$, $SCF_2H$, $C_1$-$C_3$ alkylsulfonyl or $SO_2CF_2H$;
$R_2$ is H, $C_1$-$C_4$ alkyl, $C_1$-$C_2$ haloalkyl, CN, OH, $C_1$-$C_2$ alkoxy, $NH_2$, $NHCH_3$, $N(CH_3)2$, $C_1C_2$ alkyl substituted by CN, $C_1$-$C_2$ alkoxy or $C_1$-$C_2$ alkylthio, $C_3$-$C_4$ cycloalkyl, $C_3$-$C_4$ alkenyl, $C_3$-$C_4$ alkynyl or $C(O)R_5$;
$R_3$ is H, $C_1C_4$ alkyl or $C_1$-$C_2$ haloalkyl; or
$R_2$ and $R_3$ may be taken together as $-(CH_2)_n-$or $-CH_2CH_2OCH_2CH_2-$ or

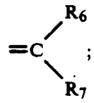

;

Ris H, F, Cl or $CH_3$;
$R_5$ is H, $C_1$-$C_3$ alkyl, $C_1$-$C_2$ alkoxy, $NH_2$, $NHCH_3$ or $N(CH_3)_2$;
$R_6$ is H, $C_1$-$C_2$ alkyl or phenyl;
$R_7$ is H or $CH_3$;
n is 2, 3, 4 or 5;
p is 0 or 1;

A is

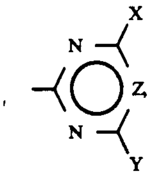, 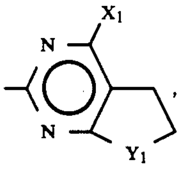, 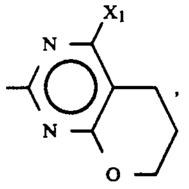,

A-1 A-2 A-3

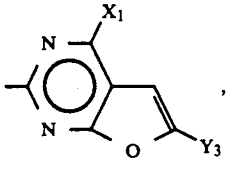, 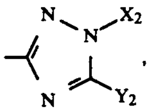,

A-4 A-5

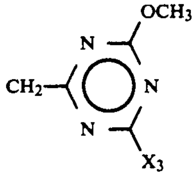 or 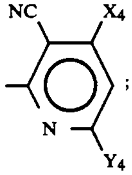;

A-6 A-7

X is H, $C_1$–$C_4$ alkyl, $C_1$–$C_4$ alkoxy, $C_1$–$C_4$ haloalkoxy, $C_1$–$C_4$ haloalky 1, $C_1$–$C_4$ haloalkylthio, $C_1$–$C_4$ alkylthio, halogen, $C_2$–$C_5$ alkoxyalkyl, $C_2$–$C_5$ alkoxyalkoxy, amino, $C_1$–$C_3$ alkylamino or di($C_1$–$C_3$ alkyl-)amino;

Y is H, $C_1$–$C_4$ alkyl, $C_1$–$C_4$ alkoxy, $C_1$–$C_4$ haloalkoxy, $C_1$–$C_4$ alkylthio, $C_1$–$C_4$ alkylthio, $C_2$–$C_5$ alkoxyalkyl, $C_2$–$C_5$ alkoxyalkoxy, amino, $C_1$–$C_3$ alkylamino, di($C_1$–$C_3$ alkyl) amino, $C_3$–$C_4$ alkenyloxy, $C_3$–$C_4$ alkynyloxy, $C_2$–$C_5$ alkylthioalkyl, $C_2$–$C_5$ alkylsulfinylalkyl, $C_2$–$C_5$ alkylsulfonylalkyl, $C_1$–$C_4$ haloalkyl, $C_2$–$C_4$ alkynyl, $C_3$–$C_5$ cycloalkyl, azido, cyano,

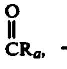, 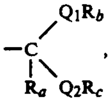, 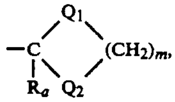, 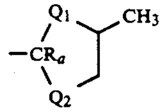

m is 2 or 3;

$Q_1$ and $Q_2$ are independently O or S;

$R_a$ is H or $C_1$–$C_3$ alkyl;

$R_b$ and $R_c$ are independently $C_1$–$C_3$ alkyl;

Z is CH, N, $CCH_3$, $CC_2H_5$, CCl or CBr;

$Y_1$ is O or $CH_2$;

$X_1$ is $CH_3$, $OCH_3$, $OC_2H_5$ or $OCF_2H$;

$X_2$ is $CH_3$, $C_2H_5$ or $CH_2CF_3$;

$Y_2$ is $OCH_3$, $OC_2H_5$, $SCH_3$, $SC_2H_5$, $CH_3$ or $CH_2CH_3$;

$X_3$ is $CH_3$ or $OCH_3$;

$Y_3$ is H or $CH_3$;

$X_4$ is $CH_3$, $OCH_3$, $OC_2H_5$, $CH_2OCH_3$ or Cl; and $Y_4$ is $CH_3$, $OCH_3$, $OC_2H_5$ or Cl;

and their agriculturally suitable salts; provided that 1) when X is halogen, then Z is CH and Y is $OCH_3$, $OC_2H_5$, $NH_2$, $NHCH_3$, $N(CH_3)_2$, $OCF_2H$, $OCF_2Br$ or $N(OCH_3)CH_3$;

2) when X and/or Y is $C_1$ haloalkoxy, then Z is CH;

3) when W is S, then R is H, A is A-1, Z is CH or N, and Y is $CH_3$, $OCH_3$, $OC_2H_5$, $CH_2OCH_3$, $C_2H_5$, $CF_3$, $SCH_3$, $OCH_2CH{=}CH_2$, $OCH_2C{\equiv}CH$, $OCH_2CH_2OCH_3$, $CH(OCH_3)_2$ or

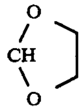;

4) when the total number of carbon atoms of X and Y is greater than four, then the combined number of carbons of $R_2$ and $R_3$ is less than or equal to six; and 5) $X_4$ and $Y_4$ are not simultaneously Cl.

In the above definitions, the term "alkyl," used either alone or in compound words such as "alkylthio" or "haloalkyl," denotes straight chain or branched alkylm e.g., methyl, ethyl, n-propyl, isopropyl or the different butyl isomers.

Alkoxy denotes methoxy, ethoxy, n-propoxy, isopropoxy and the different butoxy isomers.

Alkenyl denotes straight chain or branched alkenes, e.g., vinyl, 1-propenyl, 2-propenyl, 3-propenyl and the different butenyl isomers.

Alkynyl denotes straight chain or branched alkynes, e.g., ethynyl, 1-propynyl, 2-propynyl and the different butynyl isomers.

The term "halogen," either alone or in compound words such as "haloalkyl," denotes fluorine, chlorine, bromine or iodine. Further, when used in compound words such as "haloalkyl" said alkyl may be monohalogenated or fully substituted with halogen atoms, which may be the same or different. Examples of haloalkyl include $CH_2CH_2F$, $CF_2CF_3$ and $CH_2CHFCl$.

The total number of carbon atoms in a substituent group is indicated by the Ci-Cj prefix where i and j are numbers from 1 to 4. For example, $C_3$–$C_4$ alkenyl would designate propenyl through butenyl.

Compounds of the invention preferred for reasons of increased ease of synthesis and/or greater herbicidal efficacy are:

1. Compounds of Formula I wherein $R_4$ is H;

2. Compounds of Preferred 1 wherein $R_2$ is $C_1$–$C_2$ haloalkyl, OH, $C_1$–$C_2$ alkoxy, $NH_2$, $NHCH_3$, $N(CH_3)_2$, $C_1$–$C_2$ alkyl substituted by $C_1$–$C_2$ alkylthio, $C_3$–$C_4$ cycloalkyl or $C(O)R_5$;

$R_3$ is H, $C_1$–$C_4$ alkyl or $C_1$–$C_2$ haloalkyl; or $R_2$ and $R_3$ are taken together as $-(CH_2)_n-$ or

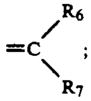;

and n is 2 or 3.

3. Compounds of Preferred 2 wherein

W is O;

X is $C_1$–$C_2$ alkyl, $C_1$–$C_2$ alkoxy, F, Cl, Br, I, $OCF_2H$, $CH_2F$, $CF_3$, $OCH_2CH_2F$, $OCH_2CHF_2$, $OCH_2CF_3$, $CH_2Cl$ or $CH_2Br$;

Y is H, $C_1$–$C_2$ alkyl, $C_1$–$C_2$ alkoxy, $CH_2OCH_3$, $CH_2OCH_2CH_3$, $NHCH_3$, $N(OCH_3)CH_3$, $N(CH_3)_2$, $CF_3$, $SCH_3$, $OCH_2CH{=}CH_2$, $OCH_2C{\equiv}CH$, $OCH_2CH_2OCH_3$, $CH_2SCH_3$, $C(O)R_a$,

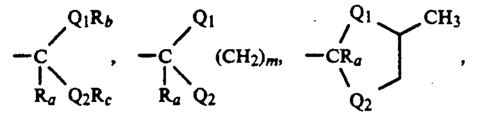

$OCF_2H$, $SCF_2H$, $OCF_2Br$, cyclopropyl, $C\equiv CH$ or $C\equiv CCH_3$; and Z is CH or N.

4. Compounds of Preferred 3 wherein $R_2$ is $NH_2$, $NHCH_3$, $N(CH_3)_2$, $CF_3$, $CF_2H$, OH, $OCH_3$, $CH_2SCH_3$, cyclopropyl or $C(O)R_5$;

$R_3$ is H, $CH_3$ or $CH_2CH_3$; or $R_2$ and $R_3$ are taken together as $-(CH_2)_n-$ or

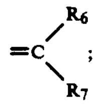

$R_5$ is H, $CH_3$, $OCH_3$, $NH_2$, $NHCH_3$ or $N(CH_3)_2$; and $R_6$ is H or $C_1$-$C_2$ alkyl.

5. Compounds of Preferred 4 wherein

A is A-1;

X is $CH_3$, $OCH_3$, $OCH_2CH_3$, Cl, $OCF_2H$ or $OCH_2CF_3$; and

Y is $CH_3$, $OCH_3$, $CH_2CH_3$, $CH_2OCH_3$, $NHCH_3$ or $CH(OCH_3)_2$.

6. Compounds of Preferred 5 wherein

R is H;

$R_1$ is H; and

P is O.

7. Compounds of Preferred 1 wherein $R_2$ is H, $C_1$-$C_4$ alkyl, CN, $C_1$-$C_2$ alkyl substituted by CN or $C_1$-$C_2$ alkoxy, $C_3$-$C_4$ alkenyl or $C_3$-$C_4$ alkynyl;

$R_3$ is H, $C_1$-$C_4$ alkyl or $C_1$-$C_2$ haloalkyl; or $R_2$ and $R_3$ are taken together as $-(CH_2)_n-$ or $-CH_2CH_2OCH_2CH_2-$; and n is 4 or 5.

8. Compounds of Preferred 7 wherein

W is O;

X is $C_1$-$C_2$ alkyl, $C_1$-$C_2$ alkoxy, F, Cl, Br, I, $OCF_2H$, $CH_2F$, $CF_3$, $OCH_2CH_2F$, $OCH_2CHF_2$, $OCH_2CF_3$, $CH_2Cl$ or $CH_2Br$;

Y is H, $C_1$-$C_2$ alkyl, $C_1$-$C_2$ alkoxy, $CH_2OCH_3$, $CH_2OCH_2CH_3$, $NHCH_3$, $N(OCH_3)CH_3$, $N(CH_3)_2$, $CF_3$, $SCH_3$, $OCH_2CH{=}CH_2$, $OCH_2C\equiv CH$, $OCH_2CH_2OCH_3$, $CH_2SCH_3$, $C(O)R_a$,

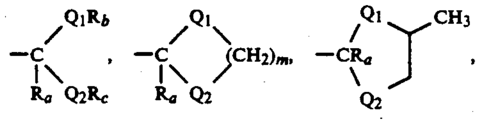

$OCF_2F$, $SCF_2H$, $OCF_2Br$, cyclopropyl, $C\equiv CH$ or $C\equiv CCH_3$; and Z is CH or N.

9. Compounds of Preferred 8 wherein $R_2$ is H, $C_1$-$C_4$ alkyl, CN, $CH_2CN$, $CH_2OCH_3$, alkyl or propargyl; and $R_3$ is H, $CH_3$ or $CH_2CH_3$.

10. Compounds of Preferred 9 wherein

A is A-1;

X is $CH_3$, $OCH_3$, $OCH_2CH_3$, Cl, $OCF_2H$ or $OCH_2CF_3$; and

Y is $CH_3$, $OCH_3$, $CH_2CH_3$, $CH_2OCH_3$, $NHCH_3$ or $CH(OCH_3)_2$.

11. Compounds of Preferred 10 wherein

R is H;

$R_1$ is H; and p is O.

12. Compounds of Formula I wherein $R_4$ is F, Cl or $CH_3$.

13. Compounds of Preferred 12 wherein $R_2$ is $C_1$-$C_2$ haloalkyl, OH, $C_1$-$C_2$ alkoxy, $NH_2$, $NHCH_3$, $N(CH_3)_2$, $C_1$-$C_2$ alkyl substituted by $C_1$-$C_2$ alkylthio, $C_3$-$C_4$ cycloalkyl or $C(O)R_5$;

$R_3$ is H, $C_1$-$C_4$ alkyl or $C_1$-$C_2$ haloalkyl; or $R_2$ and $R_3$ are taken together as $-(CH_2)_n-$, or

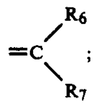

and n is 2 or 3.

14. Compounds of Preferred 13 wherein

W is O;

X is $C_1$-$C_2$ alkyl, $C_1$-$C_2$ alkoxy, F, Cl, Br, I, $OCF_2H$, $CH_2F$, $CF_3$, $OCH_2CH_2F$, $OCH_2CHF_2$, $OCH_2CF_3$, $CH_2Cl$ or $CH_2Br$;

Y is H, $C_1$-$C_2$ alkyl, $C_1$-$C_2$ alkoxy, $CH_2OCH_3$, $CH_2OCH_2CH_3$, $NHCH_3$, $N(OCH_3)CH_3$, $N(CH_3)_2$, $CF_3$, $SCH_3$, $OCH_2CH{=}CH_2$, $OCH_2C\equiv CH$, $OCH_2CH_2OCH_3$, $CH_2SCH_3$, $C(O)R_a$,

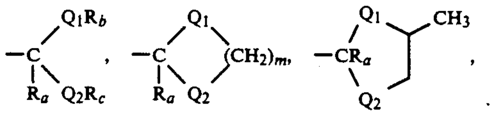

$OCF_2H$, $SCF_2H$, $OCF_2Br$, cyclopropyl, $C\equiv CH$ or $C\equiv CCH_3$; and Z is CH or N.

15. Compounds of Preferred 14 wherein $R_2$ is $NH_2$, $NHCH_3$, $N(CH_3)_2$, $CF_3$, $CF_2H$, OH, $OCH_3$, $CH_2SCH_3$, cyclopropyl or $C(O)R_5$;

$R_3$ is H, $CH_3$ or $CH_2CH_3$; or $R_2$ and $R_3$ are taken together as $-(CH_2)_n-$, or

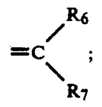

$R_5$ is H, $CH_3$, $OCH_3$, $NH_2$, $NHCH_3$ or $N(CH_3)_2$; and $R_6$ is H or $C_1$-$C_2$ alkyl.

16. Compounds of Preferred 15 wherein

A is A-1;

X is $CH_3$, $OCH_3$, $OCH_2CH_3$, Cl, $OCF_2H$ or $OCH_2CF_3$; and

Y is $CH_3$, $OCH_3$, $CH_2CH_3$, $CH_{20}CH_3$, $NHCH_3$ or $CH(OCH_3)_2$.

17. Compounds of Preferred 16 wherein

R is H;

$R_1$ is H; and p is O.

18. Compounds of Preferred 12 wherein $R_2$ is H, $C_1$-$C_4$ alkyl, CN, $C_1$-$C_2$ alkyl substituted by CN or $C_1$-$C_2$ alkoxy, $C_3$-$C_4$ alkenyl or $C_3$-$C_4$ alkynyl;

$R_3$ is H, $C_1$-$C_4$ alkyl or $C_1$-$C_2$ haloalkyl; or $R_2$ and $R_3$ are taken together as $-(CH_2)_n-$ or $-CH_2CH_2OCH_2CH_2-$; and n is 4 or 5.

19. Compounds of Preferred 18 wherein

W is O;

X is $C_1$-$C_2$ alkyl, $C_1$-$C_2$ alkoxy, F, Cl, Br, I, $OCF_2H$, $CH_2F$, $CF_3$, $OCH_2CH_2F$, $OCH_2CHF_2$, $OCH_2CF_3$, $CH_2Cl$ or $CH_2Br$;

Y is H, $C_1$-$C_2$ alkyl, $C_1$-$C_2$ alkoxy, $CH_2OCH_3$, $CH_2OCH_2CH_3$, $NHCH_3$, $N(OCH_3)CH_3$, $N(CH_3)_2$, $CF_3$, $SCH_3$, $OCH_2CH{=}CH_2$, $OCH_2C{\equiv}CH$, $OCH_2CH_2OCH_3$, $CH_2SCH_3$, $C(O)R_a$,

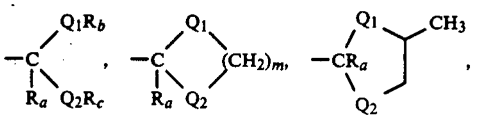

$OCF_2F$, $SCF_2F$, $OCF_2Br$, cyclopropyl, $C{\equiv}CH$ or $C{\equiv}CCH_3$; and Z is CH or N.

20. Compounds of Preferred 19 wherein $R_2$ is H, $C_1$-$C_4$ alkyl, CN, $CH_2CN$, $CH_2OCH_3$, allyl or propargyl; and $R_3$ is H, $CH_3$ or $CH_2CH_3$.

21. Compounds of Preferred 20 wherein

A is A-1;

$CH_3$, $OCH_3$, $OCH_2CH_3$, Cl, $OCF_2H$ or $OCH_2CF_3$; and

Y is $CH_3$, $OCH_3$, $CH_2CH_3$, $CH_2OCH_3$, $NHCH_3$ or $CH(OCH_3)_2$.

22. Compounds of Preferred 21 wherein

R is H;

$R_1$ is H; and p is O.

Compounds of the invention specifically preferred for reasons of greatest ease of synthesis and/or greatest herbicidal efficacy are N-[[(4,6-dimethoxy-2-pyrimidinyl)amino]carbonyl]-6-(dimethylamino)-2-pyridinesulfonamide, m.p. 141°-143° C.; 6-(dimethylamino)-N-[[[4-ethoxy-6-(methylamino)-1,3,5-triazin-2-yl]amino]carbonyl]-2-pyridinesulfonamide, m.p. 186°-188° C.; and N-[[[(4-ethoxy-6-(dimethylamino)-1,3,5-traizin-2-yl ]amino]carbonyl]-6-(methylamino)-2-pyridinesulfonamide, m.p. 116°-117° C.

This invention also comPrises intermediates of Formula II utilized in the Preparation of the compounds of Formula I.

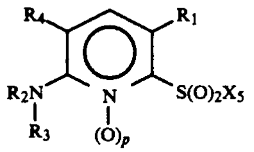

wherein $R_1$, $R_2$, $R_3$, $R_4$ and p are as previously defined; and $X_5$ is Cl, $NH_2$ or $NHC(CH_3)_3$;

provided that when $R_1$ is H, $R_3$ is H, $R_4$ is H, p is O and $X_5$ is $NH_2$, then $R_2$ is other than H.

The compounds of this invention are highly active as preemergent and/or postemergent herbicides or plant growth regulants. Some of the compounds demonstrate selective safety toward cereal crops, maize (corn), cotton and oilseed rape. The invention comprises in addition to the novel compounds agriculturally suitable compositions containing said novel compounds and a method of using said compounds and/or compositions as preemergent and/or postemergent herbicides or plant growth regulants.

DETAILED DESCRIPTION OF THE INVENTION

Compounds of Formula I can be prepared by the methods described in Equations 1 and 2.

Equation 1

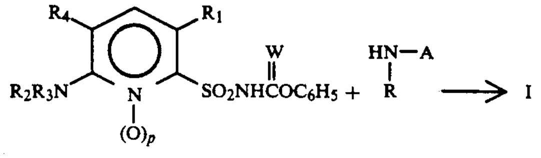

(2) (3)

The reaction shown in Equation 1 is carried out by contacting a phenyl carbamate or phenyl thiocarbamate of Formula (2) with an aminoheterocycle of Formula (3) in an inert organic solvent such as dioxane or tetrahydrofuran at temperatures of about 20° C. to 100° C. for a period of about one-half to twenty-four hours. The product can be isolated by evaporation of the reaction solvent and purified by triturating the residue with solvents such as 1-chlorobutane or ethyl ether and filtering, by recrystallizing from mixtures of solvents such as 1,2-dichloroethane, 1-chlorobutane and heptane or by chromatography on silica gel.

Equation 2

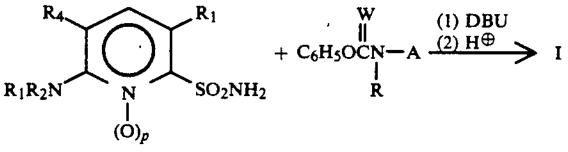

(4) (5)

The reaction of Equation 2 can be carried out by contacting a sulfonamide of Formula (4) with a heterocyclic phenyl carbamate of Formula (5) in the presence of 1,8-diazabicyclo[5,4,0]undec-7-ene (DBU), by methods analogous to those described in South African patent Application 830441. The phenyl carbamates of Formula (5) can be prepared by methods (or modifications thereof) described in South African Patent Application 825671 and South African Paten Application 825045.

Phenylcarbamates and phenylthiocarbamates of Formula (2) (Equation 1) can be prepared from sulfonamides of Formula (4) (Equation 2) by methods described (or modifications thereof) in U.S. Pat. No. 4,443,243. The sulfonamides (4) can be prepared via the routes shown in Equations 4-7, or by modifications thereof.

Equation 3

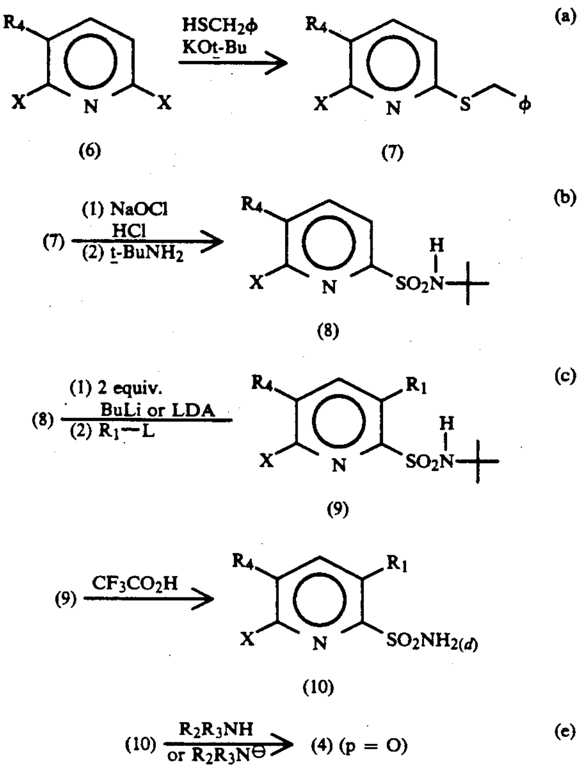

wherein:

X is F or Cl, and

L is a leaving group such as Cl, Br, I, alkyl sulfide, etc.; and with the provision that when $R_1=H$, then Step (3c) is omitted.

Dihalopyridine (6) (The Chemistry of Heterocyclic Compounds, Vol. 14, Wiley-Interscience, New York (1964) is contacted with benzyl mercaptan in the presence of potassium tert-butoxide in a solvent such as dimethylformamide to produce the sulfide (7). The product is isolated by partitioning the reaction mixture between water and ether (Equation 3a).

The sulfide (7) is converted to tert-butyl sulfonamide (8) by treatment with hypochlorite solution followed by tert-butylamine using the methods described in South African patent Application 848845 (Equation 3b).

Metallation of compound (8) by treatment with two equivalents of a strong base such as n-butyllithium or lithium diisopropylamide (LDA) followed by treatment with an appropriate electrophile ($R_1$—L) produces compound (9). An appropriate choice of electrophile $R_1$—L would be evident to one skilled in the art (Equation 3c).

Contacting tert-butylsulfonamide (9) with trifluoroacetic acid affords sulfonamide (10). The product may be isolated by evaporation of the volatiles followed by trituration of the residue with an organic solvent such as ether (Equation 3d).

Treatment of (10) with at least two equivalents of ammonia or of a primary or secondary amine or with the anion of a primary or secondary amide or of a cyanamide produces sulfonamide (4) (p=0). The product may be isolated by evaporating the volatiles in vacuo and triturating the residue with water or by partitioning the mixture between water and an organic solvent (Equation 3e).

Equation 4

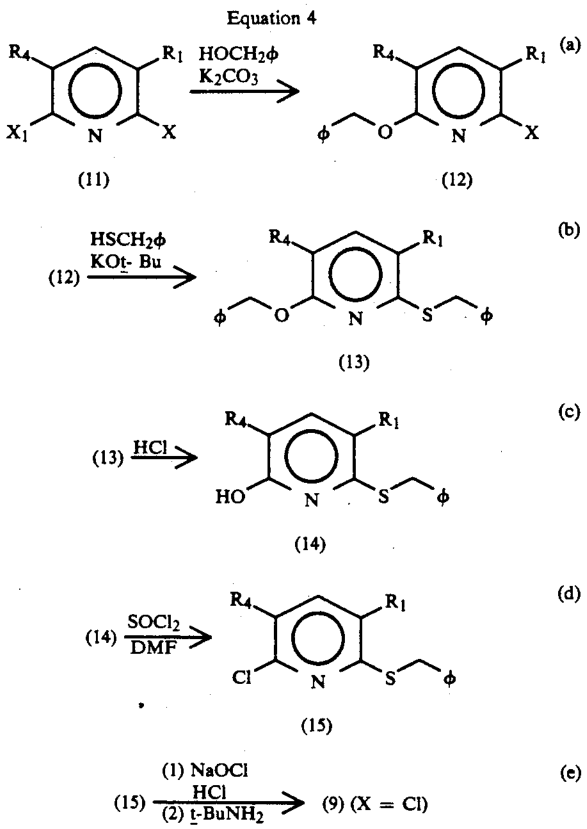

wherein: X and $X_1$ may be independently F, Cl or Br.

The dihalopyride (11) (*The Chemistry of Heterocyclic Compounds*, Vol. 14, Wiley-Interscience New York (1964)) is contacted with benzyl alcohol in the presence of an acid acceptor such as potassium carbonate in an inert solvent such as dimethyl sulfoxide to produce the ether (12). The product is isolated by partitioning the reaction mixture between water and ether (Equation 4a).

The compound (12) is converted to sulfide (13) as described previously for Equation 3a (Equation 4b). Treatment of (13) with concentrated hydrochloric acid produces the pyridinol (14). The product is isolated by partitioning the reaction mixture between water and an organic solvent (Equation 4c).

The pyridinol (14) is converted to chloride (15) by refluxing with thionyl chloride in the presence of dimethylformamide (DMF). The product is isolated by evaporation of the volatiles in vacuo and partitioning the residue between water and an organic solvent (Equation 4d).

The chloride (15) is converted to sulfonamide (9) (X=Cl) as described previously for Equation 3b (Equation 4e).

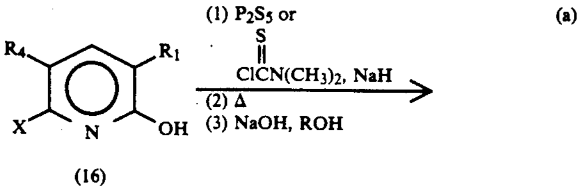

-continued

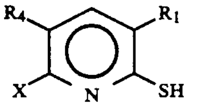

(17)

(b)

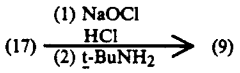

wherein: X is F, Cl or Br.

The hydroxylpyridine (16) (*The Chemistry of Heterocyclic Compounds*), Vol. 14, Wiley-Interscience, New York (1964)) is converted to mercaptopyridine (17) by treatment with phosphorous pentasulfide or via the thiocarbamate according to the procedure of Newman, et al. in *J. Org. Chem.* 31 3980 (1966) (Equation 5a).

Mercaptopyridine (17) is converted to sulfonamide (9) as described previously for Equation 3b (Equation 5b).

(a)

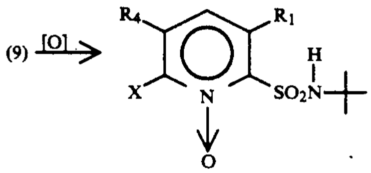

(18)

(b)

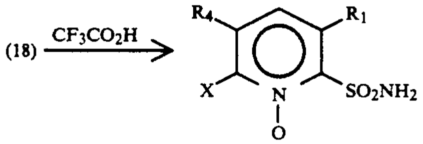

(19)

(c)

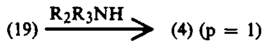

wherein:

X is F, Cl or Br.

Sulfonamide (9) may be converted to the N-oxide (18) by methods such as those described (or modifications thereof) in Evans, et al., *Rec. Trav.* 78 408 (1959). Some of the oxidants of choice for this transformation are m-chloroperoxybenzoic acid, peracetic acid, etc. (Equation 6a).

Compound (18) may be converted to sulfonamide (19) as described previously for Equation 3d (Equation 6b).

Sulfonamide (19) may be converted to sulfonamide (4) (p=1) as described previously for Equation 3e (Equation 6c).

(a)

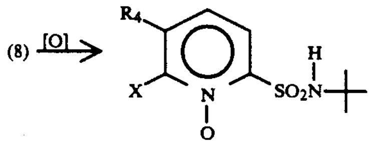

(20)

-continued

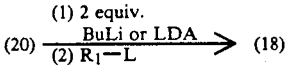

wherein:

X is F or Cl, and

In cases where the substituent $R_1$ is sensitive to oxidation, this substituent may be introduced subsequent to the N-oxidation reaction. Thus, the sulfonamide (8) is converted to the N-oxide (20) by methods described for Equation 6a (Equation 7a).

The N-oxide (20) is metallated and reacted with an electrophile ($R_1$—L) to produce sulfonamide (18) as described previously for Equation 3c (Equation 7b).

For further details pertaining to lithiations of pyridine ring systems see, Epsztajn et al., *Tetrahedron Lett.*, 4739 (1980) Snieckus et al., *J. Am. Chem. Soc.*, 102, 1457 (1980); Kuraishi et al., *Tet. Lett.*, 2049 (1983); Meyers et al., *J. Org. Chem.*, 2633 (1982); Taylor et al., *J. Org. Chem.*, 48, 4156 (1983) and Breant et al., *Synthesis*, 822 (1983).

For a general treatment of pyridines and pyridine N-oxides see, Katritzky, A. R., and Rees, C. W., "Comprehensive Heterocyclic Chemistry", Vol. 2, Pergamon Press, Oxford, New York, Part 2A, 1984.

Phenyl carbamates and phenyl thiocarbamates (5) of Equation 2 can be prepared from heterocyclic amines (3) by methods, or modifications thereof known to those skilled in the art, described in South African patent Application 82/5671 and South African patent Application 82/5045.

The synthesis of heterocyclic amines such as those represented by Formula 3 (Equation 1) has been reviewed in "The Chemistry of Heterocyclic Compounds," a series published by Interscience Publ., New York and London. Aminopyrimidines are described by D. J. Brown in "The Pyrimidines," Vol. XVI of the series mentioned above which is herein incorporated by reference. The 2-amino-1,3,5-triazines of Formula 3, where A is A-1 and Z is N, can be prepared according to the methods described by E. M. Smolin and L. Rapaport in "s-Triazines and Derivatives," Vol. XIII.

Pyrimidines of Formula 3, where A is A-1 and Y is an acetal or thioacetal substituent, can be prepared by methods taught in European Patent Application No. 84,224 (published Jul. 27, 1983).

Pyrimidines of Formula 3, where A is A-1 and Y is cyclopropyl or $OCF_2H$ can be synthesized according to the methods taught in U.S. Pat. No. 4,515,626 and U.S. Pat. No. 4,540,782, respectively.

Compounds of Formula 3, where A is A-2 or A-3, can be prepared by U.S. Pat. No. 4,339,267.

Compounds of Formula 3, where A is A-4, can be prepared by methods taught in U.S. Pat. No. 4,487.626.

Additional references dealing with the synthesis of bicyclic pyrimidines of Formula 3, where A is A-2, A-3, or A-4 are Braker, Sheehan, Spitzmiller and Lott, *J. Am. Chem. Soc.*, 69, 3072 (1947); Mitler and Bhattachanya, *Quart. J. Indian Chem. Soc.*, 4, 152 (1927); Shrage and Hitchings, *J. Org. Chem.*, 16, 1153 (1951); Caldwell, Kornfeld and Donnell, *J. Am. Chem., Soc.*, 63, 2188 (1941): and Fissekis, Myles and Brown, *J. Org. Chem.*, 29, 2670 (1964).

Compounds of Formula 3, where A is A-5, can be prepared by methods taught in U.S. Pat. No. 4,421,550.

Compounds of Formula 3, where A is A-6, can be prepared by methods taught in U.S. Pat. No. 4,496,392.

Compounds of Formula 3, where A is A-7, can be prepared by methods taught in EP-A-125,864.

Agriculturally suitable salts of compounds of Formula I are also useful herbicides and can be prepared by well-known methods including those described in U.S. Pat. No. 4,127,405.

The following Example illustrates the synthesis of the compounds of this invention. Temperatures are reported in degrees Celsius. Abbreviations for nuclear magnetic resonance (NMR) are s=singlet, d=doublet, dd=doublet of doublets, br32 broad, and peak positions are reported as parts per million downfield from internal tetramethylsilane. The NMR spectra were measured at 200 MHz.

EXAMPLE 1

Step A

N-(1,1-dimethylethyl)-6-fluoro-2-pyridinesulfonamide

To 13.46 g (120 mmol) potassium tert-butoxide dissolved in 200 ml dry DMF was added dropwise 11.8 ml (12.5 g, 200 mmol) benzyl mercaptan while maintaining a temperature of 0° C. to 5° C. This mixture was warmed to room temperature for 15 min, then cooled to −30° C., when 9.1 ml (11.5 g, 100 mmol) 2,6-difluoropyridine was added all at once. The reaction mixture was stirred 2 hr at 0° C., then at room temperature overnight. The mixture was then poured into 800 ml ice-water and extracted into 800 ml of ether. The ether layer was washed with three 200-ml portions of water, dried over magnesium sulfate, filtered and concentrated in vacuo to leave 21.97 g of a yellow oil.

This crude sulfide was dissolved in 400 ml of methylene chloride, 200 ml of water was added and the mixture cooled to 0° C. Then 28.4 ml (341 mmol) of concentrated hydrochloric acid was added, followed by dropwise addition with vigorous stirring of 484 ml (341 mmol) of 5.25% sodium hypochlorite (Clorox ®) while maintaining a temperature of 0° C. to 5° C. After stirring another 20 min at 0° C., the mixture was separated and the organic phase was dried over magnesium sulfate, filtered and concentrated in vacuo, maintaining a temperature of no higher than 25° C.

The residue was dissolved in 100 ml of methylene chloride and added dropwise to 25 ml (17.4 g, 238 mmol) tert-bulylamine in 200 ml of methylene chloride, maintaining a temperature of 20° C. to 25° C. The mixture was stirred 3 days at room temperature, then washed with 100 ml of water, dried over magnesium sulfate, filtered and concentrated in vacuo to leave a dark oil, which was triturated with hexanes to afford 15.90 g of olive-green solid, m.p. 88° C. to 90° C.

NMR ($CDCL_3$): δ 1.25 (s, 9H), 4.96 (br s, 1H), 7.13 (dd, 1H), 7.95 (m, 1H), 8.02 (dd, 1H).

Step B 6-Fluoropyridine-2-sulfonamide

To 100 ml trifluoroacetic acid was added 11.6 g (50 mmol) of N-(1,1-dimethylethyl)-6-fluoro-2-pyridinesulfonamide and the mixture was refluxed for two days. The volatiles were then removed in vacuo and the residue triturated with ether to afford 7.23 g of tan solid, m.p. 110° C. to 111° C.

NMR ($CDCl_3$) δ 7.30 (d, 1H), 8.00 (d, 1H), 8.17 (dd, 1H).

Step C 6-(Methylamino)pyridine-2-sulfonamide

To 10 ml of condensed methylamine was added 1.86 g (10 mmol) of 6-fluoropyridine-2-sulfonamide. The mixture was allowed to reflux under a dry-ice condenser for 4 hr, then excess amine was allowed to evaporate overnight. The residue was crystallized with water to yield 1.64 g of tan solid, m.p. 124° C. to 26° C.

NMR ($CDCl_3$): δ 2.64 (s, 3H), 6.12 (br s, 2H), 6.30 (d, 1H), 6.86 (d, 1H), 7.23 (dd, 1H).

Step D

2-[[(4,6-dimethoxypyrimidin-2-yl) aminocarbonyl]-aminosulfonly]-6-(methylamino)pyridine To a suspension of 0.20 g (1.0 mmol) of 6-(methylamino)pyridine-2-sulfonamide and 0.28 g (1.0 mmol) of 4,6-dimethoxypyrimidin-2-yl phenyl carbamate in 1.0 ml of acetonitrile was added 0.20 ml (0.20 g, 1.3 mmol) of 1,8-diazabicyclo[5,4,0]undec-7-ene. The mixture was stirred at room temperature for 1 hr, then 3 ml of water was added. Dropwise addition of 1N hydrochloric acid precipitated a solid which was filtered and washed with water to afford 0.21 g of the title compound as a white powder, m.p. 166° C. to 168° C.

NMR($CDCl_3+CF_3CO_2D$): δ 3.09 (s, 3H), 4.01 (s, 6H), 5.88 (s, 1H), 7.10 (d, 1H), 7.51 (d, 1H), 7.94 (dd, 1H).

By applying the procedures of Example 1 and those described in Equations 1 through 7, the compounds in Tables I through IV can be prepared by one skilled in the art (melting points are in ° C).

GENERAL STRUCTURES FOR TABLES

General Structure 1

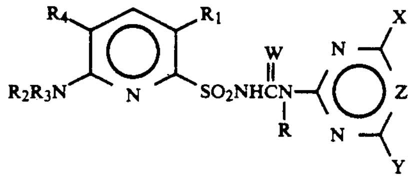

General Structure 2

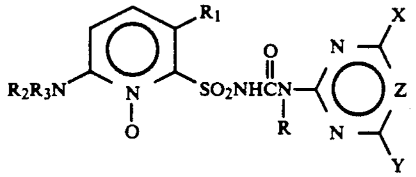

General Structure 3

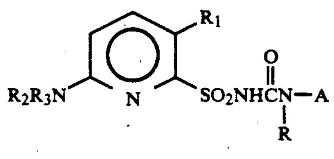

General Structure 4

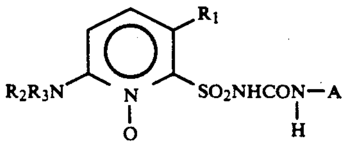

TABLE I

| | | General Structure I | | | | | | |
|---|---|---|---|---|---|---|---|---|
| $R_1$ | $R_2$ | $R_3$ | $R_4$ | W | R | X | Y | Z |
| H | H | H | H | O | H | $OCH_3$ | $OCH_3$ | CH |
| H | H | H | H | O | H | Cl | $OCH_3$ | CH |
| H | H | H | H | O | H | $CH_3$ | $OCH_3$ | CH |
| H | H | H | H | O | H | $CH_3$ | $CH_3$ | CH |
| H | H | H | H | O | H | $OCH_3$ | $OCH_3$ | N |
| H | H | H | H | O | H | $CH_3$ | $OCH_3$ | N |
| H | H | H | H | O | H | $CH_3$ | $CH_3$ | N |
| H | H | H | H | O | H | $OCH_2CH_3$ | $OCH_2CH_3$ | N |
| H | H | H | H | O | H | $NHCH_3$ | $OCH_2CH_3$ | N |
| H | H | H | H | O | H | $N(CH_3)_2$ | $OCH_2CH_3$ | N |
| H | H | H | H | O | H | $N(CH_3)_2$ | $OCH_3$ | N |
| H | H | H | H | O | H | $N(CH_3)_2$ | $OCH_2CF_3$ | N |
| H | H | H | H | O | $CH_3$ | $CH_3$ | $OCH_3$ | N |
| H | H | H | H | S | H | $OCH_3$ | $OCH_3$ | CH |
| H | H | H | H | S | H | Cl | $OCH_3$ | CH |
| H | H | H | H | S | H | $CH_3$ | $OCH_3$ | CH |
| H | H | H | H | S | H | $CH_3$ | $CH_3$ | CH |
| H | H | H | H | S | H | $OCH_3$ | $OCH_3$ | N |
| H | H | H | H | S | H | $CH_3$ | $OCH_3$ | N |
| H | H | $CH_3$ | H | O | H | $OCH_3$ | $OCH_3$ | CH |
| H | H | $CH_3$ | H | O | H | Cl | $OCH_3$ | CH |
| H | H | $CH_3$ | H | O | H | $CH_3$ | $OCH_3$ | CH |
| H | H | $CH_3$ | H | O | H | $CH_3$ | $CH_3$ | CH |
| H | H | $CH_3$ | H | O | H | $OCH_3$ | $OCH_3$ | N |
| H | H | $CH_3$ | H | O | H | $CH_3$ | $OCH_3$ | N |
| H | H | $CH_3$ | H | O | H | $CH_3$ | $CH_3$ | N |
| H | H | $CH_3$ | H | O | H | $OCH_2CH_3$ | $OCH_2CH_3$ | N |
| H | H | $CH_3$ | H | O | H | $NHCH_3$ | $OCH_2CH_3$ | N |
| H | H | $CH_3$ | H | O | H | $N(CH_3)_2$ | $OCH_2CH_3$ | N |
| H | H | $CH_3$ | H | O | H | $N(CH_3)_2$ | $OCH_3$ | N |
| H | H | $CH_3$ | H | O | H | $N(CH_3)_2$ | $OCH_2CF_3$ | N |
| H | H | $CH_3$ | H | O | $CH_3$ | $CH_3$ | $OCH_3$ | N |
| H | H | $CH_3$ | H | S | H | $OCH_3$ | $OCH_3$ | CH |
| H | H | $CH_3$ | H | S | H | Cl | $OCH_3$ | CH |
| H | H | $CH_3$ | H | S | H | $CH_3$ | $OCH_3$ | CH |
| H | H | $CH_3$ | H | S | H | $CH_3$ | $CH_3$ | CH |
| H | H | $CH_3$ | H | S | H | $OCH_3$ | $OCH_3$ | N |
| H | H | $CH_3$ | H | S | H | $CH_3$ | $OCH_3$ | N |
| H | H | $CH_2CH_3$ | H | O | H | $OCH_3$ | $OCH_3$ | CH |
| H | H | $CH_2CH_3$ | H | O | H | Cl | $OCH_3$ | CH |
| H | H | $CH_2CH_3$ | H | O | H | $CH_3$ | $OCH_3$ | CH |
| H | H | $CH_2CH_3$ | H | O | H | $CH_3$ | $CH_3$ | CH |
| H | H | $CH_2CH_3$ | H | O | H | $OCH_3$ | $OCH_3$ | N |
| H | H | $CH_2CH_3$ | H | O | H | $CH_3$ | $OCH_3$ | N |
| H | H | $CH_2CH_3$ | H | O | H | $CH_3$ | $CH_3$ | N |
| H | H | $CH_2CH_3$ | H | O | H | $OCH_2CH_3$ | $OCH_2CH_3$ | N |
| H | H | $CH_2CH_3$ | H | O | H | $NHCH_3$ | $OCH_2CH_3$ | N |
| H | H | $CH_2CH_3$ | H | O | H | $N(CH_3)_2$ | $OCH_2CH_3$ | N |
| H | H | $CH_2CH_3$ | H | O | H | $N(CH_3)_2$ | $OCH_3$ | N |
| H | H | $CH_2CH_3$ | H | O | H | $N(CH_3)_2$ | $OCH_2CF_3$ | N |
| H | H | $CH_2CH_3$ | H | O | $CH_3$ | $CH_3$ | $OCH_3$ | N |
| H | H | $CH_2CH_3$ | H | S | H | $OCH_3$ | $OCH_3$ | CH |
| H | H | $CH_2CH_3$ | H | S | H | Cl | $OCH_3$ | CH |
| H | H | $CH_2CH_3$ | H | S | H | $CH_3$ | $OCH_3$ | CH |
| H | H | $CH_2CH_3$ | H | S | H | $CH_3$ | $CH_3$ | CH |
| H | H | $CH_2CH_3$ | H | S | H | $OCH_3$ | $OCH_3$ | N |
| H | H | $CH_2CH_3$ | H | S | H | $CH_3$ | $OCH_3$ | N |
| H | H | $CH_2CF_3$ | H | O | H | $OCH_3$ | $OCH_3$ | CH |
| H | H | $CH_2CF_3$ | H | O | H | Cl | $OCH_3$ | CH |
| H | H | $CH_2CF_3$ | H | O | H | $CH_3$ | $OCH_3$ | CH |
| H | H | $CH_2CF_3$ | H | O | H | $CH_3$ | $CH_3$ | CH |
| H | H | $CH_2CF_3$ | H | O | H | $OCH_3$ | $OCH_3$ | N |
| H | H | $CH_2CF_3$ | H | O | H | $CH_3$ | $OCH_3$ | N |
| H | H | $CH_2CF_3$ | H | O | H | $CH_3$ | $CH_3$ | N |
| H | H | $CH_2CF_3$ | H | O | H | $OCH_2CH_3$ | $OCH_2CH_3$ | N |
| H | H | $CH_2CF_3$ | H | O | H | $NHCH_3$ | $OCH_2CH_3$ | N |
| H | H | $CH_2CF_3$ | H | O | H | $N(CH_3)_2$ | $OCH_2CH_3$ | N |
| H | H | $CH_2CF_3$ | H | O | H | $N(CH_3)_2$ | $OCH_3$ | N |
| H | H | $CH_2CF_3$ | H | O | H | $N(CH_3)_2$ | $OCH_2CF_3$ | N |
| H | H | $CH_2CF_3$ | H | O | $CH_3$ | $CH_3$ | $OCH_3$ | N |
| H | H | $CH_2CF_3$ | H | S | H | $OCH_3$ | $OCH_3$ | CH |
| H | H | $CH_2CF_3$ | H | S | H | Cl | $OCH_3$ | CH |
| H | H | $CH_2CF_3$ | H | S | H | $CH_3$ | $OCH_3$ | CH |
| H | H | $CH_2CF_3$ | H | S | H | $CH_3$ | $CH_3$ | CH |
| H | H | $CH_2CF_3$ | H | S | H | $OCH_3$ | $OCH_3$ | N |
| H | H | $CH_2CF_3$ | H | S | H | $CH_3$ | $OCH_3$ | N |
| H | $CH_2CH_2Cl$ | H | H | O | H | $OCH_3$ | $OCH_3$ | CH |
| H | $CH_2CH_2Cl$ | H | H | O | H | Cl | $OCH_3$ | CH |
| H | $CH_2CH_2Cl$ | H | H | O | H | $CH_3$ | $OCH_3$ | CH |
| H | $CH_2CH_2Cl$ | H | H | O | H | $CH_3$ | $CH_3$ | CH |

TABLE I-continued

| | | | | | | | | |
|---|---|---|---|---|---|---|---|---|
| H | $CH_2CH_2Cl$ | H | H | O | H | $OCH_3$ | $OCH_3$ | N |
| H | $CH_2CH_2Cl$ | H | H | O | H | $CH_3$ | $OCH_3$ | N |
| H | $CH_2CH_2Cl$ | H | H | O | H | $CH_3$ | $CH_3$ | N |
| H | $CH_2CH_2Cl$ | H | H | O | H | $OCH_2CH_3$ | $OCH_2CH_3$ | N |
| H | $CH_2CH_2Cl$ | H | H | O | H | $NHCH_3$ | $OCH_2CH_3$ | N |
| H | $CH_2CH_2Cl$ | H | H | O | H | $N(CH_3)_2$ | $OCH_2CH_3$ | N |
| H | $CH_2CH_2Cl$ | H | H | O | H | $N(CH_3)_2$ | $OCH_2CF_3$ | N |
| H | $CH_2CH_2Cl$ | H | H | O | $CH_3$ | $CH_3$ | $OCH_3$ | N |
| H | $CH_2CH_2Cl$ | H | H | S | H | $OCH_3$ | $OCH_3$ | CH |
| H | $CH_2CH_2Cl$ | H | H | S | H | Cl | $OCH_3$ | CH |
| H | $CH_2CH_2Cl$ | H | H | S | H | $CH_3$ | $OCH_3$ | CH |
| H | $CH_2CH_2Cl$ | H | H | S | H | $CH_3$ | $CH_3$ | CH |
| H | $CH_2CH_2Cl$ | H | H | S | H | $OCH_3$ | $OCH_3$ | N |
| H | $CH_2CH_2Cl$ | H | H | S | H | $CH_3$ | $OCH_3$ | N |
| H | $CH_2CN$ | H | H | O | H | $OCH_3$ | $OCH_3$ | CH |
| H | $CH_2CN$ | H | H | O | H | CL | $OCH_3$ | CH |
| H | $CH_2CN$ | H | H | O | H | $CH_3$ | $OCH_3$ | CH |
| H | $CH_2CN$ | H | H | O | H | $CH_3$ | $CH_3$ | CH |
| H | $CH_2CN$ | H | H | O | H | $OCH_3$ | $OCH_3$ | N |
| H | $CH_2CN$ | H | H | O | H | $CH_3$ | $OCH_3$ | N |
| H | $CH_2CN$ | H | H | O | H | $CH_3$ | $CH_3$ | N |
| H | $CH_2CN$ | H | H | O | H | $OCH_2CH_3$ | $OCH_2CH_3$ | N |
| H | $CH_2CN$ | H | H | O | H | $NHCH_3$ | $OCH_2CH_3$ | N |
| H | $CH_2CN$ | H | H | O | H | $N(CH_3)_2$ | $OCH_2CH_3$ | N |
| H | $CH_2CN$ | H | H | O | H | $N(CH_3)_2$ | $OCH_3$ | N |
| H | $CH_2CN$ | H | H | O | H | $N(CH_3)_2$ | $OCH_2CF_3$ | N |
| H | $CH_2CN$ | H | H | O | $CH_3$ | $CH_3$ | $OCH_3$ | N |
| H | $CH_2CN$ | H | H | S | H | $OCH_3$ | $OCH_3$ | CH |
| H | $CH_2CN$ | H | H | S | H | Cl | $OCH_3$ | CH |
| H | $CH_2CN$ | H | H | S | H | $CH_3$ | $OCH_3$ | CH |
| H | $CH_2CN$ | H | H | S | H | $CH_3$ | $CH_3$ | CH |
| H | $CH_2CN$ | H | H | S | H | $OCH_3$ | $OCH_3$ | N |
| H | $CH_2CN$ | H | H | S | H | $CH_3$ | $OCH_3$ | N |
| H | $CH_2CH{=}CH_2$ | H | H | O | H | $OCH_3$ | $OCH_3$ | CH |
| H | $CH_2CH{=}CH_2$ | H | H | O | H | Cl | $OCH_3$ | CH |
| H | $CH_2CH{=}CH_2$ | H | H | O | H | $CH_3$ | $OCH_3$ | CH |
| H | $CH_2CH{=}CH_2$ | H | H | O | H | $CH_3$ | $CH_3$ | CH |
| H | $CH_2CH{=}CH_2$ | H | H | O | H | $OCH_3$ | $OCH_3$ | N |
| H | $CH_2CH{=}CH_2$ | H | H | O | H | $CH_3$ | $OCH_3$ | N |
| H | $CH_2CH{=}CH_2$ | H | H | O | H | $CH_3$ | $CH_3$ | N |
| H | $CH_2CH{=}CH_2$ | H | H | O | H | $OCH_2CH_3$ | $OCH_2CH_3$ | N |
| H | $CH_2CH{=}CH_2$ | H | H | O | H | $NHCH_3$ | $OCH_2CH_3$ | N |
| H | $CH_2CH{=}CH_2$ | H | H | O | H | $N(CH_3)_2$ | $OCH_2CH_3$ | N |
| H | $CH_2CH{=}CH_2$ | H | H | O | H | $N(CH_3)_2$ | $OCH_3$ | N |
| H | $CH_2CH{=}CH_2$ | H | H | O | H | $N(CH_3)_2$ | $OCH_2CF_3$ | N |
| H | $CH_2CH{=}CH_2$ | H | H | O | $CH_3$ | $CH_3$ | $OCH_3$ | N |
| H | $CH_2CH{=}CH_2$ | H | H | S | H | $OCH_3$ | $OCH_3$ | CH |
| H | $CH_2CH{=}CH_2$ | H | H | S | H | Cl | $OCH_3$ | CH |
| H | $CH_2CH{=}CH_2$ | H | H | S | H | $CH_3$ | $OCH_3$ | CH |
| H | $CH_2CH{=}CH_2$ | H | H | S | H | $CH_3$ | $CH_3$ | CH |
| H | $CH_2CH{=}CH_2$ | H | H | S | H | $OCH_3$ | $OCH_3$ | N |
| H | $CH_2CH{=}CH_2$ | H | H | S | H | $CH_3$ | $OCH_3$ | N |
| H | $CH_2C{\equiv}CH$ | H | H | O | H | $OCH_3$ | $OCH_3$ | CH |
| H | $CH_2C{\equiv}CH$ | H | H | O | H | Cl | $OCH_3$ | CH |
| H | $CH_2C{\equiv}CH$ | H | H | O | H | $CH_3$ | $OCH_3$ | CH |
| H | $CH_2C{\equiv}CH$ | H | H | O | H | $CH_3$ | $CH_3$ | CH |
| H | $CH_2C{\equiv}CH$ | H | H | O | H | $OCH_3$ | $OCH_3$ | N |
| H | $CH_2C{\equiv}CH$ | H | H | O | H | $CH_3$ | $OCH_3$ | N |
| H | $CH_2C{\equiv}CH$ | H | H | O | H | $CH_3$ | $CH_3$ | N |
| H | $CH_2C{\equiv}CH$ | H | H | O | H | $OCH_2CH_3$ | $OCH_2CH_3$ | N |
| H | $CH_2C{\equiv}CH$ | H | H | O | H | $NHCH_3$ | $OCH_2CH_3$ | N |
| H | $CH_2C{\equiv}CH$ | H | H | O | H | $N(CH_3)_2$ | $OCH_2CH_3$ | N |
| H | $CH_2C{\equiv}CH$ | H | H | O | H | $N(CH_3)_2$ | $OCH_3$ | N |
| H | $CH_2C{\equiv}CH$ | H | H | O | H | $N(CH_3)_2$ | $OCH_2CF_3$ | N |
| H | $CH_2C{\equiv}CH$ | H | H | O | $CH_3$ | $CH_3$ | $OCH_3$ | N |
| H | $CH_2C{\equiv}CH$ | H | H | S | H | $OCH_3$ | $OCH_3$ | CH |
| H | $CH_2C{\equiv}CH$ | H | H | S | H | Cl | $OCH_3$ | CH |
| H | $CH_2C{\equiv}CH$ | H | H | S | H | $CH_3$ | $OCH_3$ | CH |
| H | $CH_2C{\equiv}CH$ | H | H | S | H | $CH_3$ | $CH_3$ | CH |
| H | $CH_2C{\equiv}CH$ | H | H | S | H | $OCH_3$ | $OCH_3$ | N |
| H | $CH_2C{\equiv}CH$ | H | H | S | H | $CH_3$ | $OCH_3$ | N |
| H | $CH_2CH_2OCH_3$ | H | H | O | H | $OCH_3$ | $OCH_3$ | CH |
| H | $CH_2CH_2OCH_3$ | H | H | O | H | Cl | $OCH_3$ | CH |
| H | $CH_2CH_2OCH_3$ | H | H | O | H | $CH_3$ | $OCH_3$ | CH |
| H | $CH_2CH_2OCH_3$ | H | H | O | H | $CH_3$ | $CH_3$ | CH |
| H | $CH_2CH_2OCH_3$ | H | H | O | H | $OCH_3$ | $OCH_3$ | N |
| H | $CH_2CH_2OCH_3$ | H | H | O | H | $CH_3$ | $OCH_3$ | N |
| H | $CH_2CH_2OCH_3$ | H | H | O | H | $CH_3$ | $CH_3$ | N |
| H | $CH_2CH_2OCH_3$ | H | H | O | H | $OCH_2CH_3$ | $OCH_2CH_3$ | N |
| H | $CH_2CH_2OCH_3$ | H | H | O | H | $NHCH_3$ | $OCH_2CH_3$ | N |
| H | $CH_2CH_2OCH_3$ | H | H | O | H | $N(CH_3)_2$ | $OCH_2CH_3$ | N |
| H | $CH_2CH_2OCH_3$ | H | H | O | H | $N(CH_3)_2$ | $OCH_3$ | N |

TABLE I-continued

| | | | | | | | | |
|---|---|---|---|---|---|---|---|---|
| H | $CH_2CH_2OCH_3$ | H | H | O | H | $N(CH_3)_2$ | $OCH_2CF_3$ | N |
| H | $CH_2CH_2OCH_3$ | H | H | O | $CH_3$ | $CH_3$ | $OCH_3$ | N |
| H | $CH_2CH_2OCH_3$ | H | H | S | H | $OCH_3$ | $OCH_3$ | CH |
| H | $CH_2CH_2OCH_3$ | H | H | S | H | Cl | $OCH_3$ | CH |
| H | $CH_2CH_2OCH_3$ | H | H | S | H | $CH_3$ | $OCH_3$ | CH |
| H | $CH_2CH_2OCH_3$ | H | H | S | H | $CH_3$ | $CH_3$ | CH |
| H | $CH_2CH_2OCH_3$ | H | H | S | H | $OCH_3$ | $OCH_3$ | N |
| H | $CH_2CH_2OCH_3$ | H | H | S | H | $CH_3$ | $OCH_3$ | N |
| H | cyclo-$C_3H_7$ | H | H | O | H | $OCH_3$ | $OCH_3$ | CH |
| H | cyclo-$C_3H_7$ | H | H | O | H | Cl | $OCH_3$ | CH |
| H | cyclo-$C_3H_7$ | H | H | O | H | $CH_3$ | $OCH_3$ | CH |
| H | cyclo-$C_3H_7$ | H | H | O | H | $CH_3$ | $CH_3$ | CH |
| H | cyclo-$C_3H_7$ | H | H | O | H | $OCH_3$ | $OCH_3$ | N |
| H | cyclo-$C_3H_7$ | H | H | O | H | $CH_3$ | $OCH_3$ | N |
| H | cyclo-$C_3H_7$ | H | H | O | H | $N(CH_3)_2$ | $OCH_3$ | N |
| H | cyclo-$C_3H_7$ | H | H | O | H | $OCH_2CH_3$ | $OCH_2CH_3$ | N |
| H | cyclo-$C_3H_7$ | H | H | O | H | $NHCH_3$ | $OCH_2CH_3$ | N |
| H | cyclo-$C_3H_7$ | H | H | O | H | $N(CH_3)_2$ | $OCH_2CH_3$ | N |
| H | cyclo-$C_3H_7$ | H | H | O | H | $N(CH_3)_2$ | $OCH_3$ | N |
| H | cyclo-$C_3H_7$ | H | H | O | H | $N(CH_3)_2$ | $OCH_2CF_3$ | N |
| H | cyclo-$C_3H_7$ | H | H | O | $CH_3$ | $CH_3$ | $OCH_3$ | N |
| H | cyclo-$C_3H_7$ | H | H | S | H | $OCH_3$ | $OCH_3$ | CH |
| H | cyclo-$C_3H_7$ | H | H | S | H | Cl | $OCH_3$ | CH |
| H | cyclo-$C_3H_7$ | H | H | S | H | $CH_3$ | $OCH_3$ | CH |
| H | cyclo-$C_3H_7$ | H | H | S | H | $CH_3$ | $CH_3$ | CH |
| H | cyclo-$C_3H_7$ | H | H | S | H | $OCH_3$ | $OCH_3$ | N |
| H | cyclo-$C_3H_7$ | H | H | S | H | $CH_3$ | $OCH_3$ | N |
| H | $CH_3$ | $CH_3$ | H | O | H | $OCH_3$ | $OCH_3$ | CH |
| H | $CH_3$ | $CH_3$ | H | O | H | Cl | $OCH_3$ | CH |
| H | $CH_3$ | $CH_3$ | H | O | H | $CH_3$ | $OCH_3$ | CH |
| H | $CH_3$ | $CH_3$ | H | O | H | $CH_3$ | $CH_3$ | CH |
| H | $CH_3$ | $CH_3$ | H | O | H | $OCH_3$ | $OCH_3$ | N |
| H | $CH_3$ | $CH_3$ | H | O | H | $CH_3$ | $OCH_3$ | N |
| H | $CH_3$ | $CH_3$ | H | O | H | $CH_3$ | $CH_3$ | N |
| H | $CH_3$ | $CH_3$ | H | O | H | $OCH_2CH_3$ | $OCH_2CH_3$ | N |
| H | $CH_3$ | $CH_3$ | H | O | H | $NHCH_3$ | $OCH_2CH_3$ | N |
| H | $CH_3$ | $CH_3$ | H | O | H | $N(CH_3)_2$ | $OCH_2CH_3$ | N |
| H | $CH_3$ | $CH_3$ | H | O | H | $N(CH_3)_2$ | $OCH_3$ | N |
| H | $CH_3$ | $CH_3$ | H | O | H | $N(CH_3)_2$ | $OCH_2CF_3$ | N |
| H | $CH_3$ | $CH_3$ | H | O | $CH_3$ | $CH_3$ | $OCH_3$ | N |
| H | $CH_3$ | $CH_3$ | H | S | H | $OCH_3$ | $OCH_3$ | CH |
| H | $CH_3$ | $CH_3$ | H | S | H | Cl | $OCH_3$ | CH |
| H | $CH_3$ | $CH_3$ | H | S | H | $CH_3$ | $OCH_3$ | CH |
| H | $CH_3$ | $CH_3$ | H | S | H | $CH_3$ | $CH_3$ | CH |
| H | $CH_3$ | $CH_3$ | H | S | H | $OCH_3$ | $OCH_3$ | N |
| H | $CH_3$ | $CH_3$ | H | S | H | $CH_3$ | $OCH_3$ | N |
| H | $CH_3$ | $CH_3$ | H | O | H | $OCH_3$ | $OCH_3$ | CH |
| H | $CH_3$ | $CH_3$ | H | O | H | Cl | $OCH_3$ | CH |
| H | $CH_3$ | $CH_3$ | H | O | H | $CH_3$ | $OCH_3$ | CH |
| H | $CH_3$ | $CH_3$ | H | O | H | $CH_3$ | $CH_3$ | CH |
| H | $CH_3$ | $CH_3$ | H | O | H | $OCH_3$ | $OCH_3$ | N |
| H | $CH_3$ | $CH_3$ | H | O | H | $CH_3$ | $OCH_3$ | N |
| H | $CH_3$ | $CH_3$ | H | O | H | $CH_3$ | $CH_3$ | N |
| H | $CH_3$ | $CH_3$ | H | O | H | $OCH_2CH_3$ | $OCH_2CH_3$ | N |
| H | $CH_3$ | $CH_3$ | H | O | H | $NHCH_3$ | $OCH_2CH_3$ | N |
| H | $CH_3$ | $CH_3$ | H | O | H | $N(CH_3)_2$ | $OCH_2CH_3$ | N |
| H | $CH_3$ | $CH_3$ | H | O | H | $N(CH_3)_2$ | $OCH_3$ | N |
| H | $CH_3$ | $CH_3$ | H | O | H | $N(CH_3)_2$ | $OCH_2CF_3$ | N |
| H | $CH_3$ | $CH_3$ | H | O | $CH_3$ | $CH_3$ | $OCH_3$ | N |
| H | $CH_3$ | $CH_3$ | H | S | H | $OCH_3$ | $OCH_3$ | CH |
| H | $CH_3$ | $CH_3$ | H | S | H | Cl | $OCH_3$ | CH |
| H | $CH_3$ | $CH_3$ | H | S | H | $CH_3$ | $OCH_3$ | CH |
| H | $CH_3$ | $CH_3$ | H | S | H | $CH_3$ | $CH_3$ | CH |
| H | $CH_3$ | $CH_3$ | H | S | H | $OCH_3$ | $OCH_3$ | N |
| H | $CH_3$ | $CH_3$ | H | S | H | $CH_3$ | $OCH_3$ | N |
| H | $CH_3$ | $CH_3$ | Cl | O | H | $OCH_3$ | $OCH_3$ | CH |
| H | $CH_3$ | $CH_3$ | Cl | O | H | Cl | $OCH_3$ | CH |
| H | $CH_3$ | $CH_3$ | Cl | O | H | $CH_3$ | $OCH_3$ | CH |
| H | $CH_3$ | $CH_3$ | Cl | O | H | $CH_3$ | $CH_3$ | CH |
| H | $CH_3$ | $CH_3$ | Cl | O | H | $OCH_3$ | $OCH_3$ | N |
| H | $CH_3$ | $CH_3$ | Cl | O | H | $CH_3$ | $OCH_3$ | N |
| H | $CH_3$ | $CH_3$ | Cl | O | H | $CH_3$ | $CH_3$ | N |
| H | $CH_3$ | $CH_3$ | Cl | O | H | $OCH_2CH_3$ | $OCH_2CH_3$ | N |
| H | $CH_3$ | $CH_3$ | Cl | O | H | $NHCH_3$ | $OCH_2CH_3$ | N |
| H | $CH_3$ | $CH_3$ | Cl | O | H | $N(CH_3)_2$ | $OCH_2CH_3$ | N |
| H | $CH_3$ | $CH_3$ | Cl | O | H | $N(CH_3)_2$ | $OCH_3$ | N |
| H | $CH_3$ | $CH_3$ | Cl | O | H | $N(CH_3)_2$ | $OCH_2CF_3$ | N |
| H | $CH_3$ | $CH_3$ | Cl | O | $CH_3$ | $CH_3$ | $OCH_3$ | N |
| H | $CH_3$ | $CH_3$ | Cl | S | H | $OCH_3$ | $OCH_3$ | CH |
| H | $CH_3$ | $CH_3$ | Cl | S | H | Cl | $OCH_3$ | CH |
| H | $CH_3$ | $CH_3$ | Cl | S | H | $CH_3$ | $OCH_3$ | CH |
| H | $CH_3$ | $CH_3$ | Cl | S | H | $CH_3$ | $CH_3$ | CH |

TABLE I-continued

| | | | | | | | | |
|---|---|---|---|---|---|---|---|---|
| H | $CH_3$ | $CH_3$ | Cl | S | H | $OCH_3$ | $OCH_3$ | N |
| H | $CH_3$ | $CH_3$ | Cl | S | H | $CH_3$ | $OCH_3$ | N |
| H | $CH_3$ | $CH_3$ | Cl | O | H | $OCH_3$ | $OCH_3$ | CH |
| H | $CH_3$ | $CH_3$ | Cl | O | H | Cl | $OCH_3$ | CH |
| H | $CH_3$ | $CH_3$ | Cl | O | H | $CH_3$ | $OCH_3$ | CH |
| H | $CH_3$ | $CH_3$ | Cl | O | H | $CH_3$ | $CH_3$ | CH |
| H | $CH_3$ | $CH_3$ | Cl | O | H | $OCH_3$ | $OCH_3$ | N |
| H | $CH_3$ | $CH_3$ | Cl | O | H | $CH_3$ | $OCH_3$ | N |
| H | $CH_3$ | $CH_3$ | Cl | O | H | $CH_3$ | $CH_3$ | N |
| H | $CH_3$ | $CH_3$ | Cl | O | H | $OCH_2CH_3$ | $OCH_2CH_3$ | N |
| H | $CH_3$ | $CH_3$ | Cl | O | H | $NHCH_3$ | $OCH_2CH_3$ | N |
| H | $CH_3$ | $CH_3$ | Cl | O | H | $N(CH_3)_2$ | $OCH_2CH_3$ | N |
| H | $CH_3$ | $CH_3$ | Cl | O | H | $N(CH_3)_2$ | $OCH_3$ | N |
| H | $CH_3$ | $CH_3$ | Cl | O | H | $N(CH_3)_2$ | $OCH_2CF_3$ | N |
| H | $CH_3$ | $CH_3$ | Cl | O | $CH_3$ | $CH_3$ | $OCH_3$ | N |
| H | $CH_3$ | $CH_3$ | Cl | S | H | $OCH_3$ | $OCH_3$ | CH |
| H | $CH_3$ | $CH_3$ | Cl | S | H | Cl | $OCH_3$ | CH |
| H | $CH_3$ | $CH_3$ | Cl | S | H | $CH_3$ | $OCH_3$ | CH |
| H | $CH_3$ | $CH_3$ | Cl | S | H | $CH_3$ | $CH_3$ | CH |
| H | $CH_3$ | $CH_3$ | Cl | S | H | $OCH_3$ | $OCH_3$ | N |
| H | $CH_3$ | $CH_3$ | Cl | S | H | $CH_3$ | $OCH_3$ | N |
| H | $CH_3$ | $CH_3$ | $CH_3$ | O | H | $OCH_3$ | $OCH_3$ | CH |
| H | $CH_3$ | $CH_3$ | $CH_3$ | O | H | Cl | $OCH_3$ | CH |
| H | $CH_3$ | $CH_3$ | $CH_3$ | O | H | $CH_3$ | $OCH_3$ | CH |
| H | $CH_3$ | $CH_3$ | $CH_3$ | O | H | $CH_3$ | $CH_3$ | CH |
| H | $CH_3$ | $CH_3$ | $CH_3$ | O | H | $OCH_3$ | $OCH_3$ | N |
| H | $CH_3$ | $CH_3$ | $CH_3$ | O | H | $CH_3$ | $OCH_3$ | N |
| H | $CH_3$ | $CH_3$ | $CH_3$ | O | H | $CH_3$ | $CH_3$ | N |
| H | $CH_3$ | $CH_3$ | $CH_3$ | O | H | $OCH_2CH_3$ | $OCH_2CH_3$ | N |
| H | $CH_3$ | $CH_3$ | $CH_3$ | O | H | $NHCH_3$ | $OCH_2CH_3$ | N |
| H | $CH_3$ | $CH_3$ | $CH_3$ | O | H | $N(CH_3)_2$ | $OCH_2CH_3$ | N |
| H | $CH_3$ | $CH_3$ | $CH_3$ | O | H | $N(CH_3)_2$ | $OCH_3$ | N |
| H | $CH_3$ | $CH_3$ | $CH_3$ | O | H | $N(CH_3)_2$ | $OCH_2CF_3$ | N |
| H | $CH_3$ | $CH_3$ | $CH_3$ | O | $CH_3$ | $CH_3$ | $OCH_3$ | N |
| H | $CH_3$ | $CH_3$ | $CH_3$ | S | H | $OCH_3$ | $OCH_3$ | CH |
| H | $CH_3$ | $CH_3$ | $CH_3$ | S | H | Cl | $OCH_3$ | CH |
| H | $CH_3$ | $CH_3$ | $CH_3$ | S | H | $CH_3$ | $OCH_3$ | CH |
| H | $CH_3$ | $CH_3$ | $CH_3$ | S | H | $CH_3$ | $CH_3$ | CH |
| H | $CH_3$ | $CH_3$ | $CH_3$ | S | H | $OCH_3$ | $OCH_3$ | N |
| H | $CH_3$ | $CH_3$ | $CH_3$ | S | H | $CH_3$ | $OCH_3$ | N |
| H | $CH_3$ | $CH_3$ | $CH_3$ | O | H | $OCH_3$ | $OCH_3$ | CH |
| H | $CH_3$ | $CH_3$ | $CH_3$ | O | H | Cl | $OCH_3$ | CH |
| H | $CH_3$ | $CH_3$ | $CH_3$ | O | H | $CH_3$ | $OCH_3$ | CH |
| H | $CH_3$ | $CH_3$ | $CH_3$ | O | H | $CH_3$ | $CH_3$ | CH |
| H | $CH_3$ | $CH_3$ | CH | O | H | $OCH_3$ | $OCH_3$ | N |
| H | $CH_3$ | $CH_3$ | $CH_3$ | O | H | $CH_3$ | $OCH_3$ | N |
| H | $CH_3$ | $CH_3$ | $CH_3$ | O | H | $CH_3$ | $CH_3$ | N |
| H | $CH_3$ | $CH_3$ | $CH_3$ | O | H | $OCH_2CH_3$ | $OCH_2CH_3$ | N |
| H | $CH_3$ | $CH_3$ | $CH_3$ | O | H | $NHCH_3$ | $OCH_2CH_3$ | N |
| H | $CH_3$ | $CH_3$ | $CH_3$ | O | H | $N(CH_3)_2$ | $OCH_2CH_3$ | N |
| H | $CH_3$ | $CH_3$ | $CH_3$ | O | H | $N(CH_3)_2$ | $OCH_3$ | N |
| H | $CH_3$ | $CH_3$ | $CH_3$ | O | H | $N(CH_3)_2$ | $OCH_2CF_3$ | N |
| H | $CH_3$ | $CH_3$ | $CH_3$ | O | $CH_3$ | $CH_3$ | $OCH_3$ | N |
| H | $CH_3$ | $CH_3$ | $CH_3$ | S | H | $OCH_3$ | $OCH_3$ | CH |
| H | $CH_3$ | $CH_3$ | $CH_3$ | S | H | Cl | $OCH_3$ | CH |
| H | $CH_3$ | $CH_3$ | $CH_3$ | S | H | $CH_3$ | $OCH_3$ | CH |
| H | $CH_3$ | $CH_3$ | $CH_3$ | S | H | $CH_3$ | $CH_3$ | CH |
| H | $CH_3$ | $CH_3$ | $CH_3$ | S | H | $OCH_3$ | $OCH_3$ | N |
| H | $CH_3$ | $CH_3$ | $CH_3$ | S | H | $CH_3$ | $OCH_3$ | N |
| H | $CH_2CH{=}CH_2$ | $CH_3$ | H | O | H | $OCH_3$ | $OCH_3$ | CH |
| H | $CH_2CH{=}CH_2$ | $CH_3$ | H | O | H | Cl | $OCH_3$ | CH |
| H | $CH_2CH{=}CH_2$ | $CH_3$ | H | O | H | $CH_3$ | $OCH_3$ | CH |
| H | $CH_2CH{=}CH_2$ | $CH_3$ | H | O | H | $CH_3$ | $CH_3$ | CH |
| H | $CH_2CH{=}CH_2$ | $CH_3$ | H | O | H | $OCH_3$ | $OCH_3$ | N |
| H | $CH_2CH{=}CH_2$ | $CH_3$ | H | O | H | $CH_3$ | $OCH_3$ | N |
| H | $CH_2CH{=}CH_2$ | $CH_3$ | H | O | H | $CH_3$ | $CH_3$ | N |
| H | $CH_2CH{=}CH_2$ | $CH_3$ | H | O | H | $OCH_2CH_3$ | $OCH_2CH_3$ | N |
| H | $CH_2CH{=}CH_2$ | $CH_3$ | H | O | H | $NHCH_3$ | $OCH_2CH_3$ | N |
| H | $CH_2CH{=}CH_2$ | $CH_3$ | H | O | H | $N(CH_3)_2$ | $OCH_2CH_3$ | N |
| H | $CH_2CH{=}CH_2$ | $CH_3$ | H | O | H | $N(CH_3)_2$ | $OCH_3$ | N |
| H | $CH_2CH{=}CH_2$ | $CH_3$ | H | O | H | $N(CH_3)_2$ | $OCH_2CF_3$ | N |
| H | $CH_2CH{=}CH_2$ | $CH_3$ | H | O | $CH_3$ | $CH_3$ | $OCH_3$ | N |
| H | $CH_2CH{=}CH_2$ | $CH_3$ | H | S | H | $OCH_3$ | $OCH_3$ | CH |
| H | $CH_2CH{=}CH_2$ | $CH_3$ | H | S | H | Cl | $OCH_3$ | CH |
| H | $CH_2CH{=}CH_2$ | $CH_3$ | H | S | H | $CH_3$ | $OCH_3$ | CH |
| H | $CH_2CH{=}CH_2$ | $CH_3$ | H | S | H | $CH_3$ | $CH_3$ | CH |
| H | $CH_2CH{=}CH_2$ | $CH_3$ | H | S | H | $OCH_3$ | $OCH_3$ | N |
| H | $CH_2CH{=}CH_2$ | $CH_3$ | H | S | H | $CH_3$ | $OCH_3$ | N |
| H | $CH_2C{\equiv}CH$ | $CH_3$ | H | O | H | $OCH_3$ | $OCH_3$ | CH |
| H | $CH_2C{\equiv}CH$ | $CH_3$ | H | O | H | Cl | $OCH_3$ | CH |
| H | $CH_2C{\equiv}CH$ | $CH_3$ | H | O | H | $CH_3$ | $OCH_3$ | CH |
| H | $CH_2C{\equiv}CH$ | $CH_3$ | H | O | H | $CH_3$ | $CH_3$ | CH |

TABLE I-continued

| | | | | | | | | |
|---|---|---|---|---|---|---|---|---|
| H | $CH_2C{\equiv}CH$ | $CH_3$ | H | O | H | $OCH_3$ | $OCH_3$ | N |
| H | $CH_2C{\equiv}CH$ | $CH_3$ | H | O | H | $CH_3$ | $OCH_3$ | N |
| H | $CH_2C{\equiv}CH$ | $CH_3$ | H | O | H | $CH_3$ | $CH_3$ | N |
| H | $CH_2C{\equiv}CH$ | $CH_3$ | H | O | H | $OCH_2CH_3$ | $OCH_2CH_3$ | N |
| H | $CH_2C{\equiv}CH$ | $CH_3$ | H | O | H | $NHCH_3$ | $OCH_2CH_3$ | N |
| H | $CH_2C{\equiv}CH$ | $CH_3$ | H | O | H | $N(CH_3)_2$ | $OCH_2CH_3$ | N |
| H | $CH_2C{\equiv}CH$ | $CH_3$ | H | O | H | $N(CH_3)_2$ | $OCH_3$ | N |
| H | $CH_2C{\equiv}CH$ | $CH_3$ | H | O | H | $N(CH_3)_2$ | $OCH_2CF_3$ | N |
| H | $CH_2C{\equiv}CH$ | $CH_3$ | H | O | $CH_3$ | $CH_3$ | $OCH_3$ | N |
| H | $CH_2C{\equiv}CH$ | $CH_3$ | H | S | H | $OCH_3$ | $OCH_3$ | CH |
| H | $CH_2C{\equiv}CH$ | $CH_3$ | H | S | H | Cl | $OCH_3$ | CH |
| H | $CH_2C{\equiv}CH$ | $CH_3$ | H | S | H | $CH_3$ | $OCH_3$ | CH |
| H | $CH_2C{\equiv}CH$ | $CH_3$ | H | S | H | $CH_3$ | $CH_3$ | CH |
| H | $CH_2C{\equiv}CH$ | $CH_3$ | H | S | H | $OCH_3$ | $OCH_3$ | N |
| H | $CH_2C{\equiv}CH$ | $CH_3$ | H | S | H | $CH_3$ | $OCH_3$ | N |
| H | $CH_2CH_3$ | $CH_2CH_3$ | H | O | H | $OCH_3$ | $OCH_3$ | CH |
| H | $CH_2CH_3$ | $CH_2CH_3$ | H | O | H | Cl | $OCH_3$ | CH |
| H | $CH_2CH_3$ | $CH_2CH_3$ | H | O | H | $CH_3$ | $OCH_3$ | CH |
| H | $CH_2CH_3$ | $CH_2CH_3$ | H | O | H | $CH_3$ | $CH_3$ | CH |
| H | $CH_2CH_3$ | $CH_2CH_3$ | H | O | H | $OCH_3$ | $OCH_3$ | N |
| H | $CH_2CH_3$ | $CH_2CH_3$ | H | O | H | $CH_3$ | $OCH_3$ | N |
| H | $CH_2CH_3$ | $CH_2CH_3$ | H | O | H | $CH_3$ | $CH_3$ | N |
| H | $CH_2CH_3$ | $CH_2CH_3$ | H | O | H | $OCH_2CH_3$ | $OCH_2CH_3$ | N |
| H | $CH_2CH_3$ | $CH_2CH_3$ | H | O | H | $NHCH_3$ | $OCH_2CH_3$ | N |
| H | $CH_2CH_3$ | $CH_2CH_3$ | H | O | H | $N(CH_3)_2$ | $OCH_2CH_3$ | N |
| H | $CH_2CH_2$ | $CH_2CH_3$ | H | O | H | $N(CH_3)_2$ | $OCH_3$ | N |
| H | $CH_2CH_3$ | $CH_2CH_3$ | H | O | H | $N(CH_3)_2$ | $OCH_2CF_3$ | N |
| H | $CH_2CH_3$ | $CH_2CH_3$ | H | O | $CH_3$ | $CH_3$ | $OCH_3$ | N |
| H | $CH_2CH_3$ | $CH_2CH_3$ | H | S | H | $OCH_3$ | $OCH_3$ | CH |
| H | $CH_2CH_3$ | $CH_2CH_3$ | H | S | H | Cl | $OCH_3$ | CH |
| H | $CH_2CH_3$ | $CH_2CH_3$ | H | S | H | $CH_3$ | $OCH_3$ | CH |
| H | $CH_2CH_3$ | $CH_2CH_3$ | H | S | H | $CH_3$ | $CH_3$ | CH |
| H | $CH_2CH_3$ | $CH_2CH_3$ | H | S | H | $OCH_3$ | $OCH_3$ | N |
| H | $CH_2CH_3$ | $CH_2CH_3$ | H | S | H | $CH_3$ | $OCH_3$ | N |
| H | $OCH_3$ | $CH_3$ | H | O | H | $OCH_3$ | $OCH_3$ | CH |
| H | $OCH_3$ | $CH_3$ | H | O | H | Cl | $OCH_3$ | CH |
| H | $OCH_3$ | $CH_3$ | H | O | H | $CH_3$ | $OCH_3$ | CH |
| H | $OCH_3$ | $CH_3$ | H | O | H | $CH_3$ | $CH_3$ | CH |
| H | $OCH_3$ | $CH_3$ | H | O | H | $OCH_3$ | $OCH_3$ | NO |
| H | $OCH_3$ | $CH_3$ | H | O | H | $CH_3$ | $OCH_3$ | N |
| H | $OCH_3$ | $CH_3$ | H | O | H | $CH_3$ | $CH_3$ | N |
| H | $OCH_3$ | $CH_3$ | H | O | H | $OCH_2CH_3$ | $OCH_2CH_3$ | N |
| H | $OCH_3$ | $CH_3$ | H | O | H | $NHCH_3$ | $OCH_2CH_3$ | N |
| H | $OCH_3$ | $CH_3$ | H | O | H | $N(CH_3)_2$ | $OCH_3CH_3$ | N |
| H | $OCH_3$ | $CH_3$ | H | O | H | $N(CH_3)_2$ | $OCH_3$ | N |
| H | $OCH_3$ | $CH_3$ | H | O | H | $N(CH_3)_2$ | $OCH_2CF_3$ | N |
| H | $OCH_3$ | $CH_3$ | H | O | $CH_3$ | $CH_3$ | $OCH_3$ | N |
| H | $OCH_3$ | $CH_3$ | H | S | H | $OCH_3$ | $OCH_3$ | CH |
| H | $OCH_3$ | $CH_3$ | H | S | H | Cl | $OCH_3$ | CH |
| H | $OCH_3$ | $CH_3$ | H | S | H | $CH_3$ | $OCH_3$ | CH |
| H | $OCH_3$ | $CH_3$ | H | S | H | $CH_3$ | $CH_3$ | CH |
| H | $OCH_3$ | $CH_3$ | H | S | H | $OCH_3$ | $OCH_3$ | N |
| H | $OCH_3$ | $CH_3$ | H | S | H | $CH_3$ | $OCH_3$ | N |
| H | $NHCH_3$ | $CH_3$ | H | O | H | $OCH_3$ | $OCH_3$ | CH |
| H | $NHCH_3$ | $CH_3$ | H | O | H | Cl | $OCH_3$ | CH |
| H | $NHCH_3$ | $CH_3$ | H | O | H | $CH_3$ | $OCH_3$ | CH |
| H | $NHCH_3$ | $CH_3$ | H | O | H | $CH_3$ | $CH_3$ | CH |
| H | $NHCH_3$ | $CH_3$ | H | O | H | $OCH_3$ | $OCH_3$ | N |
| H | $NHCH_3$ | $CH_3$ | H | O | H | $CH_3$ | $OCH_3$ | N |
| H | $NHCH_3$ | $CH_3$ | H | O | H | $CH_3$ | $CH_3$ | N |
| H | $NHCH_3$ | $CH_3$ | H | O | H | $OCH_2CH_3$ | $OCH_2CH_3$ | N |
| H | $NHCH_3$ | $CH_3$ | H | O | H | $NHCH_3$ | $OCH_2CH_3$ | N |
| H | $NHCH_3$ | $CH_3$ | H | O | H | $N(CH_3)_2$ | $OCH_2CH_3$ | N |
| H | $NHCH_3$ | $CH_3$ | H | O | H | $N(CH_3)_2$ | $OCH_3$ | N |
| H | $NHCH_3$ | $CH_3$ | H | O | H | $N(CH_3)_2$ | $OCH_2CF_3$ | N |
| H | $NHCH_3$ | $CH_3$ | H | O | $CH_3$ | $CH_3$ | $OCH_3$ | N |
| H | $NHCH_3$ | $CH_3$ | H | S | H | $OCH_3$ | $OCH_3$ | CH |
| H | $NHCH_3$ | $CH_3$ | H | S | H | Cl | $OCH_3$ | CH |
| H | $NHCH_3$ | $CH_3$ | H | S | H | $CH_3$ | $OCH_3$ | CH |
| H | $NHCH_3$ | $CH_3$ | H | S | H | $CH_3$ | $CH_3$ | CH |
| H | $NHCH_3$ | $CH_3$ | H | S | H | $OCH_3$ | $OCH_3$ | N |
| H | $NHCH_3$ | $CH_3$ | H | S | H | $CH_3$ | $OCH_3$ | N |
| H | $N(CH_3)_2$ | $CH_3$ | H | O | H | $OCH_3$ | $OCH_3$ | CH |
| H | $N(CH_3)_2$ | $CH_3$ | H | O | H | Cl | $OCH_3$ | CH |
| H | $N(CH_3)_2$ | $CH_3$ | H | O | H | $CH_3$ | $OCH_3$ | CH |
| H | $N(CH_3)_2$ | $CH_3$ | H | O | H | $CH_3$ | $CH_3$ | CH |
| H | $N(CH_3)_2$ | $CH_3$ | H | O | H | $OCH_3$ | $OCH_3$ | N |
| H | $N(CH_3)_2$ | $CH_3$ | H | O | H | $CH_3$ | $OCH_3$ | N |
| H | $N(CH_3)_2$ | $CH_3$ | H | O | H | $CH_3$ | $CH_3$ | N |
| H | $N(CH_3)_2$ | $CH_3$ | H | O | H | $OCH_2CH_3$ | $OCH_2CH_3$ | N |
| H | $N(CH_3)_2$ | $CH_3$ | H | O | H | $NHCH_3$ | $OCH_2CH_3$ | N |
| H | $N(CH_3)_2$ | $CH_3$ | H | O | H | $N(CH_3)_2$ | $OCH_2CH_3$ | N |

TABLE I-continued

| | | | | | | | | |
|---|---|---|---|---|---|---|---|---|
| H | $N(CH_3)_2$ | $CH_3$ | H | O | H | $N(CH_3)_2$ | $OCH_3$ | N |
| H | $N(CH_3)_2$ | $CH_3$ | H | O | H | $N(CH_3)_2$ | $OCH_2CF_3$ | N |
| H | $N(CH_3)_2$ | $CH_3$ | H | O | $CH_3$ | $CH_3$ | $OCH_3$ | N |
| H | $N(CH_3)_2$ | $CH_3$ | H | S | H | $OCH_3$ | $OCH_3$ | CH |
| H | $N(CH_3)_2$ | $CH_3$ | H | S | H | Cl | $OCH_3$ | CH |
| H | $N(CH_3)_2$ | $CH_3$ | H | S | H | $CH_3$ | $OCH_3$ | CH |
| H | $N(CH_3)_2$ | $CH_3$ | H | S | H | $CH_3$ | $CH_3$ | CH |
| H | $N(CH_3)_2$ | $CH_3$ | H | S | H | $OCH_3$ | $OCH_3$ | N |
| H | $N(CH_3)_2$ | $CH_3$ | H | S | H | $CH_3$ | $OCH_3$ | N |
| H | OH | $CH_3$ | H | O | H | $OCH_3$ | $OCH_3$ | CH |
| H | OH | $CH_3$ | H | O | H | Cl | $OCH_3$ | CH |
| H | OH | $CH_3$ | H | O | H | $CH_3$ | $OCH_3$ | CH |
| H | OH | $CH_3$ | H | O | H | $CH_3$ | $CH_3$ | CH |
| H | OH | $CH_3$ | H | O | H | $OCH_3$ | $OCH_3$ | N |
| H | OH | $CH_3$ | H | O | H | $CH_3$ | $OCH_3$ | N |
| H | OH | $CH_3$ | H | O | H | $CH_3$ | $CH_3$ | N |
| H | OH | $CH_3$ | H | O | H | $OCH_2CH_3$ | $OCH_2CH_3$ | N |
| H | OH | $CH_3$ | H | O | H | $NHCH_3$ | $OCH_2CH_3$ | N |
| H | OH | $CH_3$ | H | O | H | $N(CH_3)_2$ | $OCH_2CH_3$ | N |
| H | OH | $CH_3$ | H | O | H | $N(CH_3)_2$ | $OCH_3$ | N |
| H | OH | $CH_3$ | H | O | H | $N(CH_3)_2$ | $OCH_2CF_3$ | N |
| H | OH | $CH_3$ | H | O | $CH_3$ | $CH_3$ | $OCH_3$ | N |
| H | OH | $CH_3$ | H | S | H | $OCH_3$ | $OCH_3$ | CH |
| H | OH | $CH_3$ | H | S | H | Cl | $OCH_3$ | CH |
| H | OH | $CH_3$ | H | S | H | $CH_3$ | $OCH_3$ | CH |
| H | OH | $CH_3$ | H | S | H | $CH_3$ | $CH_3$ | CH |
| H | OH | $CH_3$ | H | S | H | $OCH_3$ | $OCH_3$ | N |
| H | OH | $CH_3$ | H | S | H | $CH_3$ | $OCH_3$ | N |
| H | $NH_2$ | $CH_3$ | H | O | H | $OCH_3$ | $OCH_3$ | CH |
| H | $NH_2$ | $CH_3$ | H | O | H | Cl | $OCH_3$ | CH |
| H | $NH_2$ | $CH_3$ | H | O | H | $CH_3$ | $OCH_3$ | CH |
| H | $NH_2$ | $CH_3$ | H | O | H | $CH_3$ | $CH_3$ | CH |
| H | $NH_2$ | $CH_3$ | H | O | H | $OCH_3$ | $OCH_3$ | N |
| H | $NH_2$ | $CH_3$ | H | O | H | $CH_3$ | $OCH_3$ | N |
| H | $NH_2$ | $CH_3$ | H | O | H | $CH_3$ | $CH_3$ | N |
| H | $NH_2$ | $CH_3$ | H | O | H | $OCH_2CH_3$ | $OCH_2CH_3$ | N |
| H | $NH_2$ | $CH_3$ | H | O | H | $NHCH_3$ | $OCH_2CH_3$ | N |
| H | $NH_2$ | $CH_3$ | H | O | H | $N(CH_3)_2$ | $OCH_2CH_3$ | N |
| H | $NH_2$ | $CH_3$ | H | O | H | $N(CH_3)_2$ | $OCH_3$ | N |
| H | $NH_2$ | $CH_3$ | H | O | H | $N(CH_3)_2$ | $OCH_2CF_3$ | N |
| H | $NH_2$ | $CH_3$ | H | O | $CH_3$ | $CH_3$ | $OCH_3$ | N |
| H | $NH_2$ | $CH_3$ | H | S | H | $OCH_3$ | $OCH_3$ | CH |
| H | $NH_2$ | $CH_3$ | H | S | H | Cl | $OCH_3$ | CH |
| H | $NH_2$ | $CH_3$ | H | S | H | $CH_3$ | $OCH_3$ | CH |
| H | $NH_2$ | $CH_3$ | H | S | H | $CH_3$ | $CH_3$ | CH |
| H | $NH_2$ | $CH_3$ | H | S | H | $OCH_3$ | $OCH_3$ | N |
| H | $NH_2$ | $CH_3$ | H | S | H | $CH_3$ | $OCH_3$ | N |
| H | CN | $CH_3$ | H | O | H | $OCH_3$ | $OCH_3$ | CH |
| H | CN | $CH_3$ | H | O | H | Cl | $OCH_3$ | CH |
| H | CN | $CH_3$ | H | O | H | $CH_3$ | $OCH_3$ | CH |
| H | CN | $CH_3$ | H | O | H | $CH_3$ | $CH_3$ | CH |
| H | CN | $CH_3$ | H | O | H | $OCH_3$ | $OCH_3$ | N |
| H | CN | $CH_3$ | H | O | H | $CH_3$ | $OCH_3$ | N |
| H | CN | $CH_3$ | H | O | H | $CH_3$ | $CH_3$ | N |
| H | CN | $CH_3$ | H | O | H | $OCH_2CH_3$ | $OCH_2CH_3$ | N |
| H | CN | $CH_3$ | H | O | H | $NHCH_3$ | $OCH_2CH_3$ | N |
| H | CN | $CH_3$ | H | O | H | $N(CH_3)_2$ | $OCH_2CH_3$ | N |
| H | CN | $CH_3$ | H | O | H | $N(CH_3)_2$ | $OCH_3$ | N |
| H | CN | $CH_3$ | H | O | H | $N(CH_3)_2$ | $OCH_2CF_3$ | N |
| H | CN | $CH_3$ | H | O | $CH_3$ | $CH_3$ | $OCH_3$ | N |
| H | CN | $CH_3$ | H | S | H | $OCH_3$ | $OCH_3$ | CH |
| H | CN | $CH_3$ | H | S | H | Cl | $OCH_3$ | CH |
| H | CN | $CH_3$ | H | S | H | $CH_3$ | $OCH_3$ | CH |
| H | CN | $CH_3$ | H | S | H | $CH_3$ | $CH_3$ | CH |
| H | CN | $CH_3$ | H | S | H | $OCH_3$ | $OCH_3$ | N |
| H | CN | $CH_3$ | H | S | H | $CH_3$ | $OCH_3$ | N |
| H | $COCH_3$ | $CH_3$ | H | O | H | $OCH_3$ | $OCH_3$ | CH |
| H | $COCH_3$ | $CH_3$ | H | O | H | Cl | $OCH_3$ | CH |
| H | $COCH_3$ | $CH_3$ | H | O | H | $CH_3$ | $OCH_3$ | CH |
| H | $COCH_3$ | $CH_3$ | H | O | H | $CH_3$ | $CH_3$ | CH |
| H | $COCH_3$ | $CH_3$ | H | O | H | $OCH_3$ | $OCH_3$ | N |
| H | $COCH_3$ | $CH_3$ | H | O | H | $CH_3$ | $OCH_3$ | N |
| H | $COCH_3$ | $CH_3$ | H | O | H | $CH_3$ | $CH_3$ | N |
| H | $COCH_3$ | $CH_3$ | H | O | H | $OCH_2CH_3$ | $OCH_2CH_3$ | N |
| H | $COCH_3$ | $CH_3$ | H | O | H | $NHCH_3$ | $OCH_2CH_3$ | N |
| H | $COCH_3$ | $CH_3$ | H | O | H | $N(CH_3)_2$ | $OCH_2CH_3$ | N |
| H | $COCH_3$ | $CH_3$ | H | O | H | $N(CH_3)2$ | $OCH_3$ | N |
| H | $COCH_3$ | $CH_3$ | H | O | H | $N(CH_3)_2$ | $OCH_2CF_3$ | N |
| H | $COCH_3$ | $CH_3$ | H | O | $CH_3$ | $CH_3$ | $OCH_3$ | N |
| H | $COCH_3$ | $CH_3$ | H | S | H | $OCH_3$ | $OCH_3$ | CH |
| H | $COCH_3$ | $CH_3$ | H | S | H | Cl | $OCH_3$ | CH |
| H | $COCH_3$ | $CH_3$ | H | S | H | $CH_3$ | $OCH_3$ | CH |

TABLE I-continued

| | | | | | | | | |
|---|---|---|---|---|---|---|---|---|
| H | $COCH_3$ | $CH_3$ | H | S | H | $CH_3$ | $CH_3$ | CH |
| H | $COCH_3$ | $CH_3$ | H | S | H | $OCH_3$ | $OCH_3$ | N |
| H | $COCH_3$ | $CH_3$ | H | S | H | $CH_3$ | $OCH_3$ | N |
| H | $CO_2CH_3$ | $CH_3$ | H | O | H | $OCH_3$ | $OCH_3$ | CH |
| H | $CO_2CH_3$ | $CH_3$ | H | O | H | Cl | $OCH_3$ | CH |
| H | $CO_2CH_3$ | $CH_3$ | H | O | H | $CH_3$ | $OCH_3$ | CH |
| H | $CO_2CH_3$ | $CH_3$ | H | O | H | $CH_3$ | $CH_3$ | CH |
| H | $CO_2CH_3$ | $CH_3$ | H | O | H | $OCH_3$ | $OCH_3$ | N |
| H | $CO_2CH_3$ | $CH_3$ | H | O | H | $CH_3$ | $OCH_3$ | N |
| H | $CO_2CH_3$ | $CH_3$ | H | O | H | $CH_3$ | $CH_3$ | N |
| H | $CO_2CH_3$ | $CH_3$ | H | O | H | $OCH_2CH_3$ | $OCH_2CH_3$ | N |
| H | $CO_2CH_3$ | $CH_3$ | H | O | H | $NHCH_3$ | $OCH_2CH_3$ | N |
| H | $CO_2CH_3$ | $CH_3$ | H | O | H | $N(CH_3)_2$ | $OCH_2CH_3$ | N |
| H | $CO_2CH_3$ | $CH_3$ | H | O | H | $N(CH_3)_2$ | $OCH_3$ | N |
| H | $CO_2CH_3$ | $CH_3$ | H | O | H | $N(CH_3)_2$ | $OCH_2CF_3$ | N |
| H | $CO_2CH_3$ | $CH_3$ | H | O | $CH_3$ | $CH_3$ | $OCH_3$ | N |
| H | $CO_2CH_3$ | $CH_3$ | H | S | H | $OCH_3$ | $OCH_3$ | CH |
| H | $CO_2CH_3$ | $CH_3$ | H | S | H | Cl | $OCH_3$ | CH |
| H | $CO_2CH_3$ | $CH_3$ | H | S | H | $CH_3$ | $OCH_3$ | CH |
| H | $CO_2CH_3$ | $CH_3$ | H | S | H | $CH_3$ | $CH_3$ | CH |
| H | $CO_2CH_3$ | $CH_3$ | H | S | H | $OCH_3$ | $OCH_3$ | N |
| H | $CO_2CH_3$ | $CH_3$ | H | S | H | $CH_3$ | $OCH_3$ | N |
| H | $CON(CH_3)_2$ | $CH_3$ | H | O | H | $OCH_3$ | $OCH_3$ | CH |
| H | $CON(CH_3)_2$ | $CH_3$ | H | O | H | Cl | $OCH_3$ | CH |
| H | $CON(CH_3)_2$ | $CH_3$ | H | O | H | $CH_3$ | $OCH_3$ | CH |
| H | $CON(CH_3)_2$ | $CH_3$ | H | O | H | $CH_3$ | $CH_3$ | CH |
| H | $CON(CH_3)_2$ | $CH_3$ | H | O | H | $OCH_3$ | $OCH_3$ | N |
| H | $CON(CH_3)_2$ | $CH_3$ | H | O | H | $CH_3$ | $OCH_3$ | N |
| H | $CON(CH_3)_2$ | $CH_3$ | H | O | H | $CH_3$ | $CH_3$ | N |
| H | $CON(CH_3)_2$ | $CH_3$ | H | O | H | $OCH_2CH_3$ | $OCH_2CH_3$ | N |
| H | $CON(CH_3)_2$ | $CH_3$ | H | O | H | $NHCH_3$ | $OCH_2CH_3$ | N |
| H | $CON(CH_3)_2$ | $CH_3$ | H | O | H | $N(CH_3)_2$ | $OCH_2CH_3$ | N |
| H | $CON(CH_3)_2$ | $CH_3$ | H | O | H | $N(CH_3)_2$ | $OCH_3$ | N |
| H | $CON(CH_3)_2$ | $CH_3$ | H | O | H | $N(CH_3)_2$ | $OCH_2CF_3$ | N |
| H | $CON(CH_3)_2$ | $CH_3$ | H | O | $CH_3$ | $CH_3$ | $OCH_3$ | N |
| H | $CON(CH_3)_2$ | $CH_3$ | H | S | H | $OCH_3$ | $OCH_3$ | CH |
| H | $CON(CH_3)_2$ | $CH_3$ | H | S | H | Cl | $OCH_3$ | CH |
| H | $CON(CH_3)_2$ | $CH_3$ | H | S | H | $CH_3$ | $OCH_3$ | CH |
| H | $CON(CH_3)_2$ | $CH_3$ | H | S | H | $CH_3$ | $CH_3$ | CH |
| H | $CON(CH_3)_2$ | $CH_3$ | H | S | H | $OCH_3$ | $OCH_3$ | N |
| H | $CON(CH_3)_2$ | $CH_3$ | H | S | H | $CH_3$ | $OCH_3$ | N |
| H | $—CH_2CH_2CH_2—$ | | H | O | H | $OCH_3$ | $OCH_3$ | CH |
| H | $—CH_2CH_2CH_2—$ | | H | O | H | Cl | $OCH_3$ | CH |
| H | $—CH_2CH_2CH_2—$ | | H | O | H | $CH_3$ | $OCH_3$ | CH |
| H | $—CH_2CH_2CH_2—$ | | H | O | H | $CH_3$ | $CH_3$ | CH |
| H | $—CH_2CH_2CH_2—$ | | H | O | H | $OCH_3$ | $OCH_3$ | N |
| H | $—CH_2CH_2CH_2—$ | | H | O | H | $CH_3$ | $OCH_3$ | N |
| H | $—CH_2CH_2CH_2—$ | | H | O | H | $CH_3$ | $CH_3$ | N |
| H | $—CH_2CH_2CH_2—$ | | H | O | H | $OCH_2CH_3$ | $OCH_2CH_3$ | N |
| H | $—CH_2CH_2CH_2—$ | | H | O | H | $NHCH_3$ | $OCH_2CH_3$ | N |
| H | $—CH_2CH_2CH_2—$ | | H | O | H | $N(CH_3)_2$ | $OCH_2CH_3$ | N |
| H | $—CH_2CH_2CH_2—$ | | H | O | H | $N(CH_3)_2$ | $OCH_3$ | N |
| H | $—CH_2CH_2CH_2—$ | | H | O | H | $N(CH_3)_2$ | $OCH_2CF_3$ | N |
| H | $—CH_2CH_2CH_2—$ | | H | O | $CH_3$ | $CH_3$ | $OCH_3$ | N |
| H | $—CH_2CH_2CH_2—$ | | H | S | H | $OCH_3$ | $OCH_3$ | CH |
| H | $—CH_2CH_2CH_2—$ | | H | S | H | Cl | $OCH_3$ | CH |
| H | $—CH_2CH_2CH_2—$ | | H | S | H | $CH_3$ | $OCH_3$ | CH |
| H | $—CH_2CH_2CH_2—$ | | H | S | H | $CH_3$ | $CH_3$ | CH |
| H | $—CH_2CH_2CH_2—$ | | H | S | H | $OCH_3$ | $OCH_3$ | N |
| H | $—CH_2CH_2CH_2—$ | | H | S | H | $CH_3$ | $OCH_3$ | N |
| H | $—CH_2CH_2OCH_2CH_2—$ | | H | O | H | $OCH_3$ | $OCH_3$ | CH |
| H | $—CH_2CH_2OCH_2CH_2—$ | | H | O | H | Cl | $OCH_3$ | CH |
| H | $—CH_2CH_2OCH_2CH_2—$ | | H | O | H | $CH_3$ | $OCH_3$ | CH |
| H | $—CH_2CH_2OCH_2CH_2—$ | | H | O | H | $CH_3$ | $CH_3$ | CH |
| H | $—CH_2CH_2OCH_2CH_2—$ | | H | O | H | $OCH_3$ | $OCH_3$ | N |
| H | $—CH_2CH_2OCH_2CH_2—$ | | H | O | H | $CH_3$ | $OCH_3$ | N |
| H | $—CH_2CH_2OCH_2CH_2—$ | | H | O | H | $CH_3$ | $CH_3$ | N |
| H | $—CH_2CH_2OCH_2CH_2—$ | | H | O | H | $OCH_2CH_3$ | $OCH_2CH_3$ | N |
| H | $—CH_2CH_2OCH_2CH_2—$ | | H | O | H | $NHCH_3$ | $OCH_2CH_3$ | N |
| H | $—CH_2CH_2OCH_2CH_2—$ | | H | O | H | $N(CH_3)_2$ | $OCH_2CH_3$ | N |
| H | $—CH_2CH_2OCH_2CH_2—$ | | H | O | H | $N(CH_3)_2$ | $OCH_3$ | N |
| H | $—CH_2CH_2OCH_2CH_2—$ | | H | O | H | $N(CH_3)_2$ | $OCH_2CF_3$ | N |
| H | $—CH_2CH_2OCH_2CH_2—$ | | H | O | $CH_3$ | $CH_3$ | $OCH_3$ | N |
| H | $—CH_2CH_2OCH_2CH_2—$ | | H | S | H | $OCH_3$ | $OCH_3$ | CH |
| H | $—CH_2CH_2OCH_2CH_2—$ | | H | S | H | Cl | $OCH_3$ | CH |
| H | $—CH_2CH_2OCH_2CH_2—$ | | H | S | H | $CH_3$ | $OCH_3$ | CH |
| H | $—CH_2CH_2OCH_2CH_2—$ | | H | S | H | $CH_3$ | $CH_3$ | CH |
| H | $—CH_2CH_2OCH_2CH_2—$ | | H | S | H | $OCH_3$ | $OCH_3$ | N |
| H | $—CH_2CH_2OCH_2CH_2—$ | | H | S | H | $CH_3$ | $OCH_3$ | N |
| Cl | H | H | H | O | H | $OCH_3$ | $OCH_3$ | CH |
| Cl | H | H | H | O | H | Cl | $OCH_3$ | CH |
| Cl | H | H | H | O | H | $CH_3$ | $OCH_3$ | CH |

TABLE I-continued

| | | | | | | | | |
|---|---|---|---|---|---|---|---|---|
| Cl | H | H | H | O | H | $CH_3$ | $CH_3$ | CH |
| Cl | H | H | H | O | H | $OCH_3$ | $OCH_3$ | N |
| Cl | H | H | H | O | H | $CH_3$ | $OCH_3$ | N |
| Cl | H | H | H | O | H | $CH_3$ | $CH_3$ | N |
| Cl | H | H | H | O | H | $OCH_2CH_3$ | $OCH_2CH_3$ | N |
| Cl | H | H | H | O | H | $NHCH_3$ | $OCH_2CH_3$ | N |
| Cl | H | H | H | O | H | $N(CH_3)_2$ | $OCH_2CH_3$ | N |
| Cl | H | H | H | O | H | $N(CH_3)_2$ | $OCH_3$ | N |
| Cl | H | H | H | O | H | $N(CH_3)_2$ | $OCH_2CF_3$ | N |
| Cl | H | H | H | O | $CH_3$ | $CH_3$ | $OCH_3$ | N |
| Cl | H | H | H | S | H | $OCH_3$ | $OCH_3$ | CH |
| Cl | H | H | H | S | H | Cl | $OCH_3$ | CH |
| Cl | H | H | H | S | H | $CH_3$ | $OCH_3$ | CH |
| Cl | H | H | H | S | H | $CH_3$ | $CH_3$ | CH |
| Cl | H | H | H | S | H | $OCH_3$ | $OCH_3$ | N |
| Cl | H | H | H | S | H | $CH_3$ | $OCH_3$ | N |
| Cl | H | $CH_3$ | H | O | H | $OCH_3$ | $OCH_3$ | CH |
| Cl | H | $CH_3$ | H | O | H | Cl | $OCH_3$ | CH |
| Cl | H | $CH_3$ | H | O | H | $CH_3$ | $OCH_3$ | CH |
| Cl | H | $CH_3$ | H | O | H | $CH_3$ | $CH_3$ | CH |
| Cl | H | $CH_3$ | H | O | H | $OCH_3$ | $OCH_3$ | N |
| Cl | H | $CH_3$ | H | O | H | $CH_3$ | $OCH_3$ | N |
| Cl | H | $CH_3$ | H | O | H | $CH_3$ | $CH_3$ | N |
| Cl | H | $CH_3$ | H | O | H | $OCH_2CH_3$ | $OCH_2CH_3$ | N |
| Cl | H | $CH_3$ | H | O | H | $NHCH_3$ | $OCH_2CH_3$ | N |
| Cl | H | $CH_3$ | H | O | H | $N(CH_3)_2$ | $OCH_2CH_3$ | N |
| Cl | H | $CH_3$ | H | O | H | $N(CH_3)_2$ | $OCH_3$ | N |
| Cl | H | $CH_3$ | H | O | H | $N(CH_3)_2$ | $OCH_2CF_3$ | N |
| Cl | H | $CH_3$ | H | O | $CH_3$ | $CH_3$ | $OCH_3$ | N |
| Cl | H | $CH_3$ | H | S | H | $OCH_3$ | $OCH_3$ | CH |
| Cl | H | $CH_3$ | H | S | H | Cl | $OCH_3$ | CH |
| Cl | H | $CH_3$ | H | S | H | $CH_3$ | $OCH_3$ | CH |
| Cl | H | $CH_3$ | H | S | H | $CH_3$ | $CH_3$ | CH |
| Cl | H | $CH_3$ | H | S | H | $OCH_3$ | $OCH_3$ | N |
| Cl | H | $CH_3$ | H | S | H | $CH_3$ | $OCH_3$ | N |
| Cl | H | H | $CH_3$ | O | H | $OCH_3$ | $OCH_3$ | CH |
| Cl | H | H | $CH_3$ | O | H | Cl | $OCH_3$ | CH |
| Cl | H | H | $CH_3$ | O | H | $CH_3$ | $OCH_3$ | CH |
| Cl | H | H | $CH_3$ | O | H | $CH_3$ | $CH_3$ | CH |
| Cl | H | H | $CH_3$ | O | H | $OCH_3$ | $OCH_3$ | N |
| Cl | H | H | $CH_3$ | O | H | $CH_3$ | $OCH_3$ | N |
| Cl | H | H | $CH_3$ | O | H | $CH_3$ | $CH_3$ | N |
| Cl | H | H | $CH_3$ | O | H | $OCH_2CH_3$ | $OCH_2CH_3$ | N |
| Cl | H | H | $CH_3$ | O | H | $NHCH_3$ | $OCH_2CH_3$ | N |
| Cl | H | H | $CH_3$ | O | H | $N(CH_3)_2$ | $OCH_2CH_3$ | N |
| Cl | H | H | $CH_3$ | O | H | $N(CH_3)_2$ | $OCH_3$ | N |
| Cl | H | H | $CH_3$ | O | H | $N(CH_3)_2$ | $OCH_2CF_3$ | N |
| Cl | H | H | $CH_3$ | O | $CH_3$ | $CH_3$ | $OCH_3$ | N |
| Cl | H | H | $CH_3$ | S | H | $OCH_3$ | $OCH_3$ | CH |
| Cl | H | H | $CH_3$ | S | H | Cl | $OCH_3$ | CH |
| Cl | H | H | $CH_3$ | S | H | $CH_3$ | $OCH_3$ | CH |
| Cl | H | H | $CH_3$ | S | H | $CH_3$ | $CH_3$ | CH |
| Cl | H | H | $CH_3$ | S | H | $OCH_3$ | $OCH_3$ | N |
| Cl | H | H | $CH_3$ | S | H | $CH_3$ | $OCH_3$ | N |
| Cl | H | $CH_3$ | $CH_3$ | O | H | $OCH_3$ | $OCH_3$ | CH |
| Cl | H | $CH_3$ | $CH_3$ | O | H | Cl | $OCH_3$ | CH |
| Cl | H | $CH_3$ | $CH_3$ | O | H | $CH_3$ | $OCH_3$ | CH |
| Cl | H | $CH_3$ | $CH_3$ | O | H | $CH_3$ | $CH_3$ | CH |
| Cl | H | $CH_3$ | $CH_3$ | O | H | $OCH_3$ | $OCH_3$ | N |
| Cl | H | $CH_3$ | $CH_3$ | O | H | $CH_3$ | $OCH_3$ | N |
| Cl | H | $CH_3$ | $CH_3$ | O | H | $CH_3$ | $CH_3$ | N |
| Cl | H | $CH_3$ | $CH_3$ | O | H | $OCH_2CH_3$ | $OCH_2CH_3$ | N |
| Cl | H | $CH_3$ | $CH_3$ | O | H | $NHCH_3$ | $OCH_2CH_3$ | N |
| Cl | H | $CH_3$ | $CH_3$ | O | H | $N(CH_3)_2$ | $OCH_2CH_3$ | N |
| Cl | H | $CH_3$ | $CH_3$ | O | H | $N(CH_3)_2$ | $OCH_3$ | N |
| Cl | H | $CH_3$ | $CH_3$ | O | H | $N(CH_3)_2$ | $OCH_2CF_3$ | N |
| Cl | H | $CH_3$ | $CH_3$ | O | $CH_3$ | $CH_3$ | $OCH_3$ | N |
| Cl | H | $CH_3$ | $CH_3$ | S | H | $OCH_3$ | $OCH_3$ | CH |
| Cl | H | $CH_3$ | $CH_3$ | S | H | Cl | $OCH_3$ | CH |
| Cl | H | $CH_3$ | $CH_3$ | S | H | $CH_3$ | $OCH_3$ | CH |
| Cl | H | $CH_3$ | $CH_3$ | S | H | $CH_3$ | $CH_3$ | CH |
| Cl | H | $CH_3$ | $CH_3$ | S | H | $OCH_3$ | $OCH_3$ | N |
| Cl | H | $CH_3$ | $CH_3$ | S | H | $CH_3$ | $OCH_3$ | N |
| Cl | H | H | Cl | O | H | $OCH_3$ | $OCH_3$ | CH |
| Cl | H | H | Cl | O | H | Cl | $OCH_3$ | CH |
| Cl | H | H | Cl | O | H | $CH_3$ | $OCH_3$ | CH |
| Cl | H | H | Cl | O | H | $CH_3$ | $CH_3$ | CH |
| Cl | H | H | Cl | O | H | $OCH_3$ | $OCH_3$ | N |
| Cl | H | H | Cl | O | H | $CH_3$ | $OCH_3$ | N |
| Cl | H | H | Cl | O | H | $CH_3$ | $CH_3$ | N |
| Cl | H | H | Cl | O | H | $OCH_2CH_3$ | $OCH_2CH_3$ | N |
| Cl | H | H | Cl | O | H | $NHCH_3$ | $OCH_2CH_3$ | N |

TABLE I-continued

| | | | | | | | | |
|---|---|---|---|---|---|---|---|---|
| Cl | H | H | Cl | O | H | $N(CH_3)_2$ | $OCH_2CH_3$ | N |
| Cl | H | H | Cl | O | H | $N(CH_3)_2$ | $OCH_3$ | N |
| Cl | H | H | Cl | O | H | $N(CH_3)_2$ | $OCH_2CF_3$ | N |
| Cl | H | H | Cl | O | $CH_3$ | $CH_3$ | $OCH_3$ | N |
| Cl | H | H | Cl | S | H | $OCH_3$ | $OCH_3$ | CH |
| Cl | H | H | Cl | S | H | Cl | $OCH_3$ | CH |
| Cl | H | H | Cl | S | H | $CH_3$ | $OCH_3$ | CH |
| Cl | H | H | Cl | S | H | $CH_3$ | $CH_3$ | CH |
| Cl | H | H | Cl | S | H | $OCH_3$ | $OCH_3$ | N |
| Cl | H | H | Cl | S | H | $CH_3$ | $OCH_3$ | N |
| Cl | H | $CH_3$ | Cl | O | H | $OCH_3$ | $OCH_3$ | CH |
| Cl | H | $CH_3$ | Cl | O | H | Cl | $OCH_3$ | CH |
| Cl | H | $CH_3$ | Cl | O | H | $CH_3$ | $OCH_3$ | CH |
| Cl | H | $CH_3$ | Cl | O | H | $CH_3$ | $CH_3$ | CH |
| Cl | H | $CH_3$ | Cl | O | H | $OCH_3$ | $OCH_3$ | N |
| Cl | H | $CH_3$ | Cl | O | H | $CH_3$ | $OCH_3$ | N |
| Cl | H | $CH_3$ | Cl | O | H | $CH_3$ | $CH_3$ | N |
| Cl | H | $CH_3$ | Cl | O | H | $OCH_2CH_3$ | $OCH_2CH_3$ | N |
| Cl | H | $CH_3$ | Cl | O | H | $NHCH_3$ | $OCH_2CH_3$ | N |
| Cl | H | $CH_3$ | Cl | O | H | $N(CH_3)_2$ | $OCH_2CH_3$ | N |
| Cl | H | $CH_3$ | Cl | O | H | $N(CH_3)_2$ | $OCH_3$ | N |
| Cl | H | $CH_3$ | Cl | O | H | $N(CH_3)_2$ | $OCH_2CF_3$ | N |
| Cl | H | $CH_3$ | Cl | O | $CH_3$ | $CH_3$ | $OCH_3$ | N |
| Cl | H | $CH_3$ | Cl | S | H | $OCH_3$ | $OCH_3$ | CH |
| Cl | H | $CH_3$ | Cl | S | H | Cl | $OCH_3$ | CH |
| Cl | H | $CH_3$ | Cl | S | H | $CH_3$ | $OCH_3$ | CH |
| Cl | H | $CH_3$ | Cl | S | H | $CH_3$ | $CH_3$ | CH |
| Cl | H | $CH_3$ | Cl | S | H | $OCH_3$ | $OCH_3$ | N |
| Cl | H | $CH_3$ | Cl | S | H | $CH_3$ | $OCH_3$ | N |
| Cl | H | $CH_2CH_3$ | H | O | H | $OCH_3$ | $OCH_3$ | CH |
| Cl | H | $CH_2CH_3$ | H | O | H | Cl | $OCH_3$ | CH |
| Cl | H | $CH_2CH_3$ | H | O | H | $CH_3$ | $OCH_3$ | CH |
| Cl | H | $CH_2CH_3$ | H | O | H | $CH_3$ | $CH_3$ | CH |
| Cl | H | $CH_2CH_3$ | H | O | H | $OCH_3$ | $OCH_3$ | N |
| Cl | H | $CH_2CH_3$ | H | O | H | $CH_3$ | $OCH_3$ | N |
| Cl | H | $CH_2CH_3$ | H | O | H | $CH_3$ | $CH_3$ | N |
| Cl | H | $CH_2CH_3$ | H | O | H | $OCH_2CH_3$ | $OCH_2CH_3$ | N |
| Cl | H | $CH_2CH_3$ | H | O | H | $NHCH_3$ | $OCH_2CH_3$ | N |
| Cl | H | $CH_2CH_3$ | H | O | H | $N(CH_3)_2$ | $OCH_2CH_3$ | N |
| Cl | H | $CH_2CH_3$ | H | O | H | $N(CH_3)_2$ | $OCH_3$ | N |
| Cl | H | $CH_2CH_3$ | H | O | H | $N(CH_3)_2$ | $OCH_2CF_3$ | N |
| Cl | H | $CH_2CH_3$ | H | O | $CH_3$ | $CH_3$ | $OCH_3$ | N |
| Cl | H | $CH_2CH_3$ | H | S | H | $OCH_3$ | $OCH_3$ | CH |
| Cl | H | $CH_2CH_3$ | H | S | H | Cl | $OCH_3$ | CH |
| Cl | H | $CH_2CH_3$ | H | S | H | $CH_3$ | $OCH_3$ | CH |
| Cl | H | $CH_2CH_3$ | H | S | H | $CH_3$ | $CH_3$ | CH |
| Cl | H | $CH_2CH_3$ | H | S | H | $OCH_3$ | $OCH_3$ | N |
| Cl | H | $CH_2CH_3$ | H | S | H | $CH_3$ | $OCH_3$ | N |
| Cl | H | $CH_2CF_3$ | H | O | H | $OCH_3$ | $OCH_3$ | CH |
| Cl | H | $CH_2CF_3$ | H | O | H | Cl | $OCH_3$ | CH |
| Cl | H | $CH_2CF_3$ | H | O | H | $CH_3$ | $OCH_3$ | CH |
| Cl | H | $CH_2CF_3$ | H | O | H | $CH_3$ | $CH_3$ | CH |
| Cl | H | $CH_2CF_3$ | H | O | H | $OCH_3$ | $OCH_3$ | N |
| Cl | H | $CH_2CF_3$ | H | O | H | $CH_3$ | $OCH_3$ | N |
| Cl | H | $CH_2CF_3$ | H | O | H | $CH_3$ | $CH_3$ | N |
| Cl | H | $CH_2CF_3$ | H | O | H | $OCH_2CH_3$ | $OCH_2CH_3$ | N |
| Cl | H | $CH_2CF_3$ | H | O | H | $NHCH_3$ | $OCH_2CH_3$ | N |
| Cl | H | $CH_2CF_3$ | H | O | H | $N(CH_3)_2$ | $OCH_2CH_3$ | N |
| Cl | H | $CH_2CF_3$ | H | O | H | $N(CH_3)_2$ | $OCH_3$ | N |
| Cl | H | $CH_2CF_3$ | H | O | H | $N(CH_3)_2$ | $OCH_2CF_3$ | N |
| Cl | H | $CH_2CF_3$ | H | O | $CH_3$ | $CH_3$ | $OCH_3$ | N |
| Cl | H | $CH_2CF_3$ | H | S | H | $OCH_3$ | $OCH_3$ | CH |
| Cl | H | $CH_2CF_3$ | H | S | H | Cl | $OCH_3$ | CH |
| Cl | H | $CH_2CF_3$ | H | S | H | $CH_3$ | $OCH_3$ | CH |
| Cl | H | $CH_2CF_3$ | H | S | H | $CH_3$ | $CH_3$ | CH |
| Cl | H | $CH_2CF_3$ | H | S | H | $OCH_3$ | $OCH_3$ | N |
| Cl | H | $CH_2CF_3$ | H | S | H | $CH_3$ | $OCH_3$ | N |
| Cl | $CH_2CH_2Cl$ | H | H | O | H | $OCH_3$ | $OCH_3$ | CH |
| Cl | $CH_2CH_2Cl$ | H | H | O | H | Cl | $OCH_3$ | CH |
| Cl | $CH_2CH_2Cl$ | H | H | O | H | $CH_3$ | $OCH_3$ | CH |
| Cl | $CH_2CH_2Cl$ | H | H | O | H | $CH_3$ | $CH_3$ | CH |
| Cl | $CH_2CH_2Cl$ | H | H | O | H | $OCH_3$ | $OCH_3$ | N |
| Cl | $CH_2CH_2Cl$ | H | H | O | H | $CH_3$ | $OCH_3$ | N |
| Cl | $CH_2CH_2Cl$ | H | H | O | H | $CH_3$ | $CH_3$ | N |
| Cl | $CH_2CH_2Cl$ | H | H | O | H | $OCH_2CH_3$ | $OCH_2CH_3$ | N |
| Cl | $CH_2CH_2Cl$ | H | H | O | H | $NHCH_3$ | $OCH_2CH_3$ | N |
| Cl | $CH_2CH_2Cl$ | H | H | O | H | $N(CH_3)_2$ | $OCH_2CH_3$ | N |
| Cl | $CH_2CH_2Cl$ | H | H | O | H | $N(CH_3)_2$ | $OCH_3$ | N |
| Cl | $CH_2CH_2Cl$ | H | H | O | H | $N(CH_3)_2$ | $OCH_2CF_3$ | N |
| Cl | $CH_2CH_2Cl$ | H | H | O | $CH_3$ | $CH_3$ | $OCH_3$ | N |
| Cl | $CH_2CH_2Cl$ | H | H | S | H | $OCH_3$ | $OCH_3$ | CH |
| Cl | $CH_2CH_2Cl$ | H | H | S | H | Cl | $OCH_3$ | CH |

TABLE I-continued

| | | | | | | | | |
|---|---|---|---|---|---|---|---|---|
| Cl | $CH_2CH_2Cl$ | H | H | S | H | $CH_3$ | $OCH_3$ | CH |
| Cl | $CH_2CH_2Cl$ | H | H | S | H | $CH_3$ | $CH_3$ | CH |
| Cl | $CH_2CH_2Cl$ | H | H | S | H | $OCH_3$ | $OCH_3$ | N |
| Cl | $CH_2CH_2Cl$ | H | H | S | H | $CH_3$ | $OCH_3$ | N |
| Cl | $CH_2CN$ | H | H | O | H | $OCH_3$ | $OCH_3$ | CH |
| Cl | $CH_2CN$ | H | H | O | H | Cl | $OCH_3$ | CH |
| Cl | $CH_2CN$ | H | H | O | H | $CH_3$ | $OCH_3$ | CH |
| Cl | $CH_2CN$ | H | H | O | H | $CH_3$ | $CH_3$ | CH |
| Cl | $CH_2CN$ | H | H | O | H | $OCH_3$ | $OCH_3$ | N |
| Cl | $CH_2CN$ | H | H | O | H | $CH_3$ | $OCH_3$ | N |
| Cl | $CH_2CN$ | H | H | O | H | $CH_3$ | $CH_3$ | N |
| Cl | $CH_2CN$ | H | H | O | H | $OCH_2CH_3$ | $OCH_2CH_3$ | N |
| Cl | $CH_2CN$ | H | H | O | H | $NHCH_3$ | $OCH_2CH_3$ | N |
| Cl | $CH_2CN$ | H | H | O | H | $N(CH_3)_2$ | $OCH_2CH_3$ | N |
| Cl | $CH_2CN$ | H | H | O | H | $N(CH_3)_2$ | $OCH_3$ | N |
| Cl | $CH_2CN$ | H | H | O | H | $N(CH_3)_2$ | $OCH_2CF_3$ | N |
| Cl | $CH_2CN$ | H | H | O | $CH_3$ | $CH_3$ | $OCH_3$ | N |
| Cl | $CH_2CN$ | H | H | S | H | $OCH_3$ | $OCH_3$ | CH |
| Cl | $CH_2CN$ | H | H | S | H | Cl | $OCH_3$ | CH |
| Cl | $CH_2CN$ | H | H | S | H | $CH_3$ | $OCH_3$ | CH |
| Cl | $CH_2CN$ | H | H | S | H | $CH_3$ | $CH_3$ | CH |
| Cl | CH CN | H | H | S | H | $OCH_3$ | $OCH_3$ | N |
| Cl | $CH_2CN$ | H | H | S | H | $CH_3$ | $OCH_3$ | N |
| Cl | $CH_2CH{=}CH_2$ | H | H | O | H | $OCH_3$ | $OCH_3$ | CH |
| Cl | $CH_2CH{=}CH_2$ | H | H | O | H | Cl | $OCH_3$ | CH |
| Cl | $CH_2CH{=}CH_2$ | H | H | O | H | $CH_3$ | $OCH_3$ | CH |
| Cl | $CH_2CH{=}CH_2$ | H | H | O | H | $CH_3$ | $CH_3$ | CH |
| Cl | $CH_2CH{=}CH_2$ | H | H | O | H | $OCH_3$ | $OCH_3$ | N |
| Cl | $CH_2CH{=}CH_2$ | H | H | O | H | $CH_3$ | $OCH_3$ | N |
| Cl | $CH_2CH{=}CH_2$ | H | H | O | H | $CH_3$ | $CH_3$ | N |
| Cl | $CH_2CH{=}CH_2$ | H | H | O | H | $OCH_2CH_3$ | $OCH_2CH_3$ | N |
| Cl | $CH_2CH{=}CH_2$ | H | H | O | H | $NHCH_3$ | $OCH_2CH_3$ | N |
| Cl | $CH_2CH{=}CH_2$ | H | H | O | H | $N(CH_3)_2$ | $OCH_2CH_3$ | N |
| Cl | $CH_2CH{=}CH_2$ | H | H | O | H | $N(CH_3)_2$ | $OCH_3$ | N |
| Cl | $CH_2CH{=}CH_2$ | H | H | O | H | $N(CH_3)_2$ | $OCH_2CF_3$ | N |
| Cl | $CH_2CH{=}CH_2$ | H | H | O | $CH_3$ | $CH_3$ | $OCH_3$ | N |
| Cl | $CH_2CH{=}CH_2$ | H | H | S | H | $OCH_3$ | $OCH_3$ | CH |
| Cl | $CH_2CH{=}CH_2$ | H | H | S | H | Cl | $OCH_3$ | CH |
| Cl | $CH_2CH{=}CH_2$ | H | H | S | H | $CH_3$ | $OCH_3$ | CH |
| Cl | $CH_2CH{=}CH_2$ | H | H | S | H | $CH_3$ | $CH_3$ | CH |
| Cl | $CH_2CH{=}CH_2$ | H | H | S | H | $OCH_3$ | $OCH_3$ | N |
| Cl | $CH_2CH{=}CH_2$ | H | H | S | H | $CH_3$ | $OCH_3$ | N |
| Cl | $CH_2C{\equiv}CH$ | H | H | O | H | $OCH_3$ | $OCH_3$ | CH |
| Cl | $CH_2C{\equiv}CH$ | H | H | O | H | Cl | $OCH_3$ | CH |
| Cl | $CH_2C{\equiv}CH$ | H | H | O | H | $CH_3$ | $OCH_3$ | CH |
| Cl | $CH_2C{\equiv}CH$ | H | H | O | H | $CH_3$ | $CH_3$ | CH |
| Cl | $CH_2C{\equiv}CH$ | H | H | O | H | $OCH_3$ | $OCH_3$ | N |
| Cl | $CH_2C{\equiv}CH$ | H | H | O | H | $CH_3$ | $OCH_3$ | N |
| Cl | $CH_2C{\equiv}CH$ | H | H | O | H | $CH_3$ | $CH_3$ | N |
| Cl | $CH_2C{\equiv}CH$ | H | H | O | H | $OCH_2CH_3$ | $OCH_2CH_3$ | N |
| Cl | $CH_2C{\equiv}CH$ | H | H | O | H | $NHCH_3$ | $OCH_2CH_3$ | N |
| Cl | $CH_2C{\equiv}CH$ | H | H | O | H | $N(CH_3)_2$ | $OCH_2CH_3$ | N |
| Cl | $CH_2C{\equiv}CH$ | H | H | O | H | $N(CH_3)_2$ | $OCH_3$ | N |
| Cl | $CH_2C{\equiv}CH$ | H | H | O | H | $N(CH_3)_2$ | $OCH_2CF_3$ | N |
| Cl | $CH_2C{\equiv}CH$ | H | H | O | $CH_3$ | $CH_3$ | $OCH_3$ | N |
| Cl | $CH_2C{\equiv}CH$ | H | H | S | H | $OCH_3$ | $OCH_3$ | CH |
| Cl | $CH_2C{\equiv}CH$ | H | H | S | H | Cl | $OCH_3$ | CH |
| Cl | $CH_2C{\equiv}CH$ | H | H | S | H | $CH_3$ | $OCH_3$ | CH |
| Cl | $CH_2C{\equiv}CH$ | H | H | S | H | $CH_3$ | $CH_3$ | CH |
| Cl | $CH_2C{\equiv}CH$ | H | H | S | H | $OCH_3$ | $OCH_3$ | N |
| Cl | $CH_2C{\equiv}CH$ | H | H | S | H | $CH_3$ | $OCH_3$ | N |
| Cl | $CH_2CH_2OCH_3$ | H | H | O | H | $OCH_3$ | $OCH_3$ | CH |
| Cl | $CH_2CH_2OCH_3$ | H | H | O | H | Cl | $OCH_3$ | CH |
| Cl | $CH_2CH_2OCH_3$ | H | H | O | H | $CH_3$ | $OCH_3$ | CH |
| Cl | $CH_2CH_2OCH_3$ | H | H | O | H | $CH_3$ | $CH_3$ | CH |
| Cl | $CH_2CH_2OCH_3$ | H | H | O | H | $OCH_3$ | $OCH_3$ | N |
| Cl | $CH_2CH_2OCH_3$ | H | H | O | H | $CH_3$ | $OCH_3$ | N |
| Cl | $CH_2CH_2OCH_3$ | H | H | O | H | $CH_3$ | $CH_3$ | N |
| Cl | $CH_2CH_2OCH_3$ | H | H | O | H | $OCH_2CH_3$ | $OCH_2CH_3$ | N |
| Cl | $CH_2CH_2OCH_3$ | H | H | O | H | $NHCH_3$ | $OCH_2CH_3$ | N |
| Cl | $CH_2CH_2OCH_3$ | H | H | O | H | $N(CH_3)_2$ | $OCH_2CH_3$ | N |
| Cl | $CH_2CH_2OCH_3$ | H | H | O | H | $N(CH_3)_2$ | $OCH_3$ | N |
| Cl | $CH_2CH_2OCH_3$ | H | H | O | H | $N(CH_3)_2$ | $OCH_2CF_3$ | N |
| Cl | $CH_2CH_2OCH_3$ | H | H | O | $CH_3$ | $CH_3$ | $OCH_3$ | N |
| Cl | $CH_2CH_2OCH_3$ | H | H | S | H | $OCH_3$ | $OCH_3$ | CH |
| Cl | $CH_2CH_2OCH_3$ | H | H | S | H | Cl | $OCH_3$ | CH |
| Cl | $CH_2CH_2OCH_3$ | H | H | S | H | $CH_3$ | $OCH_3$ | CH |
| Cl | $CH_2CH_2OCH_3$ | H | H | S | H | $CH_3$ | $CH_3$ | CH |
| Cl | $CH_2CH_2OCH_3$ | H | H | S | H | $OCH_3$ | $OCH_3$ | N |
| Cl | $CH_2CH_2OCH_3$ | H | H | S | H | $CH_3$ | $OCH_3$ | N |
| Cl | cyclo-$C_3H_7$ | H | H | O | H | $OCH_3$ | $OCH_3$ | CH |
| Cl | cyclo-$C_3H_7$ | H | H | O | H | Cl | $OCH_3$ | CH |

TABLE I-continued

| | | | | | | | | |
|---|---|---|---|---|---|---|---|---|
| Cl | cyclo-C$_3$H$_7$ | H | H | O | H | CH$_3$ | OCH$_3$ | CH |
| Cl | cyclo-C$_3$H$_7$ | H | H | O | H$_3$ | CH$_3$ | CH | CH |
| Cl | cyclo-C$_3$H$_7$ | H | H | O | H | OCH$_3$ | OCH$_3$ | N |
| Cl | cyclo-C$_3$H$_7$ | H | H | O | H | CH$_3$ | OCH$_3$ | N |
| Cl | cyclo-C$_3$H$_7$ | H | H | O | H | CH$_3$ | CH$_3$ | N |
| Cl | cyclo-C$_3$H$_7$ | H | H | O | H | OCH$_2$CH$_3$ | OCH$_2$CH$_3$ | N |
| Cl | cyclo-C$_3$H$_7$ | H | H | O | H | NHCH$_3$ | OCH$_2$CH$_3$ | N |
| Cl | cyclo-C$_3$H$_7$ | H | H | O | H | N(CH$_3$)$_2$ | OCH$_2$CH$_3$ | N |
| Cl | cyclo-C$_3$H$_7$ | H | H | O | H | N(CH$_3$)$_2$ | OCH$_3$ | N |
| Cl | cyclo-C$_3$H$_7$ | H | H | O | H | N(CH$_3$)$_2$ | OCH$_2$CF$_3$ | N |
| Cl | cyclo-C$_3$H$_7$ | H | H | O | CH$_3$ | CH$_3$ | OCH$_3$ | N |
| Cl | cyclo-C$_3$H$_7$ | H | H | S | H | OCH$_3$ | OCH$_3$ | CH |
| Cl | cyclo-C$_3$H$_7$ | H | H | S | H | Cl | OCH$_3$ | CH |
| Cl | cyclo-C$_3$H$_7$ | H | H | S | H | CH$_3$ | OCH$_3$ | CH |
| Cl | cyclo-C$_3$H$_7$ | H | H | S | H | CH$_3$ | CH$_3$ | CH |
| Cl | cyclo-C$_3$H$_7$ | H | H | S | H | OCH$_3$ | OCH$_3$ | N |
| Cl | cyclo-C$_3$H$_7$ | H | H | S | H | CH$_3$ | OCH$_3$ | N |
| Cl | CH$_3$ | CH$_3$ | H | O | H | OCH$_3$ | OCH$_3$ | CH |
| Cl | CH$_3$ | CH$_3$ | H | O | H | Cl | OCH$_3$ | CH |
| Cl | CH$_3$ | CH$_3$ | H | O | H | CH$_3$ | OCH$_3$ | CH |
| Cl | CH$_3$ | CH$_3$ | H | O | H | CH$_3$ | CH$_3$ | CH |
| Cl | CH$_3$ | CH$_3$ | H | O | H | OCH$_3$ | OCH$_3$ | N |
| Cl | CH$_3$ | CH$_3$ | H | O | H | CH$_3$ | OCH$_3$ | N |
| Cl | CH$_3$ | CH$_3$ | H | O | H | CH$_3$ | CH$_3$ | N |
| Cl | CH$_3$ | CH$_3$ | H | O | H | OCH$_2$CH$_3$ | OCH$_2$CH$_3$ | N |
| Cl | CH$_3$ | CH$_3$ | H | O | H | NHCH$_3$ | OCH$_2$CH$_3$ | N |
| Cl | CH$_3$ | CH$_3$ | H | O | H | N(CH$_3$)$_2$ | OCH$_2$CH$_3$ | N |
| Cl | CH$_3$ | CH$_3$ | H | O | H | N(CH$_3$)$_2$ | OCH$_3$ | N |
| Cl | CH$_3$ | CH$_3$ | H | O | H | N(CH$_3$)$_2$ | OCH$_2$CF$_3$ | N |
| Cl | CH$_3$ | CH$_3$ | H | O | CH$_3$ | CH$_3$ | OCH$_3$ | N |
| Cl | CH$_3$ | CH$_3$ | H | S | H | OCH$_3$ | OCH$_3$ | CH |
| Cl | CH$_3$ | CH$_3$ | H | S | H | Cl | OCH$_3$ | CH |
| Cl | CH$_3$ | CH$_3$ | H | S | H | CH$_3$ | OCH$_3$ | CH |
| Cl | CH$_3$ | CH$_3$ | H | S | H | CH$_3$ | CH$_3$ | CH |
| Cl | CH$_3$ | CH$_3$ | H | S | H | OCH$_3$ | OCH$_3$ | N |
| Cl | CH$_3$ | CH$_3$ | H | S | H | CH$_3$ | OCH$_3$ | N |
| Cl | CH$_3$ | CH$_2$CH$_3$ | H | O | H | OCH$_3$ | OCH$_3$ | CH |
| Cl | CH$_3$ | CH$_2$CH$_3$ | H | O | H | Cl | OCH$_3$ | CH |
| Cl | CH$_3$ | CH$_2$CH$_3$ | H | O | H | CH$_3$ | OCH$_3$ | CH |
| Cl | CH$_3$ | CH$_2$CH$_3$ | H | O | H | CH$_3$ | CH$_3$ | CH |
| Cl | CH$_3$ | CH$_2$CH$_3$ | H | O | H | OCH$_3$ | OCH$_3$ | N |
| Cl | CH$_3$ | CH$_2$CH$_3$ | H | O | H | CH$_3$ | OCH$_3$ | N |
| Cl | CH$_3$ | CH$_2$CH$_3$ | H | O | H | CH$_3$ | CH$_3$ | N |
| Cl | CH$_3$ | CH$_2$CH$_3$ | H | O | H | OCH$_2$CH$_3$ | OCH$_2$CH$_3$ | N |
| Cl | CH$_3$ | CH$_2$CH$_3$ | H | O | H | NHCH$_3$ | OCH$_2$CH$_3$ | N |
| Cl | CH$_3$ | CH$_2$CH$_3$ | H | O | H | N(CH$_3$)$_2$ | OCH$_2$CH$_3$ | N |
| Cl | CH$_3$ | CH$_2$CH$_3$ | H | O | H | N(CH$_3$)$_2$ | OCH$_3$ | N |
| Cl | CH$_3$ | CH$_2$CH$_3$ | H | O | H | N(CH$_3$)$_2$ | OCH$_2$CF$_3$ | N |
| Cl | CH$_3$ | CH$_2$CH$_3$ | H | O | CH$_3$ | CH$_3$ | OCH$_3$ | N |
| Cl | CH$_3$ | CH$_2$CH$_3$ | H | S | H | OCH$_3$ | OCH$_3$ | CH |
| Cl | CH$_3$ | CH$_2$CH$_3$ | H | S | H | Cl | OCH$_3$ | CH |
| Cl | CH$_3$ | CH$_2$CH$_3$ | H | S | H | CH$_3$ | OCH$_3$ | CH |
| Cl | CH$_3$ | CH$_2$CH$_3$ | H | S | H | CH$_3$ | CH$_3$ | CH |
| Cl | CH$_3$ | CH$_2$CH$_3$ | H | S | H | OCH$_3$ | OCH$_3$ | N |
| Cl | CH$_3$ | CH$_2$CH$_3$ | H | S | H | CH$_3$ | OCH$_3$ | N |
| Cl | CH$_3$ | CH$_3$ | CH$_3$ | O | H | OCH$_3$ | OCH$_3$ | CH |
| Cl | CH$_3$ | CH$_3$ | CH$_3$ | O | H | Cl | OCH$_3$ | CH |
| Cl | CH$_3$ | CH$_3$ | CH$_3$ | O | H | CH$_3$ | OCH$_3$ | CH |
| Cl | CH$_3$ | CH$_3$ | CH$_3$ | O | H | CH$_3$ | CH$_3$ | CH |
| Cl | CH$_3$ | CH$_3$ | CH$_3$ | O | H | OCH$_3$ | OCH$_3$ | N |
| Cl | CH$_3$ | CH$_3$ | CH$_3$ | O | H | CH$_3$ | OCH$_3$ | N |
| Cl | CH$_3$ | CH$_3$ | CH$_3$ | O | H | CH$_3$ | CH$_3$ | N |
| Cl | CH$_3$ | CH$_3$ | CH$_3$ | O | H | OCH$_2$CH$_3$ | OCH$_2$CH$_3$ | N |
| Cl | CH$_3$ | CH$_3$ | CH$_3$ | O | H | NHCH$_3$ | OCH$_2$CH$_3$ | N |
| Cl | CH$_3$ | CH$_3$ | CH$_3$ | O | H | N(CH$_3$)$_2$ | OCH$_2$CH$_3$ | N |
| Cl | CH$_3$ | CH$_3$ | CH$_3$ | O | H | N(CH$_3$)$_2$ | OCH$_3$ | N |
| Cl | CH$_3$ | CH$_3$ | CH$_3$ | O | H | N(CH$_3$)$_2$ | OCH$_2$CF$_3$ | N |
| Cl | CH$_3$ | CH$_3$ | CH$_3$ | O | CH$_3$ | CH$_3$ | OCH$_3$ | N |
| Cl | CH$_3$ | CH$_3$ | CH$_3$ | S | H | OCH$_3$ | OCH$_3$ | CH |
| Cl | CH$_3$ | CH$_3$ | CH$_3$ | S | H | Cl | OCH$_3$ | CH |
| Cl | CH$_3$ | CH$_3$ | CH$_3$ | S | H | CH$_3$ | OCH$_3$ | CH |
| Cl | CH$_3$ | CH$_3$ | CH$_3$ | S | H | CH$_3$ | CH$_3$ | CH |
| Cl | CH$_3$ | CH$_3$ | CH$_3$ | S | H | OCH$_3$ | OCH$_3$ | N |
| Cl | CH$_3$ | CH$_3$ | CH$_3$ | S | H | CH$_3$ | OCH$_3$ | N |
| Cl | CH$_3$ | CH$_3$ | Cl | O | H | OCH$_3$ | OCH$_3$ | CH |
| Cl | CH$_3$ | CH$_3$ | Cl | O | H | Cl | OCH$_3$ | CH |
| Cl | CH$_3$ | CH$_3$ | Cl$_1$ | O | H | CH$_3$ | OCH$_3$ | CH |
| Cl | CH$_3$ | CH$_3$ | Cl | O | H | CH$_3$ | CH$_3$ | CH |
| Cl | CH$_3$ | CH$_3$ | Cl | O | H | OCH$_3$ | OCH$_3$ | N |
| Cl | CH$_3$ | CH$_3$ | Cl | O | H | CH$_3$ | OCH$_3$ | N |
| Cl | CH$_3$ | CH$_3$ | Cl | O | H | NHCH$_3$ | OCH$_2$CF$_3$ | N |
| Cl | CH$_3$ | CH$_3$ | Cl | O | H | OCH$_2$CH$_3$ | OCH$_2$CH$_3$ | N |

TABLE I-continued

| | | | | | | | | |
|---|---|---|---|---|---|---|---|---|
| Cl | $CH_3$ | $CH_3$ | Cl | O | H | $NHCH_3$ | $OCH_2CH_3$ | N |
| Cl | $CH_3$ | $CH_3$ | Cl | O | H | $N(CH_3)_2$ | $OCH_2CH_3$ | N |
| Cl | $CH_3$ | $CH_3$ | Cl | O | H | $N(CH_3)_2$ | $OCH_3$ | N |
| Cl | $CH_3$ | $CH_3$ | Cl | O | H | $N(CH_3)_2$ | $OCH_2CF_3$ | N |
| Cl | $CH_3$ | $CH_3$ | Cl | O | $CH_3$ | $CH_3$ | $OCH_3$ | N |
| Cl | $CH_3$ | $CH_3$ | Cl | S | H | $OCH_3$ | $OCH_3$ | CH |
| Cl | $CH_3$ | $CH_3$ | Cl | S | H | Cl | $OCH_3$ | CH |
| Cl | $CH_3$ | $CH_3$ | Cl | S | H | $CH_3$ | $OCH_3$ | CH |
| Cl | $CH_3$ | $CH_3$ | Cl | S | H | $CH_3$ | $CH_3$ | CH |
| Cl | $CH_3$ | $CH_3$ | Cl | S | H | $OCH_3$ | $OCH_3$ | N |
| Cl | $CH_3$ | $CH_3$ | Cl | S | H | $CH_3$ | $OCH_3$ | N |
| Cl | $CH_2CH_3$ | $CH_2CH_3$ | H | O | H | $OCH_3$ | $OCH_3$ | CH |
| Cl | $CH_2CH_3$ | $CH_2CH_3$ | H | O | H | Cl | $OCH_3$ | CH |
| Cl | $CH_2CH_3$ | $CH_2CH_3$ | H | O | H | $CH_3$ | $OCH_3$ | CH |
| Cl | $CH_2CH_3$ | $CH_2CH_3$ | H | O | H | $CH_3$ | $CH_3$ | CH |
| Cl | $CH_2CH_3$ | $CH_2CH_3$ | H | O | H | $OCH_3$ | $OCH_3$ | N |
| Cl | $CH_2CH_3$ | $CH_2CH_3$ | H | O | H | $CH_3$ | $OCH_3$ | N |
| Cl | $CH_2CH_3$ | $CH_2CH_3$ | H | O | H | $CH_3$ | $CH_3$ | N |
| Cl | $CH_2CH_3$ | $CH_2CH_3$ | H | O | H | $OCH_2CH_3$ | $OCH_2CH_3$ | N |
| Cl | $CH_2CH_3$ | $CH_2CH_3$ | H | O | H | $NHCH_3$ | $OCH_2CH_3$ | N |
| Cl | $CH_2CH_3$ | $CH_2CH_3$ | H | O | H | $N(CH_3)_2$ | $OCH_2CH_3$ | N |
| Cl | $CH_2CH_3$ | $CH_2CH_3$ | H | O | H | $N(CH_3)_2$ | $OCH_3$ | N |
| Cl | $CH_2CH_3$ | $CH_2CH_3$ | H | O | H | $N(CH_3)_2$ | $OCH_2CF_3$ | N |
| Cl | $CH_2CH_3$ | $CH_2CH_3$ | H | O | $CH_3$ | $CH_3$ | $OCH_3$ | N |
| Cl | $CH_2CH_3$ | $CH_2CH_3$ | H | S | H | $OCH_3$ | $OCH_3$ | CH |
| Cl | $CH_2CH_3$ | $CH_2CH_3$ | H | S | H | Cl | $OCH_3$ | CH |
| Cl | $CH_2CH_3$ | $CH_2CH_3$ | H | S | H | $CH_3$ | $OCH_3$ | CH |
| Cl | $CH_2CH_3$ | $CH_2CH_3$ | H | S | H | $CH_3$ | $CH_3$ | CH |
| Cl | $CH_2CH_3$ | $CH_2CH_3$ | H | S | H | $OCH_3$ | $OCH_3$ | N |
| Cl | $CH_2CH_3$ | $CH_2CH_3$ | H | S | H | $CH_3$ | $OCH_3$ | N |
| Cl | $OCH_3$ | $CH_3$ | H | O | H | $OCH_3$ | $OCH_3$ | CH |
| Cl | $OCH_3$ | $CH_3$ | H | O | H | Cl | $OCH_3$ | CH |
| Cl | $OCH_3$ | $CH_3$ | H | O | H | $CH_3$ | $OCH_3$ | CH |
| Cl | $OCH_3$ | $CH_3$ | H | O | H | $CH_3$ | $CH_3$ | CH |
| Cl | $OCH_3$ | $CH_3$ | H | O | H | $OCH_3$ | $OCH_3$ | N |
| Cl | $OCH_3$ | $CH_3$ | H | O | H | $CH_3$ | $OCH_3$ | N |
| Cl | $OCH_3$ | $CH_3$ | H | O | H | $CH_3$ | $CH_3$ | N |
| Cl | $OCH_3$ | $CH_3$ | H | O | H | $OCH_2CH_3$ | $OCH_2CH_3$ | N |
| Cl | $OCH_3$ | $CH_3$ | H | O | H | $NHCH_3$ | $OCH_2CH_3$ | N |
| Cl | $OCH_3$ | $CH_3$ | H | O | H | $N(CH_3)_2$ | $OCH_2CH_3$ | N |
| Cl | $OCH_3$ | $CH_3$ | H | O | H | $N(CH_3)_2$ | $OCH_3$ | N |
| Cl | $OCH_3$ | $CH_3$ | H | O | H | $N(CH_3)_2$ | $OCH_2CF_3$ | N |
| Cl | $OCH_3$ | $CH_3$ | H | O | $CH_3$ | $CH_3$ | $OCH_3$ | N |
| Cl | $OCH_3$ | $CH_3$ | H | S | H | $OCH_3$ | $OCH_3$ | CH |
| Cl | $OCH_3$ | $CH_3$ | H | S | H | Cl | $OCH_3$ | CH |
| Cl | $OCH_3$ | $CH_3$ | H | S | H | $CH_3$ | $OCH_3$ | CH |
| Cl | $OCH_3$ | $CH_3$ | H | S | H | $CH_3$ | $CH_3$ | CH |
| Cl | $OCH_3$ | $CH_3$ | H | S | H | $OCH_3$ | $OCH_3$ | N |
| Cl | $OCH_3$ | $CH_3$ | H | S | H | $CH_3$ | $OCH_3$ | N |
| Cl | $NHCH_3$ | $CH_3$ | H | O | H | $OCH_3$ | $OCH_3$ | CH |
| Cl | $NHCH_3$ | $CH_3$ | H | O | H | Cl | $OCH_3$ | CH |
| Cl | $NHCH_3$ | $CH_3$ | H | O | H | $CH_3$ | $OCH_3$ | CH |
| Cl | $NHCH_3$ | $CH_3$ | H | O | H | $CH_3$ | $CH_3$ | CH |
| Cl | $NHCH_3$ | $CH_3$ | H | O | H | $OCH_3$ | $OCH_3$ | N |
| Cl | $NHCH_3$ | $CH_3$ | H | O | H | $CH_3$ | $OCH_3$ | N |
| Cl | $NHCH_3$ | $CH_3$ | H | O | $H_3$ | $CH_3$ | CH | N |
| Cl | $NHCH_3$ | $CH_3$ | H | O | H | $OCH_2CH_3$ | $OCH_2CH_3$ | N |
| Cl | $NHCH_3$ | $CH_3$ | H | O | H | $NHCH_3$ | $OCH_2CH_3$ | N |
| Cl | $NHCH_3$ | $CH_3$ | H | O | H | $N(CH_3)_2$ | $OCH_2CH_3$ | N |
| Cl | $NHCH_3$ | $CH_3$ | H | O | H | $N(CH_3)_2$ | $OCH_3$ | N |
| Cl | $NHCH_3$ | $CH_3$ | H | O | H | $N(CH_3)_2$ | $OCH_2CF_3$ | N |
| Cl | $NHCH_3$ | $CH_3$ | H | O | $CH_3$ | $CH_3$ | $OCH_3$ | N |
| Cl | $NHCH_3$ | $CH_3$ | H | S | H | $OCH_3$ | $OCH_3$ | CH |
| Cl | $NHCH_3$ | $CH_3$ | H | S | H | Cl | $OCH_3$ | CH |
| Cl | $NHCH_3$ | $CH_3$ | H | S | H | $CH_3$ | $OCH_3$ | CH |
| Cl | $NHCH_3$ | $CH_3$ | H | S | H | $CH_3$ | $CH_3$ | CH |
| Cl | $NHCH_3$ | $CH_3$ | H | S | H | $OCH_3$ | $OCH_3$ | N |
| Cl | $NHCH_3$ | $CH_3$ | H | S | H | $CH_3$ | $OCH_3$ | N |
| Cl | $N(CH_3)_2$ | $CH_3$ | H | O | H | $OCH_3$ | $OCH_3$ | CH |
| Cl | $N(CH_3)_2$ | $CH_3$ | H | O | H | Cl | $OCH_3$ | CH |
| Cl | $N(CH_3)_2$ | $CH_3$ | H | O | H | $CH_3$ | $OCH_3$ | CH |
| Cl | $N(CH_3)_2$ | $CH_3$ | H | O | H | $CH_3$ | $CH_3$ | CH |
| Cl | $N(CH_3)_2$ | $CH_3$ | H | O | H | $OCH_3$ | $OCH_3$ | N |
| Cl | $N(CH_3)_2$ | $CH_3$ | H | O | H | $CH_3$ | $OCH_3$ | N |
| Cl | $N(CH_3)_2$ | $CH_3$ | H | O | H | $CH_3$ | $CH_3$ | N |
| Cl | $N(CH_3)_2$ | $CH_3$ | H | O | H | $OCH_2CH_3$ | $OCH_2CH_3$ | N |
| Cl | $N(CH_3)_2$ | $CH_3$ | H | O | H | $NHCH_3$ | $OCH_2CH_3$ | N |
| Cl | $N(CH_3)_2$ | $CH_3$ | H | O | H | $N(CH_3)_2$ | $OCH_2CH_3$ | N |
| Cl | $N(CH_3)_2$ | $CH_3$ | H | O | H | $N(CH_3)_2$ | $OCH_3$ | N |

-continued

| | | | | | | | | |
|---|---|---|---|---|---|---|---|---|
| Cl | $N(CH_3)_2$ | $CH_3$ | H | O | H | $N(CH_3)_2$ | $OCH_2CF3$ | N |
| Cl | $N(CH_3)_2$ | $CH_3$ | H | O | $CH_3$ | $CH_3$ | $OCH_3$ | N |
| Cl | $N(CH_3)_2$ | $CH_3$ | H | S | H | $OCH_3$ | $OCH_3$ | CH |
| Cl | $N(CH_3)_2$ | $CH_3$ | H | S | H | Cl | OCH | $CH_3$ |
| Cl | $N(CH_3)_2$ | $CH_3$ | H | S | H | $CH_3$ | $OCH_3$ | CH |
| Cl | $N(CH_3)_2$ | $CH_3$ | H | S | H | $CH_3$ | $CH_3$ | CH |
| Cl | $N(CH_3)_2$ | $CH_3$ | H | S | H | $OCH_3$ | $OCH_3$ | N |
| Cl | $N(CH_3)_2$ | $CH_3$ | H | S | H | $CH_3$ | $OCH_3$ | N |
| Cl | $—CH_2CH_2CH_2—$ | | H | O | H | $OCH_3$ | $OCH_3$ | CH |
| Cl | $—CH_2CH_2CH_2—$ | | H | O | H | Cl | $OCH_3$ | CH |
| Cl | $—CH_2CH_2CH_2—$ | | H | O | H | $CH_3$ | $OCH_3$ | CH |
| Cl | $—CH_2CH_2CH_2—$ | | H | O | H | $CH_3$ | $CH_3$ | CH |
| Cl | $—CH_2CH_2CH_2—$ | | H | O | H | $OCH_3$ | $OCH_3$ | N |
| Cl | $—CH_2CH_2CH_2—$ | | H | O | H | $CH_3$ | $OCH_3$ | N |
| Cl | $—CH_2CH_2CH_2—$ | | H | O | H | $CH_3$ | $CH_3$ | N |
| Cl | $—CH_2CH_2CH_2—$ | | H | O | H | $OCH_2CH_3$ | $OCH_2CH_3$ | N |
| Cl | $—CH_2CH_2CH_2—$ | | H | O | H | $NHCH_3$ | $OCH_2CH_3$ | N |
| Cl | $—CH_2CH_2CH_2—$ | | H | O | H | $N(CH_3)_2$ | $OCH_2CH_3$ | N |
| Cl | $—CH_2CH_2CH_2—$ | | H | O | H | $N(CH_3)_2$ | $OCH_3$ | N |
| Cl | $—CH_2CH_2CH_2—$ | | H | O | H | $N(CH_3)_2$ | $OCH_2CF_3$ | N |
| Cl | $—CH_2CH_2CH_2—$ | | H | O | $CH_3$ | $CH_3$ | $OCH_3$ | N |
| Cl | $—CH_2CH_2CH_2—$ | | H | S | H | $OCH_3$ | $OCH_3$ | CH |
| Cl | $—CH_2CH_2CH_2—$ | | H | S | H | Cl | $OCH_3$ | CH |
| Cl | $—CH_2CH_2CH_2—$ | | H | S | H | $CH_3$ | $OCH_3$ | CH |
| Cl | $—CH_2CH_2CH_2—$ | | H | S | H | $CH_3$ | $CH_3$ | CH |
| Cl | $—CH_2CH_2CH_2—$ | | H | S | H | $OCH_3$ | $OCH_3$ | N |
| Cl | $—CH_2CH_2CH_2—$ | | H | S | H | $CH_3$ | $OCH_3$ | N |
| Cl | $—CH_2CH_2OCH_2CH_2—$ | | H | O | H | $OCH_3$ | $OCH_3$ | CH |
| Cl | $—CH_2CH_2OCH_2CH_2—$ | | H | O | H | Cl | $OCH_3$ | CH |
| Cl | $—CH_2CH_2OCH_2CH_2—$ | | H | O | H | $CH_3$ | $OCH_3$ | CH |
| Cl | $—CH_2CH_2OCH_2CH_2—$ | | H | O | H | $CH_3$ | $CH_3$ | CH |
| Cl | $—CH_2CH_2OCH_2CH_2—$ | | H | O | H | $OCH_3$ | $OCH_3$ | N |
| Cl | $—CH_2CH_2OCH_2CH_2—$ | | H | O | H | $CH_3$ | $OCH_3$ | N |
| Cl | $—CH_2CH_2OCH_2CH_2—$ | | H | O | H | $CH_3$ | $CH_3$ | N |
| Cl | $—CH_2CH_2OCH_2CH_2—$ | | H | O | H | $OCH_2CH_3$ | $OCH_2CH_3$ | N |
| Cl | $—CH_2CH_2OCH_2CH_2—$ | | H | O | H | $NHCH_3$ | $OCH_2CH_3$ | N |
| Cl | $—CH_2CH_2OCH_2CH_2—$ | | H | O | H | $N(CH_3)_2$ | $OCH_2CH_3$ | N |
| Cl | $—CH_2CH_2OCH_2CH_2—$ | | H | O | H | $N(CH_3)_2$ | $OCH_3$ | N |
| Cl | $—CH_2CH_2OCH_2CH_2—$ | | H | O | H | $N(CH_3)_2$ | $OCH_2CF_3$ | N |
| Cl | $—CH_2CH_2OCH_2CH_2—$ | | H | O | $CH_3$ | $CH_3$ | $OCH_3$ | N |
| Cl | $—CH_2CH_2OCH_2CH_2—$ | | H | S | H | $OCH_3$ | $OCH_3$ | CH |
| Cl | $—CH_2CH_2OCH_2CH_2—$ | | H | S | H | Cl | $OCH_3$ | CH |
| Cl | $—CH_2CH_2OCH_2CH_2—$ | | H | S | H | $CH_3$ | $OCH_3$ | CH |
| Cl | $—CH_2CH_2OCH_2CH_2—$ | | H | S | H | $CH_3$ | $CH_3$ | CH |
| Cl | $—CH_2CH_2OCH_2CH_2—$ | | H | S | H | $OCH_3$ | $OCH_3$ | N |
| Cl | $—CH_2CH_2OCH_2CH_2—$ | | H | S | H | $CH_3$ | $OCH_3$ | N |
| $CH_3$ | H | H | H | O | H | $OCH_3$ | $OCH_3$ | CH |
| $CH_3$ | H | H | H | O | H | Cl | $OCH_3$ | CH |
| $CH_3$ | H | H | H | O | H | $CH_3$ | $OCH_3$ | CH |
| $CH_3$ | H | H | H | O | H | $CH_3$ | $CH_3$ | CH |
| $CH_3$ | H | H | H | O | H | $OCH_3$ | $OCH_3$ | N |
| $CH_3$ | H | H | H | O | H | $CH_3$ | $OCH_3$ | N |
| $CH_3$ | H | H | H | O | H | $CH_3$ | $CH_3$ | N |
| $CH_3$ | H | H | H | O | H | $OCH_2CH_3$ | $OCH_2CH_3$ | N |
| $CH_3$ | H | H | H | O | H | $NHCH_3$ | $OCH_2CH_3$ | N |
| $CH_3$ | H | H | H | O | H | $N(CH_3)_2$ | $OCH_2CH_3$ | N |
| $CH_3$ | H | H | H | O | H | $N(CH_3)_2$ | $OCH_3$ | N |
| $CH_3$ | H | H | H | O | H | $N(CH_3)_2$ | $OCH_2CF_3$ | N |
| $CH_3$ | H | H | H | O | $CH_3$ | $CH_3$ | $OCH_3$ | N |
| $CH_3$ | H | H | H | S | H | $OCH_3$ | $OCH_3$ | CH |
| $CH_3$ | H | H | H | S | H | Cl | $OCH_3$ | CH |
| $CH_3$ | H | H | H | S | H | $CH_3$ | $OCH_3$ | CH |
| $CH_3$ | H | H | H | S | H | $CH_3$ | $CH_3$ | CH |
| $CH_3$ | H | H | H | S | H | $OCH_3$ | $OCH_3$ | N |
| $CH_3$ | H | H | H | S | H | $CH_3$ | $OCH_3$ | N |
| $CH_3$ | H | $CH_3$ | H | O | H | $OCH_3$ | $OCH_3$ | CH |
| $CH_3$ | H | $CH_3$ | H | O | H | Cl | $OCH_3$ | CH |
| $CH_3$ | H | $CH_3$ | H | O | H | $CH_3$ | $OCH_3$ | CH |
| $CH_3$ | H | $CH_3$ | H | O | H | $CH_3$ | $CH_3$ | CH |
| $CH_3$ | H | $CH_3$ | H | O | H | $OCH_3$ | $OCH_3$ | N |
| $CH_3$ | H | $CH_3$ | H | O | H | $CH_3$ | $OCH_3$ | N |
| $CH_3$ | H | $CH_3$ | H | O | H | $CH_3$ | $CH_3$ | N |
| $CH_3$ | H | $CH_3$ | H | O | H | $OCH_2CH_3$ | $OCH_2CH_3$ | N |
| $CH_3$ | H | $CH_3$ | H | O | H | $NHCH_3$ | $OCH_2CH_3$ | N |
| $CH_3$ | H | $CH_3$ | H | O | H | $N(CH_3)_2$ | $OCH_2CH_3$ | N |
| $CH_3$ | H | $CH_3$ | H | O | H | $N(CH_3)_2$ | $OCH_3$ | N |
| $CH_3$ | H | $CH_3$ | H | O | H | $N(CH_3)_2$ | $OCH_2CF_3$ | N |
| $CH_3$ | H | $CH_3$ | H | O | $CH_3$ | $CH_3$ | $OCH_3$ | N |
| $CH_3$ | H | $CH_3$ | H | S | H | $OCH_3$ | $OCH_3$ | CH |
| $CH_3$ | H | $CH_3$ | H | S | H | Cl | $OCH_3$ | CH |
| $CH_3$ | H | $CH_3$ | H | S | H | $CH_3$ | $OCH_3$ | CH |
| $CH_3$ | H | $CH_3$ | H | S | H | $CH_3$ | $CH_3$ | CH |

-continued

| | | | | | | | | |
|---|---|---|---|---|---|---|---|---|
| $CH_3$ | H | $CH_3$ | H | S | H | $OCH_3$ | $OCH_3$ | N |
| $CH_3$ | H | $CH_3$ | H | S | H | $CH_3$ | $OCH_3$ | N |
| $CH_3$ | H | $CH_2CH_3$ | H | O | H | $OCH_3$ | $OCH_3$ | CH |
| $CH_3$ | H | $CH_2CH_3$ | H | O | H | $Cl_3$ | OCH | CH |
| $CH_3$ | H | $CH_2CH_3$ | H | O | H | $CH_3$ | $OCH_3$ | CH |
| $CH_3$ | H | $CH_2CH_3$ | H | O | H | $CH_3$ | $CH_3$ | CH |
| $CH_3$ | H | $CH_2CH_3$ | H | O | H | $OCH_3$ | $OCH_3$ | N |
| $CH_3$ | H | $CH_2CH_3$ | H | O | H | $CH_3$ | $OCH_3$ | N |
| $CH_3$ | H | $CH_2CH_3$ | H | O | H | $CH_3$ | $CH_3$ | N |
| $CH_3$ | H | $CH_2CH_3$ | H | O | H | $OCH_2CH_3$ | $OCH_2CH_3$ | N |
| $CH_3$ | H | $CH_2CH_3$ | H | O | H | $NHCH_3$ | $OCH_2CH_3$ | N |
| $CH_3$ | H | $CH_2CH_3$ | H | O | H | $N(CH_3)_2$ | $OCH_2CH_3$ | N |
| $CH_3$ | H | $CH_2CH_3$ | H | O | H | $N(CH_3)_2$ | $OCH_3$ | N |
| $CH_3$ | H | $CH_2CH_3$ | H | O | H | $N(CH_3)_2$ | $OCH_2CF_3$ | N |
| $CH_3$ | H | $CH_2CH_3$ | H | O | $CH_3$ | $CH_3$ | $OCH_3$ | N |
| $CH_3$ | H | $CH_2CH_3$ | H | S | H | $OCH_3$ | $OCH_3$ | CH |
| $CH_3$ | H | $CH_2CH_3$ | H | S | H | Cl | $OCH_3$ | CH |
| $CH_3$ | H | $CH_2CH_3$ | H | S | H | $CH_3$ | $OCH_3$ | CH |
| $CH_3$ | H | $CH_2CH_3$ | H | S | H | $CH_3$ | $CH_3$ | CH |
| $CH_3$ | H | $CH_2CH_3$ | H | S | H | $OCH_3$ | $OCH_3$ | N |
| $CH_3$ | H | $CH_2CH_3$ | H | S | H | $CH_3$ | $OCH_3$ | N |
| $CH_3$ | H | $CH_2CF_3$ | H | O | H | $OCH_3$ | $OCH_3$ | CH |
| $CH_3$ | H | $CH_2CF_3$ | H | O | H | Cl | $OCH_3$ | CH |
| $CH_3$ | H | $CH_2CF_3$ | H | O | H | $CH_3$ | $OCH_3$ | CH |
| $CH_3$ | H | $CH_2CF_3$ | H | O | H | $CH_3$ | $CH_3$ | CH |
| $CH_3$ | H | $CH_2CF_3$ | H | O | H | $OCH_3$ | $OCH_3$ | N |
| $CH_3$ | H | $CH_2CF_3$ | H | O | H | $CH_3$ | $OCH_3$ | N |
| $CH_3$ | H | $CH_2CF_3$ | H | O | H | $CH_3$ | $CH_3$ | N |
| $CH_3$ | H | $CH_2CF_3$ | H | O | H | $OCH_2CH_3$ | $OCH_2CH_3$ | N |
| $CH_3$ | H | $CH_2CF_3$ | H | O | H | $NHCH_3$ | $OCH_2CH_3$ | N |
| $CH_3$ | H | $CH_2CF_3$ | H | O | H | $N(CH_3)_2$ | $OCH_2CH_3$ | N |
| $CH_3$ | H | $CH_2CF_3$ | H | O | H | $N(CH_3)_2$ | $OCH_3$ | N |
| $CH_3$ | H | $CH_2CF_3$ | H | O | H | $N(CH_3)_2$ | $OCH_2CF_3$ | N |
| $CH_3$ | H | $CH_2CF_3$ | H | O | $CH_3$ | $CH_3$ | $OCH_3$ | N |
| $CH_3$ | H | $CH_2CF_3$ | H | S | H | $OCH_3$ | $OCH_3$ | CH |
| $CH_3$ | H | $CH_2CF_3$ | H | S | H | Cl | $OCH_3$ | CH |
| $CH_3$ | H | $CH_2CF_3$ | H | S | H | $CH_3$ | $OCH_3$ | CH |
| $CH_3$ | H | $CH_2CF_3$ | H | S | H | $CH_3$ | $CH_3$ | CH |
| $CH_3$ | H | $CH_2CF_3$ | H | S | H | $OCH_3$ | $OCH_3$ | N |
| $CH_3$ | H | $CH_2CF_3$ | H | S | H | $CH_3$ | $OCH_3$ | N |
| $CH_3$ | $CH_2CH_2Cl$ | H | H | O | H | $OCH_3$ | $OCH_3$ | CH |
| $CH_3$ | $CH_2CH_2Cl$ | H | H | O | H | Cl | $OCH_3$ | CH |
| $CH_3$ | $CH_2CH_2Cl$ | H | H | O | H | $CH_3$ | $OCH_3$ | CH |
| $CH_3$ | $CH_2CH_2Cl$ | H | H | O | H | $CH_3$ | $CH_3$ | CH |
| $CH_3$ | $CH_2CH_2Cl$ | H | H | O | H | $OCH_3$ | $OCH_3$ | N |
| $CH_3$ | $CH_2CH_2Cl$ | H | H | O | H | $CH_3$ | $OCH_3$ | N |
| $CH_3$ | $CH_2CH_2Cl$ | H | H | O | H | $CH_3$ | $CH_3$ | N |
| $CH_3$ | $CH_2CH_2Cl$ | H | H | O | H | $OCH_2CH_3$ | $OCH_2CH_3$ | N |
| $CH_3$ | $CH_2CH_2Cl$ | H | H | O | H | $NHCH_3$ | $OCH_2CH_3$ | N |
| $CH_3$ | $CH_2CH_2Cl$ | H | H | O | H | $N(CH_3)_2$ | $OCH_2CH_3$ | N |
| $CH_3$ | $CH_2CH_2Cl$ | H | H | O | H | $N(CH_3)_2$ | $OCH_3$ | N |
| $CH_3$ | $CH_2CH_2Cl$ | H | H | O | H | $N(CH_3)_2$ | $OCH_2CF_3$ | N |
| $CH_3$ | $CH_2CH_2Cl$ | H | H | O | $CH_3$ | $CH_3$ | $OCH_3$ | N |
| $CH_3$ | $CH_2CH_2Cl$ | H | H | S | H | $OCH_3$ | $OCH_3$ | CH |
| $CH_3$ | $CH_2CH_2Cl$ | H | H | S | H | Cl | $OCH_3$ | CH |
| $CH_3$ | $CH_2CH_2Cl$ | H | H | S | H | $CH_3$ | $OCH_3$ | CH |
| $CH_3$ | $CH_2CH_2Cl$ | H | H | S | H | $CH_3$ | $CH_3$ | CH |
| $CH_3$ | $CH_2CH_2Cl$ | H | H | S | H | $OCH_3$ | $OCH_3$ | N |
| $CH_3$ | $CH_2CH_2Cl$ | H | H | S | H | $CH_3$ | $OCH_3$ | N |
| $CH_3$ | $CH_2CN$ | H | H | O | H | $OCH_3$ | $OCH_3$ | CH |
| $CH_3$ | $CH_2CN$ | H | H | O | H | Cl | $OCH_3$ | CH |
| $CH_3$ | $CH_2CN$ | H | H | O | H | $CH_3$ | $OCH_3$ | CH |
| $CH_3$ | $CH_2CN$ | H | H | O | H | $CH_3$ | $CH_3$ | CH |
| $CH_3$ | $CH_2CN$ | H | H | O | H | $OCH_3$ | $OCH_3$ | N |
| $CH_3$ | $CH_2CN$ | H | H | O | H | $CH_3$ | $OCH_3$ | N |
| $CH_3$ | $CH_2CN$ | H | H | O | H | $CH_3$ | $CH_3$ | N |
| $CH_3$ | $CH_2CN$ | H | H | O | H | $OCH_2CH_3$ | $OCH_2CH_3$ | N |
| $CH_3$ | $CH_2CN$ | H | H | O | H | $NHCH_3$ | $OCH_2CH_3$ | N |
| CH | $CH_2CN$ | H | H | O | H | $N(CH_3)_2$ | $OCH_2CH_3$ | N |
| $CH_3$ | $CH_2CN$ | H | H | O | H | $N(CH_3)_2$ | $OCH_3$ | N |
| $CH_3$ | $CH_2CN$ | H | H | O | H | $N(CH_3)_2$ | $OCH_2CF_3$ | N |
| $CH_3$ | $CH_2CN$ | H | H | O | $CH_3$ | $CH_3$ | $OCH_3$ | N |
| $CH_3$ | $CH_2CN$ | H | H | S | H | $OCH_3$ | $OCH_3$ | CH |
| $CH_3$ | $CH_2CN$ | H | H | S | H | Cl | $OCH_3$ | CH |
| $CH_3$ | $CH_2CN$ | H | H | S | H | $CH_3$ | $OCH_3$ | CH |
| $CH_3$ | $CH_2CN$ | H | H | S | H | $CH_3$ | $CH_3$ | CH |
| $CH_3$ | $CH_2CN$ | H | H | S | H | $OCH_3$ | $OCH_3$ | N |
| $CH_3$ | $CH_2CN$ | H | H | S | H | $CH_3$ | $OCH_3$ | N |
| $CH_3$ | $CH_2CH{=}CH_2$ | H | H | O | H | $OCH_3$ | $OCH_3$ | CH |
| $CH_3$ | $CH_2CH{=}CH_2$ | H | H | O | H | Cl | $OCH_3$ | CH |
| $CH_3$ | $CH_2CH{=}CH_2$ | H | H | O | H | $CH_3$ | $OCH_3$ | CH |
| $CH_3$ | $CH_2CH{=}CH_2$ | H | H | O | H | $CH_3$ | $CH_3$ | CH |

-continued

| | | | | | | | | |
|---|---|---|---|---|---|---|---|---|
| $CH_3$ | $CH_2CH{=}CH_2$ | H | H | O | H | $OCH_3$ | $OCH_3$ | N |
| $CH_3$ | $CH_2CH{=}CH_2$ | H | H | O | H | $CH_3$ | $OCH_3$ | N |
| $CH_3$ | $CH_2CH{=}CH_2$ | H | H | O | H | $CH_3$ | $CH_3$ | N |
| $CH_3$ | $CH_2CH{=}CH_2$ | H | H | O | H | $OCH_2CH_3$ | $OCH_2CH_3$ | N |
| $CH_3$ | $CH_2CH{=}CH_2$ | H | H | O | H | $NHCH_3$ | $OCH_2CH_3$ | N |
| $CH_3$ | $CH_2CH{=}CH_2$ | H | H | O | H | $N(CH_3)_2$ | $OCH_2CH_3$ | N |
| $CH_3$ | $CH_2CH{=}CH_2$ | H | H | O | H | $N(CH_3)_2$ | $OCH_3$ | N |
| $CH_3$ | $CH_2CH{=}CH_2$ | H | H | O | H | $N(CH_3)_2$ | $OCH_2CF_3$ | N |
| $CH_3$ | $CH_2CH{=}CH_2$ | H | H | O | $CH_3$ | $CH_3$ | $OCH_3$ | N |
| $CH_3$ | $CH_2CH{=}CH_2$ | H | H | S | H | $OCH_3$ | $OCH_3$ | CH |
| $CH_3$ | $CH_2CH{=}CH_2$ | H | H | S | H | Cl | $OCH_3$ | CH |
| $CH_3$ | $CH_2CH{=}CH_2$ | H | H | S | H | $CH_3$ | $OCH_3$ | CH |
| $CH_3$ | $CH_2CH{=}CH_2$ | H | H | S | H | $CH_3$ | $CH_3$ | CH |
| $CH_3$ | $CH_2CH{=}CH_2$ | H | H | S | H | $OCH_3$ | $OCH_3$ | N |
| $CH_3$ | $CH_2CH{=}CH_2$ | H | H | S | H | $CH_3$ | $OCH_3$ | N |
| $CH_3$ | $CH_2C{\equiv}CH$ | H | H | O | H | $OCH_3$ | $OCH_3$ | CH |
| $CH_3$ | $CH_2C{\equiv}CH$ | H | H | O | H | $Cl_3$ | OCH | CH |
| $CH_3$ | $CH_2C{\equiv}CH$ | H | H | O | H | $CH_3$ | $OCH_3$ | CH |
| $CH_3$ | $CH_2C{\equiv}CH$ | H | H | O | H | $CH_3$ | $CH_3$ | CH |
| $CH_3$ | $CH_2C{\equiv}CH$ | H | H | O | H | $OCH_3$ | $OCH_3$ | N |
| $CH_3$ | $CH_2C{\equiv}CH$ | H | H | O | H | $CH_3$ | $OCH_3$ | N |
| $CH_3$ | $CH_2C{\equiv}CH$ | H | H | O | H | $CH_3$ | $CH_3$ | N |
| $CH_3$ | $CH_2C{\equiv}CH$ | H | H | O | H | $OCH_2CH_3$ | $OCH_2CH_3$ | N |
| $CH_3$ | $CH_2C{\equiv}CH$ | H | H | O | H | $NHCH_3$ | $OCH_2CH_3$ | N |
| $CH_3$ | $CH_2C{\equiv}CH$ | H | H | O | H | $N(CH_3)_2$ | $OCH_2CH_3$ | N |
| $CH_3$ | $CH_2C{\equiv}CH$ | H | H | O | H | $N(CH_3)_2$ | $OCH_3$ | N |
| $CH_3$ | $CH_2C{\equiv}CH$ | H | H | O | H | $N(CH_3)_2$ | $OCH_2CF_3$ | N |
| $CH_3$ | $CH_2C{\equiv}CH$ | H | H | O | $CH_3$ | $CH_3$ | $OCH_3$ | N |
| $CH_3$ | $CH_2C{\equiv}CH$ | H | H | S | H | $OCH_3$ | $OCH_3$ | CH |
| $CH_3$ | $CH_2C{\equiv}CH$ | H | H | S | H | Cl | $OCH_3$ | CH |
| $CH_3$ | $CH_2C{\equiv}CH$ | H | H | S | H | $CH_3$ | $OCH_3$ | CH |
| $CH_3$ | $CH_2C{\equiv}CH$ | H | H | S | H | $CH_3$ | $CH_3$ | CH |
| $CH_3$ | $CH_2C{\equiv}CH$ | H | H | S | H | $OCH_3$ | $OCH_3$ | N |
| $CH_3$ | $CH_2C{\equiv}CH$ | H | H | S | H | $CH_3$ | $OCH_3$ | N |
| $CH_3$ | $CH_2CH_2OCH_3$ | H | H | O | H | $OCH_3$ | $OCH_3$ | CH |
| $CH_3$ | $CH_2CH_2OCH_3$ | H | H | O | H | Cl | $OCH_3$ | CH |
| $CH_3$ | $CH_2CH_2OCH_3$ | H | H | O | H | $CH_3$ | $OCH_3$ | CH |
| $CH_3$ | $CH_2CH_2OCH_3$ | H | H | O | H | $CH_3$ | $CH_3$ | CH |
| $CH_3$ | $CH_2CH_2OCH_3$ | H | H | O | H | $OCH_3$ | $OCH_3$ | N |
| $CH_3$ | $CH_2CH_2OCH_3$ | H | H | O | H | $CH_3$ | $OCH_3$ | N |
| $CH_3$ | $CH_2CH_2OCH_3$ | H | H | O | H | $CH_3$ | $CH_3$ | N |
| $CH_3$ | $CH_2CH_2OCH_3$ | H | H | O | H | $OCH_2CH_3$ | $OCH_2CH_3$ | N |
| $CH_3$ | $CH_2CH_2OCH_3$ | H | H | O | H | $NHCH_3$ | $OCH_2CH_3$ | N |
| $CH_3$ | $CH_2CH_2OCH_3$ | H | H | O | H | $N(CH_3)_2$ | $OCH_2CH_3$ | N |
| $CH_3$ | $CH_2CH_2OCH_3$ | H | H | O | H | $N(CH_3)_2$ | $OCH_3$ | N |
| $CH_3$ | $CH_2CH_2OCH_3$ | H | H | O | H | $N(CH_3)_2$ | $OCH_2CF_3$ | N |
| $CH_3$ | $CH_2CH_2OCH_3$ | H | H | O | $CH_3$ | $CH_3$ | $OCH_3$ | N |
| $CH_3$ | $CH_2CH_2OCH_3$ | H | H | S | H | $OCH_3$ | $OCH_3$ | CH |
| $CH_3$ | $CH_2CH_2OCH_3$ | H | H | S | H | Cl | $OCH_3$ | CH |
| $CH_3$ | $CH_2CH_2OCH_3$ | H | H | S | H | $CH_3$ | $OCH_3$ | CH |
| $CH_3$ | $CH_2CH_2OCH_3$ | H | H | S | H | $CH_3$ | $CH_3$ | CH |
| $CH_3$ | $CH_2CH_2OCH_3$ | H | H | S | H | $OCH_3$ | $OCH_3$ | N |
| $CH_3$ | $CH_2CH_2OCH_3$ | H | H | S | H | $CH_3$ | $OCH_3$ | N |
| $CH_3$ | cyclo-$C_3H_7$ | H | H | O | H | $OCH_3$ | $OCH_3$ | CH |
| $CH_3$ | cyclo-$C_3H_7$ | H | H | O | H | $Cl_3$ | OCH | CH |
| $CH_3$ | cyclo-$C_3H_7$ | H | H | O | H | $CH_3$ | $OCH_3$ | CH |
| $CH_3$ | cyclo-$C_3H_7$ | H | H | O | H | $CH_3$ | $CH_3$ | CH |
| $CH_3$ | cyclo-$C_3H_7$ | H | H | O | H | $OCH_3$ | $OCH_3$ | N |
| $CH_3$ | cyclo-$C_3H_7$ | H | H | O | H | $CH_3$ | $OCH_3$ | N |
| $CH_3$ | cyclo-$C_3H_7$ | H | H | O | H | $CH_3$ | $CH_3$ | N |
| $CH_3$ | cyclo-$C_3H_7$ | H | H | O | H | $OCH_2CH_3$ | $OCH_2CH_3$ | N |
| $CH_3$ | cyclo-$C_3H_7$ | H | H | O | H | $NHCH_3$ | $OCH_2CH_3$ | N |
| $CH_3$ | cyclo-$C_3H_7$ | H | H | O | H | $N(CH_3)_2$ | $OCH_2CH_3$ | N |
| $CH_3$ | cyclo-$C_3H_7$ | H | H | O | H | $N(CH_3)_2$ | $OCH_3$ | N |
| $CH_3$ | cyclo-$C_3H_7$ | H | H | O | H | $N(CH_3)_2$ | $OCH_2CF_3$ | N |
| $CH_3$ | cyclo-$C_3H_7$ | H | H | O | $CH_3$ | $CH_3$ | $OCH_3$ | N |
| $CH_3$ | cyclo-$C_3H_7$ | H | H | S | H | $OCH_3$ | $OCH_3$ | CH |
| $CH_3$ | cyclo-$C_3H_7$ | H | H | S | H | Cl | $OCH_3$ | CH |
| $CH_3$ | cyclo-$C_3H_7$ | H | H | S | H | $CH_3$ | $OCH_3$ | CH |
| $CH_3$ | cyclo-$C_3H_7$ | H | H | S | H | $CH_3$ | $CH_3$ | CH |
| $CH_3$ | cyclo-$C_3H_7$ | H | H | S | H | $OCH_3$ | $OCH_3$ | N |
| $CH_3$ | cyclo-$C_3H_7$ | H | H | S | H | $CH_3$ | $OCH_3$ | N |
| $CH_3$ | $CH_3$ | $CH_3$ | H | O | H | $OCH_3$ | $OCH_3$ | CH |
| $CH_3$ | $CH_3$ | $CH_3$ | H | O | H | Cl | $OCH_3$ | CH |
| $CH_3$ | $CH_3$ | $CH_3$ | H | O | H | $CH_3$ | $OCH_3$ | CH |
| $CH_3$ | $CH_3$ | $CH_3$ | H | O | H | $CH_3$ | $CH_3$ | CH |
| $CH_3$ | $CH_3$ | $CH_3$ | H | O | H | $OCH_3$ | $OCH_3$ | N |
| $CH_3$ | $CH_3$ | $CH_3$ | H | O | H | $CH_3$ | $OCH_3$ | N |
| $CH_3$ | $CH_3$ | $CH_3$ | H | O | H | $CH_3$ | $CH_3$ | N |
| $CH_3$ | $CH_3$ | $CH_3$ | H | O | H | $OCH_2CH_3$ | $OCH_2CH_3$ | N |
| $CH_3$ | $CH_3$ | $CH_3$ | H | O | H | $NHCH_3$ | $OCH_2CH_3$ | N |
| $CH_3$ | $CH_3$ | $CH_3$ | H | O | H | $N(CH_3)_2$ | $OCH_2CH_3$ | N |

-continued

| | | | | | | | | |
|---|---|---|---|---|---|---|---|---|
| $CH_3$ | $CH_3$ | $CH_3$ | H | O | H | $N(CH_3)_2$ | $OCH_3$ | N |
| $CH_3$ | $CH_3$ | $CH_3$ | H | O | H | $N(CH_3)_2$ | $OCH_2CF_3$ | N |
| $CH_3$ | $CH_3$ | $CH_3$ | H | O | $CH_3$ | $CH_3$ | $OCH_3$ | N |
| $CH_3$ | $CH_3$ | $CH_3$ | H | S | H | $OCH_3$ | $OCH_3$ | CH |
| $CH_3$ | $CH_3$ | $CH_3$ | H | S | H | Cl | $OCH_3$ | CH |
| $CH_3$ | $CH_3$ | $CH_3$ | H | S | H | $CH_3$ | $OCH_3$ | CH |
| $CH_3$ | $CH_3$ | $CH_3$ | H | S | H | $CH_3$ | $CH_3$ | CH |
| $CH_3$ | $CH_3$ | $CH_3$ | H | S | H | $OCH_3$ | $OCH_3$ | N |
| $CH_3$ | $CH_3$ | $CH_3$ | H | S | H | $CH_3$ | $OCH_3$ | N |
| $CH_3$ | $CH_3$ | $CH_2CH_3$ | H | O | H | $OCH_3$ | $OCH_3$ | CH |
| $CH_3$ | $CH_3$ | $CH_2CH_3$ | H | O | H | Cl | $OCH_3$ | CH |
| $CH_3$ | $CH_3$ | $CH_2CH_3$ | H | O | H | $CH_3$ | $OCH_3$ | CH |
| $CH_3$ | $CH_3$ | $CH_2CH_3$ | H | O | H | $CH_3$ | $CH_3$ | CH |
| $CH_3$ | $CH_3$ | $CH_2CH_3$ | H | O | H | $OCH_3$ | $OCH_3$ | N |
| $CH_3$ | $CH_3$ | $CH_2CH_3$ | H | O | H | $CH_3$ | $OCH_3$ | N |
| $CH_3$ | $CH_3$ | $CH_2CH_3$ | H | O | H | $CH_3$ | $CH_3$ | N |
| $CH_3$ | $CH_3$ | $CH_2CH_3$ | H | O | H | $OCH_2CH_3$ | $OCH_2CH_3$ | N |
| $CH_3$ | $CH_3$ | $CH_2CH_3$ | H | O | H | $NHCH_3$ | $OCH_2CH_3$ | N |
| $CH_3$ | $CH_3$ | $CH_2CH_3$ | H | O | H | $N(CH_3)_2$ | $OCH_2CH_3$ | N |
| $CH_3$ | $CH_3$ | $CH_2CH_3$ | H | O | H | $N(CH_3)_2$ | $OCH_3$ | N |
| $CH_3$ | $CH_3$ | $CH_2CH_3$ | H | O | H | $N(CH_3)_2$ | $OCH_2CF_3$ | N |
| $CH_3$ | $CH_3$ | $CH_2CH_3$ | H | O | $CH_3$ | $CH_3$ | $OCH_3$ | N |
| $CH_3$ | $CH_3$ | $CH_2CH_3$ | H | S | H | $OCH_3$ | $OCH_3$ | CH |
| $CH_3$ | $CH_3$ | $CH_2CH_3$ | H | S | H | Cl | $OCH_3$ | CH |
| $CH_3$ | $CH_3$ | $CH_2CH_3$ | H | S | H | $CH_3$ | $OCH_3$ | CH |
| $CH_3$ | $CH_3$ | $CH_2CH_3$ | H | S | H | $CH_3$ | $CH_3$ | CH |
| $CH_3$ | $CH_3$ | $CH_2CH_3$ | H | S | H | $OCH_3$ | $OCH_3$ | N |
| $CH_3$ | $CH_3$ | $CH_2CH_3$ | H | S | H | $CH_3$ | $OCH_3$ | N |
| $CH_3$ | $CH_2CH_3$ | $CH_2CH_3$ | H | O | H | $OCH_3$ | $OCH_3$ | CH |
| $CH_3$ | $CH_2CH_3$ | $CH_2CH_3$ | H | O | H | Cl | $OCH_3$ | CH |
| $CH_3$ | $CH_2CH_3$ | $CH_2CH_3$ | H | O | H | $CH_3$ | $OCH_3$ | CH |
| $CH_3$ | $CH_2CH_3$ | $CH_2CH_3$ | H | O | H | $CH_3$ | $CH_3$ | CH |
| $CH_3$ | $CH_2CH_3$ | $CH_2CH_3$ | H | O | H | $OCH_3$ | $OCH_3$ | N |
| $CH_3$ | $CH_2CH_3$ | $CH_2CH_3$ | H | O | H | $CH_3$ | $OCH_3$ | N |
| $CH_3$ | $CH_2CH_3$ | $CH_2CH_3$ | H | O | H | $CH_3$ | $CH_3$ | N |
| $CH_3$ | $CH_2CH_3$ | $CH_2CH_3$ | H | O | H | $OCH_2CH_3$ | $OCH_2CH_3$ | N |
| $CH_3$ | $CH_2CH_3$ | $CH_2CH_3$ | H | O | H | $NHCH_3$ | $OCH_2CH_3$ | N |
| $CH_3$ | $CH_2CH_3$ | $CH_2CH_3$ | H | O | H | $N(CH_3)_2$ | $OCH_2CH_3$ | N |
| $CH_3$ | $CH_2CH_3$ | $CH_2CH_3$ | H | O | H | $N(CH_3)_2$ | $OCH_3$ | N |
| $CH_3$ | $CH_2CH_3$ | $CH_2CH_3$ | H | O | H | $N(CH_3)_2$ | $OCH_2CF_3$ | N |
| $CH_3$ | $CH_2CH_3$ | $CH_2CH_3$ | H | O | $CH_3$ | $CH_3$ | $OCH_3$ | N |
| $CH_3$ | $CH_2CH_3$ | $CH_2CH_3$ | H | S | H | $OCH_3$ | $OCH_3$ | CH |
| $CH_3$ | $CH_2CH_3$ | $CH_2CH_3$ | H | S | H | Cl | $OCH_3$ | CH |
| $CH_3$ | $CH_2CH_3$ | $CH_2CH_3$ | H | S | H | $CH_3$ | $OCH_3$ | CH |
| $CH_3$ | $CH_2CH_3$ | $CH_2CH_3$ | H | S | H | $CH_3$ | $CH_3$ | CH |
| $CH_3$ | $CH_2CH_3$ | $CH_2CH_3$ | H | S | H | $OCH_3$ | $OCH_3$ | N |
| $CH_3$ | $CH_2CH_3$ | $CH_2CH_3$ | H | S | H | $CH_3$ | $OCH_3$ | N |
| $CH_3$ | $OCH_3$ | $CH_3$ | H | O | H | $OCH_3$ | $OCH_3$ | CH |
| $CH_3$ | $OCH_3$ | $CH_3$ | H | O | H | $Cl_3$ | OCH | CH |
| $CH_3$ | $OCH_3$ | $CH_3$ | H | O | H | $CH_3$ | $OCH_3$ | CH |
| $CH_3$ | $OCH_3$ | $CH_3$ | H | O | H | $CH_3$ | $CH_3$ | CH |
| $CH_3$ | $OCH_3$ | $CH_3$ | H | O | H | $OCH_3$ | $OCH_3$ | N |
| $CH_3$ | $OCH_3$ | $CH_3$ | H | O | H | $CH_3$ | $OCH_3$ | N |
| $CH_3$ | $OCH_3$ | $CH_3$ | H | O | $H_3$ | CH | $CH_3$ | N |
| $CH_3$ | $OCH_3$ | $CH_3$ | H | O | H | $OCH_2CH_3$ | $OCH_2CH_3$ | N |
| $CH_3$ | $OCH_3$ | $CH_3$ | H | O | H | $NHCH_3$ | $OCH_2CH_3$ | N |
| $CH_3$ | $OCH_3$ | $CH_3$ | H | O | H | $N(CH_3)_2$ | $OCH_2CH_3$ | N |
| $CH_3$ | $OCH_3$ | $CH_3$ | H | O | H | $N(CH_3)_2$ | $OCH_3$ | N |
| $CH_3$ | $OCH_3$ | $CH_3$ | H | O | H | $N(CH_3)_2$ | $OCH_2CF_3$ | N |
| $CH_3$ | $OCH_3$ | $CH_3$ | H | O | $CH_3$ | $CH_3$ | $OCH_3$ | N |
| $CH_3$ | $OCH_3$ | $CH_3$ | H | S | H | $OCH_3$ | $OCH_3$ | CH |
| $CH_3$ | $OCH_3$ | $CH_3$ | H | S | H | Cl | $OCH_3$ | CH |
| $CH_3$ | $OCH_3$ | $CH_3$ | H | S | H | $CH_3$ | $OCH_3$ | CH |
| $CH_3$ | $OCH_3$ | $CH_3$ | H | S | H | $CH_3$ | $CH_3$ | CH |
| $CH_3$ | $OCH_3$ | $CH_3$ | H | S | H | $OCH_3$ | $OCH_3$ | N |
| $CH_3$ | $OCH_3$ | $CH_3$ | H | S | H | $CH_3$ | $OCH_3$ | N |
| $CH_3$ | $NHCH_3$ | $CH_3$ | H | O | H | $OCH_3$ | $OCH_3$ | CH |
| $CH_3$ | $NHCH_3$ | $CH_3$ | H | O | H | Cl | $OCH_3$ | CH |
| $CH_3$ | $NHCH_3$ | $CH_3$ | H | O | H | $CH_3$ | $OCH_3$ | CH |
| $CH_3$ | $NHCH_3$ | $CH_3$ | H | O | H | $CH_3$ | $CH_3$ | CH |
| $CH_3$ | $NHCH_3$ | $CH_3$ | H | O | H | $OCH_3$ | $OCH_3$ | N |
| $CH_3$ | $NHCH_3$ | $CH_3$ | H | O | H | $CH_3$ | $OCH_3$ | N |
| $CH_3$ | $NHCH_3$ | $CH_3$ | H | O | H | $CH_3$ | $CH_3$ | N |
| $CH_3$ | $NHCH_3$ | $CH_3$ | H | O | H | $OCH_2CH_3$ | $OCH_2CH_3$ | N |
| $CH_3$ | $NHCH_3$ | $CH_3$ | H | O | H | $NHCH_3$ | $OCH_2CH_3$ | N |
| $CH_3$ | $NHCH_3$ | $CH_3$ | H | O | H | $N(CH_3)_2$ | $OCH_2CH_3$ | N |
| $CH_3$ | $NHCH_3$ | $CH_3$ | H | O | H | $N(CH_3)_2$ | $OCH_3$ | N |
| $CH_3$ | $NHCH_3$ | $CH_3$ | H | O | H | $N(CH_3)_2$ | $OCH_2CF_3$ | N |
| $CH_3$ | $NHCH_3$ | $CH_3$ | H | O | $CH_3$ | $CH_3$ | $OCH_3$ | N |
| $CH_3$ | $NHCH_3$ | $CH_3$ | H | S | H | $OCH_3$ | $OCH_3$ | CH |
| $CH_3$ | $NHCH_3$ | $CH_3$ | H | S | H | Cl | $OCH_3$ | CH |
| $CH_3$ | $NHCH_3$ | $CH_3$ | H | S | H | $CH_3$ | $OCH_3$ | CH |

-continued

| | | | | | | | | |
|---|---|---|---|---|---|---|---|---|
| $CH_3$ | $NHCH_3$ | $CH_3$ | H | S | H | $CH_3$ | $CH_3$ | CH |
| $CH_3$ | $NHCH_3$ | $CH_3$ | H | S | H | $OCH_3$ | $OCH_3$ | N |
| $CH_3$ | $NHCH_3$ | $CH_3$ | H | S | H | $CH_3$ | $OCH_3$ | N |
| $CH_3$ | $N(CH_3)_2$ | $CH_3$ | H | O | H | $OCH_3$ | $OCH_3$ | CH |
| $CH_3$ | $N(CH_3)_2$ | $CH_3$ | H | O | H | Cl | $OCH_3$ | CH |
| $CH_3$ | $N(CH_3)_2$ | $CH_3$ | H | O | H | $CH_3$ | $OCH_3$ | CH |
| $CH_3$ | $N(CH_3)_2$ | $CH_3$ | H | O | H | $CH_3$ | $CH_3$ | CH |
| $CH_3$ | $N(CH_3)_2$ | $CH_3$ | H | O | H | $OCH_3$ | $OCH_3$ | N |
| $CH_3$ | $N(CH_3)_2$ | $CH_3$ | H | O | H | $CH_3$ | $OCH_3$ | N |
| $CH_3$ | $N(CH_3)_2$ | $CH_3$ | H | O | H | $CH_3$ | $CH_3$ | N |
| $CH_3$ | $N(CH_3)_2$ | $CH_3$ | H | O | H | $OCH_2CH_3$ | $OCH_2CH_3$ | N |
| $CH_3$ | $N(CH_3)_2$ | $CH_3$ | H | O | H | $NHCH_3$ | $OCH_2CH_3$ | N |
| $CH_3$ | $N(CH_3)_2$ | $CH_3$ | H | O | H | $N(CH_3)_2$ | $OCH_2CH_3$ | N |
| $CH_3$ | $N(CH_3)_2$ | $CH_3$ | H | O | H | $N(CH_3)_2$ | $OCH_3$ | N |
| $CH_3$ | $N(CH_3)_2$ | $CH_3$ | H | O | H | $N(CH_3)_2$ | $OCH_2CF_3$ | N |
| $CH_3$ | $N(CH_3)_2$ | $CH_3$ | H | O | $CH_3$ | $CH_3$ | $OCH_3$ | N |
| $CH_3$ | $N(CH_3)_2$ | $CH_3$ | H | S | H | $OCH_3$ | $OCH_3$ | CH |
| $CH_3$ | $N(CH_3)_2$ | $CH_3$ | H | S | H | Cl | $OCH_3$ | CH |
| $CH_3$ | $N(CH_3)_2$ | $CH_3$ | H | S | H | $CH_3$ | $OCH_3$ | CH |
| $CH_3$ | $N(CH_3)_2$ | $CH_3$ | H | S | H | $CH_3$ | $CH_3$ | CH |
| $CH_3$ | $N(CH_3)_2$ | $CH_3$ | H | S | H | $OCH_3$ | $OCH_3$ | N |
| $CH_3$ | $N(CH_3)_2$ | $CH_3$ | H | S | H | $CH_3$ | $OCH_3$ | N |
| $CH_3$ | $-CH_2CH_2CH_2-$ | | H | O | H | $OCH_3$ | $OCH_3$ | CH |
| $CH_3$ | $-CH_2CH_2CH_2-$ | | H | O | H | Cl | $OCH_3$ | CH |
| $CH_3$ | $-CH_2CH_2CH_2-$ | | H | O | H | $CH_3$ | $OCH_3$ | CH |
| $CH_3$ | $-CH_2CH_2CH_2-$ | | H | O | H | $CH_3$ | $CH_3$ | CH |
| $CH_3$ | $-CH_2CH_2CH_2-$ | | H | O | H | $OCH_3$ | $OCH_3$ | N |
| $CH_3$ | $-CH_2CH_2CH_2-$ | | H | O | H | $CH_3$ | $OCH_3$ | N |
| $CH_3$ | $-CH_2CH_2CH_2-$ | | H | O | H | $CH_3$ | $CH_3$ | N |
| $CH_3$ | $-CH_2CH_2CH_2-$ | | H | O | H | $OCH_2CH_3$ | $OCH_2CH_3$ | N |
| $CH_3$ | $-CH_2CH_2CH_2-$ | | H | O | H | $NHCH_3$ | $OCH_2CH_3$ | N |
| $CH_3$ | $-CH_2CH_2CH_2-$ | | H | O | H | $N(CH_3)_2$ | $OCH_2CH_3$ | N |
| $CH_3$ | $-CH_2CH_2CH_2-$ | | H | O | H | $N(CH_3)_2$ | $OCH_3$ | N |
| $CH_3$ | $-CH_2CH_2CH_2-$ | | H | O | H | $N(CH_3)_2$ | $OCH_2CF_3$ | N |
| $CH_3$ | $-CH_2CH_2CH_2-$ | | H | O | $CH_3$ | $CH_3$ | $OCH_3$ | N |
| $CH_3$ | $-CH_2CH_2CH_2-$ | | H | S | H | $OCH_3$ | $OCH_3$ | CH |
| $CH_3$ | $-CH_2CH_2CH_2-$ | | H | S | H | Cl | $OCH_3$ | CH |
| $CH_3$ | $-CH_2CH_2CH_2-$ | | H | S | H | $CH_3$ | $OCH_3$ | CH |
| $CH_3$ | $-CH_2CH_2CH_2-$ | | H | S | H | $CH_3$ | $CH_3$ | CH |
| $CH_3$ | $-CH_2CH_2CH_2-$ | | H | S | H | $OCH_3$ | $OCH_3$ | N |
| $CH_3$ | $-CH_2CH_2CH_2-$ | | H | S | H | $CH_3$ | $OCH_3$ | N |
| $CH_3$ | $-CH_2CH_2OCH_2CH_2-$ | | H | O | H | $OCH_3$ | $OCH_3$ | CH |
| $CH_3$ | $-CH_2CH_2OCH_2CH_2-$ | | H | O | H | Cl | $OCH_3$ | CH |
| $CH_3$ | $-CH_2CH_2OCH_2CH_2-$ | | H | O | H | $CH_3$ | $OCH_3$ | CH |
| $CH_3$ | $-CH_2CH_2OCH_2CH_2-$ | | H | O | H | $CH_3$ | $CH_3$ | CH |
| $CH_3$ | $-CH_2CH_2OCH_2CH_2-$ | | H | O | H | $OCH_3$ | $OCH_3$ | N |
| $CH_3$ | $-CH_2CH_2OCH_2CH_2-$ | | H | O | H | $CH_3$ | $OCH_3$ | N |
| $CH_3$ | $-CH_2CH_2OCH_2CH_2-$ | | H | O | H | $CH_3$ | $CH_3$ | N |
| $CH_3$ | $-CH_2CH_2OCH_2CH_2-$ | | H | O | H | $OCH_2CH_3$ | $OCH_2CH_3$ | N |
| $CH_3$ | $-CH_2CH_2OCH_2CH_2-$ | | H | O | H | $NHCH_3$ | $OCH_2CH_3$ | N |
| $CH_3$ | $-CH_2CH_2OCH_2CH_2-$ | | H | O | H | $N(CH_3)_2$ | $OCH_2CH_3$ | N |
| $CH_3$ | $-CH_2CH_2OCH_2CH_2-$ | | H | O | H | $N(CH_3)_2$ | $OCH_3$ | N |
| $CH_3$ | $-CH_2CH_2OCH_2CH_2-$ | | H | O | H | $N(CH_3)_2$ | $OCH_2CF_3$ | N |
| $CH_3$ | $-CH_2CH_2OCH_2CH_2-$ | | H | O | $CH_3$ | $CH_3$ | $OCH_3$ | N |
| $CH_3$ | $-CH_2CH_2OCH_2CH_2-$ | | H | S | H | $OCH_3$ | $OCH_3$ | CH |
| $CH_3$ | $-CH_2CH_2OCH_2CH_2-$ | | H | S | H | Cl | $OCH_3$ | CH |
| $CH_3$ | $-CH_2CH_2OCH_2CH_2-$ | | H | S | H | $CH_3$ | $OCH_3$ | CH |
| $CH_3$ | $-CH_2CH_2OCH_2CH_2-$ | | H | S | H | $CH_3$ | $CH_3$ | CH |
| $CH_3$ | $-CH_2CH_2OCH_2CH_2-$ | | H | S | H | $OCH_3$ | $OCH_3$ | N |
| $CH_3$ | $-CH_2CH_2OCH_2CH_2-$ | | H | S | H | $CH_3$ | $OCH_3$ | N |
| $SCH_3$ | H | H | H | O | H | $OCH_3$ | $OCH_3$ | CH |
| $SCH_3$ | H | H | H | O | H | Cl | $OCH_3$ | CH |
| $SCH_3$ | H | H | H | O | H | $CH_3$ | $OCH_3$ | CH |
| $SCH_3$ | H | H | H | O | H | $CH_3$ | $CH_3$ | CH |
| $SCH_3$ | H | H | H | O | H | $OCH_3$ | $OCH_3$ | N |
| $SCH_3$ | H | H | H | O | H | $CH_3$ | $OCH_3$ | N |
| $SCH_3$ | H | H | H | O | H | $CH_3$ | $CH_3$ | N |
| $SCH_3$ | H | H | H | O | H | $OCH_2CH_3$ | $OCH_2CH_3$ | N |
| $SCH_3$ | H | H | H | O | H | $NHCH_3$ | $OCH_2CH_3$ | N |
| $SCH_3$ | H | H | H | O | H | $N(CH_3)_2$ | $OCH_2CH_3$ | N |
| $SCH_3$ | H | H | H | O | H | $N(CH_3)_2$ | $OCH_3$ | N |
| $SCH_3$ | H | H | H | O | H | $N(CH_3)_2$ | $OCH_2CF_3$ | N |
| $SCH_3$ | H | H | H | O | $CH_3$ | $CH_3$ | $OCH_3$ | N |
| $SCH_3$ | H | H | H | S | H | $OCH_3$ | $OCH_3$ | CH |
| $SCH_3$ | H | H | H | S | H | Cl | $OCH_3$ | CH |
| $SCH_3$ | H | H | H | S | H | $CH_3$ | $OCH_3$ | CH |
| $SCH_3$ | H | H | H | S | H | $CH_3$ | $CH_3$ | CH |
| $SCH_3$ | H | H | H | S | H | $OCH_3$ | $OCH_3$ | N |
| $SCH_3$ | H | H | H | S | H | $CH_3$ | $OCH_3$ | N |
| $SCH_3$ | H | $CH_3$ | H | O | H | $OCH_3$ | $OCH_3$ | CH |
| $SCH_3$ | H | $CH_3$ | H | O | H | Cl | $OCH_3$ | CH |
| $SCH_3$ | H | $CH_3$ | H | O | H | $CH_3$ | $OCH_3$ | CH |

-continued

| | | | | | | | | |
|---|---|---|---|---|---|---|---|---|
| $SCH_3$ | H | $CH_3$ | H | O | H | $CH_3$ | $CH_3$ | CH |
| $SCH_3$ | H | $CH_3$ | H | O | H | $OCH_3$ | $OCH_3$ | N |
| $SCH_3$ | H | $CH_3$ | H | O | H | $CH_3$ | $OCH_3$ | N |
| $SCH_3$ | H | $CH_3$ | H | O | H | $CH_3$ | $CH_3$ | N |
| $SCH_3$ | H | $CH_3$ | H | O | H | $OCH_2CH_3$ | $OCH_2CH_3$ | N |
| $SCH_3$ | H | $CH_3$ | H | O | H | $NHCH_3$ | $OCH_2CH_3$ | N |
| $SCH_3$ | H | $CH_3$ | H | O | H | $N(CH_3)_2$ | $OCH_2CH_3$ | N |
| $SCH_3$ | H | $CH_3$ | H | O | H | $N(CH_3)_2$ | $OCH_3$ | N |
| $SCH_3$ | H | $CH_3$ | H | O | H | $N(CH_3)_2$ | $OCH_2CF_3$ | N |
| $SCH_3$ | H | $CH_3$ | H | O | $CH_3$ | $CH_3$ | $OCH_3$ | N |
| $SCH_3$ | H | $CH_3$ | H | S | H | $OCH_3$ | $OCH_3$ | CH |
| $SCH_3$ | H | $CH_3$ | H | S | H | Cl | $OCH_3$ | CH |
| $SCH_3$ | H | $CH_3$ | H | S | H | $CH_3$ | $OCH_3$ | CH |
| $SCH_3$ | H | $CH_3$ | H | S | H | $CH_3$ | $CH_3$ | CH |
| $SCH_3$ | H | $CH_3$ | H | S | H | $OCH_3$ | $OCH_3$ | N |
| $SCH_3$ | H | $CH_3$ | H | S | H | $CH_3$ | $OCH_3$ | N |
| $SCH_3$ | H | $CH_2CH_3$ | H | O | H | $OCH_3$ | $OCH_3$ | CH |
| $SCH_3$ | H | $CH_2CH_3$ | H | O | H | Cl | $OCH_3$ | CH |
| $SCH_3$ | H | $CH_2CH_3$ | H | O | H | $CH_3$ | $OCH_3$ | CH |
| $SCH_3$ | H | $CH_2CH_3$ | H | O | H | $CH_3$ | $CH_3$ | CH |
| $SCH_3$ | H | $CH_2CH_3$ | H | O | H | $OCH_3$ | $OCH_3$ | N |
| $SCH_3$ | H | $CH_2CH_3$ | H | O | H | $CH_3$ | $OCH_3$ | N |
| $SCH_3$ | H | $CH_2CH_3$ | H | O | H | $CH_3$ | $CH_3$ | N |
| $SCH_3$ | H | $CH_2CH_3$ | H | O | H | $OCH_2CH_3$ | $OCH_2CH_3$ | N |
| $SCH_3$ | H | $CH_2CH_3$ | H | O | H | $NHCH_3$ | $OCH_2CH_3$ | N |
| $SCH_3$ | H | $CH_2CH_3$ | H | O | H | $N(CH_3)_2$ | $OCH_2CH_3$ | N |
| $SCH_3$ | H | $CH_2CH_3$ | H | O | H | $N(CH_3)_2$ | $OCH_3$ | N |
| $SCH_3$ | H | $CH_2CH_3$ | H | O | H | $N(CH_3)_2$ | $OCH_2CF_3$ | N |
| $SCH_3$ | H | $CH_2CH_3$ | H | O | $CH_3$ | $CH_3$ | $OCH_3$ | N |
| $SCH_3$ | H | $CH_2CH_3$ | H | S | H | $OCH_3$ | $OCH_3$ | CH |
| $SCH_3$ | H | $CH_2CH_3$ | H | S | H | Cl | $OCH_3$ | CH |
| $SCH_3$ | H | $CH_2CH_3$ | H | S | H | $CH_3$ | $OCH_3$ | CH |
| $SCH_3$ | H | $CH_2CH_3$ | H | S | H | $CH_3$ | $CH_3$ | CH |
| $SCH_3$ | H | $CH_2CH_3$ | H | S | H | $OCH_3$ | $OCH_3$ | N |
| $SCH_3$ | H | $CH_2CH_3$ | H | S | H | $CH_3$ | $OCH_3$ | N |
| $SCH_3$ | H | $CH_2CF_3$ | H | O | H | $OCH_3$ | $OCH_3$ | CH |
| $SCH_3$ | H | $CH_2CF_3$ | H | O | H | Cl | $OCH_3$ | CH |
| $SCH_3$ | H | $CH_2CF_3$ | H | O | H | $CH_3$ | $OCH_3$ | CH |
| $SCH_3$ | H | $CH_2CF_3$ | H | O | H | $CH_3$ | $CH_3$ | CH |
| $SCH_3$ | H | $CH_2CF_3$ | H | O | H | $OCH_3$ | $OCH_3$ | N |
| $SCH_3$ | H | $CH_2CF_3$ | H | O | H | $CH_3$ | $OCH_3$ | N |
| $SCH_3$ | H | $CH_2CF_3$ | H | O | H | $CH_3$ | $CH_3$ | N |
| $SCH_3$ | H | $CH_2CF_3$ | H | O | H | $OCH_2CH_3$ | $OCH_2CH_3$ | N |
| $SCH_3$ | H | $CH_2CF_3$ | H | O | H | $NHCH_3$ | $OCH_2CH_3$ | N |
| $SCH_3$ | H | $CH_2CF_3$ | H | O | H | $N(CH_3)_2$ | $OCH_2CH_3$ | N |
| $SCH_3$ | H | $CH_2CF_3$ | H | O | H | $N(CH_3)_2$ | $OCH_3$ | N |
| $SCH_3$ | H | $CH_2CF_3$ | H | O | H | $N(CH_3)_2$ | $OCH_2CF_3$ | N |
| $SCH_3$ | H | $CH_2CF_3$ | H | O | $CH_3$ | $CH_3$ | $OCH_3$ | N |
| $SCH_3$ | H | $CH_2CF_3$ | H | S | H | $OCH_3$ | $OCH_3$ | CH |
| $SCH_3$ | H | $CH_2CF_3$ | H | S | H | Cl | $OCH_3$ | CH |
| $SCH_3$ | H | $CH_2CF_3$ | H | S | H | $CH_3$ | $OCH_3$ | CH |
| $SCH_3$ | H | $CH_2CF_3$ | H | S | H | $CH_3$ | $CH_3$ | CH |
| $SCH_3$ | H | $CH_2CF_3$ | H | S | H | $OCH_3$ | $OCH_3$ | N |
| $SCH_3$ | H | $CH_2CF_3$ | H | S | H | $CH_3$ | $OCH_3$ | N |
| $SCH_3$ | $CH_2CH_2Cl$ | H | H | O | H | $OCH_3$ | $OCH_3$ | CH |
| $SCH_3$ | $CH_2CH_2Cl$ | H | H | O | H | Cl | $OCH_3$ | CH |
| $SCH_3$ | $CH_2CH_2Cl$ | H | H | O | H | $CH_3$ | $OCH_3$ | CH |
| $SCH_3$ | $CH_2CH_2Cl$ | H | H | O | H | $CH_3$ | $CH_3$ | CH |
| $SCH_3$ | $CH_2CH_2Cl$ | H | H | O | H | $OCH_3$ | $OCH_3$ | N |
| $SCH_3$ | $CH_2CH_2Cl$ | H | H | O | H | $CH_3$ | $OCH_3$ | N |
| $SCH_3$ | $CH_2CH_2Cl$ | H | H | O | H | $CH_3$ | $CH_3$ | N |
| $SCH_3$ | $CH_2CH_2Cl$ | H | H | O | H | $OCH_2CH_3$ | $OCH_2CH_3$ | N |
| $SCH_3$ | $CH_2CH_2Cl$ | H | H | O | H | $NHCH_3$ | $OCH_2CH_3$ | N |
| $SCH_3$ | $CH_2CH_2Cl$ | H | H | O | H | $N(CH_3)_2$ | $OCH_2CH_3$ | N |
| $SCH_3$ | $CH_2CH_2Cl$ | H | H | O | H | $N(CH_3)_2$ | $OCH_3$ | N |
| $SCH_3$ | $CH_2CH_2Cl$ | H | H | O | H | $N(CH_3)_2$ | $OCH_2CF_3$ | N |
| $SCH_3$ | $CH_2CH_2Cl$ | H | H | O | $CH_3$ | $CH_3$ | $OCH_3$ | N |
| $SCH_3$ | $CH_2CH_2Cl$ | H | H | S | H | $OCH_3$ | $OCH_3$ | CH |
| $SCH_3$ | $CH_2CH_2Cl$ | H | H | S | H | Cl | $OCH_3$ | CH |
| $SCH_3$ | $CH_2CH_2Cl$ | H | H | S | H | $CH_3$ | $OCH_3$ | CH |
| $SCH_3$ | $CH_2CH_2Cl$ | H | H | S | H | $CH_3$ | $CH_3$ | CH |
| $SCH_3$ | $CH_2CH_2Cl$ | H | H | S | H | $OCH_3$ | $OCH_3$ | N |
| $SCH_3$ | $CH_2CH_2Cl$ | H | H | S | H | $CH_3$ | $OCH_3$ | N |
| $SCH_3$ | $CH_2CN$ | H | H | O | H | $OCH_3$ | $OCH_3$ | CH |
| $SCH_3$ | $CH_2CN$ | H | H | O | H | Cl | $OCH_3$ | CH |
| $SCH_3$ | $CH_2CN$ | H | H | O | H | $CH_3$ | $OCH_3$ | CH |
| $SCH_3$ | $CH_2CN$ | H | H | O | H | $CH_3$ | $CH_3$ | CH |
| $SCH_3$ | $CH_2CN$ | H | H | O | H | $OCH_3$ | $OCH_3$ | N |
| $SCH_3$ | $CH_2CN$ | H | H | O | H | $CH_3$ | $OCH_3$ | N |
| $SCH_3$ | $CH_2CN$ | H | H | O | H | $CH_3$ | $CH_3$ | N |
| $SCH_3$ | $CH_2CN$ | H | H | O | H | $OCH_2CH_3$ | $OCH_2CH_3$ | N |
| $SCH_3$ | $CH_2CN$ | H | H | O | H | $NHCH_3$ | $OCH_2CH_3$ | N |

-continued

| | | | | | | | | |
|---|---|---|---|---|---|---|---|---|
| $SCH_3$ | $CH_2CN$ | H | H | O | H | $N(CH_3)_2$ | $OCH_2CH_3$ | N |
| $SCH_3$ | $CH_2CN$ | H | H | O | H | $N(CH_3)_2$ | $OCH_3$ | N |
| $SCH_3$ | $CH_2CN$ | H | H | O | H | $N(CH_3)_2$ | $OCH_2CF_3$ | N |
| $SCH_3$ | $CH_2CN$ | H | H | O | $CH_3$ | $CH_3$ | $OCH_3$ | N |
| $SCH_3$ | $CH_2CN$ | H | H | S | H | $OCH_3$ | $OCH_3$ | CH |
| $SCH_3$ | $CH_2CN$ | H | H | S | H | Cl | $OCH_3$ | CH |
| $SCH_3$ | $CH_2CN$ | H | H | S | H | $CH_3$ | $OCH_3$ | CH |
| $SCH_3$ | $CH_2CN$ | H | H | S | H | $CH_3$ | $CH_3$ | CH |
| $SCH_3$ | $CH_2CN$ | H | H | S | H | $OCH_3$ | $OCH_3$ | N |
| $SCH_3$ | $CH_2CN$ | H | H | S | H | $CH_3$ | $OCH_3$ | N |
| $SCH_3$ | $CH_2CH{=}CH_2$ | H | H | O | H | $OCH_3$ | $OCH_3$ | CH |
| $SCH_3$ | $CH_2CH{=}CH_2$ | H | H | O | H | Cl | $OCH_3$ | CH |
| $SCH_3$ | $CH_2CH{=}CH_2$ | H | H | O | H | $CH_3$ | $OCH_3$ | CH |
| $SCH_3$ | $CH_2CH{=}CH_2$ | H | H | O | H | $CH_3$ | $CH_3$ | CH |
| $SCH_3$ | $CH_2CH{=}CH_2$ | H | H | O | H | $OCH_3$ | $OCH_3$ | N |
| $SCH_3$ | $CH_2CH{=}CH_2$ | H | H | O | H | $CH_3$ | $OCH_3$ | N |
| $SCH_3$ | $CH_2CH{=}CH_2$ | H | H | O | H | $CH_3$ | $CH_3$ | N |
| $SCH_3$ | $CH_2CH{=}CH_2$ | H | H | O | H | $OCH_2CH_3$ | $OCH_2CH_3$ | N |
| $SCH_3$ | $CH_2CH{=}CH_2$ | H | H | O | H | $NHCH_3$ | $OCH_2CH_3$ | N |
| $SCH_3$ | $CH_2CH{=}CH_2$ | H | H | O | H | $N(CH_3)_2$ | $OCH_2CH_3$ | N |
| $SCH_3$ | $CH_2CH{=}CH_2$ | H | H | O | H | $N(CH_3)_2$ | $OCH_3$ | N |
| $SCH_3$ | $CH_2CH{=}CH_2$ | H | H | O | H | $N(CH_3)_2$ | $OCH_2CF_3$ | N |
| $SCH_3$ | $CH_2CH{=}CH_2$ | H | H | O | $CH_3$ | $CH_3$ | $OCH_3$ | N |
| $SCH_3$ | $CH_2CH{=}CH_2$ | H | H | S | H | $OCH_3$ | $OCH_3$ | CH |
| $SCH_3$ | $CH_2CH{=}CH_2$ | H | H | S | H | Cl | $OCH_3$ | CH |
| $SCH_3$ | $CH_2CH{=}CH_2$ | H | H | S | H | $CH_3$ | $OCH_3$ | CH |
| $SCH_3$ | $CH_2CH{=}CH_2$ | H | H | S | H | $CH_3$ | $CH_3$ | CH |
| $SCH_3$ | $CH_2CH{=}CH_2$ | H | H | S | H | $OCH_3$ | $OCH_3$ | N |
| $SCH_3$ | $CH_2CH{=}CH_2$ | H | H | S | H | $CH_3$ | $OCH_3$ | N |
| $SCH_3$ | $CH_2C{\equiv}CH$ | H | H | O | H | $OCH_3$ | $OCH_3$ | CH |
| $SCH_3$ | $CH_2C{\equiv}CH$ | H | H | O | H | Cl | $OCH_3$ | CH |
| $SCH_3$ | $CH_2C{\equiv}CH$ | H | H | O | H | $CH_3$ | $OCH_3$ | CH |
| $SCH_3$ | $CH_2C{\equiv}CH$ | H | H | O | H | $CH_3$ | $CH_3$ | CH |
| $SCH_3$ | $CH_2C{\equiv}CH$ | H | H | O | H | $OCH_3$ | $OCH_3$ | N |
| $SCH_3$ | $CH_2C{\equiv}CH$ | H | H | O | H | $CH_3$ | $OCH_3$ | N |
| $SCH_3$ | $CH_2C{\equiv}CH$ | H | H | O | H | $CH_3$ | $CH_3$ | N |
| $SCH_3$ | $CH_2C{\equiv}CH$ | H | H | O | H | $OCH_2CH_3$ | $OCH_2CH_3$ | N |
| $SCH_3$ | $CH_2C{\equiv}CH$ | H | H | O | H | $NHCH_3$ | $OCH_2CH_3$ | N |
| $SCH_3$ | $CH_2C{\equiv}CH$ | H | H | O | H | $N(CH_3)_2$ | $OCH_2CH_3$ | N |
| $SCH_3$ | $CH_2C{\equiv}CH$ | H | H | O | H | $N(CH_3)_2$ | $OCH_3$ | N |
| $SCH_3$ | $CH_2C{\equiv}CH$ | H | H | O | H | $N(CH_3)_2$ | $OCH_2CF_3$ | N |
| $SCH_3$ | $CH_2C{\equiv}CH$ | H | H | O | $CH_3$ | $CH_3$ | $OCH_3$ | N |
| $SCH_3$ | $CH_2C{\equiv}CH$ | H | H | S | H | $OCH_3$ | $OCH_3$ | CH |
| $SCH_3$ | $CH_2C{\equiv}CH$ | H | H | S | H | Cl | $OCH_3$ | CH |
| $SCH_3$ | $CH_2C{\equiv}CH$ | H | H | S | H | $CH_3$ | $OCH_3$ | CH |
| $SCH_3$ | $CH_2C{\equiv}CH$ | H | H | S | H | $CH_3$ | $CH_3$ | CH |
| $SCH_3$ | $CH_2C{\equiv}CH$ | H | H | S | H | $OCH_3$ | $OCH_3$ | N |
| $SCH_3$ | $CH_2C{\equiv}CH$ | H | H | S | H | $CH_3$ | $OCH_3$ | N |
| $SCH_3$ | $CH_2CH_2OCH_3$ | H | H | O | H | $OCH_3$ | $OCH_3$ | CH |
| $SCH_3$ | $CH_2CH_2OCH_3$ | H | H | O | H | Cl | $OCH_3$ | CH |
| $SCH_3$ | $CH_2CH_2OCH_3$ | H | H | O | H | $CH_3$ | $OCH_3$ | CH |
| $SCH_3$ | $CH_2CH_2OCH_3$ | H | H | O | H | $CH_3$ | $CH_3$ | CH |
| $SCH_3$ | $CH_2CH_2OCH_3$ | H | H | O | H | $OCH_3$ | $OCH_3$ | N |
| $SCH_3$ | $CH_2CH_2OCH_3$ | H | H | O | H | $CH_3$ | $OCH_3$ | N |
| $SCH_3$ | $CH_2CH_2OCH_3$ | H | H | O | H | $CH_3$ | $CH_3$ | N |
| $SCH_3$ | $CH_2CH_2OCH_3$ | H | H | O | H | $OCH_2CH_3$ | $OCH_2CH_3$ | N |
| $SCH_3$ | $CH_2CH_2OCH_3$ | H | H | O | H | $NHCH_3$ | $OCH_2CH_3$ | N |
| $SCH_3$ | $CH_2CH_2OCH_3$ | H | H | O | H | $N(CH_3)_2$ | $OCH_2CH_3$ | N |
| $SCH_3$ | $CH_2CH_2OCH_3$ | H | H | O | H | $N(CH_3)_2$ | $OCH_3$ | N |
| $SCH_3$ | $CH_2CH_2OCH_3$ | H | H | O | H | $N(CH_3)_2$ | $OCH_2CF_3$ | N |
| $SCH_3$ | $CH_2CH_2OCH_3$ | H | H | O | $CH_3$ | $CH_3$ | $OCH_3$ | N |
| $SCH_3$ | $CH_2CH_2OCH_3$ | H | H | S | H | $OCH_3$ | $OCH_3$ | CH |
| $SCH_3$ | $CH_2CH_2OCH_3$ | H | H | S | H | Cl | $OCH_3$ | CH |
| $SCH_3$ | $CH_2CH_2OCH_3$ | H | H | S | H | $CH_3$ | $OCH_3$ | CH |
| $SCH_3$ | $CH_2CH_2OCH_3$ | H | H | S | H | $CH_3$ | $CH_3$ | CH |
| $SCH_3$ | $CH_2CH_2OCH_3$ | H | H | S | H | $OCH_3$ | $OCH_3$ | N |
| $SCH_3$ | $CH_2CH_2OCH_3$ | H | H | S | H | $CH_3$ | $OCH_3$ | N |
| $SCH_3$ | cyclo-$C_3H_7$ | H | H | O | H | $OCH_3$ | $OCH_3$ | CH |
| $SCH_3$ | cyclo-$C_3H_7$ | H | H | O | H | Cl | $OCH_3$ | CH |
| $SCH_3$ | cyclo-$C_3H_7$ | H | H | O | H | $CH_3$ | $OCH_3$ | CH |
| $SCH_3$ | cyclo-$C_3H_7$ | H | H | O | H | $CH_3$ | $CH_3$ | CH |
| $SCH_3$ | cyclo-$C_3H_7$ | H | H | O | H | $OCH_3$ | $OCH_3$ | N |
| $SCH_3$ | cyclo-$C_3H_7$ | H | H | O | H | $CH_3$ | $OCH_3$ | N |
| $SCH_3$ | cyclo-$C_3H_7$ | H | H | O | H | $CH_3$ | $CH_3$ | N |
| $SCH_3$ | cyclo-$C_3H_7$ | H | H | O | H | $OCH_2CH_3$ | $OCH_2CH_3$ | N |
| $SCH_3$ | cyclo-$C_3H_7$ | H | H | O | H | $NHCH_3$ | $OCH_2CH_3$ | N |
| $SCH_3$ | cyclo-$C_3H_7$ | H | H | O | H | $N(CH_3)_2$ | $OCH_2CH_3$ | N |
| $SCH_3$ | cyclo-$C_3H_7$ | H | H | O | H | $N(CH_3)_2$ | $OCH_3$ | N |
| $SCH_3$ | cyclo-$C_3H_7$ | H | H | O | H | $N(CH_3)_2$ | $OCH_2CF_3$ | N |
| $SCH_3$ | cyclo-$C_3H_7$ | H | H | O | $CH_3$ | $CH_3$ | $OCH_3$ | N |
| $SCH_3$ | cyclo-$C_3H_7$ | H | H | S | H | $OCH_3$ | $OCH_3$ | CH |
| $SCH_3$ | cyclo-$C_3H_7$ | H | H | S | H | Cl | $OCH_3$ | CH |

-continued

| | | | | | | | | |
|---|---|---|---|---|---|---|---|---|
| $SCH_3$ | cyclo-$C_3H_7$ | H | H | S | H | $CH_3$ | $OCH_3$ | CH |
| $SCH_3$ | cyclo-$C_3H_7$ | H | H | S | H | $CH_3$ | $CH_3$ | CH |
| $SCH_3$ | cyclo-$C_3H_7$ | H | H | S | H | $OCH_3$ | $OCH_3$ | N |
| $SCH_3$ | cyclo-$C_3H_7$ | H | H | S | H | $CH_3$ | $OCH_3$ | N |
| $SCH_3$ | $CH_3$ | $CH_3$ | H | O | H | $OCH_3$ | $OCH_3$ | CH |
| $SCH_3$ | $CH_3$ | $CH_3$ | H | O | H | Cl | $OCH_3$ | CH |
| $SCH_3$ | $CH_3$ | $CH_3$ | H | O | H | $CH_3$ | $OCH_3$ | CH |
| $SCH_3$ | $CH_3$ | $CH_3$ | H | O | H | $CH_3$ | $CH_3$ | CH |
| $SCH_3$ | $CH_3$ | $CH_3$ | H | O | H | $OCH_3$ | $OCH_3$ | N |
| $SCH_3$ | $CH_3$ | $CH_3$ | H | O | H | $CH_3$ | $OCH_3$ | N |
| $SCH_3$ | $CH_3$ | $CH_3$ | H | O | H | $CH_3$ | $CH_3$ | N |
| $SCH_3$ | $CH_3$ | $CH_3$ | H | O | H | $OCH_2CH_3$ | $OCH_2CH_3$ | N |
| $SCH_3$ | $CH_3$ | $CH_3$ | H | O | H | $NHCH_3$ | $OCH_2CH_3$ | N |
| $SCH_3$ | $CH_3$ | $CH_3$ | H | O | H | $N(CH_3)_2$ | $OCH_2CH_3$ | N |
| $SCH_3$ | $CH_3$ | $CH_3$ | H | O | H | $N(CH_3)_2$ | $OCH_3$ | N |
| $SCH_3$ | $CH_3$ | $CH_3$ | H | O | H | $N(CH_3)_2$ | $OCH_2CF_3$ | N |
| $SCH_3$ | $CH_3$ | $CH_3$ | H | O | $CH_3$ | $CH_3$ | $OCH_3$ | N |
| $SCH_3$ | $CH_3$ | $CH_3$ | H | S | H | $OCH_3$ | $OCH_3$ | CH |
| $SCH_3$ | $CH_3$ | $CH_3$ | H | S | H | Cl | $OCH_3$ | CH |
| $SCH_3$ | $CH_3$ | $CH_3$ | H | S | H | $CH_3$ | $OCH_3$ | CH |
| $SCH_3$ | $CH_3$ | $CH_3$ | H | S | H | $CH_3$ | $CH_3$ | CH |
| $SCH_3$ | $CH_3$ | $CH_3$ | H | S | H | $OCH_3$ | $OCH_3$ | N |
| $SCH_3$ | $CH_3$ | $CH_3$ | H | S | H | $CH_3$ | $OCH_3$ | N |
| $SCH_3$ | $CH_3$ | $CH_2CH_3$ | H | O | H | $OCH_3$ | $OCH_3$ | CH |
| $SCH_3$ | $CH_3$ | $CH_2CH_3$ | H | O | H | Cl | $OCH_3$ | CH |
| $SCH_3$ | $CH_3$ | $CH_2CH_3$ | H | O | H | $CH_3$ | $OCH_3$ | CH |
| $SCH_3$ | $CH_3$ | $CH_2CH_3$ | H | O | H | $CH_3$ | $CH_3$ | CH |
| $SCH_3$ | $CH_3$ | $CH_2CH_3$ | H | O | H | $OCH_3$ | $OCH_3$ | N |
| $SCH_3$ | $CH_3$ | $CH_2CH_3$ | H | O | H | $CH_3$ | $OCH_3$ | N |
| $SCH_3$ | $CH_3$ | $CH_2CH_3$ | H | O | H | $CH_3$ | $CH_3$ | N |
| $SCH_3$ | $CH_3$ | $CH_2CH_3$ | H | O | H | $OCH_2CH_3$ | $OCH_2CH_3$ | N |
| $SCH_3$ | $CH_3$ | $CH_2CH_3$ | H | O | H | $NHCH_3$ | $OCH_2CH_3$ | N |
| $SCH_3$ | $CH_3$ | $CH_2CH_3$ | H | O | H | $N(CH_3)_2$ | $OCH_2CH_3$ | N |
| $SCH_3$ | $CH_3$ | $CH_2CH_3$ | H | O | H | $N(CH_3)_2$ | $OCH_3$ | N |
| $SCH_3$ | $CH_3$ | $CH_2CH_3$ | H | O | H | $N(CH_3)_2$ | $OCH_2CF_3$ | N |
| $SCH_3$ | $CH_3$ | $CH_2CH_3$ | H | O | $CH_3$ | $CH_3$ | $OCH_3$ | N |
| $SCH_3$ | $CH_3$ | $CH_2CH_3$ | H | S | H | $OCH_3$ | $OCH_3$ | CH |
| $SCH_3$ | $CH_3$ | $CH_2CH_3$ | H | S | H | Cl | $OCH_3$ | CH |
| $SCH_3$ | $CH_3$ | $CH_2CH_3$ | H | S | H | $CH_3$ | $OCH_3$ | CH |
| $SCH_3$ | $CH_3$ | $CH_2CH_3$ | H | S | H | $CH_3$ | $CH_3$ | CH |
| $SCH_3$ | $CH_3$ | $CH_2CH_3$ | H | S | H | $OCH_3$ | $OCH_3$ | N |
| $SCH_3$ | $CH_3$ | $CH_2CH_3$ | H | S | H | $CH_3$ | $OCH_3$ | N |
| $SCH_3$ | $CH_2CH_3$ | $CH_2CH_3$ | H | O | H | $OCH_3$ | $OCH_3$ | CH |
| $SCH_3$ | $CH_2CH_3$ | $CH_2CH_3$ | H | O | H | Cl | $OCH_3$ | CH |
| $SCH_3$ | $CH_2CH_3$ | $CH_2CH_3$ | H | O | H | $CH_3$ | $OCH_3$ | CH |
| $SCH_3$ | $CH_2CH_3$ | $CH_2CH_3$ | H | O | H | $CH_3$ | $CH_3$ | CH |
| $SCH_3$ | $CH_2CH_3$ | $CH_2CH_3$ | H | O | H | $OCH_3$ | $OCH_3$ | N |
| $SCH_3$ | $CH_2CH_3$ | $CH_2CH_3$ | H | O | H | $CH_3$ | $OCH_3$ | N |
| $SCH_3$ | $CH_2CH_3$ | $CH_2CH_3$ | H | O | H | $CH_3$ | $CH_3$ | N |
| $SCH_3$ | $CH_2CH_3$ | $CH_2CH_3$ | H | O | H | $OCH_2CH_3$ | $OCH_2CH_3$ | N |
| $SCH_3$ | $CH_2CH_3$ | $CH_2CH_3$ | H | O | H | $NHCH_3$ | $OCH_2CH_3$ | N |
| $SCH_3$ | $CH_2CH_3$ | $CH_2CH_3$ | H | O | H | $N(CH_3)_2$ | $OCH_2CH_3$ | N |
| $SCH_3$ | $CH_2CH_3$ | $CH_2CH_3$ | H | O | H | $N(CH_3)_2$ | $OCH_3$ | N |
| $SCH_3$ | $CH_2CH_3$ | $CH_2CH_3$ | H | O | H | $N(CH_3)_2$ | $OCH_2CF_3$ | N |
| $SCH_3$ | $CH_2CH_3$ | $CH_2CH_3$ | H | O | $CH_3$ | $CH_3$ | $OCH_3$ | N |
| $SCH_3$ | $CH_2CH_3$ | $CH_2CH_3$ | H | S | H | $OCH_3$ | $OCH_3$ | CH |
| $SCH_3$ | $CH_2CH_3$ | $CH_2CH_3$ | H | S | H | Cl | $OCH_3$ | CH |
| $SCH_3$ | $CH_2CH_3$ | $CH_2CH_3$ | H | S | H | $CH_3$ | $OCH_3$ | CH |
| $SCH_3$ | $CH_2CH_3$ | $CH_2CH_3$ | H | S | H | $CH_3$ | $CH_3$ | CH |
| $SCH_3$ | $CH_2CH_3$ | $CH_2CH_3$ | H | S | H | $OCH_3$ | $OCH_3$ | N |
| $SCH_3$ | $CH_2CH_3$ | $CH_2CH_3$ | H | S | H | $CH_3$ | $OCH_3$ | N |
| $SCH_3$ | $OCH_3$ | $CH_3$ | H | O | H | $OCH_3$ | $OCH_3$ | CH |
| $SCH_3$ | $OCH_3$ | $CH_3$ | H | O | H | Cl | $OCH_3$ | CH |
| $SCH_3$ | $OCH_3$ | $CH_3$ | H | O | H | $CH_3$ | $OCH_3$ | CH |
| $SCH_3$ | $OCH_3$ | $CH_3$ | H | O | H | $CH_3$ | $CH_3$ | CH |
| $SCH_3$ | $OCH_3$ | $CH_3$ | H | O | H | $OCH_3$ | $OCH_3$ | N |
| $SCH_3$ | $OCH_3$ | $CH_3$ | H | O | H | $CH_3$ | $OCH_3$ | N |
| $SCH_3$ | $OCH_3$ | $CH_3$ | H | O | H | $CH_3$ | $CH_3$ | N |
| $SCH_3$ | $OCH_3$ | $CH_3$ | H | O | H | $OCH_2CH_3$ | $OCH_2CH_3$ | N |
| $SCH_3$ | $OCH_3$ | $CH_3$ | H | O | H | $NHCH_3$ | $OCH_2CH_3$ | N |
| $SCH_3$ | $OCH_3$ | $CH_3$ | H | O | H | $N(CH_3)_2$ | $OCH_2CH_3$ | N |
| $SCH_3$ | $OCH_3$ | $CH_3$ | H | O | H | $N(CH_3)_2$ | $OCH_3$ | N |
| $SCH_3$ | $OCH_3$ | $CH_3$ | H | O | H | $N(CH_3)_2$ | $OCH_2CF_3$ | N |
| $SCH_3$ | $OCH_3$ | $CH_3$ | H | O | $CH_3$ | $CH_3$ | $OCH_3$ | N |
| $SCH_3$ | $OCH_3$ | $CH_3$ | H | S | H | $OCH_3$ | $OCH_3$ | CH |
| $SCH_3$ | $OCH_3$ | $CH_3$ | H | S | H | Cl | $OCH_3$ | CH |
| $SCH_3$ | $OCH_3$ | $CH_3$ | H | S | H | $CH_3$ | $OCH_3$ | CH |
| $SCH_3$ | $OCH_3$ | $CH_3$ | H | S | H | $CH_3$ | $CH_3$ | CH |
| $SCH_3$ | $OCH_3$ | $CH_3$ | H | S | H | $OCH_3$ | $OCH_3$ | N |
| $SCH_3$ | $OCH_3$ | $CH_3$ | H | S | H | $CH_3$ | $OCH_3$ | N |
| $SCH_3$ | $NHCH_3$ | $CH_3$ | H | O | H | $OCH_3$ | $OCH_3$ | CH |
| $SCH_3$ | $NHCH_3$ | $CH_3$ | H | O | H | Cl | $OCH_3$ | CH |

-continued

| | | | | | | | | |
|---|---|---|---|---|---|---|---|---|
| $SCH_3$ | $NHCH_3$ | $CH_3$ | H | O | H | $CH_3$ | $OCH_3$ | CH |
| $SCH_3$ | $NHCH_3$ | $CH_3$ | H | O | H | $CH_3$ | $CH_3$ | CH |
| $SCH_3$ | $NHCH_3$ | $CH_3$ | H | O | H | $OCH_3$ | $OCH_3$ | N |
| $SCH_3$ | $NHCH_3$ | $CH_3$ | H | O | H | $CH_3$ | $OCH_3$ | N |
| $SCH_3$ | $NHCH_3$ | $CH_3$ | H | O | H | $CH_3$ | $CH_3$ | N |
| $SCH_3$ | $NHCH_3$ | $CH_3$ | H | O | H | $OCH_2CH_3$ | $OCH_2CH_3$ | N |
| $SCH_3$ | $NHCH_3$ | $CH_3$ | H | O | H | $NHCH_3$ | $OCH_2CH_3$ | N |
| $SCH_3$ | $NHCH_3$ | $CH_3$ | H | O | H | $N(CH_3)_2$ | $OCH_2CH_3$ | N |
| $SCH_3$ | $NHCH_3$ | $CH_3$ | H | O | H | $N(CH_3)_2$ | $OCH_3$ | N |
| $SCH_3$ | $NHCH_3$ | $CH_3$ | H | O | H | $N(CH_3)_2$ | $OCH_2CF_3$ | N |
| $SCH_3$ | $NHCH_3$ | $CH_3$ | H | O | $CH_3$ | $CH_3$ | $OCH_3$ | N |
| $SCH_3$ | $NHCH_3$ | $CH_3$ | H | S | H | $OCH_3$ | $OCH_3$ | CH |
| $SCH_3$ | $NHCH_3$ | $CH_3$ | H | S | H | Cl | $OCH_3$ | CH |
| $SCH_3$ | $NHCH_3$ | $CH_3$ | H | S | H | $CH_3$ | $OCH_3$ | CH |
| $SCH_3$ | $NHCH_3$ | $CH_3$ | H | S | H | $CH_3$ | $CH_3$ | CH |
| $SCH_3$ | $NHCH_3$ | $CH_3$ | H | S | H | $OCH_3$ | $OCH_3$ | N |
| $SCH_3$ | $NHCH_3$ | $CH_3$ | H | S | H | $CH_3$ | $OCH_3$ | N |
| $SCH_3$ | $N(CH_3)_2$ | $CH_3$ | H | O | H | $OCH_3$ | $OCH_3$ | CH |
| $SCH_3$ | $N(CH_3)_2$ | $CH_3$ | H | O | H | Cl | $OCH_3$ | CH |
| $SCH_3$ | $N(CH_3)_2$ | $CH_3$ | H | O | H | $CH_3$ | $OCH_3$ | CH |
| $SCH_3$ | $N(CH_3)_2$ | $CH_3$ | H | O | H | $CH_3$ | $CH_3$ | CH |
| $SCH_3$ | $N(CH_3)_2$ | $CH_3$ | H | O | H | $OCH_3$ | $OCH_3$ | N |
| $SCH_3$ | $N(CH_3)_2$ | $CH_3$ | H | O | H | $CH_3$ | $OCH_3$ | N |
| $SCH_3$ | $N(CH_3)_2$ | $CH_3$ | H | O | H | $CH_3$ | $CH_3$ | N |
| $SCH_3$ | $N(CH_3)_2$ | $CH_3$ | H | O | H | $OCH_2CH_3$ | $OCH_2CH_3$ | N |
| $SCH_3$ | $N(CH_3)_2$ | $CH_3$ | H | O | H | $NHCH_3$ | $OCH_2CH_3$ | N |
| $SCH_3$ | $N(CH_3)_2$ | $CH_3$ | H | O | H | $N(CH_3)_2$ | $OCH_2CH_3$ | N |
| $SCH_3$ | $N(CH_3)_2$ | $CH_3$ | H | O | H | $N(CH_3)_2$ | $OCH_3$ | N |
| $SCH_3$ | $N(CH_3)_2$ | $CH_3$ | H | O | H | $N(CH_3)_2$ | $OCH_2CF_3$ | N |
| $SCH_3$ | $N(CH_3)_2$ | $CH_3$ | H | O | $CH_3$ | $CH_3$ | $OCH_3$ | N |
| $SCH_3$ | $N(CH_3)_2$ | $CH_3$ | H | S | H | $OCH_3$ | $OCH_3$ | CH |
| $SCH_3$ | $N(CH_3)_2$ | $CH_3$ | H | S | H | Cl | $OCH_3$ | CH |
| $SCH_3$ | $N(CH_3)_2$ | $CH_3$ | H | S | H | $CH_3$ | $OCH_3$ | CH |
| $SCH_3$ | $N(CH_3)_2$ | $CH_3$ | H | S | H | $CH_3$ | $CH_3$ | CH |
| $SCH_3$ | $N(CH_3)_2$ | $CH_3$ | H | S | H | $OCH_3$ | $OCH_3$ | N |
| $SCH_3$ | $N(CH_3)_2$ | $CH_3$ | H | S | H | $CH_3$ | $OCH_3$ | N |
| $SCH_3$ | $-CH_2CH_2CH_2-$ | | H | O | H | $OCH_3$ | $OCH_3$ | CH |
| $SCH_3$ | $-CH_2CH_2CH_2-$ | | H | O | H | Cl | $OCH_3$ | CH |
| $SCH_3$ | $-CH_2CH_2CH_2-$ | | H | O | H | $CH_3$ | $OCH_3$ | CH |
| $SCH_3$ | $-CH_2CH_2CH_2-$ | | H | O | H | $CH_3$ | $CH_3$ | CH |
| $SCH_3$ | $-CH_2CH_2CH_2-$ | | H | O | H | $OCH_3$ | $OCH_3$ | N |
| $SCH_3$ | $-CH_2CH_2CH_2-$ | | H | O | H | $CH_3$ | $OCH_3$ | N |
| $SCH_3$ | $-CH_2CH_2CH_2-$ | | H | O | H | $CH_3$ | $CH_3$ | N |
| $SCH_3$ | $-CH_2CH_2CH_2-$ | | H | O | H | $OCH_2CH_3$ | $OCH_2CH_3$ | N |
| $SCH_3$ | $-CH_2CH_2CH_2-$ | | H | O | H | $NHCH_3$ | $OCH_2CH_3$ | N |
| $SCH_3$ | $-CH_2CH_2CH_2-$ | | H | O | H | $N(CH_3)_2$ | $OCH_2CH_3$ | N |
| $SCH_3$ | $-CH_2CH_2CH_2-$ | | H | O | H | $N(CH_3)_2$ | $OCH_3$ | N |
| $SCH_3$ | $-CH_2CH_2CH_2-$ | | H | O | H | $N(CH_3)_2$ | $OCH_2CF_3$ | N |
| $SCH_3$ | $-CH_2CH_2CH_2-$ | | H | O | $CH_3$ | $CH_3$ | $OCH_3$ | N |
| $SCH_3$ | $-CH_2CH_2CH_2-$ | | H | S | H | $OCH_3$ | $OCH_3$ | CH |
| $SCH_3$ | $-CH_2CH_2CH_2-$ | | H | S | H | Cl | $OCH_3$ | CH |
| $SCH_3$ | $-CH_2CH_2CH_2-$ | | H | S | H | $CH_3$ | $OCH_3$ | CH |
| $SCH_3$ | $-CH_2CH_2CH_2-$ | | H | S | H | $CH_3$ | $CH_3$ | CH |
| $SCH_3$ | $-CH_2CH_2CH_2-$ | | H | S | H | $OCH_3$ | $OCH_3$ | N |
| $SCH_3$ | $-CH_2CH_2CH_2-$ | | H | S | H | $CH_3$ | $OCH_3$ | N |
| $SCH_3$ | $-CH_2CH_2OCH_2CH_2-$ | | H | O | H | $OCH_3$ | $OCH_3$ | CH |
| $SCH_3$ | $-CH_2CH_2OCH_2CH_2-$ | | H | O | H | Cl | $OCH_3$ | CH |
| $SCH_3$ | $-CH_2CH_2OCH_2CH_2-$ | | H | O | H | $CH_3$ | $OCH_3$ | CH |
| $SCH_3$ | $-CH_2CH_2OCH_2CH_2-$ | | H | O | H | $CH_3$ | $CH_3$ | CH |
| $SCH_3$ | $-CH_2CH_2OCH_2CH_2-$ | | H | O | H | $OCH_3$ | $OCH_3$ | N |
| $SCH_3$ | $-CH_2CH_2OCH_2CH_2-$ | | H | O | H | $CH_3$ | $OCH_3$ | N |
| $SCH_3$ | $-CH_2CH_2OCH_2CH_2-$ | | H | O | H | $CH_3$ | $CH_3$ | N |
| $SCH_3$ | $-CH_2CH_2OCH_2CH_2-$ | | H | O | H | $OCH_2CH_3$ | $OCH_2CH_3$ | N |
| $SCH_3$ | $-CH_2CH_2OCH_2CH_2-$ | | H | O | H | $NHCH_3$ | $OCH_2CH_3$ | N |
| $SCH_3$ | $-CH_2CH_2OCH_2CH_2-$ | | H | O | H | $N(CH_3)_2$ | $OCH_2CH_3$ | N |
| $SCH_3$ | $-CH_2CH_2OCH_2CH_2-$ | | H | O | H | $N(CH_3)_2$ | $OCH_3$ | N |
| $SCH_3$ | $-CH_2CH_2OCH_2CH_2-$ | | H | O | H | $N(CH_3)_2$ | $OCH_2CF_3$ | N |
| $SCH_3$ | $-CH_2CH_2OCH_2CH_2-$ | | H | O | $CH_3$ | $CH_3$ | $OCH_3$ | N |
| $SCH_3$ | $-CH_2CH_2OCH_2CH_2-$ | | H | S | H | $OCH_3$ | $OCH_3$ | CH |
| $SCH_3$ | $-CH_2CH_2OCH_2CH_2-$ | | H | S | H | Cl | $OCH_3$ | CH |
| $SCH_3$ | $-CH_2CH_2OCH_2CH_2-$ | | H | S | H | $CH_3$ | $OCH_3$ | CH |
| $SCH_3$ | $-CH_2CH_2OCH_2CH_2-$ | | H | S | H | $CH_3$ | $CH_3$ | CH |
| $SCH_3$ | $-CH_2CH_2OCH_2CH_2-$ | | H | S | H | $OCH_3$ | $OCH_3$ | N |
| $SCH_3$ | $-CH_2CH_2OCH_2CH_2-$ | | H | S | H | $CH_3$ | $OCH_3$ | N |
| $SO_2CH_3$ | $CH_3$ | $CH_3$ | H | O | H | $OCH_3$ | $OCH_3$ | CH |
| $SO_2CH_2CH_3$ | H | H | H | O | H | $OCH_3$ | $OCH_3$ | CH |
| $SO_2CH_2CH_3$ | H | H | H | O | H | Cl | $OCH_3$ | CH |
| $SO_2CH_2CH_3$ | H | H | H | O | H | $CH_3$ | $OCH_3$ | CH |
| $SO_2CH_2CH_3$ | H | H | H | O | H | $CH_3$ | $CH_3$ | CH |
| $SO_2CH_2CH_3$ | H | H | H | O | H | $OCH_3$ | $OCH_3$ | N |
| $SO_2CH_2CH_3$ | H | H | H | O | H | $CH_3$ | $OCH_3$ | N |
| $SO_2CH_2CH_3$ | H | H | H | O | H | $CH_3$ | $CH_3$ | N |

-continued

| | | | | | | | | |
|---|---|---|---|---|---|---|---|---|
| $SO_2CH_2CH_3$ | H | H | H | O | H | $OCH_2CH_3$ | $OCH_2CH_3$ | N |
| $SO_2CH_2CH_3$ | H | H | H | O | H | $NHCH_3$ | $OCH_2CH_3$ | N |
| $SO_2CH_2CH_3$ | H | H | H | O | H | $N(CH_3)_2$ | $OCH_2CH_3$ | N |
| $SO_2CH_2CH_3$ | H | H | H | O | H | $N(CH_3)_2$ | $OCH_3$ | N |
| $SO_2CH_2CH_3$ | H | H | H | O | H | $N(CH_3)_2$ | $OCH_2CF_3$ | N |
| $SO_2CH_2CH_3$ | H | H | H | O | $CH_3$ | $CH_3$ | $OCH_3$ | N |
| $SO_2CH_2CH_3$ | H | H | H | S | H | $OCH_3$ | $OCH_3$ | CH |
| $SO_2CH_2CH_3$ | H | H | H | S | H | Cl | $OCH_3$ | CH |
| $SO_2CH_2CH_3$ | H | H | H | S | H | $CH_3$ | $OCH_3$ | CH |
| $SO_2CH_2CH_3$ | H | H | H | S | H | $CH_3$ | $CH_3$ | CH |
| $SO_2CH_2CH_3$ | H | H | H | S | H | $OCH_3$ | $OCH_3$ | N |
| $SO_2CH_2CH_3$ | H | H | H | S | H | $CH_3$ | $OCH_3$ | N |
| $SO_2CH_2CH_3$ | H | $CH_3$ | H | O | H | $OCH_3$ | $OCH_3$ | CH |
| $SO_2CH_2CH_3$ | H | $CH_3$ | H | O | H | Cl | $OCH_3$ | CH |
| $SO_2CH_2CH_3$ | H | $CH_3$ | H | O | H | $CH_3$ | $OCH_3$ | CH |
| $SO_2CH_2CH_3$ | H | $CH_3$ | H | O | H | $CH_3$ | $CH_3$ | CH |
| $SO_2CH_2CH_3$ | H | $CH_3$ | H | O | H | $OCH_3$ | $OCH_3$ | N |
| $SO_2CH_2CH_3$ | H | $CH_3$ | H | O | H | $CH_3$ | $OCH_3$ | N |
| $SO_2CH_2CH_3$ | H | $CH_3$ | H | O | H | $CH_3$ | $CH_3$ | N |
| $SO_2CH_2CH_3$ | H | $CH_3$ | H | O | H | $OCH_2CH_3$ | $OCH_2CH_3$ | N |
| $SO_2CH_2CH_3$ | H | $CH_3$ | H | O | H | $NHCH_3$ | $OCH_2CH_3$ | N |
| $SO_2CH_2CH_3$ | H | $CH_3$ | H | O | H | $N(CH_3)_2$ | $OCH_2CH_3$ | N |
| $SO_2CH_2CH_3$ | H | $CH_3$ | H | O | H | $N(CH_3)_2$ | $OCH_3$ | N |
| $SO_2CH_2CH_3$ | H | $CH_3$ | H | O | H | $N(CH_3)_2$ | $OCH_2CF_3$ | N |
| $SO_2CH_2CH_3$ | H | $CH_3$ | H | O | $CH_3$ | $CH_3$ | $OCH_3$ | N |
| $SO_2CH_2CH_3$ | H | $CH_3$ | H | S | H | $OCH_3$ | $OCH_3$ | CH |
| $SO_2CH_2CH_3$ | H | $CH_3$ | H | S | H | Cl | $OCH_3$ | CH |
| $SO_2CH_2CH_3$ | H | $CH_3$ | H | S | H | $CH_3$ | $OCH_3$ | CH |
| $SO_2CH_2CH_3$ | H | $CH_3$ | H | S | H | $CH_3$ | $CH_3$ | CH |
| $SO_2CH_2CH_3$ | H | $CH_3$ | H | S | H | $OCH_3$ | $OCH_3$ | N |
| $SO_2CH_2CH_3$ | H | $CH_3$ | H | S | H | $CH_3$ | $OCH_3$ | N |
| $SO_2CH_2CH_3$ | H | $CH_2CH_3$ | H | O | H | $OCH_3$ | $OCH_3$ | CH |
| $SO_2CH_2CH_3$ | H | $CH_2CH_3$ | H | O | H | Cl | $OCH_3$ | CH |
| $SO_2CH_2CH_3$ | H | $CH_2CH_3$ | H | O | H | $CH_3$ | $OCH_3$ | CH |
| $SO_2CH_2CH_3$ | H | $CH_2CH_3$ | H | O | H | $CH_3$ | $CH_3$ | CH |
| $SO_2CH_2CH_3$ | H | $CH_2CH_3$ | H | O | H | $OCH_3$ | $OCH_3$ | N |
| $SO_2CH_2CH_3$ | H | $CH_2CH_3$ | H | O | H | $CH_3$ | $OCH_3$ | N |
| $SO_2CH_2CH_3$ | H | $CH_2CH_3$ | H | O | H | $CH_3$ | $CH_3$ | N |
| $SO_2CH_2CH_3$ | H | $CH_2CH_3$ | H | O | H | $OCH_2CH_3$ | $OCH_2CH_3$ | N |
| $SO_2CH_2CH_3$ | H | $CH_2CH_3$ | H | O | H | $NHCH_3$ | $OCH_2CH_3$ | N |
| $SO_2CH_2CH_3$ | H | $CH_2CH_3$ | H | O | H | $N(CH_3)_2$ | $OCH_2CH_3$ | N |
| $SO_2CH_2CH_3$ | H | $CH_2CH_3$ | H | O | H | $N(CH_3)_2$ | $OCH_3$ | N |
| $SO_2CH_2CH_3$ | H | $CH_2CH_3$ | H | O | H | $N(CH_3)_2$ | $OCH_2CF_3$ | N |
| $SO_2CH_2CH_3$ | H | $CH_2CH_3$ | H | O | $CH_3$ | $CH_3$ | $OCH_3$ | N |
| $SO_2CH_2CH_3$ | H | $CH_2CH_3$ | H | S | H | $OCH_3$ | $OCH_3$ | CH |
| $SO_2CH_2CH_3$ | H | $CH_2CH_3$ | H | S | H | Cl | $OCH_3$ | CH |
| $SO_2CH_2CH_3$ | H | $CH_2CH_3$ | H | S | H | $CH_3$ | $OCH_3$ | CH |
| $SO_2CH_2CH_3$ | H | $CH_2CH_3$ | H | S | H | $CH_3$ | $CH_3$ | CH |
| $SO_2CH_2CH_3$ | H | $CH_2CH_3$ | H | S | H | $OCH_3$ | $OCH_3$ | N |
| $SO_2CH_2CH_3$ | H | $CH_2CH_3$ | H | S | H | $CH_3$ | $OCH_3$ | N |
| $SO_2CH_2CH_3$ | H | $CH_2CF_3$ | H | O | H | $OCH_3$ | $OCH_3$ | CH |
| $SO_2CH_2CH_3$ | H | $CH_2CF_3$ | H | O | H | Cl | $OCH_3$ | CH |
| $SO_2CH_2CH_3$ | H | $CH_2CF_3$ | H | O | H | $CH_3$ | $OCH_3$ | CH |
| $SO_2CH_2CH_3$ | H | $CH_2CF_3$ | H | O | H | $CH_3$ | $CH_3$ | CH |
| $SO_2CH_2CH_3$ | H | $CH_2CF_3$ | H | O | H | $OCH_3$ | $OCH_3$ | N |
| $SO_2CH_2CH_3$ | H | $CH_2CF_3$ | H | O | H | $CH_3$ | $OCH_3$ | N |
| $SO_2CH_2CH_3$ | H | $CH_2CF_3$ | H | O | H | $CH_3$ | $CH_3$ | N |
| $SO_2CH_2CH_3$ | H | $CH_2CF_3$ | H | O | H | $OCH_2CH_3$ | $OCH_2CH_3$ | N |
| $SO_2CH_2CH_3$ | H | $CH_2CF_3$ | H | O | H | $NHCH_3$ | $OCH_2CH_3$ | N |
| $SO_2CH_2CH_3$ | H | $CH_2CF_3$ | H | O | H | $N(CH_3)_2$ | $OCH_2CH_3$ | N |
| $SO_2CH_2CH_3$ | H | $CH_2CF_3$ | H | O | H | $N(CH_3)_2$ | $OCH_3$ | N |
| $SO_2CH_2CH_3$ | H | $CH_2CF_3$ | H | O | H | $N(CH_3)_2$ | $OCH_2CF_3$ | N |
| $SO_2CH_2CH_3$ | H | $CH_2CF_3$ | H | O | $CH_3$ | $CH_3$ | $OCH_3$ | N |
| $SO_2CH_2CH_3$ | H | $CH_2CF_3$ | H | S | H | $OCH_3$ | $OCH_3$ | CH |
| $SO_2CH_2CH_3$ | H | $CH_2CF_3$ | H | S | H | Cl | $OCH_3$ | CH |
| $SO_2CH_2CH_3$ | H | $CH_2CF_3$ | H | S | H | $CH_3$ | $OCH_3$ | CH |
| $SO_2CH_2CH_3$ | H | $CH_2CF_3$ | H | S | H | $CH_3$ | $CH_3$ | CH |
| $SO_2CH_2CH_3$ | H | $CH_2CF_3$ | H | S | H | $OCH_3$ | $OCH_3$ | N |
| $SO_2CH_2CH_3$ | H | $CH_2CF_3$ | H | S | H | $CH_3$ | $OCH_3$ | N |
| $SO_2CH_2CH_3$ | $CH_2CH_2Cl$ | H | H | O | H | $OCH_3$ | $OCH_3$ | CH |
| $SO_2CH_2CH_3$ | $CH_2CH_2Cl$ | H | H | O | H | Cl | $OCH_3$ | CH |
| $SO_2CH_2CH_3$ | $CH_2CH_2Cl$ | H | H | O | H | $CH_3$ | $OCH_3$ | CH |
| $SO_2CH_2CH_3$ | $CH_2CH_2Cl$ | H | H | O | H | $CH_3$ | $CH_3$ | CH |
| $SO_2CH_2CH_3$ | $CH_2CH_2Cl$ | H | H | O | H | $OCH_3$ | $OCH_3$ | N |
| $SO_2CH_2CH_3$ | $CH_2CH_2Cl$ | H | H | O | H | $CH_3$ | $OCH_3$ | N |
| $SO_2CH_2CH_3$ | $CH_2CH_2Cl$ | H | H | O | H | $CH_3$ | $CH_3$ | N |
| $SO_2CH_2CH_3$ | $CH_2CH_2Cl$ | H | H | O | H | $OCH_2CH_3$ | $OCH_2CH_3$ | N |
| $SO_2CH_2CH_3$ | $CH_2CH_2Cl$ | H | H | O | H | $NHCH_3$ | $OCH_2CH_3$ | N |
| $SO_2CH_2CH_3$ | $CH_2CH_2Cl$ | H | H | O | H | $N(CH_3)_2$ | $OCH_2CH_3$ | N |
| $SO_2CH_2CH_3$ | $CH_2CH_2Cl$ | H | H | O | H | $N(CH_3)_2$ | $OCH_3$ | N |
| $SO_2CH_2CH_3$ | $CH_2CH_2Cl$ | H | H | O | H | $N(CH_3)_2$ | $OCH_2CF_3$ | N |
| $SO_2CH_2CH_3$ | $CH_2CH_2Cl$ | H | H | O | $CH_3$ | $CH_3$ | $OCH_3$ | N |

-continued

| | | | | | | | | |
|---|---|---|---|---|---|---|---|---|
| $SO_2CH_2CH_3$ | $CH_2CH_2Cl$ | H | H | S | H | $OCH_3$ | $OCH_3$ | CH |
| $SO_2CH_2CH_3$ | $CH_2CH_2Cl$ | H | H | S | H | Cl | $OCH_3$ | CH |
| $SO_2CH_2CH_3$ | $CH_2CH_2Cl$ | H | H | S | H | $CH_3$ | $OCH_3$ | CH |
| $SO_2CH_2CH_3$ | $CH_2CH_2Cl$ | H | H | S | H | $CH_3$ | $CH_3$ | CH |
| $SO_2CH_2CH_3$ | $CH_2CH_2Cl$ | H | H | S | H | $OCH_3$ | $OCH_3$ | N |
| $SO_2CH_2CH_3$ | $CH_2CH_2Cl$ | H | H | S | H | $CH_3$ | $OCH_3$ | N |
| $SO_2CH_2CH_3$ | $CH_2CN$ | H | H | O | H | $OCH_3$ | $OCH_3$ | CH |
| $SO_2CH_2CH_3$ | $CH_2CN$ | H | H | O | H | Cl | $OCH_3$ | CH |
| $SO_2CH_2CH_3$ | $CH_2CN$ | H | H | O | H | $CH_3$ | $OCH_3$ | CH |
| $SO_2CH_2CH_3$ | $CH_2CN$ | H | H | O | H | $CH_3$ | $CH_3$ | CH |
| $SO_2CH_2CH_3$ | $CH_2CN$ | H | H | O | H | $OCH_3$ | $OCH_3$ | N |
| $SO_2CH_2CH_3$ | $CH_2CN$ | H | H | O | H | $CH_3$ | $OCH_3$ | N |
| $SO_2CH_2CH_3$ | $CH_2CN$ | H | H | O | H | $CH_3$ | $CH_3$ | N |
| $SO_2CH_2CH_3$ | $CH_2CN$ | H | H | O | H | $OCH_2CH_3$ | $OCH_2CH_3$ | N |
| $SO_2CH_2CH_3$ | $CH_2CN$ | H | H | O | H | $NHCH_3$ | $OCH_2CH_3$ | N |
| $SO_2CH_2CH_3$ | $CH_2CN$ | H | H | O | H | $N(CH_3)_2$ | $OCH_2CH_3$ | N |
| $SO_2CH_2CH_3$ | $CH_2CN$ | H | H | O | H | $N(CH_3)_2$ | $OCH_3$ | N |
| $SO_2CH_2CH_3$ | $CH_2CN$ | H | H | O | H | $N(CH_3)_2$ | $OCH_2CF_3$ | N |
| $SO_2CH_2CH_3$ | $CH_2CN$ | H | H | O | $CH_3$ | $CH_3$ | $OCH_3$ | N |
| $SO_2CH_2CH_3$ | $CH_2CN$ | H | H | S | H | $OCH_3$ | $OCH_3$ | CH |
| $SO_2CH_2CH_3$ | $CH_2CN$ | H | H | S | H | Cl | $OCH_3$ | CH |
| $SO_2CH_2CH_3$ | $CH_2CN$ | H | H | S | H | $CH_3$ | $OCH_3$ | CH |
| $SO_2CH_2CH_3$ | $CH_2CN$ | H | H | S | H | $CH_3$ | $CH_3$ | CH |
| $SO_2CH_2CH_3$ | CH CN | H | H | S | H | $OCH_3$ | $OCH_3$ | N |
| $SO_2CH_2CH_3$ | $CH_2CN$ | H | H | S | H | $CH_3$ | $OCH_3$ | N |
| $SO_2CH_2CH_3$ | $CH_2CH{=}CH_2$ | H | H | O | H | $OCH_3$ | $OCH_3$ | CH |
| $SO_2CH_2CH_3$ | $CH_2CH{=}CH_2$ | H | H | O | H | Cl | $OCH_3$ | CH |
| $SO_2CH_2CH_3$ | $CH_2CH{=}CH_2$ | H | H | O | H | $CH_3$ | $OCH_3$ | CH |
| $SO_2CH_2CH_3$ | $CH_2CH{=}CH_2$ | H | H | O | H | $CH_3$ | $CH_3$ | CH |
| $SO_2CH_2CH_3$ | $CH_2CH{=}CH_2$ | H | H | O | H | $OCH_3$ | $OCH_3$ | N |
| $SO_2CH_2CH_3$ | $CH_2CH{=}CH_2$ | H | H | O | H | $CH_3$ | $OCH_3$ | N |
| $SO_2CH_2CH_3$ | $CH_2CH{=}CH_2$ | H | H | O | H | $CH_3$ | $CH_3$ | N |
| $SO_2CH_2CH_3$ | $CH_2CH{=}CH_2$ | H | H | O | H | $OCH_2CH_3$ | $OCH_2CH_3$ | N |
| $SO_2CH_2CH_3$ | $CH_2CH{=}CH_2$ | H | H | O | H | $NHCH_3$ | $OCH_2CH_3$ | N |
| $SO_2CH_2CH_3$ | $CH_2CH{=}CH_2$ | H | H | O | H | $N(CH_3)_2$ | $OCH_2CH_3$ | N |
| $SO_2CH_2CH_3$ | $CH_2CH{=}CH_2$ | H | H | O | H | $N(CH_3)_2$ | $OCH_3$ | N |
| $SO_2CH_2CH_3$ | $CH_2CH{=}CH_2$ | H | H | O | H | $N(CH_3)_2$ | $OCH_2CF_3$ | N |
| $SO_2CH_2CH_3$ | $CH_2CH{=}CH_2$ | H | H | O | $CH_3$ | $CH_3$ | $OCH_3$ | N |
| $SO_2CH_2CH_3$ | $CH_2CH{=}CH_2$ | H | H | S | H | $OCH_3$ | $OCH_3$ | CH |
| $SO_2CH_2CH_3$ | $CH_2CH{=}CH_2$ | H | H | S | H | Cl | $OCH_3$ | CH |
| $SO_2CH_2CH_3$ | $CH_2CH{=}CH_2$ | H | H | S | H | $CH_3$ | $OCH_3$ | CH |
| $SO_2CH_2CH_3$ | $CH_2CH{=}CH_2$ | H | H | S | H | $CH_3$ | $CH_3$ | CH |
| $SO_2CH_2CH_3$ | $CH_2CH{=}CH_2$ | H | H | S | H | $OCH_3$ | $OCH_3$ | N |
| $SO_2CH_2CH_3$ | $CH_2CH{=}CH_2$ | H | H | S | H | $CH_3$ | $OCH_3$ | N |
| $SO_2CH_2CH_3$ | $CH_2C{\equiv}CH$ | H | H | O | H | $OCH_3$ | $OCH_3$ | CH |
| $SO_2CH_2CH_3$ | $CH_2C{\equiv}CH$ | H | H | O | H | Cl | $OCH_3$ | CH |
| $SO_2CH_2CH_3$ | $CH_2C{\equiv}CH$ | H | H | O | H | $CH_3$ | $OCH_3$ | CH |
| $SO_2CH_2CH_3$ | $CH_2C{\equiv}CH$ | H | H | O | H | $CH_3$ | $CH_3$ | CH |
| $SO_2CH_2CH_3$ | $CH_2C{\equiv}CH$ | H | H | O | H | $OCH_3$ | $OCH_3$ | N |
| $SO_2CH_2CH_3$ | $CH_2C{\equiv}CH$ | H | H | O | H | $CH_3$ | $OCH_3$ | N |
| $SO_2CH_2CH_3$ | $CH_2C{\equiv}CH$ | H | H | O | H | $CH_3$ | $CH_3$ | N |
| $SO_2CH_2CH_3$ | $CH_2C{\equiv}CH$ | H | H | O | H | $OCH_2CH_3$ | $OCH_2CH_3$ | N |
| $SO_2CH_2CH_3$ | $CH_2C{\equiv}CH$ | H | H | O | H | $NHCH_3$ | $OCH_2CH_3$ | N |
| $SO_2CH_2CH_3$ | $CH_2C{\equiv}CH$ | H | H | O | H | $N(CH_3)_2$ | $OCH_2CH_3$ | N |
| $SO_2CH_2CH_3$ | $CH_2C{\equiv}CH$ | H | H | O | H | $N(CH_3)_2$ | $OCH_3$ | N |
| $SO_2CH_2CH_3$ | $CH_2C{\equiv}CH$ | H | H | O | H | $N(CH_3)_2$ | $OCH_2CF_3$ | N |
| $SO_2CH_2CH_3$ | $CH_2C{\equiv}CH$ | H | H | O | $CH_3$ | $CH_3$ | $OCH_3$ | N |
| $SO_2CH_2CH_3$ | $CH_2C{\equiv}CH$ | H | H | S | H | $OCH_3$ | $OCH_3$ | CH |
| $SO_2CH_2CH_3$ | $CH_2C{\equiv}CH$ | H | H | S | H | Cl | $OCH_3$ | CH |
| $SO_2CH_2CH_3$ | $CH_2C{\equiv}CH$ | H | H | S | H | $CH_3$ | $OCH_3$ | CH |
| $SO_2CH_2CH_3$ | $CH_2C{\equiv}CH$ | H | H | S | H | $CH_3$ | $CH_3$ | CH |
| $SO_2CH_2CH_3$ | $CH_2C{\equiv}CH$ | H | H | S | H | $OCH_3$ | $OCH_3$ | N |
| $SO_2CH_2CH_3$ | $CH_2C{\equiv}CH$ | H | H | S | H | $CH_3$ | $OCH_3$ | N |
| $SO_2CH_2CH_3$ | $CH_2CH_2OCH_3$ | H | H | O | H | $OCH_3$ | $OCH_3$ | CH |
| $SO_2CH_2CH_3$ | $CH_2CH_2OCH_3$ | H | H | O | H | Cl | $OCH_3$ | CH |
| $SO_2CH_2CH_3$ | $CH_2CH_2OCH_3$ | H | H | O | H | $CH_3$ | $OCH_3$ | CH |
| $SO_2CH_2CH_3$ | $CH_2CH_2OCH_3$ | H | H | O | H | $CH_3$ | $CH_3$ | CH |
| $SO_2CH_2CH_3$ | $CH_2CH_2OCH_3$ | H | H | O | H | $OCH_3$ | $OCH_3$ | N |
| $SO_2CH_2CH_3$ | $CH_2CH_2OCH_3$ | H | H | O | H | $CH_3$ | $OCH_3$ | N |
| $SO_2CH_2CH_3$ | $CH_2CH_2OCH_3$ | H | H | O | H | $CH_3$ | $CH_3$ | N |
| $SO_2CH_2CH_3$ | $CH_2CH_2OCH_3$ | H | H | O | H | $OCH_2CH_3$ | $OCH_2CH_3$ | N |
| $SO_2CH_2CH_3$ | $CH_2CH_2OCH_3$ | H | H | O | H | $NHCH_3$ | $OCH_2CH_3$ | N |
| $SO_2CH_2CH_3$ | $CH_2CH_2OCH_3$ | H | H | O | H | $N(CH_3)_2$ | $OCH_2CH_3$ | N |
| $SO_2CH_2CH_3$ | $CH_2CH_2OCH_3$ | H | H | O | H | $N(CH_3)_2$ | $OCH_3$ | N |
| $SO_2CH_2CH_3$ | $CH_2CH_2OCH_3$ | H | H | O | H | $N(CH_3)_2$ | $OCH_2CF_3$ | N |
| $SO_2CH_2CH_3$ | $CH_2CH_2OCH_3$ | H | H | O | $CH_3$ | $CH_3$ | $OCH_3$ | N |
| $SO_2CH_2CH_3$ | $CH_2CH_2OCH_3$ | H | H | S | H | $OCH_3$ | $OCH_3$ | CH |
| $SO_2CH_2CH_3$ | $CH_2CH_2OCH_3$ | H | H | S | H | Cl | $OCH_3$ | CH |

-continued

| | | | | | | | | |
|---|---|---|---|---|---|---|---|---|
| $SO_2CH_2CH_3$ | $CH_2CH_2OCH_3$ | H | H | S | H | $CH_3$ | $OCH_3$ | CH |
| $SO_2CH_2CH_3$ | $CH_2CH_2OCH_3$ | H | H | S | H | $CH_3$ | $CH_3$ | CH |
| $SO_2CH_2CH_3$ | $CH_2CH_2OCH_3$ | H | H | S | H | $OCH_3$ | $OCH_3$ | N |
| $SO_2CH_2CH_3$ | $CH_2CH_2OCH_3$ | H | H | S | H | $CH_3$ | $OCH_3$ | N |
| $SO_2CH_2CH_3$ | cyclo-$C_3H_7$ | H | H | O | H | $OCH_3$ | $OCH_3$ | CH |
| $SO_2CH_2CH_3$ | cyclo-$C_3H_7$ | H | H | O | H | Cl | $OCH_3$ | CH |
| $SO_2CH_2CH_3$ | cyclo-$C_3H_7$ | H | H | O | H | $CH_3$ | $OCH_3$ | CH |
| $SO_2CH_2CH_3$ | cyclo-$C_3H_7$ | H | H | O | H | $CH_3$ | $CH_3$ | CH |
| $SO_2CH_2CH_3$ | cyclo-$C_3H_7$ | H | H | O | H | $OCH_3$ | $OCH_3$ | N |
| $SO_2CH_2CH_3$ | cyclo-$C_3H_7$ | H | H | O | H | $CH_3$ | $OCH_3$ | N |
| $SO_2CH_2CH_3$ | cyclo-$C_3H_7$ | H | H | O | H | $CH_3$ | $CH_3$ | N |
| $SO_2CH_2CH_3$ | cyclo-$C_3H_7$ | H | H | O | H | $OCH_2CH_3$ | $OCH_2CH_3$ | N |
| $SO_2CH_2CH_3$ | cyclo-$C_3H_7$ | H | H | O | H | $NHCH_3$ | $OCH_2CH_3$ | N |
| $SO_2CH_2CH_3$ | cyclo-$C_3H_7$ | H | H | O | H | $N(CH_3)_2$ | $OCH_2CH_3$ | N |
| $SO_2CH_2CH_3$ | cyclo-$C_3H_7$ | H | H | O | H | $N(CH_3)_2$ | $OCH_3$ | N |
| $SO_2CH_2CH_3$ | cyclo-$C_3H_7$ | H | H | O | H | $N(CH_3)_2$ | $OCH_2CF_3$ | N |
| $SO_2CH_2CH_3$ | cyclo-$C_3H_7$ | H | H | O | $CH_3$ | $CH_3$ | $OCH_3$ | N |
| $SO_2CH_2CH_3$ | cyclo-$C_3H_7$ | H | H | S | H | $OCH_3$ | $OCH_3$ | CH |
| $SO_2CH_2CH_3$ | cyclo-$C_3H_7$ | H | H | S | H | Cl | $OCH_3$ | CH |
| $SO_2CH_2CH_3$ | cyclo-$C_3H_7$ | H | H | S | H | $CH_3$ | $OCH_3$ | CH |
| $SO_2CH_2CH_3$ | cyclo-$C_3H_7$ | H | H | S | H | $CH_3$ | $CH_3$ | CH |
| $SO_2CH_2CH_3$ | cyclo-$C_3H_7$ | H | H | S | H | $OCH_3$ | $OCH_3$ | N |
| $SO_2CH_2CH_3$ | cyclo-$C_3H_7$ | H | H | S | H | $CH_3$ | $OCH_3$ | N |
| $SO_2CH_2CH_3$ | $CH_3$ | $CH_3$ | H | O | H | $OCH_3$ | $OCH_3$ | CH |
| $SO_2CH_2CH_3$ | $CH_3$ | $CH_3$ | H | O | H | Cl | $OCH_3$ | CH |
| $SO_2CH_2CH_3$ | $CH_3$ | $CH_3$ | H | O | H | $CH_3$ | $OCH_3$ | CH |
| $SO_2CH_2CH_3$ | $CH_3$ | $CH_3$ | H | O | H | $CH_3$ | $CH_3$ | CH |
| $SO_2CH_2CH_3$ | $CH_3$ | $CH_3$ | H | O | H | $OCH_3$ | $OCH_3$ | N |
| $SO_2CH_2CH_3$ | $CH_3$ | $CH_3$ | H | O | H | $CH_3$ | $OCH_3$ | N |
| $SO_2CH_2CH_3$ | $CH_3$ | $CH_3$ | H | O | H | $CH_3$ | $CH_3$ | N |
| $SO_2CH_2CH_3$ | $CH_3$ | $CH_3$ | H | O | H | $OCH_2CH_3$ | $OCH_2CH_3$ | N |
| $SO_2CH_2CH_3$ | $CH_3$ | $CH_3$ | H | O | H | $NHCH_3$ | $OCH_2CH_3$ | N |
| $SO_2CH_2CH_3$ | $CH_3$ | $CH_3$ | H | O | H | $N(CH_3)_2$ | $OCH_2CH_3$ | N |
| $SO_2CH_2CH_3$ | $CH_3$ | $CH_3$ | H | O | H | $N(CH_3)_2$ | $OCH_3$ | N |
| $SO_2CH_2CH_3$ | $CH_3$ | $CH_3$ | H | O | H | $N(CH_3)_2$ | $OCH_2CF_3$ | N |
| $SO_2CH_2CH_3$ | $CH_3$ | $CH_3$ | H | O | $CH_3$ | $CH_3$ | $OCH_3$ | N |
| $SO_2CH_2CH_3$ | $CH_3$ | $CH_3$ | H | S | H | $OCH_3$ | $OCH_3$ | CH |
| $SO_2CH_2CH_3$ | $CH_3$ | $CH_3$ | H | S | H | Cl | $OCH_3$ | CH |
| $SO_2CH_2CH_3$ | $CH_3$ | $CH_3$ | H | S | H | $CH_3$ | $OCH_3$ | CH |
| $SO_2CH_2CH_3$ | $CH_3$ | $CH_3$ | H | S | H | $CH_3$ | $CH_3$ | CH |
| $SO_2CH_2CH_3$ | $CH_3$ | $CH_3$ | H | S | H | $OCH_3$ | $OCH_3$ | N |
| $SO_2CH_2CH_3$ | $CH_3$ | $CH_3$ | H | S | H | $CH_3$ | $OCH_3$ | N |
| $SO_2CH_2CH_3$ | $CH_3$ | $CH_2CH_3$ | H | O | H | $OCH_3$ | $OCH_3$ | CH |
| $SO_2CH_2CH_3$ | $CH_3$ | $CH_2CH_3$ | H | O | H | Cl | $OCH_3$ | CH |
| $SO_2CH_2CH_3$ | $CH_3$ | $CH_2CH_3$ | H | O | H | $CH_3$ | $OCH_3$ | CH |
| $SO_2CH_2CH_3$ | $CH_3$ | $CH_2CH_3$ | H | O | H | $CH_3$ | $CH_3$ | CH |
| $SO_2CH_2CH_3$ | $CH_3$ | $CH_2CH_3$ | H | O | H | $OCH_3$ | $OCH_3$ | N |
| $SO_2CH_2CH_3$ | $CH_3$ | $CH_2CH_3$ | H | O | H | $CH_3$ | $OCH_3$ | N |
| $SO_2CH_2CH_3$ | $CH_3$ | $CH_2CH_3$ | H | O | H | $CH_3$ | $CH_3$ | N |
| $SO_2CH_2CH_3$ | $CH_3$ | $CH_2CH_3$ | H | O | H | $OCH_2CH_3$ | $OCH_2CH_3$ | N |
| $SO_2CH_2CH_3$ | $CH_3$ | $CH_2CH_3$ | H | O | H | $NHCH_3$ | $OCH_2CH_3$ | N |
| $SO_2CH_2CH_3$ | $CH_3$ | $CH_2CH_3$ | H | O | H | $N(CH_3)_2$ | $OCH_2CH_3$ | N |
| $SO_2CH_2CH_3$ | $CH_3$ | $CH_2CH_3$ | H | O | H | $N(CH_3)_2$ | $OCH_3$ | N |
| $SO_2CH_2CH_3$ | $CH_3$ | $CH_2CH_3$ | H | O | H | $N(CH_3)_2$ | $OCH_2CF_3$ | N |
| $SO_2CH_2CH_3$ | $CH_3$ | $CH_2CH_3$ | H | O | $CH_3$ | $CH_3$ | $OCH_3$ | N |
| $SO_2CH_2CH_3$ | $CH_3$ | $CH_2CH_3$ | H | S | H | $OCH_3$ | $OCH_3$ | CH |
| $SO_2CH_2CH_3$ | $CH_3$ | $CH_2CH_3$ | H | S | H | Cl | $OCH_3$ | CH |
| $SO_2CH_2CH_3$ | $CH_3$ | $CH_2CH_3$ | H | S | H | $CH_3$ | $OCH_3$ | CH |
| $SO_2CH_2CH_3$ | $CH_3$ | $CH_2CH_3$ | H | S | H | $CH_3$ | $CH_3$ | CH |
| $SO_2CH_2CH_3$ | $CH_3$ | $CH_2CH_3$ | H | S | H | $OCH_3$ | $OCH_3$ | N |
| $SO_2CH_2CH_3$ | $CH_3$ | $CH_2CH_3$ | H | S | H | $CH_3$ | $OCH_3$ | N |
| $SO_2CH_2CH_3$ | $CH_2CH_3$ | $CH_2CH_3$ | H | O | H | $OCH_3$ | $OCH_3$ | CH |
| $SO_2CH_2CH_3$ | $CH_2CH_3$ | $CH_2CH_3$ | H | O | H | Cl | $OCH_3$ | CH |
| $SO_2CH_2CH_3$ | $CH_2CH_3$ | $CH_2CH_3$ | H | O | H | $CH_3$ | $OCH_3$ | CH |
| $SO_2CH_2CH_3$ | $CH_2CH_3$ | $CH_2CH_3$ | H | O | H | $CH_3$ | $CH_3$ | CH |
| $SO_2CH_2CH_3$ | $CH_2CH_3$ | $CH_2CH_3$ | H | O | H | $OCH_3$ | $OCH_3$ | N |
| $SO_2CH_2CH_3$ | $CH_2CH_3$ | $CH_2CH_3$ | H | O | H | $CH_3$ | $OCH_3$ | N |
| $SO_2CH_2CH_3$ | $CH_2CH_3$ | $CH_2CH_3$ | H | O | H | $CH_3$ | $CH_3$ | N |
| $SO_2CH_2CH_3$ | $CH_2CH_3$ | $CH_2CH_3$ | H | O | H | $OCH_2CH_3$ | $OCH_2CH_3$ | N |
| $SO_2CH_2CH_3$ | $CH_2CH_3$ | $CH_2CH_3$ | H | O | H | $NHCH_3$ | $OCH_2CH_3$ | N |
| $SO_2CH_2CH_3$ | $CH_2CH_3$ | $CH_2CH_3$ | H | O | H | $N(CH_3)_2$ | $OCH_2CH_3$ | N |
| $SO_2CH_2CH_3$ | $CH_2CH_3$ | $CH_2CH_3$ | H | O | H | $N(CH_3)_2$ | $OCH_3$ | N |
| $SO_2CH_2CH_3$ | $CH_2CH_3$ | $CH_2CH_3$ | H | O | H | $N(CH_3)_2$ | $OCH_2CF_3$ | N |
| $SO_2CH_2CH_3$ | $CH_2CH_3$ | $CH_2CH_3$ | H | O | $CH_3$ | $CH_3$ | $OCH_3$ | N |
| $SO_2CH_2CH_3$ | $CH_2CH_3$ | $CH_2CH_3$ | H | S | H | $OCH_3$ | $OCH_3$ | CH |
| $SO_2CH_2CH_3$ | $CH_2CH_3$ | $CH_2CH_3$ | H | S | H | Cl | $OCH_3$ | CH |
| $SO_2CH_2CH_3$ | $CH_2CH_3$ | $CH_2CH_3$ | H | S | H | $CH_3$ | $OCH_3$ | CH |
| $SO_2CH_2CH_3$ | $CH_2CH_3$ | $CH_2CH_3$ | H | S | H | $CH_3$ | $CH_3$ | CH |
| $SO_2CH_2CH_3$ | $CH_2CH_3$ | $CH_2CH_3$ | H | S | H | $OCH_3$ | $OCH_3$ | N |
| $SO_2CH_2CH_3$ | $CH_2CH_3$ | $CH_2CH_3$ | H | S | H | $CH_3$ | $OCH_3$ | N |
| $SO_2CH_2CH_3$ | $OCH_3$ | $CH_3$ | H | O | H | $OCH_3$ | $OCH_3$ | CH |
| $SO_2CH_2CH_3$ | $OCH_3$ | $CH_3$ | H | O | H | Cl | $OCH_3$ | CH |

-continued

| | | | | | | | | |
|---|---|---|---|---|---|---|---|---|
| $SO_2CH_2CH_3$ | $OCH_3$ | $CH_3$ | H | O | H | $CH_3$ | $OCH_3$ | CH |
| $SO_2CH_2CH_3$ | $OCH_3$ | $CH_3$ | H | O | H | $CH_3$ | $CH_3$ | CH |
| $SO_2CH_2CH_3$ | $OCH_3$ | $CH_3$ | H | O | H | $OCH_3$ | $OCH_3$ | N |
| $SO_2CH_2CH_3$ | $OCH_3$ | $CH_3$ | H | O | H | $CH_3$ | $OCH_3$ | N |
| $SO_2CH_2CH_3$ | $OCH_3$ | $CH_3$ | H | O | H | $CH_3$ | $CH_3$ | N |
| $SO_2CH_2CH_3$ | $OCH_3$ | $CH_3$ | H | O | H | $OCH_2CH_3$ | $OCH_2CH_3$ | N |
| $SO_2CH_2CH_3$ | $OCH_3$ | $CH_3$ | H | O | H | $NHCH_3$ | $OCH_2CH_3$ | N |
| $SO_2CH_2CH_3$ | $OCH_3$ | $CH_3$ | H | O | H | $N(CH_3)_2$ | $OCH_2CH_3$ | N |
| $SO_2CH_2CH_3$ | $OCH_3$ | $CH_3$ | H | O | H | $N(CH_3)_2$ | $OCH_3$ | N |
| $SO_2CH_2CH_3$ | $OCH_3$ | $CH_3$ | H | O | H | $N(CH_3)_2$ | $OCH_2CF_3$ | N |
| $SO_2CH_2CH_3$ | $OCH_3$ | $CH_3$ | H | O | $CH_3$ | $CH_3$ | $OCH_3$ | N |
| $SO_2CH_2CH_3$ | $OCH_3$ | $CH_3$ | H | S | H | $OCH_3$ | $OCH_3$ | CH |
| $SO_2CH_2CH_3$ | $OCH_3$ | $CH_3$ | H | S | H | Cl | $OCH_3$ | CH |
| $SO_2CH_2CH_3$ | $OCH_3$ | $CH_3$ | H | S | H | $CH_3$ | $OCH_3$ | CH |
| $SO_2CH_2CH_3$ | $OCH_3$ | $CH_3$ | H | S | H | $CH_3$ | $CH_3$ | CH |
| $SO_2CH_2CH_3$ | $OCH_3$ | $CH_3$ | H | S | H | $OCH_3$ | $OCH_3$ | N |
| $SO_2CH_2CH_3$ | $OCH_3$ | $CH_3$ | H | S | H | $CH_3$ | $OCH_3$ | N |
| $SO_2CH_2CH_3$ | $NHCH_3$ | $CH_3$ | H | O | H | $OCH_3$ | $OCH_3$ | CH |
| $SO_2CH_2CH_3$ | $NHCH_3$ | $CH_3$ | H | O | H | Cl | $OCH_3$ | CH |
| $SO_2CH_2CH_3$ | $NHCH_3$ | $CH_3$ | H | O | H | $CH_3$ | $OCH_3$ | CH |
| $SO_2CH_2CH_3$ | $NHCH_3$ | $CH_3$ | H | O | H | $CH_3$ | $CH_3$ | CH |
| $SO_2CH_2CH_3$ | $NHCH_3$ | $CH_3$ | H | O | H | $OCH_3$ | $OCH_3$ | N |
| $SO_2CH_2CH_3$ | $NHCH_3$ | $CH_3$ | H | O | H | $CH_3$ | $OCH_3$ | N |
| $SO_2CH_2CH_3$ | $NHCH_3$ | $CH_3$ | H | O | H | $CH_3$ | $CH_3$ | N |
| $SO_2CH_2CH_3$ | $NHCH_3$ | $CH_3$ | H | O | H | $OCH_2CH_3$ | $OCH_2CH_3$ | N |
| $SO_2CH_2CH_3$ | $NHCH_3$ | $CH_3$ | H | O | H | $NHCH_3$ | $OCH_2CH_3$ | N |
| $SO_2CH_2CH_3$ | $NHCH_3$ | $CH_3$ | H | O | H | $N(CH_3)_2$ | $OCH_2CH_3$ | N |
| $SO_2CH_2CH_3$ | $NHCH_3$ | $CH_3$ | H | O | H | $N(CH_3)_2$ | $OCH_3$ | N |
| $SO_2CH_2CH_3$ | $NHCH_3$ | $CH_3$ | H | O | H | $N(CH_3)_2$ | $OCH_2CF_3$ | N |
| $SO_2CH_2CH_3$ | $NHCH_3$ | $CH_3$ | H | O | $CH_3$ | $CH_3$ | $OCH_3$ | N |
| $SO_2CH_2CH_3$ | $NHCH_3$ | $CH_3$ | H | S | H | $OCH_3$ | $OCH_3$ | CH |
| $SO_2CH_2CH_3$ | $NHCH_3$ | $CH_3$ | H | S | H | Cl | $OCH_3$ | CH |
| $SO_2CH_2CH_3$ | $NHCH_3$ | $CH_3$ | H | S | H | $CH_3$ | $OCH_3$ | CH |
| $SO_2CH_2CH_3$ | $NHCH_3$ | $CH_3$ | H | S | H | $CH_3$ | $CH_3$ | CH |
| $SO_2CH_2CH_3$ | $NHCH_3$ | $CH_3$ | H | S | H | $OCH_3$ | $OCH_3$ | N |
| $SO_2CH_2CH_3$ | $NHCH_3$ | $CH_3$ | H | S | H | $CH_3$ | $OCH_3$ | N |
| $SO_2CH_2CH_3$ | $N(CH_3)_2$ | $CH_3$ | H | O | H | $OCH_3$ | $OCH_3$ | CH |
| $SO_2CH_2CH_3$ | $N(CH_3)_2$ | $CH_3$ | H | O | H | Cl | $OCH_3$ | CH |
| $SO_2CH_2CH_3$ | $N(CH_3)_2$ | $CH_3$ | H | O | H | $CH_3$ | $OCH_3$ | CH |
| $SO_2CH_2CH_3$ | $N(CH_3)_2$ | $CH_3$ | H | O | H | $CH_3$ | $CH_3$ | CH |
| $SO_2CH_2CH_3$ | $N(CH_3)_2$ | $CH_3$ | H | O | H | $OCH_3$ | $OCH_3$ | N |
| $SO_2CH_2CH_3$ | $N(CH_3)_2$ | $CH_3$ | H | O | H | $CH_3$ | $OCH_3$ | N |
| $SO_2CH_2CH_3$ | $N(CH_3)_2$ | $CH_3$ | H | O | H | $CH_3$ | $CH_3$ | N |
| $SO_2CH_2CH_3$ | $N(CH_3)_2$ | $CH_3$ | H | O | H | $OCH_2CH_3$ | $OCH_2CH_3$ | N |
| $SO_2CH_2CH_3$ | $N(CH_3)_2$ | $CH_3$ | H | O | H | $NHCH_3$ | $OCH_2CH_3$ | N |
| $SO_2CH_2CH_3$ | $N(CH_3)_2$ | $CH_3$ | H | O | H | $N(CH_3)_2$ | $OCH_2CH_3$ | N |
| $SO_2CH_2CH_3$ | $N(CH_3)_2$ | $CH_3$ | H | O | H | $N(CH_3)_2$ | $OCH_3$ | N |
| $SO_2CH_2CH_3$ | $N(CH_3)_2$ | $CH_3$ | H | O | H | $N(CH_3)_2$ | $OCH_2CF_3$ | N |
| $SO_2CH_2CH_3$ | $N(CH_3)_2$ | $CH_3$ | H | O | $CH_3$ | $CH_3$ | $OCH_3$ | N |
| $SO_2CH_2CH_3$ | $N(CH_3)_2$ | $CH_3$ | H | S | H | $OCH_3$ | $OCH_3$ | CH |
| $SO_2CH_2CH_3$ | $N(CH_3)_2$ | $CH_3$ | H | S | H | Cl | $OCH_3$ | CH |
| $SO_2CH_2CH_3$ | $N(CH_3)_2$ | $CH_3$ | H | S | H | $CH_3$ | $OCH_3$ | CH |
| $SO_2CH_2CH_3$ | $N(CH_3)_2$ | $CH_3$ | H | S | H | $CH_3$ | $CH_3$ | CH |
| $SO_2CH_2CH_3$ | $N(CH_3)_2$ | $CH_3$ | H | S | H | $OCH_3$ | $OCH_3$ | N |
| $SO_2CH_2CH_3$ | $N(CH_3)_2$ | $CH_3$ | H | S | H | $CH_3$ | $OCH_3$ | N |
| $SO_2CH_2CH_3$ | $—CH_2CH_2CH_2—$ | | H | O | H | $OCH_3$ | $OCH_3$ | CH |
| $SO_2CH_2CH_3$ | $—CH_2CH_2CH_2—$ | | H | O | H | Cl | $OCH_3$ | CH |
| $SO_2CH_2CH_3$ | $—CH_2CH_2CH_2—$ | | H | O | H | $CH_3$ | $OCH_3$ | CH |
| $SO_2CH_2CH_3$ | $—CH_2CH_2CH_2—$ | | H | O | H | $CH_3$ | $CH_3$ | CH |
| $SO_2CH_2CH_3$ | $—CH_2CH_2CH_2—$ | | H | O | H | $OCH_3$ | $OCH_3$ | N |
| $SO_2CH_2CH_3$ | $—CH_2CH_2CH_2—$ | | H | O | H | $CH_3$ | $OCH_3$ | N |
| $SO_2CH_2CH_3$ | $—CH_2CH_2CH_2—$ | | H | O | H | $CH_3$ | $CH_3$ | N |
| $SO_2CH_2CH_3$ | $—CH_2CH_2CH_2—$ | | H | O | H | $OCH_2CH_3$ | $OCH_2CH_3$ | N |
| $SO_2CH_2CH_3$ | $—CH_2CH_2CH_2—$ | | H | O | H | $NHCH_3$ | $OCH_2CH_3$ | N |
| $SO_2CH_2CH_3$ | $—CH_2CH_2CH_2—$ | | H | O | H | $N(CH_3)_2$ | $OCH_2CH_3$ | N |
| $SO_2CH_2CH_3$ | $—CH_2CH_2CH_2—$ | | H | O | H | $N(CH_3)_2$ | $OCH_3$ | N |
| $SO_2CH_2CH_3$ | $—CH_2CH_2CH_2—$ | | H | O | H | $N(CH_3)_2$ | $OCH_2CF_3$ | N |
| $SO_2CH_2CH_3$ | $—CH_2CH_2CH_2—$ | | H | O | $CH_3$ | $CH_3$ | $OCH_3$ | N |
| $SO_2CH_2CH_3$ | $—CH_2CH_2CH_2—$ | | H | S | H | $OCH_3$ | $OCH_3$ | CH |
| $SO_2CH_2CH_3$ | $—CH_2CH_2CH_2—$ | | H | S | H | Cl | $OCH_3$ | CH |
| $SO_2CH_2CH_3$ | $—CH_2CH_2CH_2—$ | | H | S | H | $CH_3$ | $OCH_3$ | CH |
| $SO_2CH_2CH_3$ | $—CH_2CH_2CH_2—$ | | H | S | H | $CH_3$ | $CH_3$ | CH |
| $SO_2CH_2CH_3$ | $—CH_2CH_2CH_2—$ | | H | S | H | $OCH_3$ | $OCH_3$ | N |
| $SO_2CH_2CH_3$ | $—CH_2CH_2CH_2—$ | | H | S | H | $CH_3$ | $OCH_3$ | N |
| $SO_2CH_2CH_3$ | $—CH_2CH_2OCH_2CH_2—$ | | H | O | H | $OCH_3$ | $OCH_3$ | CH |
| $SO_2CH_2CH_3$ | $—CH_2CH_2OCH_2CH_2—$ | | H | O | H | Cl | $OCH_3$ | CH |
| $SO_2CH_2CH_3$ | $—CH_2CH_2OCH_2CH_2—$ | | H | O | H | $CH_3$ | $OCH_3$ | CH |
| $SO_2CH_2CH_3$ | $—CH_2CH_2OCH_2CH_2—$ | | H | O | H | $CH_3$ | $CH_3$ | CH |
| $SO_2CH_2CH_3$ | $—CH_2CH_2OCH_2CH_2—$ | | H | O | H | $OCH_3$ | $OCH_3$ | N |
| $SO_2CH_2CH_3$ | $—CH_2CH_2OCH_2CH_2—$ | | H | O | H | $CH_3$ | $OCH_3$ | N |
| $SO_2CH_2CH_3$ | $—CH_2CH_2OCH_2CH_2—$ | | H | O | H | $CH_3$ | $CH_3$ | N |
| $SO_2CH_2CH_3$ | $—CH_2CH_2OCH_2CH_2—$ | | H | O | H | $OCH_2CH_3$ | $OCH_2CH_3$ | N |

-continued

| | | | | | | | | |
|---|---|---|---|---|---|---|---|---|
| $SO_2CH_2CH_3$ | $-CH_2CH_2OCH_2CH_2-$ | | H | O | H | $NHCH_3$ | $OCH_2CH_3$ | N |
| $SO_2CH_2CH_3$ | $-CH_2CH_2OCH_2CH_2-$ | | H | O | H | $N(CH_3)_2$ | $OCH_2CH_3$ | N |
| $SO_2CH_2CH_3$ | $-CH_2CH_2OCH_2CH_2-$ | | H | O | H | $N(CH_3)_2$ | $OCH_3$ | N |
| $SO_2CH_2CH_3$ | $-CH_2CH_2OCH_2CH_2-$ | | H | O | H | $N(CH_3)_2$ | $OCH_2CF_3$ | N |
| $SO_2CH_2CH_3$ | $-CH_2CH_2OCH_2CH_2-$ | | H | O | $CH_3$ | $CH_3$ | $OCH_3$ | N |
| $SO_2CH_2CH_3$ | $-CH_2CH_2OCH_2CH_2-$ | | H | S | H | $OCH_3$ | $OCH_3$ | CH |
| $SO_2CH_2CH_3$ | $-CH_2CH_2OCH_2CH_2-$ | | H | S | H | Cl | $OCH_3$ | CH |
| $SO_2CH_2CH_3$ | $-CH_2CH_2OCH_2CH_2-$ | | H | S | H | $CH_3$ | $OCH_3$ | CH |
| $SO_2CH_2CH_3$ | $-CH_2CH_2OCH_2CH_2-$ | | H | S | H | $CH_3$ | $CH_3$ | CH |
| $SO_2CH_2CH_3$ | $-CH_2CH_2OCH_2CH_2-$ | | H | S | H | $OCH_3$ | $OCH_3$ | N |
| $SO_2CH_2CH_3$ | $-CH_2CH_2OCH_2CH_2-$ | | H | S | H | $CH_3$ | $OCH_3$ | N |
| Br | $CH_3$ | H | H | O | H | $OCH_3$ | $OCH_3$ | CH |
| Br | $CH_3$ | H | H | O | H | Cl | $OCH_3$ | CH |
| Br | $CH_3$ | H | H | O | H | $CH_3$ | $OCH_3$ | CH |
| Br | $CH_3$ | H | H | O | H | $CH_3$ | $CH_3$ | CH |
| Br | $CH_3$ | H | H | O | H | $OCH_3$ | $OCH_3$ | N |
| Br | $CH_3$ | H | H | O | H | $CH_3$ | $OCH_3$ | N |
| Br | $CH_3$ | H | H | O | H | $CH_3$ | $CH_3$ | N |
| Br | $CH_3$ | H | H | O | H | $OCH_2CH_3$ | $OCH_2CH_3$ | N |
| Br | $CH_3$ | H | H | O | H | $NHCH_3$ | $OCH_2CH_3$ | N |
| Br | $CH_3$ | H | H | O | H | $N(CH_3)_2$ | $OCH_2CH_3$ | N |
| Br | $CH_3$ | H | H | O | H | $N(CH_3)_2$ | $OCH_3$ | N |
| Br | $CH_3$ | H | H | O | H | $N(CH_3)_2$ | $OCH_2CF_3$ | N |
| Br | $CH_3$ | H | H | O | $CH_3$ | $CH_3$ | $OCH_3$ | N |
| Br | $CH_3$ | H | H | S | H | $OCH_3$ | $OCH_3$ | CH |
| Br | $CH_3$ | H | H | S | H | Cl | $OCH_3$ | CH |
| Br | $CH_3$ | H | H | S | H | $CH_3$ | $OCH_3$ | CH |
| Br | $CH_3$ | H | H | S | H | $CH_3$ | $CH_3$ | CH |
| Br | $CH_3$ | H | H | S | H | $OCH_3$ | $OCH_3$ | N |
| Br | $CH_3$ | H | H | S | H | $CH_3$ | $OCH_3$ | N |
| Br | $CH_2CH{=}CH_2$ | H | H | O | H | $OCH_3$ | $OCH_3$ | CH |
| Br | $CH_2CH{=}CH_2$ | H | H | O | H | Cl | $OCH_3$ | CH |
| Br | $CH_2CH{=}CH_2$ | H | H | O | H | $CH_3$ | $OCH_3$ | CH |
| Br | $CH_2CH{=}CH_2$ | H | H | O | H | $CH_3$ | $CH_3$ | CH |
| Br | $CH_2CH{=}CH_2$ | H | H | O | H | $OCH_3$ | $OCH_3$ | N |
| Br | $CH_2CH{=}CH_2$ | H | H | O | H | $CH_3$ | $OCH_3$ | N |
| Br | $CH_2CH{=}CH_2$ | H | H | O | H | $CH_3$ | $CH_3$ | N |
| Br | $CH_2CH{=}CH_2$ | H | H | O | H | $OCH_2CH_3$ | $OCH_2CH_3$ | N |
| Br | $CH_2CH{=}CH_2$ | H | H | O | H | $NHCH_3$ | $OCH_2CH_3$ | N |
| Br | $CH_2CH{=}CH_2$ | H | H | O | H | $N(CH_3)_2$ | $OCH_2CH_3$ | N |
| Br | $CH_2CH{=}CH_2$ | H | H | O | H | $N(CH_3)_2$ | $OCH_3$ | N |
| Br | $CH_2CH{=}CH_2$ | H | H | O | H | $N(CH_3)_2$ | $OCH_2CF_3$ | N |
| Br | $CH_2CH{=}CH_2$ | H | H | O | $CH_3$ | $CH_3$ | $OCH_3$ | N |
| Br | $CH_2CH{=}CH_2$ | H | H | S | H | $OCH_3$ | $OCH_3$ | CH |
| Br | $CH_2CH{=}CH_2$ | H | H | S | H | Cl | $OCH_3$ | CH |
| Br | $CH_2CH{=}CH_2$ | H | H | S | H | $CH_3$ | $OCH_3$ | CH |
| Br | $CH_2CH{=}CH_2$ | H | H | S | H | $CH_3$ | $CH_3$ | CH |
| Br | $CH_2CH{=}CH_2$ | H | H | S | H | $OCH_3$ | $OCH_3$ | N |
| Br | $CH_2CH{=}CH_2$ | H | H | S | H | $CH_3$ | $OCH_3$ | N |
| Br | $CH_3$ | $CH_3$ | H | O | H | $OCH_3$ | $OCH_3$ | CH |
| Br | $CH_3$ | $CH_3$ | H | O | H | Cl | $OCH_3$ | CH |
| Br | $CH_3$ | $CH_3$ | H | O | H | $CH_3$ | $OCH_3$ | CH |
| Br | $CH_3$ | $CH_3$ | H | O | H | $CH_3$ | $CH_3$ | CH |
| Br | $CH_3$ | $CH_3$ | H | O | H | $OCH_3$ | $OCH_3$ | N |
| Br | $CH_3$ | $CH_3$ | H | O | H | $CH_3$ | $OCH_3$ | N |
| Br | $CH_3$ | $CH_3$ | H | O | H | $CH_3$ | $CH_3$ | N |
| Br | $CH_3$ | $CH_3$ | H | O | H | $OCH_2CH_3$ | $OCH_2CH_3$ | N |
| Br | $CH_3$ | $CH_3$ | H | O | H | $NHCH_3$ | $OCH_2CH_3$ | N |
| Br | $CH_3$ | $CH_3$ | H | O | H | $N(CH_3)_2$ | $OCH_2CH_3$ | N |
| Br | $CH_3$ | $CH_3$ | H | O | H | $N(CH_3)_2$ | $OCH_3$ | N |
| Br | $CH_3$ | $CH_3$ | H | O | H | $N(CH_3)_2$ | $OCH_2CF_3$ | N |
| Br | $CH_3$ | $CH_3$ | H | O | $CH_3$ | $CH_3$ | $OCH_3$ | N |
| Br | $CH_3$ | $CH_3$ | H | S | H | $OCH_3$ | $OCH_3$ | CH |
| Br | $CH_3$ | $CH_3$ | H | S | H | Cl | $OCH_3$ | CH |
| Br | $CH_3$ | $CH_3$ | H | S | H | $CH_3$ | $OCH_3$ | CH |
| Br | $CH_3$ | $CH_3$ | H | S | H | $CH_3$ | $CH_3$ | CH |
| Br | $CH_3$ | $CH_3$ | H | S | H | $OCH_3$ | $OCH_3$ | N |
| Br | $CH_3$ | $CH_3$ | H | S | H | $CH_3$ | $OCH_3$ | N |
| Br | $-CH_2CH_2CH_2-$ | | H | O | H | $OCH_3$ | $OCH_3$ | CH |
| Br | $-CH_2CH_2CH_2-$ | | H | O | H | Cl | $OCH_3$ | CH |
| Br | $-CH_2CH_2CH_2-$ | | H | O | H | $CH_3$ | $OCH_3$ | CH |
| Br | $-CH_2CH_2CH_2-$ | | H | O | H | $CH_3$ | $CH_3$ | CH |
| Br | $-CH_2CH_2CH_2-$ | | H | O | H | $OCH_3$ | $OCH_3$ | N |
| Br | $-CH_2CH_2CH_2-$ | | H | O | H | $CH_3$ | $OCH_3$ | N |
| Br | $-CH_2CH_2CH_2-$ | | H | O | H | $CH_3$ | $CH_3$ | N |
| Br | $-CH_2CH_2CH_2-$ | | H | O | H | $OCH_2CH_3$ | $OCH_2CH_3$ | N |
| Br | $-CH_2CH_2CH_2-$ | | H | O | H | $NHCH_3$ | $OCH_2CH_3$ | N |
| Br | $-CH_2CH_2CH_2-$ | | H | O | H | $N(CH_3)_2$ | $OCH_2CH_3$ | N |
| Br | $-CH_2CH_2CH_2-$ | | H | O | H | $N(CH_3)_2$ | $OCH_3$ | N |
| Br | $-CH_2CH_2CH_2-$ | | H | O | H | $N(CH_3)_2$ | $OCH_2CF_3$ | N |
| Br | $-CH_2CH_2CH_2-$ | | H | O | $CH_3$ | $CH_3$ | $OCH_3$ | N |
| Br | $-CH_2CH_2CH_2-$ | | H | S | H | $OCH_3$ | $OCH_3$ | CH |

-continued

| | | | | | | | | |
|---|---|---|---|---|---|---|---|---|
| Br | $-CH_2CH_2CH_2-$ | | H | S | H | Cl | $OCH_3$ | CH |
| Br | $-CH_2CH_2CH_2-$ | | H | S | H | $CH_3$ | $OCH_3$ | CH |
| Br | $-CH_2CH_2CH_2-$ | | H | S | H | $CH_3$ | $CH_3$ | CH |
| Br | $-CH_2CH_2CH_2-$ | | H | S | H | $OCH_3$ | $OCH_3$ | N |
| Br | $-CH_2CH_2CH_2-$ | | H | S | H | $CH_3$ | $OCH_3$ | N |
| $CH_2CH_3$ | $CH_3$ | H | H | O | H | $OCH_3$ | $OCH_3$ | CH |
| $CH_2CH_3$ | $CH_3$ | H | H | O | H | Cl | $OCH_3$ | CH |
| $CH_2CH_3$ | $CH_3$ | H | H | O | H | $CH_3$ | $OCH_3$ | CH |
| $CH_2CH_3$ | $CH_3$ | H | H | O | H | $CH_3$ | $CH_3$ | CH |
| $CH_2CH_3$ | $CH_3$ | H | H | O | H | $OCH_3$ | $OCH_3$ | N |
| $CH_2CH_3$ | $CH_3$ | H | H | O | H | $CH_3$ | $OCH_3$ | N |
| $CH_2CH_3$ | $CH_3$ | H | H | O | H | $CH_3$ | $CH_3$ | N |
| $CH_2CH_3$ | $CH_3$ | H | H | O | H | $OCH_2CH_3$ | $OCH_2CH_3$ | N |
| $CH_2CH_3$ | $CH_3$ | H | H | O | H | $NHCH_3$ | $OCH_2CH_3$ | N |
| $CH_2CH_3$ | $CH_3$ | H | H | O | H | $N(CH_3)_2$ | $OCH_2CH_3$ | N |
| $CH_2CH_3$ | $CH_3$ | H | H | O | H | $N(CH_3)_2$ | $OCH_3$ | N |
| $CH_2CH_3$ | $CH_3$ | H | H | O | H | $N(CH_3)_2$ | $OCH_2CF_3$ | N |
| $CH_2CH_3$ | $CH_3$ | H | H | O | $CH_3$ | $CH_3$ | $OCH_3$ | N |
| $CH_2CH_3$ | $CH_3$ | H | H | S | H | $OCH_3$ | $OCH_3$ | CH |
| $CH_2CH_3$ | $CH_3$ | H | H | S | H | Cl | $OCH_3$ | CH |
| $CH_2CH_3$ | $CH_3$ | H | H | S | H | $CH_3$ | $OCH_3$ | CH |
| $CH_2CH_3$ | $CH_3$ | H | H | S | H | $CH_3$ | $CH_3$ | CH |
| $CH_2CH_3$ | $CH_3$ | H | H | S | H | $OCH_3$ | $OCH_3$ | N |
| $CH_2CH_3$ | $CH_3$ | H | H | S | H | $CH_3$ | $OCH_3$ | N |
| $CH_2CH_3$ | $CH_2CH{=}CH_2$ | H | H | O | H | $OCH_3$ | $OCH_3$ | CH |
| $CH_2CH_3$ | $CH_2CH{=}CH_2$ | H | H | O | H | Cl | $OCH_3$ | CH |
| $CH_2CH_3$ | $CH_2CH{=}CH_2$ | H | H | O | H | $CH_3$ | $OCH_3$ | CH |
| $CH_2CH_3$ | $CH_2CH{=}CH_2$ | H | H | O | H | $CH_3$ | $CH_3$ | CH |
| $CH_2CH_3$ | $CH_2CH{=}CH_2$ | H | H | O | H | $OCH_3$ | $OCH_3$ | N |
| $CH_2CH_3$ | $CH_2CH{=}CH_2$ | H | H | O | H | $CH_3$ | $OCH_3$ | N |
| $CH_2CH_3$ | $CH_2CH{=}CH_2$ | H | H | O | H | $CH_3$ | $CH_3$ | N |
| $CH_2CH_3$ | $CH_2CH{=}CH_2$ | H | H | O | H | $OCH_2CH_3$ | $OCH_2CH_3$ | N |
| $CH_2CH_3$ | $CH_2CH{=}CH_2$ | H | H | O | H | $NHCH_3$ | $OCH_2CH_3$ | N |
| $CH_2CH_3$ | $CH_2CH{=}CH_2$ | H | H | O | H | $N(CH_3)_2$ | $OCH_2CH_3$ | N |
| $CH_2CH_3$ | $CH_2CH{=}CH_2$ | H | H | O | H | $N(CH_3)_2$ | $OCH_3$ | N |
| $CH_2CH_3$ | $CH_2CH{=}CH_2$ | H | H | O | H | $N(CH_3)_2$ | $OCH_2CF_3$ | N |
| $CH_2CH_3$ | $CH_2CH{=}CH_2$ | H | H | O | $CH_3$ | $CH_3$ | $OCH_3$ | N |
| $CH_2CH_3$ | $CH_2CH{=}CH_2$ | H | H | S | H | $OCH_3$ | $OCH_3$ | CH |
| $CH_2CH_3$ | $CH_2CH{=}CH_2$ | H | H | S | H | Cl | $OCH_3$ | CH |
| $CH_2CH_3$ | $CH_2CH{=}CH_2$ | H | H | S | H | $CH_3$ | $OCH_3$ | CH |
| $CH_2CH_3$ | $CH_2CH{=}CH_2$ | H | H | S | H | $CH_3$ | $CH_3$ | CH |
| $CH_2CH_3$ | $CH_2CH{=}CH_2$ | H | H | S | H | $OCH_3$ | $OCH_3$ | N |
| $CH_2CH_3$ | $CH_2CH{=}CH_2$ | H | H | S | H | $CH_3$ | $OCH_3$ | N |
| $CH_2CH_3$ | $CH_3$ | $CH_3$ | H | O | H | $OCH_3$ | $OCH_3$ | CH |
| $CH_2CH_3$ | $CH_3$ | $CH_3$ | H | O | H | Cl | $OCH_3$ | CH |
| $CH_2CH_3$ | $CH_3$ | $CH_3$ | H | O | H | $CH_3$ | $OCH_3$ | CH |
| $CH_2CH_3$ | $CH_3$ | $CH_3$ | H | O | H | $CH_3$ | $CH_3$ | CH |
| $CH_2CH_3$ | $CH_3$ | $CH_3$ | H | O | H | $OCH_3$ | $OCH_3$ | N |
| $CH_2CH_3$ | $CH_3$ | $CH_3$ | H | O | H | $CH_3$ | $OCH_3$ | N |
| $CH_2CH_3$ | $CH_3$ | $CH_3$ | H | O | H | $CH_3$ | $CH_3$ | N |
| $CH_2CH_3$ | $CH_3$ | $CH_3$ | H | O | H | $OCH_2CH_3$ | $OCH_2CH_3$ | N |
| $CH_2CH_3$ | $CH_3$ | $CH_3$ | H | O | H | $NHCH_3$ | $OCH_2CH_3$ | N |
| $CH_2CH_3$ | $CH_3$ | $CH_3$ | H | O | H | $N(CH_3)_2$ | $OCH_2CH_3$ | N |
| $CH_2CH_3$ | $CH_3$ | $CH_3$ | H | O | H | $N(CH_3)_2$ | $OCH_3$ | N |
| $CH_2CH_3$ | $CH_3$ | $CH_3$ | H | O | H | $N(CH_3)_2$ | $OCH_2CF_3$ | N |
| $CH_2CH_3$ | $CH_3$ | $CH_3$ | H | O | $CH_3$ | $CH_3$ | $OCH_3$ | N |
| $CH_2CH_3$ | $CH_3$ | $CH_3$ | H | S | H | $OCH_3$ | $OCH_3$ | CH |
| $CH_2CH_3$ | $CH_3$ | $CH_3$ | H | S | H | Cl | $OCH_3$ | CH |
| $CH_2CH_3$ | $CH_3$ | $CH_3$ | H | S | H | $CH_3$ | $OCH_3$ | CH |
| $CH_2CH_3$ | $CH_3$ | $CH_3$ | H | S | H | $CH_3$ | $CH_3$ | CH |
| $CH_2CH_3$ | $CH_3$ | $CH_3$ | H | S | H | $OCH_3$ | $OCH_3$ | N |
| $CH_2CH_3$ | $CH_3$ | $CH_3$ | H | S | H | $CH_3$ | $OCH_3$ | N |
| $CH_2CH_3$ | $-CH_2CH_2CH_2-$ | | H | O | H | $OCH_3$ | $OCH_3$ | CH |
| $CH_2CH_3$ | $-CH_2CH_2CH_2-$ | | H | O | H | Cl | $OCH_3$ | CH |
| $CH_2CH_3$ | $-CH_2CH_2CH_2-$ | | H | O | H | $CH_3$ | $OCH_3$ | CH |
| $CH_2CH_3$ | $-CH_2CH_2CH_2-$ | | H | O | H | $CH_3$ | $CH_3$ | CH |
| $CH_2CH_3$ | $-CH_2CH_2CH_2-$ | | H | O | H | $OCH_3$ | $OCH_3$ | N |
| $CH_2CH_3$ | $-CH_2CH_2CH_2-$ | | H | O | H | $CH_3$ | $OCH_3$ | N |
| $CH_2CH_3$ | $-CH_2CH_2CH_2-$ | | H | O | H | $CH_3$ | $CH_3$ | N |
| $CH_2CH_3$ | $-CH_2CH_2CH_2-$ | | H | O | H | $OCH_2CH_3$ | $OCH_2CH_3$ | N |
| $CH_2CH_3$ | $-CH_2CH_2CH_2-$ | | H | O | H | $NHCH_3$ | $OCH_2CH_3$ | N |
| $CH_2CH_3$ | $-CH_2CH_2CH_2-$ | | H | O | H | $N(CH_3)_2$ | $OCH_2CH_3$ | N |
| $CH_2CH_3$ | $-CH_2CH_2CH_2-$ | | H | O | H | $N(CH_3)_2$ | $OCH_3$ | N |
| $CH_2CH_3$ | $-CH_2CH_2CH_2-$ | | H | O | H | $N(CH_3)_2$ | $OCH_2CF_3$ | N |
| $CH_2CH_3$ | $-CH_2CH_2CH_2-$ | | H | O | $CH_3$ | $CH_3$ | $OCH_3$ | N |
| $CH_2CH_3$ | $-CH_2CH_2CH_2-$ | | H | S | H | $OCH_3$ | $OCH_3$ | CH |
| $CH_2CH_3$ | $-CH_2CH_2CH_2-$ | | H | S | H | Cl | $OCH_3$ | CH |
| $CH_2CH_3$ | $-CH_2CH_2CH_2-$ | | H | S | H | $CH_3$ | $OCH_3$ | CH |
| $CH_2CH_3$ | $-CH_2CH_2CH_2-$ | | H | S | H | $CH_3$ | $CH_3$ | CH |
| $CH_2CH_3$ | $-CH_2CH_2CH_2-$ | | H | S | H | $OCH_3$ | $OCH_3$ | N |
| $CH_2CH_3$ | $-CH_2CH_2CH_2-$ | | H | S | H | $CH_3$ | $OCH_3$ | N |
| $CF_3$ | $CH_3$ | $CH_3$ | H | O | H | $OCH_3$ | $OCH_3$ | CH |

-continued

| | | | | | | | | | |
|---|---|---|---|---|---|---|---|---|---|
| $CF_3$ | $CH_3$ | | $CH_3$ | H | O | H | Cl | $OCH_3$ | CH |
| $CF_3$ | $CH_3$ | | $CH_3$ | H | O | H | $CH_3$ | $OCH_3$ | CH |
| $CF_3$ | $CH_3$ | | $CH_3$ | H | O | H | $CH_3$ | $CH_3$ | CH |
| $CF_3$ | $CH_3$ | | $CH_3$ | H | O | H | $OCH_3$ | $OCH_3$ | N |
| $CF_3$ | $CH_3$ | | $CH_3$ | H | O | H | $CH_3$ | $OCH_3$ | N |
| $CF_3$ | $CH_3$ | | $CH_3$ | H | O | H | $CH_3$ | $CH_3$ | N |
| $CF_3$ | $CH_3$ | | $CH_3$ | H | O | H | $OCH_2CH_3$ | $OCH_2CH_3$ | N |
| $CF_3$ | $CH_3$ | | $CH_3$ | H | O | H | $NHCH_3$ | $OCH_2CH_3$ | N |
| $CF_3$ | $CH_3$ | | $CH_3$ | H | O | H | $N(CH_3)_2$ | $OCH_2CH_3$ | N |
| $CF_3$ | $CH_3$ | | $CH_3$ | H | O | H | $N(CH_3)_2$ | $OCH_3$ | N |
| $CF_3$ | $CH_3$ | | $CH_3$ | H | O | H | $N(CH_3)_2$ | $OCH_2CF_3$ | N |
| $CF_3$ | $CH_3$ | | $CH_3$ | H | O | $CH_3$ | $CH_3$ | $OCH_3$ | N |
| $CF_3$ | $CH_3$ | | $CH_3$ | H | S | H | $OCH_3$ | $OCH_3$ | CH |
| $CF_3$ | $CH_3$ | | $CH_3$ | H | S | H | Cl | $OCH_3$ | CH |
| $CF_3$ | $CH_3$ | | $CH_3$ | H | S | H | $CH_3$ | $OCH_3$ | CH |
| $CF_3$ | $CH_3$ | | $CH_3$ | H | S | H | $CH_3$ | $CH_3$ | CH |
| $CF_3$ | $CH_3$ | | $CH_3$ | H | S | H | $OCH_3$ | $OCH_3$ | N |
| $CF_3$ | $CH_3$ | | $CH_3$ | H | S | H | $CH_3$ | $OCH_3$ | N |
| $CF_3$ | | $-CH_2CH_2CH_2-$ | | H | O | H | $OCH_3$ | $OCH_3$ | CH |
| $CF_3$ | | $-CH_2CH_2CH_2-$ | | H | O | H | Cl | $OCH_3$ | CH |
| $CF_3$ | | $-CH_2CH_2CH_2-$ | | H | O | H | $CH_3$ | $OCH_3$ | CH |
| $CF_3$ | | $-CH_2CH_2CH_2-$ | | H | O | H | $CH_3$ | $CH_3$ | CH |
| $CF_3$ | | $-CH_2CH_2CH_2-$ | | H | O | H | $OCH_3$ | $OCH_3$ | N |
| $CF_3$ | | $-CH_2CH_2CH_2-$ | | H | O | H | $CH_3$ | $OCH_3$ | N |
| $CF_3$ | | $-CH_2CH_2CH_2-$ | | H | O | H | $CH_3$ | $CH_3$ | N |
| $CF_3$ | | $-CH_2CH_2CH_2-$ | | H | O | H | $OCH_2CH_3$ | $OCH_2CH_3$ | N |
| $CF_3$ | | $-CH_2CH_2CH_2-$ | | H | O | H | $NHCH_3$ | $OCH_2CH_3$ | N |
| $CF_3$ | | $-CH_2CH_2CH_2-$ | | H | O | H | $N(CH_3)_2$ | $OCH_2CH_3$ | N |
| $CF_3$ | | $-CH_2CH_2CH_2-$ | | H | O | H | $N(CH_3)_2$ | $OCH_3$ | N |
| $CF_3$ | | $-CH_2CH_2CH_2-$ | | H | O | H | $N(CH_3)_2$ | $OCH_2CF_3$ | N |
| $CF_3$ | | $-CH_2CH_2CH_2-$ | | H | O | $CH_3$ | $CH_3$ | $OCH_3$ | N |
| $CF_3$ | | $-CH_2CH_2CH_2-$ | | H | S | H | $OCH_3$ | $OCH_3$ | CH |
| $CF_3$ | | $-CH_2CH_2CH_2-$ | | H | S | H | Cl | $OCH_3$ | CH |
| $CF_3$ | | $-CH_2CH_2CH_2-$ | | H | S | H | $CH_3$ | $OCH_3$ | CH |
| $CF_3$ | | $-CH_2CH_2CH_2-$ | | H | S | H | $CH_3$ | $CH_3$ | CH |
| $CF_3$ | | $-CH_2CH_2CH_2-$ | | H | S | H | $OCH_3$ | $OCH_3$ | N |
| $CF_3$ | | $-CH_2CH_2CH_2-$ | | H | S | H | $CH_3$ | $OCH_3$ | N |
| $CF_3$ | $CH_3$ | | $CH_3$ | H | O | H | $OCH_3$ | $OCH_3$ | CH |
| $CF_3$ | $CH_3$ | | $CH_3$ | H | O | H | Cl | $OCH_3$ | CH |
| $CF_3$ | $CH_3$ | | $CH_3$ | H | O | H | $CH_3$ | $OCH_3$ | CH |
| $CF_3$ | $CH_3$ | | $CH_3$ | H | O | H | $CH_3$ | $CH_3$ | CH |
| $CF_3$ | $CH_3$ | | $CH_3$ | H | O | H | $OCH_3$ | $OCH_3$ | N |
| $CF_3$ | $CH_3$ | | $CH_3$ | H | O | H | $CH_3$ | $OCH_3$ | N |
| $CF_3$ | $CH_3$ | | $CH_3$ | H | O | H | $CH_3$ | $CH_3$ | N |
| $CF_3$ | $CH_3$ | | $CH_3$ | H | O | H | $OCH_2CH_3$ | $OCH_2CH_3$ | N |
| $CF_3$ | $CH_3$ | | $CH_3$ | H | O | H | $NHCH_3$ | $OCH_2CH_3$ | N |
| $CF_3$ | $CH_3$ | | $CH_3$ | H | O | H | $N(CH_3)_2$ | $OCH_2CH_3$ | N |
| $CF_3$ | $CH_3$ | | $CH_3$ | H | O | H | $N(CH_3)_2$ | $OCH_3$ | N |
| $CF_3$ | $CH_3$ | | $CH_3$ | H | O | H | $N(CH_3)_2$ | $OCH_2CF_3$ | N |
| $CF_3$ | $CH_3$ | | $CH_3$ | H | O | $CH_3$ | $CH_3$ | $OCH_3$ | N |
| $CF_3$ | $CH_3$ | | $CH_3$ | H | S | H | $OCH_3$ | $OCH_3$ | CH |
| $CF_3$ | $CH_3$ | | $CH_3$ | H | S | H | Cl | $OCH_3$ | CH |
| $CF_3$ | $CH_3$ | | $CH_3$ | H | S | H | $CH_3$ | $OCH_3$ | CH |
| $CF_3$ | $CH_3$ | | $CH_3$ | H | S | H | $CH_3$ | $CH_3$ | CH |
| $CF_3$ | $CH_3$ | | $CH_3$ | H | S | H | $OCH_3$ | $OCH_3$ | N |
| $CF_3$ | $CH_3$ | | $CH_3$ | H | S | H | $CH_3$ | $OCH_3$ | N |
| $CF_3$ | | $-CH_2CH_2CH_2-$ | | H | O | H | $OCH_3$ | $OCH_3$ | CH |
| $CF_3$ | | $-CH_2CH_2CH_2-$ | | H | O | H | Cl | $OCH_3$ | CH |
| $CF_3$ | | $-CH_2CH_2CH_2-$ | | H | O | H | $CH_3$ | $OCH_3$ | CH |
| $CF_3$ | | $-CH_2CH_2CH_2-$ | | H | O | H | $CH_3$ | $CH_3$ | CH |
| $CF_3$ | | $-CH_2CH_2CH_2-$ | | H | O | H | $OCH_3$ | $OCH_3$ | N |
| $CF_3$ | | $-CH_2CH_2CH_2-$ | | H | O | H | $CH_3$ | $OCH_3$ | N |
| $CF_3$ | | $-CH_2CH_2CH_2-$ | | H | O | H | $CH_3$ | $CH_3$ | N |
| $CF_3$ | | $-CH_2CH_2CH_2-$ | | H | O | H | $OCH_2CH_3$ | $OCH_2CH_3$ | N |
| $CF_3$ | | $-CH_2CH_2CH_2-$ | | H | O | H | $NHCH_3$ | $OCH_2CH_3$ | N |
| $CF_3$ | | $-CH_2CH_2CH_2-$ | | H | O | H | $N(CH_3)_2$ | $OCH_2CH_3$ | N |
| $CF_3$ | | $-CH_2CH_2CH_2-$ | | H | O | H | $N(CH_3)_2$ | $OCH_3$ | N |
| $CF_3$ | | $-CH_2CH_2CH_2-$ | | H | O | H | $N(CH_3)_2$ | $OCH_2CF_3$ | N |
| $CF_3$ | | $-CH_2CH_2CH_2-$ | | H | O | $CH_3$ | $CH_3$ | $OCH_3$ | N |
| $CF_3$ | | $-CH_2CH_2CH_2-$ | | H | S | H | $OCH_3$ | $OCH_3$ | CH |
| $CF_3$ | | $-CH_2CH_2CH_2-$ | | H | S | H | Cl | $OCH_3$ | CH |
| $CF_3$ | | $-CH_2CH_2CH_2-$ | | H | S | H | $CH_3$ | $OCH_3$ | CH |
| $CF_3$ | | $-CH_2CH_2CH_2-$ | | H | S | H | $CH_3$ | $CH_3$ | CH |
| $CF_3$ | | $-CH_2CH_2CH_2-$ | | H | S | H | $OCH_3$ | $OCH_3$ | N |
| $CF_3$ | | $-CH_2CH_2CH_2-$ | | H | S | H | $CH_3$ | $OCH_3$ | N |
| $CH_2CH_2Cl$ | $CH_3$ | | H | H | O | H | $OCH_3$ | $OCH_3$ | CH |
| $CH_2CH_2Cl$ | $CH_3$ | | H | H | O | H | Cl | $OCH_3$ | CH |
| $CH_2CH_2Cl$ | $CH_3$ | | H | H | O | H | $CH_3$ | $OCH_3$ | CH |
| $CH_2CH_2Cl$ | $CH_3$ | | H | H | O | H | $CH_3$ | $CH_3$ | CH |
| $CH_2CH_2Cl$ | $CH_3$ | | H | H | O | H | $OCH_3$ | $OCH_3$ | N |
| $CH_2CH_2Cl$ | $CH_3$ | | H | H | O | H | $CH_3$ | $OCH_3$ | N |
| $CH_2CH_2Cl$ | $CH_3$ | | H | H | O | H | $CH_3$ | $CH_3$ | N |

-continued

| | | | | | | | | |
|---|---|---|---|---|---|---|---|---|
| $CH_2CH_2Cl$ | $CH_3$ | H | H | O | H | $OCH_2CH_3$ | $OCH_2CH_3$ | N |
| $CH_2CH_2Cl$ | $CH_3$ | H | H | O | H | $NHCH_3$ | $OCH_2CH_3$ | N |
| $CH_2CH_2Cl$ | $CH_3$ | H | H | O | H | $N(CH_3)_2$ | $OCH_2CH_3$ | N |
| $CH_2CH_2Cl$ | $CH_3$ | H | H | O | H | $N(CH_3)_2$ | $OCH_3$ | N |
| $CH_2CH_2Cl$ | $CH_3$ | H | H | O | H | $N(CH_3)_2$ | $OCH_2CF_3$ | N |
| $CH_2CH_2Cl$ | $CH_3$ | H | H | O | $CH_3$ | $CH_3$ | $OCH_3$ | N |
| $CH_2CH_2Cl$ | $CH_3$ | H | H | S | H | $OCH_3$ | $OCH_3$ | CH |
| $CH_2CH_2Cl$ | $CH_3$ | H | H | S | H | Cl | $OCH_3$ | CH |
| $CH_2CH_2Cl$ | $CH_3$ | H | H | S | H | $CH_3$ | $OCH_3$ | CH |
| $CH_2CH_2Cl$ | $CH_3$ | H | H | S | H | $CH_3$ | $CH_3$ | CH |
| $CH_2CH_2Cl$ | $CH_3$ | H | H | S | H | $OCH_3$ | $OCH_3$ | N |
| $CH_2CH_2Cl$ | $CH_3$ | H | H | S | H | $CH_3$ | $OCH_3$ | N |
| $CH_2CH_2Cl$ | $CH_2CH{=}CH_2$ | H | H | O | H | $OCH_3$ | $OCH_3$ | CH |
| $CH_2CH_2Cl$ | $CH_2CH{=}CH_2$ | H | H | O | H | Cl | $OCH_3$ | CH |
| $CH_2CH_2Cl$ | $CH_2CH{=}CH_2$ | H | H | O | H | $CH_3$ | $OCH_3$ | CH |
| $CH_2CH_2Cl$ | $CH_2CH{=}CH_2$ | H | H | O | H | $CH_3$ | $CH_3$ | CH |
| $CH_2CH_2Cl$ | $CH_2CH{=}CH_2$ | H | H | O | H | $OCH_3$ | $OCH_3$ | N |
| $CH_2CH_2Cl$ | $CH_2CH{=}CH_2$ | H | H | O | H | $CH_3$ | $OCH_3$ | N |
| $CH_2CH_2Cl$ | $CH_2CH{=}CH_2$ | H | H | O | H | $CH_3$ | $CH_3$ | N |
| $CH_2CH_2Cl$ | $CH_2CH{=}CH_2$ | H | H | O | H | $OCH_2CH_3$ | $OCH_2CH_3$ | N |
| $CH_2CH_2Cl$ | $CH_2CH{=}CH_2$ | H | H | O | H | $NHCH_3$ | $OCH_2CH_3$ | N |
| $CH_2CH_2Cl$ | $CH_2CH{=}CH_2$ | H | H | O | H | $N(CH_3)_2$ | $OCH_2CH_3$ | N |
| $CH_2CH_2Cl$ | $CH_2CH{=}CH_2$ | H | H | O | H | $N(CH_3)_2$ | $OCH_3$ | N |
| $CH_2CH_2Cl$ | $CH_2CH{=}CH_2$ | H | H | O | H | $N(CH_3)_2$ | $OCH_2CF_3$ | N |
| $CH_2CH_2Cl$ | $CH_2CH{=}CH_2$ | H | H | O | $CH_3$ | $CH_3$ | $OCH_3$ | N |
| $CH_2CH_2Cl$ | $CH_2CH{=}CH_2$ | H | H | S | H | $OCH_3$ | $OCH_3$ | CH |
| $CH_2CH_2Cl$ | $CH_2CH{=}CH_2$ | H | H | S | H | Cl | $OCH_3$ | CH |
| $CH_2CH_2Cl$ | $CH_2CH{=}CH_2$ | H | H | S | H | $CH_3$ | $OCH_3$ | CH |
| $CH_2CH_2Cl$ | $CH_2CH{=}CH_2$ | H | H | S | H | $CH_3$ | $CH_3$ | CH |
| $CH_2CH_2Cl$ | $CH_2CH{=}CH_2$ | H | H | S | H | $OCH_3$ | $OCH_3$ | N |
| $CH_2CH_2Cl$ | $CH_2CH{=}CH_2$ | H | H | S | H | $CH_3$ | $OCH_3$ | N |
| $CH_2CH_2Cl$ | $CH_3$ | $CH_3$ | H | O | H | $OCH_3$ | $OCH_3$ | CH |
| $CH_2CH_2Cl$ | $CH_3$ | $CH_3$ | H | O | H | Cl | $OCH_3$ | CH |
| $CH_2CH_2Cl$ | $CH_3$ | $CH_3$ | H | O | H | $CH_3$ | $OCH_3$ | CH |
| $CH_2CH_2Cl$ | $CH_3$ | $CH_3$ | H | O | H | $CH_3$ | $CH_3$ | CH |
| $CH_2CH_2Cl$ | $CH_3$ | $CH_3$ | H | O | H | $OCH_3$ | $OCH_3$ | N |
| $CH_2CH_2Cl$ | $CH_3$ | $CH_3$ | H | O | H | $CH_3$ | $OCH_3$ | N |
| $CH_2CH_2Cl$ | $CH_3$ | $CH_3$ | H | O | H | $CH_3$ | $CH_3$ | N |
| $CH_2CH_2Cl$ | $CH_3$ | $CH_3$ | H | O | H | $OCH_2CH_3$ | $OCH_2CH_3$ | N |
| $CH_2CH_2Cl$ | $CH_3$ | $CH_3$ | H | O | H | $NHCH_3$ | $OCH_2CH_3$ | N |
| $CH_2CH_2Cl$ | $CH_3$ | $CH_3$ | H | O | H | $N(CH_3)_2$ | $OCH_2CH_3$ | N |
| $CH_2CH_2Cl$ | $CH_3$ | $CH_3$ | H | O | H | $N(CH_3)_2$ | $OCH_3$ | N |
| $CH_2CH_2Cl$ | $CH_3$ | $CH_3$ | H | O | H | $N(CH_3)_2$ | $OCH_2CF_3$ | N |
| $CH_2CH_2Cl$ | $CH_3$ | $CH_3$ | H | O | $CH_3$ | $CH_3$ | $OCH_3$ | N |
| $CH_2CH_2Cl$ | $CH_3$ | $CH_3$ | H | S | H | $OCH_3$ | $OCH_3$ | CH |
| $CH_2CH_2Cl$ | $CH_3$ | $CH_3$ | H | S | H | Cl | $OCH_3$ | CH |
| $CH_2CH_2Cl$ | $CH_3$ | $CH_3$ | H | S | H | $CH_3$ | $OCH_3$ | CH |
| $CH_2CH_2Cl$ | $CH_3$ | $CH_3$ | H | S | H | $CH_3$ | $CH_3$ | CH |
| $CH_2CH_2Cl$ | $CH_3$ | $CH_3$ | H | S | H | $OCH_3$ | $OCH_3$ | N |
| $CH_2CH_2Cl$ | $CH_3$ | $CH_3$ | H | S | H | $CH_3$ | $OCH_3$ | N |
| $CH_2CH_2Cl$ | $-CH_2CH_2CH_2-$ | | H | O | H | $OCH_3$ | $OCH_3$ | CH |
| $CH_2CH_2Cl$ | $-CH_2CH_2CH_2-$ | | H | O | H | Cl | $OCH_3$ | CH |
| $CH_2CH_2Cl$ | $-CH_2CH_2CH_2-$ | | H | O | H | $CH_3$ | $OCH_3$ | CH |
| $CH_2CH_2Cl$ | $-CH_2CH_2CH_2-$ | | H | O | H | $CH_3$ | $CH_3$ | CH |
| $CH_2CH_2Cl$ | $-CH_2CH_2CH_2-$ | | H | O | H | $OCH_3$ | $OCH_3$ | N |
| $CH_2CH_2Cl$ | $-CH_2CH_2CH_2-$ | | H | O | H | $CH_3$ | $OCH_3$ | N |
| $CH_2CH_2Cl$ | $-CH_2CH_2CH_2-$ | | H | O | H | $CH_3$ | $CH_3$ | N |
| $CH_2CH_2Cl$ | $-CH_2CH_2CH_2-$ | | H | O | H | $OCH_2CH_3$ | $OCH_2CH_3$ | N |
| $CH_2CH_2Cl$ | $-CH_2CH_2CH_2-$ | | H | O | H | $NHCH_3$ | $OCH_2CH_3$ | N |
| $CH_2CH_2Cl$ | $-CH_2CH_2CH_2-$ | | H | O | H | $N(CH_3)_2$ | $OCH_2CH_3$ | N |
| $CH_2CH_2Cl$ | $-CH_2CH_2CH_2-$ | | H | O | H | $N(CH_3)_2$ | $OCH_3$ | N |
| $CH_2CH_2Cl$ | $-CH_2CH_2CH_2-$ | | H | O | H | $N(CH_3)_2$ | $OCH_2CF_3$ | N |
| $CH_2CH_2Cl$ | $-CH_2CH_2CH_2-$ | | H | O | $CH_3$ | $CH_3$ | $OCH_3$ | N |
| $CH_2CH_2Cl$ | $-CH_2CH_2CH_2-$ | | H | S | H | $OCH_3$ | $OCH_3$ | CH |
| $CH_2CH_2Cl$ | $-CH_2CH_2CH_2-$ | | H | S | H | Cl | $OCH_3$ | CH |
| $CH_2CH_2Cl$ | $-CH_2CH_2CH_2-$ | | H | S | H | $CH_3$ | $OCH_3$ | CH |
| $CH_2CH_2Cl$ | $-CH_2CH_2CH_2-$ | | H | S | H | $CH_3$ | $CH_3$ | CH |
| $CH_2CH_2Cl$ | $-CH_2CH_2CH_2-$ | | H | S | H | $OCH_3$ | $OCH_3$ | N |
| $CH_2CH_2Cl$ | $-CH_2CH_2CH_2-$ | | H | S | H | $CH_3$ | $OCH_3$ | N |
| $OCH_3$ | $CH_3$ | H | H | O | H | $OCH_3$ | $OCH_3$ | CH |
| $OCH_3$ | $CH_3$ | H | H | O | H | Cl | $OCH_3$ | CH |
| $OCH_3$ | $CH_3$ | H | H | O | H | $CH_3$ | $OCH_3$ | CH |
| $OCH_3$ | $CH_3$ | H | H | O | H | $CH_3$ | $CH_3$ | CH |
| $OCH_3$ | $CH_3$ | H | H | O | H | $OCH_3$ | $OCH_3$ | N |
| $OCH_3$ | $CH_3$ | H | H | O | H | $CH_3$ | $OCH_3$ | N |
| $OCH_3$ | $CH_3$ | H | H | O | H | $CH_3$ | $CH_3$ | N |
| $OCH_3$ | $CH_3$ | H | H | O | H | $OCH_2CH_3$ | $OCH_2CH_3$ | N |
| $OCH_3$ | $CH_3$ | H | H | O | H | $NHCH_3$ | $OCH_2CH_3$ | N |
| $OCH_3$ | $CH_3$ | H | H | O | H | $N(CH_3)_2$ | $OCH_2CH_3$ | N |
| $OCH_3$ | $CH_3$ | H | H | O | H | $N(CH_3)_2$ | $OCH_3$ | N |
| $OCH_3$ | $CH_3$ | H | H | O | H | $N(CH_3)_2$ | $OCH_2CF_3$ | N |
| $OCH_3$ | $CH_3$ | H | H | O | $CH_3$ | $CH_3$ | $OCH_3$ | N |

-continued

| | | | | | | | | |
|---|---|---|---|---|---|---|---|---|
| $OCH_3$ | $CH_3$ | H | H | S | H | $OCH_3$ | $OCH_3$ | CH |
| $OCH_3$ | $CH_3$ | H | H | S | H | Cl | $OCH_3$ | CH |
| $OCH_3$ | $CH_3$ | H | H | S | H | $CH_3$ | $OCH_3$ | CH |
| $OCH_3$ | $CH_3$ | H | H | S | H | $CH_3$ | $CH_3$ | CH |
| $OCH_3$ | $CH_3$ | H | H | S | H | $OCH_3$ | $OCH_3$ | N |
| $OCH_3$ | $CH_3$ | H | H | S | H | $CH_3$ | $OCH_3$ | N |
| $OCH_3$ | $CH_2CH{=}CH_2$ | H | H | O | H | $OCH_3$ | $OCH_3$ | CH |
| $OCH_3$ | $CH_2CH{=}CH_2$ | H | H | O | H | Cl | $OCH_3$ | CH |
| $OCH_3$ | $CH_2CH{=}CH_2$ | H | H | O | H | $CH_3$ | $OCH_3$ | CH |
| $OCH_3$ | $CH_2CH{=}CH_2$ | H | H | O | H | $CH_3$ | $CH_3$ | CH |
| $OCH_3$ | $CH_2CH{=}CH_2$ | H | H | O | H | $OCH_3$ | $OCH_3$ | N |
| $OCH_3$ | $CH_2CH{=}CH_2$ | H | H | O | H | $CH_3$ | $OCH_3$ | N |
| $OCH_3$ | $CH_2CH{=}CH_2$ | H | H | O | H | $CH_3$ | $CH_3$ | N |
| $OCH_3$ | $CH_2CH{=}CH_2$ | H | H | O | H | $OCH_2CH_3$ | $OCH_2CH_3$ | N |
| $OCH_3$ | $CH_2CH{=}CH_2$ | H | H | O | H | $NHCH_3$ | $OCH_2CH_3$ | N |
| $OCH_3$ | $CH_2CH{=}CH_2$ | H | H | O | H | $N(CH_3)_2$ | $OCH_2CH_3$ | N |
| $OCH_3$ | $CH_2CH{=}CH_2$ | H | H | O | H | $N(CH_3)_2$ | $OCH_3$ | N |
| $OCH_3$ | $CH_2CH{=}CH_2$ | H | H | O | H | $N(CH_3)_2$ | $OCH_2CF_3$ | N |
| $OCH_3$ | $CH_2CH{=}CH_2$ | H | H | O | $CH_3$ | $CH_3$ | $OCH_3$ | N |
| $OCH_3$ | $CH_2CH{=}CH_2$ | H | H | S | H | $OCH_3$ | $OCH_3$ | CH |
| $OCH_3$ | $CH_2CH{=}CH_2$ | H | H | S | H | Cl | $OCH_3$ | CH |
| $OCH_3$ | $CH_2CH{=}CH_2$ | H | H | S | H | $CH_3$ | $OCH_3$ | CH |
| $OCH_3$ | $CH_2CH{=}CH_2$ | H | H | S | H | $CH_3$ | $CH_3$ | CH |
| $OCH_3$ | $CH_2CH{=}CH_2$ | H | H | S | H | $OCH_3$ | $OCH_3$ | N |
| $OCH_3$ | $CH_2CH{=}CH_2$ | H | H | S | H | $CH_3$ | $OCH_3$ | N |
| $OCH_3$ | $CH_3$ | $CH_3$ | H | O | H | $OCH_3$ | $OCH_3$ | CH |
| $OCH_3$ | $CH_3$ | $CH_3$ | H | O | H | Cl | $OCH_3$ | CH |
| $OCH_3$ | $CH_3$ | $CH_3$ | H | O | H | $CH_3$ | $OCH_3$ | CH |
| $OCH_3$ | $CH_3$ | $CH_3$ | H | O | H | $CH_3$ | $CH_3$ | CH |
| $OCH_3$ | $CH_3$ | $CH_3$ | H | O | H | $OCH_3$ | $OCH_3$ | N |
| $OCH_3$ | $CH_3$ | $CH_3$ | H | O | H | $CH_3$ | $OCH_3$ | N |
| $OCH_3$ | $CH_3$ | $CH_3$ | H | O | H | $CH_3$ | $CH_3$ | N |
| $OCH_3$ | $CH_3$ | $CH_3$ | H | O | H | $OCH_2CH_3$ | $OCH_2CH_3$ | N |
| $OCH_3$ | $CH_3$ | $CH_3$ | H | O | H | $NHCH_3$ | $OCH_2CH_3$ | N |
| $OCH_3$ | $CH_3$ | $CH_3$ | H | O | H | $N(CH_3)_2$ | $OCH_2CH_3$ | N |
| $OCH_3$ | $CH_3$ | $CH_3$ | H | O | H | $N(CH_3)_2$ | $OCH_3$ | N |
| $OCH_3$ | $CH_3$ | $CH_3$ | H | O | H | $N(CH_3)_2$ | $OCH_2CF_3$ | N |
| $OCH_3$ | $CH_3$ | $CH_3$ | H | O | $CH_3$ | $CH_3$ | $OCH_3$ | N |
| $OCH_3$ | $CH_3$ | $CH_3$ | H | S | H | $OCH_3$ | $OCH_3$ | CH |
| $OCH_3$ | $CH_3$ | $CH_3$ | H | S | H | Cl | $OCH_3$ | CH |
| $OCH_3$ | $CH_3$ | $CH_3$ | H | S | H | $CH_3$ | $OCH_3$ | CH |
| $OCH_3$ | $CH_3$ | $CH_3$ | H | S | H | $CH_3$ | $CH_3$ | CH |
| $OCH_3$ | $CH_3$ | $CH_3$ | H | S | H | $OCH_3$ | $OCH_3$ | N |
| $OCH_3$ | $CH_3$ | $CH_3$ | H | S | H | $CH_3$ | $OCH_3$ | N |
| $OCH_3$ | $-CH_2CH_2CH_2-$ | | H | O | H | $OCH_3$ | $OCH_3$ | CH |
| $OCH_3$ | $-CH_2CH_2CH_2-$ | | H | O | H | Cl | $OCH_3$ | CH |
| $OCH_3$ | $-CH_2CH_2CH_2-$ | | H | O | H | $CH_3$ | $OCH_3$ | CH |
| $OCH_3$ | $-CH_2CH_2CH_2-$ | | H | O | H | $CH_3$ | $CH_3$ | CH |
| $OCH_3$ | $-CH_2CH_2CH_2-$ | | H | O | H | $OCH_3$ | $OCH_3$ | N |
| $OCH_3$ | $-CH_2CH_2CH_2-$ | | H | O | H | $CH_3$ | $OCH_3$ | N |
| $OCH_3$ | $-CH_2CH_2CH_2-$ | | H | O | H | $CH_3$ | $CH_3$ | N |
| $OCH_3$ | $-CH_2CH_2CH_2-$ | | H | O | H | $OCH_2CH_3$ | $OCH_2CH_3$ | N |
| $OCH_3$ | $-CH_2CH_2CH_2-$ | | H | O | H | $NHCH_3$ | $OCH_2CH_3$ | N |
| $OCH_3$ | $-CH_2CH_2CH_2-$ | | H | O | H | $N(CH_3)_2$ | $OCH_2CH_3$ | N |
| $OCH_3$ | $-CH_2CH_2CH_2-$ | | H | O | H | $N(CH_3)_2$ | $OCH_3$ | N |
| $OCH_3$ | $-CH_2CH_2CH_2-$ | | H | O | H | $N(CH_3)_2$ | $OCH_2CF_3$ | N |
| $OCH_3$ | $-CH_2CH_2CH_2-$ | | H | O | $CH_3$ | $CH_3$ | $OCH_3$ | N |
| $OCH_3$ | $-CH_2CH_2CH_2-$ | | H | S | H | $OCH_3$ | $OCH_3$ | CH |
| $OCH_3$ | $-CH_2CH_2CH_2-$ | | H | S | H | Cl | $OCH_3$ | CH |
| $OCH_3$ | $-CH_2CH_2CH_2-$ | | H | S | H | $CH_3$ | $OCH_3$ | CH |
| $OCH_3$ | $-CH_2CH_2CH_2-$ | | H | S | H | $CH_3$ | $CH_3$ | CH |
| $OCH_3$ | $-CH_2CH_2CH_2-$ | | H | S | H | $OCH_3$ | $OCH_3$ | N |
| $OCH_3$ | $-CH_2CH_2CH_2-$ | | H | S | H | $CH_3$ | $OCH_3$ | N |
| $OCF_2H$ | $CH_3$ | H | H | O | H | $OCH_3$ | $OCH_3$ | CH |
| $OCF_2H$ | $CH_3$ | H | H | O | H | Cl | $OCH_3$ | CH |
| $OCF_2H$ | $CH_3$ | H | H | O | H | $CH_3$ | $OCH_3$ | CH |
| $OCF_2H$ | $CH_3$ | H | H | O | H | $CH_3$ | $CH_3$ | CH |
| $OCF_2H$ | $CH_3$ | H | H | O | H | $OCH_3$ | $OCH_3$ | N |
| $OCF_2H$ | $CH_3$ | H | H | O | H | $CH_3$ | $OCH_3$ | N |
| $OCF_2H$ | $CH_3$ | H | H | O | H | $CH_3$ | $CH_3$ | N |
| $OCF_2H$ | $CH_3$ | H | H | O | H | $OCH_2CH_3$ | $OCH_2CH_3$ | N |
| $OCF_2H$ | $CH_3$ | H | H | O | H | $NHCH_3$ | $OCH_2CH_3$ | N |
| $OCF_2H$ | $CH_3$ | H | H | O | H | $N(CH_3)_2$ | $OCH_2CH_3$ | N |
| $OCF_2H$ | $CH_3$ | H | H | O | H | $N(CH_3)_2$ | $OCH_3$ | N |
| $OCF_2H$ | $CH_3$ | H | H | O | H | $N(CH_3)_2$ | $OCH_2CF_3$ | N |
| $OCF_2H$ | $CH_3$ | H | H | O | $CH_3$ | $CH_3$ | $OCH_3$ | N |
| $OCF_2H$ | $CH_3$ | H | H | S | H | $OCH_3$ | $OCH_3$ | CH |
| $OCF_2H$ | $CH_3$ | H | H | S | H | Cl | $OCH_3$ | CH |
| $OCF_2H$ | $CH_3$ | H | H | S | H | $CH_3$ | $OCH_3$ | CH |
| $OCF_2H$ | $CH_3$ | H | H | S | H | $CH_3$ | $CH_3$ | CH |
| $OCF_2H$ | $CH_3$ | H | H | S | H | $OCH_3$ | $OCH_3$ | N |
| $OCF_2H$ | $CH_3$ | H | H | S | H | $CH_3$ | $OCH_3$ | N |

-continued

| | | | | | | | | |
|---|---|---|---|---|---|---|---|---|
| $OCF_2H$ | $CH_2CH{=}CH_2$ | H | H | O | H | $OCH_3$ | $OCH_3$ | CH |
| $OCF_2H$ | $CH_2CH{=}CH_2$ | H | H | O | H | Cl | $OCH_3$ | CH |
| $OCF_2H$ | $CH_2CH{=}CH_2$ | H | H | O | H | $CH_3$ | $OCH_3$ | CH |
| $OCF_2H$ | $CH_2CH{=}CH_2$ | H | H | O | H | $CH_3$ | $CH_3$ | CH |
| $OCF_2H$ | $CH_2CH{=}CH_2$ | H | H | O | H | $OCH_3$ | $OCH_3$ | N |
| $OCF_2H$ | $CH_2CH{=}CH_2$ | H | H | O | H | $CH_3$ | $OCH_3$ | N |
| $OCF_2H$ | $CH_2CH{=}CH_2$ | H | H | O | H | $CH_3$ | $CH_3$ | N |
| $OCF_2H$ | $CH_2CH{=}CH_2$ | H | H | O | H | $OCH_2CH_3$ | $OCH_2CH_3$ | N |
| $OCF_2H$ | $CH_2CH{=}CH_2$ | H | H | O | H | $NHCH_3$ | $OCH_2CH_3$ | N |
| $OCF_2H$ | $CH_2CH{=}CH_2$ | H | H | O | H | $N(CH_3)_2$ | $OCH_2CH_3$ | N |
| $OCF_2H$ | $CH_2CH{=}CH_2$ | H | H | O | H | $N(CH_3)_2$ | $OCH_3$ | N |
| $OCF_2H$ | $CH_2CH{=}CH_2$ | H | H | O | H | $N(CH_3)_2$ | $OCH_2CF_3$ | N |
| $OCF_2H$ | $CH_2CH{=}CH_2$ | H | H | O | $CH_3$ | $CH_3$ | $OCH_3$ | N |
| $OCF_2H$ | $CH_2CH{=}CH_2$ | H | H | S | H | $OCH_3$ | $OCH_3$ | CH |
| $OCF_2H$ | $CH_2CH{=}CH_2$ | H | H | S | H | Cl | $OCH_3$ | CH |
| $OCF_2H$ | $CH_2CH{=}CH_2$ | H | H | S | H | $CH_3$ | $OCH_3$ | CH |
| $OCF_2H$ | $CH_2CH{=}CH_2$ | H | H | S | H | $CH_3$ | $CH_3$ | CH |
| $OCF_2H$ | $CH_2CH{=}CH_2$ | H | H | S | H | $OCH_3$ | $OCH_3$ | N |
| $OCF_2H$ | $CH_2CH{=}CH_2$ | H | H | S | H | $CH_3$ | $OCH_3$ | N |
| $OCF_2H$ | $CH_3$ | $CH_3$ | H | O | H | $OCH_3$ | $OCH_3$ | CH |
| $OCF_2H$ | $CH_3$ | $CH_3$ | H | O | H | Cl | $OCH_3$ | CH |
| $OCF_2H$ | $CH_3$ | $CH_3$ | H | O | H | $CH_3$ | $OCH_3$ | CH |
| $OCF_2H$ | $CH_3$ | $CH_3$ | H | O | H | $CH_3$ | $CH_3$ | CH |
| $OCF_2H$ | $CH_3$ | $CH_3$ | H | O | H | $OCH_3$ | $OCH_3$ | N |
| $OCF_2H$ | $CH_3$ | $CH_3$ | H | O | H | $CH_3$ | $OCH_3$ | N |
| $OCF_2H$ | $CH_3$ | $CH_3$ | H | O | H | $CH_3$ | $CH_3$ | N |
| $OCF_2H$ | $CH_3$ | $CH_3$ | H | O | H | $OCH_2CH_3$ | $OCH_2CH_3$ | N |
| $OCF_2H$ | $CH_3$ | $CH_3$ | H | O | H | $NHCH_3$ | $OCH_2CH_3$ | N |
| $OCF_2H$ | $CH_3$ | $CH_3$ | H | O | H | $N(CH_3)_2$ | $OCH_2CH_3$ | N |
| $OCF_2H$ | $CH_3$ | $CH_3$ | H | O | H | $N(CH_3)_2$ | $OCH_3$ | N |
| $OCF_2H$ | $CH_3$ | $CH_3$ | H | O | H | $N(CH_3)_2$ | $OCH_2CF_3$ | N |
| $OCF_2H$ | $CH_3$ | $CH_3$ | H | O | $CH_3$ | $CH_3$ | $OCH_3$ | N |
| $OCF_2H$ | $CH_3$ | $CH_3$ | H | S | H | $OCH_3$ | $OCH_3$ | CH |
| $OCF_2H$ | $CH_3$ | $CH_3$ | H | S | H | Cl | $OCH_3$ | CH |
| $OCF_2H$ | $CH_3$ | $CH_3$ | H | S | H | $CH_3$ | $OCH_3$ | CH |
| $OCF_2H$ | $CH_3$ | $CH_3$ | H | S | H | $CH_3$ | $CH_3$ | CH |
| $OCF_2H$ | $CH_3$ | $CH_3$ | H | S | H | $OCH_3$ | $OCH_3$ | N |
| $OCF_2H$ | $CH_3$ | $CH_3$ | H | S | H | $CH_3$ | $OCH_3$ | N |
| $OCF_2H$ | $-CH_2CH_2CH_2-$ | | H | O | H | $OCH_3$ | $OCH_3$ | CH |
| $OCF_2H$ | $-CH_2CH_2CH_2-$ | | H | O | H | Cl | $OCH_3$ | CH |
| $OCF_2H$ | $-CH_2CH_2CH_2-$ | | H | O | H | $CH_3$ | $OCH_3$ | CH |
| $OCF_2H$ | $-CH_2CH_2CH_2-$ | | H | O | H | $CH_3$ | $CH_3$ | CH |
| $OCF_2H$ | $-CH_2CH_2CH_2-$ | | H | O | H | $OCH_3$ | $OCH_3$ | N |
| $OCF_2H$ | $-CH_2CH_2CH_2-$ | | H | O | H | $CH_3$ | $OCH_3$ | N |
| $OCF_2H$ | $-CH_2CH_2CH_2-$ | | H | O | H | $CH_3$ | $CH_3$ | N |
| $OCF_2H$ | $-CH_2CH_2CH_2-$ | | H | O | H | $OCH_2CH_3$ | $OCH_2CH_3$ | N |
| $OCF_2H$ | $-CH_2CH_2CH_2-$ | | H | O | H | $NHCH_3$ | $OCH_2CH_3$ | N |
| $OCF_2H$ | $-CH_2CH_2CH_2-$ | | H | O | H | $N(CH_3)_2$ | $OCH_2CH_3$ | N |
| $OCF_2H$ | $-CH_2CH_2CH_2-$ | | H | O | H | $N(CH_3)_2$ | $OCH_3$ | N |
| $OCF_2H$ | $-CH_2CH_2CH_2-$ | | H | O | H | $N(CH_3)_2$ | $OCH_2CF_3$ | N |
| $OCF_2H$ | $-CH_2CH_2CH_2-$ | | H | O | $CH_3$ | $CH_3$ | $OCH_3$ | N |
| $OCF_2H$ | $-CH_2CH_2CH_2-$ | | H | S | H | $OCH_3$ | $OCH_3$ | CH |
| $OCF_2H$ | $-CH_2CH_2CH_2-$ | | H | S | H | Cl | $OCH_3$ | CH |
| $OCF_2H$ | $-CH_2CH_2CH_2-$ | | H | S | H | $CH_3$ | $OCH_3$ | CH |
| $OCF_2H$ | $-CH_2CH_2CH_2-$ | | H | S | H | $CH_3$ | $CH_3$ | CH |
| $OCF_2H$ | $-CH_2CH_2CH_2-$ | | H | S | H | $OCH_3$ | $OCH_3$ | N |
| $OCF_2H$ | $-CH_2CH_2CH_2-$ | | H | S | H | $CH_3$ | $OCH_3$ | N |
| $SCF_2H$ | $CH_3$ | H | H | O | H | $OCH_3$ | $OCH_3$ | CH |
| $SCF_2H$ | $CH_3$ | H | H | O | H | Cl | $OCH_3$ | CH |
| $SCF_2H$ | $CH_3$ | H | H | O | H | $CH_3$ | $OCH_3$ | CH |
| $SCF_2H$ | $CH_3$ | H | H | O | H | $CH_3$ | $CH_3$ | CH |
| $SCF_2H$ | $CH_3$ | H | H | O | H | $OCH_3$ | $OCH_3$ | N |
| $SCF_2H$ | $CH_3$ | H | H | O | H | $CH_3$ | $OCH_3$ | N |
| $SCF_2H$ | $CH_3$ | H | H | O | H | $CH_3$ | $CH_3$ | N |
| $SCF_2H$ | $CH_3$ | H | H | O | H | $OCH_2CH_3$ | $OCH_2CH_3$ | N |
| $SCF_2H$ | $CH_3$ | H | H | O | H | $NHCH_3$ | $OCH_2CH_3$ | N |
| $SCF_2H$ | $CH_3$ | H | H | O | H | $N(CH_3)_2$ | $OCH_2CH_3$ | N |
| $SCF_2H$ | $CH_3$ | H | H | O | H | $N(CH_3)_2$ | $OCH_3$ | N |
| $SCF_2H$ | $CH_3$ | H | H | O | H | $N(CH_3)_2$ | $OCH_2CF_3$ | N |
| $SCF_2H$ | $CH_3$ | H | H | O | $CH_3$ | $CH_3$ | $OCH_3$ | N |
| $SCF_2H$ | $CH_3$ | H | H | S | H | $OCH_3$ | $OCH_3$ | CH |
| $SCF_2H$ | $CH_3$ | H | H | S | H | Cl | $OCH_3$ | CH |
| $SCF_2H$ | $CH_3$ | H | H | S | H | $CH_3$ | $OCH_3$ | CH |
| $SCF_2H$ | $CH_3$ | H | H | S | H | $CH_3$ | $CH_3$ | CH |
| $SCF_2H$ | $CH_3$ | H | H | S | H | $OCH_3$ | $OCH_3$ | N |
| $SCF_2H$ | $CH_3$ | H | H | S | H | $CH_3$ | $OCH_3$ | N |
| $SCF_2H$ | $CH_2CH{=}CH_2$ | H | H | O | H | $OCH_3$ | $OCH_3$ | CH |
| $SCF_2H$ | $CH_2CH{=}CH_2$ | H | H | O | H | Cl | $OCH_3$ | CH |
| $SCF_2H$ | $CH_2CH{=}CH_2$ | H | H | O | H | $CH_3$ | $OCH_3$ | CH |
| $SCF_2H$ | $CH_2CH{=}CH_2$ | H | H | O | H | $CH_3$ | $CH_3$ | CH |
| $SCF_2H$ | $CH_2CH{=}CH_2$ | H | H | O | H | $OCH_3$ | $OCH_3$ | N |
| $SCF_2H$ | $CH_2CH{=}CH_2$ | H | H | O | H | $CH_3$ | $OCH_3$ | N |

-continued

| | | | | | | | | |
|---|---|---|---|---|---|---|---|---|
| $SCF_2H$ | $CH_2CH{=}CH_2$ | H | H | O | H | $CH_3$ | $CH_3$ | N |
| $SCF_2H$ | $CH_2CH{=}CH_2$ | H | H | O | H | $OCH_2CH_3$ | $OCH_2CH_3$ | N |
| $SCF_2H$ | $CH_2CH{=}CH_2$ | H | H | O | H | $NHCH_3$ | $OCH_2CH_3$ | N |
| $SCF_2H$ | $CH_2CH{=}CH_2$ | H | H | O | H | $N(CH_3)_2$ | $OCH_2CH_3$ | N |
| $SCF_2H$ | $CH_2CH{=}CH_2$ | H | H | O | H | $N(CH_3)_2$ | $OCH_3$ | N |
| $SCF_2H$ | $CH_2CH{=}CH_2$ | H | H | O | H | $N(CH_3)_2$ | $OCH_2CF_3$ | N |
| $SCF_2H$ | $CH_2CH{=}CH_2$ | H | H | O | $CH_3$ | $CH_3$ | $OCH_3$ | N |
| $SCF_2H$ | $CH_2CH{=}CH_2$ | H | H | S | H | $OCH_3$ | $OCH_3$ | CH |
| $SCF_2H$ | $CH_2CH{=}CH_2$ | H | H | S | H | Cl | $OCH_3$ | CH |
| $SCF_2H$ | $CH_2CH{=}CH_2$ | H | H | S | H | $CH_3$ | $OCH_3$ | CH |
| $SCF_2H$ | $CH_2CH{=}CH_2$ | H | H | S | H | $CH_3$ | $CH_3$ | CH |
| $SCF_2H$ | $CH_2CH{=}CH_2$ | H | H | S | H | $OCH_3$ | $OCH_3$ | N |
| $SCF_2H$ | $CH_2CH{=}CH_2$ | H | H | S | H | $CH_3$ | $OCH_3$ | N |
| $SCF_2H$ | $CH_3$ | $CH_3$ | H | O | H | $OCH_3$ | $OCH_3$ | CH |
| $SCF_2H$ | $CH_3$ | $CH_3$ | H | O | H | Cl | $OCH_3$ | CH |
| $SCF_2H$ | $CH_3$ | $CH_3$ | H | O | H | $CH_3$ | $OCH_3$ | CH |
| $SCF_2H$ | $CH_3$ | $CH_3$ | H | O | H | $CH_3$ | $CH_3$ | CH |
| $SCF_2H$ | $CH_3$ | $CH_3$ | H | O | H | $OCH_3$ | $OCH_3$ | N |
| $SCF_2H$ | $CH_3$ | $CH_3$ | H | O | H | $CH_3$ | $OCH_3$ | N |
| $SCF_2H$ | $CH_3$ | $CH_3$ | H | O | H | $CH_3$ | $CH_3$ | N |
| $SCF_2H$ | $CH_3$ | $CH_3$ | H | O | H | $OCH_2CH_3$ | $OCH_2CH_3$ | N |
| $SCF_2H$ | $CH_3$ | $CH_3$ | H | O | H | $NHCH_3$ | $OCH_2CH_3$ | N |
| $SCF_2H$ | $CH_3$ | $CH_3$ | H | O | H | $N(CH_3)_2$ | $OCH_2CH_3$ | N |
| $SCF_2H$ | $CH_3$ | $CH_3$ | H | O | H | $N(CH_3)_2$ | $OCH_3$ | N |
| $SCF_2H$ | $CH_3$ | $CH_3$ | H | O | H | $N(CH_3)_2$ | $OCH_2CF_3$ | N |
| $SCF_2H$ | $CH_3$ | $CH_3$ | H | O | $CH_3$ | $CH_3$ | $OCH_3$ | N |
| $SCF_2H$ | $CH_3$ | $CH_3$ | H | S | H | $OCH_3$ | $OCH_3$ | CH |
| $SCF_2H$ | $CH_3$ | $CH_3$ | H | S | H | Cl | $OCH_3$ | CH |
| $SCF_2H$ | $CH_3$ | $CH_3$ | H | S | H | $CH_3$ | $OCH_3$ | CH |
| $SCF_2H$ | $CH_3$ | $CH_3$ | H | S | H | $CH_3$ | $CH_3$ | CH |
| $SCF_2H$ | $CH_3$ | $CH_3$ | H | S | H | $OCH_3$ | $OCH_3$ | N |
| $SCF_2H$ | $CH_3$ | $CH_3$ | H | S | H | $CH_3$ | $OCH_3$ | N |
| $SCF_2H$ | $—CH_2CH_2CH_2—$ | | H | O | H | $OCH_3$ | $OCH_3$ | CH |
| $SCF_2H$ | $—CH_2CH_2CH_2—$ | | H | O | H | Cl | $OCH_3$ | CH |
| $SCF_2H$ | $—CH_2CH_2CH_2—$ | | H | O | H | $CH_3$ | $OCH_3$ | CH |
| $SCF_2H$ | $—CH_2CH_2CH_2—$ | | H | O | H | $CH_3$ | $CH_3$ | CH |
| $SCF_2H$ | $—CH_2CH_2CH_2—$ | | H | O | H | $OCH_3$ | $OCH_3$ | N |
| $SCF_2H$ | $—CH_2CH_2CH_2—$ | | H | O | H | $CH_3$ | $OCH_3$ | N |
| $SCF_2H$ | $—CH_2CH_2CH_2—$ | | H | O | H | $CH_3$ | $CH_3$ | N |
| $SCF_2H$ | $—CH_2CH_2CH_2—$ | | H | O | H | $OCH_2CH_3$ | $OCH_2CH_3$ | N |
| $SCF_2H$ | $—CH_2CH_2CH_2—$ | | H | O | H | $NHCH_3$ | $OCH_2CH_3$ | N |
| $SCF_2H$ | $—CH_2CH_2CH_2—$ | | H | O | H | $N(CH_3)_2$ | $OCH_2CH_3$ | N |
| $SCF_2H$ | $—CH_2CH_2CH_2—$ | | H | O | H | $N(CH_3)_2$ | $OCH_3$ | N |
| $SCF_2H$ | $—CH_2CH_2CH_2—$ | | H | O | H | $N(CH_3)_2$ | $OCH_2CF_3$ | N |
| $SCF_2H$ | $—CH_2CH_2CH_2—$ | | H | O | $CH_3$ | $CH_3$ | $OCH_3$ | N |
| $SCF_2H$ | $—CH_2CH_2CH_2—$ | | H | S | H | $OCH_3$ | $OCH_3$ | CH |
| $SCF_2H$ | $—CH_2CH_2CH_2—$ | | H | S | H | Cl | $OCH_3$ | CH |
| $SCF_2H$ | $—CH_2CH_2CH_2—$ | | H | S | H | $CH_3$ | $OCH_3$ | CH |
| $SCF_2H$ | $—CH_2CH_2CH_2—$ | | H | S | H | $CH_3$ | $CH_3$ | CH |
| $SCF_2H$ | $—CH_2CH_2CH_2—$ | | H | S | H | $OCH_3$ | $OCH_3$ | N |
| $SCF_2H$ | $—CH_2CH_2CH_2—$ | | H | S | H | $CH_3$ | $OCH_3$ | N |
| $NO_2$ | $CH_3$ | H | H | O | H | $OCH_3$ | $OCH_3$ | CH |
| $NO_2$ | $CH_3$ | H | H | O | H | Cl | $OCH_3$ | CH |
| $NO_2$ | $CH_3$ | H | H | O | H | $CH_3$ | $OCH_3$ | CH |
| $NO_2$ | $CH_3$ | H | H | O | H | $CH_3$ | $CH_3$ | CH |
| $NO_2$ | $CH_3$ | H | H | O | H | $OCH_3$ | $OCH_3$ | N |
| $NO_2$ | $CH_3$ | H | H | O | H | $CH_3$ | $OCH_3$ | N |
| $NO_2$ | $CH_3$ | H | H | O | H | $CH_3$ | $CH_3$ | N |
| $NO_2$ | $CH_3$ | H | H | O | H | $OCH_2CH_3$ | $OCH_2CH_3$ | N |
| $NO_2$ | $CH_3$ | H | H | O | H | $NHCH_3$ | $OCH_2CH_3$ | N |
| $NO_2$ | $CH_3$ | H | H | O | H | $N(CH_3)_2$ | $OCH_2CH_3$ | N |
| $NO_2$ | $CH_3$ | H | H | O | H | $N(CH_3)_2$ | $OCH_3$ | N |
| $NO_2$ | $CH_3$ | H | H | O | H | $N(CH_3)_2$ | $OCH_2CF_3$ | N |
| $NO_2$ | $CH_3$ | H | H | O | $CH_3$ | $CH_3$ | $OCH_3$ | N |
| $NO_2$ | $CH_3$ | H | H | S | H | $OCH_3$ | $OCH_3$ | CH |
| $NO_2$ | $CH_3$ | H | H | S | H | Cl | $OCH_3$ | CH |
| $NO_2$ | $CH_3$ | H | H | S | H | $CH_3$ | $OCH_3$ | CH |
| $NO_2$ | $CH_3$ | H | H | S | H | $CH_3$ | $CH_3$ | CH |
| $NO_2$ | $CH_3$ | H | H | S | H | $OCH_3$ | $OCH_3$ | N |
| $NO_2$ | $CH_3$ | H | H | S | H | $CH_3$ | $OCH_3$ | N |
| $NO_2$ | $CH_2CH{=}CH_2$ | H | H | O | H | $OCH_3$ | $OCH_3$ | CH |
| $NO_2$ | $CH_2CH{=}CH_2$ | H | H | O | H | Cl | $OCH_3$ | CH |
| $NO_2$ | $CH_2CH{=}CH_2$ | H | H | O | H | $CH_3$ | $OCH_3$ | CH |
| $NO_2$ | $CH_2CH{=}CH_2$ | H | H | O | H | $CH_3$ | $CH_3$ | CH |
| $NO_2$ | $CH_2CH{=}CH_2$ | H | H | O | H | $OCH_3$ | $OCH_3$ | N |
| $NO_2$ | $CH_2CH{=}CH_2$ | H | H | O | H | $CH_3$ | $OCH_3$ | N |
| $NO_2$ | $CH_2CH{=}CH_2$ | H | H | O | H | $CH_3$ | $CH_3$ | N |
| $NO_2$ | $CH_2CH{=}CH_2$ | H | H | O | H | $OCH_2CH_3$ | $OCH_2CH_3$ | N |
| $NO_2$ | $CH_2CH{=}CH_2$ | H | H | O | H | $NHCH_3$ | $OCH_2CH_3$ | N |
| $NO_2$ | $CH_2CH{=}CH_2$ | H | H | O | H | $N(CH_3)_2$ | $OCH_2CH_3$ | N |
| $NO_2$ | $CH_2CH{=}CH_2$ | H | H | O | H | $N(CH_3)_2$ | $OCH_3$ | N |
| $NO_2$ | $CH_2CH{=}CH_2$ | H | H | O | H | $N(CH_3)_2$ | $OCH_2CF_3$ | N |

-continued

| | | | | | | | | |
|---|---|---|---|---|---|---|---|---|
| $NO_2$ | $CH_2CH{=}CH_2$ | H | H | O | $CH_3$ | $CH_3$ | $OCH_3$ | N |
| $NO_2$ | $CH_2CH{=}CH_2$ | H | H | S | H | $OCH_3$ | $OCH_3$ | CH |
| $NO_2$ | $CH_2CH{=}CH_2$ | H | H | S | H | Cl | $OCH_3$ | CH |
| $NO_2$ | $CH_2CH{=}CH_2$ | H | H | S | H | $CH_3$ | $OCH_3$ | CH |
| $NO_2$ | $CH_2CH{=}CH_2$ | H | H | S | H | $CH_3$ | $CH_3$ | CH |
| $NO_2$ | $CH_2CH{=}CH_2$ | H | H | S | H | $OCH_3$ | $OCH_3$ | N |
| $NO_2$ | $CH_2CH{=}CH_2$ | H | H | S | H | $CH_3$ | $OCH_3$ | N |
| $NO_2$ | $CH_3$ | $CH_3$ | H | O | H | $OCH_3$ | $OCH_3$ | CH |
| $NO_2$ | $CH_3$ | $CH_3$ | H | O | H | Cl | $OCH_3$ | CH |
| $NO_2$ | $CH_3$ | $CH_3$ | H | O | H | $CH_3$ | $OCH_3$ | CH |
| $NO_2$ | $CH_3$ | $CH_3$ | H | O | H | $CH_3$ | $CH_3$ | CH |
| $NO_2$ | $CH_3$ | $CH_3$ | H | O | H | $OCH_3$ | $OCH_3$ | N |
| $NO_2$ | $CH_3$ | $CH_3$ | H | O | H | $CH_3$ | $OCH_3$ | N |
| $NO_2$ | $CH_3$ | $CH_3$ | H | O | H | $CH_3$ | $CH_3$ | N |
| $NO_2$ | $CH_3$ | $CH_3$ | H | O | H | $OCH_2CH_3$ | $OCH_2CH_3$ | N |
| $NO_2$ | $CH_3$ | $CH_3$ | H | O | H | $NHCH_3$ | $OCH_2CH_3$ | N |
| $NO_2$ | $CH_3$ | $CH_3$ | H | O | H | $N(CH_3)_2$ | $OCH_2CH_3$ | N |
| $NO_2$ | $CH_3$ | $CH_3$ | H | O | H | $N(CH_3)_2$ | $OCH_3$ | N |
| $NO_2$ | $CH_3$ | $CH_3$ | H | O | H | $N(CH_3)_2$ | $OCH_2CF_3$ | N |
| $NO_2$ | $CH_3$ | $CH_3$ | H | O | $CH_3$ | $CH_3$ | $OCH_3$ | N |
| $NO_2$ | $CH_3$ | $CH_3$ | H | S | H | $OCH_3$ | $OCH_3$ | CH |
| $NO_2$ | $CH_3$ | $CH_3$ | H | S | H | Cl | $OCH_3$ | CH |
| $NO_2$ | $CH_3$ | $CH_3$ | H | S | H | $CH_3$ | $OCH_3$ | CH |
| $NO_2$ | $CH_3$ | $CH_3$ | H | S | H | $CH_3$ | $CH_3$ | CH |
| $NO_2$ | $CH_3$ | $CH_3$ | H | S | H | $OCH_3$ | $OCH_3$ | N |
| $NO_2$ | $CH_3$ | $CH_3$ | H | S | H | $CH_3$ | $OCH_3$ | N |
| $NO_2$ | $-CH_2CH_2CH_2-$ | | H | O | H | $OCH_3$ | $OCH_3$ | CH |
| $NO_2$ | $-CH_2CH_2CH_2-$ | | H | O | H | Cl | $OCH_3$ | CH |
| $NO_2$ | $-CH_2CH_2CH_2-$ | | H | O | H | $CH_3$ | $OCH_3$ | CH |
| $NO_2$ | $-CH_2CH_2CH_2-$ | | H | O | H | $CH_3$ | $CH_3$ | CH |
| $NO_2$ | $-CH_2CH_2CH_2-$ | | H | O | H | $OCH_3$ | $OCH_3$ | N |
| $NO_2$ | $-CH_2CH_2CH_2-$ | | H | O | H | $CH_3$ | $OCH_3$ | N |
| $NO_2$ | $-CH_2CH_2CH_2-$ | | H | O | H | $CH_3$ | $CH_3$ | N |
| $NO_2$ | $-CH_2CH_2CH_2-$ | | H | O | H | $OCH_2CH_3$ | $OCH_2CH_3$ | N |
| $NO_2$ | $-CH_2CH_2CH_2-$ | | H | O | H | $NHCH_3$ | $OCH_2CH_3$ | N |
| $NO_2$ | $-CH_2CH_2CH_2-$ | | H | O | H | $N(CH_3)_2$ | $OCH_2CH_3$ | N |
| $NO_2$ | $-CH_2CH_2CH_2-$ | | H | O | H | $N(CH_3)_2$ | $OCH_3$ | N |
| $NO_2$ | $-CH_2CH_2CH_2-$ | | H | O | H | $N(CH_3)_2$ | $OCH_2CF_3$ | N |
| $NO_2$ | $-CH_2CH_2CH_2-$ | | H | O | $CH_3$ | $CH_3$ | $OCH_3$ | N |
| $NO_2$ | $-CH_2CH_2CH_2-$ | | H | S | H | $OCH_3$ | $OCH_3$ | CH |
| $NO_2$ | $-CH_2CH_2CH_2-$ | | H | S | H | Cl | $OCH_3$ | CH |
| $NO_2$ | $-CH_2CH_2CH_2-$ | | H | S | H | $CH_3$ | $OCH_3$ | CH |
| $NO_2$ | $-CH_2CH_2CH_2-$ | | H | S | H | $CH_3$ | $CH_3$ | CH |
| $NO_2$ | $-CH_2CH_2CH_2-$ | | H | S | H | $OCH_3$ | $OCH_3$ | N |
| $NO_2$ | $-CH_2CH_2CH_2-$ | | H | S | H | $CH_3$ | $OCH_3$ | N |
| $SO_2CF_2H$ | $CH_3$ | H | H | O | H | $OCH_3$ | $OCH_3$ | CH |
| $SO_2CF_2H$ | $CH_3$ | H | H | O | H | Cl | $OCH_3$ | CH |
| $SO_2CF_2H$ | $CH_3$ | H | H | O | H | $CH_3$ | $OCH_3$ | CH |
| $SO_2CF_2H$ | $CH_3$ | H | H | O | H | $CH_3$ | $CH_3$ | CH |
| $SO_2CF_2H$ | $CH_3$ | H | H | O | H | $OCH_3$ | $OCH_3$ | N |
| $SO_2CF_2H$ | $CH_3$ | H | H | O | H | $CH_3$ | $OCH_3$ | N |
| $SO_2CF_2H$ | $CH_3$ | H | H | O | H | $CH_3$ | $CH_3$ | N |
| $SO_2CF_2H$ | $CH_3$ | H | H | O | H | $OCH_2CH_3$ | $OCH_2CH_3$ | N |
| $SO_2CF_2H$ | $CH_3$ | H | H | O | H | $NHCH_3$ | $OCH_2CH_3$ | N |
| $SO_2CF_2H$ | $CH_3$ | H | H | O | H | $N(CH_3)_2$ | $OCH_2CH_3$ | N |
| $SO_2CF_2H$ | $CH_3$ | H | H | O | H | $N(CH_3)_2$ | $OCH_3$ | N |
| $SO_2CF_2H$ | $CH_3$ | H | H | O | H | $N(CH_3)_2$ | $OCH_2CF_3$ | N |
| $SO_2CF_2H$ | $CH_3$ | H | H | O | $CH_3$ | $CH_3$ | $OCH_3$ | N |
| $SO_2CF_2H$ | $CH_3$ | H | H | SO | H | $OCH_3$ | $OCH_3$ | CH |
| $SO_2CF_2H$ | $CH_3$ | H | H | S | H | Cl | $OCH_3$ | CH |
| $SO_2CF_2H$ | $CH_3$ | H | H | S | H | $CH_3$ | $OCH_3$ | CH |
| $SO_2CF_2H$ | $CH_3$ | H | H | S | H | $CH_3$ | $CH_3$ | CH |
| $SO_2CF_2H$ | $CH_3$ | H | H | S | H | $OCH_3$ | $OCH_3$ | N |
| $SO_2CF_2H$ | $CH_3$ | H | H | S | H | $CH_3$ | $OCH_3$ | N |
| $SO_2CF_2H$ | $CH_2CH{=}CH_2$ | H | H | O | H | $OCH_3$ | $OCH_3$ | CH |
| $SO_2CF_2H$ | $CH_2CH{=}CH_2$ | H | H | O | H | Cl | $OCH_3$ | CH |
| $SO_2CF_2H$ | $CH_2CH{=}CH_2$ | H | H | O | H | $CH_3$ | $OCH_3$ | CH |
| $SO_2CF_2H$ | $CH_2CH{=}CH_2$ | H | H | O | H | $CH_3$ | $CH_3$ | CH |
| $SO_2CF_2H$ | $CH_2CH{=}CH_2$ | H | H | O | H | $OCH_3$ | $OCH_3$ | N |
| $SO_2CF_2H$ | $CH_2CH{=}CH_2$ | H | H | O | H | $CH_3$ | $OCH_3$ | N |
| $SO_2CF_2H$ | $CH_2CH{=}CH_2$ | H | H | O | H | $CH_3$ | $CH_3$ | N |
| $SO_2CF_2H$ | $CH_2CH{=}CH_2$ | H | H | O | H | $OCH_2CH_3$ | $OCH_2CH_3$ | N |
| $SO_2CF_2H$ | $CH_2CH{=}CH_2$ | H | H | O | H | $NHCH_3$ | $OCH_2CH_3$ | N |
| $SO_2CF_2H$ | $CH_2CH{=}CH_2$ | H | H | O | H | $N(CH_3)_2$ | $OCH_2CH_3$ | N |
| $SO_2CF_2H$ | $CH_2CH{=}CH_2$ | H | H | O | H | $N(CH_3)_2$ | $OCH_3$ | N |
| $SO_2CF_2H$ | $CH_2CH{=}CH_2$ | H | H | O | H | $N(CH_3)_2$ | $OCH_2CF_3$ | N |
| $SO_2CF_2H$ | $CH_2CH{=}CH_2$ | H | H | O | $CH_3$ | $CH_3$ | $OCH_3$ | N |
| $SO_2CF_2H$ | $CH_2CH{=}CH_2$ | H | H | S | H | $OCH_3$ | $OCH_3$ | CH |
| $SO_2CF_2H$ | $CH_2CH{=}CH_2$ | H | H | S | H | Cl | $OCH_3$ | CH |
| $SO_2CF_2H$ | $CH_2CH{=}CH_2$ | H | H | S | H | $CH_3$ | $OCH_3$ | CH |
| $SO_2CF_2H$ | $CH_2CH{=}CH_2$ | H | H | S | H | $CH_3$ | $CH_3$ | CH |
| $SO_2CF_2H$ | $CH_2CH{=}CH_2$ | H | H | S | H | $OCH_3$ | $OCH_3$ | N |

-continued

| | | | | | | | | |
|---|---|---|---|---|---|---|---|---|
| $SO_2CF_2H$ | $CH_2CH{=}CH_2$ | H | H | S | H | $CH_3$ | $OCH_3$ | N |
| $SO_2CF_2H$ | $CH_3$ | $CH_3$ | H | OS | H | $OCH_3$ | $OCH_3$ | CH |
| $SO_2CF_2H$ | $CH_3$ | $CH_3$ | H | O | H | Cl | $OCH_3$ | CH |
| $SO_2CF_2H$ | $CH_3$ | $CH_3$ | H | O | H | $CH_3$ | $OCH_3$ | CH |
| $SO_2CF_2H$ | $CH_3$ | $CH_3$ | H | O | H | $CH_3$ | $CH_3$ | CH |
| $SO_2CF_2H$ | $CH_3$ | $CH_3$ | H | O | H | $OCH_3$ | $OCH_3$ | N |
| $SO_2CF_2H$ | $CH_3$ | $CH_3$ | H | O | H | $CH_3$ | $OCH_3$ | N |
| $SO_2CF_2H$ | $CH_3$ | $CH_3$ | H | O | H | $CH_3$ | $CH_3$ | N |
| $SO_2CF_2H$ | $CH_3$ | $CH_3$ | H | O | H | $OCH_2CH_3$ | $OCH_2CH_3$ | N |
| $SO_2CF_2H$ | $CH_3$ | $CH_3$ | H | O | H | $NHCH_3$ | $OCH_2CH_3$ | N |
| $SO_2CF_2H$ | $CH_3$ | $CH_3$ | H | O | H | $N(CH_3)_2$ | $OCH_2CH_3$ | N |
| $SO_2CF_2H$ | $CH_3$ | $CH_3$ | H | O | H | $N(CH_3)_2$ | $OCH_3$ | N |
| $SO_2CF_2H$ | $CH_3$ | $CH_3$ | H | O | H | $N(CH_3)_2$ | $OCH_2CF_3$ | N |
| $SO_2CF_2H$ | $CH_3$ | $CH_3$ | H | O | $CH_3$ | $CH_3$ | $OCH_3$ | N |
| $SO_2CF_2H$ | $CH_3$ | $CH_3$ | H | S | H | $OCH_3$ | $OCH_3$ | CH |
| $SO_2CF_2H$ | $CH_3$ | $CH_3$ | H | S | H | Cl | $OCH_3$ | CH |
| $SO_2CF_2H$ | $CH_3$ | $CH_3$ | H | S | H | $CH_3$ | $OCH_3$ | CH |
| $SO_2CF_2H$ | $CH_3$ | $CH_3$ | H | S | H | $CH_3$ | $CH_3$ | CH |
| $SO_2CF_2H$ | $CH_3$ | $CH_3$ | H | S | H | $OCH_3$ | $OCH_3$ | N |
| $SO_2CF_2H$ | $CH_3$ | $CH_3$ | H | S | H | $CH_3$ | $OCH_3$ | N |
| $SO_2CF_2H$ | $-CH_2CH_2CH_2-$ | | H | O | H | $OCH_3$ | $OCH_3$ | CH |
| $SO_2CF_2H$ | $-CH_2CH_2CH_2-$ | | H | O | H | Cl | $OCH_3$ | CH |
| $SO_2CF_2H$ | $-CH_2CH_2CH_2-$ | | H | O | H | $CH_3$ | $OCH_3$ | CH |
| $SO_2CF_2H$ | $-CH_2CH_2CH_2-$ | | H | O | H | $CH_3$ | $CH_3$ | CH |
| $SO_2CF_2H$ | $-CH_2CH_2CH_2-$ | | H | O | H | $OCH_3$ | $OCH_3$ | N |
| $SO_2CF_2H$ | $-CH_2CH_2CH_2-$ | | H | O | H | $CH_3$ | $OCH_3$ | N |
| $SO_2CF_2H$ | $-CH_2CH_2CH_2-$ | | H | O | H | $CH_3$ | $CH_3$ | N |
| $SO_2CF_2H$ | $-CH_2CH_2CH_2-$ | | H | O | H | $OCH_2CH_3$ | $OCH_2CH_3$ | N |
| $SO_2CF_2H$ | $-CH_2CH_2CH_2-$ | | H | O | H | $NHCH_3$ | $OCH_2CH_3$ | N |
| $SO_2CF_2H$ | $-CH_2CH_2CH_2-$ | | H | O | H | $N(CH_3)_2$ | $OCH_2CH_3$ | N |
| $SO_2CF_2H$ | $-CH_2CH_2CH_2-$ | | H | O | H | $N(CH_3)_2$ | $OCH_3$ | N |
| $SO_2CF_2H$ | $-CH_2CH_2CH_2-$ | | H | O | H | $N(CH_3)_2$ | $OCH_2CF_3$ | N |
| $SO_2CF_2H$ | $-CH_2CH_2CH_2-$ | | H | O | $CH_3$ | $CH_3$ | $OCH_3$ | N |
| $SO_2CF_2H$ | $-CH_2CH_2CH_2-$ | | H | S | H | $OCH_3$ | $OCH_3$ | CH |
| $SO_2CF_2H$ | $-CH_2CH_2CH_2-$ | | H | S | H | Cl | $OCH_3$ | CH |
| $SO_2CF_2H$ | $-CH_2CH_2CH_2-$ | | H | S | H | $CH_3$ | $OCH_3$ | CH |
| $SO_2CF_2H$ | $-CH_2CH_2CH_2-$ | | H | S | H | $CH_3$ | $CH_3$ | CH |
| $SO_2CF_2H$ | $-CH_2CH_2CH_2-$ | | H | S | H | $OCH_3$ | $OCH_3$ | N |
| $SO_2CF_2H$ | $-CH_2CH_2CH_2-$ | | H | S | H | $CH_3$ | $OCH_3$ | N |

TABLE II

GENERAL STRUCTURE 2

| $R_1$ | $R_2$ | $R_3$ | R | X | Y | Z |
|---|---|---|---|---|---|---|
| H | H | H | H | $OCH_3$ | $OCH_3$ | CH |
| H | H | H | H | Cl | $OCH_3$ | CH |
| H | H | H | H | $CH_3$ | $OCH_3$ | CH |
| H | H | H | H | $CH_3$ | $CH_3$ | CH |
| H | H | H | H | $OCH_3$ | $OCH_3$ | N |
| H | H | H | H | $CH_3$ | $OCH_3$ | N |
| H | H | H | H | $NHCH_3$ | $OCH_2CH_3$ | N |
| H | H | H | $CH_3$ | $CH_3$ | $OCH_3$ | N |
| H | $CH_3$ | H | H | $OCH_3$ | $OCH_3$ | CH |
| H | $CH_3$ | H | H | Cl | $OCH_3$ | CH |
| H | $CH_3$ | H | H | $CH_3$ | $OCH_3$ | CH |
| H | $CH_3$ | H | H | $CH_3$ | $CH_3$ | CH |
| H | $CH_3$ | H | H | $OCH_3$ | $OCH_3$ | N |
| H | $CH_3$ | H | H | $CH_3$ | $OCH_3$ | N |
| H | $CH_3$ | H | H | $NHCH_3$ | $OCH_2CH_3$ | N |
| H | $CH_3$ | H | $CH_3$ | $CH_3$ | $OCH_3$ | N |
| H | $CH_2CH_3$ | H | H | $OCH_3$ | $OCH_3$ | CH |
| H | $CH_2CH_3$ | H | H | Cl | $OCH_3$ | CH |
| H | $CH_2CH_3$ | H | H | $CH_3$ | $OCH_3$ | CH |
| H | $CH_2CH_3$ | H | H | $CH_3$ | $CH_3$ | CH |
| H | $CH_2CH_3$ | H | H | $OCH_3$ | $OCH_3$ | N |
| H | $CH_2CH_3$ | H | H | $CH_3$ | $OCH_3$ | N |
| H | $CH_2CH_3$ | H | H | $NHCH_3$ | $OCH_2CH_3$ | N |
| H | $CH_2CH_3$ | H | $CH_3$ | $CH_3$ | $OCH_3$ | N |
| H | $CH_2CF_3$ | H | H | $OCH_3$ | $OCH_3$ | CH |
| H | $CH_2CF_3$ | H | H | Cl | $OCH_3$ | CH |
| H | $CH_2CF_3$ | H | H | $CH_3$ | $OCH_3$ | CH |
| H | $CH_2CF_3$ | H | H | $CH_3$ | $CH_3$ | CH |
| H | $CH_2CF_3$ | H | H | $OCH_3$ | $OCH_3$ | N |
| H | $CH_2CF_3$ | H | H | $CH_3$ | $OCH_3$ | N |
| H | $CH_2CF_3$ | H | H | $NHCH_3$ | $OCH_2CH_3$ | N |
| H | $CH_2CF_3$ | H | $CH_3$ | $CH_3$ | $OCH_3$ | N |
| H | $CH_2CH{=}CH_2$ | H | H | $OCH_3$ | $OCH_3$ | CH |
| H | $CH_2CH{=}CH_2$ | H | H | Cl | $OCH_3$ | CH |
| H | $CH_2CH{=}CH_2$ | H | H | $CH_3$ | $OCH_3$ | CH |
| H | $CH_2CH{=}CH_2$ | H | H | $CH_3$ | $CH_3$ | CH |
| H | $CH_2CH{=}CH_2$ | H | H | $OCH_3$ | $OCH_3$ | N |

TABLE II-continued

GENERAL STRUCTURE 2

| $R_1$ | $R_2$ | $R_3$ | R | X | Y | Z |
|---|---|---|---|---|---|---|
| H | $CH_2CH{=}CH_2$ | H | H | $CH_3$ | $OCH_3$ | N |
| H | $CH_2CH{=}CH_2$ | H | H | $NHCH_3$ | $OCH_2CH_3$ | N |
| H | $CH_2CH{=}CH_2$ | H | $CH_3$ | $CH_3$ | $OCH_3$ | N |
| H | $CH_2C{\equiv}CH$ | H | H | $OCH_3$ | $OCH_3$ | CH |
| H | $CH_2C{\equiv}CH$ | H | H | Cl | $OCH_3$ | CH |
| H | $CH_2C{\equiv}CH$ | H | H | $CH_3$ | $OCH_3$ | CH |
| H | $CH_2C{\equiv}CH$ | H | H | $CH_3$ | $CH_3$ | CH |
| H | $CH_2C{\equiv}CH$ | H | H | $OCH_3$ | $OCH_3$ | N |
| H | $CH_2C{\equiv}CH$ | H | H | $CH_3$ | $OCH_3$ | N |
| H | $CH_2C{\equiv}CH$ | H | H | $NHCH_3$ | $OCH_2CH_3$ | N |
| H | $CH_2C{\equiv}CH$ | H | $CH_3$ | $CH_3$ | $OCH_3$ | N |
| H | $CH_2CH_2Cl$ | H | H | $OCH_3$ | $OCH_3$ | CH |
| H | $CH_2CH_2Cl$ | H | H | Cl | $OCH_3$ | CH |
| H | $CH_2CH_2Cl$ | H | H | $CH_3$ | $OCH_3$ | CH |
| H | $CH_2CH_2Cl$ | H | H | $CH_3$ | $CH_3$ | CH |
| H | $CH_2CH_2Cl$ | H | H | $OCH_3$ | $OCH_3$ | N |
| H | $CH_2CH_2Cl$ | H | H | $CH_3$ | $OCH_3$ | N |
| H | $CH_2CH_2Cl$ | H | H | $NHCH_3$ | $OCH_2CH_3$ | N |
| H | $CH_2CH_2Cl$ | H | $CH_3$ | $CH_3$ | $OCH_3$ | N |
| H | $CH_2CN$ | H | H | $OCH_3$ | $OCH_3$ | CH |
| H | $CH_2CN$ | H | H | Cl | $OCH_3$ | CH |
| H | $CH_2CN$ | H | H | $CH_3$ | $OCH_3$ | CH |
| H | $CH_2CN$ | H | H | $CH_3$ | $CH_3$ | CH |
| H | $CH_2CN$ | H | H | $OCH_3$ | $OCH_3$ | N |
| H | $CH_2CN$ | H | H | $CH_3$ | $OCH_3$ | N |
| H | $CH_2CN$ | H | H | $NHCH_3$ | $OCH_2CH_3$ | N |
| H | $CH_2CN$ | H | $CH_3$ | $CH_3$ | $OCH_3$ | N |
| H | $CH_2CH_2OCH_3$ | H | H | $OCH_3$ | $OCH_3$ | CH |
| H | $CH_2CH_2OCH_3$ | H | H | Cl | $OCH_3$ | CH |
| H | $CH_2CH_2OCH_3$ | H | H | $CH_3$ | $OCH_3$ | CH |
| H | $CH_2CH_2OCH_3$ | H | H | $CH_3$ | $CH_3$ | CH |
| H | $CH_2CH_2OCH_3$ | H | H | $OCH_3$ | $OCH_3$ | N |
| H | $CH_2CH_2OCH_3$ | H | H | $CH_3$ | $OCH_3$ | N |
| H | $CH_2CH_2OCH_3$ | H | H | $NHCH_3$ | $OCH_2CH_3$ | N |
| H | $CH_2CH_2OCH_3$ | H | $CH_3$ | $CH_3$ | $OCH_3$ | N |
| H | cyclo-$C_3H_7$ | H | H | $OCH_3$ | $OCH_3$ | CH |
| H | cyclo-$C_3H_7$ | H | H | Cl | $OCH_3$ | CH |
| H | cyclo-$C_3H_7$ | H | H | $CH_3$ | $OCH_3$ | CH |
| H | cyclo-$C_3H_7$ | H | H | $CH_3$ | $CH_3$ | CH |
| H | cyclo-$C_3H_7$ | H | H | $OCH_3$ | $OCH_3$ | N |
| H | cyclo-$C_3H_7$ | H | H | $CH_3$ | $OCH_3$ | N |
| H | cyclo-$C_3H_7$ | H | H | $NHCH_3$ | $OCH_2CH_3$ | N |
| H | cyclo-$C_3H_7$ | H | $CH_3$ | $CH_3$ | $OCH_3$ | N |
| H | $CH_3$ | $CH_3$ | H | $OCH_3$ | $OCH_3$ | CH |
| H | $CH_3$ | $CH_3$ | H | Cl | $OCH_3$ | CH |
| H | $CH_3$ | $CH_3$ | H | $CH_3$ | $OCH_3$ | CH |
| H | $CH_3$ | $CH_3$ | H | $CH_3$ | $CH_3$ | CH |
| H | $CH_3$ | $CH_3$ | H | $OCH_3$ | $OCH_3$ | N |
| H | $CH_3$ | $CH_3$ | H | $CH_3$ | $OCH_3$ | N |
| H | $CH_3$ | $CH_3$ | H | $NHCH_3$ | $OCH_2CH_3$ | N |
| H | $CH_3$ | $CH_3$ | $CH_3$ | $CH_3$ | $OCH_3$ | N |
| H | $CH_2CH_3$ | $CH_3$ | H | $OCH_3$ | $OCH_3$ | CH |
| H | $CH_2CH_3$ | $CH_3$ | H | Cl | $OCH_3$ | CH |
| H | $CH_2CH_3$ | $CH_3$ | H | $CH_3$ | $OCH_3$ | CH |
| H | $CH_2CH_3$ | $CH_3$ | H | $CH_3$ | $CH_3$ | CH |
| H | $CH_2CH_3$ | $CH_3$ | H | $OCH_3$ | $OCH_3$ | N |
| H | $CH_2CH_3$ | $CH_3$ | H | $CH_3$ | $OCH_3$ | N |
| H | $CH_2CH_3$ | $CH_3$ | H | $NHCH_3$ | $OCH_2CH_3$ | N |
| H | $CH_2CH_3$ | $CH_3$ | $CH_3$ | $CH_3$ | $OCH_3$ | N |
| H | $CH_2CH_3$ | $CH_2CH_3$ | H | $OCH_3$ | $OCH_3$ | CH |
| H | $CH_2CH_3$ | $CH_2CH_3$ | H | Cl | $OCH_3$ | CH |
| H | $CH_2CH_3$ | $CH_2CH_3$ | H | $CH_3$ | $OCH_3$ | CH |
| H | $CH_2CH_3$ | $CH_2CH_3$ | H | $CH_3$ | $CH_3$ | CH |
| H | $CH_2CH_3$ | $CH_2CH_3$ | H | $OCH_3$ | $OCH_3$ | N |
| H | $CH_2CH_3$ | $CH_2CH_3$ | H | $CH_3$ | $OCH_3$ | N |
| H | $CH_2CH_3$ | $CH_2CH_3$ | H | $NHCH_3$ | $OCH_2CH_3$ | N |
| H | $CH_2CH_3$ | $CH_2CH_3$ | $CH_3$ | $CH_3$ | $OCH_3$ | N |
| H | $OCH_3$ | $CH_3$ | H | $OCH_3$ | $OCH_3$ | CH |
| H | $OCH_3$ | $CH_3$ | H | Cl | $OCH_3$ | CH |
| H | $OCH_3$ | $CH_3$ | H | $CH_3$ | $OCH_3$ | CH |
| H | $OCH_3$ | $CH_3$ | H | $CH_3$ | $CH_3$ | CH |
| H | $OCH_3$ | $CH_3$ | H | $OCH_3$ | $OCH_3$ | N |
| H | $OCH_3$ | $CH_3$ | H | $CH_3$ | $OCH_3$ | N |
| H | $OCH_3$ | $CH_3$ | H | $NHCH_3$ | $OCH_2CH_3$ | N |
| H | $OCH_3$ | $CH_3$ | $CH_3$ | $CH_3$ | $OCH_3$ | N |
| H | $N(CH_3)_2$ | $CH_3$ | H | $OCH_3$ | $OCH_3$ | CH |
| H | $N(CH_3)_2$ | $CH_3$ | H | Cl | $OCH_3$ | CH |
| H | $N(CH_3)_2$ | $CH_3$ | H | $CH_3$ | $OCH_3$ | CH |
| H | $N(CH_3)_2$ | $CH_3$ | H | $CH_3$ | $CH_3$ | CH |
| H | $N(CH_3)_2$ | $CH_3$ | H | $OCH_3$ | $OCH_3$ | N |

TABLE II-continued

GENERAL STRUCTURE 2

| $R_1$ | $R_2$ | $R_3$ | R | X | Y | Z |
|---|---|---|---|---|---|---|
| H | $N(CH_3)_2$ | $CH_3$ | H | $CH_3$ | $OCH_3$ | N |
| H | $N(CH_3)_2$ | $CH_3$ | H | $NHCH_3$ | $OCH_2CH_3$ | N |
| H | $N(CH_3)_2$ | $CH_3$ | $CH_3$ | $CH_3$ | $OCH_3$ | N |
| H | $—CH_2CH_2CH_2—$ | | H | $OCH_3$ | $OCH_3$ | CH |
| H | $—CH_2CH_2CH_2—$ | | H | Cl | $OCH_3$ | CH |
| H | $—CH_2CH_2CH_2—$ | | H | $CH_3$ | $OCH_3$ | CH |
| H | $—CH_2CH_2CH_2—$ | | H | $CH_3$ | $CH_3$ | CH |
| H | $—CH_2CH_2CH_2—$ | | H | $OCH_3$ | $OCH_3$ | N |
| H | $—CH_2CH_2CH_2—$ | | H | $CH_3$ | $OCH_3$ | N |
| H | $—CH_2CH_2CH_2—$ | | H | $NHCH_3$ | $OCH_2CH_3$ | N |
| H | $—CH_2CH_2CH_2—$ | | $CH_3$ | $CH_3$ | $OCH_3$ | N |
| Cl | H | H | H | $OCH_3$ | $OCH_3$ | CH |
| Cl | H | H | H | Cl | $OCH_3$ | CH |
| Cl | H | H | H | $CH_3$ | $OCH_3$ | CH |
| Cl | H | H | H | $CH_3$ | $CH_3$ | CH |
| Cl | H | H | H | $OCH_3$ | $OCH_3$ | N |
| Cl | H | H | H | $CH_3$ | $OCH_3$ | N |
| Cl | H | H | H | $NHCH_3$ | $OCH_2CH_3$ | N |
| Cl | H | H | $CH_3$ | $CH_3$ | $OCH_3$ | N |
| Cl | H | $CH_3$ | H | $OCH_3$ | $OCH_3$ | CH |
| Cl | H | $CH_3$ | H | Cl | $OCH_3$ | CH |
| Cl | H | $CH_3$ | H | $CH_3$ | $OCH_3$ | CH |
| Cl | H | $CH_3$ | H | $CH_3$ | $CH_3$ | CH |
| Cl | H | $CH_3$ | H | $OCH_3$ | $OCH_3$ | N |
| Cl | H | $CH_3$ | H | $CH_3$ | $OCH_3$ | N |
| Cl | H | $CH_3$ | H | $NHCH_3$ | $OCH_2CH_3$ | N |
| Cl | H | $CH_3$ | $CH_3$ | $CH_3$ | $OCH_3$ | N |
| Cl | H | $CH_2CH_3$ | H | $OCH_3$ | $OCH_3$ | CH |
| Cl | H | $CH_2CH_3$ | H | Cl | $OCH_3$ | CH |
| Cl | H | $CH_2CH_3$ | H | $CH_3$ | $OCH_3$ | CH |
| Cl | H | $CH_2CH_3$ | H | $CH_3$ | $CH_3$ | CH |
| Cl | H | $CH_2CH_3$ | H | $OCH_3$ | $OCH_3$ | N |
| Cl | H | $CH_2CH_3$ | H | $CH_3$ | $OCH_3$ | N |
| Cl | H | $CH_2CH_3$ | H | $NHCH_3$ | $OCH_2CH_3$ | N |
| Cl | H | $CH_2CH_3$ | $CH_3$ | $CH_3$ | $OCH_3$ | N |
| Cl | H | $CH_2CF_3$ | H | $OCH_3$ | $OCH_3$ | CH |
| Cl | H | $CH_2CF_3$ | H | Cl | $OCH_3$ | CH |
| Cl | H | $CH_2CF_3$ | H | $CH_3$ | $OCH_3$ | CH |
| Cl | H | $CH_2CF_3$ | H | $CH_3$ | $CH_3$ | CH |
| Cl | H | $CH_2CF_3$ | H | $OCH_3$ | $OCH_3$ | N |
| Cl | H | $CH_2CF_3$ | H | $CH_3$ | $OCH_3$ | N |
| Cl | H | $CH_2CF_3$ | H | $NHCH_3$ | $OCH_2CH_3$ | N |
| Cl | H | $CH_2CF_3$ | $CH_3$ | $CH_3$ | $OCH_3$ | N |
| Cl | $CH_2CH=CH_2$ | H | H | $OCH_3$ | $OCH_3$ | CH |
| Cl | $CH_2CH=CH_2$ | H | H | Cl | $OCH_3$ | CH |
| Cl | $CH_2CH=CH_2$ | H | H | $CH_3$ | $OCH_3$ | CH |
| Cl | $CH_2CH=CH_2$ | H | H | $CH_3$ | $CH_3$ | CH |
| Cl | $CH_2CH=CH_2$ | H | H | $OCH_3$ | $OCH_3$ | N |
| Cl | $CH_2CH=CH_2$ | H | H | $CH_3$ | $OCH_3$ | N |
| Cl | $CH_2CH=CH_2$ | H | H | $NHCH_3$ | $OCH_2CH_3$ | N |
| Cl | $CH_2CH=CH_2$ | H | $CH_3$ | $CH_3$ | $OCH_3$ | N |
| Cl | $CH_2C\equiv CH$ | H | H | $OCH_3$ | $OCH_3$ | CH |
| Cl | $CH_2C\equiv CH$ | H | H | Cl | $OCH_3$ | CH |
| Cl | $CH_2C\equiv CH$ | H | H | $CH_3$ | $OCH_3$ | CH |
| Cl | $CH_2C\equiv CH$ | H | H | $CH_3$ | $CH_3$ | CH |
| Cl | $CH_2C\equiv CH$ | H | H | $OCH_3$ | $OCH_3$ | N |
| Cl | $CH_2C\equiv CH$ | H | H | $CH_3$ | $OCH_3$ | N |
| Cl | $CH_2C\equiv CH$ | H | H | $NHCH_3$ | $OCH_2CH_3$ | N |
| Cl | $CH_2C\equiv CH$ | H | $CH_3$ | $CH_3$ | $OCH_3$ | N |
| Cl | $CH_2CH_2Cl$ | H | H | $OCH_3$ | $OCH_3$ | CH |
| Cl | $CH_2CH_2Cl$ | H | H | Cl | $OCH_3$ | CH |
| Cl | $CH_2CH_2Cl$ | H | H | $CH_3$ | $OCH_3$ | CH |
| Cl | $CH_2CH_2Cl$ | H | H | $CH_3$ | $CH_3$ | CH |
| Cl | $CH_2CH_2Cl$ | H | H | $OCH_3$ | $OCH_3$ | N |
| Cl | $CH_2CH_2Cl$ | H | H | $CH_3$ | $OCH_3$ | N |
| Cl | $CH_2CH_2Cl$ | H | H | $NHCH_3$ | $OCH_2CH_3$ | N |
| Cl | $CH_2CH_2Cl$ | H | $CH_3$ | $CH_3$ | $OCH_3$ | N |
| Cl | $CH_2CN$ | H | H | $OCH_3$ | $OCH_3$ | CH |
| Cl | $CH_2CN$ | H | H | Cl | $OCH_3$ | CH |
| Cl | $CH_2CN$ | H | H | $CH_3$ | $OCH_3$ | CH |
| Cl | $CH_2CN$ | H | H | $CH_3$ | $CH_3$ | CH |
| Cl | $CH_2CN$ | H | H | $OCH_3$ | $OCH_3$ | N |
| Cl | $CH_2CN$ | H | H | $CH_3$ | $OCH_3$ | N |
| Cl | $CH_2CN$ | H | H | $NHCH_3$ | $OCH_2CH_3$ | N |
| Cl | $CH_2CN$ | H | $CH_3$ | $CH_3$ | $OCH_3$ | N |
| Cl | $CH_2CH_2OCH_3$ | H | H | $OCH_3$ | $OCH_3$ | CH |
| Cl | $CH_2CH_2OCH_3$ | H | H | Cl | $OCH_3$ | CH |
| Cl | $CH_2CH_2OCH_3$ | H | H | $CH_3$ | $OCH_3$ | CH |
| Cl | $CH_2CH_2OCH_3$ | H | H | $CH_3$ | $CH_3$ | CH |
| Cl | $CH_2CH_2OCH_3$ | H | H | $OCH_3$ | $OCH_3$ | N |

TABLE II-continued

GENERAL STRUCTURE 2

| $R_1$ | $R_2$ | $R_3$ | R | X | Y | Z |
|---|---|---|---|---|---|---|
| Cl | $CH_2CH_2OCH_3$ | H | H | $CH_3$ | $OCH_3$ | N |
| Cl | $CH_2CH_2OCH_3$ | H | H | $NHCH_3$ | $OCH_2CH_3$ | N |
| Cl | $CH_2CH_2OCH_3$ | H | $CH_3$ | $CH_3$ | $OCH_3$ | N |
| Cl | cyclo-$C_3H_7$ | H | H | $OCH_3$ | $OCH_3$ | CH |
| Cl | cyclo-$C_3H_7$ | H | H | Cl | $OCH_3$ | CH |
| Cl | cyclo-$C_3H_7$ | H | H | $CH_3$ | $OCH_3$ | CH |
| Cl | cyclo-$C_3H_7$ | H | H | $CH_3$ | $CH_3$ | CH |
| Cl | cyclo-$C_3H_7$ | H | H | $OCH_3$ | $OCH_3$ | N |
| Cl | cyclo-$C_3H_7$ | H | H | $CH_3$ | $OCH_3$ | N |
| Cl | cyclo-$C_3H_7$ | H | H | $NHCH_3$ | $OCH_2CH_3$ | N |
| Cl | cyclo-$C_3H_7$ | H | $CH_3$ | $CH_3$ | $OCH_3$ | N |
| Cl | $CH_3$ | $CH_3$ | H | $OCH_3$ | $OCH_3$ | CH |
| Cl | $CH_3$ | $CH_3$ | H | Cl | $OCH_3$ | CH |
| Cl | $CH_3$ | $CH_3$ | H | $CH_3$ | $OCH_3$ | CH |
| Cl | $CH_3$ | $CH_3$ | H | $CH_3$ | $CH_3$ | CH |
| Cl | $CH_3$ | $CH_3$ | H | $OCH_3$ | $OCH_3$ | N |
| Cl | $CH_3$ | $CH_3$ | H | $CH_3$ | $OCH_3$ | N |
| Cl | $CH_3$ | $CH_3$ | H | $NHCH_3$ | $OCH_2CH_3$ | N |
| Cl | $CH_3$ | $CH_3$ | $CH_3$ | $CH_3$ | $OCH_3$ | N |
| Cl | $CH_2CH_3$ | $CH_3$ | H | $OCH_3$ | $OCH_3$ | CH |
| Cl | $CH_2CH_3$ | $CH_3$ | H | Cl | $OCH_3$ | CH |
| Cl | $CH_2CH_3$ | $CH_3$ | H | $CH_3$ | $OCH_3$ | CH |
| Cl | $CH_2CH_3$ | $CH_3$ | H | $CH_3$ | $CH_3$ | CH |
| Cl | $CH_2CH_3$ | $CH_3$ | H | $OCH_3$ | $OCH_3$ | N |
| Cl | $CH_2CH_3$ | $CH_3$ | H | $CH_3$ | $OCH_3$ | N |
| Cl | $CH_2CH_3$ | $CH_3$ | H | $NHCH_3$ | $OCH_2CH_3$ | N |
| Cl | $CH_2CH_3$ | $CH_3$ | $CH_3$ | $CH_3$ | $OCH_3$ | N |
| Cl | $CH_2CH_3$ | $CH_2CH_3$ | H | $OCH_3$ | $OCH_3$ | CH |
| Cl | $CH_2CH_3$ | $CH_2CH_3$ | H | Cl | $OCH_3$ | CH |
| Cl | $CH_2CH_3$ | $CH_2CH_3$ | H | $CH_3$ | $OCH_3$ | CH |
| Cl | $CH_2CH_3$ | $CH_2CH_3$ | H | $CH_3$ | $CH_3$ | CH |
| Cl | $CH_2CH_3$ | $CH_2CH_3$ | H | $OCH_3$ | $OCH_3$ | N |
| Cl | $CH_2CH_3$ | $CH_2CH_3$ | H | $CH_3$ | $OCH_3$ | N |
| Cl | $CH_2CH_3$ | $CH_2CH_3$ | H | $NHCH_3$ | $OCH_2CH_3$ | N |
| Cl | $CH_2CH_3$ | $CH_2CH_3$ | $CH_3$ | $CH_3$ | $OCH_3$ | N |
| Cl | $OCH_3$ | $CH_3$ | H | $OCH_3$ | $OCH_3$ | CH |
| Cl | $OCH_3$ | $CH_3$ | H | Cl | $OCH_3$ | CH |
| Cl | $OCH_3$ | $CH_3$ | H | $CH_3$ | $OCH_3$ | CH |
| Cl | $OCH_3$ | $CH_3$ | H | $CH_3$ | $CH_3$ | CH |
| Cl | $OCH_3$ | $CH_3$ | H | $OCH_3$ | $OCH_3$ | N |
| Cl | $OCH_3$ | $CH_3$ | H | $CH_3$ | $OCH_3$ | N |
| Cl | $OCH_3$ | $CH_3$ | H | $NHCH_3$ | $OCH_2CH_3$ | N |
| Cl | $OCH_3$ | $CH_3$ | $CH_3$ | $CH_3$ | $OCH_3$ | N |
| Cl | $N(CH_3)_2$ | $CH_3$ | H | $OCH_3$ | $OCH_3$ | CH |
| Cl | $N(CH_3)_2$ | $CH_3$ | H | Cl | $OCH_3$ | CH |
| Cl | $N(CH_3)_2$ | $CH_3$ | H | $CH_3$ | $OCH_3$ | CH |
| Cl | $N(CH_3)_2$ | $CH_3$ | H | $CH_3$ | $CH_3$ | CH |
| Cl | $N(CH_3)_2$ | $CH_3$ | H | $OCH_3$ | $OCH_3$ | N |
| Cl | $N(CH_3)_2$ | $CH_3$ | H | $CH_3$ | $OCH_3$ | N |
| Cl | $N(CH_3)_2$ | $CH_3$ | H | $NHCH_3$ | $OCH_2CH_3$ | N |
| Cl | $N(CH_3)_2$ | $CH_3$ | $CH_3$ | $CH_3$ | $OCH_3$ | N |
| Cl | $-CH_2CH_2CH_2-$ | | H | $OCH_3$ | $OCH_3$ | CH |
| Cl | $-CH_2CH_2CH_2-$ | | H | Cl | $OCH_3$ | CH |
| Cl | $-CH_2CH_2CH_2-$ | | H | $CH_3$ | $OCH_3$ | CH |
| Cl | $-CH_2CH_2CH_2-$ | | H | $CH_3$ | $CH_3$ | CH |
| Cl | $-CH_2CH_2CH_2-$ | | H | $OCH_3$ | $OCH_3$ | N |
| Cl | $-CH_2CH_2CH_2-$ | | H | $CH_3$ | $OCH_3$ | N |
| Cl | $-CH_2CH_2CH_2-$ | | H | $NHCH_3$ | $OCH_2CH_3$ | N |
| Cl | $-CH_2CH_2CH_2-$ | | $CH_3$ | $CH_3$ | $OCH_3$ | N |
| $CH_3$ | H | H | H | $OCH_3$ | $OCH_3$ | CH |
| $CH_3$ | H | H | H | Cl | $OCH_3$ | CH |
| $CH_3$ | H | H | H | $CH_3$ | $OCH_3$ | CH |
| $CH_3$ | H | H | H | $CH_3$ | $CH_3$ | CH |
| $CH_3$ | H | H | H | $OCH_3$ | $OCH_3$ | N |
| $CH_3$ | H | H | H | $CH_3$ | $OCH_3$ | N |
| $CH_3$ | H | H | H | $NHCH_3$ | $OCH_2CH_3$ | N |
| $CH_3$ | H | H | $CH_3$ | $CH_3$ | $OCH_3$ | N |
| $CH_3$ | H | $CH_3$ | H | $OCH_3$ | $OCH_3$ | CH |
| $CH_3$ | H | $CH_3$ | H | Cl | $OCH_3$ | CH |
| $CH_3$ | H | $CH_3$ | H | $CH_3$ | $OCH_3$ | CH |
| $CH_3$ | H | $CH_3$ | H | $CH_3$ | $CH_3$ | CH |
| $CH_3$ | H | $CH_3$ | H | $OCH_3$ | $OCH_3$ | N |
| $CH_3$ | H | $CH_3$ | H | $CH_3$ | $OCH_3$ | N |
| $CH_3$ | H | $CH_3$ | H | $NHCH_3$ | $OCH_2CH_3$ | N |
| $CH_3$ | H | $CH_3$ | $CH_3$ | $CH_3$ | $OCH_3$ | N |
| $CH_3$ | H | $CH_2CH_3$ | H | $OCH_3$ | $OCH_3$ | CH |
| $CH_3$ | H | $CH_2CH_3$ | H | Cl | $OCH_3$ | CH |
| $CH_3$ | H | $CH_2CH_3$ | H | $CH_3$ | $OCH_3$ | CH |
| $CH_3$ | H | $CH_2CH_3$ | H | $CH_3$ | $CH_3$ | CH |
| $CH_3$ | H | $CH_2CH_3$ | H | $OCH_3$ | $OCH_3$ | N |

TABLE II-continued

GENERAL STRUCTURE 2

| $R_1$ | $R_2$ | $R_3$ | R | X | Y | Z |
|---|---|---|---|---|---|---|
| $CH_3$ | H | $CH_2CH_3$ | H | $CH_3$ | $OCH_3$ | N |
| $CH_3$ | H | $CH_2CH_3$ | H | $NHCH_3$ | $OCH_2CH_3$ | N |
| $CH_3$ | H | $CH_2CH_3$ | $CH_3$ | $CH_3$ | $OCH_3$ | N |
| $CH_3$ | H | $CH_2CF_3$ | H | $OCH_3$ | $OCH_3$ | CH |
| $CH_3$ | H | $CH_2CF_3$ | H | Cl | $OCH_3$ | CH |
| $CH_3$ | H | $CH_2CF_3$ | H | $CH_3$ | $OCH_3$ | CH |
| $CH_3$ | H | $CH_2CF_3$ | H | $CH_3$ | $CH_3$ | CH |
| $CH_3$ | H | $CH_2CF_3$ | H | $OCH_3$ | $OCH_3$ | N |
| $CH_3$ | H | $CH_2CF_3$ | H | $CH_3$ | $OCH_3$ | N |
| $CH_3$ | H | $CH_2CF_3$ | H | $NHCH_3$ | $OCH_2CH_3$ | N |
| $CH_3$ | H | $CH_2CF_3$ | $CH_3$ | $CH_3$ | $OCH_3$ | N |
| $CH_3$ | $CH_2CH{=}CH_2$ | H | H | $OCH_3$ | $OCH_3$ | CH |
| $CH_3$ | $CH_2CH{=}CH_2$ | H | H | Cl | $OCH_3$ | CH |
| $CH_3$ | $CH_2CH{=}CH_2$ | H | H | $CH_3$ | $OCH_3$ | CH |
| $CH_3$ | $CH_2CH{=}CH_2$ | H | H | $CH_3$ | $CH_3$ | CH |
| $CH_3$ | $CH_2CH{=}CH_2$ | H | H | $OCH_3$ | $OCH_3$ | N |
| $CH_3$ | $CH_2CH{=}CH_2$ | H | H | $CH_3$ | $OCH_3$ | N |
| $CH_3$ | $CH_2CH{=}CH_2$ | H | H | $NHCH_3$ | $OCH_2CH_3$ | N |
| $CH_3$ | $CH_2CH{=}CH_2$ | H | $CH_3$ | $CH_3$ | $OCH_3$ | N |
| $CH_3$ | $CH_2C{\equiv}CH$ | H | H | $OCH_3$ | $OCH_3$ | CH |
| $CH_3$ | $CH_2C{\equiv}CH$ | H | H | Cl | $OCH_3$ | CH |
| $CH_3$ | $CH_2C{\equiv}CH$ | H | H | $CH_3$ | $OCH_3$ | CH |
| $CH_3$ | $CH_2C{\equiv}CH$ | H | H | $CH_3$ | $CH_3$ | CH |
| $CH_3$ | $CH_2C{\equiv}CH$ | H | H | $OCH_3$ | $OCH_3$ | N |
| $CH_3$ | $CH_2C{\equiv}CH$ | H | H | $CH_3$ | $OCH_3$ | N |
| $CH_3$ | $CH_2C{\equiv}CH$ | H | H | $NHCH_3$ | $OCH_2CH_3$ | N |
| $CH_3$ | $CH_2C{\equiv}CH$ | H | $CH_3$ | $CH_3$ | $OCH_3$ | N |
| $CH_3$ | $CH_2CH_2Cl$ | H | H | $OCH_3$ | $OCH_3$ | CH |
| $CH_3$ | $CH_2CH_2Cl$ | H | H | Cl | $OCH_3$ | CH |
| $CH_3$ | $CH_2CH_2Cl$ | H | H | $CH_3$ | $OCH_3$ | CH |
| $CH_3$ | $CH_2CH_2Cl$ | H | H | $CH_3$ | $CH_3$ | CH |
| $CH_3$ | $CH_2CH_2Cl$ | H | H | $OCH_3$ | $OCH_3$ | N |
| $CH_3$ | $CH_2CH_2Cl$ | H | H | $CH_3$ | $OCH_3$ | N |
| $CH_3$ | $CH_2CH_2Cl$ | H | H | $NHCH_3$ | $OCH_2CH_3$ | N |
| $CH_3$ | $CH_2CH_2Cl$ | H | $CH_3$ | $CH_3$ | $OCH_3$ | N |
| $CH_3$ | $CH_2CN$ | H | H | $OCH_3$ | $OCH_3$ | CH |
| $CH_3$ | $CH_2CN$ | H | H | Cl | $OCH_3$ | CH |
| $CH_3$ | $CH_2CN$ | H | H | $CH_3$ | $OCH_3$ | CH |
| $CH_3$ | $CH_2CN$ | H | H | $CH_3$ | $CH_3$ | CH |
| $CH_3$ | $CH_2CN$ | H | H | $OCH_3$ | $OCH_3$ | N |
| $CH_3$ | $CH_2CN$ | H | H | $CH_3$ | $OCH_3$ | N |
| $CH_3$ | $CH_2CN$ | H | H | $NHCH_3$ | $OCH_2CH_3$ | N |
| $CH_3$ | $CH_2CN$ | H | $CH_3$ | $CH_3$ | $OCH_3$ | N |
| $CH_3$ | $CH_2CH_2OCH_3$ | H | H | $OCH_3$ | $OCH_3$ | CH |
| $CH_3$ | $CH_2CH_2OCH_3$ | H | H | Cl | $OCH_3$ | CH |
| $CH_3$ | $CH_2CH_2OCH_3$ | H | H | $CH_3$ | $OCH_3$ | CH |
| $CH_3$ | $CH_2CH_2OCH_3$ | H | H | $CH_3$ | $CH_3$ | CH |
| $CH_3$ | $CH_2CH_2OCH_3$ | H | H | $OCH_3$ | $OCH_3$ | N |
| $CH_3$ | $CH_2CH_2OCH_3$ | H | H | $CH_3$ | $OCH_3$ | N |
| $CH_3$ | $CH_2CH_2OCH_3$ | H | H | $NHCH_3$ | $OCH_2CH_3$ | N |
| $CH_3$ | $CH_2CH_2OCH_3$ | H | $CH_3$ | $CH_3$ | $OCH_3$ | N |
| $CH_3$ | cyclo-$C_3H_7$ | H | H | $OCH_3$ | $OCH_3$ | CH |
| $CH_3$ | cyclo-$C_3H_7$ | H | H | Cl | $OCH_3$ | CH |
| $CH_3$ | cyclo-$C_3H_7$ | H | H | $CH_3$ | $OCH_3$ | CH |
| $CH_3$ | cyclo-$C_3H_7$ | H | H | $CH_3$ | $CH_3$ | CH |
| $CH_3$ | cyclo-$C_3H_7$ | H | H | $OCH_3$ | $OCH_3$ | N |
| $CH_3$ | cyclo-$C_3H_7$ | H | H | $CH_3$ | $OCH_3$ | N |
| $CH_3$ | cyclo-$C_3H_7$ | H | H | $NHCH_3$ | $OCH_2CH_3$ | N |
| $CH_3$ | cyclo-$C_3H_7$ | H | $CH_3$ | $CH_3$ | $OCH_3$ | N |
| $CH_3$ | $CH_3$ | $CH_3$ | H | $OCH_3$ | $OCH_3$ | CH |
| $CH_3$ | $CH_3$ | $CH_3$ | H | Cl | $OCH_3$ | CH |
| $CH_3$ | $CH_3$ | $CH_3$ | H | $CH_3$ | $OCH_3$ | CH |
| $CH_3$ | $CH_3$ | $CH_3$ | H | $CH_3$ | $CH_3$ | CH |
| $CH_3$ | $CH_3$ | $CH_3$ | H | $OCH_3$ | $OCH_3$ | N |
| $CH_3$ | $CH_3$ | $CH_3$ | H | $CH_3$ | $OCH_3$ | N |
| $CH_3$ | $CH_3$ | $CH_3$ | H | $NHCH_3$ | $OCH_2CH_3$ | N |
| $CH_3$ | $CH_3$ | $CH_3$ | $CH_3$ | $CH_3$ | $OCH_3$ | N |
| $CH_3$ | $CH_2CH_3$ | $CH_3$ | H | $OCH_3$ | $OCH_3$ | CH |
| $CH_3$ | $CH_2CH_3$ | $CH_3$ | H | Cl | $OCH_3$ | CH |
| $CH_3$ | $CH_2CH_3$ | $CH_3$ | H | $CH_3$ | $OCH_3$ | CH |
| $CH_3$ | $CH_2CH_3$ | $CH_3$ | H | $CH_3$ | $CH_3$ | CH |
| $CH_3$ | $CH_2CH_3$ | $CH_3$ | H | $OCH_3$ | $OCH_3$ | N |
| $CH_3$ | $CH_2CH_3$ | $CH_3$ | H | $CH_3$ | $OCH_3$ | N |
| $CH_3$ | $CH_2CH_3$ | $CH_3$ | H | $NHCH_3$ | $OCH_2CH_3$ | N |
| $CH_3$ | $CH_2CH_3$ | $CH_3$ | $CH_3$ | $CH_3$ | $OCH_3$ | N |
| $CH_3$ | $CH_2CH_3$ | $CH_2CH_3$ | H | $OCH_3$ | $OCH_3$ | CH |
| $CH_3$ | $CH_2CH_3$ | $CH_2CH_3$ | H | Cl | $OCH_3$ | CH |
| $CH_3$ | $CH_2CH_3$ | $CH_2CH_3$ | H | $CH_3$ | $OCH_3$ | CH |
| $CH_3$ | $CH_2CH_3$ | $CH_2CH_3$ | H | $CH_3$ | $CH_3$ | CH |
| $CH_3$ | $CH_2CH_3$ | $CH_2CH_3$ | H | $OCH_3$ | $OCH_3$ | N |

TABLE II-continued

GENERAL STRUCTURE 2

| $R_1$ | $R_2$ | $R_3$ | R | X | Y | Z |
|---|---|---|---|---|---|---|
| $CH_3$ | $CH_2CH_3$ | $CH_2CH_3$ | H | $CH_3$ | $OCH_3$ | N |
| $CH_3$ | $CH_2CH_3$ | $CH_2CH_3$ | H | $NHCH_3$ | $OCH_2CH_3$ | N |
| $CH_3$ | $CH_2CH_3$ | $CH_2CH_3$ | $CH_3$ | $CH_3$ | $OCH_3$ | N |
| $CH_3$ | $OCH_3$ | $CH_3$ | H | $OCH_3$ | $OCH_3$ | CH |
| $CH_3$ | $OCH_3$ | $CH_3$ | H | Cl | $OCH_3$ | CH |
| $CH_3$ | $OCH_3$ | $CH_3$ | H | $CH_3$ | $OCH_3$ | CH |
| $CH_3$ | $OCH_3$ | $CH_3$ | H | $CH_3$ | $CH_3$ | CH |
| $CH_3$ | $OCH_3$ | $CH_3$ | H | $OCH_3$ | $OCH_3$ | N |
| $CH_3$ | $OCH_3$ | $CH_3$ | H | $CH_3$ | $OCH_3$ | N |
| $CH_3$ | $OCH_3$ | $CH_3$ | H | $NHCH_3$ | $OCH_2CH_3$ | N |
| $CH_3$ | $OCH_3$ | $CH_3$ | $CH_3$ | $CH_3$ | $OCH_3$ | N |
| $CH_3$ | $N(CH_3)_2$ | $CH_3$ | H | $OCH_3$ | $OCH_3$ | CH |
| $CH_3$ | $N(CH_3)_2$ | $CH_3$ | H | Cl | $OCH_3$ | CH |
| $CH_3$ | $N(CH_3)_2$ | $CH_3$ | H | $CH_3$ | $OCH_3$ | CH |
| $CH_3$ | $N(CH_3)_2$ | $CH_3$ | H | $CH_3$ | $CH_3$ | CH |
| $CH_3$ | $N(CH_3)_2$ | $CH_3$ | H | $OCH_3$ | $OCH_3$ | N |
| $CH_3$ | $N(CH_3)_2$ | $CH_3$ | H | $CH_3$ | $OCH_3$ | N |
| $CH_3$ | $N(CH_3)_2$ | $CH_3$ | H | $NHCH_3$ | $OCH_2CH_3$ | N |
| $CH_3$ | $N(CH_3)_2$ | $CH_3$ | $CH_3$ | $CH_3$ | $OCH_3$ | N |
| $CH_3$ | $-CH_2CH_2CH_2-$ | | H | $OCH_3$ | $OCH_3$ | CH |
| $CH_3$ | $-CH_2CH_2CH_2-$ | | H | Cl | $OCH_3$ | CH |
| $CH_3$ | $-CH_2CH_2CH_2-$ | | H | $CH_3$ | $OCH_3$ | CH |
| $CH_3$ | $-CH_2CH_2CH_2-$ | | H | $CH_3$ | $CH_3$ | CH |
| $CH_3$ | $-CH_2CH_2CH_2-$ | | H | $OCH_3$ | $OCH_3$ | N |
| $CH_3$ | $-CH_2CH_2CH_2-$ | | H | $CH_3$ | $OCH_3$ | N |
| $CH_3$ | $-CH_2CH_2CH_2-$ | | H | $NHCH_3$ | $OCH_2CH_3$ | N |
| $CH_3$ | $-CH_2CH_2CH_2-$ | | $CH_3$ | $CH_3$ | $OCH_3$ | N |
| $SCH_3$ | H | H | H | $OCH_3$ | $OCH_3$ | CH |
| $SCH_3$ | H | H | H | Cl | $OCH_3$ | CH |
| $SCH_3$ | H | H | H | $CH_3$ | $OCH_3$ | CH |
| $SCH_3$ | H | H | H | $CH_3$ | $CH_3$ | CH |
| $SCH_3$ | H | H | H | $OCH_3$ | $OCH_3$ | N |
| $SCH_3$ | H | H | H | $CH_3$ | $OCH_3$ | N |
| $SCH_3$ | H | H | H | $NHCH_3$ | $OCH_2CH_3$ | N |
| $SCH_3$ | H | H | $CH_3$ | $CH_3$ | $OCH_3$ | N |
| $SCH_3$ | H | $CH_3$ | H | $OCH_3$ | $OCH_3$ | CH |
| $SCH_3$ | H | $CH_3$ | H | Cl | $OCH_3$ | CH |
| $SCH_3$ | H | $CH_3$ | H | $CH_3$ | $OCH_3$ | CH |
| $SCH_3$ | H | $CH_3$ | H | $CH_3$ | $CH_3$ | CH |
| $SCH_3$ | H | $CH_3$ | H | $OCH_3$ | $OCH_3$ | N |
| $SCH_3$ | H | $CH_3$ | H | $CH_3$ | $OCH_3$ | N |
| $SCH_3$ | H | $CH_3$ | H | $NHCH_3$ | $OCH_2CH_3$ | N |
| $SCH_3$ | H | $CH_3$ | $CH_3$ | $CH_3$ | $OCH_3$ | N |
| $SCH_3$ | H | $CH_2CH_3$ | H | $OCH_3$ | $OCH_3$ | CH |
| $SCH_3$ | H | $CH_2CH_3$ | H | Cl | $OCH_3$ | CH |
| $SCH_3$ | H | $CH_2CH_3$ | H | $CH_3$ | $OCH_3$ | CH |
| $SCH_3$ | H | $CH_2CH_3$ | H | $CH_3$ | $CH_3$ | CH |
| $SCH_3$ | H | $CH_2CH_3$ | H | $OCH_3$ | $OCH_3$ | N |
| $SCH_3$ | H | $CH_2CH_3$ | H | $CH_3$ | $OCH_3$ | N |
| $SCH_3$ | H | $CH_2CH_3$ | H | $NHCH_3$ | $OCH_2CH_3$ | N |
| $SCH_3$ | H | $CH_2CH_3$ | $CH_3$ | $CH_3$ | $OCH_3$ | N |
| $SCH_3$ | H | $CH_2CF_3$ | H | $OCH_3$ | $OCH_3$ | CH |
| $SCH_3$ | H | $CH_2CF_3$ | H | Cl | $OCH_3$ | CH |
| $SCH_3$ | H | $CH_2CF_3$ | H | $CH_3$ | $OCH_3$ | CH |
| $SCH_3$ | H | $CH_2CF_3$ | H | $CH_3$ | $CH_3$ | CH |
| $SCH_3$ | H | $CH_2CF_3$ | H | $OCH_3$ | $OCH_3$ | N |
| $SCH_3$ | H | $CH_2CF_3$ | H | $CH_3$ | $OCH_3$ | N |
| $SCH_3$ | H | $CH_2CF_3$ | H | $NHCH_3$ | $OCH_2CH_3$ | N |
| $SCH_3$ | H | $CH_2CF_3$ | $CH_3$ | $CH_3$ | $OCH_3$ | N |
| $SCH_3$ | $CH_2CH{=}CH_2$ | H | H | $OCH_3$ | $OCH_3$ | CH |
| $SCH_3$ | $CH_2CH{=}CH_2$ | H | H | Cl | $OCH_3$ | CH |
| $SCH_3$ | $CH_2CH{=}CH_2$ | H | H | $CH_3$ | $OCH_3$ | CH |
| $SCH_3$ | $CH_2CH{=}CH_2$ | H | H | $CH_3$ | $CH_3$ | CH |
| $SCH_3$ | $CH_2CH{=}CH_2$ | H | H | $OCH_3$ | $OCH_3$ | N |
| $SCH_3$ | $CH_2CH{=}CH_2$ | H | H | $CH_3$ | $OCH_3$ | N |
| $SCH_3$ | $CH_2CH{=}CH_2$ | H | H | $NHCH_3$ | $OCH_2CH_3$ | N |
| $SCH_3$ | $CH_2CH{=}CH_2$ | H | $CH_3$ | $CH_3$ | $OCH_3$ | N |
| $SCH_3$ | $CH_2C{\equiv}CH$ | H | H | $OCH_3$ | $OCH_3$ | CH |
| $SCH_3$ | $CH_2C{\equiv}CH$ | H | H | Cl | $OCH_3$ | CH |
| $SCH_3$ | $CH_2C{\equiv}CH$ | H | H | $CH_3$ | $OCH_3$ | CH |
| $SCH_3$ | $CH_2C{\equiv}CH$ | H | H | $CH_3$ | $CH_3$ | CH |
| $SCH_3$ | $CH_2C{\equiv}CH$ | H | H | $OCH_3$ | $OCH_3$ | N |
| $SCH_3$ | $CH_2C{\equiv}CH$ | H | H | $CH_3$ | $OCH_3$ | N |
| $SCH_3$ | $CH_2C{\equiv}CH$ | H | H | $NHCH_3$ | $OCH_2CH_3$ | N |
| $SCH_3$ | $CH_2C{\equiv}CH$ | H | $CH_3$ | $CH_3$ | $OCH_3$ | N |
| $SCH_3$ | $CH_2CH_2Cl$ | H | H | $OCH_3$ | $OCH_3$ | CH |
| $SCH_3$ | $CH_2CH_2Cl$ | H | H | Cl | $OCH_3$ | CH |
| $SCH_3$ | $CH_2CH_2Cl$ | H | H | $CH_3$ | $OCH_3$ | CH |
| $SCH_3$ | $CH_2CH_2Cl$ | H | H | $CH_3$ | $CH_3$ | CH |
| $SCH_3$ | $CH_2CH_2Cl$ | H | H | $OCH_3$ | $OCH_3$ | N |

TABLE II-continued

GENERAL STRUCTURE 2

| $R_1$ | $R_2$ | $R_3$ | R | X | Y | Z |
|---|---|---|---|---|---|---|
| $SCH_3$ | $CH_2CH_2Cl$ | H | H | $CH_3$ | $OCH_3$ | N |
| $SCH_3$ | $CH_2CH_2Cl$ | H | H | $NHCH_3$ | $OCH_2CH_3$ | N |
| $SCH_3$ | $CH_2CH_2Cl$ | H | $CH_3$ | $CH_3$ | $OCH_3$ | N |
| $SCH_3$ | $CH_2CN$ | H | H | $OCH_3$ | $OCH_3$ | CH |
| $SCH_3$ | $CH_2CN$ | H | H | Cl | $OCH_3$ | CH |
| $SCH_3$ | $CH_2CN$ | H | H | $CH_3$ | $OCH_3$ | CH |
| $SCH_3$ | $CH_2CN$ | H | H | $CH_3$ | $CH_3$ | CH |
| $SCH_3$ | $CH_2CN$ | H | H | $OCH_3$ | $OCH_3$ | N |
| $SCH_3$ | $CH_2CN$ | H | H | $CH_3$ | $OCH_3$ | N |
| $SCH_3$ | $CH_2CN$ | H | H | $NHCH_3$ | $OCH_2CH_3$ | N |
| $SCH_3$ | $CH_2CN$ | H | $CH_3$ | $CH_3$ | $OCH_3$ | N |
| $SCH_3$ | $CH_2CH_2OCH_3$ | H | H | $OCH_3$ | $OCH_3$ | CH |
| $SCH_3$ | $CH_2CH_2OCH_3$ | H | H | Cl | $OCH_3$ | CH |
| $SCH_3$ | $CH_2CH_2OCH_3$ | H | H | $CH_3$ | $OCH_3$ | CH |
| $SCH_3$ | $CH_2CH_2OCH_3$ | H | H | $CH_3$ | $CH_3$ | CH |
| $SCH_3$ | $CH_2CH_2OCH_3$ | H | H | $OCH_3$ | $OCH_3$ | N |
| $SCH_3$ | $CH_2CH_2OCH_3$ | H | H | $CH_3$ | $OCH_3$ | N |
| $SCH_3$ | $CH_2CH_2OCH_3$ | H | H | $NHCH_3$ | $OCH_2CH_3$ | N |
| $SCH_3$ | $CH_2CH_2OCH_3$ | H | $CH_3$ | $CH_3$ | $OCH_3$ | N |
| $SCH_3$ | cyclo-$C_3H_7$ | H | H | $OCH_3$ | $OCH_3$ | CH |
| $SCH_3$ | cyclo-$C_3H_7$ | H | H | Cl | $OCH_3$ | CH |
| $SCH_3$ | cyclo-$C_3H_7$ | H | H | $CH_3$ | $OCH_3$ | CH |
| $SCH_3$ | cyclo-$C_3H_7$ | H | H | $CH_3$ | $CH_3$ | CH |
| $SCH_3$ | cyclo-$C_3H_7$ | H | H | $OCH_3$ | $OCH_3$ | N |
| $SCH_3$ | cyclo-$C_3H_7$ | H | H | $CH_3$ | $OCH_3$ | N |
| $SCH_3$ | cyclo-$C_3H_7$ | H | H | $NHCH_3$ | $OCH_2CH_3$ | N |
| $SCH_3$ | cyclo-$C_3H_7$ | H | $CH_3$ | $CH_3$ | $OCH_3$ | N |
| $SCH_3$ | $CH_3$ | $CH_3$ | H | $OCH_3$ | $OCH_3$ | CH |
| $SCH_3$ | $CH_3$ | $CH_3$ | H | Cl | $OCH_3$ | CH |
| $SCH_3$ | $CH_3$ | $CH_3$ | H | $CH_3$ | $OCH_3$ | CH |
| $SCH_3$ | $CH_3$ | $CH_3$ | H | $CH_3$ | $CH_3$ | CH |
| $SCH_3$ | $CH_3$ | $CH_3$ | H | $OCH_3$ | $OCH_3$ | N |
| $SCH_3$ | $CH_3$ | $CH_3$ | H | $CH_3$ | $OCH_3$ | N |
| $SCH_3$ | $CH_3$ | $CH_3$ | H | $NHCH_3$ | $OCH_2CH_3$ | N |
| $SCH_3$ | $CH_3$ | $CH_3$ | $CH_3$ | $CH_3$ | $OCH_3$ | N |
| $SCH_3$ | $CH_2CH_3$ | $CH_3$ | H | $OCH_3$ | $OCH_3$ | CH |
| $SCH_3$ | $CH_2CH_3$ | $CH_3$ | H | Cl | $OCH_3$ | CH |
| $SCH_3$ | $CH_2CH_3$ | $CH_3$ | H | $CH_3$ | $OCH_3$ | CH |
| $SCH_3$ | $CH_2CH_3$ | $CH_3$ | H | $CH_3$ | $CH_3$ | CH |
| $SCH_3$ | $CH_2CH_3$ | $CH_3$ | H | $OCH_3$ | $OCH_3$ | N |
| $SCH_3$ | $CH_2CH_3$ | $CH_3$ | H | $CH_3$ | $OCH_3$ | N |
| $SCH_3$ | $CH_2CH_3$ | $CH_3$ | H | $NHCH_3$ | $OCH_2CH_3$ | N |
| $SCH_3$ | $CH_2CH_3$ | $CH_3$ | $CH_3$ | $CH_3$ | $OCH_3$ | N |
| $SCH_3$ | $CH_2CH_3$ | $CH_2CH_3$ | H | $OCH_3$ | $OCH_3$ | CH |
| $SCH_3$ | $CH_2CH_3$ | $CH_2CH_3$ | H | Cl | $OCH_3$ | CH |
| $SCH_3$ | $CH_2CH_3$ | $CH_2CH_3$ | H | $CH_3$ | $OCH_3$ | CH |
| $SCH_3$ | $CH_2CH_3$ | $CH_2CH_3$ | H | $CH_3$ | $CH_3$ | CH |
| $SCH_3$ | $CH_2CH_3$ | $CH_2CH_3$ | H | $OCH_3$ | $OCH_3$ | N |
| $SCH_3$ | $CH_2CH_3$ | $CH_2CH_3$ | H | $CH_3$ | $OCH_3$ | N |
| $SCH_3$ | $CH_2CH_3$ | $CH_2CH_3$ | H | $NHCH_3$ | $OCH_2CH_3$ | N |
| $SCH_3$ | $CH_2CH_3$ | $CH_2CH_3$ | $CH_3$ | $CH_3$ | $OCH_3$ | N |
| $SCH_3$ | $OCH_3$ | $CH_3$ | H | $OCH_3$ | $OCH_3$ | CH |
| $SCH_3$ | $OCH_3$ | $CH_3$ | H | Cl | $OCH_3$ | CH |
| $SCH_3$ | $OCH_3$ | $CH_3$ | H | $CH_3$ | $OCH_3$ | CH |
| $SCH_3$ | $OCH_3$ | $CH_3$ | H | $CH_3$ | $CH_3$ | CH |
| $SCH_3$ | $OCH_3$ | $CH_3$ | H | $OCH_3$ | $OCH_3$ | N |
| $SCH_3$ | $OCH_3$ | $CH_3$ | H | $CH_3$ | $OCH_3$ | N |
| $SCH_3$ | $OCH_3$ | $CH_3$ | H | $NHCH_3$ | $OCH_2CH_3$ | N |
| $SCH_3$ | $OCH_3$ | $CH_3$ | $CH_3$ | $CH_3$ | $OCH_3$ | N |
| $SCH_3$ | $N(CH_3)_2$ | $CH_3$ | H | $OCH_3$ | $OCH_3$ | CH |
| $SCH_3$ | $N(CH_3)_2$ | $CH_3$ | H | Cl | $OCH_3$ | CH |
| $SCH_3$ | $N(CH_3)_2$ | $CH_3$ | H | $CH_3$ | $OCH_3$ | CH |
| $SCH_3$ | $N(CH_3)_2$ | $CH_3$ | H | $CH_3$ | $CH_3$ | CH |
| $SCH_3$ | $N(CH_3)_2$ | $CH_3$ | H | $OCH_3$ | $OCH_3$ | N |
| $SCH_3$ | $N(CH_3)_2$ | $CH_3$ | H | $CH_3$ | $OCH_3$ | N |
| $SCH_3$ | $N(CH_3)_2$ | $CH_3$ | H | $NHCH_3$ | $OCH_2CH_3$ | N |
| $SCH_3$ | $N(CH_3)_2$ | $CH_3$ | $CH_3$ | $CH_3$ | $OCH_3$ | N |
| $SCH_3$ | $-CH_2CH_2CH_2-$ | | H | $OCH_3$ | $OCH_3$ | CH |
| $SCH_3$ | $-CH_2CH_2CH_2-$ | | H | Cl | $OCH_3$ | CH |
| $SCH_3$ | $-CH_2CH_2CH_2-$ | | H | $CH_3$ | $OCH_3$ | CH |
| $SCH_3$ | $-CH_2CH_2CH_2-$ | | H | $CH_3$ | $CH_3$ | CH |
| $SCH_3$ | $-CH_2CH_2CH_2-$ | | H | $OCH_3$ | $OCH_3$ | N |
| $SCH_3$ | $-CH_2CH_2CH_2-$ | | H | $CH_3$ | $OCH_3$ | N |
| $SCH_3$ | $-CH_2CH_2CH_2-$ | | H | $NHCH_3$ | $OCH_2CH_3$ | N |
| $SCH_3$ | $-CH_2CH_2CH_2-$ | | $CH_3$ | $CH_3$ | $OCH_3$ | N |
| $SO_2CH_2CH_3$ | H | H | H | $OCH_3$ | $OCH_3$ | CH |
| $SO_2CH_2CH_3$ | H | H | H | Cl | $OCH_3$ | CH |
| $SO_2CH_2CH_3$ | H | H | H | $CH_3$ | $OCH_3$ | CH |
| $SO_2CH_2CH_3$ | H | H | H | $CH_3$ | $CH_3$ | CH |
| $SO_2CH_2CH_3$ | H | H | H | $OCH_3$ | $OCH_3$ | N |

TABLE II-continued

GENERAL STRUCTURE 2

| $R_1$ | $R_2$ | $R_3$ | R | X | Y | Z |
|---|---|---|---|---|---|---|
| $SO_2CH_2CH_3$ | H | H | H | $CH_3$ | $OCH_3$ | N |
| $SO_2CH_2CH_3$ | H | H | H | $NHCH_3$ | $OCH_2CH_3$ | N |
| $SO_2CH_2CH_3$ | H | H | $CH_3$ | $CH_3$ | $OCH_3$ | N |
| $SO_2CH_2CH_3$ | H | $CH_3$ | H | $OCH_3$ | $OCH_3$ | CH |
| $SO_2CH_2CH_3$ | H | $CH_3$ | H | Cl | $OCH_3$ | CH |
| $SO_2CH_2CH_3$ | H | $CH_3$ | H | $CH_3$ | $OCH_3$ | CH |
| $SO_2CH_2CH_3$ | H | $CH_3$ | H | $CH_3$ | $CH_3$ | CH |
| $SO_2CH_2CH_3$ | H | $CH_3$ | H | $OCH_3$ | $OCH_3$ | N |
| $SO_2CH_2CH_3$ | H | $CH_3$ | H | $CH_3$ | $OCH_3$ | N |
| $SO_2CH_2CH_3$ | H | $CH_3$ | H | $NHCH_3$ | $OCH_2CH_3$ | N |
| $SO_2CH_2CH_3$ | H | $CH_3$ | $CH_3$ | $CH_3$ | $OCH_3$ | N |
| $SO_2CH_2CH_3$ | H | $CH_2CH_3$ | H | $OCH_3$ | $OCH_3$ | CH |
| $SO_2CH_2CH_3$ | H | $CH_2CH_3$ | H | Cl | $OCH_3$ | CH |
| $SO_2CH_2CH_3$ | H | $CH_2CH_3$ | H | $CH_3$ | $OCH_3$ | CH |
| $SO_2CH_2CH_3$ | H | $CH_2CH_3$ | H | $CH_3$ | $CH_3$ | CH |
| $SO_2CH_2CH_3$ | H | $CH_2CH_3$ | H | $OCH_3$ | $OCH_3$ | N |
| $SO_2CH_2CH_3$ | H | $CH_2CH_3$ | H | $CH_3$ | $OCH_3$ | N |
| $SO_2CH_2CH_3$ | H | $CH_2CH_3$ | H | $NHCH_3$ | $OCH_2CH_3$ | N |
| $SO_2CH_2CH_3$ | H | $CH_2CH_3$ | $CH_3$ | $CH_3$ | $OCH_3$ | N |
| $SO_2CH_2CH_3$ | H | $CH_2CF_3$ | H | $OCH_3$ | $OCH_3$ | CH |
| $SO_2CH_2CH_3$ | H | $CH_2CF_3$ | H | Cl | $OCH_3$ | CH |
| $SO_2CH_2CH_3$ | H | $CH_2CF_3$ | H | $CH_3$ | $OCH_3$ | CH |
| $SO_2CH_2CH_3$ | H | $CH_2CF_3$ | H | $CH_3$ | $CH_3$ | CH |
| $SO_2CH_2CH_3$ | H | $CH_2CF_3$ | H | $OCH_3$ | $OCH_3$ | N |
| $SO_2CH_2CH_3$ | H | $CH_2CF_3$ | H | $CH_3$ | $OCH_3$ | N |
| $SO_2CH_2CH_3$ | H | $CH_2CF_3$ | H | $NHCH_3$ | $OCH_2CH_3$ | N |
| $SO_2CH_2CH_3$ | H | $CH_2CF_3$ | $CH_3$ | $CH_3$ | $OCH_3$ | N |
| $SO_2CH_2CH_3$ | $CH_2CH{=}CH_2$ | H | H | $OCH_3$ | $OCH_3$ | CH |
| $SO_2CH_2CH_3$ | $CH_2CH{=}CH_2$ | H | H | Cl | $OCH_3$ | CH |
| $SO_2CH_2CH_3$ | $CH_2CH{=}CH_2$ | H | H | $CH_3$ | $OCH_3$ | CH |
| $SO_2CH_2CH_3$ | $CH_2CH{=}CH_2$ | H | H | $CH_3$ | $CH_3$ | CH |
| $SO_2CH_2CH_3$ | $CH_2CH{=}CH_2$ | H | H | $OCH_3$ | $OCH_3$ | N |
| $SO_2CH_2CH_3$ | $CH_2CH{=}CH_2$ | H | H | $CH_3$ | $OCH_3$ | N |
| $SO_2CH_2CH_3$ | $CH_2CH{=}CH_2$ | H | H | $NHCH_3$ | $OCH_2CH_3$ | N |
| $SO_2CH_2CH_3$ | $CH_2CH{=}CH_2$ | H | $CH_3$ | $CH_3$ | $OCH_3$ | N |
| $SO_2CH_2CH_3$ | $CH_2C\equiv CH$ | H | H | $OCH_3$ | $OCH_3$ | CH |
| $SO_2CH_2CH_3$ | $CH_2C\equiv CH$ | H | H | Cl | $OCH_3$ | CH |
| $SO_2CH_2CH_3$ | $CH_2C\equiv CH$ | H | H | $CH_3$ | $OCH_3$ | CH |
| $SO_2CH_2CH_3$ | $CH_2C\equiv CH$ | H | H | $CH_3$ | $CH_3$ | CH |
| $SO_2CH_2CH_3$ | $CH_2C\equiv CH$ | H | H | $OCH_3$ | $OCH_3$ | N |
| $SO_2CH_2CH_3$ | $CH_2C\equiv CH$ | H | H | $CH_3$ | $OCH_3$ | N |
| $SO_2CH_2CH_3$ | $CH_2C\equiv CH$ | H | H | $NHCH_3$ | $OCH_2CH_3$ | N |
| $SO_2CH_2CH_3$ | $CH_2C\equiv CH$ | H | $CH_3$ | $CH_3$ | $OCH_3$ | N |
| $SO_2CH_2CH_3$ | $CH_2CH_2Cl$ | H | H | $OCH_3$ | $OCH_3$ | CH |
| $SO_2CH_2CH_3$ | $CH_2CH_2Cl$ | H | H | Cl | $OCH_3$ | CH |
| $SO_2CH_2CH_3$ | $CH_2CH_2Cl$ | H | H | $CH_3$ | $OCH_3$ | CH |
| $SO_2CH_2CH_3$ | $CH_2CH_2Cl$ | H | H | $CH_3$ | $CH_3$ | CH |
| $SO_2CH_2CH_3$ | $CH_2CH_2Cl$ | H | H | $OCH_3$ | $OCH_3$ | N |
| $SO_2CH_2CH_3$ | $CH_2CH_2Cl$ | H | H | $CH_3$ | $OCH_3$ | N |
| $SO_2CH_2CH_3$ | $CH_2CH_2Cl$ | H | H | $NHCH_3$ | $OCH_2CH_3$ | N |
| $SO_2CH_2CH_3$ | $CH_2CH_2Cl$ | H | $CH_3$ | $CH_3$ | $OCH_3$ | N |
| $SO_2CH_2CH_3$ | $CH_2CN$ | H | H | $OCH_3$ | $OCH_3$ | CH |
| $SO_2CH_2CH_3$ | $CH_2CN$ | H | H | Cl | $OCH_3$ | CH |
| $SO_2CH_2CH_3$ | $CH_2CN$ | H | H | $CH_3$ | $OCH_3$ | CH |
| $SO_2CH_2CH_3$ | $CH_2CN$ | H | H | $CH_3$ | $CH_3$ | CH |
| $SO_2CH_2CH_3$ | $CH_2CN$ | H | H | $OCH_3$ | $OCH_3$ | N |
| $SO_2CH_2CH_3$ | $CH_2CN$ | H | H | $CH_3$ | $OCH_3$ | N |
| $SO_2CH_2CH_3$ | $CH_2CN$ | H | H | $NHCH_3$ | $OCH_2CH_3$ | N |
| $SO_2CH_2CH_3$ | $CH_2CN$ | H | $CH_3$ | $CH_3$ | $OCH_3$ | N |
| $SO_2CH_2CH_3$ | $CH_2CH_2OCH_3$ | H | H | $OCH_3$ | $OCH_3$ | CH |
| $SO_2CH_2CH_3$ | $CH_2CH_2OCH_3$ | H | H | Cl | $OCH_3$ | CH |
| $SO_2CH_2CH_3$ | $CH_2CH_2OCH_3$ | H | H | $CH_3$ | $OCH_3$ | CH |
| $SO_2CH_2CH_3$ | $CH_2CH_2OCH_3$ | H | H | $CH_3$ | $CH_3$ | CH |
| $SO_2CH_2CH_3$ | $CH_2CH_2OCH_3$ | H | H | $OCH_3$ | $OCH_3$ | N |
| $SO_2CH_2CH_3$ | $CH_2CH_2OCH_3$ | H | H | $CH_3$ | $OCH_3$ | N |
| $SO_2CH_2CH_3$ | $CH_2CH_2OCH_3$ | H | H | $NHCH_3$ | $OCH_2CH_3$ | N |
| $SO_2CH_2CH_3$ | $CH_2CH_2OCH_3$ | H | $CH_3$ | $CH_3$ | $OCH_3$ | N |
| $SO_2CH_2CH_3$ | cyclo-$C_3H_7$ | H | H | $OCH_3$ | $OCH_3$ | CH |
| $SO_2CH_2CH_3$ | cyclo-$C_3H_7$ | H | H | Cl | $OCH_3$ | CH |
| $SO_2CH_2CH_3$ | cyclo-$C_3H_7$ | H | H | $CH_3$ | $OCH_3$ | CH |
| $SO_2CH_2CH_3$ | cyclo-$C_3H_7$ | H | H | $CH_3$ | $CH_3$ | CH |
| $SO_2CH_2CH_3$ | cyclo-$C_3H_7$ | H | H | $OCH_3$ | $OCH_3$ | N |
| $SO_2CH_2CH_3$ | cyclo-$C_3H_7$ | H | H | $CH_3$ | $OCH_3$ | N |
| $SO_2CH_2CH_3$ | cyclo-$C_3H_7$ | H | H | $NHCH_3$ | $OCH_2CH_3$ | N |
| $SO_2CH_2CH_3$ | cyclo-$C_3H_7$ | H | $CH_3$ | $CH_3$ | $OCH_3$ | N |
| $SO_2CH_2CH_3$ | $CH_3$ | $CH_3$ | H | $OCH_3$ | $OCH_3$ | CH |
| $SO_2CH_2CH_3$ | $CH_3$ | $CH_3$ | H | Cl | $OCH_3$ | CH |
| $SO_2CH_2CH_3$ | $CH_3$ | $CH_3$ | H | $CH_3$ | $OCH_3$ | CH |
| $SO_2CH_2CH_3$ | $CH_3$ | $CH_3$ | H | $CH_3$ | $CH_3$ | CH |
| $SO_2CH_2CH_3$ | $CH_3$ | $CH_3$ | H | $OCH_3$ | $OCH_3$ | N |

TABLE II-continued

GENERAL STRUCTURE 2

| $R_1$ | $R_2$ | $R_3$ | R | X | Y | Z |
|---|---|---|---|---|---|---|
| $SO_2CH_2CH_3$ | $CH_3$ | $CH_3$ | H | $CH_3$ | $OCH_3$ | N |
| $SO_2CH_2CH_3$ | $CH_3$ | $CH_3$ | H | $NHCH_3$ | $OCH_2CH_3$ | N |
| $SO_2CH_2CH_3$ | $CH_3$ | $CH_3$ | $CH_3$ | $CH_3$ | $OCH_3$ | N |
| $SO_2CH_2CH_3$ | $CH_2CH_3$ | $CH_3$ | H | $OCH_3$ | $OCH_3$ | CH |
| $SO_2CH_2CH_3$ | $CH_2CH_3$ | $CH_3$ | H | Cl | $OCH_3$ | CH |
| $SO_2CH_2CH_3$ | $CH_2CH_3$ | $CH_3$ | H | $CH_3$ | $OCH_3$ | CH |
| $SO_2CH_2CH_3$ | $CH_2CH_3$ | $CH_3$ | H | $CH_3$ | $CH_3$ | CH |
| $SO_2CH_2CH_3$ | $CH_2CH_3$ | $CH_3$ | H | $OCH_3$ | $OCH_3$ | N |
| $SO_2CH_2CH_3$ | $CH_2CH_3$ | $CH_3$ | H | $CH_3$ | $OCH_3$ | N |
| $SO_2CH_2CH_3$ | $CH_2CH_3$ | $CH_3$ | H | $NHCH_3$ | $OCH_2CH_3$ | N |
| $SO_2CH_2CH_3$ | $CH_2CH_3$ | $CH_3$ | $CH_3$ | $CH_3$ | $OCH_3$ | N |
| $SO_2CH_2CH_3$ | $CH_2CH_3$ | $CH_2CH_3$ | H | $OCH_3$ | $OCH_3$ | CH |
| $SO_2CH_2CH_3$ | $CH_2CH_3$ | $CH_2CH_3$ | H | Cl | $OCH_3$ | CH |
| $SO_2CH_2CH_3$ | $CH_2CH_3$ | $CH_2CH_3$ | H | $CH_3$ | $CH_3$ | CH |
| $SO_2CH_2CH_3$ | $CH_2CH_3$ | $CH_2CH_3$ | H | $OCH_3$ | $OCH_3$ | N |
| $SO_2CH_2CH_3$ | $CH_2CH_3$ | $CH_2CH_3$ | H | $CH_3$ | $OCH_3$ | N |
| $SO_2CH_2CH_3$ | $CH_2CH_3$ | $CH_2CH_3$ | H | $NHCH_3$ | $OCH_2CH_3$ | N |
| $SO_2CH_2CH_3$ | $CH_2CH_3$ | $CH_2CH_3$ | $CH_3$ | $CH_3$ | $OCH_3$ | N |
| $SO_2CH_2CH_3$ | $OCH_3$ | $CH_3$ | H | $OCH_3$ | $OCH_3$ | CH |
| $SO_2CH_2CH_3$ | $OCH_3$ | $CH_3$ | H | Cl | $OCH_3$ | CH |
| $SO_2CH_2CH_3$ | $OCH_3$ | $CH_3$ | H | $CH_3$ | $OCH_3$ | CH |
| $SO_2CH_2CH_3$ | $OCH_3$ | $CH_3$ | H | $CH_3$ | $CH_3$ | CH |
| $SO_2CH_2CH_3$ | $OCH_3$ | $CH_3$ | H | $OCH_3$ | $OCH_3$ | N |
| $SO_2CH_2CH_3$ | $OCH_3$ | $CH_3$ | H | $CH_3$ | $OCH_3$ | N |
| $SO_2CH_2CH_3$ | $OCH_3$ | $CH_3$ | H | $NHCH_3$ | $OCH_2CH_3$ | N |
| $SO_2CH_2CH_3$ | $OCH_3$ | $CH_3$ | $CH_3$ | $CH_3$ | $OCH_3$ | N |
| $SO_2CH_2CH_3$ | $N(CH_3)_2$ | $CH_3$ | H | $OCH_3$ | $OCH_3$ | CH |
| $SO_2CH_2CH_3$ | $N(CH_3)_2$ | $CH_3$ | H | Cl | $OCH_3$ | CH |
| $SO_2CH_2CH_3$ | $N(CH_3)_2$ | $CH_3$ | H | $CH_3$ | $OCH_3$ | CH |
| $SO_2CH_2CH_3$ | $N(CH_3)_2$ | $CH_3$ | H | $CH_3$ | $CH_3$ | CH |
| $SO_2CH_2CH_3$ | $N(CH_3)_2$ | $CH_3$ | H | $OCH_3$ | $OCH_3$ | N |
| $SO_2CH_2CH_3$ | $N(CH_3)_2$ | $CH_3$ | H | $CH_3$ | $OCH_3$ | N |
| $SO_2CH_2CH_3$ | $N(CH_3)_2$ | $CH_3$ | H | $NHCH_3$ | $OCH_2CH_3$ | N |
| $SO_2CH_2CH_3$ | $N(CH_3)_2$ | $CH_3$ | $CH_3$ | $CH_3$ | $OCH_3$ | N |
| $SO_2CH_2CH_3$ | $-CH_2CH_2CH_2-$ | | H | $OCH_3$ | $OCH_3$ | CH |
| $SO_2CH_2CH_3$ | $-CH_2CH_2CH_2-$ | | H | Cl | $OCH_3$ | CH |
| $SO_2CH_2CH_3$ | $-CH_2CH_2CH_2-$ | | H | $CH_3$ | $OCH_3$ | CH |
| $SO_2CH_2CH_3$ | $-CH_2CH_2CH_2-$ | | H | $CH_3$ | $CH_3$ | CH |
| $SO_2CH_2CH_3$ | $-CH_2CH_2CH_2-$ | | H | $OCH_3$ | $OCH_3$ | N |
| $SO_2CH_2CH_3$ | $-CH_2CH_2CH_2-$ | | H | $CH_3$ | $OCH_3$ | N |
| $SO_2CH_2CH_3$ | $-CH_2CH_2CH_2-$ | | H | $NHCH_3$ | $OCH_2CH_3$ | N |
| $SO_2CH_2CH_3$ | $-CH_2CH_2CH_2-$ | | $CH_3$ | $CH_3$ | $OCH_3$ | N |
| Br | $CH_3$ | H | H | $OCH_3$ | $OCH_3$ | CH |
| Br | $CH_3$ | H | H | Cl | $OCH_3$ | CH |
| Br | $CH_3$ | H | H | $CH_3$ | $OCH_3$ | CH |
| Br | $CH_3$ | H | H | $CH_3$ | $CH_3$ | CH |
| Br | $CH_3$ | H | H | $OCH_3$ | $OCH_3$ | N |
| Br | $CH_3$ | H | H | $CH_3$ | $OCH_3$ | N |
| Br | $CH_3$ | H | H | $NHCH_3$ | $OCH_2CH_3$ | N |
| Br | $CH_3$ | H | $CH_3$ | $CH_3$ | $OCH_3$ | N |
| Br | $CH_2CH{=}CH_2$ | H | H | $OCH_3$ | $OCH_3$ | CH |
| Br | $CH_2CH{=}CH_2$ | H | H | Cl | $OCH_3$ | CH |
| Br | $CH_2CH{=}CH_2$ | H | H | $CH_3$ | $OCH_3$ | CH |
| Br | $CH_2CH{=}CH_2$ | H | H | $CH_3$ | $CH_3$ | CH |
| Br | $CH_2CH{=}CH_2$ | H | H | $OCH_3$ | $OCH_3$ | N |
| Br | $CH_2CH{=}CH_2$ | H | H | $CH_3$ | $OCH_3$ | N |
| Br | $CH_2CH{=}CH_2$ | H | H | $NHCH_3$ | $OCH_2CH_3$ | N |
| Br | $CH_2CH{=}CH_2$ | H | $CH_3$ | $CH_3$ | $OCH_3$ | N |
| Br | $CH_3$ | $CH_3$ | H | $OCH_3$ | $OCH_3$ | CH |
| Br | $CH_3$ | $CH_3$ | H | Cl | $OCH_3$ | CH |
| Br | $CH_3$ | $CH_3$ | H | $CH_3$ | $OCH_3$ | CH |
| Br | $CH_3$ | $CH_3$ | H | $CH_3$ | $CH_3$ | CH |
| Br | $CH_3$ | $CH_3$ | H | $OCH_3$ | $OCH_3$ | N |
| Br | $CH_3$ | $CH_3$ | H | $CH_3$ | $OCH_3$ | N |
| Br | $CH_3$ | $CH_3$ | H | $NHCH_3$ | $OCH_2CH_3$ | N |
| Br | $CH_3$ | $CH_3$ | $CH_3$ | $CH_3$ | $OCH_3$ | N |
| Br | $-CH_2CH_2CH_2-$ | | H | $OCH_3$ | $OCH_3$ | CH |
| Br | $-CH_2CH_2CH_2-$ | | H | Cl | $OCH_3$ | CH |
| Br | $-CH_2CH_2CH_2-$ | | H | $CH_3$ | $OCH_3$ | CH |
| Br | $-CH_2CH_2CH_2-$ | | H | $CH_3$ | $CH_3$ | CH |
| Br | $-CH_2CH_2CH_2-$ | | H | $OCH_3$ | $OCH_3$ | N |
| Br | $-CH_2CH_2CH_2-$ | | H | $CH_3$ | $OCH_3$ | N |
| Br | $-CH_2CH_2CH_2-$ | | H | $NHCH_3$ | $OCH_2CH_3$ | N |
| Br | $-CH_2CH_2CH_2-$ | | $CH_3$ | $CH_3$ | $OCH_3$ | N |
| $CH_2CH_3$ | $CH_3$ | H | H | $OCH_3$ | $OCH_3$ | CH |
| $CH_2CH_3$ | $CH_3$ | H | H | Cl | $OCH_3$ | CH |
| $CH_2CH_3$ | $CH_3$ | H | H | $CH_3$ | $OCH_3$ | CH |
| $CH_2CH_3$ | $CH_3$ | H | H | $CH_3$ | $CH_3$ | CH |
| $CH_2CH_3$ | $CH_3$ | H | H | $OCH_3$ | $OCH_3$ | N |
| $CH_2CH_3$ | $CH_3$ | H | H | $CH_3$ | $OCH_3$ | N |

TABLE II-continued

GENERAL STRUCTURE 2

| $R_1$ | $R_2$ | $R_3$ | R | X | Y | Z |
|---|---|---|---|---|---|---|
| $CH_2CH_3$ | $CH_3$ | H | H | $NHCH_3$ | $OCH_2CH_3$ | N |
| $CH_2CH_3$ | $CH_3$ | H | $CH_3$ | $CH_3$ | $OCH_3$ | N |
| $CH_2CH_3$ | $CH_2CH{=}CH_2$ | H | H | $OCH_3$ | $OCH_3$ | CH |
| $CH_2CH_3$ | $CH_2CH{=}CH_2$ | H | H | Cl | $OCH_3$ | CH |
| $CH_2CH_3$ | $CH_2CH{=}CH_2$ | H | H | $CH_3$ | $OCH_3$ | CH |
| $CH_2CH_3$ | $CH_2CH{=}CH_2$ | H | H | $CH_3$ | $CH_3$ | CH |
| $CH_2CH_3$ | $CH_2CH{=}CH_2$ | H | H | $OCH_3$ | $OCH_3$ | N |
| $CH_2CH_3$ | $CH_2CH{=}CH_2$ | H | H | $CH_3$ | $OCH_3$ | N |
| $CH_2CH_3$ | $CH_2CH{=}CH_2$ | H | H | $NHCH_3$ | $OCH_2CH_3$ | N |
| $CH_2CH_3$ | $CH_2CH{=}CH_2$ | H | $CH_3$ | $CH_3$ | $OCH_3$ | N |
| $CH_2CH_3$ | $CH_3$ | $CH_3$ | H | $OCH_3$ | $OCH_3$ | CH |
| $CH_2CH_3$ | $CH_3$ | $CH_3$ | H | Cl | $OCH_3$ | CH |
| $CH_2CH_3$ | $CH_3$ | $CH_3$ | H | $CH_3$ | $OCH_3$ | CH |
| $CH_2CH_3$ | $CH_3$ | $CH_3$ | H | $CH_3$ | $CH_3$ | CH |
| $CH_2CH_3$ | $CH_3$ | $CH_3$ | H | $OCH_3$ | $OCH_3$ | N |
| $CH_2CH_3$ | $CH_3$ | $CH_3$ | H | $CH_3$ | $OCH_3$ | N |
| $CH_2CH_3$ | $CH_3$ | $CH_3$ | H | $NHCH_3$ | $OCH_2CH_3$ | N |
| $CH_2CH_3$ | $CH_3$ | $CH_3$ | $CH_3$ | $CH_3$ | $OCH_3$ | N |
| $CH_2CH_3$ | $-CH_2CH_2CH_2-$ | | H | $OCH_3$ | $OCH_3$ | CH |
| $CH_2CH_3$ | $-CH_2CH_2CH_2-$ | | H | Cl | $OCH_3$ | CH |
| $CH_2CH_3$ | $-CH_2CH_2CH_2-$ | | H | $CH_3$ | $OCH_3$ | CH |
| $CH_2CH_3$ | $-CH_2CH_2CH_2-$ | | H | $CH_3$ | $CH_3$ | CH |
| $CH_2CH_3$ | $-CH_2CH_2CH_2-$ | | H | $OCH_3$ | $OCH_3$ | N |
| $CH_2CH_3$ | $-CH_2CH_2CH_2-$ | | H | $CH_3$ | $OCH_3$ | N |
| $CH_2CH_3$ | $-CH_2CH_2CH_2-$ | | H | $NHCH_3$ | $OCH_2CH_3$ | N |
| $CH_2CH_3$ | $-CH_2CH_2CH_2-$ | | $CH_3$ | $CH_3$ | $OCH_3$ | N |
| $CF_3$ | $CH_3$ | H | H | $OCH_3$ | $OCH_3$ | CH |
| $CF_3$ | $CH_3$ | H | H | Cl | $OCH_3$ | CH |
| $CF_3$ | $CH_3$ | H | H | $CH_3$ | $OCH_3$ | CH |
| $CF_3$ | $CH_3$ | H | H | $CH_3$ | $CH_3$ | CH |
| $CF_3$ | $CH_3$ | H | H | $OCH_3$ | $OCH_3$ | N |
| $CF_3$ | $CH_3$ | H | H | $CH_3$ | $OCH_3$ | N |
| $CF_3$ | $CH_3$ | H | H | $NHCH_3$ | $OCH_2CH_3$ | N |
| $CF_3$ | $CH_3$ | H | $CH_3$ | $CH_3$ | $OCH_3$ | N |
| $CF_3$ | $CH_2CH{=}CH_2$ | H | H | $OCH_3$ | $OCH_3$ | CH |
| $CF_3$ | $CH_2CH{=}CH_2$ | H | H | Cl | $OCH_3$ | CH |
| $CF_3$ | $CH_2CH{=}CH_2$ | H | H | $CH_3$ | $OCH_3$ | CH |
| $CF_3$ | $CH_2CH{=}CH_2$ | H | H | $CH_3$ | $CH_3$ | CH |
| $CF_3$ | $CH_2CH{=}CH_2$ | H | H | $OCH_3$ | $OCH_3$ | N |
| $CF_3$ | $CH_2CH{=}CH_2$ | H | H | $CH_3$ | $OCH_3$ | N |
| $CF_3$ | $CH_2CH{=}CH_2$ | H | H | $NHCH_3$ | $OCH_2CH_3$ | N |
| $CF_3$ | $CH_2CH{=}CH_2$ | H | $CH_3$ | $CH_3$ | $OCH_3$ | N |
| $CF_3$ | $CH_3$ | $CH_3$ | H | $OCH_3$ | $OCH_3$ | CH |
| $CF_3$ | $CH_3$ | $CH_3$ | H | Cl | $OCH_3$ | CH |
| $CF_3$ | $CH_3$ | $CH_3$ | H | $CH_3$ | $OCH_3$ | CH |
| $CF_3$ | $CH_3$ | $CH_3$ | H | $CH_3$ | $CH_3$ | CH |
| $CF_3$ | $CH_3$ | $CH_3$ | H | $OCH_3$ | $OCH_3$ | N |
| $CF_3$ | $CH_3$ | $CH_3$ | H | $CH_3$ | $OCH_3$ | N |
| $CF_3$ | $CH_3$ | $CH_3$ | H | $NHCH_3$ | $OCH_2CH_3$ | N |
| $CF_3$ | $CH_3$ | $CH_3$ | $CH_3$ | $CH_3$ | $OCH_3$ | N |
| $CF_3$ | $-CH_2CH_2CH_2-$ | | H | $OCH_3$ | $OCH_3$ | CH |
| $CF_3$ | $-CH_2CH_2CH_2-$ | | H | Cl | $OCH_3$ | CH |
| $CF_3$ | $-CH_2CH_2CH_2-$ | | H | $CH_3$ | $OCH_3$ | CH |
| $CF_3$ | $-CH_2CH_2CH_2-$ | | H | $CH_3$ | $CH_3$ | CH |
| $CF_3$ | $-CH_2CH_2CH_2-$ | | H | $OCH_3$ | $OCH_3$ | N |
| $CF_3$ | $-CH_2CH_2CH_2-$ | | H | $CH_3$ | $OCH_3$ | N |
| $CF_3$ | $-CH_2CH_2CH_2-$ | | H | $NHCH_3$ | $OCH_2CH_3$ | N |
| $CF_3$ | $-CH_2CH_2CH_2-$ | | $CH_3$ | $CH_3$ | $OCH_3$ | N |
| $OCH_3$ | $CH_3$ | H | H | $OCH_3$ | $OCH_3$ | CH |
| $OCH_3$ | $CH_3$ | H | H | Cl | $OCH_3$ | CH |
| $OCH_3$ | $CH_3$ | H | H | $CH_3$ | $OCH_3$ | CH |
| $OCH_3$ | $CH_3$ | H | H | $CH_3$ | $CH_3$ | CH |
| $OCH_3$ | $CH_3$ | H | H | $OCH_3$ | $OCH_3$ | N |
| $OCH_3$ | $CH_3$ | H | H | $CH_3$ | $OCH_3$ | N |
| $OCH_3$ | $CH_3$ | H | H | $NHCH_3$ | $OCH_2CH_3$ | N |
| $OCH_3$ | $CH_3$ | H | $CH_3$ | $CH_3$ | $OCH_3$ | N |
| $OCH_3$ | $CH_2CH{=}CH_2$ | H | H | $OCH_3$ | $OCH_3$ | CH |
| $OCH_3$ | $CH_2CH{=}CH_2$ | H | H | Cl | $OCH_3$ | CH |
| $OCH_3$ | $CH_2CH{=}CH_2$ | H | H | $CH_3$ | $OCH_3$ | CH |
| $OCH_3$ | $CH_2CH{=}CH_2$ | H | H | $CH_3$ | $CH_3$ | CH |
| $OCH_3$ | $CH_2CH{=}CH_2$ | H | H | $OCH_3$ | $OCH_3$ | N |
| $OCH_3$ | $CH_2CH{=}CH_2$ | H | H | $CH_3$ | $OCH_3$ | N |
| $OCH_3$ | $CH_2CH{=}CH_2$ | H | H | $NHCH_3$ | $OCH_2CH_3$ | N |
| $OCH_3$ | $CH_2CH{=}CH_2$ | H | $CH_3$ | $CH_3$ | $OCH_3$ | N |
| $OCH_3$ | $CH_3$ | $CH_3$ | H | $OCH_3$ | $OCH_3$ | CH |
| $OCH_3$ | $CH_3$ | $CH_3$ | H | Cl | $OCH_3$ | CH |
| $OCH_3$ | $CH_3$ | $CH_3$ | H | $CH_3$ | $OCH_3$ | CH |
| $OCH_3$ | $CH_3$ | $CH_3$ | H | $CH_3$ | $CH_3$ | CH |
| $OCH_3$ | $CH_3$ | $CH_3$ | H | $OCH_3$ | $OCH_3$ | N |
| $OCH_3$ | $CH_3$ | $CH_3$ | H | $CH_3$ | $OCH_3$ | N |

TABLE II-continued

GENERAL STRUCTURE 2

| $R_1$ | $R_2$ | $R_3$ | R | X | Y | Z |
|---|---|---|---|---|---|---|
| $OCH_3$ | $CH_3$ | $CH_3$ | H | $NHCH_3$ | $OCH_2CH_3$ | N |
| $OCH_3$ | $CH_3$ | $CH_3$ | $CH_3$ | $CH_3$ | $OCH_3$ | N |
| $OCH_3$ | $-CH_2CH_2CH_2-$ | | H | $OCH_3$ | $OCH_3$ | CH |
| $OCH_3$ | $-CH_2CH_2CH_2-$ | | H | Cl | $OCH_3$ | CH |
| $OCH_3$ | $-CH_2CH_2CH_2-$ | | H | $CH_3$ | $OCH_3$ | CH |
| $OCH_3$ | $-CH_2CH_2CH_2-$ | | H | $CH_3$ | $CH_3$ | CH |
| $OCH_3$ | $-CH_2CH_2CH_2-$ | | H | $OCH_3$ | $OCH_3$ | N |
| $OCH_3$ | $-CH_2CH_2CH_2-$ | | H | $CH_3$ | $OCH_3$ | N |
| $OCH_3$ | $-CH_2CH_2CH_2-$ | | H | $NHCH_3$ | $OCH_2CH_3$ | N |
| $OCH_3$ | $-CH_2CH_2CH_2-$ | | $CH_3$ | $CH_3$ | $OCH_3$ | N |
| $OCF_2H$ | $CH_3$ | H | H | $OCH_3$ | $OCH_3$ | CH |
| $OCF_2H$ | $CH_3$ | H | H | Cl | $OCH_3$ | CH |
| $OCF_2H$ | $CH_3$ | H | H | $CH_3$ | $OCH_3$ | CH |
| $OCF_2H$ | $CH_3$ | H | H | $CH_3$ | $CH_3$ | CH |
| $OCF_2H$ | $CH_3$ | H | H | $OCH_3$ | $OCH_3$ | N |
| $OCF_2H$ | $CH_3$ | H | H | $CH_3$ | $OCH_3$ | N |
| $OCF_2H$ | $CH_3$ | H | H | $NHCH_3$ | $OCH_2CH_3$ | N |
| $OCF_2H$ | $CH_3$ | H | $CH_3$ | $CH_3$ | $OCH_3$ | N |
| $OCF_2H$ | $CH_2CH{=}CH_2$ | H | H | $OCH_3$ | $OCH_3$ | CH |
| $OCF_2H$ | $CH_2CH{=}CH_2$ | H | H | Cl | $OCH_3$ | CH |
| $OCF_2H$ | $CH_2CH{=}CH_2$ | H | H | $CH_3$ | $OCH_3$ | CH |
| $OCF_2H$ | $CH_2CH{=}CH_2$ | H | H | $CH_3$ | $CH_3$ | CH |
| $OCF_2H$ | $CH_2CH{=}CH_2$ | H | H | $OCH_3$ | $OCH_3$ | N |
| $OCF_2H$ | $CH_2CH{=}CH_2$ | H | H | $CH_3$ | $OCH_3$ | N |
| $OCF_2H$ | $CH_2CH{=}CH_2$ | H | H | $NHCH_3$ | $OCH_2CH_3$ | N |
| $OCF_2H$ | $CH_2CH{=}CH_2$ | H | $CH_3$ | $CH_3$ | $OCH_3$ | N |
| $OCF_2H$ | $CH_3$ | $CH_3$ | H | $OCH_3$ | $OCH_3$ | CH |
| $OCF_2H$ | $CH_3$ | $CH_3$ | H | Cl | $OCH_3$ | CH |
| $OCF_2H$ | $CH_3$ | $CH_3$ | H | $CH_3$ | $OCH_3$ | CH |
| $OCF_2H$ | $CH_3$ | $CH_3$ | H | $CH_3$ | $CH_3$ | CH |
| $OCF_2H$ | $CH_3$ | $CH_3$ | H | $OCH_3$ | $OCH_3$ | N |
| $OCF_2H$ | $CH_3$ | $CH_3$ | H | $CH_3$ | $OCH_3$ | N |
| $OCF_2H$ | $CH_3$ | $CH_3$ | H | $NHCH_3$ | $OCH_2CH_3$ | N |
| $OCF_2H$ | $CH_3$ | $CH_3$ | $CH_3$ | $CH_3$ | $OCH_3$ | N |
| $OCF_2H$ | $-CH_2CH_2CH_2-$ | | H | $OCH_3$ | $OCH_3$ | CH |
| $OCF_2H$ | $-CH_2CH_2CH_2-$ | | H | Cl | $OCH_3$ | CH |
| $OCF_2H$ | $-CH_2CH_2CH_2-$ | | H | $CH_3$ | $OCH_3$ | CH |
| $OCF_2H$ | $-CH_2CH_2CH_2-$ | | H | $CH_3$ | $CH_3$ | CH |
| $OCF_2H$ | $-CH_2CH_2CH_2-$ | | H | $OCH_3$ | $OCH_3$ | N |
| $OCF_2H$ | $-CH_2CH_2CH_2-$ | | H | $CH_3$ | $OCH_3$ | N |
| $OCF_2H$ | $-CH_2CH_2CH_2-$ | | H | $NHCH_3$ | $OCH_2CH_3$ | N |
| $OCF_2H$ | $-CH_2CH_2CH_2-$ | | $CH_3$ | $CH_3$ | $OCH_3$ | N |
| $SCF_2H$ | $CH_3$ | H | H | $OCH_3$ | $OCH_3$ | CH |
| $SCF_2H$ | $CH_3$ | H | H | Cl | $OCH_3$ | CH |
| $SCF_2H$ | $CH_3$ | H | H | $CH_3$ | $OCH_3$ | CH |
| $SCF_2H$ | $CH_3$ | H | H | $CH_3$ | $CH_3$ | CH |
| $SCF_2H$ | $CH_3$ | H | H | $OCH_3$ | $OCH_3$ | N |
| $SCF_2H$ | $CH_3$ | H | H | $CH_3$ | $OCH_3$ | N |
| $SCF_2H$ | $CH_3$ | H | H | $NHCH_3$ | $OCH_2CH_3$ | N |
| $SCF_2H$ | $CH_3$ | H | $CH_3$ | $CH_3$ | $OCH_3$ | N |
| $SCF_2H$ | $CH_2CH{=}CH_2$ | H | H | $OCH_3$ | $OCH_3$ | CH |
| $SCF_2H$ | $CH_2CH{=}CH_2$ | H | H | Cl | $OCH_3$ | CH |
| $SCF_2H$ | $CH_2CH{=}CH_2$ | H | H | $CH_3$ | $OCH_3$ | CH |
| $SCF_2H$ | $CH_2CH{=}CH_2$ | H | H | $CH_3$ | $CH_3$ | CH |
| $SCF_2H$ | $CH_2CH{=}CH_2$ | H | H | $OCH_3$ | $OCH_3$ | N |
| $SCF_2H$ | $CH_2CH{=}CH_2$ | H | H | $CH_3$ | $OCH_3$ | N |
| $SCF_2H$ | $CH_2CH{=}CH_2$ | H | H | $NHCH_3$ | $OCH_2CH_3$ | N |
| $SCF_2H$ | $CH_2CH{=}CH_2$ | H | $CH_3$ | $CH_3$ | $OCH_3$ | N |
| $SCF_2H$ | $CH_3$ | $CH_3$ | H | $OCH_3$ | $OCH_3$ | CH |
| $SCF_2H$ | $CH_3$ | $CH_3$ | H | Cl | $OCH_3$ | CH |
| $SCF_2H$ | $CH_3$ | $CH_3$ | H | $CH_3$ | $OCH_3$ | CH |
| $SCF_2H$ | $CH_3$ | $CH_3$ | H | $CH_3$ | $CH_3$ | CH |
| $SCF_2H$ | $CH_3$ | $CH_3$ | H | $OCH_3$ | $OCH_3$ | N |
| $SCF_2H$ | $CH_3$ | $CH_3$ | H | $CH_3$ | $OCH_3$ | N |
| $SCF_2H$ | $CH_3$ | $CH_3$ | H | $NHCH_3$ | $OCH_2CH_3$ | N |
| $SCF_2H$ | $CH_3$ | $CH_3$ | $CH_3$ | $CH_3$ | $OCH_3$ | N |
| $SCF_2H$ | $-CH_2CH_2CH_2-$ | | H | $OCH_3$ | $OCH_3$ | CH |
| $SCF_2H$ | $-CH_2CH_2CH_2-$ | | H | Cl | $OCH_3$ | CH |
| $SCF_2H$ | $-CH_2CH_2CH_2-$ | | H | $CH_3$ | $OCH_3$ | CH |
| $SCF_2H$ | $-CH_2CH_2CH_2-$ | | H | $CH_3$ | $CH_3$ | CH |
| $SCF_2H$ | $-CH_2CH_2CH_2-$ | | H | $OCH_3$ | $OCH_3$ | N |
| $SCF_2H$ | $-CH_2CH_2CH_2-$ | | H | $CH_3$ | $OCH_3$ | N |
| $SCF_2H$ | $-CH_2CH_2CH_2-$ | | H | $NHCH_3$ | $OCH_2CH_3$ | N |
| $SCF_2H$ | $-CH_2CH_2CH_2-$ | | $CH_3$ | $CH_3$ | $OCH_3$ | N |
| $SO_2CF_2H$ | $CH_3$ | H | H | $OCH_3$ | $OCH_3$ | CH |
| $SO_2CF_2H$ | $CH_3$ | H | H | Cl | $OCH_3$ | CH |
| $SO_2CF_2H$ | $CH_3$ | H | H | $CH_3$ | $OCH_3$ | CH |
| $SO_2CF_2H$ | $CH_3$ | H | H | $CH_3$ | $CH_3$ | CH |
| $SO_2CF_2H$ | $CH_3$ | H | H | $OCH_3$ | $OCH_3$ | N |
| $SO_2CF_2H$ | $CH_3$ | H | H | $CH_3$ | $OCH_3$ | N |

TABLE II-continued

GENERAL STRUCTURE 2

| $R_1$ | $R_2$ | $R_3$ | R | X | Y | Z |
|---|---|---|---|---|---|---|
| $SO_2CF_2H$ | $CH_3$ | H | H | $NHCH_3$ | $OCH_2CH_3$ | N |
| $SO_2CF_2H$ | $CH_3$ | H | $CH_3$ | $CH_3$ | $OCH_3$ | N |
| $SO_2CF_2H$ | $CH_2CH{=}CH_2$ | H | H | $OCH_3$ | $OCH_3$ | CH |
| $SO_2CF_2H$ | $CH_2CH{=}CH_2$ | H | H | Cl | $OCH_3$ | CH |
| $SO_2CF_2H$ | $CH_2CH{=}CH_2$ | H | H | $CH_3$ | $OCH_3$ | CH |
| $SO_2CF_2H$ | $CH_2CH{=}CH_2$ | H | H | $CH_3$ | $CH_3$ | CH |
| $SO_2CF_2H$ | $CH_2CH{=}CH_2$ | H | H | $OCH_3$ | $OCH_3$ | N |
| $SO_2CF_2H$ | $CH_2CH{=}CH_2$ | H | H | $CH_3$ | $OCH_3$ | N |
| $SO_2CF_2H$ | $CH_2CH{=}CH_2$ | H | H | $NHCH_3$ | $OCH_2CH_3$ | N |
| $SO_2CF_2H$ | $CH_2CH{=}CH_2$ | H | $CH_3$ | $CH_3$ | $OCH_3$ | N |
| $SO_2CF_2H$ | $CH_3$ | $CH_3$ | H | $OCH_3$ | $OCH_3$ | CH |
| $SO_2CF_2H$ | $CH_3$ | $CH_3$ | H | Cl | $OCH_3$ | CH |
| $SO_2CF_2H$ | $CH_3$ | $CH_3$ | H | $CH_3$ | $OCH_3$ | CH |
| $SO_2CF_2H$ | $CH_3$ | $CH_3$ | H | $CH_3$ | $CH_3$ | CH |
| $SO_2CF_2H$ | $CH_3$ | $CH_3$ | H | $OCH_3$ | $OCH_3$ | N |
| $SO_2CF_2H$ | $CH_3$ | $CH_3$ | H | $CH_3$ | $OCH_3$ | N |
| $SO_2CF_2H$ | $CH_3$ | $CH_3$ | H | $NHCH_3$ | $OCH_2CH_3$ | N |
| $SO_2CF_2H$ | $CH_3$ | $CH_3$ | $CH_3$ | $CH_3$ | $OCH_3$ | N |
| $SO_2CF_2H$ | $-CH_2CH_2CH_2-$ | | H | $OCH_3$ | $OCH_3$ | CH |
| $SO_2CF_2H$ | $-CH_2CH_2CH_2-$ | | H | Cl | $OCH_3$ | CH |
| $SO_2CF_2H$ | $-CH_2CH_2CH_2-$ | | H | $CH_3$ | $OCH_3$ | CH |
| $SO_2CF_2H$ | $-CH_2CH_2CH_2-$ | | H | $CH_3$ | $CH_3$ | CH |
| $SO_2CF_2H$ | $-CH_2CH_2CH_2-$ | | H | $OCH_3$ | $OCH_3$ | N |
| $SO_2CF_2H$ | $-CH_2CH_2CH_2-$ | | H | $CH_3$ | $OCH_3$ | N |
| $SO_2CF_2H$ | $-CH_2CH_2CH_2-$ | | H | $NHCH_3$ | $OCH_2CH_3$ | N |
| $SO_2CF_2H$ | $-CH_2CH_2CH_2-$ | | $CH_3$ | $CH_3$ | $OCH_3$ | N |

TABLE III

GENERAL STRUCTURE 3

| $R_1$ | $R_2$ | $R_3$ | A |
|---|---|---|---|
| H | H | H | A-2 ($X_1 = CH_3$, $Y_1 = CH_2$) |
| H | H | H | A-3 ($X_1 = CH_3$) |
| H | H | H | A-3 ($X_1 = OCH_3$) |
| H | H | H | A-4 ($X_1 = CH_3$, $Y_3 = CH_3$) |
| H | H | H | A-4 ($X_1 = CH_3$, $Y_3 = OCH_3$) |
| H | H | H | A-4 ($X_1 = OCH_3$, $Y_3 = CH_3$) |
| H | H | H | A-5 ($X_2 = CH_3$, $Y_2 = OCH_3$) |
| H | H | H | A-5 ($X_2 = CH_3$, $Y_2 = SCH_3$) |
| H | H | H | A-6 ($X_3 = OCH_3$) |
| H | H | H | A-7 ($X_4 = OCH_3$, $Y_4 = OCH_3$) |
| H | H | H | A-7 ($X_4 = CH_3$, $Y_4 = OCH_3$) |
| H | H | H | A-7 ($X_4 = OCH_3$, $Y_4 = CH_3$) |
| H | H | $CH_3$ | A-2 ($X_1 = CH_3$, $Y_1 = CH_2$) |
| H | H | $CH_3$ | A-3 ($X_1 = CH_3$) |
| H | H | $CH_3$ | A-3 ($X_1 = OCH_3$) |
| H | H | $CH_3$ | A-4 ($X_1 = CH_3$, $Y_3 = CH_3$) |
| H | H | $CH_3$ | A-4 ($X_1 = CH_3$, $Y_3 = OCH_3$) |
| H | H | $CH_3$ | A-4 ($X_1 = OCH_3$, $Y_3 = CH_3$) |
| H | H | $CH_3$ | A-5 ($X_2 = CH_3$, $Y_2 = OCH_3$) |
| H | H | $CH_3$ | A-5 ($X_2 = CH_3$, $Y_2 = SCH_3$) |
| H | H | $CH_3$ | A-6 ($X_3 = OCH_3$) |
| H | H | $CH_3$ | A-7 ($X_4 = OCH_3$, $Y_4 = OCH_3$) |
| H | H | $CH_3$ | A-7 ($X_4 = CH_3$, $Y_4 = OCH_3$) |
| H | H | $CH_3$ | A-7 ($X_4 = OCH_3$, $Y_4 = CH_3$) |
| H | H | $CH_2CH_3$ | A-2 ($X_1 = CH_3$, $Y_1 = CH_2$) |
| H | H | $CH_2CH_3$ | A-3 ($X_1 = CH_3$) |
| H | H | $CH_2CH_3$ | A-3 ($X_1 = OCH_3$) |
| H | H | $CH_2CH_3$ | A-4 ($X_1 = CH_3$, $Y_3 = CH_3$) |
| H | H | $CH_2CH_3$ | A-4 ($X_1 = CH_3$, $Y_3 = OCH_3$) |
| H | H | $CH_2CH_3$ | A-4 ($X_1 = OCH_3$, $Y_3 = CH_3$) |
| H | H | $CH_2CH_3$ | A-5 ($X_2 = CH_3$, $Y_2 = OCH_3$) |
| H | H | $CH_2CH_3$ | A-5 ($X_2 = CH_3$, $Y_2 = SCH_3$) |
| H | H | $CH_2CH_3$ | A-6 ($X_3 = OCH_3$) |
| H | H | $CH_2CH_3$ | A-7 ($X_4 = OCH_3$, $Y_4 = OCH_3$) |
| H | H | $CH_2CH_3$ | A-7 ($X_4 = CH_3$, $Y_4 = OCH_3$) |
| H | H | $CH_2CH_3$ | A-7 ($X_4 = OCH_3$, $Y_4 = CH_3$) |
| H | $CH_2CF_3$ | H | A-2 ($X_1 = CH_3$, $Y_1 = CH_2$) |
| H | $CH_2CF_3$ | H | A-3 ($X_1 = CH_3$) |
| H | $CH_2CF_3$ | H | A-3 ($X_1 = OCH_3$) |
| H | $CH_2CF_3$ | H | A-4 ($X_1 = CH_3$, $Y_3 = CH_3$) |
| H | $CH_2CF_3$ | H | A-4 ($X_1 = CH_3$, $Y_3 = OCH_3$) |
| H | $CH_2CF_3$ | H | A-4 ($X_1 = OCH_3$, $Y_3 = CH_3$) |
| H | $CH_2CF_3$ | H | A-5 ($X_2 = CH_3$, $Y_2 = OCH_3$) |
| H | $CH_2CF_3$ | H | A-5 ($X_2 = CH_3$, $Y_2 = SCH_3$) |
| H | $CH_2CF_3$ | H | A-6 ($X_3 = OCH_3$) |
| H | $CH_2CF_3$ | H | A-7 ($X_4 = OCH_3$, $Y_4 = OCH_3$) |
| H | $CH_2CF_3$ | H | A-7 ($X_4 = CH_3$, $Y_4 = OCH_3$) |

TABLE III-continued

GENERAL STRUCTURE 3

| $R_1$ | $R_2$ | $R_3$ | A |
|---|---|---|---|
| H | $CH_2CF_3$ | H | A-7 ($X_4$ = $OCH_3$, $Y_4$ = $CH_3$) |
| H | $CH_2CH_2Cl$ | H | A-2 ($X_1$ = $CH_3$, $Y_1$ = $CH_2$) |
| H | $CH_2CH_2Cl$ | H | A-3 ($X_1$ = $CH_3$) |
| H | $CH_2CH_2Cl$ | H | A-3 ($X_1$ = $OCH_3$) |
| H | $CH_2CH_2Cl$ | H | A-4 ($X_1$ = $CH_3$, $Y_3$ = $CH_3$) |
| H | $CH_2CH_2Cl$ | H | A-4 ($X_1$ = $CH_3$, $Y_3$ = $OCH_3$) |
| H | $CH_2CH_2Cl$ | H | A-4 ($X_1$ = $OCH_3$, $Y_3$ = $CH_3$) |
| H | $CH_2CH_2Cl$ | H | A-5 ($X_2$ = $CH_3$, $Y_2$ = $OCH_3$) |
| H | $CH_2CH_2Cl$ | H | A-5 ($X_2$ = $CH_3$, $Y_2$ = $SCH_3$) |
| H | $CH_2CH_2Cl$ | H | A-6 ($X_3$ = $OCH_3$) |
| H | $CH_2CH_2Cl$ | H | A-7 ($X_4$ = $OCH_3$, $Y_4$ = $OCH_3$) |
| H | $CH_2CH_2Cl$ | H | A-7 ($X_4$ = $CH_3$, $Y_4$ = $OCH_3$) |
| H | $CH_2CH_2Cl$ | H | A-7 ($X_4$ = $OCH_3$, $Y_4$ = $CH_3$) |
| H | $CH_2CN$ | H | A-2 ($X_1$ = $CH_3$, $Y_1$ = $CH_2$) |
| H | $CH_2CN$ | H | A-3 ($X_1$ = $CH_3$) |
| H | $CH_2CN$ | H | A-3 ($X_1$ = $OCH_3$) |
| H | $CH_2CN$ | H | A-4 ($X_1$ = $CH_3$, $Y_3$ = $CH_3$) |
| H | $CH_2CN$ | H | A-4 ($X_1$ = $CH_3$, $Y_3$ = $OCH_3$) |
| H | $CH_2CN$ | H | A-4 ($X_1$ = $OCH_3$, $Y_3$ = $CH_3$) |
| H | $CH_2CN$ | H | A-5 ($X_2$ = $CH_3$, $Y_2$ = $OCH_3$) |
| H | $CH_2CN$ | H | A-5 ($X_2$ = $CH_3$, $Y_2$ = $SCH_3$) |
| H | $CH_2CN$ | H | A-6 ($X_3$ = $OCH_3$) |
| H | $CH_2CN$ | H | A-7 ($X_4$ = $OCH_3$, $Y_4$ = $OCH_3$) |
| H | $CH_2CN$ | H | A-7 ($X_4$ = $CH_3$, $Y_4$ = $OCH_3$) |
| H | $CH_2CN$ | H | A-7 ($X_4$ = $OCH_3$, $Y_4$ = $CH_3$) |
| H | $CH_2CH_2OCH_3$ | H | A-2 ($X_1$ = $CH_3$, $Y_1$ = $CH_2$) |
| H | $CH_2CH_2OCH_3$ | H | A-3 ($X_1$ = $CH_3$) |
| H | $CH_2CH_2OCH_3$ | H | A-3 ($X_1$ = $OCH_3$) |
| H | $CH_2CH_2OCH_3$ | H | A-4 ($X_1$ = $CH_3$, $Y_3$ = $CH_3$) |
| H | $CH_2CH_2OCH_3$ | H | A-4 ($X_1$ = $CH_3$, $Y_3$ = $OCH_3$) |
| H | $CH_2CH_2OCH_3$ | H | A-4 ($X_1$ = $OCH_3$, $Y_3$ = $CH_3$) |
| H | $CH_2CH_2OCH_3$ | H | A-5 ($X_2$ = $CH_3$, $Y_2$ = $OCH_3$) |
| H | $CH_2CH_2OCH_3$ | H | A-5 ($X_2$ = $CH_3$, $Y_2$ = $SCH_3$) |
| H | $CH_2CH_2OCH_3$ | H | A-6 ($X_3$ = $OCH_3$) |
| H | $CH_2CH_2OCH_3$ | H | A-7 ($X_4$ = $OCH_3$, $Y_4$ = $OCH_3$) |
| H | $CH_2CH_2OCH_3$ | H | A-7 ($X_4$ = $CH_3$, $Y_4$ = $OCH_3$) |
| H | $CH_2CH_2OCH_3$ | H | A-7 ($X_4$ = $OCH_3$, $Y_4$ = $CH_3$) |
| H | $CH_2CH{=}CH_2$ | H | A-2 ($X_1$ = $CH_3$, $Y_1$ = $CH_2$) |
| H | $CH_2CH{=}CH_2$ | H | A-3 ($X_1$ = $CH_3$) |
| H | $CH_2CH{=}CH_2$ | H | A-3 ($X_1$ = $OCH_3$) |
| H | $CH_2CH{=}CH_2$ | H | A-4 ($X_1$ = $CH_3$, $Y_3$ = $CH_3$) |
| H | $CH_2CH{=}CH_2$ | H | A-4 ($X_1$ = $CH_3$, $Y_3$ = $OCH_3$) |
| H | $CH_2CH{=}CH_2$ | H | A-4 ($X_1$ = $OCH_3$, $Y_3$ = $CH_3$) |
| H | $CH_2CH{=}CH_2$ | H | A-5 ($X_2$ = $CH_3$, $Y_2$ = $OCH_3$) |
| H | $CH_2CH{=}CH_2$ | H | A-5 ($X_2$ = $CH_3$, $Y_2$ = $SCH_3$) |
| H | $CH_2CH{=}CH_2$ | H | A-6 ($X_3$ = $OCH_3$) |
| H | $CH_2CH{=}CH_2$ | H | A-7 ($X_4$ = $OCH_3$, $Y_4$ = $OCH_3$) |
| H | $CH_2CH{=}CH_2$ | H | A-7 ($X_4$ = $CH_3$, $Y_4$ = $OCH_3$) |
| H | $CH_2CH{=}CH_2$ | H | A-7 ($X_4$ = $OCH_3$, $Y_4$ = $CH_3$) |
| H | $CH_2C{\equiv}CH$ | H | A-2 ($X_1$ = $CH_3$, $Y_1$ = $CH_2$) |
| H | $CH_2C{\equiv}CH$ | H | A-3 ($X_1$ = $CH_3$) |
| H | $CH_2C{\equiv}CH$ | H | A-3 ($X_1$ = $OCH_3$) |
| H | $CH_2C{\equiv}CH$ | H | A-4 ($X_1$ = $CH_3$, $Y_3$ = $CH_3$) |
| H | $CH_2C{\equiv}CH$ | H | A-4 ($X_1$ = $CH_3$, $Y_3$ = $OCH_3$) |
| H | $CH_2C{\equiv}CH$ | H | A-4 ($X_1$ = $OCH_3$, $Y_3$ = $CH_3$) |
| H | $CH_2C{\equiv}CH$ | H | A-5 ($X_2$ = $CH_3$, $Y_2$ = $OCH_3$) |
| H | $CH_2C{\equiv}CH$ | H | A-5 ($X_2$ = $CH_3$, $Y_2$ = $SCH_3$) |
| H | $CH_2C{\equiv}CH$ | H | A-6 ($X_3$ = $OCH_3$) |
| H | $CH_2C{\equiv}CH$ | H | A-7 ($X_4$ = $OCH_3$, $Y_4$ = $OCH_3$) |
| H | $CH_2C{\equiv}CH$ | H | A-7 ($X_4$ = $CH_3$, $Y_4$ = $OCH_3$) |
| H | $CH_2C{\equiv}CH$ | H | A-7 ($X_4$ = $OCH_3$, $Y_4$ = $CH_3$) |
| H | cyclo-$C_3H_7$ | H | A-2 ($X_1$ = $CH_3$, $Y_1$ = $CH_2$) |
| H | cyclo-$C_3H_7$ | H | A-3 ($X_1$ = $CH_3$) |
| H | cyclo-$C_3H_7$ | H | A-3 ($X_1$ = $OCH_3$) |
| H | cyclo-$C_3H_7$ | H | A-4 ($X_1$ = $CH_3$, $Y_3$ = $CH_3$) |
| H | cyclo-$C_3H_7$ | H | A-4 ($X_1$ = $CH_3$, $Y_3$ = $OCH_3$) |
| H | cyclo-$C_3H_7$ | H | A-4 ($X_1$ = $OCH_3$, $Y_3$ = $CH_3$) |
| H | cyclo-$C_3H_7$ | H | A-5 ($X_2$ = $CH_3$, $Y_2$ = $OCH_3$) |
| H | cyclo-$C_3H_7$ | H | A-5 ($X_2$ = $CH_3$, $Y_2$ = $SCH_3$) |
| H | cyclo-$C_3H_7$ | H | A-6 ($X_3$ = $OCH_3$) |
| H | cyclo-$C_3H_7$ | H | A-7 ($X_4$ = $OCH_3$, $Y_4$ = $OCH_3$) |
| H | cyclo-$C_3H_7$ | H | A-7 ($X_4$ = $CH_3$, $Y_4$ = $OCH_3$) |
| H | cyclo-$C_3H_7$ | H | A-7 ($X_4$ = $OCH_3$, $Y_4$ = $CH_3$) |
| H | $CH_3$ | $CH_3$ | A-2 ($X_1$ = $CH_3$, $Y_1$ = $CH_2$) |
| H | $CH_3$ | $CH_3$ | A-3 ($X_1$ = $CH_3$) |
| H | $CH_3$ | $CH_3$ | A-3 ($X_1$ = $OCH_3$) |
| H | $CH_3$ | $CH_3$ | A-4 ($X_1$ = $CH_3$, $Y_3$ = $CH_3$) |
| H | $CH_3$ | $CH_3$ | A-4 ($X_1$ = $CH_3$, $Y_3$ = $OCH_3$) |
| H | $CH_3$ | $CH_3$ | A-4 ($X_1$ = $OCH_3$, $Y_3$ = $CH_3$) |
| H | $CH_3$ | $CH_3$ | A-5 ($X_2$ = $CH_3$, $Y_2$ = $OCH_3$) |

TABLE III-continued

GENERAL STRUCTURE 3

| $R_1$ | $R_2$ | $R_3$ | A |
|---|---|---|---|
| H | $CH_3$ | $CH_3$ | A-5 ($X_2$ = $CH_3$, $Y_2$ = $SCH_3$) |
| H | $CH_3$ | $CH_3$ | A-6 ($X_3$ = $OCH_3$) |
| H | $CH_3$ | $CH_3$ | A-7 ($X_4$ = $OCH_3$, $Y_4$ = $OCH_3$) |
| H | $CH_3$ | $CH_3$ | A-7 ($X_4$ = $CH_3$, $Y_4$ = $OCH_3$) |
| H | $CH_3$ | $CH_3$ | A-7 ($X_4$ = $OCH_3$, $Y_4$ = $CH_3$) |
| H | $CH_2CH_3$ | $CH_3$ | A-2 ($X_1$ = $CH_3$, $Y_1$ = $CH_2$) |
| H | $CH_2CH_3$ | $CH_3$ | A-3 ($X_1$ = $CH_3$) |
| H | $CH_2CH_3$ | $CH_3$ | A-3 ($X_1$ = $OCH_3$) |
| H | $CH_2CH_3$ | $CH_3$ | A-4 ($X_1$ = $CH_3$, $Y_3$ = $CH_3$) |
| H | $CH_2CH_3$ | $CH_3$ | A-4 ($X_1$ = $CH_3$, $Y_3$ = $OCH_3$) |
| H | $CH_2CH_3$ | $CH_3$ | A-4 ($X_1$ = $OCH_3$, $Y_3$ = $CH_3$) |
| H | $CH_2CH_3$ | $CH_3$ | A-5 ($X_2$ = $CH_3$, $Y_2$ = $OCH_3$) |
| H | $CH_2CH_3$ | $CH_3$ | A-5 ($X_2$ = $CH_3$, $Y_2$ = $SCH_3$) |
| H | $CH_2CH_3$ | $CH_3$ | A-6 ($X_3$ = $OCH_3$) |
| H | $CH_2CH_3$ | $CH_3$ | A-7 ($X_4$ = $OCH_3$, $Y_4$ = $OCH_3$) |
| H | $CH_2CH_3$ | $CH_3$ | A-7 ($X_4$ = $CH_3$, $Y_4$ = $OCH_3$) |
| H | $CH_2CH_3$ | $CH_3$ | A-7 ($X_4$ = $OCH_3$, $Y_4$ = $CH_3$) |
| H | $CH_2CH_3$ | $CH_2CH_3$ | A-2 ($X_1$ = $CH_3$, $Y_1$ = $CH_2$) |
| H | $CH_2CH_3$ | $CH_2CH_3$ | A-3 ($X_1$ = $CH_3$) |
| H | $CH_2CH_3$ | $CH_2CH_3$ | A-3 ($X_1$ = $OCH_3$) |
| H | $CH_2CH_3$ | $CH_2CH_3$ | A-4 ($X_1$ = $CH_3$, $Y_3$ = $CH_3$) |
| H | $CH_2CH_3$ | $CH_2CH_3$ | A-4 ($X_1$ = $CH_3$, $Y_3$ = $OCH_3$) |
| H | $CH_2CH_3$ | $CH_2CH_3$ | A-4 ($X_1$ = $OCH_3$, $Y_3$ = $CH_3$) |
| H | $CH_2CH_3$ | $CH_2CH_3$ | A-5 ($X_2$ = $CH_3$, $Y_2$ = $OCH_3$) |
| H | $CH_2CH_3$ | $CH_2CH_3$ | A-5 ($X_2$ = $CH_3$, $Y_2$ = $SCH_3$) |
| H | $CH_2CH_3$ | $CH_2CH_3$ | A-6 ($X_3$ = $OCH_3$) |
| H | $CH_2CH_3$ | $CH_2CH_3$ | A-7 ($X_4$ = $OCH_3$, $Y_4$ = $OCH_3$) |
| H | $CH_2CH_3$ | $CH_2CH_3$ | A-7 ($X_4$ = $CH_3$, $Y_4$ = $OCH_3$) |
| H | $CH_2CH_3$ | $CH_2CH_3$ | A-7 ($X_4$ = $OCH_3$, $Y_4$ = $CH_3$) |
| H | $OCH_3$ | $CH_3$ | A-2 ($X_1$ = $CH_3$, $Y_1$ = $CH_2$) |
| H | $OCH_3$ | $CH_3$ | A-3 ($X_1$ = $CH_3$) |
| H | $OCH_3$ | $CH_3$ | A-3 ($X_1$ = $OCH_3$) |
| H | $OCH_3$ | $CH_3$ | A-4 ($X_1$ = $CH_3$, $Y_3$ = $CH_3$) |
| H | $OCH_3$ | $CH_3$ | A-4 ($X_1$ = $CH_3$, $Y_3$ = $OCH_3$) |
| H | $OCH_3$ | $CH_3$ | A-4 ($X_1$ = $OCH_3$, $Y_3$ = $CH_3$) |
| H | $OCH_3$ | $CH_3$ | A-5 ($X_2$ = $CH_3$, $Y_2$ = $OCH_3$) |
| H | $OCH_3$ | $CH_3$ | A-5 ($X_2$ = $CH_3$, $Y_2$ = $SCH_3$) |
| H | $OCH_3$ | $CH_3$ | A-6 ($X_3$ = $OCH_3$) |
| H | $OCH_3$ | $CH_3$ | A-7 ($X_4$ = $OCH_3$, $Y_4$ = $OCH_3$) |
| H | $OCH_3$ | $CH_3$ | A-7 ($X_4$ = $CH_3$, $Y_4$ = $OCH_3$) |
| H | $OCH_3$ | $CH_3$ | A-7 ($X_4$ = $OCH_3$, $Y_4$ = $CH_3$) |
| H | $NHCH_3$ | $CH_3$ | A-2 ($X_1$ = $CH_3$, $Y_1$ = $CH_2$) |
| H | $NHCH_3$ | $CH_3$ | A-3 ($X_1$ = $CH_3$) |
| H | $NHCH_3$ | $CH_3$ | A-3 ($X_1$ = $OCH_3$) |
| H | $NHCH_3$ | $CH_3$ | A-4 ($X_1$ = $CH_3$, $Y_3$ = $CH_3$) |
| H | $NHCH_3$ | $CH_3$ | A-4 ($X_1$ = $CH_3$, $Y_3$ = $OCH_3$) |
| H | $NHCH_3$ | $CH_3$ | A-4 ($X_1$ = $OCH_3$, $Y_3$ = $CH_3$) |
| H | $NHCH_3$ | $CH_3$ | A-5 ($X_2$ = $CH_3$, $Y_2$ = $OCH_3$) |
| H | $NHCH_3$ | $CH_3$ | A-5 ($X_2$ = $CH_3$, $Y_2$ = $SCH_3$) |
| H | $NHCH_3$ | $CH_3$ | A-6 ($X_3$ = $OCH_3$) |
| H | $NHCH_3$ | $CH_3$ | A-7 ($X_4$ = $OCH_3$, $Y_4$ = $OCH_3$) |
| H | $NHCH_3$ | $CH_3$ | A-7 ($X_4$ = $CH_3$, $Y_4$ = $OCH_3$) |
| H | $NHCH_3$ | $CH_3$ | A-7 ($X_4$ = $OCH_3$, $Y_4$ = $CH_3$) |
| H | $N(CH_3)_2$ | $CH_3$ | A-2 ($X_1$ = $CH_3$, $Y_1$ = $CH_2$) |
| H | $N(CH_3)_2$ | $CH_3$ | A-3 ($X_1$ = $CH_3$) |
| H | $N(CH_3)_2$ | $CH_3$ | A-3 ($X_1$ = $OCH_3$) |
| H | $N(CH_3)_2$ | $CH_3$ | A-4 ($X_1$ = $CH_3$, $Y_3$ = $CH_3$) |
| H | $N(CH_3)_2$ | $CH_3$ | A-4 ($X_1$ = $CH_3$, $Y_3$ = $OCH_3$) |
| H | $N(CH_3)_2$ | $CH_3$ | A-4 ($X_1$ = $OCH_3$, $Y_3$ = $CH_3$) |
| H | $N(CH_3)_2$ | $CH_3$ | A-5 ($X_2$ = $CH_3$, $Y_2$ = $OCH_3$) |
| H | $N(CH_3)_2$ | $CH_3$ | A-5 ($X_2$ = $CH_3$, $Y_2$ = $SCH_3$) |
| H | $N(CH_3)_2$ | $CH_3$ | A-6 ($X_3$ = $OCH_3$) |
| H | $N(CH_3)_2$ | $CH_3$ | A-7 ($X_4$ = $OCH_3$, $Y_4$ = $OCH_3$) |
| H | $N(CH_3)_2$ | $CH_3$ | A-7 ($X_4$ = $CH_3$, $Y_4$ = $OCH_3$) |
| H | $N(CH_3)_2$ | $CH_3$ | A-7 ($X_4$ = $OCH_3$, $Y_4$ = $CH_3$) |
| H | $—CH_2CH_2CH_2—$ | | A-2 ($X_1$ = $CH_3$, $Y_1$ = $CH_2$) |
| H | $—CH_2CH_2CH_2—$ | | A-3 ($X_1$ = $CH_3$) |
| H | $—CH_2CH_2CH_2—$ | | A-3 ($X_1$ = $OCH_3$) |
| H | $—CH_2CH_2CH_2—$ | | A-4 ($X_1$ = $CH_3$, $Y_3$ = $CH_3$) |
| H | $—CH_2CH_2CH_2—$ | | A-4 ($X_1$ = $CH_3$, $Y_3$ = $OCH_3$) |
| H | $—CH_2CH_2CH_2—$ | | A-4 ($X_1$ = $OCH_3$, $Y_3$ = $CH_3$) |
| H | $—CH_2CH_2CH_2—$ | | A-5 ($X_2$ = $CH_3$, $Y_2$ = $OCH_3$) |
| H | $—CH_2CH_2CH_2—$ | | A-5 ($X_2$ = $CH_3$, $Y_2$ = $SCH_3$) |
| H | $—CH_2CH_2CH_2—$ | | A-6 ($X_3$ = $OCH_3$) |
| H | $—CH_2CH_2CH_2—$ | | A-7 ($X_4$ = $OCH_3$, $Y_4$ = $OCH_3$) |
| H | $—CH_2CH_2CH_2—$ | | A-7 ($X_4$ = $CH_3$, $Y_4$ = $OCH_3$) |
| H | $—CH_2CH_2CH_2—$ | | A-7 ($X_4$ = $OCH_3$, $Y_4$ = $CH_3$) |
| H | $—CH_2CH_2OCH_2CH_2—$ | | A-2 ($X_1$ = $CH_3$, $Y_1$ = $CH_2$) |
| H | $—CH_2CH_2OCH_2CH_2—$ | | A-3 ($X_1$ = $CH_3$) |
| H | $—CH_2CH_2OCH_2CH_2—$ | | A-3 ($X_1$ = $OCH_3$) |

TABLE III-continued

GENERAL STRUCTURE 3

| $R_1$ | $R_2$ | $R_3$ | A |
|---|---|---|---|
| H | $-CH_2CH_2OCH_2CH_2-$ | | A-4 ($X_1 = CH_3$, $Y_3 = CH_3$) |
| H | $-CH_2CH_2OCH_2CH_2-$ | | A-4 ($X_1 = CH_3$, $Y_3 = OCH_3$) |
| H | $-CH_2CH_2OCH_2CH_2-$ | | A-4 ($X_1 = OCH_3$, $Y_3 = CH_3$) |
| H | $-CH_2CH_2OCH_2CH_2-$ | | A-5 ($X_2 = CH_3$, $Y_2 = OCH_3$) |
| H | $-CH_2CH_2OCH_2CH_2-$ | | A-5 ($X_2 = CH_3$, $Y_2 = SCH_3$) |
| H | $-CH_2CH_2OCH_2CH_2-$ | | A-6 ($X_3 = OCH_3$) |
| H | $-CH_2CH_2OCH_2CH_2-$ | | A-7 ($X_4 = OCH_3$, $Y_4 = OCH_3$) |
| H | $-CH_2CH_2OCH_2CH_2-$ | | A-7 ($X_4 = CH_3$, $Y_4 = OCH_3$) |
| H | $-CH_2CH_2OCH_2CH_2-$ | | A-7 ($X_4 = OCH_3$, $Y_4 = CH_3$) |
| Cl | H | H | A-2 ($X_1 = CH_3$, $Y_1 = CH_2$) |
| Cl | H | H | A-3 ($X_1 = CH_3$) |
| Cl | H | H | A-3 ($X_1 = OCH_3$) |
| Cl | H | H | A-4 ($X_1 = CH_3$, $Y_3 = CH_3$) |
| Cl | H | H | A-4 ($X_1 = CH_3$, $Y_3 = OCH_3$) |
| Cl | H | H | A-4 ($X_1 = OCH_3$, $Y_3 = CH_3$) |
| Cl | H | H | A-5 ($X_2 = CH_3$, $Y_2 = OCH_3$) |
| Cl | H | H | A-5 ($X_2 = CH_3$, $Y_2 = SCH_3$) |
| Cl | H | H | A-6 ($X_3 = OCH_3$) |
| Cl | H | H | A-7 ($X_4 = OCH_3$, $Y_4 = OCH_3$) |
| Cl | H | H | A-7 ($X_4 = CH_3$, $Y_4 = OCH_3$) |
| Cl | H | H | A-7 ($X_4 = OCH_3$, $Y_4 = CH_3$) |
| Cl | H | $CH_3$ | A-2 ($X_1 = CH_3$, $Y_1 = CH_2$) |
| Cl | H | $CH_3$ | A-3 ($X_1 = CH_3$) |
| Cl | H | $CH_3$ | A-3 ($X_1 = OCH_3$) |
| Cl | H | $CH_3$ | A-4 ($X_1 = CH_3$, $Y_3 = CH_3$) |
| Cl | H | $CH_3$ | A-4 ($X_1 = CH_3$, $Y_3 = OCH_3$) |
| Cl | H | $CH_3$ | A-4 ($X_1 = OCH_3$, $Y_3 = CH_3$) |
| Cl | H | $CH_3$ | A-5 ($X_2 = CH_3$, $Y_2 = OCH_3$) |
| Cl | H | $CH_3$ | A-5 ($X_2 = CH_3$, $Y_2 = SCH_3$) |
| Cl | H | $CH_3$ | A-6 ($X_3 = OCH_3$) |
| Cl | H | $CH_3$ | A-7 ($X_4 = OCH_3$, $Y_4 = OCH_3$) |
| Cl | H | $CH_3$ | A-7 ($X_4 = CH_3$, $Y_4 = OCH_3$) |
| Cl | H | $CH_3$ | A-7 ($X_4 = OCH_3$, $Y_4 = CH_3$) |
| Cl | H | $CH_2CH_3$ | A-2 ($X_1 = CH_3$, $Y_1 = CH_2$) |
| Cl | H | $CH_2CH_3$ | A-3 ($X_1 = CH_3$) |
| Cl | H | $CH_2CH_3$ | A-3 ($X_1 = OCH_3$) |
| Cl | H | $CH_2CH_3$ | A-4 ($X_1 = CH_3$, $Y_3 = CH_3$) |
| Cl | H | $CH_2CH_3$ | A-4 ($X_1 = CH_3$, $Y_3 = OCH_3$) |
| Cl | H | $CH_2CH_3$ | A-4 ($X_1 = OCH_3$, $Y_3 = CH_3$) |
| Cl | H | $CH_2CH_3$ | A-5 ($X_2 = CH_3$, $Y_2 = OCH_3$) |
| Cl | H | $CH_2CH_3$ | A-5 ($X_2 = CH_3$, $Y_2 = SCH_3$) |
| Cl | H | $CH_2CH_3$ | A-6 ($X_3 = OCH_3$) |
| Cl | H | $CH_2CH_3$ | A-7 ($X_4 = OCH_3$, $Y_4 = OCH_3$) |
| Cl | H | $CH_2CH_3$ | A-7 ($X_4 = CH_3$, $Y_4 = OCH_3$) |
| Cl | H | $CH_2CH_3$ | A-7 ($X_4 = OCH_3$, $Y_4 = CH_3$) |
| Cl | $CH_2CF_3$ | H | A-2 ($X_1 = CH_3$, $Y_1 = CH_2$) |
| Cl | $CH_2CF_3$ | H | A-3 ($X_1 = CH_3$) |
| Cl | $CH_2CF_3$ | H | A-3 ($X_1 = OCH_3$) |
| Cl | $CH_2CF_3$ | H | A-4 ($X_1 = CH_3$, $Y_3 = CH_3$) |
| Cl | $CH_2CF_3$ | H | A-4 ($X_1 = CH_3$, $Y_3 = OCH_3$) |
| Cl | $CH_2CF_3$ | H | A-4 ($X_1 = OCH_3$, $Y_3 = CH_3$) |
| Cl | $CH_2CF_3$ | H | A-5 ($X_2 = CH_3$, $Y_2 = OCH_3$) |
| Cl | $CH_2CF_3$ | H | A-5 ($X_2 = CH_3$, $Y_2 = SCH_3$) |
| Cl | $CH_2CF_3$ | H | A-6 ($X_3 = OCH_3$) |
| Cl | $CH_2CF_3$ | H | A-7 ($X_4 = OCH_3$, $Y_4 = OCH_3$) |
| Cl | $CH_2CF_3$ | H | A-7 ($X_4 = CH_3$, $Y_4 = OCH_3$) |
| Cl | $CH_2CF_3$ | H | A-7 ($X_4 = OCH_3$, $Y_4 = CH_3$) |
| Cl | $CH_2CH_2Cl$ | H | A-2 ($X_1 = CH_3$, $Y_1 = CH_2$) |
| Cl | $CH_2CH_2Cl$ | H | A-3 ($X_1 = CH_3$) |
| Cl | $CH_2CH_2Cl$ | H | A-3 ($X_1 = OCH_3$) |
| Cl | $CH_2CH_2Cl$ | H | A-4 ($X_1 = CH_3$, $Y_3 = CH_3$) |
| Cl | $CH_2CH_2Cl$ | H | A-4 ($X_1 = CH_3$, $Y_3 = OCH_3$) |
| Cl | $CH_2CH_2Cl$ | H | A-4 ($X_1 = OCH_3$, $Y_3 = CH_3$) |
| Cl | $CH_2CH_2Cl$ | H | A-5 ($X_2 = CH_3$, $Y_2 = OCH_3$) |
| Cl | $CH_2CH_2Cl$ | H | A-5 ($X_2 = CH_3$, $Y_2 = SCH_3$) |
| Cl | $CH_2CH_2Cl$ | H | A-6 ($X_3 = OCH_3$) |
| Cl | $CH_2CH_2Cl$ | H | A-7 ($X_4 = OCH_3$, $Y_4 = OCH_3$) |
| Cl | $CH_2CH_2Cl$ | H | A-7 ($X_4 = CH_3$, $Y_4 = OCH_3$) |
| Cl | $CH_2CH_2Cl$ | H | A-7 ($X_4 = OCH_3$, $Y_4 = CH_3$) |
| Cl | $CH_2CN$ | H | A-2 ($X_1 = CH_3$, $Y_1 = CH_2$) |
| Cl | $CH_2CN$ | H | A-3 ($X_1 = CH_3$) |
| Cl | $CH_2CN$ | H | A-3 ($X_1 = OCH_3$) |
| Cl | $CH_2CN$ | H | A-4 ($X_1 = CH_3$, $Y_3 = CH_3$) |
| Cl | $CH_2CN$ | H | A-4 ($X_1 = CH_3$, $Y_3 = OCH_3$) |
| Cl | $CH_2CN$ | H | A-4 ($X_1 = OCH_3$, $Y_3 = CH_3$) |
| Cl | $CH_2CN$ | H | A-5 ($X_2 = CH_3$, $Y_2 = OCH_3$) |
| Cl | $CH_2CN$ | H | A-5 ($X_2 = CH_3$, $Y_2 = SCH_3$) |
| Cl | $CH_2CN$ | H | A-6 ($X_3 = OCH_3$) |
| Cl | $CH_2CN$ | H | A-7 ($X_4 = OCH_3$, $Y_4 = OCH_3$) |
| Cl | $CH_2CN$ | H | A-7 ($X_4 = CH_3$, $Y_4 = OCH_3$) |

TABLE III-continued

GENERAL STRUCTURE 3

| $R_1$ | $R_2$ | $R_3$ | A |
|---|---|---|---|
| Cl | $CH_2CN$ | H | A-7 ($X_4$ = $OCH_3$, $Y_4$ = $CH_3$) |
| Cl | $CH_2CH_2OCH_3$ | H | A-2 ($X_1$ = $CH_3$, $Y_1$ = $CH_2$) |
| Cl | $CH_2CH_2OCH_3$ | H | A-3 ($X_1$ = $CH_3$) |
| Cl | $CH_2CH_2OCH_3$ | H | A-3 ($X_1$ = $OCH_3$) |
| Cl | $CH_2CH_2OCH_3$ | H | A-4 ($X_1$ = $CH_3$, $Y_3$ = $CH_3$) |
| Cl | $CH_2CH_2OCH_3$ | H | A-4 ($X_1$ = $CH_3$, $Y_3$ = $OCH_3$) |
| Cl | $CH_2CH_2OCH_3$ | H | A-4 ($X_1$ = $OCH_3$, $Y_3$ = $CH_3$) |
| Cl | $CH_2CH_2OCH_3$ | H | A-5 ($X_2$ = $CH_3$, $Y_2$ = $OCH_3$) |
| Cl | $CH_2CH_2OCH_3$ | H | A-5 ($X_2$ = $CH_3$, $Y_2$ = $SCH_3$) |
| Cl | $CH_2CH_2OCH_3$ | H | A-6 ($X_3$ = $OCH_3$) |
| Cl | $CH_2CH_2OCH_3$ | H | A-7 ($X_4$ = $OCH_3$, $Y_4$ = $OCH_3$) |
| Cl | $CH_2CH_2OCH_3$ | H | A-7 ($X_4$ = $CH_3$, $Y_4$ = $OCH_3$) |
| Cl | $CH_2CH_2OCH_3$ | H | A-7 ($X_4$ = $OCH_3$, $Y_4$ = $CH_3$) |
| Cl | $CH_2CH{=}CH_2$ | H | A-2 ($X_1$ = $CH_3$, $Y_1$ = $CH_2$) |
| Cl | $CH_2CH{=}CH_2$ | H | A-3 ($X_1$ = $CH_3$) |
| Cl | $CH_2CH{=}CH_2$ | H | A-3 ($X_1$ = $OCH_3$) |
| Cl | $CH_2CH{=}CH_2$ | H | A-4 ($X_1$ = $CH_3$, $Y_3$ = $CH_3$) |
| Cl | $CH_2CH{=}CH_2$ | H | A-4 ($X_1$ = $CH_3$, $Y_3$ = $OCH_3$) |
| Cl | $CH_2CH{=}CH_2$ | H | A-4 ($X_1$ = $OCH_3$, $Y_3$ = $CH_3$) |
| Cl | $CH_2CH{=}CH_2$ | H | A-5 ($X_2$ = $CH_3$, $Y_2$ = $OCH_3$) |
| Cl | $CH_2CH{=}CH_2$ | H | A-5 ($X_2$ = $CH_3$, $Y_2$ = $SCH_3$) |
| Cl | $CH_2CH{=}CH_2$ | H | A-6 ($X_3$ = $OCH_3$) |
| Cl | $CH_2CH{=}CH_2$ | H | A-7 ($X_4$ = $OCH_3$, $Y_4$ = $OCH_3$) |
| Cl | $CH_2CH{=}CH_2$ | H | A-7 ($X_4$ = $CH_3$, $Y_4$ = $OCH_3$) |
| Cl | $CH_2CH{=}CH_2$ | H | A-7 ($X_4$ = $OCH_3$, $Y_4$ = $CH_3$) |
| Cl | $CH_2C{\equiv}CH$ | H | A-2 ($X_1$ = $CH_3$, $Y_1$ = $CH_2$) |
| Cl | $CH_2C{\equiv}CH$ | H | A-3 ($X_1$ = $CH_3$) |
| Cl | $CH_2C{\equiv}CH$ | H | A-3 ($X_1$ = $OCH_3$) |
| Cl | $CH_2C{\equiv}CH$ | H | A-4 ($X_1$ = $CH_3$, $Y_3$ = $CH_3$) |
| Cl | $CH_2C{\equiv}CH$ | H | A-4 ($X_1$ = $CH_3$, $Y_3$ = $OCH_3$) |
| Cl | $CH_2C{\equiv}CH$ | H | A-4 ($X_1$ = $OCH_3$, $Y_3$ = $CH_3$) |
| Cl | $CH_2C{\equiv}CH$ | H | A-5 ($X_2$ = $CH_3$, $Y_2$ = $OCH_3$) |
| Cl | $CH_2C{\equiv}CH$ | H | A-5 ($X_2$ = $CH_3$, $Y_2$ = $SCH_3$) |
| Cl | $CH_2C{\equiv}CH$ | H | A-6 ($X_3$ = $OCH_3$) |
| Cl | $CH_2C{\equiv}CH$ | H | A-7 ($X_4$ = $OCH_3$, $Y_4$ = $OCH_3$) |
| Cl | $CH_2C{\equiv}CH$ | H | A-7 ($X_4$ = $CH_3$, $Y_4$ = $OCH_3$) |
| Cl | $CH_2C{\equiv}CH$ | H | A-7 ($X_4$ = $OCH_3$, $Y_4$ = $CH_3$) |
| Cl | cyclo-$C_3H_7$ | H | A-2 ($X_1$ = $CH_3$, $Y_1$ = $CH_2$) |
| Cl | cyclo-$C_3H_7$ | H | A-3 ($X_1$ = $CH_3$) |
| Cl | cyclo-$C_3H_7$ | H | A-3 ($X_1$ = $OCH_3$) |
| Cl | cyclo-$C_3H_7$ | H | A-4 ($X_1$ = $CH_3$, $Y_3$ = $CH_3$) |
| Cl | cyclo-$C_3H_7$ | H | A-4 ($X_1$ = $CH_3$, $Y_3$ = $OCH_3$) |
| Cl | cyclo-$C_3H_7$ | H | A-4 ($X_1$ = $OCH_3$, $Y_3$ = $CH_3$) |
| Cl | cyclo-$C_3H_7$ | H | A-5 ($X_2$ = $CH_3$, $Y_2$ = $OCH_3$) |
| Cl | cyclo-$C_3H_7$ | H | A-5 ($X_2$ = $CH_3$, $Y_2$ = $SCH_3$) |
| Cl | cyclo-$C_3H_7$ | H | A-6 ($X_3$ = $OCH_3$) |
| Cl | cyclo-$C_3H_7$ | H | A-7 ($X_4$ = $OCH_3$, $Y_4$ = $OCH_3$) |
| Cl | cyclo-$C_3H_7$ | H | A-7 ($X_4$ = $CH_3$, $Y_4$ = $OCH_3$) |
| Cl | cyclo-$C_3H_7$ | H | A-7 ($X_4$ = $OCH_3$, $Y_4$ = $CH_3$) |
| Cl | $CH_3$ | $CH_3$ | A-2 ($X_1$ = $CH_3$, $Y_1$ = $CH_2$) |
| Cl | $CH_3$ | $CH_3$ | A-3 ($X_1$ = $CH_3$) |
| Cl | $CH_3$ | $CH_3$ | A-3 ($X_1$ = $OCH_3$) |
| Cl | $CH_3$ | $CH_3$ | A-4 ($X_1$ = $CH_3$, $Y_3$ = $CH_3$) |
| Cl | $CH_3$ | $CH_3$ | A-4 ($X_1$ = $CH_3$, $Y_3$ = $OCH_3$) |
| Cl | $CH_3$ | $CH_3$ | A-4 ($X_1$ = $OCH_3$, $Y_3$ = $CH_3$) |
| Cl | $CH_3$ | $CH_3$ | A-5 ($X_2$ = $CH_3$, $Y_2$ = $OCH_3$) |
| Cl | $CH_3$ | $CH_3$ | A-5 ($X_2$ = $CH_3$, $Y_2$ = $SCH_3$) |
| Cl | $CH_3$ | $CH_3$ | A-6 ($X_3$ = $OCH_3$) |
| Cl | $CH_3$ | $CH_3$ | A-7 ($X_4$ = $OCH_3$, $Y_4$ = $OCH_3$) |
| Cl | $CH_3$ | $CH_3$ | A-7 ($X_4$ = $CH_3$, $Y_4$ = $OCH_3$) |
| Cl | $CH_3$ | $CH_3$ | A-7 ($X_4$ = $OCH_3$, $Y_4$ = $CH_3$) |
| Cl | $CH_2CH_3$ | $CH_3$ | A-2 ($X_1$ = $CH_3$, $Y_1$ = $CH_2$) |
| Cl | $CH_2CH_3$ | $CH_3$ | A-3 ($X_1$ = $CH_3$) |
| Cl | $CH_2CH_3$ | $CH_3$ | A-3 ($X_1$ = $OCH_3$) |
| Cl | $CH_2CH_3$ | $CH_3$ | A-4 ($X_1$ = $CH_3$, $Y_3$ = $CH_3$) |
| Cl | $CH_2CH_3$ | $CH_3$ | A-4 ($X_1$ = $CH_3$, $Y_3$ = $OCH_3$) |
| Cl | $CH_2CH_3$ | $CH_3$ | A-4 ($X_1$ = $OCH_3$, $Y_3$ = $CH_3$) |
| Cl | $CH_2CH_3$ | $CH_3$ | A-5 ($X_2$ = $CH_3$, $Y_2$ = $OCH_3$) |
| Cl | $CH_2CH_3$ | $CH_3$ | A-5 ($X_2$ = $CH_3$, $Y_2$ = $SCH_3$) |
| Cl | $CH_2CH_3$ | $CH_3$ | A-6 ($X_3$ = $OCH_3$) |
| Cl | $CH_2CH_3$ | $CH_3$ | A-7 ($X_4$ = $OCH_3$, $Y_4$ = $OCH_3$) |
| Cl | $CH_2CH_3$ | $CH_3$ | A-7 ($X_4$ = $CH_3$, $Y_4$ = $OCH_3$) |
| Cl | $CH_2CH_3$ | $CH_3$ | A-7 ($X_4$ = $OCH_3$, $Y_4$ = $CH_3$) |
| Cl | $CH_2CH_3$ | $CH_2CH_3$ | A-2 ($X_1$ = $CH_3$, $Y_1$ = $CH_2$) |
| Cl | $CH_2CH_3$ | $CH_2CH_3$ | A-3 ($X_1$ = $CH_3$) |
| Cl | $CH_2CH_3$ | $CH_2CH_3$ | A-3 ($X_1$ = $OCH_3$) |
| Cl | $CH_2CH_3$ | $CH_2CH_3$ | A-4 ($X_1$ = $CH_3$, $Y_3$ = $CH_3$) |
| Cl | $CH_2CH_3$ | $CH_2CH_3$ | A-4 ($X_1$ = $CH_3$, $Y_3$ = $OCH_3$) |
| Cl | $CH_2CH_3$ | $CH_2CH_3$ | A-4 ($X_1$ = $OCH_3$, $Y_3$ = $CH_3$) |
| Cl | $CH_2CH_3$ | $CH_2CH_3$ | A-5 ($X_2$ = $CH_3$, $Y_2$ = $OCH_3$) |

TABLE III-continued

GENERAL STRUCTURE 3

| $R_1$ | $R_2$ | $R_3$ | A |
|---|---|---|---|
| Cl | $CH_2CH_3$ | $CH_2CH_3$ | A-5 ($X_2 = CH_3$, $Y_2 = SCH_3$) |
| Cl | $CH_2CH_3$ | $CH_2CH_3$ | A-6 ($X_3 = OCH_3$) |
| Cl | $CH_2CH_3$ | $CH_2CH_3$ | A-7 ($X_4 = OCH_3$, $Y_4 = OCH_3$) |
| Cl | $CH_2CH_3$ | $CH_2CH_3$ | A-7 ($X_4 = CH_3$, $Y_4 = OCH_3$) |
| Cl | $CH_2CH_3$ | $CH_2CH_3$ | A-7 ($X_4 = OCH_3$, $Y_4 = CH_3$) |
| Cl | $OCH_3$ | $CH_3$ | A-2 ($X_1 = CH_3$, $Y_1 = CH_2$) |
| Cl | $OCH_3$ | $CH_3$ | A-3 ($X_1 = CH_3$) |
| Cl | $OCH_3$ | $CH_3$ | A-3 ($X_1 = OCH_3$) |
| Cl | $OCH_3$ | $CH_3$ | A-4 ($X_1 = CH_3$, $Y_3 = CH_3$) |
| Cl | $OCH_3$ | $CH_3$ | A-4 ($X_1 = CH_3$, $Y_3 = OCH_3$) |
| Cl | $OCH_3$ | $CH_3$ | A-4 ($X_1 = OCH_3$, $Y_3 = CH_3$) |
| Cl | $OCH_3$ | $CH_3$ | A-5 ($X_2 = CH_3$, $Y_2 = OCH_3$) |
| Cl | $OCH_3$ | $CH_3$ | A-5 ($X_2 = CH_3$, $Y_2 = SCH_3$) |
| Cl | $OCH_3$ | $CH_3$ | A-6 ($X_3 = OCH_3$) |
| Cl | $OCH_3$ | $CH_3$ | A-7 ($X_4 = OCH_3$, $Y_4 = OCH_3$) |
| Cl | $OCH_3$ | $CH_3$ | A-7 ($X_4 = CH_3$, $Y_4 = OCH_3$) |
| Cl | $OCH_3$ | $CH_3$ | A-7 ($X_4 = OCH_3$, $Y_4 = CH_3$) |
| Cl | $NHCH_3$ | $CH_3$ | A-2 ($X_1 = CH_3$, $Y_1 = CH_2$) |
| Cl | $NHCH_3$ | $CH_3$ | A-3 ($X_1 = CH_3$) |
| Cl | $NHCH_3$ | $CH_3$ | A-3 ($X_1 = OCH_3$) |
| Cl | $NHCH_3$ | $CH_3$ | A-4 ($X_1 = CH_3$, $Y_3 = CH_3$) |
| Cl | $NHCH_3$ | $CH_3$ | A-4 ($X_1 = CH_3$, $Y_3 = OCH_3$) |
| Cl | $NHCH_3$ | $CH_3$ | A-4 ($X_1 = OCH_3$, $Y_3 = CH_3$) |
| Cl | $NHCH_3$ | $CH_3$ | A-5 ($X_2 = CH_3$, $Y_2 = OCH_3$) |
| Cl | $NHCH_3$ | $CH_3$ | A-5 ($X_2 = CH_3$, $Y_2 = SCH_3$) |
| Cl | $NHCH_3$ | $CH_3$ | A-6 ($X_3 = OCH_3$) |
| Cl | $NHCH_3$ | $CH_3$ | A-7 ($X_4 = OCH_3$, $Y_4 = OCH_3$) |
| Cl | $NHCH_3$ | $CH_3$ | A-7 ($X_4 = CH_3$, $Y_4 = OCH_3$) |
| Cl | $NHCH_3$ | $CH_3$ | A-7 ($X_4 = OCH_3$, $Y_4 = CH_3$) |
| Cl | $N(CH_3)_2$ | $CH_3$ | A-2 ($X_1 = CH_3$, $Y_1 = CH_2$) |
| Cl | $N(CH_3)_2$ | $CH_3$ | A-3 ($X_1 = CH_3$) |
| Cl | $N(CH_3)_2$ | $CH_3$ | A-3 ($X_1 = OCH_3$) |
| Cl | $N(CH_3)_2$ | $CH_3$ | A-4 ($X_1 = CH_3$, $Y_3 = CH_3$) |
| Cl | $N(CH_3)_2$ | $CH_3$ | A-4 ($X_1 = CH_3$, $Y_3 = OCH_3$) |
| Cl | $N(CH_3)_2$ | $CH_3$ | A-4 ($X_1 = OCH_3$, $Y_3 = CH_3$) |
| Cl | $N(CH_3)_2$ | $CH_3$ | A-5 ($X_2 = CH_3$, $Y_2 = OCH_3$) |
| Cl | $N(CH_3)_2$ | $CH_3$ | A-5 ($X_2 = CH_3$, $Y_2 = SCH_3$) |
| Cl | $N(CH_3)_2$ | $CH_3$ | A-6 ($X_3 = OCH_3$) |
| Cl | $N(CH_3)_2$ | $CH_3$ | A-7 ($X_4 = OCH_3$, $Y_4 = OCH_3$) |
| Cl | $N(CH_3)_2$ | $CH_3$ | A-7 ($X_4 = CH_3$, $Y_4 = OCH_3$) |
| Cl | $N(CH_3)_2$ | $CH_3$ | A-7 ($X_4 = OCH_3$, $Y_4 = CH_3$) |
| Cl | $-CH_2CH_2CH_2-$ | | A-2 ($X_1 = CH_3$, $Y_1 = CH_2$) |
| Cl | $-CH_2CH_2CH_2-$ | | A-3 ($X_1 = CH_3$) |
| Cl | $-CH_2CH_2CH_2-$ | | A-3 ($X_1 = OCH_3$) |
| Cl | $-CH_2CH_2CH_2-$ | | A-4 ($X_1 = CH_3$, $Y_3 = CH_3$) |
| Cl | $-CH_2CH_2CH_2-$ | | A-4 ($X_1 = CH_3$, $Y_3 = OCH_3$) |
| Cl | $-CH_2CH_2CH_2-$ | | A-4 ($X_1 = OCH_3$, $Y_3 = CH_3$) |
| Cl | $-CH_2CH_2CH_2-$ | | A-5 ($X_2 = CH_3$, $Y_2 = OCH_3$) |
| Cl | $-CH_2CH_2CH_2-$ | | A-5 ($X_2 = CH_3$, $Y_2 = SCH_3$) |
| Cl | $-CH_2CH_2CH_2-$ | | A-6 ($X_3 = OCH_3$) |
| Cl | $-CH_2CH_2CH_2-$ | | A-7 ($X_4 = OCH_3$, $Y_4 = OCH_3$) |
| Cl | $-CH_2CH_2CH_2-$ | | A-7 ($X_4 = CH_3$, $Y_4 = OCH_3$) |
| Cl | $-CH_2CH_2CH_2-$ | | A-7 ($X_4 = OCH_3$, $Y_4 = CH_3$) |
| Cl | $-CH_2CH_2OCH_2CH_2-$ | | A-2 ($X_1 = CH_3$, $Y_1 = CH_2$) |
| Cl | $-CH_2CH_2OCH_2CH_2-$ | | A-3 ($X_1 = CH_3$) |
| Cl | $-CH_2CH_2OCH_2CH_2-$ | | A-3 ($X_1 = OCH_3$) |
| Cl | $-CH_2CH_2OCH_2CH_2-$ | | A-4 ($X_1 = CH_3$, $Y_3 = CH_3$) |
| Cl | $-CH_2CH_2OCH_2CH_2-$ | | A-4 ($X_1 = CH_3$, $Y_3 = OCH_3$) |
| Cl | $-CH_2CH_2OCH_2CH_2-$ | | A-4 ($X_1 = OCH_3$, $Y_3 = CH_3$) |
| Cl | $-CH_2CH_2OCH_2CH_2-$ | | A-5 ($X_2 = CH_3$, $Y_2 = OCH_3$) |
| Cl | $-CH_2CH_2OCH_2CH_2-$ | | A-5 ($X_2 = CH_3$, $Y_2 = SCH_3$) |
| Cl | $-CH_2CH_2OCH_2CH_2-$ | | A-6 ($X_3 = OCH_3$) |
| Cl | $-CH_2CH_2OCH_2CH_2-$ | | A-7 ($X_4 = OCH_3$, $Y_4 = OCH_3$) |
| Cl | $-CH_2CH_2OCH_2CH_2-$ | | A-7 ($X_4 = CH_3$, $Y_4 = OCH_3$) |
| Cl | $-CH_2CH_2OCH_2CH_2-$ | | A-7 ($X_4 = OCH_3$, $Y_4 = CH_3$) |
| $CH_3$ | H | H | A-2 ($X_1 = CH_3$, $Y_1 = CH_2$) |
| $CH_3$ | H | H | A-3 ($X_1 = CH_3$) |
| $CH_3$ | H | H | A-3 ($X_1 = OCH_3$) |
| $CH_3$ | H | H | A-4 ($X_1 = CH_3$, $Y_3 = CH_3$) |
| $CH_3$ | H | H | A-4 ($X_1 = CH_3$, $Y_3 = OCH_3$) |
| $CH_3$ | H | H | A-4 ($X_1 = OCH_3$, $Y_3 = CH_3$) |
| $CH_3$ | H | H | A-5 ($X_2 = CH_3$, $Y_2 = OCH_3$) |
| $CH_3$ | H | H | A-5 ($X_2 = CH_3$, $Y_2 = SCH_3$) |
| $CH_3$ | H | H | A-6 ($X_3 = OCH_3$) |
| $CH_3$ | H | H | A-7 ($X_4 = OCH_3$, $Y_4 = OCH_3$) |
| $CH_3$ | H | H | A-7 ($X_4 = CH_3$, $Y_4 = OCH_3$) |
| $CH_3$ | H | H | A-7 ($X_4 = OCH_3$, $Y_4 = CH_3$) |
| $CH_3$ | H | $CH_3$ | A-2 ($X_1 = CH_3$, $Y_1 = CH_2$) |
| $CH_3$ | H | $CH_3$ | A-3 ($X_1 = CH_3$) |
| $CH_3$ | H | $CH_3$ | A-3 ($X_1 = OCH_3$) |

TABLE III-continued

GENERAL STRUCTURE 3

| $R_1$ | $R_2$ | $R_3$ | A |
|---|---|---|---|
| $CH_3$ | H | $CH_3$ | A-4 ($X_1$ = $CH_3$, $Y_3$ = $CH_3$) |
| $CH_3$ | H | $CH_3$ | A-4 ($X_1$ = $CH_3$, $Y_3$ = $OCH_3$) |
| $CH_3$ | H | $CH_3$ | A-4 ($X_1$ = $OCH_3$, $Y_3$ = $CH_3$) |
| $CH_3$ | H | $CH_3$ | A-5 ($X_2$ = $CH_3$, $Y_2$ = $OCH_3$) |
| $CH_3$ | H | $CH_3$ | A-5 ($X_2$ = $CH_3$, $Y_2$ = $SCH_3$) |
| $CH_3$ | H | $CH_3$ | A-6 ($X_3$ = $OCH_3$) |
| $CH_3$ | H | $CH_3$ | A-7 ($X_4$ = $OCH_3$, $Y_4$ = $OCH_3$) |
| $CH_3$ | H | $CH_3$ | A-7 ($X_4$ = $CH_3$, $Y_4$ = $OCH_3$) |
| $CH_3$ | H | $CH_3$ | A-7 ($X_4$ = $OCH_3$, $Y_4$ = $CH_3$) |
| $CH_3$ | H | $CH_2CH_3$ | A-2 ($X_1$ = $CH_3$, $Y_1$ = $CH_2$) |
| $CH_3$ | H | $CH_2CH_3$ | A-3 ($X_1$ = $CH_3$) |
| $CH_3$ | H | $CH_2CH_3$ | A-3 ($X_1$ = $OCH_3$) |
| $CH_3$ | H | $CH_2CH_3$ | A-4 ($X_1$ = $CH_3$, $Y_3$ = $CH_3$) |
| $CH_3$ | H | $CH_2CH_3$ | A-4 ($X_1$ = $CH_3$, $Y_3$ = $OCH_3$) |
| $CH_3$ | H | $CH_2CH_3$ | A-4 ($X_1$ = $OCH_3$, $Y_3$ = $CH_3$) |
| $CH_3$ | H | $CH_2CH_3$ | A-5 ($X_2$ = $CH_3$, $Y_2$ = $OCH_3$) |
| $CH_3$ | H | $CH_2CH_3$ | A-5 ($X_2$ = $CH_3$, $Y_2$ = $SCH_3$) |
| $CH_3$ | H | $CH_2CH_3$ | A-6 ($X_3$ = $OCH_3$) |
| $CH_3$ | H | $CH_2CH_3$ | A-7 ($X_4$ = $OCH_3$, $Y_4$ = $OCH_3$) |
| $CH_3$ | H | $CH_2CH_3$ | A-7 ($X_4$ = $CH_3$, $Y_4$ = $OCH_3$) |
| $CH_3$ | H | $CH_2CH_3$ | A-7 ($X_4$ = $OCH_3$, $Y_4$ = $CH_3$) |
| $CH_3$ | $CH_2CF_3$ | H | A-2 ($X_1$ = $CH_3$, $Y_1$ = $CH_2$) |
| $CH_3$ | $CH_2CF_3$ | H | A-3 ($X_1$ = $CH_3$) |
| $CH_3$ | $CH_2CF_3$ | H | A-3 ($X_1$ = $OCH_3$) |
| $CH_3$ | $CH_2CF_3$ | H | A-4 ($X_1$ = $CH_3$, $Y_3$ = $CH_3$) |
| $CH_3$ | $CH_2CF_3$ | H | A-4 ($X_1$ = $CH_3$, $Y_3$ = $OCH_3$) |
| $CH_3$ | $CH_2CF_3$ | H | A-4 ($X_1$ = $OCH_3$, $Y_3$ = $CH_3$) |
| $CH_3$ | $CH_2CF_3$ | H | A-5 ($X_2$ = $CH_3$, $Y_2$ = $OCH_3$) |
| $CH_3$ | $CH_2CF_3$ | H | A-5 ($X_2$ = $CH_3$, $Y_2$ = $SCH_3$) |
| $CH_3$ | $CH_2CF_3$ | H | A-6 ($X_3$ = $OCH_3$) |
| $CH_3$ | $CH_2CF_3$ | H | A-7 ($X_4$ = $OCH_3$, $Y_4$ = $OCH_3$) |
| $CH_3$ | $CH_2CF_3$ | H | A-7 ($X_4$ = $CH_3$, $Y_4$ = $OCH_3$) |
| $CH_3$ | $CH_2CF_3$ | H | A-7 ($X_4$ = $OCH_3$, $Y_4$ = $CH_3$) |
| $CH_3$ | $CH_2CH_2Cl$ | H | A-2 ($X_1$ = $CH_3$, $Y_1$ = $CH_2$) |
| $CH_3$ | $CH_2CH_2Cl$ | H | A-3 ($X_1$ = $CH_3$) |
| $CH_3$ | $CH_2CH_2Cl$ | H | A-3 ($X_1$ = $OCH_3$) |
| $CH_3$ | $CH_2CH_2Cl$ | H | A-4 ($X_1$ = $CH_3$, $Y_3$ = $CH_3$) |
| $CH_3$ | $CH_2CH_2Cl$ | H | A-4 ($X_1$ = $CH_3$, $Y_3$ = $OCH_3$) |
| $CH_3$ | $CH_2CH_2Cl$ | H | A-4 ($X_1$ = $OCH_3$, $Y_3$ = $CH_3$) |
| $CH_3$ | $CH_2CH_2Cl$ | H | A-5 ($X_2$ = $CH_3$, $Y_2$ = $OCH_3$) |
| $CH_3$ | $CH_2CH_2Cl$ | H | A-5 ($X_2$ = $CH_3$, $Y_2$ = $SCH_3$) |
| $CH_3$ | $CH_2CH_2Cl$ | H | A-6 ($X_3$ = $OCH_3$) |
| $CH_3$ | $CH_2CH_2Cl$ | H | A-7 ($X_4$ = $OCH_3$, $Y_4$ = $OCH_3$) |
| $CH_3$ | $CH_2CH_2Cl$ | H | A-7 ($X_4$ = $CH_3$, $Y_4$ = $OCH_3$) |
| $CH_3$ | $CH_2CH_2Cl$ | H | A-7 ($X_4$ = $OCH_3$, $Y_4$ = $CH_3$) |
| $CH_3$ | $CH_2CN$ | H | A-2 ($X_1$ = $CH_3$, $Y_1$ = $CH_2$) |
| $CH_3$ | $CH_2CN$ | H | A-3 ($X_1$ = $CH_3$) |
| $CH_3$ | $CH_2CN$ | H | A-3 ($X_1$ = $OCH_3$) |
| $CH_3$ | $CH_2CN$ | H | A-4 ($X_1$ = $CH_3$, $Y_3$ = $CH_3$) |
| $CH_3$ | $CH_2CN$ | H | A-4 ($X_1$ = $CH_3$, $Y_3$ = $OCH_3$) |
| $CH_3$ | $CH_2CN$ | H | A-4 ($X_1$ = $OCH_3$, $Y_3$ = $CH_3$) |
| $CH_3$ | $CH_2CN$ | H | A-5 ($X_2$ = $CH_3$, $Y_2$ = $OCH_3$) |
| $CH_3$ | $CH_2CN$ | H | A-5 ($X_2$ = $CH_3$, $Y_2$ = $SCH_3$) |
| $CH_3$ | $CH_2CN$ | H | A-6 ($X_3$ = $OCH_3$) |
| $CH_3$ | $CH_2CN$ | H | A-7 ($X_4$ = $OCH_3$, $Y_4$ = $OCH_3$) |
| $CH_3$ | $CH_2CN$ | H | A-7 ($X_4$ = $CH_3$, $Y_4$ = $OCH_3$) |
| $CH_3$ | $CH_2CN$ | H | A-7 ($X_4$ = $OCH_3$, $Y_4$ = $CH_3$) |
| $CH_3$ | $CH_2CH_2OCH_3$ | H | A-2 ($X_1$ = $CH_3$, $Y_1$ = $CH_2$) |
| $CH_3$ | $CH_2CH_2OCH_3$ | H | A-3 ($X_1$ = $CH_3$) |
| $CH_3$ | $CH_2CH_2OCH_3$ | H | A-3 ($X_1$ = $OCH_3$) |
| $CH_3$ | $CH_2CH_2OCH_3$ | H | A-4 ($X_1$ = $CH_3$, $Y_3$ = $CH_3$) |
| $CH_3$ | $CH_2CH_2OCH_3$ | H | A-4 ($X_1$ = $CH_3$, $Y_3$ = $OCH_3$) |
| $CH_3$ | $CH_2CH_2OCH_3$ | H | A-4 ($X_1$ = $OCH_3$, $Y_3$ = $CH_3$) |
| $CH_3$ | $CH_2CH_2OCH_3$ | H | A-5 ($X_2$ = $CH_3$, $Y_2$ = $OCH_3$) |
| $CH_3$ | $CH_2CH_2OCH_3$ | H | A-5 ($X_2$ = $CH_3$, $Y_2$ = $SCH_3$) |
| $CH_3$ | $CH_2CH_2OCH_3$ | H | A-6 ($X_3$ = $OCH_3$) |
| $CH_3$ | $CH_2CH_2OCH_3$ | H | A-7 ($X_4$ = $OCH_3$, $Y_4$ = $OCH_3$) |
| $CH_3$ | $CH_2CH_2OCH_3$ | H | A-7 ($X_4$ = $CH_3$, $Y_4$ = $OCH_3$) |
| $CH_3$ | $CH_2CH_2OCH_3$ | H | A-7 ($X_4$ = $OCH_3$, $Y_4$ = $CH_3$) |
| $CH_3$ | $CH_2CH{=}CH_2$ | H | A-2 ($X_1$ = $CH_3$, $Y_1$ = $CH_2$) |
| $CH_3$ | $CH_2CH{=}CH_2$ | H | A-3 ($X_1$ = $CH_3$) |
| $CH_3$ | $CH_2CH{=}CH_2$ | H | A-3 ($X_1$ = $OCH_3$) |
| $CH_3$ | $CH_2CH{=}CH_2$ | H | A-4 ($X_1$ = $CH_3$, $Y_3$ = $CH_3$) |
| $CH_3$ | $CH_2CH{=}CH_2$ | H | A-4 ($X_1$ = $CH_3$, $Y_3$ = $OCH_3$) |
| $CH_3$ | $CH_2CH{=}CH_2$ | H | A-4 ($X_1$ = $OCH_3$, $Y_3$ = $CH_3$) |
| $CH_3$ | $CH_2CH{=}CH_2$ | H | A-5 ($X_2$ = $CH_3$, $Y_2$ = $OCH_3$) |
| $CH_3$ | $CH_2CH{=}CH_2$ | H | A-5 ($X_2$ = $CH_3$, $Y_2$ = $SCH_3$) |
| $CH_3$ | $CH_2CH{=}CH_2$ | H | A-6 ($X_3$ = $OCH_3$) |
| $CH_3$ | $CH_2CH{=}CH_2$ | H | A-7 ($X_4$ = $OCH_3$, $Y_4$ = $OCH_3$) |
| $CH_3$ | $CH_2CH{=}CH_2$ | H | A-7 ($X_4$ = $CH_3$, $Y_4$ = $OCH_3$) |

TABLE III-continued

GENERAL STRUCTURE 3

| $R_1$ | $R_2$ | $R_3$ | A |
|---|---|---|---|
| $CH_3$ | $CH_2CH{=}CH_2$ | H | A-7 ($X_4$ = $OCH_3$, $Y_4$ = $CH_3$) |
| $CH_3$ | $CH_2{\equiv}CH$ | H | A-2 ($X_1$ = $CH_3$, $Y_1$ = $CH_2$) |
| $CH_3$ | $CH_2{\equiv}CH$ | H | A-3 ($X_1$ = $CH_3$) |
| $CH_3$ | $CH_2{\equiv}CH$ | H | A-3 ($X_1$ = $OCH_3$) |
| $CH_3$ | $CH_2{\equiv}CH$ | H | A-4 ($X_1$ = $CH_3$, $Y_3$ = $CH_3$) |
| $CH_3$ | $CH_2{\equiv}CH$ | H | A-4 ($X_1$ = $CH_3$, $Y_3$ = $OCH_3$) |
| $CH_3$ | $CH_2{\equiv}CH$ | H | A-4 ($X_1$ = $OCH_3$, $Y_3$ = $CH_3$) |
| $CH_3$ | $CH_2{\equiv}CH$ | H | A-5 ($X_2$ = $CH_3$, $Y_2$ = $OCH_3$) |
| $CH_3$ | $CH_2{\equiv}CH$ | H | A-5 ($X_2$ = $CH_3$, $Y_2$ = $SCH_3$) |
| $CH_3$ | $CH_2{\equiv}CH$ | H | A-6 ($X_3$ = $OCH_3$) |
| $CH_3$ | $CH_2{\equiv}CH$ | H | A-7 ($X_4$ = $OCH_3$, $Y_4$ = $OCH_3$) |
| $CH_3$ | $CH_2{\equiv}CH$ | H | A-7 ($X_4$ = $CH_3$, $Y_4$ = $OCH_3$) |
| $CH_3$ | $CH_2{\equiv}CH$ | H | A-7 ($X_4$ = $OCH_3$, $Y_4$ = $CH_3$) |
| $CH_3$ | cyclo-$C_3H_7$ | H | A-2 ($X_1$ = $CH_3$, $Y_1$ = $CH_2$) |
| $CH_3$ | cyclo-$C_3H_7$ | H | A-3 ($X_1$ = $CH_3$) |
| $CH_3$ | cyclo-$C_3H_7$ | H | A-3 ($X_1$ = $OCH_3$) |
| $CH_3$ | cyclo-$C_3H_7$ | H | A-4 ($X_1$ = $CH_3$, $Y_3$ = $CH_3$) |
| $CH_3$ | cyclo-$C_3H_7$ | H | A-4 ($X_1$ = $CH_3$, $Y_3$ = $OCH_3$) |
| $CH_3$ | cyclo-$C_3H_7$ | H | A-4 ($X_1$ = $OCH_3$, $Y_3$ = $CH_3$) |
| $CH_3$ | cyclo-$C_3H_7$ | H | A-5 ($X_2$ = $CH_3$, $Y_2$ = $OCH_3$) |
| $CH_3$ | cyclo-$C_3H_7$ | H | A-5 ($X_2$ = $CH_3$, $Y_2$ = $SCH_3$) |
| $CH_3$ | cyclo-$C_3H_7$ | H | A-6 ($X_3$ = $OCH_3$) |
| $CH_3$ | cyclo-$C_3H_7$ | H | A-7 ($X_4$ = $OCH_3$, $Y_4$ = $OCH_3$) |
| $CH_3$ | cyclo-$C_3H_7$ | H | A-7 ($X_4$ = $CH_3$, $Y_4$ = $OCH_3$) |
| $CH_3$ | cyclo-$C_3H_7$ | H | A-7 ($X_4$ = $OCH_3$, $Y_4$ = $CH_3$) |
| $CH_3$ | $CH_3$ | $CH_3$ | A-2 ($X_1$ = $CH_3$, $Y_1$ = $CH_2$) |
| $CH_3$ | $CH_3$ | $CH_3$ | A-3 ($X_1$ = $CH_3$) |
| $CH_3$ | $CH_3$ | $CH_3$ | A-3 ($X_1$ = $OCH_3$) |
| $CH_3$ | $CH_3$ | $CH_3$ | A-4 ($X_1$ = $CH_3$, $Y_3$ = $CH_3$) |
| $CH_3$ | $CH_3$ | $CH_3$ | A-4 ($X_1$ = $CH_3$, $Y_3$ = $OCH_3$) |
| $CH_3$ | $CH_3$ | $CH_3$ | A-4 ($X_1$ = $OCH_3$, $Y_3$ = $CH_3$) |
| $CH_3$ | $CH_3$ | $CH_3$ | A-5 ($X_2$ = $CH_3$, $Y_2$ = $OCH_3$) |
| $CH_3$ | $CH_3$ | $CH_3$ | A-5 ($X_2$ = $CH_3$, $Y_2$ = $SCH_3$) |
| $CH_3$ | $CH_3$ | $CH_3$ | A-6 ($X_3$ = $OCH_3$) |
| $CH_3$ | $CH_3$ | $CH_3$ | A-7 ($X_4$ = $OCH_3$, $Y_4$ = $OCH_3$) |
| $CH_3$ | $CH_3$ | $CH_3$ | A-7 ($X_4$ = $CH_3$, $Y_4$ = $OCH_3$) |
| $CH_3$ | $CH_3$ | $CH_3$ | A-7 ($X_4$ = $OCH_3$, $Y_4$ = $CH_3$) |
| $CH_3$ | $CH_2CH_3$ | $CH_3$ | A-2 ($X_1$ = $CH_3$, $Y_1$ = $CH_2$) |
| $CH_3$ | $CH_2CH_3$ | $CH_3$ | A-3 ($X_1$ = $CH_3$) |
| $CH_3$ | $CH_2CH_3$ | $CH_3$ | A-3 ($X_1$ = $OCH_3$) |
| $CH_3$ | $CH_2CH_3$ | $CH_3$ | A-4 ($X_1$ = $CH_3$, $Y_3$ = $CH_3$) |
| $CH_3$ | $CH_2CH_3$ | $CH_3$ | A-4 ($X_1$ = $CH_3$, $Y_3$ = $OCH_3$) |
| $CH_3$ | $CH_2CH_3$ | $CH_3$ | A-4 ($X_1$ = $OCH_3$, $Y_3$ = $CH_3$) |
| $CH_3$ | $CH_2CH_3$ | $CH_3$ | A-5 ($X_2$ = $CH_3$, $Y_2$ = $OCH_3$) |
| $CH_3$ | $CH_2CH_3$ | $CH_3$ | A-5 ($X_2$ = $CH_3$, $Y_2$ = $SCH_3$) |
| $CH_3$ | $CH_2CH_3$ | $CH_3$ | A-6 ($X_3$ = $OCH_3$) |
| $CH_3$ | $CH_2CH_3$ | $CH_3$ | A-7 ($X_4$ = $OCH_3$, $Y_4$ = $OCH_3$) |
| $CH_3$ | $CH_2CH_3$ | $CH_3$ | A-7 ($X_4$ = $CH_3$, $Y_4$ = $OCH_3$) |
| $CH_3$ | $CH_2CH_3$ | $CH_3$ | A-7 ($X_4$ = $OCH_3$, $Y_4$ = $CH_3$) |
| $CH_3$ | $CH_2CH_3$ | $CH_2CH_3$ | A-2 ($X_1$ = $CH_3$, $Y_1$ = $CH_2$) |
| $CH_3$ | $CH_2CH_3$ | $CH_2CH_3$ | A-3 ($X_1$ = $CH_3$) |
| $CH_3$ | $CH_2CH_3$ | $CH_2CH_3$ | A-3 ($X_1$ = $OCH_3$) |
| $CH_3$ | $CH_2CH_3$ | $CH_2CH_3$ | A-4 ($X_1$ = $CH_3$, $Y_3$ = $CH_3$) |
| $CH_3$ | $CH_2CH_3$ | $CH_2CH_3$ | A-4 ($X_1$ = $CH_3$, $Y_3$ = $OCH_3$) |
| $CH_3$ | $CH_2CH_3$ | $CH_2CH_3$ | A-4 ($X_1$ = $OCH_3$, $Y_3$ = $CH_3$) |
| $CH_3$ | $CH_2CH_3$ | $CH_2CH_3$ | A-5 ($X_2$ = $CH_3$, $Y_2$ = $OCH_3$) |
| $CH_3$ | $CH_2CH_3$ | $CH_2CH_3$ | A-5 ($X_2$ = $CH_3$, $Y_2$ = $SCH_3$) |
| $CH_3$ | $CH_2CH_3$ | $CH_2CH_3$ | A-6 ($X_3$ = $OCH_3$) |
| $CH_3$ | $CH_2CH_3$ | $CH_2CH_3$ | A-7 ($X_4$ = $OCH_3$, $Y_4$ = $OCH_3$) |
| $CH_3$ | $CH_2CH_3$ | $CH_2CH_3$ | A-7 ($X_4$ = $CH_3$, $Y_4$ = $OCH_3$) |
| $CH_3$ | $CH_2CH_3$ | $CH_2CH_3$ | A-7 ($X_4$ = $OCH_3$, $Y_4$ = $CH_3$) |
| $CH_3$ | $OCH_3$ | $CH_3$ | A-2 ($X_1$ = $CH_3$, $Y_1$ = $CH_2$) |
| $CH_3$ | $OCH_3$ | $CH_3$ | A-3 ($X_1$ = $CH_3$) |
| $CH_3$ | $OCH_3$ | $CH_3$ | A-3 ($X_1$ = $OCH_3$) |
| $CH_3$ | $OCH_3$ | $CH_3$ | A-4 ($X_1$ = $CH_3$, $Y_3$ = $CH_3$) |
| $CH_3$ | $OCH_3$ | $CH_3$ | A-4 ($X_1$ = $CH_3$, $Y_3$ = $OCH_3$) |
| $CH_3$ | $OCH_3$ | $CH_3$ | A-4 ($X_1$ = $OCH_3$, $Y_3$ = $CH_3$) |
| $CH_3$ | $OCH_3$ | $CH_3$ | A-5 ($X_2$ = $CH_3$, $Y_2$ = $OCH_3$) |
| $CH_3$ | $OCH_3$ | $CH_3$ | A-5 ($X_2$ = $CH_3$, $Y_2$ = $SCH_3$) |
| $CH_3$ | $OCH_3$ | $CH_3$ | A-6 ($X_3$ = $OCH_3$) |
| $CH_3$ | $OCH_3$ | $CH_3$ | A-7 ($X_4$ = $OCH_3$, $Y_4$ = $OCH_3$) |
| $CH_3$ | $OCH_3$ | $CH_3$ | A-7 ($X_4$ = $CH_3$, $Y_4$ = $OCH_3$) |
| $CH_3$ | $OCH_3$ | $CH_3$ | A-7 ($X_4$ = $OCH_3$, $Y_4$ = $CH_3$) |
| $CH_3$ | $NHCH_3$ | $CH_3$ | A-2 ($X_1$ = $CH_3$, $Y_1$ = $CH_2$) |
| $CH_3$ | $NHCH_3$ | $CH_3$ | A-3 ($X_1$ = $CH_3$) |
| $CH_3$ | $NHCH_3$ | $CH_3$ | A-3 ($X_1$ = $OCH_3$) |
| $CH_3$ | $NHCH_3$ | $CH_3$ | A-4 ($X_1$ = $CH_3$, $Y_3$ = $CH_3$) |
| $CH_3$ | $NHCH_3$ | $CH_3$ | A-4 ($X_1$ = $CH_3$, $Y_3$ = $OCH_3$) |
| $CH_3$ | $NHCH_3$ | $CH_3$ | A-4 ($X_1$ = $OCH_3$, $Y_3$ = $CH_3$) |
| $CH_3$ | $NHCH_3$ | $CH_3$ | A-5 ($X_2$ = $CH_3$, $Y_2$ = $OCH_3$) |

TABLE III-continued

GENERAL STRUCTURE 3

| $R_1$ | $R_2$ | $R_3$ | A |
|---|---|---|---|
| $CH_3$ | $NHCH_3$ | $CH_3$ | A-5 ($X_2$ = $CH_3$, $Y_2$ = $SCH_3$) |
| $CH_3$ | $NHCH_3$ | $CH_3$ | A-6 ($X_3$ = $OCH_3$) |
| $CH_3$ | $NHCH_3$ | $CH_3$ | A-7 ($X_4$ = $OCH_3$, $Y_4$ = $OCH_3$) |
| $CH_3$ | $NHCH_3$ | $CH_3$ | A-7 ($X_4$ = $CH_3$, $Y_4$ = $OCH_3$) |
| $CH_3$ | $NHCH_3$ | $CH_3$ | A-7 ($X_4$ = $OCH_3$, $Y_4$ = $CH_3$) |
| $CH_3$ | $N(CH_3)_2$ | $CH_3$ | A-2 ($X_1$ = $CH_3$, $Y_1$ = $CH_2$) |
| $CH_3$ | $N(CH_3)_2$ | $CH_3$ | A-3 ($X_1$ = $CH_3$) |
| $CH_3$ | $N(CH_3)_2$ | $CH_3$ | A-3 ($X_1$ = $OCH_3$) |
| $CH_3$ | $N(CH_3)_2$ | $CH_3$ | A-4 ($X_1$ = $CH_3$, $Y_3$ = $CH_3$) |
| $CH_3$ | $N(CH_3)_2$ | $CH_3$ | A-4 ($X_1$ = $CH_3$, $Y_3$ = $OCH_3$) |
| $CH_3$ | $N(CH_3)_2$ | $CH_3$ | A-4 ($X_1$ = $OCH_3$, $Y_3$ = $CH_3$) |
| $CH_3$ | $N(CH_3)_2$ | $CH_3$ | A-5 ($X_2$ = $CH_3$, $Y_2$ = $OCH_3$) |
| $CH_3$ | $N(CH_3)_2$ | $CH_3$ | A-5 ($X_2$ = $CH_3$, $Y_2$ = $SCH_3$) |
| $CH_3$ | $N(CH_3)_2$ | $CH_3$ | A-6 ($X_3$ = $OCH_3$) |
| $CH_3$ | $N(CH_3)_2$ | $CH_3$ | A-7 ($X_4$ = $OCH_3$, $Y_4$ = $OCH_3$) |
| $CH_3$ | $N(CH_3)_2$ | $CH_3$ | A-7 ($X_4$ = $CH_3$, $Y_4$ = $OCH_3$) |
| $CH_3$ | $N(CH_3)_2$ | $CH_3$ | A-7 ($X_4$ = $OCH_3$, $Y_4$ = $CH_3$) |
| $CH_3$ | $—CH_2CH_2CH_2—$ | | A-2 ($X_1$ = $CH_3$, $Y_1$ = $CH_2$) |
| $CH_3$ | $—CH_2CH_2CH_2—$ | | A-3 ($X_1$ = $CH_3$) |
| $CH_3$ | $—CH_2CH_2CH_2—$ | | A-3 ($X_1$ = $OCH_3$) |
| $CH_3$ | $—CH_2CH_2CH_2—$ | | A-4 ($X_1$ = $CH_3$, $Y_3$ = $CH_3$) |
| $CH_3$ | $—CH_2CH_2CH_2—$ | | A-4 ($X_1$ = $CH_3$, $Y_3$ = $OCH_3$) |
| $CH_3$ | $—CH_2CH_2CH_2—$ | | A-4 ($X_1$ = $OCH_3$, $Y_3$ = $CH_3$) |
| $CH_3$ | $—CH_2CH_2CH_2—$ | | A-5 ($X_2$ = $CH_3$, $Y_2$ = $OCH_3$) |
| $CH_3$ | $—CH_2CH_2CH_2—$ | | A-5 ($X_2$ = $CH_3$, $Y_2$ = $SCH_3$) |
| $CH_3$ | $—CH_2CH_2CH_2—$ | | A-6 ($X_3$ = $OCH_3$) |
| $CH_3$ | $—CH_2CH_2CH_2—$ | | A-7 ($X_4$ = $OCH_3$, $Y_4$ = $OCH_3$) |
| $CH_3$ | $—CH_2CH_2CH_2—$ | | A-7 ($X_4$ = $CH_3$, $Y_4$ = $OCH_3$) |
| $CH_3$ | $—CH_2CH_2CH_2—$ | | A-7 ($X_4$ = $OCH_3$, $Y_4$ = $CH_3$) |
| $CH_3$ | $—CH_2CH_2OCH_2CH_2—$ | | A-2 ($X_1$ = $CH_3$, $Y_1$ = $CH_2$) |
| $CH_3$ | $—CH_2CH_2OCH_2CH_2—$ | | A-3 ($X_1$ = $CH_3$) |
| $CH_3$ | $—CH_2CH_2OCH_2CH_2—$ | | A-3 ($X_1$ = $OCH_3$) |
| $CH_3$ | $—CH_2CH_2OCH_2CH_2—$ | | A-4 ($X_1$ = $CH_3$, $Y_3$ = $CH_3$) |
| $CH_3$ | $—CH_2CH_2OCH_2CH_2—$ | | A-4 ($X_1$ = $CH_3$, $Y_3$ = $OCH_3$) |
| $CH_3$ | $—CH_2CH_2OCH_2CH_2—$ | | A-4 ($X_1$ = $OCH_3$, $Y_3$ = $CH_3$) |
| $CH_3$ | $—CH_2CH_2OCH_2CH_2—$ | | A-5 ($X_2$ = $CH_3$, $Y_2$ = $OCH_3$) |
| $CH_3$ | $—CH_2CH_2OCH_2CH_2—$ | | A-5 ($X_2$ = $CH_3$, $Y_2$ = $SCH_3$) |
| $CH_3$ | $—CH_2CH_2OCH_2CH_2—$ | | A-6 ($X_3$ = $OCH_3$) |
| $CH_3$ | $—CH_2CH_2OCH_2CH_2—$ | | A-7 ($X_4$ = $OCH_3$, $Y_4$ = $OCH_3$) |
| $CH_3$ | $—CH_2CH_2OCH_2CH_2—$ | | A-7 ($X_4$ = $CH_3$, $Y_4$ = $OCH_3$) |
| $CH_3$ | $—CH_2CH_2OCH_2CH_2—$ | | A-7 ($X_4$ = $OCH_3$, $Y_4$ = $CH_3$) |
| $SCH_3$ | H | H | A-2 ($X_1$ = $CH_3$, $Y_1$ = $CH_2$) |
| $SCH_3$ | H | H | A-3 ($X_1$ = $CH_3$) |
| $SCH_3$ | H | H | A-3 ($X_1$ = $OCH_3$) |
| $SCH_3$ | H | H | A-4 ($X_1$ = $CH_3$, $Y_3$ = $CH_3$) |
| $SCH_3$ | H | H | A-4 ($X_1$ = $CH_3$, $Y_3$ = $OCH_3$) |
| $SCH_3$ | H | H | A-4 ($X_1$ = $OCH_3$, $Y_3$ = $CH_3$) |
| $SCH_3$ | H | H | A-5 ($X_2$ = $CH_3$, $Y_2$ = $OCH_3$) |
| $SCH_3$ | H | H | A-5 ($X_2$ = $CH_3$, $Y_2$ = $SCH_3$) |
| $SCH_3$ | H | H | A-6 ($X_3$ = $OCH_3$) |
| $SCH_3$ | H | H | A-7 ($X_4$ = $OCH_3$, $Y_4$ = $OCH_3$) |
| $SCH_3$ | H | H | A-7 ($X_4$ = $CH_3$, $Y_4$ = $OCH_3$) |
| $SCH_3$ | H | H | A-7 ($X_4$ = $OCH_3$, $Y_4$ = $CH_3$) |
| $SCH_3$ | H | $CH_3$ | A-2 ($X_1$ = $CH_3$, $Y_1$ = $CH_2$) |
| $SCH_3$ | H | $CH_3$ | A-3 ($X_1$ = $CH_3$) |
| $SCH_3$ | H | $CH_3$ | A-3 ($X_1$ = $OCH_3$) |
| $SCH_3$ | H | $CH_3$ | A-4 ($X_1$ = $CH_3$, $Y_3$ = $CH_3$) |
| $SCH_3$ | H | $CH_3$ | A-4 ($X_1$ = $CH_3$, $Y_3$ = $OCH_3$) |
| $SCH_3$ | H | $CH_3$ | A-4 ($X_1$ = $OCH_3$, $Y_3$ = $CH_3$) |
| $SCH_3$ | H | $CH_3$ | A-5 ($X_2$ = $CH_3$, $Y_2$ = $OCH_3$) |
| $SCH_3$ | H | $CH_3$ | A-5 ($X_2$ = $CH_3$, $Y_2$ = $SCH_3$) |
| $SCH_3$ | H | $CH_3$ | A-6 ($X_3$ = $OCH_3$) |
| $SCH_3$ | H | $CH_3$ | A-7 ($X_4$ = $OCH_3$, $Y_4$ = $OCH_3$) |
| $SCH_3$ | H | $CH_3$ | A-7 ($X_4$ = $CH_3$, $Y_4$ = $OCH_3$) |
| $SCH_3$ | H | $CH_3$ | A-7 ($X_4$ = $OCH_3$, $Y_4$ = $CH_3$) |
| $SCH_3$ | H | $CH_2CH_3$ | A-2 ($X_1$ = $CH_3$, $Y_1$ = $CH_2$) |
| $SCH_3$ | H | $CH_2CH_3$ | A-3 ($X_1$ = $CH_3$) |
| $SCH_3$ | H | $CH_2CH_3$ | A-3 ($X_1$ = $OCH_3$) |
| $SCH_3$ | H | $CH_2CH_3$ | A-4 ($X_1$ = $CH_3$, $Y_3$ = $CH_3$) |
| $SCH_3$ | H | $CH_2CH_3$ | A-4 ($X_1$ = $CH_3$, $Y_3$ = $OCH_3$) |
| $SCH_3$ | H | $CH_2CH_3$ | A-4 ($X_1$ = $OCH_3$, $Y_3$ = $CH_3$) |
| $SCH_3$ | H | $CH_2CH_3$ | A-5 ($X_2$ = $CH_3$, $Y_2$ = $OCH_3$) |
| $SCH_3$ | H | $CH_2CH_3$ | A-5 ($X_2$ = $CH_3$, $Y_2$ = $SCH_3$) |
| $SCH_3$ | H | $CH_2CH_3$ | A-6 ($X_3$ = $OCH_3$) |
| $SCH_3$ | H | $CH_2CH_3$ | A-7 ($X_4$ = $OCH_3$, $Y_4$ = $OCH_3$) |
| $SCH_3$ | H | $CH_2CH_3$ | A-7 ($X_4$ = $CH_3$, $Y_4$ = $OCH_3$) |
| $SCH_3$ | H | $CH_2CH_3$ | A-7 ($X_4$ = $OCH_3$, $Y_4$ = $CH_3$) |
| $SCH_3$ | $CH_2CF_3$ | H | A-2 ($X_1$ = $CH_3$, $Y_1$ = $CH_2$) |
| $SCH_3$ | $CH_2CF_3$ | H | A-3 ($X_1$ = $CH_3$) |
| $SCH_3$ | $CH_2CF_3$ | H | A-3 ($X_1$ = $OCH_3$) |

TABLE III-continued

GENERAL STRUCTURE 3

| $R_1$ | $R_2$ | $R_3$ | A |
|---|---|---|---|
| $SCH_3$ | $CH_2CF_3$ | H | A-4 ($X_1 = CH_3$, $Y_3 = CH_3$) |
| $SCH_3$ | $CH_2CF_3$ | H | A-4 ($X_1 = CH_3$, $Y_3 = OCH_3$) |
| $SCH_3$ | $CH_2CF_3$ | H | A-4 ($X_1 = OCH_3$, $Y_3 = CH_3$) |
| $SCH_3$ | $CH_2CF_3$ | H | A-5 ($X_2 = CH_3$, $Y_2 = OCH_3$) |
| $SCH_3$ | $CH_2CF_3$ | H | A-5 ($X_2 = CH_3$, $Y_2 = SCH_3$) |
| $SCH_3$ | $CH_2CF_3$ | H | A-6 ($X_3 = OCH_3$) |
| $SCH_3$ | $CH_2CF_3$ | H | A-7 ($X_4 = OCH_3$, $Y_4 = OCH_3$) |
| $SCH_3$ | $CH_2CF_3$ | H | A-7 ($X_4 = CH_3$, $Y_4 = OCH_3$) |
| $SCH_3$ | $CH_2CF_3$ | H | A-7 ($X_4 = OCH_3$, $Y_4 = CH_3$) |
| $SCH_3$ | $CH_2CH_2Cl$ | H | A-2 ($X_1 = CH_3$, $Y_1 = CH_2$) |
| $SCH_3$ | $CH_2CH_2Cl$ | H | A-3 ($X_1 = CH_3$) |
| $SCH_3$ | $CH_2CH_2Cl$ | H | A-3 ($X_1 = OCH_3$) |
| $SCH_3$ | $CH_2CH_2Cl$ | H | A-4 ($X_1 = CH_3$, $Y_3 = CH_3$) |
| $SCH_3$ | $CH_2CH_2Cl$ | H | A-4 ($X_1 = CH_3$, $Y_3 = OCH_3$) |
| $SCH_3$ | $CH_2CH_2Cl$ | H | A-4 ($X_1 = OCH_3$, $Y_3 = CH_3$) |
| $SCH_3$ | $CH_2CH_2Cl$ | H | A-5 ($X_2 = CH_3$, $Y_1 = OCH_3$) |
| $SCH_3$ | $CH_2CH_2Cl$ | H | A-5 ($X_2 = CH_3$, $Y_2 = SCH_3$) |
| $SCH_3$ | $CH_2CH_2Cl$ | H | A-6 ($X_3 = OCH_3$) |
| $SCH_3$ | $CH_2CH_2Cl$ | H | A-7 ($X_4 = OCH_3$, $Y_4 = OCH_3$) |
| $SCH_3$ | $CH_2CH_2Cl$ | H | A-7 ($X_4 = CH_3$, $Y_4 = OCH_3$) |
| $SCH_3$ | $CH_2CH_2Cl$ | H | A-7 ($X_4 = OCH_3$, $Y_4 = CH_3$) |
| $SCH_3$ | $CH_2CN$ | H | A-2 ($X_1 = CH_3$, $Y_1 = CH_2$) |
| $SCH_3$ | $CH_2CN$ | H | A-3 ($X_1 = CH_3$) |
| $SCH_3$ | $CH_2CN$ | H | A-3 ($X_1 = OCH_3$) |
| $SCH_3$ | $CH_2CN$ | H | A-4 ($X_1 = CH_3$, $Y_3 = CH_3$) |
| $SCH_3$ | $CH_2CN$ | H | A-4 ($X_1 = CH_3$, $Y_3 = OCH_3$) |
| $SCH_3$ | $CH_2CN$ | H | A-4 ($X_1 = OCH_3$, $Y_3 = CH_3$) |
| $SCH_3$ | $CH_2CN$ | H | A-5 ($X_2 = CH_3$, $Y_2 = OCH_3$) |
| $SCH_3$ | $CH_2CN$ | H | A-5 ($X_2 = CH_3$, $Y_2 = SCH_3$) |
| $SCH_3$ | $CH_2CN$ | H | A-6 ($X_3 = OCH_3$) |
| $SCH_3$ | $CH_2CN$ | H | A-7 ($X_4 = OCH_3$, $Y_4 = OCH_3$) |
| $SCH_3$ | $CH_2CN$ | H | A-7 ($X_4 = CH_3$, $Y_4 = OCH_3$) |
| $SCH_3$ | $CH_2CN$ | H | A-7 ($X_4 = OCH_3$, $Y_4 = CH_3$) |
| $SCH_3$ | $CH_2CH_2OCH_3$ | H | A-2 ($X_1 = CH_3$, $Y_1 = CH_2$) |
| $SCH_3$ | $CH_2CH_2OCH_3$ | H | A-3 ($X_1 = CH_3$) |
| $SCH_3$ | $CH_2CH_2OCH_3$ | H | A-3 ($X_1 = OCH_3$) |
| $SCH_3$ | $CH_2CH_2OCH_3$ | H | A-4 ($X_1 = CH_3$, $Y_3 = CH_3$) |
| $SCH_3$ | $CH_2CH_2OCH_3$ | H | A-4 ($X_1 = CH_3$, $Y_3 = OCH_3$) |
| $SCH_3$ | $CH_2CH_2OCH_3$ | H | A-4 ($X_1 = OCH_3$, $Y_3 = CH_3$) |
| $SCH_3$ | $CH_2CH_2OCH_3$ | H | A-5 ($X_2 = CH_3$, $Y_2 = OCH_3$) |
| $SCH_3$ | $CH_2CH_2OCH_3$ | H | A-5 ($X_2 = CH_3$, $Y_2 = SCH_3$) |
| $SCH_3$ | $CH_2CH_2OCH_3$ | H | A-6 ($X_3 = OCH_3$) |
| $SCH_3$ | $CH_2CH_2OCH_3$ | H | A-7 ($X_4 = OCH_3$, $Y_4 = OCH_3$) |
| $SCH_3$ | $CH_2CH_2OCH_3$ | H | A-7 ($X_4 = CH_3$, $Y_4 = OCH_3$) |
| $SCH_3$ | $CH_2CH_2OCH_3$ | H | A-7 ($X_4 = OCH_3$, $Y_4 = CH_3$) |
| $SCH_3$ | $CH_2CH{=}CH_2$ | H | A-2 ($X_1 = CH_3$, $Y_1 = CH_2$) |
| $SCH_3$ | $CH_2CH{=}CH_2$ | H | A-3 ($X_1 = CH_3$) |
| $SCH_3$ | $CH_2CH{=}CH_2$ | H | A-3 ($X_1 = OCH_3$) |
| $SCH_3$ | $CH_2CH{=}CH_2$ | H | A-4 ($X_1 = CH_3$, $Y_3 = CH_3$) |
| $SCH_3$ | $CH_2CH{=}CH_2$ | H | A-4 ($X_1 = CH_3$, $Y_3 = OCH_3$) |
| $SCH_3$ | $CH_2CH{=}CH_2$ | H | A-4 ($X_1 = OCH_3$, $Y_3 = CH_3$) |
| $SCH_3$ | $CH_2CH{=}CH_2$ | H | A-5 ($X_2 = CH_3$, $Y_2 = OCH_3$) |
| $SCH_3$ | $CH_2CH{=}CH_2$ | H | A-5 ($X_2 = CH_3$, $Y_2 = SCH_3$) |
| $SCH_3$ | $CH_2CH{=}CH_2$ | H | A-6 ($X_3 = OCH_3$) |
| $SCH_3$ | $CH_2CH{=}CH_2$ | H | A-7 ($X_4 = OCH_3$, $Y_4 = OCH_3$) |
| $SCH_3$ | $CH_2CH{=}CH_2$ | H | A-7 ($X_4 = CH_3$, $Y_4 = OCH_3$) |
| $SCH_3$ | $CH_2CH{=}CH_2$ | H | A-7 ($X_4 = OCH_3$, $Y_4 = CH_3$) |
| $SCH_3$ | $CH_2C{\equiv}CH$ | H | A-2 ($X_1 = CH_3$, $Y_1 = CH_2$) |
| $SCH_3$ | $CH_2C{\equiv}CH$ | H | A-3 ($X_1 = CH_3$) |
| $SCH_3$ | $CH_2C{\equiv}CH$ | H | A-3 ($X_1 = OCH_3$) |
| $SCH_3$ | $CH_2C{\equiv}CH$ | H | A-4 ($X_1 = CH_3$, $Y_3 = CH_3$) |
| $SCH_3$ | $CH_2C{\equiv}CH$ | H | A-4 ($X_1 = CH_3$, $Y_3 = OCH_3$) |
| $SCH_3$ | $CH_2C{\equiv}CH$ | H | A-4 ($X_1 = OCH_3$, $Y_3 = CH_3$) |
| $SCH_3$ | $CH_2C{\equiv}CH$ | H | A-5 ($X_2 = CH_3$, $Y_2 = OCH_3$) |
| $SCH_3$ | $CH_2C{\equiv}CH$ | H | A-5 ($X_2 = CH_3$, $Y_2 = SCH_3$) |
| $SCH_3$ | $CH_2C{\equiv}CH$ | H | A-6 ($X_3 = OCH_3$) |
| $SCH_3$ | $CH_2C{\equiv}CH$ | H | A-7 ($X_4 = OCH_3$, $Y_4 = OCH_3$) |
| $SCH_3$ | $CH_2C{\equiv}CH$ | H | A-7 ($X_4 = CH_3$, $Y_4 = OCH_3$) |
| $SCH_3$ | $CH_2C{\equiv}CH$ | H | A-7 ($X_4 = OCH_3$, $Y_4 = CH_3$) |
| $SCH_3$ | cyclo-$C_3H_7$ | H | A-2 ($X_1 = CH_3$, $Y_1 = CH_2$) |
| $SCH_3$ | cyclo-$C_3H_7$ | H | A-3 ($X_1 = CH_3$) |
| $SCH_3$ | cyclo-$C_3H_7$ | H | A-3 ($X_1 = OCH_3$) |
| $SCH_3$ | cyclo-$C_3H_7$ | H | A-4 ($X_1 = CH_3$, $Y_3 = CH_3$) |
| $SCH_3$ | cyclo-$C_3H_7$ | H | A-4 ($X_1 = CH_3$, $Y_3 = OCH_3$) |
| $SCH_3$ | cyclo-$C_3H_7$ | H | A-4 ($X_1 = OCH_3$, $Y_3 = CH_3$) |
| $SCH_3$ | cyclo-$C_3H_7$ | H | A-5 ($X_2 = CH_3$, $Y_2 = OCH_3$) |

-continued

| | | | |
|---|---|---|---|
| $SCH_3$ | cyclo-$C_3H_7$ | H | A-5 ($X_2$ = $CH_3$, $Y_2$ = $SCH_3$) |
| $SCH_3$ | cyclo-$C_3H_7$ | H | A-6 ($X_3$ = $OCH_3$) |
| $SCH_3$ | cyclo-$C_3H_7$ | H | A-7 ($X_4$ = $OCH_3$, $Y_4$ = $OCH_3$) |
| $SCH_3$ | cyclo-$C_3H_7$ | H | A-7 ($X_4$ = $CH_3$, $Y_4$ = $OCH_3$) |
| $SCH_3$ | cyclo-$C_3H_7$ | H | A-7 ($X_4$ = $OCH_3$, $Y_4$ = $CH_3$) |
| $SCH_3$ | $CH_3$ | $CH_3$ | A-2 ($X_1$ = $CH_3$, $Y_1$ = $CH_2$) |
| $SCH_3$ | $CH_3$ | $CH_3$ | A-3 ($X_1$ = $CH_3$) |
| $SCH_3$ | $CH_3$ | $CH_3$ | A-3 ($X_1$ = $OCH_3$) |
| $SCH_3$ | $CH_3$ | $CH_3$ | A-4 ($X_1$ = $CH_3$, $Y_3$ = $CH_3$) |
| $SCH_3$ | $CH_3$ | $CH_3$ | A-4 ($X_1$ = $CH_3$, $Y_3$ = $OCH_3$) |
| $SCH_3$ | $CH_3$ | $CH_3$ | A-4 ($X_1$ = $OCH_3$, $Y_3$ = $CH_3$) |
| $SCH_3$ | $CH_3$ | $CH_3$ | A-5 ($X_2$ = $CH_3$, $Y_2$ = $OCH_3$) |
| $SCH_3$ | $CH_3$ | $CH_3$ | A-5 ($X_2$ = $CH_3$, $Y_2$ = $SCH_3$) |
| $SCH_3$ | $CH_3$ | $CH_3$ | A-6 ($X_3$ = $OCH_3$) |
| $SCH_3$ | $CH_3$ | $CH_3$ | A-7 ($X_4$ = $OCH_3$, $Y_4$ = $OCH_3$) |
| $SCH_3$ | $CH_3$ | $CH_3$ | A-7 ($X_4$ = $CH_3$, $Y_4$ = $OCH_3$) |
| $SCH_3$ | $CH_3$ | $CH_3$ | A-7 ($X_4$ = $OCH_3$, $Y_4$ = $CH_3$) |
| $SCH_3$ | $CH_2CH_3$ | $CH_3$ | A-2 ($X_1$ = $CH_3$, $Y_1$ = $CH_2$) |
| $SCH_3$ | $CH_2CH_3$ | $CH_3$ | A-3 ($X_1$ = $CH_3$) |
| $SCH_3$ | $CH_2CH_3$ | $CH_3$ | A-3 ($X_1$ = $OCH_3$) |
| $SCH_3$ | $CH_2CH_3$ | $CH_3$ | A-4 ($X_1$ = $CH_3$, $Y_3$ = $CH_3$) |
| $SCH_3$ | $CH_2CH_3$ | $CH_3$ | A-4 ($X_1$ = $CH_3$, $Y_3$ = $OCH_3$) |
| $SCH_3$ | $CH_2CH_3$ | $CH_3$ | A-4 ($X_1$ = $OCH_3$, $Y_3$ = $CH_3$) |
| $SCH_3$ | $CH_2CH_3$ | $CH_3$ | A-5 ($X_2$ = $CH_3$, $Y_2$ = $OCH_3$) |
| $SCH_3$ | $CH_2CH_3$ | $CH_3$ | A-5 ($X_2$ = $CH_3$, $Y_2$ = $SCH_3$) |
| $SCH_3$ | $CH_2CH_3$ | $CH_3$ | A-6 ($X_3$ = $OCH_3$) |
| $SCH_3$ | $CH_2CH_3$ | $CH_3$ | A-7 ($X_4$ = $OCH_3$, $Y_4$ = $OCH_3$) |
| $SCH_3$ | $CH_2CH_3$ | $CH_3$ | A-7 ($X_4$ = $CH_3$, $Y_4$ = $OCH_3$) |
| $SCH_3$ | $CH_2CH_3$ | $CH_3$ | A-7 ($X_4$ = $OCH_3$, $Y_4$ = $CH_3$) |
| $SCH_3$ | $CH_2CH_3$ | $CH_2CH_3$ | A-2 ($X_1$ = $CH_3$, $Y_1$ = $CH_2$) |
| $SCH_3$ | $CH_2CH_3$ | $CH_2CH_3$ | A-3 ($X_1$ = $CH_3$) |
| $SCH_3$ | $CH_2CH_3$ | $CH_2CH_3$ | A-3 ($X_1$ = $OCH_3$) |
| $SCH_3$ | $CH_2CH_3$ | $CH_2CH_3$ | A-4 ($X_1$ = $CH_3$, $Y_3$ = $CH_3$) |
| $SCH_3$ | $CH_2CH_3$ | $CH_2CH_3$ | A-4 ($X_1$ = $CH_3$, $Y_3$ = $OCH_3$) |
| $SCH_3$ | $CH_2CH_3$ | $CH_2CH_3$ | A-4 ($X_1$ = $OCH_3$, $Y_3$ = $CH_3$) |
| $SCH_3$ | $CH_2CH_3$ | $CH_2CH_3$ | A-5 ($X_2$ = $CH_3$, $Y_2$ = $OCH_3$) |
| $SCH_3$ | $CH_2CH_3$ | $CH_2CH_3$ | A-5 ($X_2$ = $CH_3$, $Y_2$ = $SCH_3$) |
| $SCH_3$ | $CH_2CH_3$ | $CH_2CH_3$ | A-6 ($X_3$ = $OCH_3$) |
| $SCH_3$ | $CH_2CH_3$ | $CH_2CH_3$ | A-7 ($X_4$ = $OCH_3$, $Y_4$ = $OCH_3$) |
| $SCH_3$ | $CH_2CH_3$ | $CH_2CH_3$ | A-7 ($X_4$ = $CH_3$, $Y_4$ = $OCH_3$) |
| $SCH_3$ | $CH_2CH_3$ | $CH_2CH_3$ | A-7 ($X_4$ = $OCH_3$, $Y_4$ = $CH_3$) |
| $SCH_3$ | $OCH_3$ | $CH_3$ | A-2 ($X_1$ = $CH_3$, $Y_1$ = $CH_2$) |
| $SCH_3$ | $OCH_3$ | $CH_3$ | A-3 ($X_1$ = $CH_3$) |
| $SCH_3$ | $OCH_3$ | $CH_3$ | A-3 ($X_1$ = $OCH_3$) |
| $SCH_3$ | $OCH_3$ | $CH_3$ | A-4 ($X_1$ = $CH_3$, $Y_3$ = $CH_3$) |
| $SCH_3$ | $OCH_3$ | $CH_3$ | A-4 ($X_1$ = $CH_3$, $Y_3$ = $OCH_3$) |
| $SCH_3$ | $OCH_3$ | $CH_3$ | A-4 ($X_1$ = $OCH_3$, $Y_3$ = $CH_3$) |
| $SCH_3$ | $OCH_3$ | $CH_3$ | A-5 ($X_2$ = $CH_3$, $Y_2$ = $OCH_3$) |
| $SCH_3$ | $OCH_3$ | $CH_3$ | A-5 ($X_2$ = $CH_3$, $Y_2$ = $SCH_3$) |
| $SCH_3$ | $OCH_3$ | $CH_3$ | A-6 ($X_3$ = $OCH_3$) |
| $SCH_3$ | $OCH_3$ | $CH_3$ | A-7 ($X_4$ = $OCH_3$, $Y_4$ = $OCH_3$) |
| $SCH_3$ | $OCH_3$ | $CH_3$ | A-7 ($X_4$ = $CH_3$, $Y_4$ = $OCH_3$) |
| $SCH_3$ | $OCH_3$ | $CH_3$ | A-7 ($X_4$ = $OCH_3$, $Y_4$ = $CH_3$) |
| $SCH_3$ | $NHCH_3$ | $CH_3$ | A-2 ($X_1$ = $CH_3$, $Y_1$ = $CH_2$) |
| $SCH_3$ | $NHCH_3$ | $CH_3$ | A-3 ($X_1$ = $CH_3$) |
| $SCH_3$ | $NHCH_3$ | $CH_3$ | A-3 ($X_1$ = $OCH_3$) |
| $SCH_3$ | $NHCH_3$ | $CH_3$ | A-4 ($X_1$ = $CH_3$, $Y_3$ = $CH_3$) |
| $SCH_3$ | $NHCH_3$ | $CH_3$ | A-4 ($X_1$ = $CH_3$, $Y_3$ = $OCH_3$) |
| $SCH_3$ | $NHCH_3$ | $CH_3$ | A-4 ($X_1$ = $OCH_3$, $Y_3$ = $CH_3$) |
| $SCH_3$ | $NHCH_3$ | $CH_3$ | A-5 ($X_2$ = $CH_3$, $Y_2$ = $OCH_3$) |
| $SCH_3$ | $NHCH_3$ | $CH_3$ | A-5 ($X_2$ = $CH_3$, $Y_2$ = $SCH_3$) |
| $SCH_3$ | $NHCH_3$ | $CH_3$ | A-6 ($X_3$ = $OCH_3$) |
| $SCH_3$ | $NHCH_3$ | $CH_3$ | A-7 ($X_4$ = $OCH_3$, $Y_4$ = $OCH_3$) |
| $SCH_3$ | $NHCH_3$ | $CH_3$ | A-7 ($X_4$ = $CH_3$, $Y_4$ = $OCH_3$) |
| $SCH_3$ | $NHCH_3$ | $CH_3$ | A-7 ($X_4$ = $OCH_3$, $Y_4$ = $CH_3$) |
| $SCH_3$ | $N(CH_3)_2$ | $CH_3$ | A-2 ($X_1$ = $CH_3$, $Y_1$ = $CH_2$) |
| $SCH_3$ | $N(CH_3)_2$ | $CH_3$ | A-3 ($X_1$ = $CH_3$) |
| $SCH_3$ | $N(CH_3)_2$ | $CH_3$ | A-3 ($X_1$ = $OCH_3$) |
| $SCH_3$ | $N(CH_3)_2$ | $CH_3$ | A-4 ($X_1$ = $CH_3$, $Y_3$ = $CH_3$) |
| $SCH_3$ | $N(CH_3)_2$ | $CH_3$ | A-4 ($X_1$ = $CH_3$, $Y_3$ = $OCH_3$) |
| $SCH_3$ | $N(CH_3)_2$ | $CH_3$ | A-4 ($X_1$ = $OCH_3$, $Y_3$ = $CH_3$) |
| $SCH_3$ | $N(CH_3)_2$ | $CH_3$ | A-5 ($X_2$ = $CH_3$, $Y_2$ = $OCH_3$) |
| $SCH_3$ | $N(CH_3)_2$ | $CH_3$ | A-5 ($X_2$ = $CH_3$, $Y_2$ = $SCH_3$) |
| $SCH_3$ | $N(CH_3)_2$ | $CH_3$ | A-6 ($X_3$ = $OCH_3$) |
| $SCH_3$ | $N(CH_3)_2$ | $CH_3$ | A-7 ($X_4$ = $OCH_3$, $Y_4$ = $OCH_3$) |
| $SCH_3$ | $N(CH_3)_2$ | $CH_3$ | A-7 ($X_4$ = $CH_3$, $Y_4$ = $OCH_3$) |
| $SCH_3$ | $N(CH_3)_2$ | $CH_3$ | A-7 ($X_4$ = $OCH_3$, $Y_4$ = $CH_3$) |
| $SCH_3$ | $-CH_2CH_2CH_2-$ | | A-2 ($X_1$ = $CH_3$, $Y_1$ = $CH_2$) |
| $SCH_3$ | $-CH_2CH_2CH_2-$ | | A-3 ($X_1$ = $CH_3$) |
| $SCH_3$ | $-CH_2CH_2CH_2-$ | | A-3 ($X_1$ = $OCH_3$) |
| $SCH_3$ | $-CH_2CH_2CH_2-$ | | A-4 ($X_1$ = $CH_3$, $Y_3$ = $CH_3$) |
| $SCH_3$ | $-CH_2CH_2CH_2-$ | | A-4 ($X_1$ = $CH_3$, $Y_3$ = $OCH_3$) |

-continued

| | | | |
|---|---|---|---|
| $SCH_3$ | $—CH_2CH_2CH_2—$ | | A-4 ($X_1 = OCH_3, Y_3 = CH_3$) |
| $SCH_3$ | $—CH_2CH_2CH_2—$ | | A-5 ($X_2 = CH_3, Y_2 = OCH_3$) |
| $SCH_3$ | $—CH_2CH_2CH_2—$ | | A-5 ($X_2 = CH_3, Y_2 = SCH_3$) |
| $SCH_3$ | $—CH_2CH_2CH_2—$ | | A-6 ($X_3 = OCH_3$) |
| $SCH_3$ | $—CH_2CH_2CH_2—$ | | A-7 ($X_4 = OCH_3, Y_4 = OCH_3$) |
| $SCH_3$ | $—CH_2CH_2CH_2—$ | | A-7 ($X_4 = CH_3, Y_4 = OCH_3$) |
| $SCH_3$ | $—CH_2CH_2CH_2—$ | | A-7 ($X_4 = OCH_3, Y_4 = CH_3$) |
| $SCH_3$ | $—CH_2CH_2OCH_2CH_2—$ | | A-2 ($X_1 = CH_3, Y_1 = CH_2$) |
| $SCH_3$ | $—CH_2CH_2OCH_2CH_2—$ | | A-3 ($X_1 = CH_3$) |
| $SCH_3$ | $—CH_2CH_2OCH_2CH_2—$ | | A-3 ($X_1 = OCH_3$) |
| $SCH_3$ | $—CH_2CH_2OCH_2CH_2—$ | | A-4 ($X_1 = CH_3, Y_3 = CH_3$) |
| $SCH_3$ | $—CH_2CH_2OCH_2CH_2—$ | | A-4 ($X_1 = CH_3, Y_3 = OCH_3$) |
| $SCH_3$ | $—CH_2CH_2OCH_2CH_2—$ | | A-4 ($X_1 = OCH_3, Y_3 = CH_3$) |
| $SCH_3$ | $—CH_2CH_2OCH_2CH_2—$ | | A-5 ($X_2 = CH_3, Y_2 = OCH_3$) |
| $SCH_3$ | $—CH_2CH_2OCH_2CH_2—$ | | A-5 ($X_2 = CH_3, Y_2 = SCH_3$) |
| $SCH_3$ | $—CH_2CH_2OCH_2CH_2—$ | | A-6 ($X_3 = OCH_3$) |
| $SCH_3$ | $—CH_2CH_2OCH_2CH_2—$ | | A-7 ($X_4 = OCH_3, Y_4 = OCH_3$) |
| $SCH_3$ | $—CH_2CH_2OCH_2CH_2—$ | | A-7 ($X_4 = CH_3, Y_4 = OCH_3$) |
| $SCH_3$ | $—CH_2CH_2OCH_2CH_2—$ | | A-7 ($X_4 = OCH_3, Y_4 = CH_3$) |
| $SO_2CH_2CH_3$ | H | H | A-2 ($X_1 = CH_3, Y_1 = CH_2$) |
| $SO_2CH_2CH_3$ | H | H | A-3 ($X_1 = CH_3$) |
| $SO_2CH_2CH_3$ | H | H | A-3 ($X_1 = OCH_3$) |
| $SO_2CH_2CH_3$ | H | H | A-4 ($X_1 = CH_3, Y_3 = CH_3$) |
| $SO_2CH_2CH_3$ | H | H | A-4 ($X_1 = CH_3, Y_3 = OCH_3$) |
| $SO_2CH_2CH_3$ | H | H | A-4 ($X_1 = OCH_3, Y_3 = CH_3$) |
| $SO_2CH_2CH_3$ | H | H | A-5 ($X_2 = CH_3, Y_2 = OCH_3$) |
| $SO_2CH_2CH_3$ | H | H | A-5 ($X_2 = CH_3, Y_2 = SCH_3$) |
| $SO_2CH_2CH_3$ | H | H | A-6 ($X_3 = OCH_3$) |
| $SO_2CH_2CH_3$ | H | H | A-7 ($X_4 = OCH_3, Y_4 = OCH_3$) |
| $SO_2CH_2CH_3$ | H | H | A-7 ($X_4 = CH_3, Y_4 = OCH_3$) |
| $SO_2CH_2CH_3$ | H | H | A-7 ($X_4 = OCH_3, Y_4 = CH_3$) |
| $SO_2CH_2CH_3$ | H | $CH_3$ | A-2 ($X_1 = CH_3, Y_1 = CH_2$) |
| $SO_2CH_2CH_3$ | H | $CH_3$ | A-3 ($X_1 = CH_3$) |
| $SO_2CH_2CH_3$ | H | $CH_3$ | A-3 ($X_1 = OCH_3$) |
| $SO_2CH_2CH_3$ | H | $CH_3$ | A-4 ($X_1 = CH_3, Y_3 = CH_3$) |
| $SO_2CH_2CH_3$ | H | $CH_3$ | A-4 ($X_1 = CH_3, Y_3 = OCH_3$) |
| $SO_2CH_2CH_3$ | H | $CH_3$ | A-4 ($X_1 = OCH_3, Y_3 = CH_3$) |
| $SO_2CH_2CH_3$ | H | $CH_3$ | A-5 ($X_2 = CH_3, Y_2 = OCH_3$) |
| $SO_2CH_2CH_3$ | H | $CH_3$ | A-5 ($X_2 = CH_3, Y_2 = SCH_3$) |
| $SO_2CH_2CH_3$ | H | $CH_3$ | A-6 ($X_3 = OCH_3$) |
| $SO_2CH_2CH_3$ | H | $CH_3$ | A-7 ($X_4 = OCH_3, Y_4 = OCH_3$) |
| $SO_2CH_2CH_3$ | H | $CH_3$ | A-7 ($X_4 = CH_3, Y_4 = OCH_3$) |
| $SO_2CH_2CH_3$ | H | $CH_3$ | A-7 ($X_4 = OCH_3, Y_4 = CH_3$) |
| $SO_2CH_2CH_3$ | H | $CH_2CH_3$ | A-2 ($X_1 = CH_3, Y_1 = CH_2$) |
| $SO_2CH_2CH_3$ | H | $CH_2CH_3$ | A-3 ($X_1 = CH_3$) |
| $SO_2CH_2CH_3$ | H | $CH_2CH_3$ | A-3 ($X_1 = OCH_3$) |
| $SO_2CH_2CH_3$ | H | $CH_2CH_3$ | A-4 ($X_1 = CH_3, Y_3 = CH_3$) |
| $SO_2CH_2CH_3$ | H | $CH_2CH_3$ | A-4 ($X_1 = CH_3, Y_3 = OCH_3$) |
| $SO_2CH_2CH_3$ | H | $CH_2CH_3$ | A-4 ($X_1 = OCH_3, Y_3 = CH_3$) |
| $SO_2CH_2CH_3$ | H | $CH_2CH_3$ | A-5 ($X_2 = CH_3, Y_2 = OCH_3$) |
| $SO_2CH_2CH_3$ | H | $CH_2CH_3$ | A-5 ($X_2 = CH_3, Y_2 = SCH_3$) |
| $SO_2CH_2CH_3$ | H | $CH_2CH_3$ | A-6 ($X_3 = OCH_3$) |
| $SO_2CH_2CH_3$ | H | $CH_2CH_3$ | A-7 ($X_4 = OCH_3, Y_4 = OCH_3$) |
| $SO_2CH_2CH_3$ | H | $CH_2CH_3$ | A-7 ($X_4 = CH_3, Y_4 = OCH_3$) |
| $SO_2CH_2CH_3$ | H | $CH_2CH_3$ | A-7 ($X_4 = OCH_3, Y_4 = CH_3$) |
| $SO_2CH_2CH_3$ | $CH_2CF_3$ | H | A-2 ($X_1 = CH_3, Y_1 = CH_2$) |
| $SO_2CH_2CH_3$ | $CH_2CF_3$ | H | A-3 ($X_1 = CH_3$) |
| $SO_2CH_2CH_3$ | $CH_2CF_3$ | H | A-3 ($X_1 = OCH_3$) |
| $SO_2CH_2CH_3$ | $CH_2CF_3$ | H | A-4 ($X_1 = CH_3, Y_3 = CH_3$) |
| $SO_2CH_2CH_3$ | $CH_2CF_3$ | H | A-4 ($X_1 = CH_3, Y_3 = OCH_3$) |
| $SO_2CH_2CH_3$ | $CH_2CF_3$ | H | A-4 ($X_1 = OCH_3, Y_3 = CH_3$) |
| $SO_2CH_2CH_3$ | $CH_2CF_3$ | H | A-5 ($X_2 = CH_3, Y_2 = OCH_3$) |
| $SO_2CH_2CH_3$ | $CH_2CF_3$ | H | A-5 ($X_2 = CH_3, Y_2 = SCH_3$) |
| $SO_2CH_2CH_3$ | $CH_2CF_3$ | H | A-6 ($X_3 = OCH_3$) |
| $SO_2CH_2CH_3$ | $CH_2CF_3$ | H | A-7 ($X_4 = OCH_3, Y_4 = OCH_3$) |
| $SO_2CH_2CH_3$ | $CH_2CF_3$ | H | A-7 ($X_4 = CH_3, Y_4 = OCH_3$) |
| $SO_2CH_2CH_3$ | $CH_2CF_3$ | H | A-7 ($X_4 = OCH_3, Y_4 = CH_3$) |
| $SO_2CH_2CH_3$ | $CH_2CH_2Cl$ | H | A-2 ($X_1 = CH_3, Y_1 = CH_2$) |
| $SO_2CH_2CH_3$ | $CH_2CH_2Cl$ | H | A-3 ($X_1 = CH_3$) |
| $SO_2CH_2CH_3$ | $CH_2CH_2Cl$ | H | A-3 ($X_1 = OCH_3$) |
| $SO_2CH_2CH_3$ | $CH_2CH_2Cl$ | H | A-4 ($X_1 = CH_3, Y_3 = CH_3$) |
| $SO_2CH_2CH_3$ | $CH_2CH_2Cl$ | H | A-4 ($X_1 = CH_3, Y_3 = OCH_3$) |
| $SO_2CH_2CH_3$ | $CH_2CH_2Cl$ | H | A-4 ($X_1 = OCH_3, Y_3 = CH_3$) |
| $SO_2CH_2CH_3$ | $CH_2CH_2Cl$ | H | A-5 ($X_2 = CH_3, Y_2 = OCH_3$) |
| $SO_2CH_2CH_3$ | $CH_2CH_2Cl$ | H | A-5 ($X_2 = CH_3, Y_2 = SCH_3$) |
| $SO_2CH_2CH_3$ | $CH_2CH_2Cl$ | H | A-6 ($X_3 = OCH_3$) |
| $SO_2CH_2CH_3$ | $CH_2CH_2Cl$ | H | A-7 ($X_4 = OCH_3, Y_4 = OCH_3$) |
| $SO_2CH_2CH_3$ | $CH_2CH_2Cl$ | H | A-7 ($X_4 = CH_3, Y_4 = OCH_3$) |
| $SO_2CH_2CH_3$ | $CH_2CH_2Cl$ | H | A-7 ($X_4 = OCH_3, Y_4 = CH_3$) |
| $SO_2CH_2CH_3$ | $CH_2CN$ | H | A-2 ($X_1 = CH_3, Y_1 = CH_2$) |
| $SO_2CH_2CH_3$ | $CH_2CN$ | H | A-3 ($X_1 = CH_3$) |
| $SO_2CH_2CH_3$ | $CH_2CN$ | H | A-3 ($X_1 = OCH_3$) |

-continued

| | | | |
|---|---|---|---|
| $SO_2CH_2CH_3$ | $CH_2CN$ | H | A-4 ($X_1 = CH_3$, $Y_3 = CH_3$) |
| $SO_2CH_2CH_3$ | $CH_2CN$ | H | A-4 ($X_1 = CH_3$, $Y_3 = OCH_3$) |
| $SO_2CH_2CH_3$ | $CH_2CN$ | H | A-4 ($X_1 = OCH_3$, $Y_3 = CH_3$) |
| $SO_2CH_2CH_3$ | $CH_2CN$ | H | A-5 ($X_2 = CH_3$, $Y_2 = OCH_3$) |
| $SO_2CH_2CH_3$ | $CH_2CN$ | H | A-5 ($X_2 = CH_3$, $Y_2 = SCH_3$) |
| $SO_2CH_2CH_3$ | $CH_2CN$ | H | A-6 ($X_3 = OCH_3$) |
| $SO_2CH_2CH_3$ | $CH_2CN$ | H | A-7 ($X_4 = OCH_3$, $Y_4 = OCH_3$) |
| $SO_2CH_2CH_3$ | $CH_2CN$ | H | A-7 ($X_4 = CH_3$, $Y_4 = OCH_3$) |
| $SO_2CH_2CH_3$ | $CH_2CN$ | H | A-7 ($X_4 = OCH_3$, $Y_4 = CH_3$) |
| $SO_2CH_2CH_3$ | $CH_2CH_2OCH_3$ | H | A-2 ($X_1 = CH_3$, $Y_1 = CH_2$) |
| $SO_2CH_2CH_3$ | $CH_2CH_2OCH_3$ | H | A-3 ($X_1 = CH_3$) |
| $SO_2CH_2CH_3$ | $CH_2CH_2OCH_3$ | H | A-3 ($X_1 = OCH_3$) |
| $SO_2CH_2CH_3$ | $CH_2CH_2OCH_3$ | H | A-4 ($X_1 = CH_3$, $Y_3 = CH_3$) |
| $SO_2CH_2CH_3$ | $CH_2CH_2OCH_3$ | H | A-4 ($X_1 = CH_3$, $Y_3 = OCH_3$) |
| $SO_2CH_2CH_3$ | $CH_2CH_2OCH_3$ | H | A-4 ($X_1 = OCH_3$, $Y_3 = CH_3$) |
| $SO_2CH_2CH_3$ | $CH_2CH_2OCH_3$ | H | A-5 ($X_2 = CH_3$, $Y_2 = OCH_3$) |
| $SO_2CH_2CH_3$ | $CH_2CH_2OCH_3$ | H | A-5 ($X_2 = CH_3$, $Y_2 = SCH_3$) |
| $SO_2CH_2CH_3$ | $CH_2CH_2OCH_3$ | H | A-6 ($X_3 = OCH_3$) |
| $SO_2CH_2CH_3$ | $CH_2CH_2OCH_3$ | H | A-7 ($X_4 = OCH_3$, $Y_4 = OCH_3$) |
| $SO_2CH_2CH_3$ | $CH_2CH_2OCH_3$ | H | A-7 ($X_4 = CH_3$, $Y_4 = OCH_3$) |
| $SO_2CH_2CH_3$ | $CH_2CH_2OCH_3$ | H | A-7 ($X_4 = OCH_3$, $Y_4 = CH_3$) |
| $SO_2CH_2CH_3$ | $CH_2CH{=}CH_2$ | H | A-2 ($X_1 = CH_3$, $Y_1 = CH_2$) |
| $SO_2CH_2CH_3$ | $CH_2CH{=}CH_2$ | H | A-3 ($X_1 = CH_3$) |
| $SO_2CH_2CH_3$ | $CH_2CH{=}CH_2$ | H | A-3 ($X_1 = OCH_3$) |
| $SO_2CH_2CH_3$ | $CH_2CH{=}CH_2$ | H | A-4 ($X_1 = CH_3$, $Y_3 = CH_3$) |
| $SO_2CH_2CH_3$ | $CH_2CH{=}CH_2$ | H | A-4 ($X_1 = CH_3$, $Y_3 = OCH_3$) |
| $SO_2CH_2CH_3$ | $CH_2CH{=}CH_2$ | H | A-4 ($X_3 = OCH_3$, $Y_3 = CH$) |
| $SO_2CH_2CH_3$ | $CH_2CH{=}CH_2$ | H | A-5 ($X_2 = CH_3$, $Y_2 = OCH_3$) |
| $SO_2CH_2CH_3$ | $CH_2CH{=}CH_2$ | H | A-5 ($X_2 = CH_3$, $Y_2 = SCH_3$) |
| $SO_2CH_2CH_3$ | $CH_2CH{=}CH_2$ | H | A-6 ($X_3 = OCH_3$) |
| $SO_2CH_2CH_3$ | $CH_2CH{=}CH_2$ | H | A-7 ($X_4 = OCH_3$, $Y_4 = OCH_3$) |
| $SO_2CH_2CH_3$ | $CH_2CH{=}CH_2$ | H | A-7 ($X_4 = CH_3$, $Y_4 = OCH_3$) |
| $SO_2CH_2CH_3$ | $CH_2CH{=}CH_2$ | H | A-7 ($X_4 = OCH_3$, $Y_4 = CH_3$) |
| $SO_2CH_2CH_3$ | $CH_2C{\equiv}CH$ | H | A-2 ($X_1 = CH_3$, $Y_1 = CH_2$) |
| $SO_2CH_2CH_3$ | $CH_2C{\equiv}CH$ | H | A-3 ($X_1 = CH_3$) |
| $SO_2CH_2CH_3$ | $CH_2C{\equiv}CH$ | H | A-3 ($X_1 = OCH_3$) |
| $SO_2CH_2CH_3$ | $CH_2C{\equiv}CH$ | H | A-4 ($X_1 = CH_3$, $Y_3 = CH_3$) |
| $SO_2CH_2CH_3$ | $CH_2C{\equiv}CH$ | H | A-4 ($X_1 = CH_3$, $Y_3 = OCH_3$) |
| $SO_2CH_2CH_3$ | $CH_2C{\equiv}CH$ | H | A-4 ($X_1 = OCH_3$, $Y_3 = CH_3$) |
| $SO_2CH_2CH_3$ | $CH_2C{\equiv}CH$ | H | A-5 ($X_2 = CH_3$, $Y_2 = OCH_3$) |
| $SO_2CH_2CH_3$ | $CH_2C{\equiv}CH$ | H | A-5 ($X_2 = CH_3$, $Y_2 = SCH_3$) |
| $SO_2CH_2CH_3$ | $CH_2C{\equiv}CH$ | H | A-6 ($X_3 = OCH_3$) |
| $SO_2CH_2CH_3$ | $CH_2C{\equiv}CH$ | H | A-7 ($X_4 = OCH_3$, $Y_4 = OCH_3$) |
| $SO_2CH_2CH_3$ | $CH_2C{\equiv}CH$ | H | A-7 ($X_4 = CH_3$, $Y_4 = OCH_3$) |
| $SO_2CH_2CH_3$ | $CH_2C{\equiv}CH$ | H | A-7 ($X_4 = OCH_3$, $Y_4 = CH_3$) |
| $SO_2CH_2CH_3$ | cyclo-$C_3H_7$ | H | A-2 ($X_1 = CH_3$, $Y_1 = CH_2$) |
| $SO_2CH_2CH_3$ | cyclo-$C_3H_7$ | H | A-3 ($X_1 = CH_3$) |
| $SO_2CH_2CH_3$ | cyclo-$C_3H_7$ | H | A-3 ($X_1 = OCH_3$) |
| $SO_2CH_2CH_3$ | cyclo-$C_3H_7$ | H | A-4 ($X_1 = CH_3$, $Y_3 = CH_3$) |
| $SO_2CH_2CH_3$ | cyclo-$C_3H_7$ | H | A-4 ($X_1 = CH_3$, $Y_3 = OCH_3$) |
| $SO_2CH_2CH_3$ | cyclo-$C_3H_7$ | H | A-4 ($X_1 = OCH_3$, $Y_3 = CH_3$) |
| $SO_2CH_2CH_3$ | cyclo-$C_3H_7$ | H | A-5 ($X_2 = CH_3$, $Y_2 = OCH_3$) |
| $SO_2CH_2CH_3$ | cyclo-$C_3H_7$ | H | A-5 ($X_2 = CH_3$, $Y_2 = SCH_3$) |
| $SO_2CH_2CH_3$ | cyclo-$C_3H_7$ | H | A-6 ($X_3 = OCH_3$) |
| $SO_2CH_2CH_3$ | cyclo-$C_3H_7$ | H | A-7 ($X_4 = OCH_3$, $Y_4 = OCH_3$) |
| $SO_2CH_2CH_3$ | cyclo-$C_3H_7$ | H | A-7 ($X_4 = CH_3$, $Y_4 = OCH_3$) |
| $SO_2CH_2CH_3$ | cyclo-$C_3H_7$ | H | A-7 ($X_4 = OCH_3$, $Y_4 = CH_3$) |
| $SO_2CH_2CH_3$ | $CH_3$ | $CH_3$ | A-2 ($X_1 = CH_3$, $Y_1 = CH_2$) |
| $SO_2CH_2CH_3$ | $CH_3$ | $CH_3$ | A-3 ($X_1 = CH_3$) |
| $SO_2CH_2CH_3$ | $CH_3$ | $CH_3$ | A-3 ($X_1 = OCH_3$) |
| $SO_2CH_2CH_3$ | $CH_3$ | $CH_3$ | A-4 ($X_1 = CH_3$, $Y_3 = CH_3$) |
| $SO_2CH_2CH_3$ | $CH_3$ | $CH_3$ | A-4 ($X_1 = CH_3$, $Y_3 = OCH_3$) |
| $SO_2CH_2CH_3$ | $CH_3$ | $CH_3$ | A-4 ($X_1 = OCH_3$, $Y_3 = CH_3$) |
| $SO_2CH_2CH_3$ | $CH_3$ | $CH_3$ | A-5 ($X_2 = CH_3$, $Y_2 = OCH_3$) |
| $SO_2CH_2CH_3$ | $CH_3$ | $CH_3$ | A-5 ($X_2 = CH_3$, $Y_2 = SCH_3$) |
| $SO_2CH_2CH_3$ | $CH_3$ | $CH_3$ | A-6 ($X_3 = OCH_3$) |
| $SO_2CH_2CH_3$ | $CH_3$ | $CH_3$ | A-7 ($X_4 = OCH_3$, $Y_4 = OCH_3$) |
| $SO_2CH_2CH_3$ | $CH_3$ | $CH_3$ | A-7 ($X_4 = CH_3$, $Y_4 = OCH_3$) |
| $SO_2CH_2CH_3$ | $CH_3$ | $CH_3$ | A-7 ($X_4 = OCH_3$, $Y_4 = CH_3$) |
| $SO_2CH_2CH_3$ | $CH_2CH_3$ | $CH_3$ | A-2 ($X_1 = CH_3$, $Y_1 = CH_2$) |
| $SO_2CH_2CH_3$ | $CH_2CH_3$ | $CH_3$ | A-3 ($X_1 = CH_3$) |
| $SO_2CH_2CH_3$ | $CH_2CH_3$ | $CH_3$ | A-3 ($X_1 = OCH_3$) |
| $SO_2CH_2CH_3$ | $CH_2CH_3$ | $CH_3$ | A-4 ($X_1 = CH_3$, $Y_3 = CH_3$) |
| $SO_2CH_2CH_3$ | $CH_2CH_3$ | $CH_3$ | A-4 ($X_1 = CH_3$, $Y_3 = OCH_3$) |
| $SO_2CH_2CH_3$ | $CH_2CH_3$ | $CH_3$ | A-4 ($X_1 = OCH_3$, $Y_3 = CH_3$) |
| $SO_2CH_2CH_3$ | $CH_2CH_3$ | $CH_3$ | A-5 ($X_2 = CH_3$, $Y_2 = OCH_3$) |
| $SO_2CH_2CH_3$ | $CH_2CH_3$ | $CH_3$ | A-5 ($X_2 = CH_3$, $Y_2 = SCH_3$) |
| $SO_2CH_2CH_3$ | $CH_2CH_3$ | $CH_3$ | A-6 ($X_3 = OCH_3$) |
| $SO_2CH_2CH_3$ | $CH_2CH_3$ | $CH_3$ | A-7 ($X_4 = OCH_3$, $Y_4 = OCH_3$) |
| $SO_2CH_2CH_3$ | $CH_2CH_3$ | $CH_3$ | A-7 ($X_4 = CH_3$, $Y_4 = OCH_3$) |
| $SO_2CH_2CH_3$ | $CH_2CH_3$ | $CH_3$ | A-7 ($X_4 = OCH_3$, $Y_4 = CH_3$) |
| $SO_2CH_2CH_3$ | $CH_2CH_3$ | $CH_2CH_3$ | A-2 ($X_1 = CH_3$, $Y_1 = CH_2$) |

-continued

| | | | |
|---|---|---|---|
| $SO_2CH_2CH_3$ | $CH_2CH_3$ | $CH_2CH_3$ | A-3 ($X_1 = CH_3$) |
| $SO_2CH_2CH_3$ | $CH_2CH_3$ | $CH_2CH_3$ | A-3 ($X_1 = OCH_3$) |
| $SO_2CH_2CH_3$ | $CH_2CH_3$ | $CH_2CH_3$ | A-4 ($X_1 = CH_3, Y_3 = CH_3$) |
| $SO_2CH_2CH_3$ | $CH_2CH_3$ | $CH_2CH_3$ | A-4 ($X_1 = CH_3, Y_3 = OCH_3$) |
| $SO_2CH_2CH_3$ | $CH_2CH_3$ | $CH_2CH_3$ | A-4 ($X_1 = OCH_3, Y_3 = CH_3$) |
| $SO_2CH_2CH_3$ | $CH_2CH_3$ | $CH_2CH_3$ | A-5 ($X_2 = CH_3, Y_2 = OCH_3$) |
| $SO_2CH_2CH_3$ | $CH_2CH_3$ | $CH_2CH_3$ | A-5 ($X_2 = CH_3, Y_2 = SCH_3$) |
| $SO_2CH_2CH_3$ | $CH_2CH_3$ | $CH_2CH_3$ | A-6 ($X_3 = OCH_3$) |
| $SO_2CH_2CH_3$ | $CH_2CH_3$ | $CH_2CH_3$ | A-7 ($X_4 = OCH_3, Y_4 = OCH_3$) |
| $SO_2CH_2CH_3$ | $CH_2CH_3$ | $CH_2CH_3$ | A-7 ($X_4 = CH_3, Y_4 = OCH_3$) |
| $SO_2CH_2CH_3$ | $CH_2CH_3$ | $CH_2CH_3$ | A-7 ($X_4 = OCH_3, Y_4 = CH_3$) |
| $SO_2CH_2CH_3$ | $OCH_3$ | $CH_3$ | A-2 ($X_1 = CH_3, Y_1 = CH_2$) |
| $SO_2CH_2CH_3$ | $OCH_3$ | $CH_3$ | A-3 ($X_1 = CH_3$) |
| $SO_2CH_2CH_3$ | $OCH_3$ | $CH_3$ | A-3 ($X_1 = OCH_3$) |
| $SO_2CH_2CH_3$ | $OCH_3$ | $CH_3$ | A-4 ($X_1 = CH_3, Y_3 = CH_3$) |
| $SO_2CH_2CH_3$ | $OCH_3$ | $CH_3$ | A-4 ($X_1 = CH_3, Y_3 = OCH_3$) |
| $SO_2CH_2CH_3$ | $OCH_3$ | $CH_3$ | A-4 ($X_1 = OCH_3, Y_3 = CH_3$) |
| $SO_2CH_2CH_3$ | $OCH_3$ | $CH_3$ | A-5 ($X_2 = CH_3, Y_2 = OCH_3$) |
| $SO_2CH_2CH_3$ | $OCH_3$ | $CH_3$ | A-5 ($X_2 = CH_3, Y_2 = SCH_3$) |
| $SO_2CH_2CH_3$ | $OCH_3$ | $CH_3$ | A-6 ($X_3 = OCH_3$) |
| $SO_2CH_2CH_3$ | $OCH_3$ | $CH_3$ | A-7 ($X_4 = OCH_3, Y_4 = OCH_3$) |
| $SO_2CH_2CH_3$ | $OCH_3$ | $CH_3$ | A-7 ($X_4 = CH_3, Y_4 = OCH_3$) |
| $SO_2CH_2CH_3$ | $OCH_3$ | $CH_3$ | A-7 ($X_4 = OCH_3, Y_4 = CH_3$) |
| $SO_2CH_2CH_3$ | $NHCH_3$ | $CH_3$ | A-2 ($X_1 = CH_3, Y_1 = CH_2$) |
| $SO_2CH_2CH_3$ | $NHCH_3$ | $CH_3$ | A-3 ($X_1 = CH_3$) |
| $SO_2CH_2CH_3$ | $NHCH_3$ | $CH_3$ | A-3 ($X_1 = OCH_3$) |
| $SO_2CH_2CH_3$ | $NHCH_3$ | $CH_3$ | A-4 ($X_1 = CH_3, Y_3 = CH_3$) |
| $SO_2CH_2CH_3$ | $NHCH_3$ | $CH_3$ | A-4 ($X_1 = CH_3, Y_3 = OCH_3$) |
| $SO_2CH_2CH_3$ | $NHCH_3$ | $CH_3$ | A-4 ($X_1 = OCH_3, Y_3 = CH_3$) |
| $SO_2CH_2CH_3$ | $NHCH_3$ | $CH_3$ | A-5 ($X_2 = CH_3, Y_2 = OCH_3$) |
| $SO_2CH_2CH_3$ | $NHCH_3$ | $CH_3$ | A-5 ($X_2 = CH_3, Y_2 = SCH_3$) |
| $SO_2CH_2CH_3$ | $NHCH_3$ | $CH_3$ | A-6 ($X_3 = OCH_3$) |
| $SO_2CH_2CH_3$ | $NHCH_3$ | $CH_3$ | A-7 ($X_4 = OCH_3, Y_4 = OCH_3$) |
| $SO_2CH_2CH_3$ | $NHCH_3$ | $CH_3$ | A-7 ($X_4 = CH_3, Y_4 = OCH_3$) |
| $SO_2CH_2CH_3$ | $NHCH_3$ | $CH_3$ | A-7 ($X_4 = OCH_3, Y_4 = CH_3$) |
| $SO_2CH_2CH_3$ | $N(CH_3)_2$ | $CH_3$ | A-2 ($X_1 = CH_3, Y_1 = CH_2$) |
| $SO_2CH_2CH_3$ | $N(CH_3)_2$ | $CH_3$ | A-3 ($X_1 = CH_3$) |
| $SO_2CH_2CH_3$ | $N(CH_3)_2$ | $CH_3$ | A-3 ($X_1 = OCH_3$) |
| $SO_2CH_2CH_3$ | $N(CH_3)_2$ | $CH_3$ | A-4 ($X_1 = CH_3, Y_3 = CH_3$) |
| $SO_2CH_2CH_3$ | $N(CH_3)_2$ | $CH_3$ | A-4 ($X_1 = CH_3, Y_3 = OCH_3$) |
| $SO_2CH_2CH_3$ | $N(CH_3)_2$ | $CH_3$ | A-4 ($X_1 = OCH_3, Y_3 = CH_3$) |
| $SO_2CH_2CH_3$ | $N(CH_3)_2$ | $CH_3$ | A-5 ($X_2 = CH_3, Y_2 = OCH_3$) |
| $SO_2CH_2CH_3$ | $N(CH_3)_2$ | $CH_3$ | A-5 ($X_2 = CH_3, Y_2 = SCH_3$) |
| $SO_2CH_2CH_3$ | $N(CH_3)_2$ | $CH_3$ | A-6 ($X_3 = OCH_3$) |
| $SO_2CH_2CH_3$ | $N(CH_3)_2$ | $CH_3$ | A-7 ($X_4 = OCH_3, Y_4 = OCH_3$) |
| $SO_2CH_2CH_3$ | $N(CH_3)_2$ | $CH_3$ | A-7 ($X_4 = CH_3, Y_4 = OCH_3$) |
| $SO_2CH_2CH_3$ | $N(CH_3)_2$ | $CH_3$ | A-7 ($X_4 = OCH_3, Y_4 = CH_3$) |
| $SO_2CH_2CH_3$ | $-CH_2CH_2CH_2-$ | | A-2 ($X_1 = CH_3, Y_1 = CH_2$) |
| $SO_2CH_2CH_3$ | $-CH_2CH_2CH_2-$ | | A-3 ($X_1 = CH_3$) |
| $SO_2CH_2CH_3$ | $-CH_2CH_2CH_2-$ | | A-3 ($X_1 = OCH_3$) |
| $SO_2CH_2CH_3$ | $-CH_2CH_2CH_2-$ | | A-4 ($X_1 = CH_3, Y_3 = CH_3$) |
| $SO_2CH_2CH_3$ | $-CH_2CH_2CH_2-$ | | A-4 ($X_1 = CH_3, Y_3 = OCH_3$) |
| $SO_2CH_2CH_3$ | $-CH_2CH_2CH_2-$ | | A-4 ($X_1 = OCH_3, Y_3 = CH_3$) |
| $SO_2CH_2CH_3$ | $-CH_2CH_2CH_2-$ | | A-5 ($X_2 = CH_3, Y_2 = OCH_3$) |
| $SO_2CH_2CH_3$ | $-CH_2CH_2CH_2-$ | | A-5 ($X_2 = CH_3, Y_2 = SCH_3$) |
| $SO_2CH_2CH_3$ | $-CH_2CH_2CH_2-$ | | A-6 ($X_3 = OCH_3$) |
| $SO_2CH_2CH_3$ | $-CH_2CH_2CH_2-$ | | A-7 ($X_4 = OCH_3, Y_4 = OCH_3$) |
| $SO_2CH_2CH_3$ | $-CH_2CH_2CH_2-$ | | A-7 ($X_4 = CH_3, Y_4 = OCH_3$) |
| $SO_2CH_2CH_3$ | $-CH_2CH_2CH_2-$ | | A-7 ($X_4 = OCH_3, Y_4 = CH_3$) |
| $SO_2CH_2CH_3$ | $-CH_2CH_2OCH_2CH_2-$ | | A-2 ($X_1 = CH_3, Y_1 = CH_2$) |
| $SO_2CH_2CH_3$ | $-CH_2CH_2OCH_2CH_2-$ | | A-3 ($X_1 = CH_3$) |
| $SO_2CH_2CH_3$ | $-CH_2CH_2OCH_2CH_2-$ | | A-3 ($X_1 = OCH_3$) |
| $SO_2CH_2CH_3$ | $-CH_2CH_2OCH_2CH_2-$ | | A-4 ($X_1 = CH_3, Y_3 = CH_3$) |
| $SO_2CH_2CH_3$ | $-CH_2CH_2OCH_2CH_2-$ | | A-4 ($X_1 = CH_3, Y_3 = OCH_3$) |
| $SO_2CH_2CH_3$ | $-CH_2CH_2OCH_2CH_2-$ | | A-4 ($X_1 = OCH_3, Y_3 = CH_3$) |
| $SO_2CH_2CH_3$ | $-CH_2CH_2OCH_2CH_2-$ | | A-5 ($X_2 = CH_3, Y_2 = OCH_3$) |
| $SO_2CH_2CH_3$ | $-CH_2CH_2OCH_2CH_2-$ | | A-5 ($X_2 = CH_3, Y_2 = SCH_3$) |
| $SO_2CH_2CH_3$ | $-CH_2CH_2OCH_2CH_2-$ | | A-6 ($X_3 = OCH_3$) |
| $SO_2CH_2CH_3$ | $-CH_2CH_2OCH_2CH_2-$ | | A-7 ($X_4 = OCH_3, Y_4 = OCH_3$) |
| $SO_2CH_2CH_3$ | $-CH_2CH_2OCH_2CH_2-$ | | A-7 ($X_4 = CH_3, Y_4 = OCH_3$) |
| $SO_2CH_2CH_3$ | $-CH_2CH_2OCH_2CH_2-$ | | A-7 ($X_4 = OCH_3, Y_4 = CH_3$) |
| Br | $CH_3$ | H | A-2 ($X_1 = CH_3, Y_1 = CH_2$) |
| Br | $CH_3$ | H | A-3 ($X_1 = CH_3$) |
| Br | $CH_3$ | H | A-3 ($X_1 = OCH_3$) |
| Br | $CH_3$ | H | A-4 ($X_1 = CH_3, Y_3 = CH_3$) |
| Br | $CH_3$ | H | A-4 ($X_1 = CH_3, Y_3 = OCH_3$) |
| Br | $CH_3$ | H | A-4 ($X_1 = OCH_3, Y_3 = CH_3$) |
| Br | $CH_3$ | H | A-5 ($X_2 = CH_3, Y_2 = OCH_3$) |
| Br | $CH_3$ | H | A-5 ($X_2 = CH_3, Y_2 = SCH_3$) |
| Br | $CH_3$ | H | A-6 ($X_3 = OCH_3$) |
| Br | $CH_3$ | H | A-7 ($X_4 = OCH_3, Y_4 = OCH_3$) |
| Br | $CH_3$ | H | A-7 ($X_4 = CH_3, Y_4 = OCH_3$) |

-continued

| | | | |
|---|---|---|---|
| Br | $CH_3$ | H | A-7 ($X_4$ = $OCH_3$, $Y_4$ = $CH_3$) |
| Br | $CH_3$ | $CH_3$ | A-2 ($X_1$ = $CH_3$, $Y_1$ = $CH_2$) |
| Br | $CH_3$ | $CH_3$ | A-3 ($X_1$ = $CH_3$) |
| Br | $CH_3$ | $CH_3$ | A-3 ($X_1$ = $OCH_3$) |
| Br | $CH_3$ | $CH_3$ | A-4 ($X_1$ = $CH_3$, $Y_3$ = $CH_3$) |
| Br | $CH_3$ | $CH_3$ | A-4 ($X_1$ = $CH_3$, $Y_3$ = $OCH_3$) |
| Br | $CH_3$ | $CH_3$ | A-4 ($X_1$ = $OCH_3$, $Y_3$ = $CH_3$) |
| Br | $CH_3$ | $CH_3$ | A-5 ($X_2$ = $CH_3$, $Y_2$ = $OCH_3$) |
| Br | $CH_3$ | $CH_3$ | A-5 ($X_2$ = $CH_3$, $Y_2$ = $SCH_3$) |
| Br | $CH_3$ | $CH_3$ | A-6 ($X_3$ = $OCH_3$) |
| Br | $CH_3$ | $CH_3$ | A-7 ($X_4$ = $OCH_3$, $Y_4$ = $OCH_3$) |
| Br | $CH_3$ | $CH_3$ | A-7 ($X_4$ = $CH_3$, $Y_4$ = $OCH_3$) |
| Br | $CH_3$ | $CH_3$ | A-7 ($X_4$ = $OCH_3$, $Y_4$ = $CH_3$) |
| Br | $CH_2CH{=}CH_2$ | H | A-2 ($X_1$ = $CH_3$, $Y_1$ = $CH_2$) |
| Br | $CH_2CH{=}CH_2$ | H | A-3 ($X_1$ = $CH_3$) |
| Br | $CH_2CH{=}CH_2$ | H | A-3 ($X_1$ = $OCH_3$) |
| Br | $CH_2CH{=}CH_2$ | H | A-4 ($X_1$ = $CH_3$, $Y_3$ = $CH_3$) |
| Br | $CH_2CH{=}CH_2$ | H | A-4 ($X_1$ = $CH_3$, $Y_3$ = $OCH_3$) |
| Br | $CH_2CH{=}CH_2$ | H | A-4 ($X_1$ = $OCH_3$, $Y_3$ = $CH_3$) |
| Br | $CH_2CH{=}CH_2$ | H | A-5 ($X_2$ = $CH_3$, $Y_2$ = $OCH_3$) |
| Br | $CH_2CH{=}CH_2$ | H | A-5 ($X_2$ = $CH_3$, $Y_2$ = $SCH_3$) |
| Br | $CH_2CH{=}CH_2$ | H | A-6 ($X_3$ = $OCH_3$) |
| Br | $CH_2CH{=}CH_2$ | H | A-7 ($X_4$ = $OCH_3$, $Y_4$ = $OCH_3$) |
| Br | $CH_2CH{=}CH_2$ | H | A-7 ($X_4$ = $CH_3$, $Y_4$ = $OCH_3$) |
| Br | $CH_2CH{=}CH_2$ | H | A-7 ($X_4$ = $OCH_3$, $Y_4$ = $CH_3$) |
| $CH_2CH_3$ | $CH_3$ | H | A-2 ($X_1$ = $CH_3$, $Y_1$ = $CH_2$) |
| $CH_2CH_3$ | $CH_3$ | H | A-3 ($X_1$ = $CH_3$) |
| $CH_2CH_3$ | $CH_3$ | H | A-3 ($X_1$ = $OCH_3$) |
| $CH_2CH_3$ | $CH_3$ | H | A-4 ($X_1$ = $CH_3$, $Y_3$ = $CH_3$) |
| $CH_2CH_3$ | $CH_3$ | H | A-4 ($X_1$ = $CH_3$, $Y_3$ = $OCH_3$) |
| $CH_2CH_3$ | $CH_3$ | H | A-4 ($X_1$ = $OCH_3$, $Y_3$ = $CH_3$) |
| $CH_2CH_3$ | $CH_3$ | H | A-5 ($X_2$ = $CH_3$, $Y_2$ = $OCH_3$) |
| $CH_2CH_3$ | $CH_3$ | H | A-5 ($X_2$ = $CH_3$, $Y_2$ = $SCH_3$) |
| $CH_2CH_3$ | $CH_3$ | H | A-6 ($X_3$ = $OCH_3$) |
| $CH_2CH_3$ | $CH_3$ | H | A-7 ($X_4$ = $OCH_3$, $Y_4$ = $OCH_3$) |
| $CH_2CH_3$ | $CH_3$ | H | A-7 ($X_4$ = $CH_3$, $Y_4$ = $OCH_3$) |
| $CH_2CH_3$ | $CH_3$ | H | A-7 ($X_4$ = $OCH_3$, $Y_4$ = $CH_3$) |
| $CH_2CH_3$ | $CH_3$ | $CH_3$ | A-2 ($X_1$ = $CH_3$, $Y_1$ = $CH_2$) |
| $CH_2CH_3$ | $CH_3$ | $CH_3$ | A-3 ($X_1$ = $CH_3$) |
| $CH_2CH_3$ | $CH_3$ | $CH_3$ | A-3 ($X_1$ = $OCH_3$) |
| $CH_2CH_3$ | $CH_3$ | $CH_3$ | A-4 ($X_1$ = $CH_3$, $Y_3$ = $CH_3$) |
| $CH_2CH_3$ | $CH_3$ | $CH_3$ | A-4 ($X_1$ = $CH_3$, $Y_3$ = $OCH_3$) |
| $CH_2CH_3$ | $CH_3$ | $CH_3$ | A-4 ($X_1$ = $OCH_3$, $Y_3$ = $CH_3$) |
| $CH_2CH_3$ | $CH_3$ | $CH_3$ | A-5 ($X_2$ = $CH_3$, $Y_2$ = $OCH_3$) |
| $CH_2CH_3$ | $CH_3$ | $CH_3$ | A-5 ($X_2$ = $CH_3$, $Y_2$ = $SCH_3$) |
| $CH_2CH_3$ | $CH_3$ | $CH_3$ | A-6 ($X_3$ = $OCH_3$) |
| $CH_2CH_3$ | $CH_3$ | $CH_3$ | A-7 ($X_4$ = $OCH_3$, $Y_4$ = $OCH_3$) |
| $CH_2CH_3$ | $CH_3$ | $CH_3$ | A-7 ($X_4$ = $CH_3$, $Y_4$ = $OCH_3$) |
| $CH_2CH_3$ | $CH_3$ | $CH_3$ | A-7 ($X_4$ = $OCH_3$, $Y_4$ = $CH_3$) |
| $CH_2CH_3$ | $CH_2CH{=}CH_2$ | H | A-2 ($X_1$ = $CH_3$, $Y_1$ = $CH_2$) |
| $CH_2CH_3$ | $CH_2CH{=}CH_2$ | H | A-3 ($X_1$ = $CH_3$) |
| $CH_2CH_3$ | $CH_2CH{=}CH_2$ | H | A-3 ($X_1$ = $OCH_3$) |
| $CH_2CH_3$ | $CH_2CH{=}CH_2$ | H | A-4 ($X_1$ = $CH_3$, $Y_3$ = $CH_3$) |
| $CH_2CH_3$ | $CH_2CH{=}CH_2$ | H | A-4 ($X_1$ = $CH_3$, $Y_3$ = $OCH_3$) |
| $CH_2CH_3$ | $CH_2CH{=}CH_2$ | H | A-4 ($X_1$ = $OCH_3$, $Y_3$ = $CH_3$) |
| $CH_2CH_3$ | $CH_2CH{=}CH_2$ | H | A-5 ($X_2$ = $CH_3$, $Y_2$ = $OCH_3$) |
| $CH_2CH_3$ | $CH_2CH{=}CH_2$ | H | A-5 ($X_2$ = $CH_3$, $Y_2$ = $SCH_3$) |
| $CH_2CH_3$ | $CH_2CH{=}CH_2$ | H | A-6 ($X_3$ = $OCH_3$) |
| $CH_2CH_3$ | $CH_2CH{=}CH_2$ | H | A-7 ($X_4$ = $OCH_3$, $Y_4$ = $OCH_3$) |
| $CH_2CH_3$ | $CH_2CH{=}CH_2$ | H | A-7 ($X_4$ = $CH_3$, $Y_4$ = $OCH_3$) |
| $CH_2CH_3$ | $CH_2CH{=}CH_2$ | H | A-7 ($X_4$ = $OCH_3$, $Y_4$ = $CH_3$) |
| $CF_3$ | $CH_3$ | H | A-2 ($X_1$ = $CH_3$, $Y_1$ = $CH_2$) |
| $CF_3$ | $CH_3$ | H | A-3 ($X_1$ = $CH_3$) |
| $CF_3$ | $CH_3$ | H | A-3 ($X_1$ = $OCH_3$) |
| $CF_3$ | $CH_3$ | H | A-4 ($X_1$ = $CH_3$, $Y_3$ = $CH_3$) |
| $CF_3$ | $CH_3$ | H | A-4 ($X_1$ = $CH_3$, $Y_3$ = $OCH_3$) |
| $CF_3$ | $CH_3$ | H | A-4 ($X_1$ = $OCH_3$, $Y_3$ = $CH_3$) |
| $CF_3$ | $CH_3$ | H | A-5 ($X_2$ = $CH_3$, $Y_2$ = $OCH_3$) |
| $CF_3$ | $CH_3$ | H | A-5 ($X_2$ = $CH_3$, $Y_2$ = $SCH_3$) |
| $CF_3$ | $CH_3$ | H | A-6 ($X_3$ = $OCH_3$) |
| $CF_3$ | $CH_3$ | H | A-7 ($X_4$ = $OCH_3$, $Y_4$ = $OCH_3$) |
| $CF_3$ | $CH_3$ | H | A-7 ($X_4$ = $CH_3$, $Y_4$ = $OCH_3$) |
| $CF_3$ | $CH_3$ | H | A-7 ($X_4$ = $OCH_3$, $Y_4$ = $CH_3$) |
| $CF_3$ | $CH_3$ | $CH_3$ | A-2 ($X_1$ = $CH_3$, $Y_1$ = $CH_2$) |
| $CF_3$ | $CH_3$ | $CH_3$ | A-3 ($X_1$ = $CH_3$) |
| $CF_3$ | $CH_3$ | $CH_3$ | A-3 ($X_1$ = $OCH_3$) |
| $CF_3$ | $CH_3$ | $CH_3$ | A-4 ($X_1$ = $CH_3$, $Y_3$ = $CH_3$) |
| $CF_3$ | $CH_3$ | $CH_3$ | A-4 ($X_1$ = $CH_3$, $Y_3$ = $OCH_3$) |
| $CF_3$ | $CH_3$ | $CH_3$ | A-4 ($X_1$ = $OCH_3$, $Y_3$ = $CH_3$) |
| $CF_3$ | $CH_3$ | $CH_3$ | A-5 ($X_2$ = $CH_3$, $Y_2$ = $OCH_3$) |
| $CF_3$ | $CH_3$ | $CH_3$ | A-5 ($X_2$ = $CH_3$, $Y_2$ = $SCH_3$) |
| $CF_3$ | $CH_3$ | $CH_3$ | A-6 ($X_3$ = $OCH_3$) |

-continued

| | | | |
|---|---|---|---|
| $CF_3$ | $CH_3$ | $CH_3$ | A-7 ($X_4$ = $OCH_3$, $Y_4$ = $OCH_3$) |
| $CF_3$ | $CH_3$ | $CH_3$ | A-7 ($X_4$ = $CH_3$, $Y_4$ = $OCH_3$) |
| $CF_3$ | $CH_3$ | $CH_3$ | A-7 ($X_4$ = $OCH_3$, $Y_4$ = $CH_3$) |
| $CF_3$ | $CH_2CH{=}CH_2$ | H | A-2 ($X_1$ = $CH_3$, $Y_1$ = $CH_2$) |
| $CF_3$ | $CH_2CH{=}CH_2$ | H | A-3 ($X_1$ = $CH_3$) |
| $CF_3$ | $CH_2CH{=}CH_2$ | H | A-3 ($X_1$ = $OCH_3$) |
| $CF_3$ | $CH_2CH{=}CH_2$ | H | A-4 ($X_1$ = $CH_3$, $Y_3$ = $CH_3$) |
| $CF_3$ | $CH_2CH{=}CH_2$ | H | A-4 ($X_1$ = $CH_3$, $Y_3$ = $OCH_3$) |
| $CF_3$ | $CH_2CH{=}CH_2$ | H | A-4 ($X_1$ = $OCH_3$, $Y_3$ = $CH_3$) |
| $CF_3$ | $CH_2CH{=}CH_2$ | H | A-5 ($X_2$ = $CH_3$, $Y_2$ = $OCH_3$) |
| $CF_3$ | $CH_2CH{=}CH_2$ | H | A-5 ($X_2$ = $CH_3$, $Y_2$ = $SCH_3$) |
| $CF_3$ | $CH_2CH{=}CH_2$ | H | A-6 ($X_3$ = $OCH_3$) |
| $CF_3$ | $CH_2CH{=}CH_2$ | H | A-7 ($X_4$ = $OCH_3$, $Y_4$ = $OCH_3$) |
| $CF_3$ | $CH_2CH{=}CH_2$ | H | A-7 ($X_4$ = $CH_3$, $Y_4$ = $OCH_3$) |
| $CF_3$ | $CH_2CH{=}CH_2$ | H | A-7 ($X_4$ = $OCH_3$, $Y_4$ = $CH_3$) |
| $OCH_3$ | $CH_3$ | H | A-2 ($X_1$ = $CH_3$, $Y_1$ = $CH_2$) |
| $OCH_3$ | $CH_3$ | H | A-3 ($X_1$ = $CH_3$) |
| $OCH_3$ | $CH_3$ | H | A-3 ($X_1$ = $OCH_3$) |
| $OCH_3$ | $CH_3$ | H | A-4 ($X_1$ = $CH_3$, $Y_3$ = $CH_3$) |
| $OCH_3$ | $CH_3$ | H | A-4 ($X_1$ = $CH_3$, $Y_3$ = $OCH_3$) |
| $OCH_3$ | $CH_3$ | H | A-4 ($X_1$ = $OCH_3$, $Y_3$ = $CH_3$) |
| $OCH_3$ | $CH_3$ | H | A-5 ($X_2$ = $CH_3$, $Y_2$ = $OCH_3$) |
| $OCH_3$ | $CH_3$ | H | A-5 ($X_2$ = $CH_3$, $Y_2$ = $SCH_3$) |
| $OCH_3$ | $CH_3$ | H | A-6 ($X_3$ = $OCH_3$) |
| $OCH_3$ | $CH_3$ | H | A-7 ($X_4$ = $OCH_3$, $Y_4$ = $OCH_3$) |
| $OCH_3$ | $CH_3$ | H | A-7 ($X_4$ = $CH_3$, $Y_4$ = $OCH_3$) |
| $OCH_3$ | $CH_3$ | H | A-7 ($X_4$ = $OCH_3$, $Y_4$ = $CH_3$) |
| $OCH_3$ | $CH_3$ | $CH_3$ | A-2 ($X_1$ = $CH_3$, $Y_1$ = $CH_2$) |
| $OCH_3$ | $CH_3$ | $CH_3$ | A-3 ($X_1$ = $CH_3$) |
| $OCH_3$ | $CH_3$ | $CH_3$ | A-3 ($X_1$ = $OCH_3$) |
| $OCH_3$ | $CH_3$ | $CH_3$ | A-4 ($X_1$ = $CH_3$, $Y_3$ = $CH_3$) |
| $OCH_3$ | $CH_3$ | $CH_3$ | A-4 ($X_1$ = $CH_3$, $Y_3$ = $OCH_3$) |
| $OCH_3$ | $CH_3$ | $CH_3$ | A-4 ($X_1$ = $OCH_3$, $Y_3$ = $CH_3$) |
| $OCH_3$ | $CH_3$ | $CH_3$ | A-5 ($X_2$ = $CH_3$, $Y_2$ = $OCH_3$) |
| $OCH_3$ | $CH_3$ | $CH_3$ | A-5 ($X_2$ = $CH_3$, $Y_2$ = $SCH_3$) |
| $OCH_3$ | $CH_3$ | $CH_3$ | A-6 ($X_3$ = $OCH_3$) |
| $OCH_3$ | $CH_3$ | $CH_3$ | A-7 ($X_4$ = $OCH_3$, $Y_4$ = $OCH_3$) |
| $OCH_3$ | $CH_3$ | $CH_3$ | A-7 ($X_4$ = $CH_3$, $Y_4$ = $OCH_3$) |
| $OCH_3$ | $CH_3$ | $CH_3$ | A-7 ($X_4$ = $OCH_3$, $Y_4$ = $CH_3$) |
| $OCH_3$ | $CH_2CH{=}CH_2$ | H | A-2 ($X_1$ = $CH_3$, $Y_1$ = $CH_2$) |
| $OCH_3$ | $CH_2CH{=}CH_2$ | H | A-3 ($X_1$ = $CH_3$) |
| $OCH_3$ | $CH_2CH{=}CH_2$ | H | A-3 ($X_1$ = $OCH_3$) |
| $OCH_3$ | $CH_2CH{=}CH_2$ | H | A-4 ($X_1$ = $CH_3$, $Y_3$ = $CH_3$) |
| $OCH_3$ | $CH_2CH{=}CH_2$ | H | A-4 ($X_1$ = $CH_3$, $Y_3$ = $OCH_3$) |
| $OCH_3$ | $CH_2CH{=}CH_2$ | H | A-4 ($X_1$ = $OCH_3$, $Y_3$ = $CH_3$) |
| $OCH_3$ | $CH_2CH{=}CH_2$ | H | A-5 ($X_2$ = $CH_3$, $Y_2$ = $OCH_3$) |
| $OCH_3$ | $CH_2CH{=}CH_2$ | H | A-5 ($X_2$ = $CH_3$, $Y_2$ = $SCH_3$) |
| $OCH_3$ | $CH_2CH{=}CH_2$ | H | A-6 ($X_3$ = $OCH_3$) |
| $OCH_3$ | $CH_2CH{=}CH_2$ | H | A-7 ($X_4$ = $OCH_3$, $Y_4$ = $OCH_3$) |
| $OCH_3$ | $CH_2CH{=}CH_2$ | H | A-7 ($X_4$ = $CH_3$, $Y_4$ = $OCH_3$) |
| $OCH_3$ | $CH_2CH{=}CH_2$ | H | A-7 ($X_4$ = $OCH_3$, $Y_4$ = $CH_3$) |
| $OCF_2H$ | $CH_3$ | H | A-2 ($X_1$ = $CH_3$, $Y_1$ = $CH_2$) |
| $OCF_2H$ | $CH_3$ | H | A-3 ($X_1$ = $CH_3$) |
| $OCF_2H$ | $CH_3$ | H | A-3 ($X_1$ = $OCH_3$) |
| $OCF_2H$ | $CH_3$ | H | A-4 ($X_1$ = $CH_3$, $Y_3$ = $CH_3$) |
| $OCF_2H$ | $CH_3$ | H | A-4 ($X_1$ = $CH_3$, $Y_3$ = $OCH_3$) |
| $OCF_2H$ | $CH_3$ | H | A-4 ($X_1$ = $OCH_3$, $Y_3$ = $CH_3$) |
| $OCF_2H$ | $CH_3$ | H | A-5 ($X_2$ = $CH_3$, $Y_2$ = $OCH_3$) |
| $OCF_2H$ | $CH_3$ | H | A-5 ($X_2$ = $CH_3$, $Y_2$ = $SCH_3$) |
| $OCF_2H$ | $CH_3$ | H | A-6 ($X_3$ = $OCH_3$) |
| $OCF_2H$ | $CH_3$ | H | A-7 ($X_4$ = $OCH_3$, $Y_4$ = $OCH_3$) |
| $OCF_2H$ | $CH_3$ | H | A-7 ($X_4$ = $CH_3$, $Y_4$ = $OCH_3$) |
| $OCF_2H$ | $CH_3$ | H | A-7 ($X_4$ = $OCH_3$, $Y_4$ = $CH_3$) |
| $OCF_2H$ | $CH_3$ | $CH_3$ | A-2 ($X_1$ = $CH_3$, $Y_1$ = $CH_2$) |
| $OCF_2H$ | $CH_3$ | $CH_3$ | A-3 ($X_1$ = $CH_3$) |
| $OCF_2H$ | $CH_3$ | $CH_3$ | A-3 ($X_1$ = $OCH_3$) |
| $OCF_2H$ | $CH_3$ | $CH_3$ | A-4 ($X_1$ = $CH_3$, $Y_3$ = $CH_3$) |
| $OCF_2H$ | $CH_3$ | $CH_3$ | A-4 ($X_1$ = $CH_3$, $Y_3$ = $OCH_3$) |
| $OCF_2H$ | $CH_3$ | $CH_3$ | A-4 ($X_1$ = $OCH_3$, $Y_3$ = $CH_3$) |
| $OCF_2H$ | $CH_3$ | $CH_3$ | A-5 ($X_2$ = $CH_3$, $Y_2$ = $OCH_3$) |
| $OCF_2H$ | $CH_3$ | $CH_3$ | A-5 ($X_2$ = $CH_3$, $Y_2$ = $SCH_3$) |
| $OCF_2H$ | $CH_3$ | $CH_3$ | A-6 ($X_3$ = $OCH_3$) |
| $OCF_2H$ | $CH_3$ | $CH_3$ | A-7 ($X_4$ = $OCH_3$, $Y_4$ = $OCH_3$) |
| $OCF_2H$ | $CH_3$ | $CH_3$ | A-7 ($X_4$ = $CH_3$, $Y_4$ = $OCH_3$) |
| $OCF_2H$ | $CH_3$ | $CH_3$ | A-7 ($X_4$ = $OCH_3$, $Y_4$ = $CH_3$) |
| $OCF_2H$ | $CH_2CH{=}CH_2$ | H | A-2 ($X_1$ = $CH_3$, $Y_1$ = $CH_2$) |
| $OCF_2H$ | $CH_2CH{=}CH_2$ | H | A-3 ($X_1$ = $CH_3$) |
| $OCF_2H$ | $CH_2CH{=}CH_2$ | H | A-3 ($X_1$ = $OCH_3$) |
| $OCF_2H$ | $CH_2CH{=}CH_2$ | H | A-4 ($X_1$ = $CH_3$, $Y_3$ = $CH_3$) |
| $OCF_2H$ | $CH_2CH{=}CH_2$ | H | A-4 ($X_1$ = $CH_3$, $Y_3$ = $OCH_3$) |
| $OCF_2H$ | $CH_2CH{=}CH_2$ | H | A-4 ($X_1$ = $OCH_3$, $Y_3$ = $CH_3$) |
| $OCF_2H$ | $CH_2CH{=}CH_2$ | H | A-5 ($X_2$ = $CH_3$, $Y_2$ = $OCH_3$) |

-continued

| | | | |
|---|---|---|---|
| $OCF_2H$ | $CH_2CH{=}CH_2$ | H | A-5 ($X_2$ = $CH_3$, $Y_2$ = $SCH_3$) |
| $OCF_2H$ | $CH_2CH{=}CH_2$ | H | A-6 ($X_3$ = $OCH_3$) |
| $OCF_2H$ | $CH_2CH{=}CH_2$ | H | A-7 ($X_4$ = $OCH_3$, $Y_4$ = $OCH_3$) |
| $OCF_2H$ | $CH_2CH{=}CH_2$ | H | A-7 ($X_4$ = $CH_3$, $Y_4$ = $OCH_3$) |
| $OCF_2H$ | $CH_2CH{=}CH_2$ | H | A-7 ($X_4$ = $OCH_3$, $Y_4$ = $CH_3$) |
| $SCF_2H$ | $CH_3$ | H | A-2 ($X_1$ = $CH_3$, $Y_1$ = $CH_2$) |
| $SCF_2H$ | $CH_3$ | H | A-3 ($X_1$ = $CH_3$) |
| $SCF_2H$ | $CH_3$ | H | A-3 ($X_1$ = $OCH_3$) |
| $SCF_2H$ | $CH_3$ | H | A-4 ($X_1$ = $CH_3$, $Y_3$ = $CH_3$) |
| $SCF_2H$ | $CH_3$ | H | A-4 ($X_1$ = $CH_3$, $Y_3$ = $OCH_3$) |
| $SCF_2H$ | $CH_3$ | H | A-4 ($X_1$ = $OCH_3$, $Y_3$ = $CH_3$) |
| $SCF_2H$ | $CH_3$ | H | A-5 ($X_2$ = $CH_3$, $Y_2$ = $OCH_3$) |
| $SCF_2H$ | $CH_3$ | H | A-5 ($X_2$ = $CH_3$, $Y_2$ = $SCH_3$) |
| $SCF_2H$ | $CH_3$ | H | A-6 ($X_3$ = $OCH_3$) |
| $SCF_2H$ | $CH_3$ | H | A-7 ($X_4$ = $OCH_3$, $Y_4$ = $OCH_3$) |
| $SCF_2H$ | $CH_3$ | H | A-7 ($X_4$ = $CH_3$, $Y_4$ = $OCH_3$) |
| $SCF_2H$ | $CH_3$ | H | A-7 ($X_4$ = $OCH_3$, $Y_4$ = $CH_3$) |
| $SCF_2H$ | $CH_3$ | $CH_3$ | A-2 ($X_1$ = $CH_3$, $Y_1$ = $CH_2$) |
| $SCF_2H$ | $CH_3$ | $CH_3$ | A-3 ($X_1$ = $CH_3$) |
| $SCF_2H$ | $CH_3$ | $CH_3$ | A-3 ($X_1$ = $OCH_3$) |
| $SCF_2H$ | $CH_3$ | $CH_3$ | A-4 ($X_1$ = $CH_3$, $Y_3$ = $CH_3$) |
| $SCF_2H$ | $CH_3$ | $CH_3$ | A-4 ($X_1$ = $CH_3$, $Y_3$ = $OCH_3$) |
| $SCF_2H$ | $CH_3$ | $CH_3$ | A-4 ($X_1$ = $OCH_3$, $Y_3$ = $CH_3$) |
| $SCF_2H$ | $CH_3$ | $CH_3$ | A-5 ($X_2$ = $CH_3$, $Y_2$ = $OCH_3$) |
| $SCF_2H$ | $CH_3$ | $CH_3$ | A-5 ($X_2$ = $CH_3$, $Y_2$ = $SCH_3$) |
| $SCF_2H$ | $CH_3$ | $CH_3$ | A-6 ($X_3$ = $OCH_3$) |
| $SCF_2H$ | $CH_3$ | $CH_3$ | A-7 ($X_4$ = $OCH_3$, $Y_4$ = $OCH_3$) |
| $SCF_2H$ | $CH_3$ | $CH_3$ | A-7 ($X_4$ = $CH_3$, $Y_4$ = $OCH_3$) |
| $SCF_2H$ | $CH_3$ | $CH_3$ | A-7 ($X_4$ = $OCH_3$, $Y_4$ = $CH_3$) |
| $SCF_2H$ | $CH_2CH{=}CH_2$ | H | A-2 ($X_1$ = $CH_3$, $Y_1$ = $CH_2$) |
| $SCF_2H$ | $CH_2CH{=}CH_2$ | H | A-3 ($X_1$ = $CH_3$) |
| $SCF_2H$ | $CH_2CH{=}CH_2$ | H | A-3 ($X_1$ = $OCH_3$) |
| $SCF_2H$ | $CH_2CH{=}CH_2$ | H | A-4 ($X_1$ = $CH_3$, $Y_3$ = $CH_3$) |
| $SCF_2H$ | $CH_2CH{=}CH_2$ | H | A-4 ($X_1$ = $CH_3$, $Y_3$ = $OCH_3$) |
| $SCF_2H$ | $CH_2CH{=}CH_2$ | H | A-4 ($X_1$ = $OCH_3$, $Y_3$ = $CH_3$) |
| $SCF_2H$ | $CH_2CH{=}CH_2$ | H | A-5 ($X_2$ = $CH_3$, $Y_2$ = $OCH_3$) |
| $SCF_2H$ | $CH_2CH{=}CH_2$ | H | A-5 ($X_2$ = $CH_3$, $Y_2$ = $SCH_3$) |
| $SCF_2H$ | $CH_2CH{=}CH_2$ | H | A-6 ($X_3$ = $OCH_3$) |
| $SCF_2H$ | $CH_2CH{=}CH_2$ | H | A-7 ($X_4$ = $OCH_3$, $Y_4$ = $OCH_3$) |
| $SCF_2H$ | $CH_2CH{=}CH_2$ | H | A-7 ($X_4$ = $CH_3$, $Y_4$ = $OCH_3$) |
| $SCF_2H$ | $CH_2CH{=}CH_2$ | H | A-7 ($X_4$ = $OCH_3$, $Y_4$ = $CH_3$) |
| $SCF_2H$ | $CH_3$ | H | A-2 ($X_1$ = $CH_3$, $Y_1$ = $CH_2$) |
| $SCF_2H$ | $CH_3$ | H | A-3 ($X_1$ = $CH_3$) |
| $SCF_2H$ | $CH_3$ | H | A-3 ($X_1$ = $OCH_3$) |
| $SCF_2H$ | $CH_3$ | H | A-4 ($X_1$ = $CH_3$, $Y_3$ = $CH_3$) |
| $SCF_2H$ | $CH_3$ | H | A-4 ($X_1$ = $CH_3$, $Y_3$ = $OCH_3$) |
| $SCF_2H$ | $CH_3$ | H | A-4 ($X_1$ = $OCH_3$, $Y_3$ = $CH_3$) |
| $SCF_2H$ | $CH_3$ | H | A-5 ($X_2$ = $CH_3$, $Y_2$ = $OCH_3$) |
| $SCF_2H$ | $CH_3$ | H | A-5 ($X_2$ = $CH_3$, $Y_2$ = $SCH_3$) |
| $SCF_2H$ | $CH_3$ | H | A-6 ($X_3$ = $OCH_3$) |
| $SCF_2H$ | $CH_3$ | H | A-7 ($X_4$ = $OCH_3$, $Y_4$ = $OCH_3$) |
| $SCF_2H$ | $CH_3$ | H | A-7 ($X_4$ = $CH_3$, $Y_4$ = $OCH_3$) |
| $SCF_2H$ | $CH_3$ | H | A-7 ($X_4$ = $OCH_3$, $Y_4$ = $CH_3$) |
| $SCF_2H$ | $CH_3$ | $CH_3$ | A-2 ($X_1$ = $CH_3$, $Y_1$ = $CH_2$) |
| $SCF_2H$ | $CH_3$ | $CH_3$ | A-3 ($X_1$ = $CH_3$) |
| $SCF_2H$ | $CH_3$ | $CH_3$ | A-3 ($X_1$ = $OCH_3$) |
| $SCF_2H$ | $CH_3$ | $CH_3$ | A-4 ($X_1$ = $CH_3$, $Y_3$ = $CH_3$) |
| $SCF_2H$ | $CH_3$ | $CH_3$ | A-4 ($X_1$ = $CH_3$, $Y_3$ = $OCH_3$) |
| $SCF_2H$ | $CH_3$ | $CH_3$ | A-4 ($X_1$ = $OCH_3$, $Y_3$ = $CH_3$) |
| $SCF_2H$ | $CH_3$ | $CH_3$ | A-5 ($X_2$ = $CH_3$, $Y_2$ = $OCH_3$) |
| $SCF_2H$ | $CH_3$ | $CH_3$ | A-5 ($X_2$ = $CH_3$, $Y_2$ = $SCH_3$) |
| $SCF_2H$ | $CH_3$ | $CH_3$ | A-6 ($X_3$ = $OCH_3$) |
| $SCF_2H$ | $CH_3$ | $CH_3$ | A-7 ($X_4$ = $OCH_3$, $Y_4$ = $OCH_3$) |
| $SCF_2H$ | $CH_3$ | $CH_3$ | A-7 ($X_4$ = $CH_3$, $Y_4$ = $OCH_3$) |
| $SCF_2H$ | $CH_3$ | $CH_3$ | A-7 ($X_4$ = $OCH_3$, $Y_4$ = $CH_3$) |
| $SCF_2H$ | $CH_2CH{=}CH_2$ | H | A-2 ($X_1$ = $CH_3$, $Y_1$ = $CH_2$) |
| $SCF_2H$ | $CH_2CH{=}CH_2$ | H | A-3 ($X_1$ = $CH_3$) |
| $SCF_2H$ | $CH_2CH{=}CH_2$ | H | A-3 ($X_1$ = $OCH_3$) |
| $SCF_2H$ | $CH_2CH{=}CH_2$ | H | A-4 ($X_1$ = $CH_3$, $Y_3$ = $CH_3$) |
| $SCF_2H$ | $CH_2CH{=}CH_2$ | H | A-4 ($X_1$ = $CH_3$, $Y_3$ = $OCH_3$) |
| $SCF_2H$ | $CH_2CH{=}CH_2$ | H | A-4 ($X_1$ = $OCH_3$, $Y_3$ = $CH_3$) |
| $SCF_2H$ | $CH_2CH{=}CH_2$ | H | A-5 ($X_2$ = $CH_3$, $Y_2$ = $OCH_3$) |
| $SCF_2H$ | $CH_2CH{=}CH_2$ | H | A-5 ($X_2$ = $CH_3$, $Y_2$ = $SCH_3$) |
| $SCF_2H$ | $CH_2CH{=}CH_2$ | H | A-6 ($X_3$ = $OCH_3$) |
| $SCF_2H$ | $CH_2CH{=}CH_2$ | H | A-7 ($X_4$ = $OCH_3$, $Y_4$ = $OCH_3$) |
| $SCF_2H$ | $CH_2CH{=}CH_2$ | H | A-7 ($X_4$ = $CH_3$, $Y_4$ = $OCH_3$) |
| $SCF_2H$ | $CH_2CH{=}CH_2$ | H | A-7 ($X_4$ = $OCH_3$, $Y_4$ = $CH_3$) |

TABLE IV

GENERAL STRUCTURE 4

| $R_1$ | $R_2$ | $R_3$ | A |
|---|---|---|---|
| H | H | H | A-2 ($X_1$ = $CH_3$, $Y_1$ = $CH_2$) |
| H | H | H | A-3 ($X_1$ = $OCH_3$) |
| H | H | H | A-4 ($X_1$ = $OCH_3$, $Y_3$ = $CH_3$) |
| H | H | H | A-5 ($X_2$ = $CH_3$, $Y_2$ = $OCH_3$) |
| H | H | H | A-6 ($X_3$ = $OCH_3$) |
| H | H | H | A-7 ($X_4$ = $OCH_3$, $Y_4$ = $OCH_3$) |
| H | $CH_3$ | H | A-2 ($X_1$ = $CH_3$, $Y_1$ = $CH_2$) |
| H | $CH_3$ | H | A-3 ($X_1$ = $OCH_3$) |
| H | $CH_3$ | H | A-4 ($X_1$ = $OCH_3$, $Y_3$ = $CH_3$) |
| H | $CH_3$ | H | A-5 ($X_2$ = $CH_3$, $Y_2$ = $OCH_3$) |
| H | $CH_3$ | H | A-6 ($X_3$ = $OCH_3$) |
| H | $CH_3$ | H | A-7 ($X_4$ = $OCH_3$, $Y_4$ = $OCH_3$) |
| H | $CH_2CH_3$ | H | A-2 ($X_1$ = $CH_3$, $Y_1$ = $CH_2$) |
| H | $CH_2CH_3$ | H | A-3 ($X_1$ = $OCH_3$) |
| H | $CH_2CH_3$ | H | A-4 ($X_1$ = $OCH_3$, $Y_3$ = $CH_3$) |
| H | $CH_2CH_3$ | H | A-5 ($X_2$ = $CH_3$, $Y_2$ = $OCH_3$) |
| H | $CH_2CH_3$ | H | A-6 ($X_3$ = $OCH_3$) |
| H | $CH_2CH_3$ | H | A-7 ($X_4$ = $OCH_3$, $Y_4$ = $OCH_3$) |
| H | $CH_2CF_3$ | H | A-2 ($X_1$ = $CH_3$, $Y_1$ = $CH_2$) |
| H | $CH_2CF_3$ | H | A-3 ($X_1$ = $OCH_3$) |
| H | $CH_2CF_3$ | H | A-4 ($X_1$ = $OCH_3$, $Y_3$ = $CH_3$) |
| H | $CH_2CF_3$ | H | A-5 ($X_2$ = $CH_3$, $Y_2$ = $OCH_3$) |
| H | $CH_2CF_3$ | H | A-6 ($X_3$ = $OCH_3$) |
| H | $CH_2CF_3$ | H | A-7 ($X_4$ = $OCH_3$, $Y_4$ = $OCH_3$) |
| H | $CH_2CH_2Cl$ | H | A-2 ($X_1$ = $CH_3$, $Y_1$ = $CH_2$) |
| H | $CH_2CH_2Cl$ | H | A-3 ($X_1$ = $OCH_3$) |
| H | $CH_2CH_2Cl$ | H | A-4 ($X_1$ = $OCH_3$, $Y_3$ = $CH_3$) |
| H | $CH_2CH_2Cl$ | H | A-5 ($X_2$ = $CH_3$, $Y_2$ = $OCH_3$) |
| H | $CH_2CH_2Cl$ | H | A-6 ($X_3$ = $OCH_3$) |
| H | $CH_2CH_2Cl$ | H | A-7 ($X_4$ = $OCH_3$, $Y_4$ = $OCH_3$) |
| H | $CH_2CN$ | H | A-2 ($X_1$ = $CH_3$, $Y_1$ = $CH_2$) |
| H | $CH_2CN$ | H | A-3 ($X_1$ = $OCH_3$) |
| H | $CH_2CN$ | H | A-4 ($X_1$ = $OCH_3$, $Y_3$ = $CH_3$) |
| H | $CH_2CN$ | H | A-5 ($X_2$ = $CH_3$, $Y_2$ = $OCH_3$) |
| H | $CH_2CN$ | H | A-6 ($X_3$ = $OCH_3$) |
| H | $CH_2CN$ | H | A-7 ($X_4$ = $OCH_3$, $Y_4$ = $OCH_3$) |
| H | $CH_2CH_2OCH_3$ | H | A-2 ($X_1$ = $CH_3$, $Y_1$ = $CH_2$) |
| H | $CH_2CH_2OCH_3$ | H | A-3 ($X_1$ = $OCH_3$) |
| H | $CH_2CH_2OCH_3$ | H | A-4 ($X_1$ = $OCH_3$, $Y_3$ = $CH_3$) |
| H | $CH_2CH_2OCH_3$ | H | A-5 ($X_2$ = $CH_3$, $Y_2$ = $OCH_3$) |
| H | $CH_2CH_2OCH_3$ | H | A-6 ($X_3$ = $OCH_3$) |
| H | $CH_2CH_2OCH_3$ | H | A-7 ($X_4$ = $OCH_3$, $Y_4$ = $OCH_3$) |
| H | $CH_2CH{=}CH_2$ | H | A-2 ($X_1$ = $CH_3$, $Y_1$ = $CH_2$) |
| H | $CH_2CH{=}CH_2$ | H | A-3 ($X_1$ = $OCH_3$) |
| H | $CH_2CH{=}CH_2$ | H | A-4 ($X_1$ = $OCH_3$, $Y_3$ = $CH_3$) |
| H | $CH_2CH{=}CH_2$ | H | A-5 ($X_2$ = $CH_3$, $Y_2$ = $OCH_3$) |
| H | $CH_2CH{=}CH_2$ | H | A-6 ($X_3$ = $OCH_3$) |
| H | $CH_2CH{=}CH_2$ | H | A-7 ($X_4$ = $OCH_3$, $Y_4$ = $OCH_3$) |
| H | $CH_2C{\equiv}CH$ | H | A-2 ($X_1$ = $CH_3$, $Y_1$ = $CH_2$) |
| H | $CH_2C{\equiv}CH$ | H | A-3 ($X_1$ = $OCH_3$) |
| H | $CH_2C{\equiv}CH$ | H | A-4 ($X_1$ = $OCH_3$, $Y_3$ = $CH_3$) |
| H | $CH_2C{\equiv}CH$ | H | A-5 ($X_2$ = $CH_3$, $Y_2$ = $OCH_3$) |
| H | $CH_2C{\equiv}CH$ | H | A-6 ($X_3$ = $OCH_3$) |
| H | $CH_2C{\equiv}CH$ | H | A-7 ($X_4$ = $OCH_3$, $Y_4$ = $OCH_3$) |
| H | cyclo-$C_3H_7$ | H | A-2 ($X_1$ = $CH_3$, $Y_1$ = $CH_2$) |
| H | cyclo-$C_3H_7$ | H | A-3 ($X_1$ = $OCH_3$) |
| H | cyclo-$C_3H_7$ | H | A-4 ($X_1$ = $OCH_3$, $Y_3$ = $CH_3$) |
| H | cyclo-$C_3H_7$ | H | A-5 ($X_2$ = $CH_3$, $Y_2$ = $OCH_3$) |
| H | cyclo-$C_3H_7$ | H | A-6 ($X_3$ = $OCH_3$) |
| H | cyclo-$C_3H_7$ | H | A-7 ($X_4$ = $OCH_3$, $Y_4$ = $OCH_3$) |
| H | $CH_3$ | $CH_3$ | A-2 ($X_1$ = $CH_3$, $Y_1$ = $CH_2$) |
| H | $CH_3$ | $CH_3$ | A-3 ($X_1$ = $OCH_3$) |
| H | $CH_3$ | $CH_3$ | A-4 ($X_1$ = $OCH_3$, $Y_3$ = $CH_3$) |
| H | $CH_3$ | $CH_3$ | A-5 ($X_2$ = $CH_3$, $Y_2$ = $OCH_3$) |
| H | $CH_3$ | $CH_3$ | A-6 ($X_3$ = $OCH_3$) |
| H | $CH_3$ | $CH_3$ | A-7 ($X_4$ = $OCH_3$, $Y_4$ = $OCH_3$) |
| H | $CH_2CH_3$ | $CH_3$ | A-2 ($X_1$ = $CH_3$, $Y_1$ = $CH_2$) |
| H | $CH_2CH_3$ | $CH_3$ | A-3 ($X_1$ = $OCH_3$) |
| H | $CH_2CH_3$ | $CH_3$ | A-4 ($X_1$ = $OCH_3$, $Y_3$ = $CH_3$) |
| H | $CH_2CH_3$ | $CH_3$ | A-5 ($X_2$ = $CH_3$, $Y_2$ = ($OCH_3$) |
| H | $CH_2CH_3$ | $CH_3$ | A-6 ($X_3$ = $OCH_3$) |
| H | $CH_2CH_3$ | $CH_3$ | A-7 ($X_4$ = $OCH_3$, $Y_4$ = $OCH_3$) |
| H | $CH_2CH_3$ | $CH_2CH_3$ | A-2 ($X_1$ = $CH_3$, $Y_1$ = $CH_2$) |
| H | $CH_2CH_3$ | $CH_2CH_3$ | A-3 ($X_1$ = $OCH_3$) |
| H | $CH_2CH_3$ | $CH_2CH_3$ | A-4 ($X_1$ = $OCH_3$, $Y_3$ = $CH_3$) |
| H | $CH_2CH_3$ | $CH_2CH_3$ | A-5 ($X_2$ = $CH_3$, $Y_2$ = $OCH_3$) |
| H | $CH_2CH_3$ | $CH_2CH_3$ | A-6 ($X_3$ = $OCH_3$) |
| H | $CH_2CH_3$ | $CH_2CH_3$ | A-7 ($X_4$ = $OCH_3$, $Y_4$ = $OCH_3$) |
| H | $OCH_3$ | $CH_3$ | A-2 ($X_1$ = $CH_3$, $Y_1$ = $CH_2$) |
| H | $OCH_3$ | $CH_3$ | A-3 ($X_1$ = $OCH_3$) |

TABLE IV-continued

GENERAL STRUCTURE 4

| $R_1$ | $R_2$ | $R_3$ | A |
|---|---|---|---|
| H | $OCH_3$ | $CH_3$ | A-4 ($X_1$ = $OCH_3$, $Y_3$ = $CH_3$) |
| H | $OCH_3$ | $CH_3$ | A-5 ($X_2$ = $CH_3$, $Y_2$ = $OCH_3$) |
| H | $OCH_3$ | $CH_3$ | A-6 ($X_3$ = $OCH_3$) |
| H | $OCH_3$ | $CH_3$ | A-7 ($X_4$ = $OCH_3$, $Y_4$ = $OCH_3$) |
| H | $NHCH_3$ | $CH_3$ | A-2 ($X_1$ = $CH_3$, $Y_1$ = $CH_2$) |
| H | $NHCH_3$ | $CH_3$ | A-3 ($X_1$ = $OCH_3$) |
| H | $NHCH_3$ | $CH_3$ | A-4 ($X_1$ = $OCH_3$, $Y_3$ = $CH_3$) |
| H | $NHCH_3$ | $CH_3$ | A-5 ($X_2$ = $CH_3$, $Y_2$ = $OCH_3$) |
| H | $NHCH_3$ | $CH_3$ | A-6 ($X_3$ = $OCH_3$) |
| H | $NHCH_3$ | $CH_3$ | A-7 ($X_4$ = $OCH_3$, $Y_4$ = $OCH_3$) |
| H | $N(CH_3)_2$ | $CH_3$ | A-2 ($X_1$ = $CH_3$, $Y_1$ = $CH_2$) |
| H | $N(CH_3)_2$ | $CH_3$ | A-3 ($X_1$ = $OCH_3$) |
| H | $N(CH_3)_2$ | $CH_3$ | A-4 ($X_1$ = $OCH_3$, $Y_3$ = $CH_3$) |
| H | $N(CH_3)_2$ | $CH_3$ | A-5 ($X_2$ = $CH_3$, $Y_2$ = $OCH_3$) |
| H | $N(CH_3)_2$ | $CH_3$ | A-6 ($X_3$ = $OCH_3$) |
| H | $N(CH_3)_2$ | $CH_3$ | A-7 ($X_4$ = $OCH_3$, $Y_4$ = $OCH_3$) |
| H | $—CH_2CH_2CH_2—$ | | A-2 ($X_1$ = $CH_3$, $Y_1$ = $CH_2$) |
| H | $—CH_2CH_2CH_2—$ | | A-3 ($X_1$ = $OCH_3$) |
| H | $—CH_2CH_2CH_2—$ | | A-4 ($X_1$ = $OCH_3$, $Y_3$ = $CH_3$) |
| H | $—CH_2CH_2CH_2—$ | | A-5 ($X_2$ = $CH_3$, $Y_2$ = $OCH_3$) |
| H | $—CH_2CH_2CH_2—$ | | A-6 ($X_3$ = $OCH_3$) |
| H | $—CH_2CH_2CH_2—$ | | A-7 ($X_4$ = $OCH_3$, $Y_4$ = $OCH_3$) |
| H | $—CH_2CH_2OCH_2CH_2—$ | | A-2 ($X_1$ = $CH_3$, $Y_1$ = $CH_2$) |
| H | $—CH_2CH_2OCH_2CH_2—$ | | A-3 ($X_1$ = $OCH_3$) |
| H | $—CH_2CH_2OCH_2CH_2—$ | | A-4 ($X_1$ = $OCH_3$, $Y_3$ = $CH_3$) |
| H | $—CH_2CH_2OCH_2CH_2—$ | | A-5 ($X_2$ = $CH_3$, $Y_2$ = ($OCH_3$)) |
| H | $—CH_2CH_2OCH_2CH_2—$ | | A-6 ($X_3$ = $OCH_3$) |
| H | $—CH_2CH_2OCH_2CH_2—$ | | A-7 ($X_4$ = $OCH_3$, $Y_4$ = $OCH_3$) |
| Cl | H | H | A-2 ($X_1$ = $CH_3$, $Y_1$ = $CH_2$) |
| Cl | H | H | A-3 ($X_1$ = $OCH_3$) |
| Cl | H | H | A-4 ($X_1$ = $OCH_3$, $Y_3$ = $CH_3$) |
| Cl | H | H | A-5 ($X_2$ = $CH_3$, $Y_2$ = $OCH_3$) |
| Cl | H | H | A-6 ($X_3$ = $OCH_3$) |
| Cl | H | H | A-7 ($X_4$ = $OCH_3$, $Y_4$ = $OCH_3$) |
| Cl | $CH_3$ | H | A-2 ($X_1$ = $CH_3$, $Y_1$ = $CH_2$) |
| Cl | $CH_3$ | H | A-3 ($X_1$ = $OCH_3$) |
| Cl | $CH_3$ | H | A-4 ($X_1$ = $OCH_3$, $Y_3$ = $CH_3$) |
| Cl | $CH_3$ | H | A-5 ($X_2$ = $CH_3$, $Y_2$ = $OCH_3$) |
| Cl | $CH_3$ | H | A-6 ($X_3$ = $OCH_3$) |
| Cl | $CH_3$ | H | A-7 ($X_4$ = $OCH_3$, $Y_4$ = $OCH_3$) |
| Cl | $CH_2CH_3$ | H | A-2 ($X_1$ = $CH_3$, $Y_1$ = $CH_2$) |
| Cl | $CH_2CH_3$ | H | A-3 ($X_1$ = $OCH_3$) |
| Cl | $CH_2CH_3$ | H | A-4 ($X_1$ = $OCH_3$, $Y_3$ = $CH_3$) |
| Cl | $CH_2CH_3$ | H | A-5 ($X_2$ = $CH_3$, $Y_2$ = $OCH_3$) |
| Cl | $CH_2CH_3$ | H | A-6 ($X_3$ = $OCH_3$) |
| Cl | $CH_2CH_3$ | H | A-7 ($X_4$ = $OCH_3$, $Y_4$ = $OCH_3$) |
| Cl | $CH_2CF_3$ | H | A-2 ($X_1$ = $CH_3$, $Y_1$ = $CH_2$) |
| Cl | $CH_2CF_3$ | H | A-3 ($X_1$ = $OCH_3$) |
| Cl | $CH_2CF_3$ | H | A-4 ($X_1$ = $OCH_3$, $Y_3$ = $CH_3$) |
| Cl | $CH_2CF_3$ | H | A-5 ($X_2$ = $CH_3$, $Y_2$ = $OCH_3$) |
| Cl | $CH_2CF_3$ | H | A-6 ($X_3$ = $OCH_3$) |
| Cl | $CH_2CF_3$ | H | A-7 ($X_4$ = $OCH_3$, $Y_4$ = $OCH_3$) |
| Cl | $CH_2CH_2Cl$ | H | A-2 ($X_1$ = $CH_3$, $Y_1$ = $CH_2$) |
| Cl | $CH_2CH_2Cl$ | H | A-3 ($X_1$ = $OCH_3$) |
| Cl | $CH_2CH_2Cl$ | H | A-4 ($X_1$ = $OCH_3$, $Y_3$ = $CH_3$) |
| Cl | $CH_2CH_2Cl$ | H | A-5 ($X_2$ = $CH_3$, $Y_2$ = $OCH_3$) |
| Cl | $CH_2CH_2Cl$ | H | A-6 ($X_3$ = $OCH_3$) |
| Cl | $CH_2CH_2Cl$ | H | A-7 ($X_4$ = $OCH_3$, $Y_4$ = $OCH_3$) |
| Cl | $CH_2CN$ | H | A-2 ($X_1$ = $CH_3$, $Y_1$ = $CH_2$) |
| Cl | $CH_2CN$ | H | A-3 ($X_1$ = $OCH_3$) |
| Cl | $CH_2CN$ | H | A-4 ($X_1$ = $OCH_3$, $Y_3$ = $CH_3$) |
| Cl | $CH_2CN$ | H | A-5 ($X_2$ = $CH_3$, $Y_2$ = ($OCH_3$)) |
| Cl | $CH_2CN$ | H | A-6 ($X_3$ = $OCH_3$) |
| Cl | $CH_2CN$ | H | A-7 ($X_4$ = $OCH_3$, $Y_4$ = $OCH_3$) |
| Cl | $CH_2CH_2OCH_3$ | H | A-2 ($X_1$ = $CH_3$, $Y_1$ = $CH_2$) |
| Cl | $CH_2CH_2OCH_3$ | H | A-3 ($X_1$ = $OCH_3$) |
| Cl | $CH_2CH_2OCH_3$ | H | A-4 ($X_1$ = $OCH_3$, $Y_3$ = $CH_3$) |
| Cl | $CH_2CH_2OCH_3$ | H | A-5 ($X_2$ = $CH_3$, $Y_2$ = $OCH_3$) |
| Cl | $CH_2CH_2OCH_3$ | H | A-6 ($X_3$ = $OCH_3$) |
| Cl | $CH_2CH_2OCH_3$ | H | A-7 ($X_4$ = $OCH_3$, $Y_4$ = $OCH_3$) |
| Cl | $CH_2CH{=}CH_2$ | H | A-2 ($X_1$ = $CH_3$, $Y_1$ = $CH_2$) |
| Cl | $CH_2CH{=}CH_2$ | H | A-3 ($X_1$ = $OCH_3$) |
| Cl | $CH_2CH{=}CH_2$ | H | A-4 ($X_1$ = $OCH_3$, $Y_3$ = $CH_3$) |
| Cl | $CH_2CH{=}CH_2$ | H | A-5 ($X_2$ = $CH_3$, $Y_2$ = $OCH_3$) |
| Cl | $CH_2CH{=}CH_2$ | H | A-6 ($X_3$ = $OCH_3$) |
| Cl | $CH_2CH{=}CH_2$ | H | A-7 ($X_4$ = $OCH_3$, $Y_4$ = $OCH_3$) |
| Cl | $CH_2C{\equiv}CH$ | H | A-2 ($X_1$ = $CH_3$, $Y_1$ = $CH_2$) |
| Cl | $CH_2C{\equiv}CH$ | H | A-3 ($X_1$ = $OCH_3$) |
| Cl | $CH_2C{\equiv}CH$ | H | A-4 ($X_1$ = $OCH_3$, $Y_3$ = $CH_3$) |
| Cl | $CH_2C{\equiv}CH$ | H | A-5 ($X_2$ = $CH_3$, $Y_2$ = $OCH_3$) |

TABLE IV-continued

GENERAL STRUCTURE 4

| $R_1$ | $R_2$ | $R_3$ | A |
|---|---|---|---|
| Cl | $CH_2C{\equiv}CH$ | H | A-6 ($X_3$ = $OCH_3$) |
| Cl | $CH_2C{\equiv}CH$ | H | A-7 ($X_4$ = $OCH_3$, $Y_4$ = $OCH_3$) |
| Cl | cyclo-$C_3H_7$ | H | A-2 ($X_1$ = $CH_3$, $Y_1$ = $CH_2$) |
| Cl | cyclo-$C_3H_7$ | H | A-3 ($X_1$ = $OCH_3$) |
| Cl | cyclo-$C_3H_7$ | H | A-4 ($X_1$ = $OCH_3$, $Y_3$ = $CH_3$) |
| Cl | cyclo-$C_3H_7$ | H | A-5 ($X_2$ = $CH_3$, $Y_2$ = $OCH_3$) |
| Cl | cyclo-$C_3H_7$ | H | A-6 ($X_3$ = $OCH_3$) |
| Cl | cyclo-$C_3H_7$ | H | A-7 ($X_4$ = $OCH_3$, $Y_4$ = $OCH_3$) |
| Cl | $CH_3$ | $CH_3$ | A-2 ($X_1$ = $CH_3$, $Y_1$ = $CH_2$) |
| Cl | $CH_3$ | $CH_3$ | A-3 ($X_1$ = $OCH_3$) |
| Cl | $CH_3$ | $CH_3$ | A-4 ($X_1$ = $OCH_3$, $Y_3$ = $CH_3$) |
| Cl | $CH_3$ | $CH_3$ | A-5 ($X_2$ = $CH_3$, $Y_2$ = $OCH_3$) |
| Cl | $CH_3$ | $CH_3$ | A-6 ($X_3$ = $OCH_3$) |
| Cl | $CH_3$ | $CH_3$ | A-7 ($X_4$ = $OCH_3$, $Y_4$ = $OCH_3$) |
| Cl | $CH_2CH_3$ | $CH_3$ | A-2 ($X_1$ = $CH_3$, $Y_1$ = $CH_2$) |
| Cl | $CH_2CH_3$ | $CH_3$ | A-3 ($X_1$ = $OCH_3$) |
| Cl | $CH_2CH_3$ | $CH_3$ | A-4 ($X_1$ = $OCH_3$, $Y_3$ = $CH_3$) |
| Cl | $CH_2CH_3$ | $CH_3$ | A-5 ($X_2$ = $CH_3$, $Y_2$ = $OCH_3$) |
| Cl | $CH_2CH_3$ | $CH_3$ | A-6 ($X_3$ = $OCH_3$) |
| Cl | $CH_2CH_3$ | $CH_3$ | A-7 ($X_4$ = $OCH_3$, $Y_4$ = $OCH_3$) |
| Cl | $CH_2CH_3$ | $CH_2CH_3$ | A-2 ($X_1$ = $CH_3$, $Y_1$ = $CH_2$) |
| Cl | $CH_2CH_3$ | $CH_2CH_3$ | A-3 ($X_1$ = $OCH_3$) |
| Cl | $CH_2CH_3$ | $CH_2CH_3$ | A-4 ($X_1$ = $OCH_3$, $Y_3$ = $CH_3$) |
| Cl | $CH_2CH_3$ | $CH_2CH_3$ | A-5 ($X_2$ = $CH_3$, $Y_2$ = $OCH_3$) |
| Cl | $CH_2CH_3$ | $CH_2CH_3$ | A-6 ($X_3$ = $OCH_3$) |
| Cl | $CH_2CH_3$ | $CH_2CH_3$ | A-7 ($X_4$ = $OCH_3$, $Y_4$ = $OCH_3$) |
| Cl | $OCH_3$ | $CH_3$ | A-2 ($X_1$ = $CH_3$, $Y_1$ = $CH_2$) |
| Cl | $OCH_3$ | $CH_3$ | A-3 ($X_1$ = $OCH_3$) |
| Cl | $OCH_3$ | $CH_3$ | A-4 ($X_1$ = $OCH_3$, $Y_3$ = $CH_3$) |
| Cl | $OCH_3$ | $CH_3$ | A-5 ($X_2$ = $CH_3$, $Y_2$ = $OCH_3$) |
| Cl | $OCH_3$ | $CH_3$ | A-6 ($X_3$ = $OCH_3$) |
| Cl | $OCH_3$ | $CH_3$ | A-7 ($X_4$ = $OCH_3$, $Y_4$ = $OCH_3$) |
| Cl | $NHCH_3$ | $CH_3$ | A-2 ($X_1$ = $CH_3$, $Y_1$ = $CH_2$) |
| Cl | $NHCH_3$ | $CH_3$ | A-3 ($X_1$ = $OCH_3$) |
| Cl | $NHCH_3$ | $CH_3$ | A-4 ($X_1$ = $OCH_3$, $Y_3$ = $CH_3$) |
| Cl | $NHCH_3$ | $CH_3$ | A-5 ($X_2$ = $CH_3$, $Y_2$ = $OCH_3$) |
| Cl | $NHCH_3$ | $CH_3$ | A-6 ($X_3$ = $OCH_3$) |
| Cl | $NHCH_3$ | $CH_3$ | A-7 ($X_4$ = $OCH_3$, $Y_4$ = $OCH_3$) |
| Cl | $N(CH_3)_2$ | $CH_3$ | A-2 ($X_1$ = $CH_3$, $Y_1$ = $CH_2$) |
| Cl | $N(CH_3)_2$ | $CH_3$ | A-3 ($X_1$ = $OCH_3$) |
| Cl | $N(CH_3)_2$ | $CH_3$ | A-4 ($X_1$ = $OCH_3$, $Y_3$ = $CH_3$) |
| Cl | $N(CH_3)_2$ | $CH_3$ | A-5 ($X_2$ = $CH_3$, $Y_2$ = $OCH_3$) |
| Cl | $N(CH_3)_2$ | $CH_3$ | A-6 ($X_3$ = $OCH_3$) |
| Cl | $N(CH_3)_2$ | $CH_3$ | A-7 ($X_4$ = $OCH_3$, $Y_4$ = $OCH_3$) |
| Cl | $-CH_2CH_2CH_2-$ | | A-2 ($X_1$ = $CH_3$, $Y_1$ = $CH_2$) |
| Cl | $-CH_2CH_2CH_2-$ | | A-3 ($X_1$ = $OCH_3$) |
| Cl | $-CH_2CH_2CH_2-$ | | A-4 ($X_1$ = $OCH_3$, $Y_3$ = $CH_3$) |
| Cl | $-CH_2CH_2CH_2-$ | | A-5 ($X_2$ = $CH_3$, $Y_2$ = $OCH_3$) |
| Cl | $-CH_2CH_2CH_2-$ | | A-6 ($X_3$ = $OCH_3$) |
| Cl | $-CH_2CH_2CH_2-$ | | A-7 ($X_4$ = $OCH_3$, $Y_4$ = $OCH_3$) |
| Cl | $-CH_2CH_2OCH_2CH_2-$ | | A-2 ($X_1$ = $CH_3$, $Y_1$ = $CH_2$) |
| Cl | $-CH_2CH_2OCH_2CH_2-$ | | A-3 ($X_1$ = $OCH_3$) |
| Cl | $-CH_2CH_2OCH_2CH_2-$ | | A-4 ($X_1$ = $OCH_3$, $Y_3$ = $CH_3$) |
| Cl | $-CH_2CH_2OCH_2CH_2-$ | | A-5 ($X_2$ = $CH_3$, $Y_2$ = ($OCH_3$)) |
| Cl | $-CH_2CH_2OCH_2CH_2-$ | | A-6 ($X_3$ = $OCH_3$) |
| Cl | $-CH_2CH_2OCH_2CH_2-$ | | A-7 ($X_4$ = $OCH_3$, $Y_4$ = $OCH_3$) |
| $CH_3$ | H | H | A-2 ($X_1$ = $CH_3$, $Y_1$ = $CH_2$) |
| $CH_3$ | H | H | A-3 ($X_1$ = $OCH_3$) |
| $CH_3$ | H | H | A-4 ($X_1$ = $OCH_3$, $Y_3$ = $CH_3$) |
| $CH_3$ | H | H | A-5 ($X_2$ = $CH_3$, $Y_2$ = $OCH_3$) |
| $CH_3$ | H | H | A-6 ($X_3$ = $OCH_3$) |
| $CH_3$ | H | H | A-7 ($X_4$ = $OCH_3$, $Y_4$ = $OCH_3$) |
| $CH_3$ | $CH_3$ | H | A-2 ($X_1$ = $CH_3$, $Y_1$ = $CH_2$) |
| $CH_3$ | $CH_3$ | H | A-3 ($X_1$ = $OCH_3$) |
| $CH_3$ | $CH_3$ | H | A-4 ($X_1$ = $OCH_3$, $Y_3$ = $CH_3$) |
| $CH_3$ | $CH_3$ | H | A-5 ($X_2$ = $CH_3$, $Y_2$ = $OCH_3$) |
| $CH_3$ | $CH_3$ | H | A-6 ($X_3$ = $OCH_3$) |
| $CH_3$ | $CH_3$ | H | A-7 ($X_4$ = $OCH_3$, $Y_4$ = $OCH_3$) |
| $CH_3$ | $CH_2CH_3$ | H | A-2 ($X_1$ = $CH_3$, $Y_1$ = $CH_2$) |
| $CH_3$ | $CH_2CH_3$ | H | A-3 ($X_1$ = $OCH_3$) |
| $CH_3$ | $CH_2CH_3$ | H | A-4 ($X_1$ = $OCH_3$, $Y_3$ = $CH_3$) |
| $CH_3$ | $CH_2CH_3$ | H | A-5 ($X_2$ = $CH_3$, $Y_2$ = $OCH_3$) |
| $CH_3$ | $CH_2CH_3$ | H | A-6 ($X_3$ = $OCH_3$) |
| $CH_3$ | $CH_2CH_3$ | H | A-7 ($X_4$ = $OCH_3$, $Y_4$ = $OCH_3$) |
| $CH_3$ | $CH_2CF_3$ | H | A-2 ($X_1$ = $CH_3$, $Y_1$ = $CH_2$) |
| $CH_3$ | $CH_2CF_3$ | H | A-3 ($X_1$ = $OCH_3$) |
| $CH_3$ | $CH_2CF_3$ | H | A-4 ($X_1$ = $OCH_3$, $Y_3$ = $CH_3$) |
| $CH_3$ | $CH_2CF_3$ | H | A-5 ($X_2$ = $CH_3$, $Y_2$ = $OCH_3$) |
| $CH_3$ | $CH_2CF_3$ | H | A-6 ($X_3$ = $OCH_3$) |
| $CH_3$ | $CH_2CF_3$ | H | A-7 ($X_4$ = $OCH_3$, $Y_4$ = $OCH_3$) |

TABLE IV-continued

GENERAL STRUCTURE 4

| $R_1$ | $R_2$ | $R_3$ | A |
|---|---|---|---|
| $CH_3$ | $CH_2CH_2Cl$ | H | A-2 ($X_1 = CH_3$, $Y_1 = CH_2$) |
| $CH_3$ | $CH_2CH_2Cl$ | H | A-3 ($X_1 = OCH_3$) |
| $CH_3$ | $CH_2CH_2Cl$ | H | A-4 ($X_1 = OCH_3$, $Y_3 = CH_3$) |
| $CH_3$ | $CH_2CH_2Cl$ | H | A-5 ($X_2 = CH_3$, $Y_2 = OCH_3$) |
| $CH_3$ | $CH_2CH_2Cl$ | H | A-6 ($X_3 = OCH_3$) |
| $CH_3$ | $CH_2CH_2Cl$ | H | A-7 ($X_4 = OCH_3$, $Y_4 = OCH_3$) |
| $CH_3$ | $CH_2CN$ | H | A-2 ($X_1 = CH_3$, $Y_1 = CH_2$) |
| $CH_3$ | $CH_2CN$ | H | A-3 ($X_1 = OCH_3$) |
| $CH_3$ | $CH_2CN$ | H | A-4 ($X_1 = OCH_3$, $Y_3 = CH_3$) |
| $CH_3$ | $CH_2CN$ | H | A-5 ($X_2 = CH_3$, $Y_2 = (OCH_3)$) |
| $CH_3$ | $CH_2CN$ | H | A-6 ($X_3 = OCH_3$) |
| $CH_3$ | $CH_2CN$ | H | A-7 ($X_4 = OCH_3$, $Y_4 = OCH_3$) |
| $CH_3$ | $CH_2CH_2OCH_3$ | H | A-2 ($X_1 = CH_3$, $Y_1 = CH_2$) |
| $CH_3$ | $CH_2CH_2OCH_3$ | H | A-3 ($X_1 = OCH_3$) |
| $CH_3$ | $CH_2CH_2OCH_3$ | H | A-4 ($X_1 = OCH_3$, $Y_3 = CH_3$) |
| $CH_3$ | $CH_2CH_2OCH_3$ | H | A-5 ($X_2 = CH_3$, $Y_2 = OCH_3$) |
| $CH_3$ | $CH_2CH_2OCH_3$ | H | A-6 ($X_3 = OCH_3$) |
| $CH_3$ | $CH_2CH_2OCH_3$ | H | A-7 ($X_4 = OCH_3$, $Y_4 = OCH_3$) |
| $CH_3$ | $CH_2CH{=}CH_2$ | H | A-2 ($X_1 = CH_3$, $Y_1 = CH_2$) |
| $CH_3$ | $CH_2CH{=}CH_2$ | H | A-3 ($X_1 = OCH_3$) |
| $CH_3$ | $CH_2CH{=}CH_2$ | H | A-4 ($X_1 = OCH_3$, $Y_3 = CH_3$) |
| $CH_3$ | $CH_2CH{=}CH_2$ | H | A-5 ($X_2 = CH_3$, $Y_2 = OCH_3$) |
| $CH_3$ | $CH_2CH{=}CH_2$ | H | A-6 ($X_3 = OCH_3$) |
| $CH_3$ | $CH_2CH{=}CH_2$ | H | A-7 ($X_4 = OCH_3$, $Y_4 = OCH_3$) |
| $CH_3$ | $CH_2C{\equiv}CH$ | H | A-2 ($X_1 = CH_3$, $Y_1 = CH_2$) |
| $CH_3$ | $CH_2C{\equiv}CH$ | H | A-3 ($X_1 = OCH_3$) |
| $CH_3$ | $CH_2C{\equiv}CH$ | H | A-4 ($X_1 = OCH_3$, $Y_3 = CH_3$) |
| $CH_3$ | $CH_2C{\equiv}CH$ | H | A-5 ($X_2 = CH_3$, $Y_2 = OCH_3$) |
| $CH_3$ | $CH_2C{\equiv}CH$ | H | A-6 ($X_3 = OCH_3$) |
| $CH_3$ | $CH_2C{\equiv}CH$ | H | A-7 ($X_4 = OCH_3$, $Y_4 = OCH_3$) |
| $CH_3$ | cyclo-$C_3H_7$ | H | A-2 ($X_1 = CH_3$, $Y_1 = CH_2$) |
| $CH_3$ | cyclo-$C_3H_7$ | H | A-3 ($X_1 = OCH_3$) |
| $CH_3$ | cyclo-$C_3H_7$ | H | A-4 ($X_1 = OCH_3$, $Y_3 = CH_3$) |
| $CH_3$ | cyclo-$C_3H_7$ | H | A-5 ($X_2 = CH_3$, $Y_2 = OCH_3$) |
| $CH_3$ | cyclo-$C_3H_7$ | H | A-6 ($X_3 = OCH_3$) |
| $CH_3$ | cyclo-$C_3H_7$ | H | A-7 ($X_4 = OCH_3$, $Y_4 = OCH_3$) |
| $CH_3$ | $CH_3$ | $CH_3$ | A-2 ($X_1 = CH_3$, $Y_1 = CH_2$) |
| $CH_3$ | $CH_3$ | $CH_3$ | A-3 ($X_1 = OCH_3$) |
| $CH_3$ | $CH_3$ | $CH_3$ | A-4 ($X_1 = OCH_3$, $Y_3 = CH_3$) |
| $CH_3$ | $CH_3$ | $CH_3$ | A-5 ($X_2 = CH_3$, $Y_2 = OCH_3$) |
| $CH_3$ | $CH_3$ | $CH_3$ | A-6 ($X_3 = OCH_3$) |
| $CH_3$ | $CH_3$ | $CH_3$ | A-7 ($X_4 = OCH_3$, $Y_4 = OCH_3$) |
| $CH_3$ | $CH_2CH_3$ | $CH_3$ | A-2 ($X_1 = CH_3$, $Y_1 = CH_2$) |
| $CH_3$ | $CH_2CH_3$ | $CH_3$ | A-3 ($X_1 = OCH_3$) |
| $CH_3$ | $CH_2CH_3$ | $CH_3$ | A-4 ($X_1 = OCH_3$, $Y_3 = CH_3$) |
| $CH_3$ | $CH_2CH_3$ | $CH_3$ | A-5 ($X_2 = CH_3$, $Y_2 = (OCH_3)$) |
| $CH_3$ | $CH_2CH_3$ | $CH_3$ | A-6 ($X_3 = OCH_3$) |
| $CH_3$ | $CH_2CH_3$ | $CH_3$ | A-7 ($X_4 = OCH_3$, $Y_4 = OCH_3$) |
| $CH_3$ | $CH_2CH_3$ | $CH_2CH_3$ | A-2 ($X_1 = CH_3$, $Y_1 = CH_2$) |
| $CH_3$ | $CH_2CH_3$ | $CH_2CH_3$ | A-3 ($X_1 = OCH_3$) |
| $CH_3$ | $CH_2CH_3$ | $CH_2CH_3$ | A-4 ($X_1 = OCH_3$, $Y_3 = CH_3$) |
| $CH_3$ | $CH_2CH_3$ | $CH_2CH_3$ | A-5 ($X_2 = CH_3$, $Y_2 = OCH_3$) |
| $CH_3$ | $CH_2CH_3$ | $CH_2CH_3$ | A-6 ($X_3 = OCH_3$) |
| $CH_3$ | $CH_2CH_3$ | $CH_2CH_3$ | A-7 ($X_4 = OCH_3$, $Y_4 = OCH_3$) |
| $CH_3$ | $OCH_3$ | $CH_3$ | A-2 ($X_1 = CH_3$, $Y_1 = CH_2$) |
| $CH_3$ | $OCH_3$ | $CH_3$ | A-3 ($X_1 = OCH_3$) |
| $CH_3$ | $OCH_3$ | $CH_3$ | A-4 ($X_1 = OCH_3$, $Y_3 = CH_3$) |
| $CH_3$ | $OCH_3$ | $CH_3$ | A-5 ($X_2 = CH_3$, $Y_2 = OCH_3$) |
| $CH_3$ | $OCH_3$ | $CH_3$ | A-6 ($X_3 = OCH_3$) |
| $CH_3$ | $OCH_3$ | $CH_3$ | A-7 ($X_4 = OCH_3$, $Y_4 = OCH_3$) |
| $CH_3$ | $NHCH_3$ | $CH_3$ | A-2 ($X_1 = CH_3$, $Y_1 = CH_2$) |
| $CH_3$ | $NHCH_3$ | $CH_3$ | A-3 ($X_1 = OCH_3$) |
| $CH_3$ | $NHCH_3$ | $CH_3$ | A-4 ($X_1 = OCH_3$, $Y_3 = CH_3$) |
| $CH_3$ | $NHCH_3$ | $CH_3$ | A-5 ($X_2 = CH_3$, $Y_2 = OCH_3$) |
| $CH_3$ | $NHCH_3$ | $CH_3$ | A-6 ($X_3 = OCH_3$) |
| $CH_3$ | $NHCH_3$ | $CH_3$ | A-7 ($X_4 = OCH_3$, $Y_4 = OCH_3$) |
| $CH_3$ | $N(CH_3)_2$ | $CH_3$ | A-2 ($X_1 = CH_3$, $Y_1 = CH_2$) |
| $CH_3$ | $N(CH_3)_2$ | $CH_3$ | A-3 ($X_1 = OCH_3$) |
| $CH_3$ | $N(CH_3)_2$ | $CH_3$ | A-4 ($X_1 = OCH_3$, $Y_3 = CH_3$) |
| $CH_3$ | $N(CH_3)_2$ | $CH_3$ | A-5 ($X_2 = CH_3$, $Y_2 = OCH_3$) |
| $CH_3$ | $N(CH_3)_2$ | $CH_3$ | A-6 ($X_3 = OCH_3$) |
| $CH_3$ | $N(CH_3)_2$ | $CH_3$ | A-7 ($X_4 = OCH_3$, $Y_4 = OCH_3$) |
| $CH_3$ | $-CH_2CH_2CH_2-$ | | A-2 ($X_1 = CH_3$, $Y_1 = CH_2$) |
| $CH_3$ | $-CH_2CH_2CH_2-$ | | A-3 ($X_1 = OCH_3$) |
| $CH_3$ | $-CH_2CH_2CH_2-$ | | A-4 ($X_1 = OCH_3$, $Y_3 = CH_3$) |
| $CH_3$ | $-CH_2CH_2CH_2-$ | | A-5 ($X_2 = CH_3$, $Y_2 = OCH_3$) |
| $CH_3$ | $-CH_2CH_2CH_2-$ | | A-6 ($X_3 = OCH_3$) |
| $CH_3$ | $-CH_2CH_2CH_2-$ | | A-7 ($X_4 = OCH_3$, $Y_4 = OCH_3$) |
| $CH_3$ | $-CH_2CH_2OCH_2CH_2-$ | | A-2 ($X_1 = CH_3$, $Y_1 = CH_2$) |
| $CH_3$ | $-CH_2CH_2OCH_2CH_2-$ | | A-3 ($X_1 = OCH_3$) |

TABLE IV-continued

GENERAL STRUCTURE 4

| $R_1$ | $R_2$ | $R_3$ | A |
|---|---|---|---|
| $CH_3$ | $—CH_2CH_2OCH_2CH_2—$ | | A-4 ($X_1$ = $OCH_3$, $Y_3$ = $CH_3$) |
| $CH_3$ | $—CH_2CH_2OCH_2CH_2—$ | | A-5 ($X_2$ = $CH_3$, $Y_2$ = ($OCH_3$)) |
| $CH_3$ | $—CH_2CH_2OCH_2CH_2—$ | | A-6 ($X_3$ = $OCH_3$) |
| $CH_3$ | $—CH_2CH_2OCH_2CH_2—$ | | A-7 ($X_4$ = $OCH_3$, $Y_4$ = $OCH_3$) |
| $SCH_3$ | H | H | A-2 ($X_1$ = $CH_3$, $Y_1$ = $CH_2$) |
| $SCH_3$ | H | H | A-3 ($X_1$ = $OCH_3$) |
| $SCH_3$ | H | H | A-4 ($X_1$ = $OCH_3$, $Y_3$ = $CH_3$) |
| $SCH_3$ | H | H | A-5 ($X_2$ = $CH_3$, $Y_2$ = $OCH_3$) |
| $SCH_3$ | H | H | A-6 ($X_3$ = $OCH_3$) |
| $SCH_3$ | H | H | A-7 ($X_4$ = $OCH_3$, $Y_4$ = $OCH_3$) |
| $SCH_3$ | $CH_3$ | H | A-2 ($X_1$ = $CH_3$, $Y_1$ = $CH_2$) |
| $SCH_3$ | $CH_3$ | H | A-3 ($X_1$ = $OCH_3$) |
| $SCH_3$ | $CH_3$ | H | A-4 ($X_1$ = $OCH_3$, $Y_3$ = $CH_3$) |
| $SCH_3$ | $CH_3$ | H | A-5 ($X_2$ = $CH_3$, $Y_2$ = $OCH_3$) |
| $SCH_3$ | $CH_3$ | H | A-6 ($X_3$ = $OCH_3$) |
| $SCH_3$ | $CH_3$ | H | A-7 ($X_4$ = $OCH_3$, $Y_4$ = $OCH_3$) |
| $SCH_3$ | $CH_2CH_3$ | H | A-2 ($X_1$ = $CH_3$, $Y_1$ = $CH_2$) |
| $SCH_3$ | $CH_2CH_3$ | H | A-3 ($X_1$ = $OCH_3$) |
| $SCH_3$ | $CH_2CH_3$ | H | A-4 ($X_1$ = $OCH_3$, $Y_3$ = $CH_3$) |
| $SCH_3$ | $CH_2CH_3$ | H | A-5 ($X_2$ = $CH_3$, $Y_2$ = $OCH_3$) |
| $SCH_3$ | $CH_2CH_3$ | H | A-6 ($X_3$ = $OCH_3$) |
| $SCH_3$ | $CH_2CH_3$ | H | A-7 ($X_4$ = $OCH_3$, $Y_4$ = $OCH_3$) |
| $SCH_3$ | $CH_2CF_3$ | H | A-2 ($X_1$ = $CH_3$, $Y_1$ = $CH_2$) |
| $SCH_3$ | $CH_2CF_3$ | H | A-3 ($X_1$ = $OCH_3$) |
| $SCH_3$ | $CH_2CF_3$ | H | A-4 ($X_1$ = $OCH_3$, $Y_3$ = $CH_3$) |
| $SCH_3$ | $CH_2CF_3$ | H | A-5 ($X_2$ = $CH_3$, $Y_2$ = $OCH_3$) |
| $SCH_3$ | $CH_2CF_3$ | H | A-6 ($X_3$ = $OCH_3$) |
| $SCH_3$ | $CH_2CF_3$ | H | A-7 ($X_4$ = $OCH_3$, $Y_4$ = $OCH_3$) |
| $SCH_3$ | $CH_2CH_2Cl$ | H | A-2 ($X_1$ = $CH_3$, $Y_1$ = $CH_2$) |
| $SCH_3$ | $CH_2CH_2Cl$ | H | A-3 ($X_1$ = $OCH_3$) |
| $SCH_3$ | $CH_2CH_2Cl$ | H | A-4 ($X_1$ = $OCH_3$, $Y_3$ = $CH_3$) |
| $SCH_3$ | $CH_2CH_2Cl$ | H | A-5 ($X_2$ = $CH_3$, $Y_2$ = $OCH_3$) |
| $SCH_3$ | $CH_2CH_2Cl$ | H | A-6 ($X_3$ = $OCH_3$) |
| $SCH_3$ | $CH_2CH_2Cl$ | H | A-7 ($X_4$ = $OCH_3$, $Y_4$ = $OCH_3$) |
| $SCH_3$ | $CH_2CN$ | H | A-2 ($X_1$ = $CH_3$, $Y_1$ = $CH_2$) |
| $SCH_3$ | $CH_2CN$ | H | A-3 ($X_1$ = $OCH_3$) |
| $SCH_3$ | $CH_2CN$ | H | A-4 ($X_1$ = $OCH_3$, $Y_3$ = $CH_3$) |
| $SCH_3$ | $CH_2CN$ | H | A-5 ($X_2$ = $CH_3$, $Y_2$ = ($OCH_3$)) |
| $SCH_3$ | $CH_2CN$ | H | A-6 ($X_3$ = $OCH_3$) |
| $SCH_3$ | $CH_2CN$ | H | A-7 ($X_4$ = $OCH_3$, $Y_4$ = $OCH_3$) |
| $SCH_3$ | $CH_2CH_2OCH_3$ | H | A-2 ($X_1$ = $CH_3$, $Y_1$ = $CH_2$) |
| $SCH_3$ | $CH_2CH_2OCH_3$ | H | A-3 ($X_1$ = $OCH_3$) |
| $SCH_3$ | $CH_2CH_2OCH_3$ | H | A-4 ($X_1$ = $OCH_3$, $Y_3$ = $CH_3$) |
| $SCH_3$ | $CH_2CH_2OCH_3$ | H | A-5 ($X_2$ = $CH_3$, $Y_2$ = $OCH_3$) |
| $SCH_3$ | $CH_2CH_2OCH_3$ | H | A-6 ($X_3$ = $OCH_3$) |
| $SCH_3$ | $CH_2CH_2OCH_3$ | H | A-7 ($X_4$ = $OCH_3$, $Y_4$ = $OCH_3$) |
| $SCH_3$ | $CH_2CH{=}CH_2$ | H | A-2 ($X_1$ = $CH_3$, $Y_1$ = $CH_2$) |
| $SCH_3$ | $CH_2CH{=}CH_2$ | H | A-3 ($X_1$ = $OCH_3$) |
| $SCH_3$ | $CH_2CH{=}CH_2$ | H | A-4 ($X_1$ = $OCH_3$, $Y_3$ = $CH_3$) |
| $SCH_3$ | $CH_2CH{=}CH_2$ | H | A-5 ($X_2$ = $CH_3$, $Y_2$ = $OCH_3$) |
| $SCH_3$ | $CH_2CH{=}CH_2$ | H | A-6 ($X_3$ = $OCH_3$) |
| $SCH_3$ | $CH_2CH{=}CH_2$ | H | A-7 ($X_4$ = $OCH_3$, $Y_4$ = $OCH_3$) |
| $SCH_3$ | $CH_2C{\equiv}CH$ | H | A-2 ($X_1$ = $CH_3$ , $Y_1$ = $CH_2$) |
| $SCH_3$ | $CH_2C{\equiv}CH$ | H | A-3 ($X_1$ = $OCH_3$) |
| $SCH_3$ | $CH_2C{\equiv}CH$ | H | A-4 ($X_1$ = $OCH_3$, $Y_3$ = $CH_3$) |
| $SCH_3$ | $CH_2C{\equiv}CH$ | H | A-5 ($X_2$ = $CH_3$, $Y_2$ = $OCH_3$) |
| $SCH_3$ | $CH_2C{\equiv}CH$ | H | A-6 ($X_3$ = $OCH_3$) |
| $SCH_3$ | $CH_2C{\equiv}CH$ | H | A-7 ($X_4$ = $OCH_3$, $Y_4$ = $OCH_3$) |
| $SCH_3$ | cyclo-$C_3H_7$ | H | A-2 ($X_1$ = $CH_3$, $Y_1$ = $CH_2$) |
| $SCH_3$ | cyclo-$C_3H_7$ | H | A-3 ($X_1$ = $OCH_3$) |
| $SCH_3$ | cyclo-$C_3H_7$ | H | A-4 ($X_1$ = $OCH_3$, $Y_3$ = $CH_3$) |
| $SCH_3$ | cyclo-$C_3H_7$ | H | A-5 ($X_2$ = $CH_3$, $Y_2$ = $OCH_3$) |
| $SCH_3$ | cyclo-$C_3H_7$ | H | A-6 ($X_3$ = $OCH_3$) |
| $SCH_3$ | cyclo-$C_3H_7$ | H | A-7 ($X_4$ = $OCH_3$, $Y_4$ = $OCH_3$) |
| $SCH_3$ | $CH_3$ | $CH_3$ | A-2 ($X_1$ = $CH_3$, $Y_1$ = $CH_2$) |
| $SCH_3$ | $CH_3$ | $CH_3$ | A-3 ($X_1$ = $OCH_3$) |
| $SCH_3$ | $CH_3$ | $CH_3$ | A-4 ($X_1$ = $OCH_3$, $Y_3$ = $CH_3$) |
| $SCH_3$ | $CH_3$ | $CH_3$ | A-5 ($X_2$ = $CH_3$, $Y_2$ = $OCH_3$) |
| $SCH_3$ | $CH_3$ | $CH_3$ | A-6 ($X_3$ = $OCH_3$) |
| $SCH_3$ | $CH_3$ | $CH_3$ | A-7 ($X_4$ = $OCH_3$, $Y_4$ = $OCH_3$) |
| $SCH_3$ | $CH_2CH_3$ | $CH_3$ | A-2 ($X_1$ = $CH_3$, $Y_1$ = $CH_2$) |
| $SCH_3$ | $CH_2CH_3$ | $CH_3$ | A-3 ($X_1$ = $OCH_3$) |
| $SCH_3$ | $CH_2CH_3$ | $CH_3$ | A-4 ($X_1$ = $OCH_3$, $Y_3$ = $CH_3$) |
| $SCH_3$ | $CH_2CH_3$ | $CH_3$ | A-5 ($X_2$ = $CH_3$, $Y_2$ = ($OCH_3$)) |
| $SCH_3$ | $CH_2CH_3$ | $CH_3$ | A-6 ($X_3$ = $OCH_3$) |
| $SCH_3$ | $CH_2CH_3$ | $CH_3$ | A-7 ($X_4$ = $OCH_3$, $Y_4$ = $OCH_3$) |
| $SCH_3$ | $CH_2CH_3$ | $CH_2CH_3$ | A-2 ($X_1$ = $CH_3$, $Y_1$ = $CH_2$) |
| $SCH_3$ | $CH_2CH_3$ | $CH_2CH_3$ | A-3 ($X_1$ = $OCH_3$) |
| $SCH_3$ | $CH_2CH_3$ | $CH_2CH_3$ | A-4 ($X_1$ = $OCH_3$, $Y_3$ = $CH_3$) |
| $SCH_3$ | $CH_2CH_3$ | $CH_2CH_3$ | A-5 ($X_2$ = $CH_3$, $Y_2$ = $OCH_3$) |

TABLE IV-continued

GENERAL STRUCTURE 4

| $R_1$ | $R_2$ | $R_3$ | A |
|---|---|---|---|
| $SCH_3$ | $CH_2CH_3$ | $CH_2CH_3$ | A-6 ($X_3 = OCH_3$) |
| $SCH_3$ | $CH_2CH_3$ | $CH_2CH_3$ | A-7 ($X_4 = OCH_3$, $Y_4 = OCH_3$) |
| $SCH_3$ | $OCH_3$ | $CH_3$ | A-2 ($X_1 = CH_3$, $Y_1 = CH_2$) |
| $SCH_3$ | $OCH_3$ | $CH_3$ | A-3 ($X_1 = OCH_3$) |
| $SCH_3$ | $OCH_3$ | $CH_3$ | A-4 ($X_1 = OCH_3$, $Y_3 = CH_3$) |
| $SCH_3$ | $OCH_3$ | $CH_3$ | A-5 ($X_2 = CH_3$, $Y_2 = OCH_3$) |
| $SCH_3$ | $OCH_3$ | $CH_3$ | A-6 ($X_3 = OCH_3$) |
| $SCH_3$ | $OCH_3$ | $CH_3$ | A-7 ($X_4 = OCH_3$, $Y_4 = OCH_3$) |
| $SCH_3$ | $NHCH_3$ | $CH_3$ | A-2 ($X_1 = CH_3$, $Y_1 = CH_2$) |
| $SCH_3$ | $NHCH_3$ | $CH_3$ | A-3 ($X_1 = OCH_3$) |
| $SCH_3$ | $NHCH_3$ | $CH_3$ | A-4 ($X_1 = OCH_3$, $Y_3 = CH_3$) |
| $SCH_3$ | $NHCH_3$ | $CH_3$ | A-5 ($X_2 = CH_3$, $Y_2 = OCH_3$) |
| $SCH_3$ | $NHCH_3$ | $CH_3$ | A-6 ($X_3 = OCH_3$) |
| $SCH_3$ | $NHCH_3$ | $CH_3$ | A-7 ($X_4 = OCH_3$, $Y_4 = OCH_3$) |
| $SCH_3$ | $N(CH_3)_2$ | $CH_3$ | A-2 ($X_1 = CH_3$, $Y_1 = CH_2$) |
| $SCH_3$ | $N(CH_3)_2$ | $CH_3$ | A-3 ($X_1 = OCH_3$) |
| $SCH_3$ | $N(CH_3)_2$ | $CH_3$ | A-4 ($X_1 = OCH_3$, $Y_3 = CH_3$) |
| $SCH_3$ | $N(CH_3)_2$ | $CH_3$ | A-5 ($X_2 = CH_3$, $Y_2 = OCH_3$) |
| $SCH_3$ | $N(CH_3)_2$ | $CH_3$ | A-6 ($X_3 = OCH_3$) |
| $SCH_3$ | $N(CH_3)_2$ | $CH_3$ | A-7 ($X_4 = OCH_3$, $Y_4 = OCH_3$) |
| $SCH_3$ | $—CH_2CH_2CH_2—$ | | A-2 ($X_1 = CH_3$, $Y_1 = CH_2$) |
| $SCH_3$ | $—CH_2CH_2CH_2—$ | | A-3 ($X_1 = OCH_3$) |
| $SCH_3$ | $—CH_2CH_2CH_2—$ | | A-4 ($X_1 = OCH_3$, $Y_3 = CH_3$) |
| $SCH_3$ | $—CH_2CH_2CH_2—$ | | A-5 ($X_2 = CH_3$, $Y_2 = OCH_3$) |
| $SCH_3$ | $—CH_2CH_2CH_2—$ | | A-6 ($X_3 = OCH_3$) |
| $SCH_3$ | $—CH_2CH_2CH_2—$ | | A-7 ($X_4 = OCH_3$, $Y_4 = OCH_3$) |
| $SCH_3$ | $—CH_2CH_2OCH_2CH_2—$ | | A-2 ($X_1 = CH_3$, $Y_1 = CH_2$) |
| $SCH_3$ | $—CH_2CH_2OCH_2CH_2—$ | | A-3 ($X_1 = OCH_3$) |
| $SCH_3$ | $—CH_2CH_2OCH_2CH_2—$ | | A-4 ($X_1 = OCH_3$, $Y_3 = CH_3$) |
| $SCH_3$ | $—CH_2CH_2OCH_2CH_2—$ | | A-5 ($X_2 = CH_3$, $Y_2 = (OCH_3)$ |
| $SCH_3$ | $—CH_2CH_2OCH_2CH_2—$ | | A-6 ($X_3 = OCH_3$) |
| $SCH_3$ | $—CH_2CH_2OCH_2CH_2—$ | | A-7 ($X_4 = OCH_3$, $Y_4 = OCH_3$) |
| $SO_2CH_2CH_3$ | H | H | A-2 ($X_1 = CH_3$, $Y_1 = CH_2$) |
| $SO_2CH_2CH_3$ | H | H | A-3 ($X_1 = OCH_3$) |
| $SO_2CH_2CH_3$ | H | H | A-4 ($X_1 = OCH_3$, $Y_3 = CH_3$) |
| $SO_2CH_2CH_3$ | H | H | A-5 ($X_2 = CH_3$, $Y_2 = OCH_3$) |
| $SO_2CH_2CH_3$ | H | H | A-6 ($X_3 = OCH_3$) |
| $SO_2CH_2CH_3$ | H | H | A-7 ($X_4 = OCH_3$, $Y_4 = OCH_3$) |
| $SO_2CH_2CH_3$ | $CH_3$ | H | A-2 ($X_1 = CH_3$, $Y_1 = CH_2$) |
| $SO_2CH_2CH_3$ | $CH_3$ | H | A-3 ($X_1 = OCH_3$) |
| $SO_2CH_2CH_3$ | $CH_3$ | H | A-4 ($X_1 = OCH_3$, $Y_3 = CH_3$) |
| $SO_2CH_2CH_3$ | $CH_3$ | H | A-5 ($X_2 = CH_3$, $Y_2 = OCH_3$) |
| $SO_2CH_2CH_3$ | $CH_3$ | H | A-6 ($X_3 = OCH_3$) |
| $SO_2CH_2CH_3$ | $CH_3$ | H | A-7 ($X_4 = OCH_3$, $Y_4 = OCH_3$) |
| $SO_2CH_2CH_3$ | $CH_2CH_3$ | H | A-2 ($X_1 = CH_3$, $Y_1 = CH_2$) |
| $SO_2CH_2CH_3$ | $CH_2CH_3$ | H | A-3 ($X_1 = OCH_3$) |
| $SO_2CH_2CH_3$ | $CH_2CH_3$ | H | A-4 ($X_1 = OCH_3$, $Y_3 = CH_3$) |
| $SO_2CH_2CH_3$ | $CH_2CH_3$ | H | A-5 ($X_2 = CH_3$, $Y_2 = OCH_3$) |
| $SO_2CH_2CH_3$ | $CH_2CH_3$ | H | A-6 ($X_3 = OCH_3$) |
| $SO_2CH_2CH_3$ | $CH_2CH_3$ | H | A-7 ($X_4 = OCH_3$, $Y_4 = OCH_3$) |
| $SO_2CH_2CH_3$ | $CH_2CF_3$ | H | A-2 ($X_1 = CH_3$, $Y_1 = CH_2$) |
| $SO_2CH_2CH_3$ | $CH_2CF_3$ | H | A-3 ($X_1 = OCH_3$) |
| $SO_2CH_2CH_3$ | $CH_2CF_3$ | H | A-4 ($X_1 = OCH_3$, $Y_3 = CH_3$) |
| $SO_2CH_2CH_3$ | $CH_2CF_3$ | H | A-5 ($X_2 = CH_3$, $Y_2 = OCH_3$) |
| $SO_2CH_2CH_3$ | $CH_2CF_3$ | H | A-6 ($X_3 = OCH_3$) |
| $SO_2CH_2CH_3$ | $CH_2CF_3$ | H | A-7 ($X_4 = OCH_3$, $Y_4 = OCH_3$) |
| $SO_2CH_2CH_3$ | $CH_2CH_2Cl$ | H | A-2 ($X_1 = CH_3$, $Y_1 = CH_2$) |
| $SO_2CH_2CH_3$ | $CH_2CH_2Cl$ | H | A-3 ($X_1 = OCH_3$) |
| $SO_2CH_2CH_3$ | $CH_2CH_2Cl$ | H | A-4 ($X_1 = OCH_3$, $Y_3 = CH_3$) |
| $SO_2CH_2CH_3$ | $CH_2CH_2Cl$ | H | A-5 ($X_2 = CH_3$, $Y_2 = OCH_3$) |
| $SO_2CH_2CH_3$ | $CH_2CH_2Cl$ | H | A-6 ($X_3 = OCH_3$) |
| $SO_2CH_2CH_3$ | $CH_2CH_2Cl$ | H | A-7 ($X_4 = OCH_3$, $Y_4 = OCH_3$) |
| $SO_2CH_2CH_3$ | $CH_2CN$ | H | A-2 ($X_1 = CH_3$, $Y_1 = CH_2$) |
| $SO_2CH_2CH_3$ | $CH_2CN$ | H | A-3 ($X_1 = OCH_3$) |
| $SO_2CH_2CH_3$ | $CH_2CN$ | H | A-4 ($X_1 = OCH_3$, $Y_3 = CH_3$) |
| $SO_2CH_2CH_3$ | $CH_2CN$ | H | A-5 ($X_2 = CH_3$, $Y_2 = (OCH_3)$ |
| $SO_2CH_2CH_3$ | $CH_2CN$ | H | A-6 ($X_3 = OCH_3$) |
| $SO_2CH_2CH_3$ | $CH_2CN$ | H | A-7 ($X_4 = OCH_3$, $Y_4 = OCH_3$) |
| $SO_2CH_2CH_3$ | $CH_2CH_2OCH_3$ | H | A-2 ($X_1 = CH_3$, $Y_1 = CH_2$) |
| $SO_2CH_2CH_3$ | $CH_2CH_2OCH_3$ | H | A-3 ($X_1 = OCH_3$) |
| $SO_2CH_2CH_3$ | $CH_2CH_2OCH_3$ | H | A-4 ($X_1 = OCH_3$, $Y_3 = CH_3$) |
| $SO_2CH_2CH_3$ | $CH_2CH_2OCH_3$ | H | A-5 ($X_2 = CH_3$, $Y_2 = OCH_3$) |
| $SO_2CH_2CH_3$ | $CH_2CH_2OCH_3$ | H | A-6 ($X_3 = OCH_3$) |
| $SO_2CH_2CH_3$ | $CH_2CH_2OCH_3$ | H | A-7 ($X_4 = OCH_3$, $Y_4 = OCH_3$) |
| $SO_2CH_2CH_3$ | $CH_2CH{=}CH_2$ | H | A-2 ($X_1 = CH_3$, $Y_1 = CH_2$) |
| $SO_2CH_2CH_3$ | $CH_2CH{=}CH_2$ | H | A-3 ($X_1 = OCH_3$) |
| $SO_2CH_2CH_3$ | $CH_2CH{=}CH_2$ | H | A-4 ($X_1 = OCH_3$, $Y_3 = CH_3$) |
| $SO_2CH_2CH_3$ | $CH_2CH{=}CH_2$ | H | A-5 ($X_2 = CH_3$, $Y_2 = OCH_3$) |
| $SO_2CH_2CH_3$ | $CH_2CH{=}CH_2$ | H | A-6 ($X_3 = OCH_3$) |
| $SO_2CH_2CH_3$ | $CH_2CH{=}CH_2$ | H | A-7 ($X_4 = OCH_3$, $Y_4 = OCH_3$) |

TABLE IV-continued

GENERAL STRUCTURE 4

| $R_1$ | $R_2$ | $R_3$ | A |
|---|---|---|---|
| $SO_2CH_2CH_3$ | $CH_2C{\equiv}CH$ | H | A-2 ($X_1$ = $CH_3$, $Y_1$ = $CH_2$) |
| $SO_2CH_2CH_3$ | $CH_2C{\equiv}CH$ | H | A-3 ($X_1$ = $OCH_3$) |
| $SO_2CH_2CH_3$ | $CH_2C{\equiv}CH$ | H | A-4 ($X_1$ = $OCH_3$, $Y_3$ = $CH_3$) |
| $SO_2CH_2CH_3$ | $CH_2C{\equiv}CH$ | H | A-5 ($X_2$ = $CH_3$, $Y_2$ = $OCH_3$) |
| $SO_2CH_2CH_3$ | $CH_2C{\equiv}CH$ | H | A-6 ($X_3$ = $OCH_3$) |
| $SO_2CH_2CH_3$ | $CH_2C{\equiv}CH$ | H | A-7 ($X_4$ = $OCH_3$, $Y_4$ = $OCH_3$) |
| $SO_2CH_2CH_3$ | cyclo-$C_3H_7$ | H | A-2 ($X_1$ = $CH_3$, $Y_1$ = $CH_2$) |
| $SO_2CH_2CH_3$ | cyclo-$C_3H_7$ | H | A-3 ($X_1$ = $OCH_3$) |
| $SO_2CH_2CH_3$ | cyclo-$C_3H_7$ | H | A-4 ($X_1$ = $OCH_3$, $Y_3$ = $CH_3$) |
| $SO_2CH_2CH_3$ | cyclo-$C_3H_7$ | H | A-5 ($X_2$ = $CH_3$, $Y_2$ = $OCH_3$) |
| $SO_2CH_2CH_3$ | cyclo-$C_3H_7$ | H | A-6 ($X_3$ = $OCH_3$) |
| $SO_2CH_2CH_3$ | cyclo-$C_3H_7$ | H | A-7 ($X_4$ = $OCH_3$, $Y_4$ = $OCH_3$) |
| $SO_2CH_2CH_3$ | $CH_3$ | $CH_3$ | A-2 ($X_1$ = $CH_3$, $Y_1$ = $CH_2$) |
| $SO_2CH_2CH_3$ | $CH_3$ | $CH_3$ | A-3 ($X_1$ = $OCH_3$) |
| $SO_2CH_2CH_3$ | $CH_3$ | $CH_3$ | A-4 ($X_1$ = $OCH_3$, $Y_3$ = $CH_3$) |
| $SO_2CH_2CH_3$ | $CH_3$ | $CH_3$ | A-5 ($X_2$ = $CH_3$, $Y_2$ = $OCH_3$) |
| $SO_2CH_2CH_3$ | $CH_3$ | $CH_3$ | A-6 ($X_3$ = $OCH_3$) |
| $SO_2CH_2CH_3$ | $CH_3$ | $CH_3$ | A-7 ($X_4$ = $OCH_3$, $Y_4$ = $OCH_3$) |
| $SO_2CH_2CH_3$ | $CH_2CH_3$ | $CH_3$ | A-2 ($X_1$ = $CH_3$, $Y_1$ = $CH_2$) |
| $SO_2CH_2CH_3$ | $CH_2CH_3$ | $CH_3$ | A-3 ($X_1$ = $OCH_3$) |
| $SO_2CH_2CH_3$ | $CH_2CH_3$ | $CH_3$ | A-4 ($X_1$ = $OCH_3$, $Y_3$ = $CH_3$) |
| $SO_2CH_2CH_3$ | $CH_2CH_3$ | $CH_3$ | A-5 ($X_2$ = $CH_3$, $Y_2$ = ($OCH_3$) |
| $SO_2CH_2CH_3$ | $CH_2CH_3$ | $CH_3$ | A-6 ($X_3$ = $OCH_3$) |
| $SO_2CH_2CH_3$ | $CH_2CH_3$ | $CH_3$ | A-7 ($X_4$ = $OCH_3$, $Y_4$ = $OCH_3$) |
| $SO_2CH_2CH_3$ | $CH_2CH_3$ | $CH_2CH_3$ | A-2 ($X_1$ = $CH_3$, $Y_1$ = $CH_2$) |
| $SO_2CH_2CH_3$ | $CH_2CH_3$ | $CH_2CH_3$ | A-3 ($X_1$ = $OCH_3$) |
| $SO_2CH_2CH_3$ | $CH_2CH_3$ | $CH_2CH_3$ | A-4 ($X_1$ = $OCH_3$, $Y_3$ = $CH_3$) |
| $SO_2CH_2CH_3$ | $CH_2CH_3$ | $CH_2CH_3$ | A-5 ($X_2$ = $CH_3$, $Y_2$ = $OCH_3$) |
| $SO_2CH_2CH_3$ | $CH_2CH_3$ | $CH_2CH_3$ | A-6 ($X_3$ = $OCH_3$) |
| $SO_2CH_2CH_3$ | $CH_2CH_3$ | $CH_2CH_3$ | A-7 ($X_4$ = $OCH_3$, $Y_4$ = $OCH_3$) |
| $SO_2CH_2CH_3$ | $OCH_3$ | $CH_3$ | A-2 ($X_1$ = $CH_3$, $Y_1$ = $CH_2$) |
| $SO_2CH_2CH_3$ | $OCH_3$ | $CH_3$ | A-3 ($X_1$ = $OCH_3$) |
| $SO_2CH_2CH_3$ | $OCH_3$ | $CH_3$ | A-4 ($X_1$ = $OCH_3$, $Y_3$ = $CH_3$) |
| $SO_2CH_2CH_3$ | $OCH_3$ | $CH_3$ | A-5 ($X_2$ = $CH_3$, $Y_2$ = $OCH_3$) |
| $SO_2CH_2CH_3$ | $OCH_3$ | $CH_3$ | A-6 ($X_3$ = $OCH_3$) |
| $SO_2CH_2CH_3$ | $OCH_3$ | $CH_3$ | A-7 ($X_4$ = $OCH_3$, $Y_4$ = $OCH_3$) |
| $SO_2CH_2CH_3$ | $NHCH_3$ | $CH_3$ | A-2 ($X_1$ = $CH_3$, $Y_1$ = $CH_2$) |
| $SO_2CH_2CH_3$ | $NHCH_3$ | $CH_3$ | A-3 ($X_1$ = $OCH_3$) |
| $SO_2CH_2CH_3$ | $NHCH_3$ | $CH_3$ | A-4 ($X_1$ = $OCH_3$, $Y_3$ = $CH_3$) |
| $SO_2CH_2CH_3$ | $NHCH_3$ | $CH_3$ | A-5 ($X_2$ = $CH_3$, $Y_2$ = $OCH_3$) |
| $SO_2CH_2CH_3$ | $NHCH_3$ | $CH_3$ | A-6 ($X_3$ = $OCH_3$) |
| $SO_2CH_2CH_3$ | $NHCH_3$ | $CH_3$ | A-7 ($X_4$ = $OCH_3$, $Y_4$ = $OCH_3$) |
| $SO_2CH_2CH_3$ | $N(CH_3)_2$ | $CH_3$ | A-2 ($X_1$ = $CH_3$, $Y_1$ = $CH_2$) |
| $SO_2CH_2CH_3$ | $N(CH_3)_2$ | $CH_3$ | A-3 ($X_1$ = $OCH_3$) |
| $SO_2CH_2CH_3$ | $N(CH_3)_2$ | $CH_3$ | A-4 ($X_1$ = $OCH_3$, $Y_3$ = $CH_3$) |
| $SO_2CH_2CH_3$ | $N(CH_3)_2$ | $CH_3$ | A-5 ($X_2$ = $CH_3$, $Y_2$ = $OCH_3$) |
| $SO_2CH_2CH_3$ | $N(CH_3)_2$ | $CH_3$ | A-6 ($X_3$ = $OCH_3$) |
| $SO_2CH_2CH_3$ | $N(CH_3)_2$ | $CH_3$ | A-7 ($X_4$ = $OCH_3$, $Y_4$ = $OCH_3$) |
| $SO_2CH_2CH_3$ | $-CH_2CH_2CH_2-$ | | A-2 ($X_1$ = $CH_3$, $Y_1$ = $CH_2$) |
| $SO_2CH_2CH_3$ | $-CH_2CH_2CH_2-$ | | A-3 ($X_1$ = $OCH_3$) |
| $SO_2CH_2CH_3$ | $-CH_2CH_2CH_2-$ | | A-4 ($X_1$ = $OCH_3$, $Y_3$ = $CH_3$) |
| $SO_2CH_2CH_3$ | $-CH_2CH_2CH_2-$ | | A-5 ($X_2$ = $CH_3$, $Y_2$ = $OCH_3$) |
| $SO_2CH_2CH_3$ | $-CH_2CH_2CH_2-$ | | A-6 ($X_3$ = $OCH_3$) |
| $SO_2CH_2CH_3$ | $-CH_2CH_2CH_2-$ | | A-7 ($X_4$ = $OCH_3$, $Y_4$ = $OCH_3$) |
| $SO_2CH_2CH_3$ | $-CH_2CH_2OCH_2CH_2-$ | | A-2 ($X_1$ = $CH_3$, $Y_1$ = $CH_2$) |
| $SO_2CH_2CH_3$ | $-CH_2CH_2OCH_2CH_2-$ | | A-3 ($X_1$ = $OCH_3$) |
| $SO_2CH_2CH_3$ | $-CH_2CH_2OCH_2CH_2-$ | | A-4 ($X_1$ = $OCH_3$, $Y_3$ = $CH_3$) |
| $SO_2CH_2CH_3$ | $-CH_2CH_2OCH_2CH_2-$ | | A-5 ($X_2$ = $CH_3$, $Y_2$ = ($OCH_3$) |
| $SO_2CH_2CH_3$ | $-CH_2CH_2OCH_2CH_2-$ | | A-6 ($X_3$ = $OCH_3$) |
| $SO_2CH_2CH_3$ | $-CH_2CH_2OCH_2CH_2-$ | | A-7 ($X_4$ = $OCH_3$, $Y_4$ = $OCH_3$) |
| Br | $CH_3$ | H | A-2 ($X_1$ = $CH_3$, $Y_1$ = $CH_2$) |
| Br | $CH_3$ | H | A-3 ($X_1$ = $OCH_3$) |
| Br | $CH_3$ | H | A-4 ($X_1$ = $OCH_3$, $Y_3$ = $CH_3$) |
| Br | $CH_3$ | H | A-5 ($X_2$ = $CH_3$, $Y_2$ = $OCH_3$) |
| Br | $CH_3$ | H | A-6 ($X_3$ = $OCH_3$) |
| Br | $CH_3$ | H | A-7 ($X_4$ = $OCH_3$, $Y_4$ = $OCH_3$) |
| Br | $CH_3$ | $CH_3$ | A-2 ($X_1$ = $CH_3$, $Y_1$ = $CH_2$) |
| Br | $CH_3$ | $CH_3$ | A-3 ($X_1$ = $OCH_3$) |
| Br | $CH_3$ | $CH_3$ | A-4 ($X_1$ = $OCH_3$, $Y_3$ = $CH_3$) |
| Br | $CH_3$ | $CH_3$ | A-5 ($X_2$ = $CH_3$, $Y_2$ = $OCH_3$) |
| Br | $CH_3$ | $CH_3$ | A-6 ($X_3$ = $OCH_3$) |
| Br | $CH_3$ | $CH_3$ | A-7 ($X_4$ = $OCH_3$, $Y_4$ = $OCH_3$) |
| Br | $CH_2CH{=}CH_2$ | H | A-2 ($X_1$ = $CH_3$, $Y_1$ = $CH_2$) |
| Br | $CH_2CH{=}CH_2$ | H | A-3 ($X_1$ = $OCH_3$) |
| Br | $CH_2CH{=}CH_2$ | H | A-4 ($X_1$ = $OCH_3$, $Y_3$ = $CH_3$) |
| Br | $CH_2CH{=}CH_2$ | H | A-5 ($X_2$ = $CH_3$, $Y_2$ = $OCH_3$) |
| Br | $CH_2CH{=}CH_2$ | H | A-6 ($X_3$ = $OCH_3$) |
| Br | $CH_2CH{=}CH_2$ | H | A-7 ($X_4$ = $OCH_3$, $Y_4$ = $OCH_3$) |
| $CH_2CH_3$ | $CH_3$ | H | A-2 ($X_1$ = $CH_3$, $Y_1$ = $CH_2$) |
| $CH_2CH_3$ | $CH_3$ | H | A-3 ($X_1$ = $OCH_3$) |

TABLE IV-continued

GENERAL STRUCTURE 4

| $R_1$ | $R_2$ | $R_3$ | A |
|---|---|---|---|
| $CH_2CH_3$ | $CH_3$ | H | A-4 ($X_1$ = $OCH_3$, $Y_3$ = $CH_3$) |
| $CH_2CH_3$ | $CH_3$ | H | A-5 ($X_2$ = $CH_3$, $Y_2$ = $OCH_3$) |
| $CH_2CH_3$ | $CH_3$ | H | A-6 ($X_3$ = $OCH_3$) |
| $CH_2CH_3$ | $CH_3$ | H | A-7 ($X_4$ = $OCH_3$, $Y_4$ = $OCH_3$) |
| $CH_2CH_3$ | $CH_3$ | $CH_3$ | A-2 ($X_1$ = $CH_3$, $Y_1$ = $CH_2$) |
| $CH_2CH_3$ | $CH_3$ | $CH_3$ | A-3 ($X_1$ = $OCH_3$) |
| $CH_2CH_3$ | $CH_3$ | $CH_3$ | A-4 ($X_1$ = $OCH_3$, $Y_3$ = $CH_3$) |
| $CH_2CH_3$ | $CH_3$ | $CH_3$ | A-5 ($X_2$ = $CH_3$, $Y_2$ = $OCH_3$) |
| $CH_2CH_3$ | $CH_3$ | $CH_3$ | A-6 ($X_3$ = $OCH_3$) |
| $CH_2CH_3$ | $CH_3$ | $CH_3$ | A-7 ($X_4$ = $OCH_3$ , $Y_4$ = $OCH_3$) |
| $CH_2CH_3$ | $CH_2CH{=}CH_2$ | H | A-2 ($X_1$ = $CH_3$, $Y_1$ = $CH_2$) |
| $CH_2CH_3$ | $CH_2CH{=}CH_2$ | H | A-3 ($X_1$ = $OCH_3$) |
| $CH_2CH_3$ | $CH_2CH{=}CH_2$ | H | A-4 ($X_1$ = $OCH_3$, $Y_3$ = $CH_3$) |
| $CH_2CH_3$ | $CH_2CH{=}CH_2$ | H | A-5 ($X_2$ = $CH_3$, $Y_2$ = ($OCH_3$) |
| $CH_2CH_3$ | $CH_2CH{=}CH_2$ | H | A-6 ($X_3$ = $OCH_3$) |
| $CH_2CH_3$ | $CH_2CH{=}CH_2$ | H | A-7 ($X_4$ = $OCH_3$, $Y_4$ = $OCH_3$) |
| $CF_3$ | $CH_3$ | H | A-2 ($X_1$ = $CH_3$, $Y_1$ = $CH_2$) |
| $CF_3$ | $CH_3$ | H | A-3 ($X_1$ = $OCH_3$) |
| $CF_3$ | $CH_3$ | H | A-4 ($X_1$ = $OCH_3$, $Y_3$ = $CH_3$) |
| $CF_3$ | $CH_3$ | H | A-5 ($X_2$ = $CH_3$, $Y_2$ = $OCH_3$) |
| $CF_3$ | $CH_3$ | H | A-6 ($X_3$ = $OCH_3$) |
| $CF_3$ | $CH_3$ | H | A-7 ($X_4$ = $OCH_3$, $Y_4$ = $OCH_3$) |
| $CF_3$ | $CH_3$ | $CH_3$ | A-2 ($X_1$ = $CH_3$, $Y_1$ = $CH_2$) |
| $CF_3$ | $CH_3$ | $CH_3$ | A-3 ($X_1$ = $OCH_3$) |
| $CF_3$ | $CH_3$ | $CH_3$ | A-4 ($X_1$ = $OCH_3$, $Y_3$ = $CH_3$) |
| $CF_3$ | $CH_3$ | $CH_3$ | A-5 ($X_2$ = $CH_3$, $Y_2$ = $OCH_3$) |
| $CF_3$ | $CH_3$ | $CH_3$ | A-6 ($X_3$ = $OCH_3$) |
| $CF_3$ | $CH_3$ | $CH_3$ | A-7 ($X_4$ = $OCH_3$, $Y_4$ = $OCH_3$) |
| $CF_3$ | $CH_2CH{=}CH_2$ | H | A-2 ($X_1$ = $CH_3$, $Y_1$ = $CH_2$) |
| $CF_3$ | $CH_2CH{=}CH_2$ | H | A-3 ($X_1$ = $OCH_3$) |
| $CF_3$ | $CH_2CH{=}CH_2$ | H | A-4 ($X_1$ = $OCH_3$, $Y_3$ = $CH_3$) |
| $CF_3$ | $CH_2CH{=}CH_2$ | H | A-5 ($X_2$ = $CH_3$, $Y_2$ = $OCH_3$) |
| $CF_3$ | $CH_2CH{=}CH_2$ | H | A-6 ($X_3$ = $OCH_3$) |
| $CF_3$ | $CH_2CH{=}CH_2$ | H | A-7 ($X_4$ = $OCH_3$, $Y_4$ = $OCH_3$) |
| $OCH_3$ | $CH_3$ | H | A-2 ($X_1$ = $CH_3$, $Y_1$ = $CH_2$) |
| $OCH_3$ | $CH_3$ | H | A-3 ($X_1$ = $OCH_3$) |
| $OCH_3$ | $CH_3$ | H | A-4 ($X_1$ = $OCH_3$, $Y_3$ = $CH_3$) |
| $OCH_3$ | $CH_3$ | H | A-5 ($X_2$ = $CH_3$, $Y_2$ = $OCH_3$) |
| $OCH_3$ | $CH_3$ | H | A-6 ($X_3$ = $OCH_3$) |
| $OCH_3$ | $CH_3$ | H | A-7 ($X_4$ = $OCH_3$, $Y_4$ = $OCH_3$) |
| $OCH_3$ | $CH_3$ | $CH_3$ | A-2 ($X_1$ = $CH_3$, $Y_1$ = $CH_2$) |
| $OCH_3$ | $CH_3$ | $CH_3$ | A-3 ($X_1$ = $OCH_3$) |
| $OCH_3$ | $CH_3$ | $CH_3$ | A-4 ($X_1$ = $OCH_3$, $Y_3$ = $CH_3$) |
| $OCH_3$ | $CH_3$ | $CH_3$ | A-5 ($X_2$ = $CH_3$, $Y_2$ = $OCH_3$) |
| $OCH_3$ | $CH_3$ | $CH_3$ | A-6 ($X_3$ = $OCH_3$) |
| $OCH_3$ | $CH_3$ | $CH_3$ | A-7 ($X_4$ = $OCH_3$, $Y_4$ = $OCH_3$) |
| $OCH_3$ | $CH_2CH{=}CH_2$ | H | A-2 ($X_1$ = $CH_3$, $Y_1$ = $CH_2$) |
| $OCH_3$ | $CH_2CH{=}CH_2$ | H | A-3 ($X_1$ = $OCH_3$) |
| $OCH_3$ | $CH_2CH{=}CH_2$ | H | A-4 ($X_1$ = $OCH_3$, $Y_3$ = $CH_3$) |
| $OCH_3$ | $CH_2CH{=}CH_2$ | H | A-5 ($X_2$ = $CH_3$, $Y_2$ = ($OCH_3$) |
| $OCH_3$ | $CH_2CH{=}CH_2$ | H | A-6 ($X_3$ = $OCH_3$) |
| $OCH_3$ | $CH_2CH{=}CH_2$ | H | A-7 ($X_4$ = $OCH_3$, $Y_4$ = $OCH_3$) |
| $OCF_2H$ | $CH_3$ | H | A-2 ($X_1$ = $CH_3$, $Y_1$ = $CH_2$) |
| $OCF_2H$ | $CH_3$ | H | A-3 ($X_1$ = $OCH_3$ ) |
| $OCF_2H$ | $CH_3$ | H | A-4 ($X_1$ = $OCH_3$, $Y_3$ = $CH_3$) |
| $OCF_2H$ | $CH_3$ | H | A-5 ($X_2$ = $CH_3$, $Y_2$ = $OCH_3$) |
| $OCF_2H$ | $CH_3$ | H | A-6 ($X_3$ = $OCH_3$) |
| $OCF_2H$ | $CH_3$ | H | A-7 ($X_4$ = $OCH_3$, $Y_4$ = $OCH_3$) |
| $OCF_2H$ | $CH_3$ | $CH_3$ | A-2 ($X_1$ = $CH_3$, $Y_1$ = $CH_2$) |
| $OCF_2H$ | $CH_3$ | $CH_3$ | A-3 ($X_1$ = $OCH_3$) |
| $OCF_2H$ | $CH_3$ | $CH_3$ | A-4 ($X_1$ = $OCH_3$, $Y_3$ = $CH_3$) |
| $OCF_2H$ | $CH_3$ | $CH_3$ | A-5 ($X_2$ = $CH_3$, $Y_2$ = $OCH_3$) |
| $OCF_2H$ | $CH_3$ | $CH_3$ | A-6 ($X_3$ = $OCH_3$) |
| $OCF_2H$ | $CH_3$ | $CH_3$ | A-7 ($X_4$ = $OCH_3$, $Y_4$ = $OCH_3$) |
| $OCF_2H$ | $CH_2CH{=}CH_2$ | H | A-2 ($X_1$ = $CH_3$, $Y_1$ = $CH_2$) |
| $OCF_2H$ | $CH_2CH{=}CH_2$ | H | A-3 ($X_1$ = $OCH_3$) |
| $OCF_2H$ | $CH_2CH{=}CH_2$ | H | A-4 ($X_1$ = $OCH_3$, $Y_3$ = $CH_3$) |
| $OCF_2H$ | $CH_2CH{=}CH_2$ | H | A-5 ($X_2$ = $CH_3$, $Y_2$ = $OCH_3$) |
| $OCF_2H$ | $CH_2CH{=}CH_2$ | H | A-6 ($X_3$ = $OCH_3$) |
| $OCF_2H$ | $CH_2CH{=}CH_2$ | H | A-7 ($X_4$ = $OCH_3$, $Y_4$ = $OCH_3$) |
| $SCF_2H$ | $CH_3$ | H | A-2 ($X_1$ = $CH_3$, $Y_1$ = $CH_2$) |
| $SCF_2H$ | $CH_3$ | H | A-3 ($X_1$ = $OCH_3$) |
| $SCF_2H$ | $CH_3$ | H | A-4 ($X_1$ = $OCH_3$, $Y_3$ = $CH_3$) |
| $SCF_2H$ | $CH_3$ | H | A-5 ($X_2$ = $CH_3$, $Y_2$ = $OCH_3$) |
| $SCF_2H$ | $CH_3$ | H | A-6 ($X_3$ = $OCH_3$ ) |
| $SCF_2H$ | $CH_3$ | H | A-7 ($X_4$ = $OCH_3$, $Y_4$ = $OCH_3$) |
| $SCF_2H$ | $CH_3$ | $CH_3$ | A-2 ($X_1$ = $CH_3$, $Y_1$ = $CH_2$) |
| $SCF_2H$ | $CH_3$ | $CH_3$ | A-3 ($X_1$ = $OCH_3$) |
| $SCF_2H$ | $CH_3$ | $CH_3$ | A-4 ($X_1$ = $OCH_3$, $Y_3$ = $CH_3$) |
| $SCF_2H$ | $CH_3$ | $CH_3$ | A-5 ($X_2$ = $CH_3$, $Y_2$ = $OCH_3$) |

TABLE IV-continued

| GENERAL STRUCTURE 4 | | | |
|---|---|---|---|
| $R_1$ | $R_2$ | $R_3$ | A |
| $SCF_2H$ | $CH_3$ | $CH_3$ | A-6 ($X_3$ = $OCH_3$) |
| $SCF_2H$ | $CH_3$ | $CH_3$ | A-7 ($X_4$ = $OCH_3$, $Y_4$ = $OCH_3$) |
| $SCF_2H$ | $CH_2CH{=}CH_2$ | H | A-2 ($X_1$ = $CH_3$, $Y_1$ = $CH_2$) |
| $SCF_2H$ | $CH_2CH{=}CH_2$ | H | A-3 ($X_1$ = $OCH_3$) |
| $SCF_2H$ | $CH_2CH{=}CH_2$ | H | A-4 ($X_1$ = $OCH_3$, $Y_3$ = $CH_3$) |
| $SCF_2H$ | $CH_2CH{=}CH_2$ | H | A-5 ($X_2$ = $CH_3$, $Y_2$ = ($OCH_3$)) |
| $SCF_2H$ | $CH_2CH{=}CH_2$ | H | A-6 ($X_3$ = $OCH_3$) |
| $SCF_2H$ | $CH_2CH{=}CH_2$ | H | A-7 ($X_4$ = $OCH_3$, $Y_4$ = $OCH_3$) |
| $SO_2CF_2H$ | $CH_3$ | H | A-2 ($X_1$ = $CH_3$, $Y_1$ = $CH_2$) |
| $SO_2CF_2H$ | $CH_3$ | H | A-3 ($X_1$ = $OCH_3$) |
| $SO_2CF_2H$ | $CH_3$ | H | A-4 ($X_1$ = $OCH_3$, $Y_3$ = $CH_3$) |
| $SO_2CF_2H$ | $CH_3$ | H | A-5 ($X_2$ = $CH_3$, $Y_2$ = $OCH_3$) |
| $SO_2CF_2H$ | $CH_3$ | H | A-6 ($X_3$ = $OCH_3$) |
| $SO_2CF_2H$ | $CH_3$ | H | A-7 ($X_4$ = $OCH_3$, $Y_4$ = $OCH_3$) |
| $SO_2CF_2H$ | $CH_3$ | $CH_3$ | A-2 ($X_1$ = $CH_3$, $Y_1$ = $CH_2$) |
| $SO_2CF_2H$ | $CH_3$ | $CH_3$ | A-3 ($X_1$ = $OCH_3$) |
| $SO_2CF_2H$ | $CH_3$ | $CH_3$ | A-4 ($X_1$ = $OCH_3$, $Y_3$ = $CH_3$) |
| $SO_2CF_2H$ | $CH_3$ | $CH_3$ | A-5 ($X_2$ = $CH_3$, $Y_2$ = $OCH_3$) |
| $SO_2CF_2H$ | $CH_3$ | $CH_3$ | A-6 ($X_3$ = $OCH_3$) |
| $SO_2CF_2H$ | $CH_3$ | $CH_3$ | A-7 ($X_4$ = $OCH_3$, $Y_4$ = $OCH_3$) |
| $SO_2CF_2H$ | $CH_2CH{=}CH_2$ | H | A-2 ($X_1$ = $CH_3$, $Y_1$ = $CH_2$) |
| $SO_2CF_2H$ | $CH_2CH{=}CH_2$ | H | A-3 ($X_1$ = $OCH_3$) |
| $SO_2CF_2H$ | $CH_2CH{=}CH_2$ | H | A-4 ($X_1$ = $OCH_3$, $Y_3$ = $CH_3$) |
| $SO_2CF_2H$ | $CH_2CH{=}CH_2$ | H | A-5 ($X_2$ = $CH_3$, $Y_2$ = $OCH_3$) |
| $SO_2CF_2H$ | $CH_2CH{=}CH_2$ | H | A-6 ($X_3$ = $OCH_3$) |
| $SO_2CF_2H$ | $CH_2CH{=}CH_2$ | H | A-7 ($X_4$ = $OCH_3$, $Y_4$ = $OCH_3$) |

Formulations

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid inert diluent(s). More specifically, they will contain these ingredients in the following approximate proportions:

| | Weight Percent* | | |
|---|---|---|---|
| Active Ingredient | Diluent(s) | Surfactant(s) | |
| Wettable Powders | 20-90 | 0-74 | 1-10 |
| Oil Suspensions, Emulsions, Solutions, (including Emulsifiable Concentrates) | 3-50 | 40-95 | 0-15 |
| Aqueous Suspension | 10-50 | 40-84 | 1-20 |
| Dusts | 1-25 | 70-99 | 0-5 |
| Granules and Pellets | 0.1-95 | 5-99.9 | 0-15 |
| High Strength Compositions | 90-99 | 0-10 | 0-2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950, Solubility under 0.1% is preferred for suspension concentrates; solution concentrates are preferably stable against phase separation at 0° C. "McCutcheon's Detergents and Emulsifiers Annual," MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering*, Dec. 4, 1967, pp. 147ff. and "Perry'Chemical Engineer's Handbook", 5th Ed., McGraw-Hill, New York, 1973, pp. 8-57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138-140, 162-164, 166, 167 and 169-182;

H. Gysin and E. Knusli, U.S. Pat. No. 2,891,855, Jun. 23, 1959, Col. 3, line 66 through Col. 5, line 17 and Examples 1-4;

G. C. Klingman, "Weed Control as a Science", John Wiley and Sons, Inc., New York, 1961, pp. 81-96; and J. D. Fryer and S. A. Evans, "Weed Control Handbook", 5th Ed., Blackwell Scientific Publications, Oxford, 1968, pp. 101–103.

In the following Examples, all parts are by weight unless otherwise indicated.

EXAMPLE 2

| Wettable Powder | |
|---|---|
| N-[[(4,6-Dimethoxy-2-pyrimidinyl)amino]-carbonyl]-6-(dimethylamino)-2-pyridine-sulfonamide | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until all the solids are essentially under 50 microns, reblended, and packaged.

EXAMPLE 3

| Wettable Powder | |
|---|---|
| 6-(Dimethylamino)-N-[[(4-ethoxy-6-(methyl-amino)-1,3,5-triazin-2-yl]amino]carbonyl]-2-pyridinesulfonamide | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles essentially all below 10 microns in diameter. The product is reblended before packaging.

EXAMPLE 4

| Granule | |
|---|---|
| Wettable Powder of Example 3 | 5% |
| attapulgite granules (U.S.S. 20 to 40 mesh; 0.84–0.42 mm) | 95% |

A slurry of wettable powder containing 25% solids is sprayed on the surface of attapulgite granules in a double-cone blender. The granules are dried and packaged.

EXAMPLE 5

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

| Extruded Pellet | |
|---|---|
| N-[[[(4-Ethoxy-6-(dimethylamino)-1,3,5-triazin-2-yl]amino]carbonyl]-6-(methyl-amino)-2-pyridinesulfonamide | 25% |
| anhydrous sodium sulfate | 10% |
| crude calcium ligninsulfonate | 5% |
| sodium alkylnaphthalenesulfonate | 1% |
| calcium/magnesium bentonite | 59% |

EXAMPLE 6

| Low Strength Granule | |
|---|---|
| N-[[(4,6-Dimethoxy-2-pyrimidinyl)amino]-carbonyl]-6-(dimethylamino)-2-pyridine-sulfonamide | 0.1% |
| attapulgite granules (U.S.S. 20 to 40 mesh) | 99.9% |

The active ingredient is dissolved in a solvent and the solution is sprayed upon dedusted granules in a double-cone blender. After spraying of the solution has been completed, the material is warmed to evaporate the solvent. The material is allowed to cool and then packaged.

EXAMPLE 7

| Granule | |
|---|---|
| 6-(Dimethylamino)-N-[[(4-ethoxy-6-(methyl-amino)-1,3,5-triazin-2-yl]amino]carbonyl]-2-pyridinesulfonamide | 80% |
| wetting agent | 1% |
| crude ligninsulfonate salt (containing 5 to 20% of the natural sugars) | 10% |
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14 to 100 mesh (1410 to 149 microns), and packaged for use.

EXAMPLE 8

| Low Strength Granule | |
|---|---|
| N-[[[(4-Ethoxy-6-(dimethylamino)-1,3,5-triazin-2-yl]amino]carbonyl]-6-(methyl-amino)-2-pyridinesulfonamide | 1% |
| N,N-dimethylformamide | 9% |
| attapulgite granules (U.S.S. 20 to 40 sieve) | 90% |

The active ingredient is dissolved in the solvent and the solution is sprayed upon dedusted granules in a double cone blender. After spraying of the solution has been completed, the blender is allowed to run for a short period and then the granules are packaged.

EXAMPLE 9

| Aqueous Suspension | |
|---|---|
| N-[[(4,6-Dimethoxy-2-pyrimidinyl)amino]-carbonyl]-6-(dimethylamino)-2-pyridine-sulfonamide | 40% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| water | 56.7% |

The ingredients are blended and ground in a sand mill to produce particles essentially all under 5 microns in size.

EXAMPLE 10

| Solution | |
|---|---|
| 6-(Dimethylamino)-N-[[(4-ethoxy-6-(methyl-amino)-1,3,5-triazin-2-yl]amino]carbonyl]-2-pyridinesulfonamide, sodium salt | 5% |
| water | 95% |

The salt is added directly to the water with stirring to produce the solution, which may then be packaged for use.

EXAMPLE 11

| High Strength Concentrate | |
|---|---|
| N-[[[(4-Ethoxy-6-(dimethylamino)-1,3,5-triazin-2-yl]amino]carbonyl]-6-(methyl-amino)-2-pyridinesulfonamide | 99% |
| silica aerogel | 0.5% |
| synthetic amorphous silica | 0.5% |

The ingredients are blended and ground in a hammer-mill to produce a material essentially all passing a U.S.S. No. 50 screen (0.3 mm opening). The concentrate may be formulated further if necessary.

EXAMPLE 12

| Wettable Powder | |
|---|---|
| N-[[(4,6-Dimethoxy-2-pyrimidinyl)amino]-carbonyl]-6-(dimethylamino)-2-pyridine-sulfonamide | 90% |
| dioctyl sodium sulfosuccinate | 0.1% |
| synthetic fine silica | 9.9% |

The ingredients are blended and ground in a hammer-mill to produce particles essentially all below 100 microns. The material is sifted through a U.S.S. No. 50 screen and then packaged.

EXAMPLE 13

| Wettable Powder | |
|---|---|
| 6-(Dimethylamino)-N-[[(4-ethoxy-6-(methyl-amino)-1,3,5-triazin-2-yl]amino]carbonyl]-2-pyridinesulfonamide | 40% |
| sodium ligninsulfonate | 20% |
| montmorillonite clay | 40% |

The ingredients are thoroughly blended, coarsely hammer-milled and then air-milled to produce particles essentially all below 10 microns in size. The material is reblended and then packaged.

EXAMPLE 14

| Oil Suspension | |
|---|---|
| N-[[[(4-Ethoxy-6-(dimethylamino)-1,3,5-triazin-2-yl]amino]carbonyl]-6-(methyl-amino)-2-pyridinesulfonamide | 35% |
| blend of polyalcohol carboxylic esters and oil soluble petroleum sulfonates | 6% |
| xylene | 59% |

-continued

The ingredients are combined and ground together in a sand mill to produce particles essentially all below 5 microns. The product can be used directly, extended with oils, or emulsified in water.

EXAMPLE 15

| Dust | |
|---|---|
| N-[[(4,6-Dimethoxy-2-pyrimidinyl)amino]-carbonyl]-6-(dimethylamino)-2-pyridine-sulfonamide | 10% |
| attapulgite | 10% |
| Pyrophyllite | 80% |

The active ingredient is blended with attapulgite and then passed through a hammer-mill to produce particles substantially all below 200 microns. The ground concentrate is then blended with powdered pyrophyllite until homogeneous.

EXAMPLE 16

| Oil Suspension | |
|---|---|
| 6-(Dimethylamino)-N-[[(4-ethoxy-6-(methyl-amino)-1,3,5-triazin-2-yl]amino]carbonyl]-2-pyridinesulfonamide | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE 17

| Wettable Powder | |
|---|---|
| N-[[[(4-Ethoxy-6-(dimethylamino)-1,3,5-triazin-2-yl]amino]carbonyl]-6-(methyl-amino)-2-pyridinesulfonamide | 20% |
| sodium alkylnaphthalenesulfonate | 4% |
| sodium ligninsulfonate | 4% |
| low viscosity methyl cellulose | 3% |
| attapulgite | 69% |

The ingredients are thoroughly blended. After grinding in a hammer-mill to produce particles essentially all below 100 microns, the material is reblended and sifted through a U.S.S. No. 50 sieve (0.3 mm opening) and packaged.

Utility

Test results indicate that the compounds of the present invention are highly active preemergent or postemergent herbicides or plant growth regulants. Many of them have utility for broad-spectrum pre-and/or post-emergence weed control in areas where complete control o% all vegetation is desired, such as around storage tanks, parking lots, drive-in theaters, billboards, highways, and railroad structures. Some compounds have utility for selective weed control in cereal crops, such as wheat and barley, corn, cotton, rape, soybean and sugarbeet, and for weed control in fallow. Some of the compounds are particularly useful for the control of grass weeds, such as wild oat, in cereal crops, such as wheat and barley. Also, some of the compounds are particularly useful for the control of weeds in cotton and/or rape. Alternatively, the subject compounds are useful to modify plant growth.

The rates of application for the compounds of the invention are determined by a number of factors, including their use as plant growth modifiers or as herbicides, the crop species involved, the types of weeds to be controlled, weather and climate, formulations selected, mode of application, amount of foliage present, etc. In general terms, the subject compounds should be applied at levels of around 0.0005 to 20 kg/ha, the lower rates being suggested for use on lighter soils and/or those having a low organic matter content, for plant growth modification or for situations where only short-term persistence is required such as herbicide for fallow land.

The compounds of this invention may be used in combination with other commercial herbicides, insecticides or fungicides. The following list exemplifies some of the herbicides suitable for use in mixtures.

| Common Name | Chemical Name |
|---|---|
| acetochlor | 2-chloro-N-(ethoxymethyl)-N-(2-ethyl-6-methylphenyl)acetamide |
| acifluorfen | 5-[2-chloro-4-(trifluoromethyl)-phenoxy]-2-nitrobenzoic acid |
| acrolein | 2-propenal |
| alachlor | 2-chloro-N-(2,6-diethylphenyl)-N-(methoxymethyl)acetamide |
| ametryn | N-ethyl-N'-(1-methylethyl)-6-(methylthio)-1,3,5-triazine-2,4-diamine |
| amitrole | 1H-1,2,4-triazol-3-amine |
| AMS | ammonium sulfamate |
| asulam | methyl [(4-aminophenyl)sulfonyl]-carbamate |
| atrazine | 6-chloro-N-ethyl-N'-(1-methylethyl)-1,3,5-triazine-2,4-diamine |
| barban | 4-chloro-2-butynyl 3-chlorocarbamate |
| benefin | N-butyl-N-ethyl-2,6-dinitro-4-(trifluoromethyl)benzenamine |
| bensulfuron methyl | 2-[[[[(4,6-dimethoxy-2-pyrimidinyl)amino]methylcarbonyl]-amino]sulfonyl]methyl]benzoic acid, methyl ester |
| bensulide | O,O-bis(1-methylethyl) S-[2-[(phenylsulfonyl)amino]-ethyl]phosphorodithioate |
| bentazon | 3-(1-methylethyl)-(1H)-2,1,3-benzothiadiazin-4(3H)-one, 2,2-dioxide |
| benzofluor | N-[4-(ethylthio)-2-(trifluoro-methyl)phenyl]methanesulfonamide |
| benzoylprop | N-benzoyl-N-(3,4-dichlorophenyl)-DL-alanine |
| bifenox | methyl 5-(2,4-dichlorophenoxy)-2-nitrobenzoate |
| bromacil | 5-bromo-6-methyl-3-(1-methylpropyl)-2,4(1H,3H)pyrimidinedione |
| bromoxynil | 3,5-dibromo-4-hydroxybenzonitrile |
| butachlor | N-(butoxymethyl)-2-chloro-N-(2,6-diethylphenyl)acetamide |
| buthidazole | 3-[5-(1,1-dimethylethyl)-1,3,4-thiadiazol-2-yl]-4-hydroxy-1-methyl-2-imidazolidinone |
| butralin | 4-(1,1-dimethylethyl)-N-(1-methyl-propyl)-2,6-dinitrobenzenamine |
| butylate | S-ethyl bis(2-methylpropyl)-carbamothioate |
| cacodylic acid | dimethyl arsinic oxide |
| CDAA | 2-chloro-N,N-di-2-propenylacetamide |
| CDEC | 2-chloroallyl diethyldithiocarbamate |

-continued

| Common Name | Chemical Name |
|---|---|
| chloramben | 3-amino-2,5-dichlorobenzoic acid |
| chlorbromuron | 3-(4-bromo-3-chlorophenyl)-1-methoxy-1-methylurea |
| chlorimuron | 2-[[[[(4-chloro-6-methoxy-2-pyrimidinyl)ethylamino]carbonyl]-amino]sulfonyl]benzoic acid, ethyl ester |
| chloroxuron | N'-[4-(4-chlorophenoxy)phenyl]-N,N-dimethylurea |
| chlorpropham | 1-methylethyl 3-chlorophenylcarbamate |
| chlorsulfuron | 2-chloro-N-[[(4-methoxy-6-methyl-1,3,5-triazin-2-yl)amino]carbonyl]benzene-sulfonamide |
| chlortoluron | N'-(3-chloro-4-methylphenyl)-N,N-dimethylurea |
| cinmethylin | exo-1-methyl-4-(1-methylethyl)-2-[(2-methylphenyl)methoxy]-7-oxabicyclo-[2.2.1]heptane |
| clethodim | (E,E)-(±)-2-[1-[[(3-chloro-2-propenyl)-oxy]imino]propyl]-5-[2-(ethylthio)-propyl]-3-hydroxy-2-cyclohexen-1-one |
| clomazone | 2-[(2-chlorophenyl)methyl]-4,4-dimethyl-3-isoxazolidinone |
| cloproxydim | (E,E)-2-[1-[[(3-chloro-2-propenyl)oxy)-imino]butyl]-5-[2-(ethylthio)propyl]-3-hydroxy-2-cyclohexen-1-one |
| clopyralid | 3,6-dichloro-2-pyridinecarboxylic acid |
| CMA | calcium salt of MAA |
| cyanazine | 2-[[4-chloro-6-(ethylamino)-1,3,5-triazin-2-yl]amino]-2-methylpropanenitrile |
| cycloate | S-ethyl cyclohexylethylcarbamothioate |
| cycluron | 3-cyclooctyl-1,1-dimethylurea |
| cyperquat | 1-methyl-4-phenylpyridinium |
| cyprazine | 2-chloro-4-(cyclopropylamino)-6-(isopropylamino)-s-triazine |
| cyprazole | N-[5-(2-chloro-1,1-dimethylethyl)-1,3,4-thiadiazol-2-yl]cyclopropanecarboxamide |
| cypromid | 3',4'-dichlorocyclopropanecarboxanilide |
| dalapon | 2,2-dichloropropanoic acid |
| dazomet | tetrahydro-3,5-dimethyl-2H-1,3,5-thiadiazine-2-thione |
| DCPA | dimethyl 2,3,5,6-tetrachloro-1,4-benzenedicarboxylate |
| desmediphan | ethyl [3-[[(phenylamino)carbonyl]oxy]-phenyl]carbamate |
| desmetryn | 2-(isopropylamino)-4-(methylamino)-6-(methylthio)-s-triazine |
| diallate | S-(2,3-dichloro-2-propenyl)bis(1-methylethyl)carbamothioate |
| dicamba | 3,6-dichloro-2-methoxybenzoic acid |
| dichlobenil | 2,6-dichlorobenzonitrile |
| dichlorprop | (±)-2-(2,4-dichlorophenoxy)propanoic acid |
| dichlofop-methyl | (±)-2-[4-(2,4-dichlorophenoxy)phenoxy]-propanoic acid, methyl ester |
| diethatyl | N-(chloroacetyl)-N-(2,6-diethylphenyl)-glycine |
| difenzoquat | 1,2-dimethyl-3,5-diphenyl-1H-pyrazolium |
| dinitramine | $N^3$,$N^3$-diethyl-2,4-dinitro-6-(trifluoro-methyl)-1,3-benzenediamine |
| dinoseb | 2-(1-methylpropyl)-4,6-dinitrophenol |
| diphenamid | N,N-dimethyl-α-phenylbenzeneacetamide |
| dipropetryn | 6-(ethylthio)-N,N'-bis(1-methylethyl)-1,3,5-triazine-2,4-diamine |
| diquat | 6,7-dihydrodipyrido[1,2-a:2',1'-c]-pyrazinedium ion |
| diuron | N'-(3,4-dichlorophenyl)-N,N-dimethylurea |
| DNOC | 2-methyl-4,6-dinitrophenol |
| DPX-M6316 | 3-[[[[(4-methoxy-6-methyl-1,3,5-triazin-2-yl)amino]carbonyl]amino]sulfonyl]-2-thiophenecarboxylic acid, methyl ester |
| DSMA | disodium salt of MAA |
| endothall | 7-oxabicyclo[2.2.1]heptane-2,3-dicarboxylic acid |
| EPTC | S-ethyl dipropylcarbamothioate |
| ethalfluralin | N-ethyl-N-(2-methyl-2-propenyl)-2,6-dinitro-4-(trifluoromethyl)-benzenamine |
| ethofumesate | (±)-2-ethoxy-2,3-dihydro-3,3-dimethyl- |

-continued

| Common Name | Chemical Name |
|---|---|
| | 5-benzofuranyl methanesulfonate |
| Express ® | 2-[[[[N-(4-methoxy-6-methyl-1,3,5-triazine-2-yl)-N-methylamino]-carbonyl]amino]sulfonyl]benzoic acid, methyl ester |
| fenac | 2,3,6-trichlorobenzeneacetic acid |
| fenoxaprop | (±)-2-[4-[(6-chloro-2-benzoxazolyl)oxy]-phenoxy]propanoic acid |
| fenuron | N,N-dimethyl-N'-phenylurea |
| fenuron TCA | Salt of fenuron and TCA |
| flamprop | N-benzoyl-N-(3-chloro-4-fluorophenyl)-DL-alanine |
| fluazifop | (±)-2-[4-[[5-(trifluoromethyl)-2-pyridinyl]oxy]phenoxy]propanoic acid |
| fluazifop-P | (R)-2-[4-[[5-(trifluoromethyl)-2-pyridinyl]oxy]phenoxy]propanoic acid |
| fluchloralin | N-(2-chloroethyl)-2,6-dinitro-N-propyl-4-(trifluoromethyl)benzenamine |
| fluometuron | N,N-dimethyl-N'-[3-(trifluoromethyl)-phenyl]urea |
| fluorochloridone | 3-chloro-4-(chloromethyl)-1-[3-(trifluoromethyl)phenyl]-2-pyrrolidinone |
| fluorodifen | p-nitrophenyl α,α,α-trifluoro-2-nitro-p-tolyl ether |
| fluoroglycofen | carboxymethyl 5-[2-chloro-4-(trifluoromethyl)phenoxy]-2-nitrobenzoate |
| fluridone | 1-methyl-3-phenyl-5-[3-(trifluoromethyl)phenyl]-4(1H)-pyridinone |
| fomesafen | 5-[2-chloro-4-(trifluoromethyl)phenoxy]-N-(methylsulfonyl)-2-nitrobenzamide |
| fosamine | ethyl hydrogen (aminocarbonyl)-phosphate |
| glyphosate | N-(phosphonomethyl)glycine |
| haloxyfop | 2-[4-[[3-chloro-5-(trifluoromethyl)-2-pyridinyl]oxy]phenoxy]propanoic acid |
| hexaflurate | potassium hexafluoroarsenate |
| hexazinone | 3-cyclohexyl-6-(dimethylamino)-1-methyl-1,3,5-triazine-2,4(1H,3H)-dione |
| imazamethabenz | 6-(4-isopropyl-4-methyl-5-oxo-2-imidazolin-2-yl)-m-toluic acid, methyl ester and 6-(4-isopropyl-4-methyl-5-oxo-2-imidazolin-2-yl)-p-toluic acid, methyl ester |
| imazapyr | (±)-2-[4,5-dihydro-4-methyl-4-(1-methylethyl)-5-oxo-1H-imidazol-2-yl]-3-pyridinecarboxylic acid |
| imazaquin | 2-[4,5-dihydro-4-methyl-4-(1-methylethyl)-5-oxo-1H-imidazol-2-yl]-3-quinolinecarboxylic acid |
| imazethapyr | (±)-2-[4,5-dihydro-4-methyl-4-(1-methylethyl)-5-oxo-1H-imidazol-2-yl]-5-ethyl-3-pyridinecarboxylic acid |
| ioxynil | 4-hydroxy-3,5-diiodobenzonitrile |
| isopropalin | 4-(1-methylethyl)-2,6-dinitro-N,N-dipropylbenzenamine |
| isoproturon | N-(4-isopropylphenyl)-N',N'-dimethylurea |
| isouron | N'-[5-(1,1-dimethylethyl)-3-isoxazolyl]-N,N-dimethylurea |
| isoxaben | N-[3-(1-ethyl-1-methylpropyl)-5-isoxazolyl]-2,6-dimethoxybenzamide |
| karbutilate | 3-[[(dimethylamino)carbonyl] amino]-phenyl-(1,1-dimethylethyl)carbamate |
| lactofen | (±)-2-ethoxy-1-methyl-2-oxoethyl 5-[2-chloro-4-(trifluoromethyl)phenoxy]-2-nitrobenzoate |
| lenacil | 3-cyclohexyl-6,7-dihydro-1H-cyclopentapyrimidine-2,4(3H,5H)-dione |
| linuron | N'-(3,4-dichlorophenyl)-N-methoxy-N-methylurea |
| MAA | methylarsonic acid |
| MAMA | monoammonium salt of MAA |
| MCPA | (4-chloro-2-methylphenoxy)acetic acid |
| MCPB | 4-(4-chloro-2-methylphenoxy)butanoic acid |
| mecoprop | (±)-2-(4-chloro-2-methylphenoxy)-propanoic acid |
| mefluidide | N-[2,4-dimethyl-5-[[(trifluoromethyl)-sulfonyl]amino]phenyl]acetamide |
| methalpropalin | N-(2-methyl-2-propenyl)-2,6-dinitro-N-propyl-4-(trifluoromethyl)benzenamide |

-continued

| Common Name | Chemical Name |
|---|---|
| methabenzthiazuron | 1,3-dimethyl-3-(2-benzothiazolyl)urea |
| metham | methylcarbamodithioic acid |
| methazole | 2-(3,4-dichlorophenyl)-4-methyl-1,2,4-oxadiazolidine-3,5-dione |
| methoxuron | N'-(3-chloro-4-methoxyphenyl)-N,N-dimethylurea |
| metolachlor | 2-chloro-N-(2-ethyl-6-methylphenyl)-N-(2-methoxy-1-methylethyl)acetamide |
| metribuzin | 4-amino-6-(1,1-dimethylethyl)-3-(methylthio)-1,2,4-triazin-5(4H)-one |
| metsulfuron methyl | 2-[[[[(4-methoxy-6-methyl-1,3,5-triazin-2-yl)amino]carbonyl]-amino]sulfonyl]benzoic acid, methyl ester |
| MH | 1,2-dihydro-3,6-pyridazinedione |
| molinate | S-ethyl hexahydro-1H-azepine-1-carbothioate |
| monolinuron | 3-(p-chlorophenyl)-1-methoxy-1-methylurea |
| monuron | N'-(4-chlorophenyl)-N,N-dimethylurea |
| monuron TCA | Salt of monuron and TCA |
| MSMA | monosodium salt of MAA |
| napropamide | N,N-diethyl-2-(1-naphthalenyloxy)-propanamide |
| naptalam | 2-[(1-naphthalenylamino)carbonyl]-benzoic acid |
| neburon | 1-butyl-3-(3,4-dichlorophenyl)-1-methylurea |
| nitralin | 4-(methylsulfonyl)-2,6-dinitro-N,N-dipropylaniline |
| nitrofen | 2,4-dichloro-1-(4-nitrophenoxy)benzene |
| nitrofluorfen | 2-chloro-1-(4-nitrophenoxy)-4-(trifluoromethyl)benzene |
| norea | N,N-dimethyl-N'-(octahydro-4,7-methano-1H-inden-5-yl)urea 3aα,-4α,5α,7α,7aα-isomer |
| norflurazon | 4-chloro-5-(methylamino)-2-[3-(trifluoromethyl)phenyl]-3(2H)-pyridazinone |
| oryzalin | 4-(dipropylamino)-3,5-dinitrobenzenesulfonamide |
| oxadiazon | 3-[2,4-dichloro-5-(1-methylethoxy)-phenyl]-5-(1,1-dimethylethyl)-1,3,4-oxadiazol-2(3H)-one |
| oxyfluorfen | 2-chloro-1-(3-ethoxy-4-nitrophenoxy)-4-(trifluoromethyl)benzene |
| paraquat | 1,1'-dimethyl-4,4'-dipyridinium ion |
| pebulate | S-propyl butylethylcarbamothioate |
| pendimethalin | N-(1-ethylpropyl)-3,4-dimethyl-2,6-dinitrobenzenamine |
| perfluidone | 1,1,1-trifluoro-N-[2-methyl-4-(phenylsulfonyl)phenyl]methanesulfonamide |
| phenmedipham | 3-[(methoxycarbonyl)amino]phenyl (3-methylphenyl)carbamate |
| picloram | 4-amino-3,5,6-trichloro-2-pyridinecarboxylic acid |
| PPG-1013 | 5-[2-chloro-4-(trifluoromethyl)-phenoxy]-2-nitroacetophenone oxime-O-acetic acid, methyl ester |
| procyazine | 2-[[4-chloro-6-(cyclopropylamino)-1,3,5-triazine-2-yl]amino]-2-methylpropanenitrile |
| profluralin | N-(cyclopropylmethyl)-2,6-dinitro-N-propyl-4-(trifluoromethyl)benzenamine |
| prometon | 6-methoxy-N,N'-bis(1-methylethyl)-1,3,5-triazine-2,4-diamine |
| prometryn | N,N'-bis(1-methylethyl)-6-(methylthio)-1,3,5-triazine-2,4-diamine |
| pronamide | 3,5-dichloro-N-(1,1-dimethyl-2-propynyl)benzamide |
| propachlor | 2-chloro-N-(1-methylethyl)-N-phenylacetamide |
| propanil | N-(3,4-dichlorophenyl)propanamide |
| propazine | 6-chloro-N,N'-bis(1-methylethyl)-1,3,5-triazine-2,4-diamine |
| propham | 1-methylethyl phenylcarbamate |
| prosulfalin | N-[[4-(dipropylamino)-3,5-dinitrophenyl]sulfonyl]-S,S-dimethylsulfilimine |
| prynachlor | 2-chloro-N-(1-methyl-2-propynyl)acet- |

-continued

| Common Name | Chemical Name |
|---|---|
| | anilide |
| pyrazon | 5-amino-4-chloro-2-phenyl-3(2H)-pyridazinone |
| quizalofop ethyl | (±)-2-[4-[(6-chloro-2-quinoxalinyl)-oxy]phenoxy]propanoic acid, ethyl ester |
| secbumeton | N-ethyl-6-methoxy-N'-(1-methylpropyl)-1,3,5-triazine-2,4-diamine |
| sethoxydim | 2-[1-(ethoxyimino)butyl]-5-[2-(ethyl-thio)propyl]-3-hydroxy-2-cyclohexen-1-one |
| siduron | N-(2-methylcyclohexyl)-N'-phenylurea |
| simazine | 6-chloro-N,N'-diethyl-1,3,5-triazine-2,4-diamine |
| sulfometuron methyl | 2-[[[[(4,6-dimethyl-2-pyrimidinyl)-amino]carbonyl]amino]sulfonyl]-benzoic acid, methyl ester |
| TCA | trichloroacetic acid |
| tebuthiuron | N-[5-(1,1-dimethylethyl)-1,3,4-thiadi-azol-2-yl]-N,N'-dimethylurea |
| terbacil | 5-chloro-3-(1,1-dimethylethyl)-6-methyl-2,4(1H,3H)-pyrimidinedione |
| terbuchlor | N-(butoxymethyl)-2-chloro-N-[2-(1,1-dimethylethyl)-6-methylphenyl]-acetamide |
| terbuthyl-azine | 2-(tert-butylamino)-4-chloro-6-(ethyl-amino)-s-triazine |

-continued

| Common Name | Chemical Name |
|---|---|
| terbutol | 2,6-di-tert-butyl-p-tolyl methylcar-bamate |
| terbutryn | N-(1,1-dimethylethyl)-N'-ethyl-6-(methylthio)-1,3,5-triazine-2,4-diamine |
| thiobencarb | S-[(4-chlorophenyl)methyl ]diethylcar-bamothioate |
| triallate | S-(2,3,3-trichloro-2-propenyl) bis(1-methylethyl)carbamothioate |
| triclopyr | [(3,5,6-trichloro-2-pyridinyl)-oxy]acetic acid |
| tridiphane | 2-(3,5-dichlorophenyl)-2-(2,2,2-trichloroethyl)oxirane |
| trifluralin | 2,6-dinitro-N,N-dipropyl-4-(tri-fluoromethyl)benzenamine |
| trimeturon | 1-(p-chlorophenyl)-2,3,3-trimethylpseu-dourea |
| 2,4-D | (2,4-dichlorophenoxy)acetic acid |
| 2,4-DB | 4-(2,4-dichlorophenoxy)butanoic acid |
| vernolate | S-propyl dipropylcarbamothioate |
| xylachlor | 2-chloro-N-(2,3-dimethylphenyl)-N-(1-methylethyl)acetamide |

Herbicidal properties of the subject compounds were discovered in a number of greenhouse tests. Test procedures and results follow.

COMPOUNDS

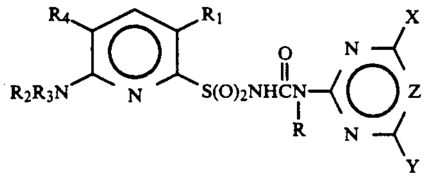

| CMPD | $R_2$ | $R_3$ | $R_1$ | $R_4$ | R | X | Y | Z | m.p. (°C.) |
|---|---|---|---|---|---|---|---|---|---|
| 1 | $CH_3$ | $CH_3$ | H | H | H | $OCH_3$ | $OCH_3$ | CH | 141–143 |
| 2 | $CH_3$ | $CH_3$ | H | H | H | Cl | $OCH_3$ | CH | 161–164 |
| 3 | $CH_3$ | $CH_3$ | H | H | H | $CH_3$ | $OCH_3$ | CH | 163–166 |
| 4 | $CH_3$ | $CH_3$ | H | H | H | $CH_3$ | $CH_3$ | CH | 165–167 |
| 5 | $CH_3$ | $CH_3$ | H | H | H | $OCH_3$ | $OCH_3$ | N | 110–122 |
| 6 | $CH_3$ | $CH_3$ | H | H | H | $CH_3$ | $OCH_3$ | N | 170–172 |
| 7 | $CH_3$ | $CH_3$ | H | H | $CH_3$ | $CH_3$ | $OCH_3$ | N | 152–154 |
| 8 | $CH_3$ | $CH_3$ | H | H | H | $NHCH_3$ | OEt | N | 186–188 |
| 9 | $CH_3$ | $CH_3$ | H | H | H | $NMe_2$ | OEt | N | 185–187 |
| 10 | $CH_3$ | $CH_3$ | H | H | H | OEt | OEt | N | 124–125 |
| 11 | $CH_3$ | $CH_3$ | H | H | H | $NMe_2$ | $OCH_2CF_3$ | N | 122–124 |
| 12 | $CH_3$ | $CH_3$ | H | H | H | $NMe_2$ | $OCH_3$ | N | 143–145 |
| 13 | $-CH_2CH_2CH_2-$ | | H | H | H | $OCH_3$ | $OCH_3$ | CH | 143–150 |
| 14 | $-CH_2CH_2CH_2-$ | | H | H | H | Cl | $OCH_3$ | CH | 110–120 |
| 15 | $-CH_2CH_2CH_2-$ | | H | H | H | $CH_3$ | $OCH_3$ | CH | 170–179 |
| 16 | $-CH_2CH_2CH_2-$ | | H | H | H | $CH_3$ | $CH_3$ | CH | 130–142 |
| 17 | $-CH_2CH_2CH_2-$ | | H | H | H | $OCH_3$ | $OCH_3$ | N | 178–184 |
| 18 | $-CH_2CH_2CH_2-$ | | H | H | H | $CH_3$ | $OCH_3$ | N | 112–167 |
| 19 | $-CH_2CH_2CH_2-$ | | H | H | $CH_3$ | $CH_3$ | $OCH_3$ | N | 132–140 |
| 20 | $CH_3$ | H | H | H | H | $OCH_3$ | $OCH_3$ | CH | 166–168 |
| 21 | $CH_3$ | H | H | H | H | Cl | $OCH_3$ | CH | 100–102 |
| 22 | $CH_3$ | H | H | H | H | $OCH_3$ | $OCH_3$ | N | 164–165 |
| 23 | $CH_3$ | H | H | H | H | $CH_3$ | $OCH_3$ | N | 168–170 |
| 24 | $CH_3$ | H | H | H | $CH_3$ | $CH_3$ | $OCH_3$ | N | 118–120 |
| 25 | $CH_3$ | H | H | H | H | $CH_3$ | $OCH_3$ | CH | 160–162 |
| 26 | $CH_3$ | H | H | H | H | $CH_3$ | $CH_3$ | CH | 182–184 |
| 27 | $CH_3$ | H | H | H | H | OEt | OEt | N | 79–81 |
| 28 | $CH_3$ | H | H | H | H | $NMe_2$ | OEt | N | 116–117 |
| 29 | $CH_3$ | H | H | H | H | $NMe_2$ | OMe | N | 194–195 |
| 30 | $CH_3$ | H | H | H | H | $NMe_2$ | $OCH_2CF_3$ | N | 115–116 |
| 31 | $CH_3$ | H | H | H | H | $NHCH_3$ | OEt | N | 114–115 |
| 32 | $-CH_2CH_2OCH_2CH_2-$ | | H | H | H | $OCH_3$ | $OCH_3$ | CH | 176–178 |
| 33 | $-CH_2CH_2OCH_2CH_2-$ | | H | H | H | Cl | $OCH_3$ | CH | 153–155 |
| 34 | $-CH_2CH_2OCH_2CH_2-$ | | H | H | H | $CH_3$ | $OCH_3$ | CH | 172–174 |
| 35 | $-CH_2CH_2OCH_2CH_2-$ | | H | H | H | $OCH_3$ | $OCH_3$ | N | 193–195 |
| 36 | $-CH_2CH_2OCH_2CH_2-$ | | H | H | H | $CH_3$ | $OCH_3$ | N | 118–119 |
| 37 | $-CH_2CH_2OCH_2CH_2-$ | | H | H | $CH_3$ | $CH_3$ | $OCH_3$ | N | 128–130 |
| 38 | $-CH_2CH_2OCH_2CH_2-$ | | H | H | H | $OCH_3$ | $OCH_3$ | N | 199–202 |
| 39 | $-CH_2CH_2OCH_2CH_2-$ | | H | H | H | $NHCH_3$ | OEt | N | 197–200 |

-continued

COMPOUNDS

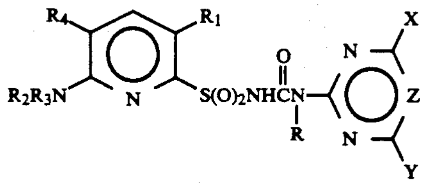

| CMPD | $R_2$ | $R_3$ | $R_1$ | $R_4$ | R | X | Y | Z | m.p. (°C.) |
|---|---|---|---|---|---|---|---|---|---|
| 40 | $CH_3$ | $OCH_3$ | H | H | H | $OCH_3$ | $OCH_3$ | CH | 148-149 |
| 41 | $CH_3$ | $OCH_3$ | H | H | H | Cl | $OCH_3$ | CH | 104-105 |
| 42 | $CH_3$ | $OCH_3$ | H | H | H | $CH_3$ | $OCH_3$ | CH | 124-126 |
| 43 | $CH_3$ | $OCH_3$ | H | H | H | $CH_3$ | $CH_3$ | CH | 167-168 |
| 44 | $CH_3$ | $OCH_3$ | H | H | H | $OCH_3$ | $OCH_3$ | N | 159-160 |
| 45 | $CH_3$ | $OCH_3$ | H | H | H | $CH_3$ | $OCH_3$ | N | 160-161 |
| 46 | $CH_3$ | $OCH_3$ | H | H | H | $NHCH_3$ | OEt | N | 167-169 |
| 47 | $CH_2CH_3$ | H | H | H | H | $OCH_3$ | $OCH_3$ | CH | 138-140 |
| 48 | $CH_2CH_3$ | H | H | H | H | Cl | $OCH_3$ | CH | 155-156 |
| 49 | $CH_2CH_3$ | H | H | H | H | $CH_3$ | $OCH_3$ | CH | 197-199 |
| 50 | $CH_2CH_3$ | H | H | H | H | $OCH_3$ | $OCH_3$ | N | 153-155 |
| 51 | $CH_2CH_3$ | H | H | H | H | $CH_3$ | $OCH_3$ | N | 144-146 |
| 52 | $CH_2CH_3$ | H | H | H | H | $NMe_2$ | $OCH_3$ | N | 160-162 |
| 53 | $CH_2CH_3$ | H | H | H | H | $NMe_2$ | $OCH_2CF_3$ | N | 138-139 |
| 54 | $CH_2CH{=}CH_2$ | H | H | H | H | $OCH_3$ | $OCH_3$ | CH | 159-160 |
| 55 | $CH_2CH{=}CH_2$ | H | H | H | H | Cl | $OCH_3$ | CH | 168-170 |
| 56 | $CH_2CH{=}CH_2$ | H | H | H | H | $CH_3$ | $OCH_3$ | CH | 162 |
| 57 | $CH_2CH{=}CH_2$ | H | H | H | H | $CH_3$ | $CH_3$ | CH | 107-108 |
| 58 | $CH_2CH{=}CH_2$ | H | H | H | H | $OCH_3$ | $OCH_3$ | N | 115-117 |
| 59 | $CH_2CH{=}CH_2$ | H | H | H | H | $CH_3$ | $OCH_3$ | N | 99-100 |
| 60 | $CH_2C{\equiv}CH$ | H | H | H | H | $OCH_3$ | $OCH_3$ | CH | 156-157 |
| 61 | $CH_2C{\equiv}CH$ | H | H | H | H | $CH_3$ | $OCH_3$ | CH | 159-160 |
| 62 | $CH_2C{\equiv}CH$ | H | H | H | H | $OCH_3$ | $OCH_3$ | N | 150-151 |
| 63 | $CH_2C{\equiv}CH$ | H | H | H | H | $CH_3$ | $OCH_3$ | N | 108-109 |
| 64 | $CH_3$ | $CH_3$ | $S(O)_2CH_3$ | H | H | $OCH_3$ | $OCH_3$ | CH | 217-219 |
| 65 | $CH_2CF_3$ | H | H | H | H | $OCH_3$ | $OCH_3$ | CH | 139-145 |
| 66 | $CH_2CF_3$ | H | H | H | H | $CH_3$ | $OCH_3$ | CH | 177-181 |
| 67 | cyclopropyl | H | H | H | H | $OCH_3$ | $OCH_3$ | CH | 117-122 |
| 68 | cyclopropyl | H | H | H | H | $CH_3$ | $OCH_3$ | CH | 175-178 |
| 69 | cyclopropyl | H | H | H | H | $OCH_3$ | $OCH_3$ | N | 120-122 |
| 70 | cyclopropyl | H | H | H | H | $CH_3$ | $OCH_3$ | N | 115-120 |
| 71 | cyclopropyl | H | H | H | H | $NMe_2$ | $OCH_3$ | N | 175-177 |
| 72 | $CH_2C{\equiv}CH$ | CH | H | H | H | $OCH_3$ | $OCH_3$ | CH | 195-199 |
| 73 | $CH_2C{\equiv}CH$ | $CH_3$ | H | H | H | Cl | $OCH_3$ | CH | 165-169 |
| 74 | $CH_2C{\equiv}CH$ | $CH_3$ | H | H | H | $CH_3$ | $OCH_3$ | CH | 158-161 |
| 75 | $CH_2C{\equiv}CH$ | $CH_3$ | H | H | H | $CH_3$ | $CH_3$ | CH | 159-170 |
| 76 | $CH_2C{\equiv}CH$ | $CH_3$ | H | H | H | $OCH_3$ | $OCH_3$ | N | 169-175 |
| 77 | $CH_2C{\equiv}CH$ | $CH_3$ | H | H | H | $CH_3$ | $OCH_3$ | N | 160-173 |
| 78 | $CH_2C{\equiv}CH$ | $CH_3$ | H | H | H | $NMe_2$ | $OCH_3$ | N | 160-173 |
| 79 | $CH_2C{\equiv}CH$ | $CH_3$ | H | H | H | $NMe_2$ | $OCH_2CF_3$ | N | 158-175(d) |
| 80 | $CH_2CH_2OH$ | $CH_3$ | H | H | H | $OCH_3$ | $OCH_3$ | CH | 150-153 |
| 81 | $CH_2CH_2OH$ | $CH_3$ | H | H | H | $CH_3$ | $OCH_3$ | CH | 148-150 |
| 82 | $CH_2CH_2OH$ | $CH_3$ | H | H | H | $CH_3$ | $OCH_3$ | N | 155-158 |
| 83 | $CH_3$ | $CH_3$ | Cl | Cl | H | $OCH_3$ | $OCH_3$ | CH | 139-145 |
| 84 | $CH_3$ | $CH_3$ | Cl | Cl | H | Cl | $CH_3$ | CH | 175-182 |
| 85 | $CH_3$ | $CH_3$ | Cl | Cl | H | $CH_3$ | $OCH_3$ | CH | 147-150 |
| 86 | $CH_3$ | $CH_3$ | Cl | Cl | H | $CH_3$ | $CH_3$ | CH | 138-143 |
| 87 | $CH_3$ | $CH_3$ | Cl | Cl | H | $OCH_3$ | $OCH_3$ | N | 185-193 |
| 88 | $CH_3$ | $CH_3$ | Cl | Cl | H | $CH_3$ | $OCH_3$ | N | 160-166 |
| 89 | $CH_3$ | $CH_3$ | Cl | Cl | H | OEt | OEt | N | 119-122 |
| 90 | $CH_3$ | $CH_3$ | Cl | Cl | H | $NHCH_3$ | OEt | N | 165-182 |
| 91 | $CH_3$ | $CH_3$ | Cl | Cl | H | $NMe_2$ | OEt | N | 128-192 |
| 92 | $CH_3$ | $CH_3$ | Cl | Cl | H | $NMe_2$ | $OCH_3$ | N | 103-165 |
| 93 | $CH_3$ | $CH_3$ | Cl | Cl | H | $NHCH_3$ | $OCH_2CF_3$ | N | 120-195 |
| 94 | $CH_3$ | $CH_3$ | Cl | Cl | H | $NMe_2$ | $OCH_2CF_3$ | N | 115-145 |
| 95 | $CH_3$ | $CH_3$ | $S(O)_2CH_2CH_2$ | H | H | $OCH_3$ | $OCH_3$ | CH | 228-231 |
| 96 | $CH_3$ | $CH_3$ | $S(O)_2CH_2CH_2$ | H | H | $CH_3$ | $OCH_3$ | CH | 208-213 |
| 97 | $CH_3$ | $CH_3$ | $S(O)_2CH_2CH_2$ | H | H | Cl | $OCH_3$ | CH | 205-209 |
| 98 | $CH_3$ | $CH_3$ | $S(O)_2CH_2CH_2$ | H | H | $CH_3$ | $CH_3$ | CH | 238-246 |

wherein Me denotes $CH_3$ and Et denotes $CH_2CH_3$.

TEST A

Seeds of barley (*Hordeum vulgare*), barnyardgrass (*Echinochloa crus-galli*), cheatgrass (*Bromus secalinu*) or downy brome (*Bromus tectorum*), cocklebur (*Xanthium pensylvanicum*), corn (*Zea mays*), cotton (*Gossypium hirsutum*), crabgrass (*Digitaria spp.*), giant foxtail (*Setaria faberi*), morninglory (*Ipomoea* spp.), rice (*Orzya sativa*), sorghum (*Sorghum bicolor*), soybean (*Glycine max*), sugarbeet (*Beta vulgaris*), velvetleaf (*Abutilon theophrasti*), wheat (*Triticum aestivum*), and wild oat (*Avena fatua*) and purple nutsedge (*Cyperus rotundus*) tubers were planted and treated preemergence with test chemicals dissolved in a non-phytotoxic solvent. At the same time, these crop and weed species were also treated with postemergence applications of test chemicals. Plants ranged in height from two to eighteen cm for postemergence treatments. Treated plants and controls were maintained in a greenhouse for sixteen days, after which all species were compared to controls and visually evaluated. The ratings, summarized in Table A, are based on a scale of 0 to 10 where 0 is no effect and 10 is complete control. A dash (-) response means no test. The accompanying descriptive symbols have the following meanings:

C=chlorosis/necrosis;
E=inhibition of emergence;
G=growth retardation;
H=formative effect; and
U=unusual pigmentation.

TABLE A

| RATE = KG/HA | CMPD 1 0.05 | CMPD 1 0.01 | CMPD 2 0.05 | CMPD 2 0.01 | CMPD 3 0.05 | CMPD 3 0.01 | CMPD 4 0.05 | CMPD 4 0.01 | CMPD 5 0.05 | CMPD 5 0.01 | CMPD 6 0.05 | CMPD 6 0.01 | CMPD 7 0.05 | CMPD 7 0.4 | CMPD 8 0.05 | CMPD 8 0.01 | CMPD 9 0.05 | CMPD 9 0.01 | CMPD 10 0.05 | CMPD 10 0.01 |
|---|---|---|---|---|---|---|---|---|---|---|---|---|---|---|---|---|---|---|---|---|
| POSTEMERGENCE | | | | | | | | | | | | | | | | | | | | |
| COTTON | 5C,9G | 2C,9G | 5C,9G | 3C,9G | 9C | 3C,9G | 3C,9G | 2C,7G | 5C,9G | 3C,7G | 3C,8G | 7G | 5C,9G | 9C | 4C,8G | 2C,3G | 3C,8G | 6G | 10C | 3C,6G |
| MORNINGGLORY | 9C | 10C | 9C | 9C | 10C | 10C | 10C | 3C,8H | 10C | 3C,8G | 10C | 9C | 3C,8G | 5C,9G | 10C | 3C,8G | 10C | 4C,8G | 10C | 10C |
| COCKLEBUR | 10C | 10C | 10C | 10C | 10C | 10C | 5C,9H | 4C,9H | 10C | 10C | 10C | 10C | 5C,9G | 5C,9G | 10C | 2C,8G | 10C | 2C,8G | 10C | 9C |
| NUTSEDGE | 10C | 10C | 10C | 10C | 10C | 10C | 9C | 4C,9G | 3C,9G | 6G | 10C | 0 | 3C,9G | 9C | 2G | 0 | 3C,6G | 4G | 9G | 0 |
| CRABGRASS | 6C,9G | 8G | 9C | 9C | 10C | 8G | 8G | 6G | 8G | 4G | 10C | 9C | 0 | 0 | 2C,4G | 3G | 0 | 0 | 4G | 0 |
| BARNYARDGRASS | 9C | 5C,9G | 10C | 5C,9G | 9C | 4C,9G | 3C,9G | 3C,8H | 5C,9G | 3C,9H | 10C | 10C | 2C,6G | 3C,7G | 4C,9H | 4G | 3C,8H | 2G | 4C,9G | 9C |
| WILD OATS | 5C,9G | 4C,8G | 5C,9G | 5C,9G | 5C,9G | 3C,9G | 4C,9G | 9G | 3C,9G | 8G | 3C,9G | 3C,9G | 0 | 2G | 2C,6G | 4G | 2G | 0 | 0 | 0 |
| WHEAT | 9G | 4G | 2C,9G | 6G | 9G | 4G | 8G | 6G | 3C,9G | 8G | 2C,9G | 9G | 0 | 2G | 2G | 0 | 2G | 0 | 0 | 0 |
| CORN | 9C | 5C,9G | 10C | 9C | 10C | 9C | 3C,9G | 9G | 9C | 9C | 10C | 10C | 0 | 2C,6G | 10C | 10C | 10C | 10C | 10C | 10C |
| SOYBEANS | 9C | 6C,9G | 9C | 5C,9G | 6C,9G | 5C,9G | 6C,9G | 3C,8G | 5C,9G | 5C,9G | 5C,9G | 5C,9G | 5C,9G | 5C,9G | 9C | 5C,9G | 6C,9G | 4C,8G | 6C,9G | 5C,9G |
| RICE | 6C,9G | 5C,9G | 9C | 5C,9G | 9C | 9C | 9C | 5C,9G | 9C | 9C | 9C | 9C | 8G | 9C | 5C,9G | 3C,8G | 9C | 4C,8G | 9C | 3C,8G |
| SORGHUM | 9C | 3C,9G | 5C,9G | 6C,9G | 9C | 3C,9G | 6C,9G | 4C,9G | 4C,9G | 9G | 10C | 9C | 3G | 8G | 4C,9G | 9G | 5C,9G | 9G | 10C | 2C,8G |
| CHEATGRASS | 5C,9G | 5C,9G | 10C | 10C | 10C | 10C | 10C | 9C | 4C,9G | 9G | — | — | — | — | — | — | — | — | — | — |
| SUGARBEETS | 10C | 10C | 10C | 9C | 10C | 9C | 9C | 9C | 9C | 9C | 10C | 5C,9H | 9C | 9C | 3C,9G | 2C,5G | 10C | 8H | 9C | 10C |
| VELVETLEAF | 9C | 9C | 10C | 10C | 10C | 10C | 5C,9H | 4C,9G | 9C | 3C,9H | 9C | 3C,9G | 8G | 5C,9G | 5C,9G | 3C,8G | 5C,9G | 7G | 3C,8G | 3C,7G |
| GIANT FOXTAIL | 9C | 4C,9G | 9C | 9C | 5C,9G | 3C,9G | 4C,9G | 3C,9G | 4C,9G | 6G | 9C | 5C,9G | 0 | 3G | 4C,9G | 3C,7G | 5C,9G | 8G | 4C,9G | 2C,4G |
| BARLEY | 5C,9G | 7G | 9C | 5C,9G | 3C,8G | 4C,9G | 8G | 5G | 9G | 4G | 9G | 4G | 0 | 2G | 2C,7G | 6G | 2C,7G | 4G | 6G | 2G |
| DOWNY BROME | — | — | — | — | — | — | — | — | — | — | 9C | 9C | 4G | 4C,9G | 3C,7G | 2C,5G | 5C,9G | 3C,8G | 4C,9G | 4G |

| RATE = KG/HA | CMPD 11 0.05 | CMPD 11 0.01 | CMPD 12 0.05 | CMPD 12 0.01 | CMPD 13 0.05 | CMPD 13 0.01 | CMPD 14 0.05 | CMPD 14 0.01 | CMPD 15 0.05 | CMPD 15 0.01 | CMPD 16 0.05 | CMPD 16 0.01 | CMPD 17 0.05 | CMPD 17 0.01 | CMPD 18 0.05 | CMPD 18 0.01 | CMPD 19 0.05 | CMPD 19 0.4 | CMPD 20 0.05 | CMPD 20 0.01 |
|---|---|---|---|---|---|---|---|---|---|---|---|---|---|---|---|---|---|---|---|---|
| POSTEMERGENCE | | | | | | | | | | | | | | | | | | | | |
| COTTON | 5G | 2G | 5C,9G | 7G | 9C | 5C,9G | 2C,8G | 7G | 9C | 3C,8G | 7G | 0 | 4C,8G | 5G | 3C,8G | 0 | 5G | 8G | 5C,9G | 3C,8G |
| MORNINGGLORY | 10C | 4C,8G | 10C | 4C,8G | 10C | 5C,9G | 3C,7G | 2C,4G | 10C | 4C,9H | 3C,7H | 3C,5H | 5C,9H | 2C,5G | 4C,8H | 2C,7G | 3C,4G | 4C,8H | 9C | 9C |
| COCKLEBUR | 10C | 3C,8G | 10C | 4C,9G | 10C | 5C,9H | 10C | 4C,9H | 5C,9H | 5C,9H | 4C,9H | 10C | 10C | 10C | 10C | 10C | 2C,7G | 4C,9H | 6C,9G | 10C |
| NUTSEDGE | 3C,5G | 4G | 10C | 0 | 10C | 8G | 3G | 0 | 4C,9G | 9G | 9G | 4G | 0 | 0 | — | 0 | 0 | 9G | 10C | 10C |
| CRABGRASS | 3C,8G | 3G | 2C,7G | 2C,5G | 10C | 6G | 2G | 0 | 7G | 5G | 4G | 0 | 2G | 3G | 2G | 0 | 0 | 2C | 10C | 4C,9G |
| BARNYARDGRASS | 3C,9G | 3C,3G | 3C,7G | 0 | 9C | 4C,9H | 4C,8H | 2C,4G | 4C,9H | 3C,7H | 2C,5G | 2G | 4C,9H | 5G | 9C | 2C,6H | 0 | 2C,6H | 10C | 9C |
| WILD OATS | 2C,7G | 2C,5G | 3C,9G | 5G | 3C,8G | 5G | 5G | 0 | 3C,9G | 2C,4G | 2C,7G | 3G | 9G | 2C,4G | 3C,8G | 3G | 0 | 2C,3G | 3C,9G | 9G |
| WHEAT | 2C,5G | 0 | 2C,5G | 2G | 9G | 2G | 2G | 0 | 9G | 4G | 4G | 3G | 9G | 5G | 9G | 2C,4G | 0 | 2G | 3C,9G | 6G |
| CORN | 10C | 3U,9G | 10C | 10C | 10C | 5C,9G | 3C,9G | 2C,8G | 10C | 9C | 3C,9G | 3C,9G | 9C | 9G | 5C,9G | 9G | 2C,6G | 3C,8H | 10C | 10C |
| SOYBEANS | 5C,9G | 4C,8H | 9C | 3C,8G | 9C | 6G | 3C,7G | 2C,7H | 6C,9G | 4C,9G | 3C,7G | 2C,7G | 4C,8G | 4C,9G | 4C,9G | 4C,9G | 6H | 2C,7H | 5C,9G | 4C,9G |
| RICE | 4C,8G | 3C,8G | 9C | 4C,8G | 9C | 9C | 4C,9G | 2C,3G | 9C | 5C,9G | 3C,8G | 0 | 9C | 5C,9G | 9C | 9C | 7G | 3C,8G | 9C | 9C |
| SORGHUM | 3C,9G | 3C,9G | 10C | 10C | 6C,9G | 9G | 9G | 8G | 9G | 3C,8G | 2C,7G | 6G | 9G | 8G | 9C | 9G | 6G | 3C,9H | 9C | 9C |
| CHEATGRASS | — | — | — | — | 5C,9G | 9G | 8G | 0 | 8G | 8G | 9G | 5G | 4C,9G | 8G | 3C,8G | 7G | 0 | 8G | — | — |
| SUGARBEETS | 9C | 4C,8G | 10C | 9C | 10C | 5C,9H | 3C,8H | 2C,5H | 9C | 4C,8H | 3C,7H | 0 | 10C | 5G | 9C | 4C,8H | 3C,7H | 3C,6H | 9C | 5C,9G |
| VELVETLEAF | 3C,7G | 6G | 5C,9G | 3C,8G | 9C | 5C,9G | 3C,8G | 6G | 10C | 5C,9H | 2C,7G | 3C,6H | 5C,9H | 3C,8H | 4C,9G | 5H | 7G | 4C,9G | 9C | 5C,9G |
| GIANT FOXTAIL | 4C,9G | 2C,5G | 9C | 3C,8G | 9C | 5C,9G | 2C,8G | 3G | 5C,9G | 2C,6G | 5G | 0 | 6G | 0 | 4G | 0 | 0 | 0 | 10C | 10C |
| BARLEY | 3C,6G | 2G | 5C,9G | 5G | 3C,9G | 5C,9G | 5G | 2G | 9G | 6G | 3G | 0 | 3C,9G | 5G | 7G | 0 | 2G | 7G | 2C,9G | 6G |
| DOWNY BROME | 9C | 2G | 10C | 2C,6G | — | — | — | — | — | — | — | — | — | — | — | — | — | — | 10C | 9C |

| RATE = KG/HA | CMPD 21 0.05 | CMPD 21 0.01 | CMPD 22 0.05 | CMPD 22 0.01 | CMPD 23 0.05 | CMPD 23 0.01 | CMPD 24 0.05 | CMPD 24 0.01 | CMPD 25 0.05 | CMPD 25 0.01 | CMPD 26 0.05 | CMPD 26 0.01 | CMPD 27 0.05 | CMPD 27 0.01 | CMPD 28 0.05 | CMPD 28 0.01 | CMPD 29 0.05 | CMPD 29 0.01 | CMPD 30 0.05 | CMPD 30 0.01 |
|---|---|---|---|---|---|---|---|---|---|---|---|---|---|---|---|---|---|---|---|---|
| POSTEMERGENCE | | | | | | | | | | | | | | | | | | | | |
| COTTON | 4C,9G | 2G | 4C,8G | 3G | 9C | 6G | 9C | 9C | 10C | 5C,9G | 9G | 0 | 7G | 5G | 4C,9G | 9G | 5C,9G | 3C,7G | 2C,9G | 0 |
| MORNINGGLORY | 9C | 3C,8G | 10C | 4C,8G | 10C | 9C | 2C,6G | 9C | 10C | 10C | 9C | 3G | 5C,9G | 9C | 5C,9G | 3C,9H | 10C | 5C,9G | 4C,9G | 3C,8G |
| COCKLEBUR | 9C | 3C,8G | 10C | 10C | 10C | 10C | 5C,9H | 9C | 9C | 9C | 9C | 7H | 10C | 3C,8H | 5C,9G | 3C,8H | 9C | 2C,8H | 4C,9G | 2C,8H |
| NUTSEDGE | 9C | 0 | 10C | 3G | 10C | 2C,5G | 0 | 4C,8G | 10C | 10C | 9C | 3C,9G | 5C,9G | 0 | 5C,9G | 2C,9G | 9G | 5C,9G | 4C,8G | 0 |

TABLE A-continued

| | | | | | | | | | | | | | | | | | | | | |
|---|---|---|---|---|---|---|---|---|---|---|---|---|---|---|---|---|---|---|---|---|
| CRABGRASS | 3C,6G | 0 | 10C | 0 | 9C | 9C | 0 | 2C,6G | 4C,9G | 6G | 2C,5G | 2G | 4C,9G | 5G | 6G | 2C | 3C,6G | 0 | 9C | 3C,5G |
| BARNYARDGRASS | 9C | 3C,8G | 9C | 5C,9G | 10C | 9C | 2G | 4C,9G | 9C | 9C | 5C,9G | 3C,5G | 4C,9G | 3C,8H | 4C,9H | 2C,5H | 3C,9H | 3C,7G | 3C,9H | 3C,7H |
| WILD OATS | 6G | 0 | 4C,9G | 3C,9G | 3C,9G | 3C,9G | 0 | 4G | 9C | 4C,8G | 3C,7G | 3C,5G | 9G | 7G | 4C,9G | 9G | 5C,9G | 4C,9G | 8G | 0 |
| WHEAT | 0 | 0 | 3C,9G | 8G | 4C,9G | 3C,9G | 0 | 3G | 4C,8G | 3C,5G | 3G | 2G | 3C,9G | 8G | 4C,9G | 3G | 5C,9G | 9G | 9G | 5G |
| CORN | 4C,9G | 6C,9G | 10C | 10C | 10C | 10C | 2C,5G | 3C,9G | 10C | 9C | 5C,9G | 4C,9G | 5C,9G | 3C,9G | 10C | 4C,9G | 9C | 5C,9G | 4C,9G | 3C,9G |
| SOYBEANS | 5C,9G | 2C,6H | 6C,9G | 5C,9G | 6C,9G | 4C,9G | 5C,9G | 5C,9G | 4C,9G | 4C,9G | 4C,9G | 3C,7H | 5C,9G | 4C,9G | 5C,9G | 4C,8G | 5C,9G | 3C,7G | 4C,9G | 3C,9G |
| RICE | 4C,9G | 8G | 9C | 4C,9G | 9C | 9C | 7G | 9C | 9C | 5C,9G | 5C,9G | 4C,9G | 9C | 9C | 9C | 5C,9G | 9C | 9C | 5C,9G | 2C,9G |
| SORGHUM | 9G | 9G | 3C,9G | 9G | 10C | 5C,9G | 2G | 9G | 9C | 9C | 4C,9G | 4C,9H | 4C,9G | 3C,9G | 9C | 5C,9G | 9C | 4C,9G | 3C,9G | 3C,9G |
| CHEATGRASS | — | — | — | — | — | — | — | — | — | — | — | — | 9C | 3C,9G | 9C | 3C,9G | 9C | 5C,9G | 5C,9G | 3C,7G |
| SUGARBEETS | 5C,9G | 4G | 10C | 4C,8G | 10C | 5C,9G | 3C,5G | 5C,9G | 10C | 5C,9G | 10C | 9C | 4C,9G | 6G | 9C | 4C,8G | 10C | 4C,9G | 3C,8G | 3C,5G |
| VELVETLEAF | 8G | 7G | 4C,9G | 3C,8H | 5C,9G | 4C,8G | 3C,9G | 5C,9G | 9C | 9C | 9C | 8G | 4C,9H | 7G | 9C | 3C,9G | 9C | 3C,9G | 3C,8H | 3C,7G |
| GIANT FOXTAIL | 6G | 2G | 9C | 2C,3G | 10C | 3C,7G | 0 | 2C,3G | 9C | 3C,9H | 3C,9G | 3C,7G | 4C,9G | 3C,9G | 4C,9G | 3C,8G | 9C | 4C,9G | 4C,9G | 3C,7G |
| BARLEY | 0 | 0 | 7G | 0 | 3C,8G | 5G | 3G | 0 | 4C,9G | 3C,7G | 3C,5G | 4G | 7G | 2G | 8G | 2G | 3C,9G | 3C,8G | 8G | 7G |
| DOWNY BROME | 5C,9G | 0 | 10C | 6G | 10C | 9C | 2C,4G | 4C,9G | 9C | 9C | 9C | 6G | — | — | — | — | — | — | — | — |
| | CMPD 31 | | CMPD 32 | | CMPD 33 | | CMPD 34 | | CMPD 35 | | CMPD 36 | | CMPD 37 | | CMPD 38 | | CMPD 39 | | CMPD 40 | |
| RATE = KG/HA | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 |
| | POSTEMERGENCE | | | | | | | | | | | | | | | | | | | |
| COTTON | 4C,9G | 5G | 9C | 4C,9G | 3C,8H | 2G | 4C,9H | 3C,8G | 9H | 2C,5G | 3C,7G | 3C,6G | 0 | 0 | 4C,9H | 7G | 3C,9H | 4G | 9C | 5C,9G |
| MORNINGGLORY | 10C | 4C,9G | 10C | 4C,9G | 3C,7G | 2H | 9C | 2C,6H | 4C,9H | 3C,7H | 4C,9G | 0 | 2C | 0 | 2C,9G | 3C,7G | 4C,9G | 3C,6H | 10C | 4C,9G |
| COCKLEBUR | 4C,9G | 7H | 10C | 8G | 10C | 4C,9G | 9C | 5C,9G | 5C,9G | 2C,5H | 2C,5G | 1C | 2C | 0 | 5C,9G | 3C,6H | 9C | 3C,6H | 10C | 5C,9G |
| NUTSEDGE | 5G | 0 | 9C | 3C,7G | 2C,9G | 0 | 3C,7G | 0 | — | 0 | 0 | 0 | 0 | 0 | 0 | 2G | 3C,8G | 0 | 10C | 9C |
| CRABGRASS | 3C,6G | 2G | 2C,5G | 0 | 0 | 0 | 0 | 0 | 0 | 0 | 2C,2G | 0 | 0 | 0 | 0 | 0 | 0 | 0 | 4C,9G | 5C,9G |
| BARNYARDGRASS | 4C,9H | 3C,7G | 4C,9H | 3C,6G | 3C,8G | 3H | 1C | 0 | 3C,7H | 2C,3G | 4C,9H | 2C,5G | 0 | 0 | 3C,6G | 0 | 4C,8H | 3C,6H | 9C | 4C,8H |
| WILD OATS | 3C,9G | 3C,9G | 3C,8G | 2G | 0 | 0 | 2C,6G | 0 | 2C,8G | 0 | 3C,6G | 0 | 0 | 0 | 3C,7G | 2G | 2G | 0 | 9G | 7G |
| WHEAT | 9G | 3C,9G | 2C,8G | 2G | 0 | 0 | 2C,6G | 0 | 2C,4G | 0 | 3C,8G | 6G | 0 | 0 | 3C,8G | 3G | 0 | 0 | 3C,9G | 6G |
| CORN | 9C | 9C | 9C | 4C,9G | 3C,9G | 2C,5G | 4C,9G | 3C,7G | 5G | 3C,7G | 9C | 8G | 2C,5G | 1C,2G | 3U,9G | 3C,8H | 9C | 4C,9G | 9C | 9C |
| SOYBEANS | 4C,9G | 4C,9G | 9C | 5C,9G | 2C,5G | 3H | 3C,8H | 4C,8G | 5G | 2C,7H | 4C,9G | 2C,8G | 1H | 1H | 4C,9G | 4C,9G | 4C,9G | 4C,9G | 9C | 5C,9G |
| RICE | 9C | 5C,9G | 5C,9G | 9C | 5C,9G | 3C,8G | 9C | 8G | 9C | 5C,9G | 9C | 2C,2G | 7G | 0 | 5C,9G | 3C,7G | 5C,9G | 2C,5G | 5C,9G | 5C,9G |
| SORGHUM | 9C | 4C,9G | 5C,9G | 4C,9G | 3C,9G | 2C,3G | 2C,9G | 2C,5G | 4C,9G | 1C,2G | 4C,9G | 1C | 1C | 0 | 4C,9G | 2C,3G | 2C,8H | 2C,5G | 5C,9G | 5C,9G |
| CHEATGRASS | 9C | 4C,9G | — | — | — | — | — | — | — | — | — | — | — | — | — | — | — | — | — | — |
| SUGARBEETS | 5C,9G | 3C,7G | 10C | 10C | 9C | 4C,9G | 10C | 3C,8G | 3C,7G | 3C,6G | 3C,8H | 3C,7G | 2C,5G | 2G | 10C | 3C,7G | 3C,3H | 0 | 10C | 9C |
| VELVETLEAF | 9C | 4C,9G | 9C | 5C,9G | 3C,7G | 3G | 9C | 4G | 7H | 3C,6G | 3C,7G | 2C,2G | 2G | 0 | 3C,7G | 3C,5H | 3C,6G | 2C,3G | 9C | 4C,9G |
| GIANT FOXTAIL | 4C,9G | 3C,9G | 9C | 3C,8G | 2G | 0 | 3C,7G | 0 | 2G | 1C | 4C,9G | 0 | 0 | 0 | 4C,9G | 0 | 3C,8G | 5G | 9C | 5C,9G |
| BARLEY | 3C,9G | 7G | 6C,9G | 5G | 3G | 0 | 9C | 5G | 5C,9G | 0 | 2C,5G | 4G | 0 | 0 | 2C,7G | 2G | 3C,6G | 3G | 9G | 3C,7G |
| DOWNY BROME | — | — | 3C,8G | 4C,9G | 2G | 0 | 9C | 0 | 8G | 2C,8G | 5C,9G | 3G | 0 | 0 | 9C | 3C,8G | 4C,8G | 0 | 9C | 5C,9G |
| | CMPD 41 | | CMPD 42 | | CMPD 43 | | CMPD 44 | | CMPD 45 | | CMPD 46 | | CMPD 47 | | CMPD 48 | | CMPD 49 | | CMPD 50 | |
| RATE = KG/HA | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 |
| | POSTEMERGENCE | | | | | | | | | | | | | | | | | | | |
| COTTON | 3C,7G | 1C | 9C | 4C,9H | 4C,8H | 3C,5G | 5C,9G | 3C,8H | 4C,9H | 4C,8H | 3C,9G | 3C,7H | 10C | 9C | 10C | 9C | 9C | 10C | 10C | 10C |
| MORNINGGLORY | 4C,9G | 3C,6H | 10C | 4C,9G | 3C,7G | 2C,4G | 9C | 4C,8G | 5C,9G | 4C,9G | 4C,8G | 3C,7G | 10C | 10C | 9C | 4C,9G | 10C | 10C | 10C | 8G |
| COCKLEBUR | 9C | 2C,5G | 10C | 5C,9G | 4C,9G | 2C,8H | 9C | 4C,8H | 10C | 4C,9G | 5C,9G | 3C,7H | 5C,9G | 3C,9G | 5C,9G | 4C,9G | 10C | 5C,9G | 10C | 9C |
| NUTSEDGE | 2C,5G | 0 | 5C,9G | 9C | 2C | 0 | 3C,7G | 2G | 3C,7G | 0 | 4G | 0 | 9C | 5G | 6C,9G | 5C,9G | 10C | 5C,9G | — | 9G |
| CRABGRASS | 2G | 0 | 3C,7G | 3G | 0 | 0 | 3C,9G | 3C,8G | 4C,9G | 5C,9G | 3C,5G | 0 | 5C,9G | 2C,6G | 9G | 4G | 10C | 4C,8G | 9C | 3C,8G |
| BARNYARDGRASS | 3C,8H | 0 | 4C,9H | 0 | 2C | 0 | 4C,9H | 4C,9G | 9C | 5C,9G | 3C,9H | 3C,5H | 9C | 9C | 5C,9G | 3C,9G | 9C | 9C | 9C | 5C,9G |
| WILD OATS | 2C,6G | 0 | 2C,9G | 3C,8G | 3G | 0 | 5C,9G | 3C,9G | 4C,9G | 4C,9G | 4C,9G | 3C,6G | 3C,9G | 9G | 8G | 6G | 5C,9G | 9G | 5C,9G | 9G |
| WHEAT | 7G | 0 | 5C,9G | 2C,8G | 5G | 0 | 9C | 4C,9G | 9C | 5C,9G | 9G | 3G | 3C,9G | 7G | 4G | 4G | 3C,9G | 9G | 3C,9G | 9G |
| CORN | 5C,9G | 3C,8H | 10C | 9C | 5C,9G | 4C,9G | 10C | 9C | 10C | 10C | 9C | 9C | 9C | 9C | 3C,9G | 9G | 4C,9G | 10C | 9C | 4C,9G |
| SOYBEANS | 3C,6G | 2C,2H | 5C,9G | 3C,9H | 3C,9G | 3C,8H | 3C,9G | 5C,9G | 5C,9G | 5C,9G | 5C,9G | 4C,9G | 9C | 9C | 5C,9G | 5C,9G | 9C | 9C | 9C | 9C |
| RICE | 9C | 3C,8G | 9C | 5C,9G | 5C,9G | 4C,9G | 9C | 9C | 5C,9G | 9C | 5C,9G | 4C,9G | 5C,9G | 5C,9G | 5C,9G | 4C,9G | 9C | 9C | 9C | 9C |
| SORGHUM | 4C,9G | 3C,9G | 5C,9G | 4C,9H | 4C,9G | 4C,8G | 9G | 4C,9G | 9C | 5C,9G | 4C,9G | 9G | 5C,9G | 3C,9G | 3C,9G | 9G | 5C,9G | 3C,9G | 6C,9G | 3C,9G |

TABLE A-continued

| | | | | | | | | | | | | | | | | | | | | |
|---|---|---|---|---|---|---|---|---|---|---|---|---|---|---|---|---|---|---|---|---|
| CHEATGRASS | — | — | — | — | — | — | — | — | — | — | — | — | 4C,8G | 3C,8G | 5C,9G | 5G | 9C | 3C,9G | 9C | 5C,9G |
| SUGARBEETS | 4C,8H | 3C,5G | 10C | 10C | 9C | 5C,9G | 9C | 5C,9G | 9C | 9C | 4C,9G | 2H | 9C | 9C | 10C | 2C,6G | 10C | 10C | 9C | 9C |
| VELVETLEAF | 4C,9G | 2C,5G | 9C | 3C,8G | 5C,9G | 3C,8H | 4C,9H | 3C,7H | 5C,9G | 3C,7G | 4C,8H | 3C,8G | 9G | 9G | 9G | 3C,8G | 10C | 10C | 9C | 3C,8G |
| GIANT FOXTAIL | 3C,7G | 0 | 5C,9G | 3C,7H | 3C,7G | 0 | 4C,9G | 3C,5G | 4C,9G | 3C,6G | 3C,9H | 2G | 10C | 5C,9G | — | 6G | 10C | 4C,9G | 9C | 4C,9G |
| BARLEY | 5G | 0 | 8G | 3C,6G | 2C,5G | 0 | 8G | 5G | 7G | 4G | 7G | 7G | 3C,9G | 4G | 6G | 3G | 4C,9G | 5G | 5C,9G | 8G |
| DOWNY BROME | 7G | 0 | 5C,9G | 3C,8G | 7G | 4G | 4C,9G | 5C,9G | 3C,8G | 5C,9G | 5C,9G | 8G | — | — | — | — | — | — | — | — |

| | CMPD 51 | | CMPD 52 | | CMPD 53 | | CMPD 54 | | CMPD 55 | | CMPD 56 | | CMPD 57 | | CMPD 58 | | CMPD 59 | | CMPD 60 | |
|---|---|---|---|---|---|---|---|---|---|---|---|---|---|---|---|---|---|---|---|---|
| RATE = KG/HA | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 |
| POSTEMERGENCE | | | | | | | | | | | | | | | | | | | | |
| COTTON | 10C | 10C | 10C | 9C | 3C,9G | 9G | 10C | 9C | 9C | 9C | 10C | 9C | 9C | 9C | 9C | 9C | 10C | 10C | 9C | 10C |
| MORNINGGLORY | 10C | 9C | 10C | 5C,9G | 5C,9G | 5C,9G | 10C | 10C | 10C | 2C,8H | 10C | 9C | 9C | 3C,8G | 9C | 3C,8H | 10C | 10C | 9C | 9C |
| COCKLEBUR | 9C | 10C | 10C | 9C | 4C,9G | 3C,8H | 9C | 5C,9G | 4C,9H | 2C,7H | 5C,9G | 9C | 5C,9G | 3C,8G | 10C | 4C,9G | 9C | 10C | 10C | 10C |
| NUTSEDGE | 3C,5G | 3G | — | 6G | 9G | 7G | 9G | 4C,9G | 7G | 3G | 9G | 2C,9G | 8G | 7G | 7G | 3G | 4G | 3G | 10C | 9C |
| CRABGRASS | 9C | 3C,9G | 4C,9G | 3C,6G | 8G | 4G | 5C,9G | 3C,8G | 3C,7G | 3G | 5C,9H | 3C,7G | 3C,8G | 3C,7G | 4C,9G | 3C,5G | 4C,9G | 3C,7G | 4C,8G | 6G |
| BARNYARDGRASS | 10C | 5C,9G | 10C | 5C,9G | 4C,9G | 4C,9G | 10C | 3C,9H | 4C,9G | 3C,8H | 5C,9G | 4C,9H | 3C,9H | 3C,5G | 9C | 9H | 9C | 4C,9H | 9C | 9H |
| WILD OATS | 5C,9G | 9G | 5C,9G | 3C,9G | 9G | 6G | 3C,9G | 2C,9G | 5G | 2G | 3C,9G | 8G | 9G | 2C,5G | 4C,9G | 3C,8G | 5C,9G | 8G | 3C,9G | 2C,9G |
| WHEAT | 5C,9G | 9G | 4C,9G | 8G | 8G | 5G | 9G | 8G | 4G | 2G | 4C,9G | 5G | 8G | 4G | 2C,9G | 9G | 4C,9G | 8G | 9G | 9G |
| CORN | 10C | 4U,9G | 9C | 9G | 3C,9G | 3C,9G | 4C,9G | 5C,9G | 3C,9G | 3C,9H | 5C,9G | 4C,9G | 3C,9G | 4C,9G | 2C,9G | 4C,9H | 9C | 4C,9G | 5C,9G | 5C,9G |
| SOYBEANS | 9C | 5C,8G | 9C | 5C,9G | 9C | 5C,9G | 9C | 9C | 3H,7G | 3C,4H | 9C | 9C | 9C | 3H,7G | 9C | 9C | 9C | 4C,9G | 9C | 9C |
| RICE | 9C | 9C | 9C | 9C | 5C,9G | 4C,8G | 5C,9G | 9C | 9C | 8G | 9C | 9C | 9C | 4C,8G | 9C | 9C | 9C | 9C | 9C | 6C,9G |
| SORGHUM | 10C | 5C,9G | 10C | 3C,9G | 4C,9G | 3C,9G | 3C,9G | 4C,9G | 4C,9G | 3C,8H | 4C,9G | 4C,9G | 3C,9G | 4C,9G | 4C,9G | 4C,9H | 5C,9G | 4C,9G | 6C,9G | 4C,9G |
| CHEATGRASS | 10C | 5C,9G | 5C,9G | 4C,9G | 4C,9G | 8G | 9C | 5C,9G | 4C,9G | 3G | 4C,9G | 3C,9G | 3C,9G | 7G | 5C,9G | 3C,7G | 5C,9G | 8G | 5C,9G | 2C,8G |
| SUGARBEETS | 6C,9G | 9C | 5C,9G | 5C,9G | 9C | 4C,8G | 9C | 9C | 4C,9H | 3H | 9C | 5C,9G | 9C | 5C,9G | 9C | 3C,7H | 9C | 4C,8H | 9C | 9C |
| VELVETLEAF | 9C | 3C,8G | 5C,9G | 8G | 3C,8G | 8G | 10C | 10C | 10C | 3C,9G | 10C | 10C | 10C | 9C | 10C | 4C,9G | 10C | 4C,9G | 10C | 9C |
| GIANT FOXTAIL | 9C | 5C,9G | 9C | 9C | 3C,9G | 6G | 9C | 9C | 3C,8G | 6G | 9C | 3C,8G | 4C,9G | 3C,7G | 9C | 3C,7G | 5C,9G | 4C,8G | 9C | 4C,9G |
| BARLEY | 8G | 6G | 5C,9G | 9G | 7G | 5G | 2C,9G | 3C,7G | 4G | 0 | 3C,9G | 6G | 3C,7G | 4G | 3C,7G | 3C,5G | 7G | 4G | 2C,9G | 8G |
| DOWNY BROME | — | — | — | — | — | — | — | — | — | — | — | — | — | — | — | — | — | — | — | — |

| | CMPD 61 | | CMPD 62 | | CMPD 63 | | CMPD 64 | | CMPD 65 | | CMPD 66 | | CMPD 67 | | CMPD 68 | | CMPD 69 | | CMPD 70 | |
|---|---|---|---|---|---|---|---|---|---|---|---|---|---|---|---|---|---|---|---|---|
| RATE = KG/HA | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 |
| POSTEMERGENCE | | | | | | | | | | | | | | | | | | | | |
| COTTON | 9C | 5C,9G | 9C | 9G | 10C | 9C | 9C | 9C | 9C | 9C | 9C | 10C | 9C | 9C | 9C | 10C | 9C | 4C,9G | 5C,9G | 10C |
| MORNINGGLORY | 10C | 9C | 10C | 9C | 10C | 9C | 10C | 10C | 10C | 10C | 10C | 10C | 10C | 10C | 9C | 4C,9G | 5C,9G | 1H | 9C | 10C |
| COCKLEBUR | 9C | 9C | 10C | 5C,9G | 10C | 5C,9G | 10C | 9C | 10C | 9C | 10C | 10C | 3C,9G | 3C,9G | 4C,9G | 4C,9G | 9C | 3C,9G | 10C | 9C |
| NUTSEDGE | 9G | 9G | 8G | — | 3G | 2G | — | 3C,9G | — | 9G | 4C,9G | — | — | 8G | — | 7G | 5G | — | 7G | — |
| CRABGRASS | 4C,8G | 7G | 9C | 8G | 3C,9G | 8G | 9C | 10C | 3C,8G | 3G | 5C,9G | 5G | 4G | 3G | 2C,8G | 6G | 7G | 3G | 8G | 4G |
| BARNYARDGRASS | 9C | 9H | 5C,9H | 3C,9G | 10C | 5C,9G | 9C | 9C | 5C,9G | 3C,9G | 9C | 3C,8H | 3C,9G | 3C,9H | 3C,9G | 2C,5H | 9H | 3C,6G | 6C,9G | 4C,9H |
| WILD OATS | 5C,9G | 2C,9G | 4C,9G | 2C,9G | 4C,9G | 8G | 5C,9G | 4C,9G | 3C,9G | 9G | 4C,9G | 4C,9G | 9G | 9G | 9G | 9G | 4C,9G | 2C,7G | 4C,9G | 8G |
| WHEAT | 2C,9G | 9G | 4C,9G | 2C,9G | 4C,9G | 9G | 4C,9G | 9G | 9G | 9G | 3C,9G | 3C,9G | 9G | 5G | 7G | 4G | 9G | 4G | 9G | 6G |
| CORN | 10C | 4C,9G | 9C | 5C,9G | 10C | 10C | 9C | 4C,9G | 3C,9G | 9G | 4C,9G | 4C,9G | 3C,9G | 2C,9G | 3C,9G | 9G | 5C,9G | 4C,9G | 5C,9G | 4C,9G |
| SOYBEANS | 9C | 9C | 5C,9G | 9C | 9C | 9C | 9C | 5C,9G | 5C,9G | 4C,9G | 9C | 4C,9H | 5C,9G | 3C,9H | 3C,9H | 3C,7H | 4C,9H | 4C,9G | 6C,9G | — |
| RICE | 9C | 6C,9G | 9C | 9C | 9C | 6C,9G | 10C | 9C | 9C | 5C,9G | 5C,9G | 4C,9G | 9C | 4C,9G | 5C,9G | 2C,9G | 5C,9G | 5C,9G | 9C | 4C,9G |
| SORGHUM | 6C,9G | 4C,9G | 5C,9G | 4C,9G | 10C | 3C,9G | 9C | 4C,9G | 9G | 4C,9G | 4C,9G | 4C,9G | 3C,9G | 3C,9H | 3C,9G | 2C,9H | 4C,9G | 4C,9G | 4C,9G | 4C,9G |
| CHEATGRASS | 6C,9G | 2C,9G | 5C,9G | 7G | 4C,9G | 9G | 9C | 3C,9G | 4C,8G | 4C,8G | 5C,9G | 4C,8G | 3C,7G | 3C,9G | 4C,9G | 2C,8G | 5C,9G | 3C,6G | 5C,9G | 4C,9G |
| SUGARBEETS | 9C | 9C | 10C | 3C,7G | 9C | 9C | 5C,9H | 5C,9H | 10C | 9C | 9C | 9C | 5C,9H | 5C,9H | 9C | 5C,9H | 5C,9G | 4C,8H | 9C | 5C,9G |
| VELVETLEAF | 9C | 9C | 9C | 4C,9G | 5C,9G | 4C,8G | 10C | 9C | 10C | 9C | 10C | 10C | 4C,9G | 5C,9G | 9C | 5C,9H | 4C,8H | 3C,7G | 4C,9G | 4C,8H |
| GIANT FOXTAIL | 9C | 4C,9G | 5C,9G | 3C,8G | 9C | 3C,8G | 10C | 5C,9G | 3C,9G | 2C,6G | 5C,9G | 3C,8G | 4C,9G | 2C,7G | 4C,9G | 3C,8G | 4C,9G | 3C,8G | 9C | 3C,8G |
| BARLEY | 3C,9G | 7G | 3C,9G | 7G | 8G | 6G | 4C,9G | 3C,9G | 4C,9G | 9G | 4C,9G | 2C,9G | 8G | 2G | 5G | 2G | 2C,8G | 5G | 2C,8G | 5G |
| DOWNY BROME | — | — | — | — | — | — | — | — | — | — | — | — | — | — | — | — | — | — | — | — |

| | CMPD 71 | | CMPD 72 | | CMPD 73 | | CMPD 74 | | CMPD 75 | | CMPD 76 | | CMPD 77 | | CMPD 78 | | CMPD 79 | | CMPD 80 | |
|---|---|---|---|---|---|---|---|---|---|---|---|---|---|---|---|---|---|---|---|---|

TABLE A-continued

| RATE = KG/HA | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 |
|---|---|---|---|---|---|---|---|---|---|---|---|---|---|---|---|---|---|---|---|---|
| | POSTEMERGENCE | | | | | | | | | | | | | | | | | | | |
| COTTON | 9C | 5C,9G | 9C | 9C | 9C | 9C | 9C | 9C | 9C | 7C | 5C,9G | 4C,9G | 9C | 5C,9G | 4C,9G | 7G | 4C,9G | 2C,3G | 10C | 5C,9G |
| MORNINGGLORY | 9C | 3C,7G | 10C | 9C | 10C | 9C | 10C | 9C | 5C,9G | 3C,7G | 10C | 5C,9G | 10C | 9C | 10C | 4C,9H | 5C,9H | 3C,8H | 4C,9G | 2C,5G |
| COCKLEBUR | 4C,9G | 3C,8G | 10C | 9C | 9C | 5C,9G | 10C | 5C,9G | 9C | 2C,7G | 9C | 4C,9H | 10C | 9C | 10C | 3C,7H | 4C,9G | 2C,7H | 10C | 3C,9H |
| NUTSEDGE | — | 5G | 10C | 10C | 3C,8G | 5G | 10C | 4C,8G | 3C,9G | 2C,7G | — | 3C,7G | 4C,8G | 5G | 9C | 2C,5G | 3G | 0 | — | 9C |
| CRABGRASS | 2C,5G | 2C,4G | 9C | 4C,7G | 4C,9G | 4C,9G | 9C | 7G | 4C,9G | 2C,8G | 5C,9G | 2C,6G | 10C | 4C,8G | 4C,8G | 3G | 3G | 2G | 3C,7G | 3G |
| BARNYARDGRASS | 3C,9H | 2C,5G | 9C | 5C,9H | 5C,9G | 4C,9G | 6C,9G | 3C,9H | 4C,8H | 3C,5G | 4C,9G | 3C,7H | 9C | 5C,9G | 3C,8H | 3C,5H | 4C,9G | 3C,8H | 9C | 5C,9G |
| WILD OATS | 3C,9G | 7G | 4C,9G | 2C,9G | 2C,8G | 6G | 6C,9G | 8G | 8G | 5G | 4C,9G | 3C,8G | 5C,9G | 3C,7G | 4C,9G | 2C,5G | 3C,9G | 3G | 9G | 6G |
| WHEAT | 9G | 5G | 5C,9G | 8G | 5G | 2G | 4C,9G | 6G | 8G | 5G | 9C | 2C,8G | 9C | 5C,9G | 9G | 4G | 3C,9G | 3C,8G | 4C,9G | 7G |
| CORN | 2C,9G | 9G | 4U,9C | 3U,9G | 9G | 9G | 9C | 3C,9G | 5C,9G | 3C,8G | 9C | 5U,9G | 9C | 5U,9C | 5C,9G | 3C,9G | 4C,9G | 4C,9G | 10C | 3U,9G |
| SOYBEANS | 3C,9H | 3C,7H | 9C | 9C | 3C,8H | 5H | 6C,9G | 5C,9G | 9C | 2C,8G | 5C,9G | 5C,9G | 9C | 5C,9G | 5C,9G | 2C,8H | 5C,9G | 3C,9H | 9C | 3C,8G |
| RICE | 5C,9G | 3C,9G | 9C | 6C,9G | 5C,9G | 8G | 6C,9G | 9C | 6C,9G | 5C,9G | 9C | 5C,9G | 9C | 9C | 9C | 9C | 4C,9G | 3C,7G | 9C | 5C,9G |
| SORGHUM | 3C,9G | 3C,9G | 9C | 4C,9G | 4C,9G | 2C,8G | 4C,9G | 4C,9G | 6C,9G | 4C,9G | 4C,9G | 4C,9G | 9C | 4C,9G | 4C,9G | 3C,9H | 4C,9G | 4C,9G | 3C,9G | 2C,9G |
| CHEATGRASS | 3C,8G | 6G | 9C | 6C,9G | 2C,8G | 2G | 6C,9G | 9G | 3C,9G | 2C,8G | 4C,9G | 2C,9G | 9C | 4C,9G | 9C | 3C,9G | 4C,9G | 2C,5G | 5C,9G | 3C,8G |
| SUGARBEETS | 4C,8H | 3C,9H | 9C | 9C | 7C | 5C,9G | 10C | 5C,9G | 9C | 9C | 10C | 9C | 10C | 10C | 10C | 4C,9H | 9C | 3C,8G | 10C | 9C |
| VELVETLEAF | 3C,7G | 2C,7G | 9C | 5C,9G | 2C,8G | 2C,6G | 10C | 5C,9G | 5C,9G | 3C,7G | 5C,9G | 2C,8G | 9C | 4C,8H | 4C,8H | 2C,6G | 3C,7G | 5G | 3C,8G | 2C,4G |
| GIANT FOXTAIL | 3C,9G | 9G | 9C | 4C,9G | 3C,8G | 3C,6G | 9C | 4C,8G | 5C,9G | 3C,7G | 5C,9G | 3C,7G | 9C | 4C,9G | 4C,9G | 3C,8G | 3C,7G | 3C,7G | 10C | 5C,9G |
| BARLEY | 3C,8G | 4G | 2C,9G | 7G | 5G | 2G | 3C,9G | 3C,5G | 7G | 5G | 2C,8G | 2C,6G | 2C,7G | 5G | 4C,9G | 2C,6G | 2C,8G | 3G | 3C,9G | 2C,9G |
| DOWNY BROME | — | — | — | — | — | — | — | — | — | — | — | — | — | — | — | — | — | — | — | — |

| | CMPD 81 | | CMPD 82 | | CMPD 83 | | CMPD 84 | | CMPD 85 | | CMPD 86 | | CMPD 87 | | CMPD 88 | | CMPD 89 | | CMPD 90 | |
|---|---|---|---|---|---|---|---|---|---|---|---|---|---|---|---|---|---|---|---|---|
| RATE = KG/HA | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 |
| | POSTEMERGENCE | | | | | | | | | | | | | | | | | | | |
| COTTON | 4C,9G | 10C | 2C,9H | 2G | 10C | 9C | 10C | 3C,5G | 9C | 9C | 3G | 3G | 5C,9G | 4C,9G | 10C | 4C,8G | 4C,9G | 5G | 5C,8G | 3C,6G |
| MORNINGGLORY | 10C | 3C,8H | 3C,7G | 2G | 8G | 10C | 9C | 3C,9G | 10C | 4C,8G | 9C | 1H | 9C | 4C,8H | 10C | 9C | 10C | 10C | 5C,9G | 4C,8G |
| COCKLEBUR | 10C | 3C,8H | 6G | 2H | 10C | 4C,9G | 9C | 6G | 10C | 4C,9G | 4C,8G | 5C,9G | 10C | 3C,7H | 10C | 5C,9G | 6C,9G | 3C,7G | 5C,9G | 3G |
| NUTSEDGE | — | 8G | 6G | — | 5C,9G | 6C,9G | 4C,9G | 0 | 6C,9G | 3C,8G | 3C,9G | 0 | 4C,9G | 0 | 5C,9G | 0 | 3C,5G | 0 | 5G | 0 |
| CRABGRASS | 4C,8G | 3C,5G | 3C,8G | 5G | 4C,8G | 2G | 0 | 0 | 3C,5G | 1C | 1C | 0 | 3G | — | 5G | 0 | 0 | 0 | 2C | 0 |
| BARNYARDGRASS | 9C | 3C,8H | 4C,9G | 7H | 10C | 9C | 9C | 3C,8H | 6C,9G | 4C,9H | 4C,8H | 3G | 4C,9H | 3C,5G | 10C | 5C,9H | 3C,7H | 0 | 3C,7H | 2C,3G |
| WILD OATS | 9G | 5G | 3C,8G | 3G | 9C | 4C,8G | 2C,5G | 2G | 3C,9G | 3C,7G | 3C,6G | 2G | 2C,5G | 4G | 3C,8G | 3C,6G | 3C,5G | 0 | 3C,5G | 0 |
| WHEAT | 8G | 3G | 3C,9G | 4G | 10C | 8G | 5G | 2G | 3C,9G | 4C,9G | 4C,8G | 4G | 5C,9G | 2C,9G | 10C | 5C,9G | 4G | 0 | 2C,6G | 4G |
| CORN | 5C,9G | 3C,9H | 9C | 3C,7H | 10C | 10C | 5U,9G | 4C,9G | 10C | 10C | 5U,9G | 2C,8G | 10C | 5U,9C | 10C | 10C | 4C,9G | 3C,8G | 4C,9G | 3C,9G |
| SOYBEANS | 9C | 3C,8H | 4C,9G | 4G | 6C,9G | 5C,9G | 4C,8H | 7G | 9C | 4C,9G | 3C,8H | 3C,7G | 9C | 4C,9G | 9C | 9C | 4C,9G | 4C,9G | 5C,9G | 4C,8G |
| RICE | 9C | 4C,9G | 5C,9G | 3C,7G | 6C,9G | 9C | 9C | 4C,8G | 9C | 9C | 9C | 3C,8G | 9C | 9C | 9C | 9C | 9C | 5G | 4C,9G | 3C,6G |
| SORGHUM | 5C,9G | 4C,9G | 4C,9G | 3C,8G | 10C | 9C | 9G | 4C,8G | 6C,9G | 3C,7G | 5C,9G | 3C,7G | 5C,9G | 2C,9G | 9C | 9C | 4C,9G | 3C,6G | 5C,9G | 4C,8H |
| CHEATGRASS | 5C,9G | 3C,6G | 7G | 2G | 9C | 9C | 4C,8G | 5G | 9C | 7G | 8G | 5G | 9C | 3C,8G | 9C | 4C,9G | 3C,8G | 0 | 5C,9G | 2C,5G |
| SUGARBEETS | 10C | 3C,6H | 3C,9G | 3H | 10C | 9C | 4C,8H | 5G | 10C | 9C | 9C | 2C,4G | 10C | 9C | 10C | 5C,9G | 9C | 3C,7G | 3C,8G | 3C,7H |
| VELVETLEAF | 3C,8G | 6G | 0 | 0 | 9C | 5C,9G | 3C,7G | 6G | 9C | 4C,9G | 4C,9G | 3C,7H | 4C,9G | 2C,8H | 6C,9G | 2C,4H | 2C,4G | 5G | 3C,7G | 2C,5G |
| GIANT FOXTAIL | 9C | 4C,9G | 3C,7G | 2G | 9C | 5C,9G | 4C,8G | 2C,5G | 9C | 2C,8G | 3C,8G | 2C,3G | 3C,7G | 2G | 5C,9G | 3C,5G | 3C,5G | 0 | 4C,8G | 3G |
| BARLEY | 5C,9G | 3C,7G | 3C,8G | 3C,7G | 5C,9G | 3C,7G | 5G | 2G | 3C,9G | 3C,6G | 7G | 4G | 6C,9G | 5G | 2C,9G | 2C,5G | 0 | 0 | 3C,5G | 0 |
| DOWNY BROME | — | — | — | — | — | — | — | — | — | — | — | — | — | — | — | — | — | — | — | — |

| | CMPD 91 | | CMPD 92 | | CMPD 93 | | CMPD 94 | | CMPD 95 | | CMPD 96 | | CMPD 97 | | CMPD 98 | |
|---|---|---|---|---|---|---|---|---|---|---|---|---|---|---|---|---|
| RATE = KG/HA | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 |
| | POSTEMERGENCE | | | | | | | | | | | | | | | |
| COTTON | 0 | 0 | 5C,9G | 3C,9G | 2C,6G | 0 | 5G | 0 | 9C | 5C,9G | 4C,9G | 3C,9G | 5C,9G | 3C,9G | 4C,9G | 8H |
| MORNINGGLORY | 1C,2H | 1H | 10C | 9C | 5C,9G | 5C,9G | 5C,9G | 2C,6H | 10C | 9C | 4C,9G | 4C,9H | 4C,9G | 4C,8H | 4C,9H | 3C,7H |
| COCKLEBUR | 2G | 0 | 5C,9G | 2C,8H | 4C,9H | 7H | 3C,8H | 3H | 10C | 9C | 5C,9G | 4C,9H | 9C | 4C,9G | 3C,9G | 3C,5G |
| NUTSEDGE | 0 | 0 | 3C,8G | 0 | 0 | 0 | 0 | 0 | 10C | 3C,8G | 9C | 3G | 5C,9G | 3G | 2C,8G | 8G |
| CRABGRASS | 0 | 0 | 2C,4G | 0 | 3G | 0 | 2G | 0 | 9C | 0 | 3G | 0 | 3C,6G | 0 | 3G | 0 |
| BARNYARDGRASS | 0 | 0 | 4C,9H | 2H | 3C,8H | 2C,5H | 6H | 4H | 5C,9G | 2C,9G | 3C,6H | 2C,5G | 5C,9G | 3C,9H | 3C,7H | 2C,4H |

TABLE A-continued

| RATE = KG/HA | CMPD 1 0.05 | CMPD 1 0.01 | CMPD 2 0.05 | CMPD 2 0.01 | CMPD 3 0.05 | CMPD 3 0.01 | CMPD 4 0.05 | CMPD 4 0.01 | CMPD 5 0.05 | CMPD 5 0.01 | CMPD 6 0.05 | CMPD 6 0.01 | CMPD 7 0.05 | CMPD 7 0.4 | CMPD 8 0.05 | CMPD 8 0.01 | CMPD 9 0.05 | CMPD 9 0.01 | CMPD 10 0.05 | CMPD 10 0.01 |
|---|---|---|---|---|---|---|---|---|---|---|---|---|---|---|---|---|---|---|---|---|
| WILD OATS | | | | | 0 | 0 | 3C,9G | 3C,9G | 8G | 4G | 7G | 5G | 5C,9G | 3C,9G | 3C,9G | 3C,7G | 9C | 2C,9G | 9G | 8G |
| WHEAT | | | | | 2G | 0 | 9G | 7G | 2C,6G | 0 | 4G | 3G | 4C,9G | 4C,9G | 9G | 9G | 4C,9G | 9G | 9G | 8G |
| CORN | | | | | 8G | 0 | 9C | 3U,9G | 9G | 9G | 3C,9G | 8G | 3C,9H | 3C,4H | 0 | 0 | 2G | 0 | 0 | 0 |
| SOYBEANS | | | | | 2C,5H | 0 | 3C,7H | 3C,7H | 5C,9G | 3C,7H | 3C,9G | 3C,8G | 9C | 5C,9G | 4C,9G | 3C,9G | 3C,8H | 4H | 4C,9G | 3C,7H |
| RICE | | | | | 4G | 0 | 9C | 9C | 2C,5G | 0 | 7G | 4G | 9C | 9C | 6C,9G | 3C,9G | 9C | 4C,9G | 5C,9G | 4C,9G |
| SORGHUM | | | | | 2C,6G | 3G | 9C | 9G | 9G | 9G | 3C,9G | 8G | 5C,9G | 4C,9G | 4C,9H | 4C,9H | 5C,9G | 4C,9G | 4C,8H | 3C,7H |
| CHEATGRASS | | | | | 3G | 0 | 9G | 8G | 7G | 0 | 3C,7G | 3G | 9C | 4C,9G | 9G | 4C,9G | 6C,9G | 9G | 4C,9G | 7G |
| SUGARBEETS | | | | | 2G | 2G | 9C | 5C,9H | 9C | 9C | 9C | 7G | 9C | 3C,5G | 3C,7G | 7G | 5C,9G | 3C,7G | 3C,5G | 1C,1H |
| VELVETLEAF | | | | | 4G | 0 | 3C,7G | 6G | 3G | 4G | 5G | 3G | 10C | 4C,9G | 5C,9H | 4C,9G | 5C,9G | 3C,8G | 3C,8H | 3C,6G |
| GIANT FOXTAIL | | | | | 4G | 0 | 5C,9G | 3C,8G | 7G | 6G | 6G | 3G | 3C,7G | 0 | 3C,6G | 2C,3G | 3C,7G | 2G | 3C,5G | 0 |
| BARLEY | | | | | 0 | 0 | 4C,9G | 6G | 2C,4G | 0 | 2C,4G | 0 | 5C,9G | 4C,9G | 9G | 7G | 4C,9G | 7G | 9G | 7G |
| DOWNY BROME | | | | | — | — | — | — | — | — | — | — | — | — | — | — | — | — | — | — |
| | | | | | | | | | PREEMERGENCE | | | | | | | | | | | |
| COTTON | 8G | 7G | 8G | 7G | 8G | 7G | 8G | 7G | 5G | 0 | 7G | 0 | 0 | 8G | 0 | — | 0 | 0 | 0 | 0 |
| MORNINGGLORY | 9G | 7G | 9G | 8G | 2C,9G | 6G | 9G | 6G | 9G | 0 | 9G | 7H | 0 | 6G | 4G | 0 | 0 | 0 | 2C,3G | 2G |
| COCKLEBUR | 3C,7H | 5G | 3C,7H | 6H | 3C,8H | 2C,4H | 3C,8H | 2C,4G | 3C,8H | 1C,4G | 8H | 3C,6H | 0 | 2G | 0 | 0 | — | 0 | 1C | 0 |
| NUTSEDGE | 10E | 10E | 10E | 9G | 10E | 10C | 10E | 10E | 3C,9G | 0 | 3G | 2G | 0 | 0 | 0 | 0 | 0 | 0 | 2G | 0 |
| CRABGRASS | 7G | 4G | 8G | 7G | 2C,9G | 4C,9G | 8G | 5G | 5C,9G | 2C | 4C,9G | 3C,8G | 0 | 0 | 1C | 0 | 0 | 0 | 2C | 0 |
| BARNYARDGRASS | 3C,9H | 2G | 3C,8H | 2C,4H | 9H | 2C,6H | 2C,2G | 2G | 4C,9H | 2C,7G | 4C,9H | 3C,8H | 0 | 0 | 3C,6H | 0 | 0 | 0 | 4C,9H | 0 |
| WILD OATS | 5G | 0 | 3C,8G | 3G | 2C,8G | 2C,2G | 2C,6G | 4G | 3C,8G | 2G | 3C,8G | 3C,8G | 0 | 0 | 2C,5G | 0 | 2C,7G | 0 | 2C,3G | 0 |
| WHEAT | 6G | 0 | 8G | 3G | 9G | 3G | 6G | 2G | 9G | 3G | 9G | 9G | 0 | 0 | 2C,4G | 0 | 0 | 0 | 3C,8G | 0 |
| CORN | 2C,7H | 1C,4G | 8G | 2C,3G | 3C,9G | 2C,8G | 3C,9G | 2C,6G | 9G | 2C,4G | 4C,9G | 9G | 0 | 0 | 9C | 0 | 3C,8H | 0 | 3C,7H | 0 |
| SOYBEANS | 4C,9H | 2G | 4C,8G | 7G | 4C,8H | 4C,8H | 4C,7G | 5G | 3C,8H | 4G | 4C,8H | 3C,8G | 0 | 3C,4H | 3C,9H | 0 | 1C | 0 | 3C,6H | 2G |
| RICE | 4C,9H | 8G | 9C | 2C,8H | 3C,9H | 9H | 9H | 2C,8G | 10E | 9H | 10H | 9H | 0 | 7G | 10H | 3C,8G | 3C,8H | 0 | 10H | 2C,4G |
| SORGHUM | 10H | 5G | 9G | 3C,8H | 3C,9H | 3C,8H | 9H | 3C,8H | 4C,9H | 9H | 10H | 9H | 0 | 0 | 9H | 7H | 3C,8H | 0 | 3C,9H | 0 |
| CHEATGRASS | 8G | 2G | 3C,8G | 3G | 3C,8G | 8G | 8G | 7G | 5C,9H | 3C,8G | — | — | — | — | — | — | — | — | — | — |
| SUGARBEETS | 1C,3G | 3G | 2C,7G | 5G | 2C,8G | 2C,7G | 6C,9G | 6G | 3C,9G | 9G | 5C,9G | 4C,9G | 3H | 8G | 2C | 0 | 8G | 0 | 2C,3G | 2G |
| VELVETLEAF | 3C,8G | 6G | 3C,8G | 2C,7G | 4C,9G | 4C,8G | 4C,9G | 7G | 2C,8G | 0 | 3C,7H | 3C,6H | 0 | 6H | 4H | 0 | 2H | 0 | 0 | 0 |
| GIANT FOXTAIL | 3C,9H | 6G | 3C,9H | 9H | 2C,9H | 3C,9H | 3C,9H | 7G | 3G | 0 | 7G | 4G | 0 | 0 | 2C | 0 | 0 | 0 | 2C,4G | 0 |
| BARLEY | 8G | 2G | 3C,8G | 0 | 9G | 5G | 8G | 0 | 4G | 0 | 8G | 8G | 0 | 0 | 8G | 0 | 0 | 0 | 5G | 2G |
| DOWNY BROME | — | — | — | — | — | — | — | — | — | — | 9H | 9H | 0 | 0 | 7G | 0 | 3C,8H | 2G | 7G | 0 |

| RATE = KG/HA | CMPD 11 0.05 | CMPD 11 0.01 | CMPD 12 0.05 | CMPD 12 0.01 | CMPD 13 0.05 | CMPD 13 0.01 | CMPD 14 0.05 | CMPD 14 0.01 | CMPD 15 0.05 | CMPD 15 0.01 | CMPD 16 0.05 | CMPD 16 0.01 | CMPD 17 0.05 | CMPD 17 0.01 | CMPD 18 0.05 | CMPD 18 0.01 | CMPD 19 0.05 | CMPD 19 0.4 | CMPD 20 0.05 | CMPD 20 0.01 |
|---|---|---|---|---|---|---|---|---|---|---|---|---|---|---|---|---|---|---|---|---|
| | | | | | | | | | PREEMERGENCE | | | | | | | | | | | |
| COTTON | 0 | 0 | 2G | 0 | 7G | 4G | 0 | 0 | 4G | 0 | 0 | 0 | 0 | 0 | 0 | 0 | 0 | 0 | 6G | 7G |
| MORNINGGLORY | 1C | 0 | 1C | 0 | 9G | 2G | 0 | 0 | 2C,4G | 0 | 0 | 0 | 6G | 0 | 2G | 0 | 0 | 1C | 9G | 9G |
| COCKLEBUR | 0 | 0 | 2C,6H | 5G | 9H | 2G | 3C,8G | 0 | 3C,7H | 0 | 0 | 0 | 2C,8H | 2C,5G | 4C,8H | 0 | 0 | 0 | 8H | 7G |
| NUTSEDGE | 0 | 0 | 5G | 0 | 10E | 0 | 0 | 0 | 9G | 8G | 8G | 10E | 2G | 0 | 0 | 0 | 0 | 7G | 10E | 0 |
| CRABGRASS | 2C,4G | 0 | 2G | 0 | 3C,7G | 0 | 2C,6G | 0 | 5C,9G | 2C,6G | 0 | 0 | 6G | 0 | 2C,5G | 3G | 0 | 0 | 3C,9G | 0 |
| BARNYARDGRASS | 2C,6H | 0 | 0 | 0 | 4C,9H | 0 | 3G | 0 | 2C,6H | 0 | 0 | 0 | 2C,7H | 4G | 4C,8H | 0 | 0 | 2G | 9H | 5G |
| WILD OATS | 2C,6G | 0 | 2C,6G | 0 | 3C,6G | 2G | 0 | 0 | 2C,5G | 0 | 0 | 0 | 2C,5G | 0 | 5G | 0 | 0 | 0 | 3C,8G | 2C,7G |
| WHEAT | 8G | 0 | 7G | 0 | 8G | 4G | 2G | 0 | 3G | 0 | 0 | 0 | 8G | 0 | 8G | 6G | 0 | 0 | 3C,8G | 3G |
| CORN | 9G | 0 | 3C,7H | 0 | 4C,9G | 3G | 2C,5G | 2G | 4C,9G | 2C,3G | 0 | 0 | 3C,9G | 3C,7G | 3C,9G | 2C,4G | 0 | 2C,6G | 9G | 9G |
| SOYBEANS | 3C,8H | 0 | 2C,7G | 0 | 7G | 6G | 1C,4G | 2G | 3C,8H | 1C,2G | 1C | 0 | 3C,8H | 1C,2G | 2C,7G | 0 | 0 | 0 | 4C,8H | 2C,8G |
| RICE | 3C,8H | 0 | 9H | 3C,8H | 10H | 2C,8H | 10H | 3G | 4C,9H | 4C,8H | 2C,3G | 0 | 10E | 4C,9H | 10H | 4C,9H | 0 | 0 | 4C,8H | 8G |
| SORGHUM | 9H | 3C,7H | 9H | 8H | 4C,9H | 3C,8H | 3C,7H | 4G | 9H | 3G | 0 | 0 | 3C,8H | 3C,7H | 3C,9H | 3C,7H | 0 | 3C,7G | 9H | 9G |
| CHEATGRASS | — | — | — | — | 9G | 8G | 7G | 0 | 8H | 8G | 7G | 0 | 9H | 6H | 9H | 7G | 0 | 2G | — | — |
| SUGARBEETS | 2C,5H | 0 | 7H | 0 | 8G | 5G | 9G | 0 | 2C,5G | 5G | 0 | 0 | 2G | 3G | 5C,9G | 4H | 0 | 7G | 9G | 2C |

TABLE A-continued

| | | | | | | | | | | | | | | | | | | | | |
|---|---|---|---|---|---|---|---|---|---|---|---|---|---|---|---|---|---|---|---|---|
| VELVETLEAF | 0 | 0 | 6H | 0 | 3C,8H | 2C,4G | 0 | 0 | 2C,7G | 3H | 0 | 0 | 2C,6H | 0 | 0 | 0 | 0 | 2C,4G | 3C,9G | 7G |
| GIANT FOXTAIL | 5G | 0 | 3C,9H | 2G | 4C,9H | 7G | 5G | 0 | 7G | 2G | 0 | 0 | 2G | 0 | 0 | 0 | 0 | 0 | 3C,9H | 0 |
| BARLEY | 8G | 0 | 0 | 0 | 4G | 4G | 0 | 3G | 8G | 2G | 2G | 0 | 7G | 6G | 6G | 0 | 0 | 5G | 8G | 0 |
| DOWNY BROME | 7G | 0 | 8H | 5G | — | — | — | — | — | — | — | — | — | — | — | — | — | — | 9H | 8G |

| | CMPD 21 | | CMPD 22 | | CMPD 23 | | CMPD 24 | | CMPD 25 | | CMPD 26 | | CMPD 27 | | CMPD 28 | | CMPD 29 | | CMPD 30 | |
|---|---|---|---|---|---|---|---|---|---|---|---|---|---|---|---|---|---|---|---|---|
| RATE = KG/HA | 0.05 | 0.01 | 0.05 | 0.01 | 0.05 | 0.01 | 0.05 | 0.4 | 0.05 | 0.01 | 0.05 | 0.01 | 0.05 | 0.01 | 0.05 | 0.01 | 0.05 | 0.01 | 0.05 | 0.01 |
| | | | | | | | | | PREEMERGENCE | | | | | | | | | | | |
| COTTON | 0 | 0 | 0 | 0 | 8G | 8G | 0 | 8G | 7G | 5G | 6G | 0 | 0 | 0 | 0 | 0 | 7G | 0 | 0 | 0 |
| MORNINGGLORY | 7G | 0 | 8G | 6G | 9G | 9G | 0 | 8G | 9G | 3G | 8H | 7G | 5G | 0 | 0 | 0 | 3G | 0 | 0 | 0 |
| COCKLEBUR | 2C,2H | 0 | 3C,8H | 2G | 8H | 7H | 0 | 2C,6H | 3C,5H | 5H | 7H | 6G | 4G | 0 | 0 | 0 | 2C,3G | 0 | 0 | 0 |
| NUTSEDGE | 0 | 0 | 0 | 0 | 9G | 7G | 0 | 0 | 0 | 0 | 10E | 0 | 0 | 0 | 0 | 0 | 0 | — | 0 | 0 |
| CRABGRASS | 4C,9G | 0 | 5C,9G | 3C,6G | 5C,9G | 4C,8G | 0 | 0 | 3C,8G | 2C,6G | 7G | 0 | 2C,5G | 0 | 4G | 0 | 2G | 0 | 0 | 0 |
| BARNYARDGRASS | 6H | 4G | 4C,8H | 2C,5H | 5C,9H | 7H | 0 | 0 | 9H | 3H | 0 | 0 | 3C,8H | 0 | 2H | 0 | 2C,7H | 0 | 0 | 0 |
| WILD OATS | 2G | 0 | 3C,8G | 2C,4G | 3C,8G | 3C,6G | 0 | 0 | 8G | 3G | 7G | 0 | 2G | 0 | 3G | 0 | 2C,7G | 0 | 2G | 0 |
| WHEAT | 0 | 0 | 9G | 8G | 3C,9G | 8G | 0 | 5G | 8G | 4G | 4G | 0 | 8G | 0 | 0 | 0 | 8G | 0 | 4G | 0 |
| CORN | 3C,8H | 0 | 3C,9G | 4G | 9C | 9G | 0 | 4C,6G | 5C,9G | 3C,8H | 5C,9H | 5G | 0 | 0 | 3C,6H | 0 | 3C,7G | 0 | 2C,8H | 2G |
| SOYBEANS | 3C,6G | 1C,2G | 9H | 3C,7H | 9H | 3C,7G | 3G | 3C,8H | 9H | 3C,3H | 7H | 3G | 2C,4G | 3G | 3C,5H | 1C,3G | 8H | 0 | 3C,3H | 0 |
| RICE | 8G | 8G | 5C,9H | 3C,8G | 10H | 9H | 2G | 7H | 10H | 9H | 10H | 8H | 3C,8H | 2G | 6H | 2G | 3C,9G | 6G | 4G | 0 |
| SORGHUM | 8H | 7G | 9H | 9G | 10H | 9H | 0 | 3C,4G | 3C,9H | 9H | 10H | 8H | 3C,8H | 0 | 3C,8H | 0 | 9G | 6G | 3C,9H | 2C,5G |
| CHEATGRASS | — | — | — | — | — | — | — | — | — | — | — | — | 7G | 0 | 8G | 0 | 8G | 0 | 6G | 0 |
| SUGARBEETS | 2C,2G | 0 | 2C,3H | 2H | 3C,9G | 3H | 2G | 6G | 9G | 9G | 9G | 6H | 2H | 0 | 2C,4G | 0 | 3G | 2G | 3G | 0 |
| VELVETLEAF | 2C,6H | 0 | 0 | 0 | 6H | 6H | 0 | 7H | 9G | 6H | 7H | 1H | 2G | 0 | 0 | 0 | 2G | 0 | 2G | 0 |
| GIANT FOXTAIL | 6G | 0 | 4G | 0 | 7G | 2G | 0 | 0 | 3C,9G | 2C,7G | 6G | 2G | 8G | 0 | 2C,6G | 2G | 5G | 0 | 3G | 0 |
| BARLEY | 0 | 0 | 8G | 8G | 8G | 3G | 0 | 0 | 3C,7G | 2C,3G | 0 | 0 | 7G | 2G | 5G | 0 | 3C,7G | 0 | 2C,4G | 0 |
| DOWNY BROME | 5G | 0 | 3C,8G | 6G | 9H | 7G | 0 | 0 | 9H | 8G | 9G | 8G | — | — | — | — | — | — | — | — |

| | CMPD 31 | | CMPD 32 | | CMPD 33 | | CMPD 34 | | CMPD 35 | | CMPD 36 | | CMPD 37 | | CMPD 38 | | CMPD 39 | | CMPD 40 | | CMPD 41 | |
|---|---|---|---|---|---|---|---|---|---|---|---|---|---|---|---|---|---|---|---|---|---|---|
| RATE = KG/HA | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 |
| | | | | | | | | | PREEMERGENCE | | | | | | | | | | | | | |
| COTTON | 2G | 0 | 4G | 0 | 0 | 0 | 2G | 0 | 0 | 0 | 0 | 0 | 0 | 0 | 0 | 0 | 2G | 0 | 8G | 5G | 0 | 0 |
| MORNINGGLORY | 3G | 0 | 4G | 2G | 2G | 0 | 2G | 0 | 0 | 0 | 0 | 0 | 0 | 0 | 0 | 0 | 3G | 0 | 5G | 2C,4G | 2C,2G | 0 |
| COCKLEBUR | 0 | 0 | 9H | 0 | 2H | 0 | 5G | 0 | 8G | 2G | 0 | 0 | 0 | 0 | 0 | 0 | 3G | 0 | 3C,6H | — | 2C,2G | 0 |
| NUTSEDGE | 8G | 0 | 0 | 0 | 0 | 0 | 0 | 0 | 0 | 0 | 0 | 0 | 0 | 0 | 0 | 0 | 10E | 0 | 10E | 10E | 10E | 0 |
| CRABGRASS | 0 | 0 | 3C,7G | 0 | 0 | 0 | 0 | 0 | 0 | 0 | 0 | 0 | 0 | 0 | 0 | 0 | 2C | 0 | 4C,9G | 2C,4G | 3C,5G | 0 |
| BARNYARDGRASS | 3C,8H | 6H | 0 | 0 | 0 | 0 | 0 | 0 | 0 | 0 | 0 | 0 | 0 | 0 | 0 | 0 | 0 | 0 | 3C,9H | 3C,5G | 3C,7G | 0 |
| WILD OATS | 1C | 0 | 2G | 0 | 0 | 0 | 2G | 0 | 0 | 0 | 0 | 0 | 0 | 0 | 0 | 0 | 0 | 0 | 9G | 3C,7G | 6G | 0 |
| WHEAT | 4G | 2G | 5G | 2G | 3G | 0 | 5G | 0 | 5G | 0 | 2C,8G | 0 | 0 | 0 | 3G | 0 | 0 | 0 | 2C,9G | 6G | 7G | 2C,5G |
| CORN | 3C,8H | 0 | 2G | 2G | 0 | 0 | 0 | 0 | 2C,7G | 0 | 2G | 0 | 0 | 0 | 2G | 0 | 0 | 0 | 3C,9G | 3C,4G | 3C,8G | 0 |
| SOYBEANS | 2G | 0 | 3C,8H | 2C,5G | 2C,4G | 0 | 2C,7G | 0 | 3C,5H | 0 | 0 | 0 | 0 | 0 | 3C,3G | 0 | 3C,7H | 0 | 3C,8H | 8G | 3C,7H | 1C |
| RICE | 8G | 3C,3G | 3C,7G | 2G | 2G | 0 | 0 | 0 | 8G | 0 | 7G | 0 | 0 | 0 | 2C,5G | 0 | 2C,5G | 0 | 9H | 3C,9H | 9H | 8H |
| SORGHUM | 9H | 3C,5G | 3C,7G | 0 | 2C,2G | 0 | 0 | 0 | 2C | 0 | 1C | 0 | 0 | 0 | 2C | 0 | 2C,4G | 0 | 5C,9H | 3C,7H | 9H | 3C,5G |
| CHEATGRASS | 8G | 4G | — | — | — | — | — | — | — | — | — | — | — | — | — | — | — | — | — | — | — | — |
| SUGARBEETS | 0 | 2H | 8G | 2G | 5G | 0 | 8G | 0 | 0 | 0 | 2G | 0 | 0 | 0 | 2H | 0 | 3H | 0 | 4C,9G | 7G | 3C,3H | 2G |
| VELVETLEAF | 2H | 0 | 4H | 0 | 2H | 0 | 1C | 0 | 0 | 0 | 0 | 0 | 0 | 0 | 0 | 0 | 0 | 0 | 3H | 0 | 0 | 0 |
| GIANT FOXTAIL | 7G | 0 | 3C,8G | 0 | 0 | 0 | 0 | 0 | 0 | 0 | 0 | 0 | 0 | 0 | 0 | 0 | 0 | 0 | 9H | 3C,5G | 5G | 0 |
| BARLEY | 3G | 0 | 9G | 4G | 2G | 0 | 7G | 0 | 2G | 0 | 0 | 0 | 0 | 0 | 3G | 0 | 0 | 0 | 3C,9G | 2C,8G | 6G | 5G |
| DOWNY BROME | — | — | 5G | 0 | 3G | 0 | 2G | 0 | 4G | 0 | 0 | 0 | 0 | 0 | 2G | 0 | 3G | 0 | 9H | 8G | 7G | 3G |

| | CMPD 42 | | CMPD 43 | | CMPD 44 | | CMPD 45 | | CMPD 46 | | CMPD 47 | | CMPD 48 | | CMPD 49 | | CMPD 50 | | CMPD 51 | |
|---|---|---|---|---|---|---|---|---|---|---|---|---|---|---|---|---|---|---|---|---|
| RATE = KG/HA | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 |
| | | | | | | | | | PREEMERGENCE | | | | | | | | | | | |

TABLE A-continued

| COTTON | 2C,8H | 2C | 0 | 0 | 3C,8H | 1C | 3C,4G | 0 | 2C,4G | 2G | 9G | 0 | 9G | 3G | 9G | 7G | 9G | 2G | 9G | 6G |
|---|---|---|---|---|---|---|---|---|---|---|---|---|---|---|---|---|---|---|---|---|
| MORNINGGLORY | 8H | 3C,5H | 2C,2H | 0 | 3C,9G | 3C,5H | 3C,5H | 0 | 3C,5H | 0 | 9G | 8G | 3C,9G | 5G | 3C,9G | 4G | 9G | 7G | 9G | 9G |
| COCKLEBUR | 8H | 3C,3H | 2C | 0 | 9H | 2C,3H | 7H | 3C,3G | 3C,2H | 0 | 3C,7H | 7G | 2G | 2G | 3C,7H | 3G | 8H | 7G | 9G | 3C,7G |
| NUTSEDGE | 10E | 0 | 10E | 0 | 10E | 10E | 0 | 0 | 10E | 0 | 8G | 0 | 4G | 0 | 5G | 0 | 10E | 0 | 7G | 10E |
| CRABGRASS | 4C,9G | 3C,5G | 3G | 0 | 5C,9G | 3C,7G | 5C,9G | 4C,8G | 3C,7G | 3G | 4C,9H | 2C,7H | 3C,8H | 4G | 5C,9H | 2C,7H | 5C,9H | 3C,8H | 5C,9H | 3C,9H |
| BARNYARDGRASS | 3C,6G | 2C | 0 | 0 | 3C,8H | 0 | 9H | 3C,8H | 3C,5H | 3H | 3C,9H | 2G | 3C,8H | 2G | 9H | 0 | 5C,9H | 2C,6H | 5C,9H | 3C,9H |
| WILD OATS | 2C,8G | 2C,6G | 0 | 0 | 3C,8G | 5G | 3C,8H | 3C,7G | 3C,7H | 0 | 8G | 2G | 2G | 0 | 2C,6G | 0 | 3C,7G | 0 | 3C,8G | 4G |
| WHEAT | 2C,8H | 6G | 2G | 0 | 9H | 8H | 9H | 3C,8H | 3C,8H | 3G | 9H | 2G | 4G | 0 | 8G | 2G | 3C,9G | 5G | 3C,9H | 7G |
| CORN | 3C,9G | 3C,3G | 2C | 0 | 4C,9H | 3C,7H | 10H | 3C,9H | 9H | 3C,5G | 3C,9G | 3C,6H | 3C,8H | 2C,6G | 3C,9H | 2C,6H | 4C,8H | 3C,7G | 5C,9H | 2C,4H |
| SOYBEANS | 3C,8H | 3C,6H | 3C,3H | 0 | 4C,8H | 3C,7H | 3C,7G | 4C,6G | 3C,8G | 3C,6G | 3C,8H | 4G | 2C,7G | 6G | 9H | 2C,6G | 3C,8G | 2C,2G | 9H | 3C,6G |
| RICE | 3C,9H | 3C,7G | 5G | 0 | 10H | 10H | 10E | 10E | 9H | 5G | 5C,9H | 2G | 3C,9H | 5G | 4C,8H | 5G | 9H | 6G | 6C,9H | 3C,8H |
| SORGHUM | 3C,9H | 3C,6G | 2C,3G | 0 | 9H | 3C,7H | 9H | 4C,8H | 3C,9H | 7G | 9H | 3C,7H | 9H | 4G | 3C,9H | 2C,3G | 3C,9H | 3C,7G | 4C,9H | 4C,9H |
| CHEATGRASS | — | — | — | — | — | — | — | — | — | — | 3C,9G | 7G | 6G | 4G | 3C,8G | 3G | 4C,9G | 3G | 4C,9G | 3C,8G |
| SUGARBEETS | 5C,9G | 4C,7H | 6G | 0 | 5C,9G | 5H | 8H | 4H | 3C,5H | 0 | 4C,9G | 5G | 2C,6G | 5G | 4C,9G | 4G | 4C,9G | 7G | 9G | 8G |
| VELVETLEAF | 4C,8H | 3C,3G | 2C,5G | 0 | 6H | 0 | 2C,2H | 0 | 5H | 0 | 3C,8G | 7G | 3C,8G | 6G | 4C,9G | 6G | 4C,8G | 0 | 4C,9G | 2G |
| GIANT FOXTAIL | 4C,9G | 5G | 3G | 0 | 3C,4G | 0 | 3C,7G | 3G | 3C,8H | 0 | 3C,9H | 5G | 2C,6H | 3G | 4C,9H | 6H | 3C,9H | 2G | 4C,9H | 3H |
| BARLEY | 3C,8G | 7G | 3G | 0 | 3C,9H | 7G | 9H | 3C,8H | 3C,7G | 4G | 6G | 0 | 7G | 2G | 5G | 5G | 8G | 0 | 8G | 2G |
| DOWNY BROME | 9H | 7G | 3G | 0 | 9H | 7G | 9H | 8G | 8H | 4G | — | — | — | — | — | — | — | — | — | — |

| | CMPD 52 | | CMPD 53 | | CMPD 54 | | CMPD 55 | | CMPD 56 | | CMPD 57 | | CMPD 58 | | CMPD 59 | | CMPD 60 | | CMPD 61 | |
|---|---|---|---|---|---|---|---|---|---|---|---|---|---|---|---|---|---|---|---|---|
| RATE = KG/HA | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 |
| | | | | | | | | | PREEMERGENCE | | | | | | | | | | | |
| COTTON | 0 | 0 | 4G | 0 | 9G | 3G | 4G | 0 | 9G | 7G | 9G | 8G | 8G | 2G | 8G | 7G | 7G | 6G | 9G | 6G |
| MORNINGGLORY | 2C,3G | 2G | 2G | 0 | 9G | 5G | 8H | 0 | 9G | 2C,6G | 9G | 7G | 5G | 4G | 9G | 8G | 9G | 6G | 9G | 9G |
| COCKLEBUR | 2G | 0 | 6G | 2G | 5G | 2G | 9H | 0 | 5H | 1H | 9H | 6H | 2G | 1H | 7H | 0 | 5G | 3G | 5H | 6G |
| NUTSEDGE | 4G | 10E | 10E | 0 | 5G | 0 | 0 | 0 | 9G | 0 | 3C,7G | 0 | 0 | 0 | 5G | 0 | 10E | 0 | 9G | 0 |
| CRABGRASS | 2C,8H | 2G | 2C,5G | 0 | 3C,9G | 7G | 2C,8H | 0 | 3C,9H | 5G | 2C,8G | 4G | 3C,8G | 5G | 4C,9G | 3C,8G | 6G | 3G | 8G | 3G |
| BARNYARDGRASS | 4G | 2G | 2C,5H | 0 | 9H | 0 | 7H | 0 | 3G | 0 | 3G | 0 | 7G | 0 | 9H | 2C,6G | 8G | 3G | 8H | 1H |
| WILD OATS | 0 | 0 | 0 | 0 | 6G | 2G | 0 | 0 | 3C,6G | 0 | 6G | 0 | 0 | 0 | 3C,3G | 0 | 6G | 2G | 6G | 2G |
| WHEAT | 2G | 0 | 0 | 0 | 7G | 2G | 0 | 0 | 8G | 0 | 6G | 0 | 8H | 2G | 8G | 7G | 8G | 4G | 9G | 5G |
| CORN | 3C,6H | 0 | 2G | 0 | 3C,9H | 3C,5G | 3C,7H | 0 | 3C,9G | 3C,5H | 3C,9H | 3C,6G | 3C,6H | 2G | 3C,9H | 3C,3H | 2C,9G | 3C,7G | 2C,9H | 3C,7H |
| SOYBEANS | 2G | 0 | 3G | 0 | 8H | 6H | 2H | 0 | 9H | 2G | 8H | 5H | 3C,7H | 2G | 4C,8H | 5G | 9H | 4G | 9H | 3C,5H |
| RICE | 2C,7H | 0 | 0 | 0 | 9H | 7G | 9G | 0 | 10H | 2G | 9H | 8H | 8G | 2G | 9G | 8G | 9H | 8G | 3C,9G | 7G |
| SORGHUM | 3C,9H | 0 | 3C,7H | 2C,5G | 3C,9H | 2C,8G | 9H | 2C,5G | 3C,9H | 3C,7G | 3C,9H | 3C,8H | 3C,8G | 2C,7G | 3C,9G | 3C,7G | 2C,9H | 3C,7G | 4C,9G | 3C,4G |
| CHEATGRASS | 2C,7G | 0 | 6G | 0 | 7G | 4G | 0 | 0 | 7G | 4G | 7G | 2G | 5G | 0 | 7G | 4G | 9G | 2G | 7G | 3G |
| SUGARBEETS | 3C,8G | 2G | 3G | 0 | 3C,7G | 2H | 5G | 0 | 6G | 2G | 3C,7G | 6G | 4C,9G | 0 | 3C,8G | 4G | 9G | 6G | 9G | 5H |
| VELVETLEAF | 6G | 2G | 10E | 3G | 9G | 3G | 8H | 0 | 7G | 5H | 8G | 5H | 2G | 0 | 7H | 3G | 9G | 6G | 2C,8G | 8H |
| GIANT FOXTAIL | 3C,8H | 6H | 2C,7H | 0 | 3G | 0 | 5G | 0 | 3C,6G | 3G | 3C,7G | 3G | 3G | 0 | 7G | 2G | 8G | 3G | 8H | 3G |
| BARLEY | 6G | 0 | 2G | 0 | 2C,6G | 4G | 7G | 0 | 4G | 0 | 4G | 0 | 3C,7G | 2G | 2C,7G | 1C | 7G | 3G | 8G | 5G |
| DOWNY BROME | — | — | — | — | — | — | — | — | — | — | — | — | — | — | — | — | — | — | — | — |

| | CMPD 62 | | CMPD 63 | | CMPD 64 | | CMPD 65 | | CMPD 66 | | CMPD 67 | | CMPD 68 | | CMPD 69 | | CMPD 70 | | CMPD 71 | |
|---|---|---|---|---|---|---|---|---|---|---|---|---|---|---|---|---|---|---|---|---|
| RATE = KG/HA | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 |
| | | | | | | | | | PREEMERGENCE | | | | | | | | | | | |
| COTTON | 7G | 4G | 9G | 9G | 9G | 2C,2G | 9G | 8G | 9G | 9G | 9G | 3G | 8G | 2G | 2G | 0 | 5G | 0 | 0 | 0 |
| MORNINGGLORY | 9G | 3G | 9G | 9G | 3C,9H | 2G | 9G | 7G | 9G | 8G | 9G | 8G | 8G | 2G | 0 | 0 | 8G | 2C,8G | 4G | 2G |
| COCKLEBUR | 3H | 3G | 6G | 6G | 8H | 2C,5G | 9G | 3G | 9H | 8H | 0 | 0 | 2G | 0 | 0 | 0 | — | 0 | 3G | 3G |
| NUTSEDGE | 10E | 0 | 2G | — | 9G | 9G | 7G | 7G | 9G | 4G | 0 | — | 7G | 4G | 0 | 0 | 10E | 0 | 0 | 0 |
| CRABGRASS | 7G | 2G | 2C,3G | 0 | 0 | 0 | 7G | 0 | 4C,8G | 7G | 5G | 2G | 2C,7H | 2G | 0 | 0 | 5G | 3G | 2G | 0 |
| BARNYARDGRASS | 8H | 4G | 4C,9H | 3C,7H | 3C,8H | 2C,6H | 2C,7H | 5H | 3C,8H | 2C,4G | 2C,8H | 4G | 3H | 2H | 2G | 0 | 3C,6H | 2G | 0 | 2G |
| WILD OATS | 5G | 3G | 3G | 0 | 3C,6G | 3G | 3C,7G | 4G | 4C,8H | 3C,6G | 2C,6G | 2G | 3G | 0 | 2C,3G | 0 | 2C,2G | 0 | 0 | 0 |
| WHEAT | 8H | 8G | 3C,9G | 8G | 3C,8G | 2C,8G | 8G | 4G | 4C,8H | 3C,7G | 6G | 0 | 4G | 0 | 0 | 0 | 5G | 0 | 0 | 0 |

TABLE A-continued

| | | | | | | | | | | | | | | | | | | | | |
|---|---|---|---|---|---|---|---|---|---|---|---|---|---|---|---|---|---|---|---|---|
| CORN | 3C,9H | 2C,3G | 9G | 3C,6G | 4C,9G | 4C,8G | 3C,9H | 2C,9G | 9H | 4C,9G | 3C,9H | 3C,6G | 2C,9G | 2C,4G | 2C,3G | 0 | 3C,9G | 2C,3G | 0 | 0 |
| SOYBEANS | 9H | 3C,8H | 9H | 9H | 9H | 4C,6G | 9H | 1C | 9H | 9H | 9H | 2C,5G | 9H | 2C,5G | 2C,5H | 0 | 8H | 5G | 3G | 0 |
| RICE | 4C,9H | 2C,8H | 10H | 4C,9H | 9H | 8H | 4C,9H | 3C,9H | 10H | 4C,9G | 9H | 3C,7H | 10H | 2C,4H | 7G | 0 | 10H | 3G | 0 | 3G |
| SORGHUM | 4C,9H | 3C,5G | 3C,9H | 4C,8H | 5C,9H | 4C,7H | 3C,9H | 2G | 5C,9G | 4C,9H | 9H | 5G | 3C,7H | 0 | 2G | 0 | 4C,9H | 2G | 2G | 0 |
| CHEATGRASS | 8H | 5G | 3C,8G | 7G | 9G | 8G | 3C,7G | 2C,8G | 9H | 3C,7G | 3C,8G | 2G | 6G | 4G | 5G | 0 | 8H | 0 | 0 | 0 |
| SUGARBEETS | 3C,9G | 7G | 9G | 7G | 9G | 7G | 3C,9G | 6G | 5C,9G | 5C,9G | 9G | 3G | 2C,8G | 3G | 2H | 0 | 5G | 0 | 0 | 0 |
| VELVETLEAF | 6H | 2G | 6G | 2G | 4C,8G | 2C,5H | 3C,9G | 2C,7G | 5C,9G | 4C,8H | 8G | 3G | 2C,7G | 0 | 0 | 0 | 0 | 0 | 2G | 0 |
| GIANT FOXTAIL | 6H | 2G | 2C,7G | 3G | 3C,8H | 2C,6G | 8G | 3G | 3C,8G | 3C,7G | 2C,9H | 7G | 3C,8H | 5H | 2G | 0 | 2C,7G | 3G | 5G | 2G |
| BARLEY | 9G | 6G | 9G | 8G | 8G | 8G | 9G | 6G | 9H | 9G | 8G | 3G | 6G | 0 | 0 | 0 | 2C,4G | 0 | 0 | 0 |
| DOWNY BROME | — | — | — | — | — | — | — | — | — | — | — | — | — | — | — | — | — | — | — | — |

| | CMPD 72 | | CMPD 73 | | CMPD 74 | | CMPD 75 | | CMPD 76 | | CMPD 77 | | CMPD 78 | | CMPD 79 | | CMPD 80 | | CMPD 81 | |
|---|---|---|---|---|---|---|---|---|---|---|---|---|---|---|---|---|---|---|---|---|
| RATE = KG/HA | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 |
| PREEMERGENCE | | | | | | | | | | | | | | | | | | | | |
| COTTON | 8G | 5G | 3G | 0 | 8G | 7G | 8G | 2G | 9G | 2G | 9G | 8G | 5G | 0 | 3G | 0 | 8G | 4G | 8G | 7G |
| MORNINGGLORY | 8G | 6G | 9G | 4G | 9G | 4G | 8G | 0 | 9G | 4G | 9H | 9G | 3G | 0 | 6G | 2G | 8G | 6G | 8G | 2H |
| COCKLEBUR | 6H | 6G | 3H | 4G | 8H | 3G | 8H | 0 | 7H | 3G | 9H | 5G | 3G | 0 | 0 | 0 | 3C,6G | 2G | 8H | 0 |
| NUTSEDGE | 9G | 5G | 9G | 10E | 10E | 3G | 10E | 0 | 9G | 0 | 5G | 6G | 0 | 0 | 10E | — | 9G | 0 | 9G | 3G |
| CRABGRASS | 8G | 6G | 2C,8G | 6G | 4C,9G | 7G | 5C,9G | 5G | 3C,8G | 3C,6G | 4C,9H | 5C,9G | 3C,6G | 0 | 4G | 0 | 9G | 8H | 4C,9H | 8G |
| BARNYARDGRASS | 3C,8H | 3C,5G | 9H | 6G | 8H | 3C,7G | 6H | 0 | 9H | 3C,6G | 9H | 3C,7H | 3C,7H | 0 | 5G | 0 | 3C,8H | 2H | 3C,9H | 3C,7H |
| WILD OATS | 2C,8G | 3G | 0 | 0 | 3C,6G | 3G | 3C,7G | 0 | 3C,7G | 0 | 3C,8G | 3C,6G | 0 | 0 | 5G | 0 | 2C,8G | 3C,7G | 4C,8G | 3C,3G |
| WHEAT | 2C,9G | 3G | 0 | 0 | 2C,8G | 2G | 3C,7G | 0 | 3C,8G | 0 | 3C,9G | 4C,9G | 0 | 0 | 2G | 0 | 2C,8G | 5G | 8G | 2C,8H |
| CORN | 2U,9G | 3C,8H | 4C,9G | 3C,6G | 3C,9G | 9G | 4C,9H | 3C,8G | 4C,9G | 2C,8G | 9H | 4C,9G | 3C,8G | 0 | 3C,7G | 2C,3G | 9G | 3C,8G | 2U,9G | 3C,8H |
| SOYBEANS | 3C,9H | 2C,7G | 3C,6H | 3G | 9H | 3C,5H | 4C,9H | 1H | 9H | 3C,7H | 9H | 4C,8H | 2C,2G | 0 | 3H | 2G | 3C,8H | 3C,7G | 3C,9H | 3C,7H |
| RICE | 4C,9H | 4C,8G | 9H | 8G | 9H | 3C,9H | 9H | 9H | 10E | 9H | 10E | 10H | 8H | 2G | 4G | 0 | 4C,9G | 7G | 3C,9G | 3C,8G |
| SORGHUM | 9G | 3C,8G | 4C,9H | 2C,8G | 4C,9H | 3C,8H | 5C,9H | 2C,9G | 3C,9H | 3C,8H | 10H | 4C,9H | 9G | 2G | 3C,8G | 0 | 9G | 3C,9G | 2C,9G | 3C,8H |
| CHEATGRASS | 4C,8G | 5G | 7G | 4G | 9H | 8H | 9H | 6G | 9H | 2C,8G | 9H | 9G | 7G | 0 | 7G | 2G | 3C,8G | 6G | 5C,9G | 8G |
| SUGARBEETS | 9G | 7G | 5G | 3G | 5C,9G | 3H | 9G | 8G | 8G | 8G | 4C,9G | 7G | 5G | — | 4G | 3G | 9G | 0 | 6G | 0 |
| VELVETLEAF | 4C,9G | 1H | 5H | 2G | 4C,9G | 3H | 3C,8G | 1H | 3C,8H | 2H | 7H | 7G | 1H | 0 | 5G | 0 | 6G | 0 | 2H,5G | 0 |
| GIANT FOXTAIL | 3C,8H | 6G | 2C,7G | 0 | 4C,8H | 6G | 3C,9H | 4G | 3C,8G | 2G | 3C,8G | 3C,6G | 3C,8G | 0 | 5G | 0 | 3C,9H | 7G | 3C,9H | 3C,9G |
| BARLEY | 4C,8G | 1C | 2C,3G | 0 | 9G | 4G | 3C,7G | 0 | 3C,9G | 2C,2G | 9H | 3C,5G | 2C,2G | 0 | 2C,3G | 0 | 2C,7G | 2C,2G | 2C,8G | 3C,7H |
| DOWNY BROME | — | — | — | — | — | — | — | — | — | — | — | — | — | — | — | — | — | — | — | — |

| | CMPD 82 | | CMPD 83 | | CMPD 84 | | CMPD 85 | | CMPD 86 | | CMPD 87 | | CMPD 88 | | CMPD 89 | | CMPD 90 | | CMPD 91 | |
|---|---|---|---|---|---|---|---|---|---|---|---|---|---|---|---|---|---|---|---|---|
| RATE = KG/HA | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 8.05 | 0.01 | 0.05 | 0.01 |
| PREEMERGENCE | | | | | | | | | | | | | | | | | | | | |
| COTTON | 8G | 5G | 6G | 5G | 5G | 2G | 3C,8G | 4G | 5G | 0 | 2C,8G | 6G | 3C,8H | 2C,5G | 3G | 0 | 0 | 0 | 0 | 0 |
| MORNINGGLORY | 9G | 2G | 1C | 3G | 0 | 0 | 3C,5G | 0 | 0 | 0 | 3C,5G | 2G | 2C,8H | 0 | 0 | 0 | 1C | 0 | 0 | 0 |
| COCKLEBUR | 7H | 0 | 2C,5G | 0 | 0 | 0 | 3C,6H | — | 2C,5G | 0 | 3C,4G | 0 | 3C,6H | 1C | 0 | 0 | 0 | 0 | 0 | 0 |
| NUTSEDGE | 8G | 0 | 9G | 0 | 5G | 0 | 2C | 0 | 0 | 0 | 0 | 0 | 2C | 0 | 0 | 0 | 0 | 0 | 0 | 0 |
| CRABGRASS | 9H | 8G | 3G | 0 | 2G | 0 | 2C,8G | 0 | 5G | 0 | 3G | 0 | 2C,8G | 3G | 0 | 0 | 0 | 0 | 0 | 0 |
| BARNYARDGRASS | 9H | 3C,8H | 8H | 8H | 7G | 0 | 4C,9H | 2H | 2C,3G | 0 | 1C | 0 | 3C,8G | 2C,3G | 0 | 0 | 0 | 0 | 0 | 0 |
| WILD OATS | 4C,9G | 2C,7G | 2C,8G | 4G | 2G | 0 | 3C,7G | 2G | 2C,4G | 0 | 3C,5G | 2G | 3C,6G | 2G | 0 | 0 | 0 | 0 | 0 | 0 |
| WHEAT | 3C,9H | 2C,7G | 6G | 2G | 0 | 0 | 2C,8G | 5G | 4G | 2G | 2C,8G | 7G | 3C,9G | 7G | 0 | 0 | 0 | 0 | 0 | 0 |
| CORN | 3C,9G | 3C,7G | 3C,8G | 0 | 3C,7G | 2G | 2C,8G | 3G | 2G | 0 | 4C,9G | 3C,5G | 3C,9G | 3C,7G | 0 | 0 | 0 | 0 | 0 | 0 |
| SOYBEANS | 4C,9G | 2C,5G | 6H | 3C,5G | 2C,2H | 0 | 3C,7H | 3C,5H | 3C,6H | 1C,2H | 3C,8H | 2C,7H | 4C,9G | 3C,5H | 2H | 0 | 1C,1H | 0 | 0 | 0 |
| RICE | 9H | 3C,9G | 9H | 9G | 9G | 7G | 4C,9G | 8G | 3C,4G | 3G | 5C,9G | 4C,8G | 10E | 9H | 0 | 0 | 2C | 0 | 0 | 0 |
| SORGHUM | 4C,9G | 3C,8H | 9G | 9G | 3C,9G | 2C,6G | 3C,9G | 3C,7G | 3C,8H | 2C,3G | 9G | 4C,8G | 4C,9G | 3C,9G | 0 | 0 | 5G | 0 | 0 | 0 |
| CHEATGRASS | 3C,9G | 8G | 8G | 7G | 4G | 0 | 8G | 8G | 6G | 0 | 8G | 3G | 9H | 8G | 0 | 0 | 0 | 0 | 0 | 0 |
| SUGARBEETS | 4C,9G | 0 | 5G | 9G | 6G | 2G | 5H | 0 | 4H | 0 | 8G | 3C,7G | 7H | 2H | 3G | 0 | 2H | 0 | 0 | 0 |
| VELVETLEAF | 6H | 0 | 7H | 1H | 2G | 0 | 7H | 2H | 2C | 0 | 2C,2H | 2H | 3C,6H | 0 | 0 | 0 | 1H | 0 | 0 | 0 |
| GIANT FOXTAIL | 3C,8G | 3G | 5G | 4G | 2G | 0 | 3C,8G | 0 | 4G | 0 | 3C,7G | 0 | 3C,8G | 2C | 0 | 0 | 0 | 0 | 0 | 0 |

TABLE A-continued

| | | | | | | | | | | | | | | | | | | | | |
|---|---|---|---|---|---|---|---|---|---|---|---|---|---|---|---|---|---|---|---|---|
| BARLEY | 3C,9G | 3C,4G | 8G | 0 | 3G | 0 | 3C,8G | 7G | 5G | 0 | 4C,9G | 7G | 9G | 2C,7G | 0 | 0 | 0 | 0 | 0 | 0 |
| DOWNY BROME | — | — | — | — | — | — | — | — | — | — | — | — | — | — | — | — | — | — | — | — |

| | CMPD 92 | | CMPD 93 | | CMPD 94 | | CMPD 95 | | CMPD 96 | | CMPD 97 | | CMPD 98 | |
|---|---|---|---|---|---|---|---|---|---|---|---|---|---|---|
| RATE = KG/HA | 0.05 | 0.01 | 0.05 | 0.01 | 0.05 | 0.01 | 0.05 | 0.01 | 0.05 | 0.01 | 0.05 | 0.01 | 0.05 | 0.01 |
| | PREEMERGENCE | | | | | | | | | | | | | |
| COTTON | 0 | 0 | 0 | 0 | 0 | 0 | 2C,9G | 6G | 2C,5G | 2G | 2C,7G | 0 | 1C | — |
| MORNINGGLORY | 2G | 0 | 0 | 0 | 0 | 0 | 3C,8H | 2C,3G | 7H | 0 | 3C,7H | 2G | 2C,5G | 0 |
| COCKLEBUR | 0 | 0 | 0 | 0 | 0 | 0 | 9H | — | 2C,7H | 2C | 3C,5H | 1H | 1C,1H | 0 |
| NUTSEDGE | 0 | 0 | 0 | 0 | 5G | 0 | 0 | 0 | 8G | — | 0 | 0 | 10E | 0 |
| CRABGRASS | 3G | 0 | 0 | 0 | 0 | 0 | 8G | 3G | 2C,2G | 0 | 8G | 2G | 6G | 0 |
| BARNYARDGRASS | 0 | 0 | 0 | 0 | 0 | 0 | 2G | 0 | 3G | 0 | 6G | 1H | 0 | 0 |
| WILD OATS | 3G | 0 | 0 | 0 | 3G | 0 | 2C,5G | 0 | 2C,5G | 2G | 2G | 0 | 2C,6G | 0 |
| WHEAT | 0 | 0 | 0 | 0 | 0 | 0 | 8G | 7G | 8G | 6G | 8G | 2G | 2C,8G | 0 |
| CORN | 1C | 0 | 0 | 0 | 0 | 0 | 3C,7G | 3G | 0 | 0 | 0 | 0 | 0 | 0 |
| SOYBEANS | 0 | 0 | 0 | 0 | 0 | 0 | 4C,9H | 3C,7G | 3C,6H | 2C,3H | 3C,7G | 3G | 3C,6G | 3H |
| RICE | 5G | 0 | 0 | 0 | 0 | 0 | 9H | 5G | 3C,7G | 0 | 3C,9H | 2G | 3C,3G | 0 |
| SORGHUM | 3C,8H | 0 | 2C | 0 | 0 | 0 | 3C,8H | 3C,3G | 3C,4G | 2G | 3C,9H | 3C,5G | 3C,7G | 0 |
| CHEATGRASS | 4G | 0 | 2G | 0 | 0 | 0 | 7G | 3G | 8G | 5G | 8G | 0 | 3C,7G | 0 |
| SUGARBEETS | 4H | 0 | 2H | 0 | 0 | 0 | 4G | 5H | 3C,6H | 5G | 5H | 3G | 4H | 2G |
| VELVETLEAF | 0 | 0 | 0 | 0 | 0 | 0 | 5H | 3H | 4H | 2C,2G | 0 | 0 | 1C | 0 |
| GIANT FOXTAIL | 3G | 0 | 0 | 0 | 2G | 0 | 2G | 0 | 2G | 0 | 3G | 0 | 0 | 0 |
| BARLEY | 0 | 0 | 0 | 0 | 0 | 0 | 3C,8G | 7G | 8G | 5G | 9G | 7G | 9G | 8G |
| DOWNY BROME | — | — | — | — | — | — | — | — | — | — | — | — | — | — |

TEST B

Seeds of barley (*Hordeum vulgare*), barnyard grass (*Echinochloa crus-galli*), blackgrass (*Alopecurus myosuroides*), cheatgrass (*Bromus secalinus*), or downy brome (*Bromus tectorum*), chickweed (*Stellaria media*), cocklebur (*Xanthium pensylvanicum*), corn (*Zea mays*), cotton (*Gossypium hirsutum*), crabgrass (*Digitaria* spp.), giant foxtail (*Setaria faberi*), green foxtail (*Setaria viridis*), jimsonweed (*Datura stramonium*), johnsongrass (*Sorghum halepense*), lambsquarters (*Chenopodium album*), morningglory (*Ipomoea* spp.), rape (*Brassica napus*), rice (*Oryza sativa*), sicklepod (*Cassia obtusifolia*), soybean (*Glycine max*), sugarbeet (*Beta vulgaris*), teaweed (*Sida spinosa*), velvetleaf (*Abutilon theophrasti*), wheat (*Triticum aestivum*), wild buckwheat (*Polygonum convolvulus*), and wild oat (*Avena fatus*) and purple nutsedge (*Cyperus rotundus*) tubers were planted and treated preemergence with test chemicals dissolved in a non-phytotoxic solvent. At the same time, these crop and weed species were also treated with postemergence applications of test chemicals. Plants ranged in height from two to eighteen cm for postemergence treatments. Treated plants and controls were maintained in a greenhouse for approximately 24 days, after which all species were compared to controls and visually evaluated. The ratings, summarized in Table B, are based on a scale of 0 to 100 where 0 is no effect and 100 is complete control. A dash (-) response means no test.

TABLE B

POSTEMERGENCE

| RATE = G/HA | CMPD 1 | | | | CMPD 2 | | | | CMPD 3 | | | | CMPD 4 | | | | CMPD 5 | | | | CMPD 6 | | | | CMPD 7 | |
|---|---|---|---|---|---|---|---|---|---|---|---|---|---|---|---|---|---|---|---|---|---|---|---|---|---|---|
| | 62 | 16 | 4 | 1 | 62 | 16 | 4 | 1 | 62 | 16 | 4 | 1 | 250 | 62 | 16 | 4 | 250 | 62 | 16 | 4 | 250 | 62 | 16 | 4 | 250 | 62 |
| GIANT FOXTAIL | 90 | 60 | 30 | 0 | 100 | 90 | 60 | 30 | 100 | 70 | 50 | 30 | 80 | 50 | 30 | 0 | 100 | 90 | 60 | 30 | 100 | 100 | 70 | 20 | 50 | 40 |
| VELVETLEAF | 90 | 80 | 70 | 50 | 100 | 100 | 100 | 90 | 100 | 70 | 50 | 30 | 100 | 100 | 90 | 60 | 100 | 90 | 70 | 60 | 100 | 100 | 90 | 40 | — | 90 |
| SUGARBEET | 100 | 90 | 60 | 0 | 100 | 100 | 100 | 90 | 100 | 100 | 90 | 80 | 100 | 100 | 90 | 40 | 100 | 100 | 100 | 90 | 100 | 100 | 100 | 70 | 100 | 100 |
| CRABGRASS | 70 | 50 | 30 | 0 | 100 | 90 | 60 | 0 | 100 | 60 | 30 | 0 | 60 | 30 | 0 | 0 | 100 | 60 | 0 | 0 | 100 | 90 | 40 | 10 | 10 | 0 |
| TEAWEED | 70 | 50 | 30 | 0 | 100 | 100 | 80 | 60 | 100 | 90 | 70 | 50 | 90 | 60 | 30 | 0 | 100 | 100 | 60 | 30 | 100 | 100 | 70 | 40 | 90 | 80 |
| JIMSONWEED | 100 | 100 | 60 | 40 | 100 | 100 | 90 | 60 | 100 | 100 | 90 | 60 | 90 | 70 | 30 | 0 | 100 | 100 | 90 | 70 | 100 | 100 | 100 | 90 | 70 | 40 |
| RICE | 90 | 60 | 30 | 0 | 90 | 80 | 70 | 50 | 90 | 70 | 50 | 30 | 90 | 70 | 50 | 30 | 100 | 100 | 100 | 80 | 100 | 100 | 100 | 80 | 80 | 40 |
| COCKLEBUR | 100 | 90 | 50 | 30 | 100 | 100 | 90 | 70 | 100 | 100 | 90 | 70 | 100 | 90 | 60 | 30 | 100 | 100 | 100 | 100 | 100 | 100 | 100 | 90 | 100 | 80 |
| COTTON | 60 | 0 | 0 | 0 | 90 | 80 | 40 | 0 | 100 | 60 | 50 | 30 | 50 | 30 | 0 | 0 | 60 | 30 | 0 | 0 | 80 | 30 | 20 | 10 | 90 | 80 |
| SOYBEAN | 100 | 60 | 40 | 20 | 100 | 100 | 90 | 80 | 100 | 100 | 80 | 70 | 100 | 60 | 40 | 0 | 100 | 100 | 100 | 70 | 100 | 100 | 100 | 80 | 90 | 80 |
| BARNYARDGRASS | 90 | 70 | 50 | 30 | 100 | 100 | 90 | 60 | 100 | 90 | 60 | 30 | 70 | 50 | 30 | 0 | 100 | 100 | 70 | 60 | 100 | 100 | 100 | 80 | 70 | 30 |
| WILD OAT | 50 | 30 | 0 | 0 | 100 | 70 | 60 | 50 | 100 | 80 | 50 | 30 | 70 | 50 | 30 | 0 | 100 | 100 | 90 | 60 | 100 | 90 | 90 | 20 | 20 | 0 |
| MORNINGGLORY | 70 | 50 | 30 | 0 | 100 | 100 | 80 | 50 | 100 | 100 | 90 | 60 | 80 | 70 | 50 | 30 | 90 | 70 | 60 | 50 | 100 | 100 | 90 | 40 | 90 | 30 |
| WHEAT | 30 | 0 | 0 | 0 | 100 | 60 | 30 | 0 | 100 | 60 | 30 | 0 | 80 | 30 | 0 | 0 | 90 | 60 | 30 | 0 | 90 | 40 | 10 | 0 | 10 | 0 |
| SICKLEPOD | 100 | 100 | 60 | 30 | 100 | 100 | 100 | 80 | 100 | 100 | 90 | 70 | 70 | 50 | 30 | 0 | 100 | 100 | 70 | 60 | 100 | 100 | 100 | 30 | 90 | 80 |
| JOHNSONGRASS | 80 | 50 | 30 | 0 | 100 | 100 | 100 | 60 | 100 | 100 | 70 | 50 | 90 | 70 | 50 | 30 | 100 | 100 | 60 | 40 | 100 | 100 | 100 | 90 | 20 | 0 |
| NUTSEDGE | 100 | 100 | 60 | 30 | 100 | 100 | 70 | 50 | 100 | 100 | 100 | 50 | 100 | 100 | 70 | 50 | 100 | 100 | 50 | 30 | 90 | 90 | 40 | 30 | 90 | 50 |
| CORN | 100 | 100 | 100 | 70 | 100 | 100 | 100 | 100 | 100 | 100 | 100 | 100 | 100 | 100 | 90 | 70 | 100 | 100 | 100 | 70 | 100 | 100 | 100 | 100 | 30 | 10 |
| WILD BUCKWHEAT | 100 | 80 | 30 | 0 | 100 | 100 | 70 | 30 | 100 | 90 | 60 | 30 | 100 | 90 | 60 | 30 | 100 | 100 | 100 | 100 | 100 | 100 | 90 | 70 | — | 100 |
| BLACKGRASS | 0 | 0 | 0 | 0 | 100 | 100 | 70 | 50 | 100 | 90 | 60 | 30 | 90 | 60 | 30 | 0 | 100 | 90 | 70 | 50 | 100 | — | 90 | 40 | — | 30 |
| RAPE | 100 | 90 | 70 | 50 | 100 | 100 | 100 | 100 | 100 | 100 | 90 | 70 | 100 | 90 | 60 | 30 | 100 | 100 | 100 | 90 | 100 | 100 | 100 | 100 | 100 | 100 |
| BARLEY | 30 | 0 | 0 | 0 | 100 | 60 | 30 | 0 | 70 | 50 | 30 | 0 | 50 | 30 | 0 | 0 | 70 | 50 | 30 | 0 | 60 | 30 | 10 | 0 | 10 | 0 |
| GREEN FOXTAIL | 70 | 30 | 0 | 0 | 100 | 90 | 70 | 50 | 100 | 70 | 50 | 30 | 70 | 30 | 0 | 0 | 100 | 90 | 60 | 30 | 100 | 90 | 60 | 20 | 40 | 30 |
| CHEATGRASS | 60 | 30 | 0 | 0 | 90 | 80 | 70 | 30 | 100 | 100 | 90 | 70 | 70 | 50 | 30 | 0 | — | — | — | — | — | — | — | — | — | — |
| LAMBSQUARTERS | 100 | 90 | 60 | 30 | 100 | 100 | 100 | 80 | 100 | 100 | 100 | 100 | 100 | 100 | 70 | 50 | 100 | 90 | 70 | 50 | 100 | 100 | 100 | 80 | 80 | 80 |
| CHICKWEED | 90 | 60 | 30 | 0 | 100 | 100 | 90 | 70 | 100 | 100 | 100 | 70 | 100 | 90 | 70 | 50 | 100 | 100 | 100 | 100 | 100 | 100 | 90 | 90 | 100 | 100 |
| DOWNY BROME | — | — | — | — | — | — | — | — | — | — | — | — | — | — | — | — | 100 | 100 | 80 | 30 | 100 | 100 | 90 | 70 | 50 | 30 |

| RATE = G/HA | CMPD 7 | | CMPD 8 | | | | CMPD 9 | | | | CMPD 10 | | | | CMPD 11 | | | | CMPD 12 | | | | CMPD 13 | | | |
|---|---|---|---|---|---|---|---|---|---|---|---|---|---|---|---|---|---|---|---|---|---|---|---|---|---|---|
| | 16 | 4 | 250 | 62 | 16 | 4 | 250 | 62 | 16 | 4 | 250 | 62 | 16 | 4 | 250 | 62 | 16 | 4 | 250 | 62 | 16 | 4 | 62 | 16 | 4 | 1 |
| GIANT FOXTAIL | — | 0 | 100 | 100 | 80 | 60 | 100 | 100 | 80 | 60 | 100 | 90 | 70 | 50 | 100 | 100 | 80 | 60 | 100 | 100 | 70 | 50 | 100 | 100 | 90 | 70 |
| VELVETLEAF | 90 | 70 | 100 | 100 | 90 | 70 | 100 | 100 | 100 | 80 | 100 | 100 | 90 | 60 | 100 | 90 | 70 | 50 | 100 | 80 | 70 | 60 | 100 | 90 | 70 | 50 |
| SUGARBEET | 90 | 80 | 100 | 100 | 90 | 70 | 100 | 100 | 100 | 90 | 100 | 100 | 90 | 70 | 100 | 100 | 100 | 100 | 100 | 100 | 90 | 70 | 100 | 100 | 100 | 70 |
| CRABGRASS | 0 | 0 | 60 | 50 | 30 | 0 | 50 | 0 | 0 | 0 | 70 | 50 | 40 | 30 | 70 | 60 | 50 | 40 | 70 | 50 | 30 | 0 | 100 | 100 | 60 | 30 |
| TEAWEED | 30 | 0 | 100 | 70 | 50 | 30 | 100 | 100 | 70 | 50 | 100 | 80 | 50 | 30 | 90 | 70 | 50 | 30 | 90 | 80 | 70 | 60 | 100 | 100 | 90 | 60 |
| JIMSONWEED | 20 | 0 | 100 | 100 | 100 | 80 | 100 | 100 | 80 | 70 | 100 | 100 | 90 | 60 | 100 | 100 | 70 | 50 | 100 | 90 | 80 | 70 | 100 | 90 | 70 | 50 |
| RICE | 30 | 0 | 90 | 80 | 70 | 60 | 90 | 80 | 70 | 60 | 100 | 100 | 90 | 70 | 80 | 70 | 60 | 50 | 90 | 80 | 70 | 60 | 100 | 100 | 100 | 70 |
| COCKLEBUR | 50 | 40 | 100 | 100 | 90 | 60 | 100 | 100 | 100 | 70 | 100 | 100 | 100 | 80 | 100 | 100 | 100 | 70 | 100 | 100 | 70 | 50 | 100 | 100 | 100 | 60 |
| COTTON | 30 | 20 | 70 | 50 | 20 | 0 | 80 | 50 | 30 | 0 | 100 | 100 | 40 | 0 | 40 | 30 | 20 | 0 | 70 | 40 | 0 | 0 | 80 | 50 | 0 | 0 |
| SOYBEAN | 70 | 40 | 100 | 100 | 100 | 100 | 100 | 100 | 100 | 90 | 100 | 100 | 100 | 100 | 100 | 100 | 100 | 90 | 100 | 100 | 100 | 60 | 100 | 100 | 100 | 70 |
| BARNYARDGRASS | 10 | 0 | 100 | 100 | 60 | 30 | 80 | 70 | 60 | 50 | 80 | 60 | 50 | 30 | 80 | 70 | 60 | 50 | 70 | 50 | 30 | 0 | 100 | 100 | 80 | 70 |
| WILD OAT | 0 | 0 | 100 | 90 | 80 | 60 | 100 | 100 | 70 | 50 | 90 | 70 | 50 | 30 | 90 | 70 | 50 | 30 | 100 | 100 | 70 | 30 | 70 | 50 | 30 | 0 |
| MORNINGGLORY | 0 | — | 100 | 100 | 90 | 80 | 100 | 90 | 80 | 70 | 100 | 100 | 100 | 60 | 100 | 90 | 80 | 70 | 90 | 80 | 60 | 30 | 100 | 90 | 70 | 50 |
| WHEAT | 0 | 0 | 80 | 70 | 50 | 30 | 90 | 60 | 30 | 0 | 90 | 60 | 30 | 0 | 70 | 60 | 50 | 30 | 70 | 50 | 30 | 0 | 60 | 30 | 0 | 0 |
| SICKLEPOD | 20 | 20 | 100 | 100 | 80 | 70 | 100 | 90 | 70 | 60 | 100 | 100 | 100 | 50 | 90 | 70 | 60 | 50 | 90 | 60 | 30 | 0 | 100 | 100 | 70 | 60 |
| JOHNSONGRASS | 0 | 0 | 100 | 100 | 70 | 60 | 100 | 100 | 80 | 60 | 100 | 100 | 70 | 50 | 100 | 100 | 90 | 80 | 100 | 100 | 100 | 70 | 100 | 70 | 50 | 30 |
| NUTSEDGE | 30 | 20 | 90 | 50 | 0 | 0 | 100 | 100 | 100 | 100 | 100 | 70 | 50 | 30 | 70 | 60 | 50 | 30 | 50 | 40 | 30 | 0 | 100 | 100 | 90 | 70 |
| CORN | 0 | 0 | 100 | 100 | 70 | 50 | 100 | 100 | 90 | 70 | 100 | 100 | 70 | 60 | 100 | 100 | 90 | 70 | 100 | 100 | 70 | 50 | 100 | 100 | 100 | 80 |
| WILD BUCKWHEAT | 40 | — | 100 | 100 | 90 | 60 | 100 | 100 | 100 | 60 | 100 | 90 | 70 | 50 | 100 | 100 | 90 | 70 | 100 | 70 | 50 | 30 | 100 | 100 | 90 | 60 |

TABLE B-continued

| | | | | | | | | | | | | | | | | | | | | | | | | | | |
|---|---|---|---|---|---|---|---|---|---|---|---|---|---|---|---|---|---|---|---|---|---|---|---|---|---|---|
| BLACKGRASS | 10 | — | 90 | 70 | 50 | 30 | 100 | 100 | 70 | 60 | 100 | 90 | 70 | 50 | 90 | 80 | 60 | 30 | 90 | 70 | 50 | 30 | 90 | 70 | 50 | 30 |
| RAPE | 90 | 80 | 30 | 0 | 0 | 0 | 90 | 60 | 30 | 0 | 100 | 70 | 50 | 30 | 100 | 100 | 70 | 50 | 90 | 80 | 60 | 30 | 100 | 100 | 100 | 90 |
| BARLEY | 0 | 0 | 70 | 50 | 30 | 0 | 70 | 50 | 30 | 0 | 60 | 30 | 0 | 0 | 70 | 60 | 50 | 30 | 70 | 50 | 30 | 0 | 70 | 50 | 30 | 0 |
| GREEN FOXTAIL | 20 | 0 | 100 | 100 | 80 | 60 | 100 | 100 | 90 | 60 | 100 | 100 | 70 | 50 | 100 | 90 | 70 | 50 | 100 | 80 | 70 | 50 | 100 | 100 | 60 | 30 |
| CHEATGRASS | — | — | — | — | — | — | — | — | — | — | — | — | — | — | — | — | — | — | — | — | — | — | — | — | — | — |
| LAMBSQUARTERS | 40 | 0 | 100 | 100 | 80 | 50 | 100 | 100 | 90 | 60 | 100 | 100 | 90 | 70 | 100 | 100 | 90 | 70 | 70 | 50 | 30 | 0 | 100 | 100 | 90 | 70 |
| CHICKWEED | 80 | 70 | 100 | 100 | 90 | 70 | 100 | 100 | 100 | 90 | 100 | 100 | 100 | 100 | 100 | 100 | 90 | 80 | 100 | 100 | 100 | 90 | 100 | 100 | 90 | 60 |
| DOWNY BROME | 20 | — | 100 | 100 | 70 | 50 | 100 | 90 | 60 | 30 | 100 | 70 | 50 | 30 | 90 | 70 | 50 | 30 | 90 | 70 | 50 | 30 | 100 | 70 | 50 | 30 |

| | CMPD 15 | | | | CMPD 20 | | | | CMPD 22 | | | | CMPD 23 | | | | CMPD 27 | | | | CMPD 28 | | | | CMPD 29 | |
|---|---|---|---|---|---|---|---|---|---|---|---|---|---|---|---|---|---|---|---|---|---|---|---|---|---|---|
| RATE = G/HA | 62 | 16 | 4 | 1 | 62 | 16 | 4 | 1 | 250 | 62 | 16 | 4 | 62 | 16 | 4 | 1 | 250 | 62 | 16 | 4 | 250 | 62 | 16 | 4 | 250 | 62 |
| GIANT FOXTAIL | 100 | 90 | 60 | 30 | 100 | 100 | 80 | 60 | 100 | 100 | 90 | 40 | 100 | 100 | 50 | 10 | 100 | 90 | 50 | 20 | 100 | 100 | 80 | 70 | 100 | 100 |
| VELVETLEAF | 100 | 100 | 90 | 60 | 100 | 90 | — | — | 100 | 100 | 90 | 80 | 100 | 100 | 80 | 40 | 100 | 90 | 70 | 40 | 100 | 100 | 100 | 80 | 100 | 90 |
| SUGARBEET | 100 | 100 | 100 | 60 | 100 | 100 | 100 | 70 | 100 | 100 | 100 | 90 | 100 | 100 | 90 | 30 | 100 | 90 | 90 | 60 | 100 | 100 | 100 | 80 | 100 | 100 |
| CRABGRASS | 100 | 70 | 50 | 30 | 100 | 80 | 80 | 20 | 100 | 100 | 60 | 30 | 100 | 80 | 30 | 10 | 100 | 50 | 50 | 40 | 100 | 80 | 30 | 30 | 50 | 50 |
| TEAWEED | 100 | 90 | 70 | 60 | 100 | 70 | 60 | 30 | 100 | 100 | 70 | 40 | 100 | 90 | 80 | 20 | 90 | 90 | 40 | 30 | 100 | 100 | 70 | 50 | 80 | 80 |
| JIMSONWEED | 100 | 80 | 60 | 50 | 100 | 100 | 90 | 50 | 100 | 100 | 90 | 90 | 100 | 100 | 100 | 80 | 100 | 100 | 100 | 60 | 100 | 100 | 100 | 90 | 100 | 90 |
| RICE | 100 | 100 | 70 | 50 | 100 | 100 | 100 | 80 | 100 | 100 | 100 | 100 | 100 | 100 | 100 | 100 | 100 | 100 | 100 | 60 | 100 | 100 | 90 | 80 | 100 | 90 |
| COCKLEBUR | 100 | 90 | 80 | 70 | 100 | 100 | 80 | 40 | 100 | 100 | 100 | 100 | 100 | 100 | 100 | 80 | 100 | 90 | 80 | 40 | 100 | 90 | 90 | 40 | 80 | 20 |
| COTTON | 100 | 60 | 30 | 0 | 90 | 70 | 50 | 30 | 80 | 50 | 20 | 10 | 70 | 50 | 10 | 10 | 70 | 50 | 20 | 0 | 90 | 90 | 50 | 10 | 70 | 60 |
| SOYBEAN | 100 | 100 | 100 | 70 | 100 | 100 | 100 | 90 | 100 | 100 | 100 | 100 | 100 | 100 | 100 | 70 | 100 | 100 | 90 | 80 | 100 | 100 | 90 | 70 | 100 | 100 |
| BARNYARDGRASS | 100 | 80 | 50 | 30 | 100 | 100 | 100 | 60 | 100 | 100 | 100 | 60 | 100 | 100 | 100 | 60 | 100 | 100 | 50 | 20 | 100 | 100 | 40 | 40 | 80 | 40 |
| WILD OAT | 80 | 50 | 30 | 0 | 90 | 80 | 70 | 40 | 100 | 100 | 100 | 40 | 100 | 100 | 70 | 40 | 100 | 90 | 70 | 40 | 100 | 100 | 90 | 50 | 100 | 100 |
| MORNINGGLORY | 100 | 90 | 60 | 30 | 100 | 100 | 90 | 70 | 100 | 100 | 100 | 90 | 100 | 100 | 90 | 30 | 100 | 90 | 90 | 70 | 100 | 100 | 100 | 90 | 100 | 80 |
| WHEAT | 60 | 30 | 0 | 0 | 90 | 70 | 10 | 0 | 80 | 80 | 10 | 0 | 80 | 40 | 10 | 0 | 100 | 70 | 20 | 0 | 80 | 40 | 10 | 0 | 100 | 100 |
| SICKLEPOD | 100 | 80 | 50 | 30 | 100 | 100 | 100 | — | 100 | 100 | 100 | 60 | 100 | 100 | 60 | 30 | 100 | 90 | 70 | 50 | 100 | 100 | 100 | 70 | 70 | 50 |
| JOHNSONGRASS | 100 | 80 | 50 | 30 | 100 | 100 | 60 | 50 | 100 | 100 | 90 | 60 | 100 | 100 | 70 | 40 | 100 | 70 | 50 | 0 | 100 | 100 | 80 | 50 | 90 | 80 |
| NUTSEDGE | 100 | 100 | 40 | 0 | 100 | 100 | 100 | 50 | 100 | 100 | 70 | 50 | 100 | 60 | 60 | 20 | 100 | 90 | 80 | 20 | 90 | 90 | 50 | 50 | 40 | 20 |
| CORN | 100 | 100 | 80 | 60 | 100 | 100 | 100 | 100 | 100 | 100 | 100 | 100 | 100 | 100 | 100 | 100 | 100 | 100 | 90 | 50 | 100 | 100 | 90 | 90 | 100 | 90 |
| WILD BUCKWHEAT | 100 | 100 | 100 | 100 | 100 | 100 | 100 | 80 | 100 | 100 | 60 | 50 | 100 | 100 | 100 | 20 | 100 | 100 | 100 | 70 | 100 | — | 100 | 40 | 100 | 100 |
| BLACKGRASS | 100 | 70 | 50 | 30 | 100 | 100 | 100 | 50 | 100 | 100 | 70 | 40 | 90 | 80 | 40 | 0 | 100 | 80 | 40 | 20 | 100 | 90 | 70 | 70 | 90 | 90 |
| RAPE | 100 | 100 | 90 | 70 | 100 | 100 | 100 | 90 | 100 | — | 100 | 100 | 100 | 100 | 100 | 90 | 100 | 100 | 90 | 0 | 100 | 70 | — | 20 | 100 | 90 |
| BARLEY | 70 | 50 | 30 | 0 | 80 | 50 | 30 | 10 | 90 | 60 | 30 | 10 | 60 | 30 | 10 | 0 | 70 | 20 | 20 | 0 | 80 | 70 | 20 | 10 | 90 | 90 |
| GREEN FOXTAIL | 70 | 50 | 30 | 0 | 100 | 100 | 80 | 70 | 100 | 100 | 70 | 40 | 100 | 100 | 40 | 30 | 100 | 90 | 70 | 30 | 100 | 100 | 100 | 90 | 90 | 70 |
| CHEATGRASS | — | — | — | — | — | — | — | — | — | — | — | — | — | — | — | — | — | — | — | — | — | — | — | — | — | — |
| LAMBSQUARTERS | 100 | 100 | 90 | 70 | 100 | 100 | 100 | 100 | 100 | 100 | 60 | 60 | 100 | 100 | 100 | 90 | 100 | 100 | 100 | 40 | 100 | 100 | 90 | 40 | 40 | 0 |
| CHICKWEED | 100 | 100 | 90 | 70 | 100 | 100 | 100 | 90 | 100 | 100 | 100 | 100 | 100 | 100 | 100 | 70 | 100 | 90 | 80 | 60 | 100 | 100 | 100 | 70 | 100 | 100 |
| DOWNY BROME | 90 | 70 | 50 | 30 | 100 | 90 | 40 | 20 | 100 | 100 | 80 | 70 | 100 | 100 | 80 | 20 | 100 | 90 | 80 | 80 | 100 | 100 | 100 | 70 | 100 | 90 |

| | CMPD 29 | | CMPD 31 | | | | CMPD 32 | | | | CMPD 40 | | | | CMPD 41 | | | | CMPD 42 | | | | CMPD 44 | | | |
|---|---|---|---|---|---|---|---|---|---|---|---|---|---|---|---|---|---|---|---|---|---|---|---|---|---|---|
| RATE = G/HA | 16 | 4 | 250 | 62 | 16 | 4 | 250 | 62 | 16 | 4 | 62 | 16 | 4 | 1 | 250 | 62 | 16 | 4 | 250 | 62 | 16 | 4 | 250 | 62 | 16 | 4 |
| GIANT FOXTAIL | 80 | 30 | 100 | 100 | 70 | 40 | 100 | 100 | 100 | 100 | 100 | 100 | 90 | 50 | 100 | 80 | 50 | 40 | 100 | 100 | 90 | 60 | 100 | 90 | 60 | 30 |
| VELVETLEAF | 70 | 40 | 100 | 100 | 100 | 80 | 100 | 100 | 100 | 80 | 100 | 100 | 90 | 30 | 100 | 90 | 20 | 0 | 100 | 100 | 100 | 90 | 100 | 100 | 80 | 70 |
| SUGARBEET | 100 | 90 | 100 | 100 | 100 | 70 | 100 | 100 | 100 | 80 | 100 | 100 | 100 | 90 | 100 | 90 | 80 | 50 | 100 | 100 | 100 | 90 | 100 | 100 | 100 | 90 |
| CRABGRASS | 20 | 0 | 80 | 40 | 10 | — | 100 | 90 | 50 | 20 | 100 | 50 | 0 | 0 | 60 | 40 | 30 | 0 | 100 | 90 | 40 | 30 | 100 | 100 | 90 | 70 |
| TEAWEED | 30 | 0 | 100 | 90 | 70 | 40 | 100 | 100 | 90 | 80 | 100 | 80 | 50 | 40 | 90 | 60 | 30 | 20 | 100 | 100 | 80 | 50 | 100 | 90 | 70 | 60 |
| JIMSONWEED | 80 | — | 100 | 100 | 100 | 80 | 100 | 100 | 80 | 60 | 100 | 100 | 100 | 60 | 100 | 100 | 60 | 30 | 100 | 100 | 100 | 90 | 100 | 100 | 100 | 90 |
| RICE | 90 | 40 | 100 | 100 | 90 | 70 | 100 | 100 | 100 | 90 | 100 | 90 | 90 | 60 | 100 | 100 | 80 | 40 | 100 | 100 | 90 | 80 | 100 | 100 | 100 | 90 |
| COCKLEBUR | 0 | 0 | 100 | 90 | 70 | 30 | 100 | 100 | 100 | 40 | 100 | 100 | 90 | 50 | 100 | 90 | 70 | 40 | 100 | 100 | 100 | 80 | 100 | 100 | 90 | 70 |
| COTTON | 50 | 40 | 90 | 60 | 40 | 10 | 90 | 90 | 90 | 50 | 90 | 50 | 20 | 0 | 80 | 40 | 0 | 0 | 100 | 90 | 80 | 20 | 90 | 80 | 60 | 40 |
| SOYBEAN | 50 | 0 | 100 | 100 | 90 | 80 | 100 | 100 | 100 | 80 | 100 | 100 | 90 | 80 | 100 | 90 | 40 | 30 | 100 | 100 | 100 | 90 | 100 | 100 | 100 | 90 |
| BARNYARDGRASS | 40 | 0 | 100 | 90 | 70 | 20 | 100 | 100 | 100 | 40 | 100 | 100 | 40 | 40 | 100 | 90 | 40 | 40 | 100 | 100 | 100 | 30 | 100 | 90 | 60 | 50 |
| WILD OAT | 90 | 60 | 90 | 80 | 70 | 70 | 90 | 80 | 50 | 40 | 100 | 90 | 70 | 40 | 70 | 70 | 50 | 40 | 100 | 90 | 70 | 40 | 100 | 100 | 70 | 70 |

TABLE B-continued

| | | | | | | | | | | | | | | | | | | | | | | | | | | |
|---|---|---|---|---|---|---|---|---|---|---|---|---|---|---|---|---|---|---|---|---|---|---|---|---|---|---|
| MORNINGGLORY | 50 | 0 | 100 | 100 | 90 | 80 | 100 | 100 | 100 | 60 | 100 | 100 | 90 | 90 | 100 | 80 | 50 | 30 | 100 | 100 | 100 | 90 | 100 | 100 | 90 | 90 |
| WHEAT | 90 | 60 | 90 | 80 | 70 | 20 | 60 | 40 | 0 | 0 | 100 | 40 | 20 | 10 | 60 | 30 | 30 | 10 | 100 | 90 | 50 | 20 | 100 | 90 | 70 | 60 |
| SICKLEPOD | 20 | 0 | 100 | 100 | 80 | 70 | 100 | 100 | 100 | 80 | 100 | 90 | 70 | 50 | 80 | 30 | 20 | 0 | 100 | 100 | 90 | 40 | 100 | 100 | 70 | 60 |
| JOHNSONGRASS | 80 | 50 | 100 | 100 | 90 | 50 | 100 | 100 | 100 | 40 | 100 | 100 | 80 | 40 | 100 | 100 | 40 | 30 | 100 | 100 | 90 | 80 | 100 | 100 | 90 | 80 |
| NUTSEDGE | 0 | 0 | 70 | 60 | 50 | 30 | 100 | 100 | 80 | 40 | 100 | 100 | 90 | 90 | 100 | 90 | 30 | 0 | 100 | 100 | 100 | 70 | 100 | 100 | 50 | 0 |
| CORN | 90 | 20 | 100 | 100 | 100 | 90 | 100 | 100 | 100 | 40 | 100 | 100 | 100 | 80 | 100 | 90 | 80 | 60 | 100 | 100 | 100 | 80 | 100 | 100 | 100 | 90 |
| WILD BUCKWHEAT | 100 | 80 | 100 | 100 | 100 | 60 | 100 | 100 | 100 | 60 | 100 | 100 | 90 | 90 | 100 | 90 | 60 | 50 | 100 | 100 | 100 | 90 | 100 | 100 | 100 | 90 |
| BLACKGRASS | 80 | 40 | 100 | 100 | 90 | 40 | 100 | 90 | — | — | 80 | 80 | 50 | 20 | 80 | 70 | 40 | 10 | 100 | 100 | 50 | 50 | 100 | 90 | 90 | 50 |
| RAPE | 90 | 90 | 90 | 60 | 0 | 0 | 100 | 100 | 100 | 90 | 100 | 100 | 100 | 100 | 100 | 100 | 100 | 90 | 100 | 100 | 100 | 100 | 100 | 100 | 100 | 90 |
| BARLEY | 80 | 50 | 70 | 70 | 30 | 10 | 100 | 70 | 60 | 10 | 90 | 50 | 40 | 10 | 40 | 40 | 20 | 10 | 90 | 70 | 70 | 40 | 100 | 60 | 40 | — |
| GREEN FOXTAIL | 60 | 40 | 100 | 100 | 90 | 60 | 100 | 100 | 70 | 40 | 100 | 100 | 90 | 60 | 100 | 90 | 40 | 30 | 100 | 100 | 80 | 50 | 100 | 100 | 70 | 60 |
| CHEATGRASS | — | — | — | — | — | — | — | — | — | — | — | — | — | — | — | — | — | — | — | — | — | — | — | — | — | — |
| LAMBSQUARTERS | 0 | 0 | 100 | 100 | 50 | 40 | 100 | 100 | 100 | 100 | 100 | 100 | 90 | 60 | 100 | 90 | 90 | 60 | 100 | 100 | 100 | 90 | 100 | 90 | 40 | — |
| CHICKWEED | 100 | 100 | 100 | 100 | 50 | 0 | 100 | 100 | 100 | 50 | 100 | 100 | 90 | 80 | 100 | 80 | 50 | 30 | 100 | 100 | 100 | 70 | 100 | 100 | 100 | 100 |
| DOWNY BROME | 80 | 40 | 100 | 100 | 80 | 40 | 100 | 70 | 60 | 30 | 100 | 90 | 80 | 50 | 100 | 80 | 40 | — | 100 | 80 | 80 | 70 | 100 | 100 | 80 | 70 |

| | CMPD 45 | | | | CMPD 46 | | | | CMPD 47 | | | | CMPD 48 | | | | CMPD 49 | | | |
|---|---|---|---|---|---|---|---|---|---|---|---|---|---|---|---|---|---|---|---|---|
| RATE = G/HA | 250 | 62 | 16 | 4 | 250 | 62 | 16 | 4 | 62 | 16 | 4 | 1 | 250 | 62 | 16 | 4 | 62 | 16 | 4 | 1 |
| GIANT FOXTAIL | 100 | 100 | 70 | 20 | 100 | 90 | 60 | 40 | 90 | 80 | 70 | 40 | 80 | 60 | 50 | 40 | 100 | 70 | 60 | 50 |
| VELVETLEAF | 100 | 90 | 80 | 40 | 100 | 100 | 90 | 80 | 100 | 100 | 70 | 60 | 100 | 90 | 80 | 70 | 100 | 100 | 90 | 70 |
| SUGARBEET | 100 | 100 | 100 | 90 | 100 | 90 | 30 | 20 | 100 | 100 | 100 | 90 | 100 | 100 | 100 | 100 | 100 | 100 | 90 | 70 |
| CRABGRASS | 100 | 100 | 90 | 70 | 80 | 40 | 20 | 0 | 50 | 40 | 20 | 0 | 40 | 30 | 20 | 0 | 70 | 50 | 40 | 30 |
| TEAWEED | 100 | 90 | 80 | 40 | 100 | 80 | 30 | 20 | 90 | 80 | 60 | 30 | 80 | 60 | 40 | 30 | 90 | 70 | 50 | 30 |
| JIMSONWEED | 100 | 100 | 100 | 90 | 100 | 100 | 80 | 40 | 100 | 100 | 90 | 60 | 100 | 90 | 85 | 80 | 100 | 100 | 90 | 80 |
| RICE | 100 | 100 | 100 | 90 | 100 | 100 | 90 | 80 | 80 | 70 | 60 | 50 | 80 | 75 | 70 | 60 | 80 | 70 | 60 | 50 |
| COCKLEBUR | 100 | 100 | 100 | 90 | 100 | 100 | 40 | 20 | 90 | 70 | 30 | 0 | 70 | 30 | 20 | 0 | 100 | 60 | 30 | 0 |
| COTTON | 90 | 70 | 20 | 0 | 90 | 70 | 30 | 10 | 90 | 60 | 30 | 0 | 100 | 90 | 50 | 30 | 90 | 80 | 70 | 40 |
| SOYBEAN | 100 | 100 | 90 | 80 | 100 | 100 | 90 | 80 | 100 | 100 | 90 | 60 | 90 | 80 | 70 | 60 | 100 | 100 | 100 | 90 |
| BARNYARDGRASS | 100 | 100 | 100 | 70 | 100 | 90 | 40 | 0 | 100 | 90 | 80 | 60 | 100 | 100 | 70 | 60 | 80 | 70 | 60 | 50 |
| WILD OAT | 100 | 100 | 70 | 70 | 100 | 70 | 70 | 40 | 100 | 70 | 60 | 50 | 70 | 50 | 30 | 0 | 70 | 60 | 50 | 30 |
| MORNINGGLORY | 100 | 90 | 90 | 70 | 100 | 90 | 90 | 60 | 100 | 90 | 60 | 30 | 90 | 80 | 70 | 50 | 90 | 85 | 80 | 50 |
| WHEAT | 100 | 100 | 90 | 60 | 100 | 50 | 10 | 0 | 90 | 70 | 50 | 30 | 60 | 30 | 0 | 0 | 80 | 70 | 60 | 50 |
| SICKLEPOD | 100 | 90 | 80 | 60 | 100 | 90 | 50 | 20 | — | 70 | — | — | — | — | — | 0 | 90 | 40 | 30 | 0 |
| JOHNSONGRASS | 100 | 100 | 100 | 90 | 100 | 90 | 80 | 40 | 100 | 90 | 80 | 50 | 100 | 80 | 50 | 30 | 100 | 100 | 70 | 40 |
| NUTSEDGE | 100 | 60 | 30 | 0 | 80 | 50 | 0 | 0 | 100 | 90 | 50 | 50 | 100 | 100 | 90 | 80 | 80 | 70 | 60 | 0 |
| CORN | 100 | 100 | 100 | 90 | 100 | 100 | 90 | 80 | 70 | 60 | 50 | 0 | 70 | 50 | 0 | 0 | 70 | 30 | 0 | 0 |
| WILD BUCKWHEAT | 100 | 100 | 90 | 70 | 100 | 90 | 90 | 70 | 90 | 70 | 60 | 50 | 100 | 90 | 80 | 70 | 100 | 100 | 100 | 70 |
| BLACKGRASS | 100 | — | 90 | 60 | 100 | 90 | 80 | 40 | 90 | 70 | 50 | 30 | 80 | 50 | 30 | 0 | 70 | 50 | 30 | 0 |
| RAPE | 100 | 100 | 100 | 90 | 30 | 10 | 0 | 0 | 100 | 100 | 100 | 100 | 100 | 100 | 100 | 90 | 100 | 100 | 90 | 80 |
| BARLEY | 100 | 70 | 40 | 20 | 60 | 60 | 20 | 0 | 70 | 50 | 30 | 0 | 60 | 50 | 40 | 30 | 70 | 60 | 50 | 40 |
| GREEN FOXTAIL | 100 | 100 | 70 | 40 | 100 | 100 | 90 | 40 | 90 | 70 | 50 | 30 | 70 | 50 | 40 | 30 | 70 | 50 | 30 | 0 |
| CHEATGRASS | — | — | — | — | — | — | — | — | — | — | — | — | — | — | — | — | — | — | — | — |
| LAMBSQUARTERS | 100 | 100 | 100 | 80 | 100 | 50 | 40 | 0 | 90 | 85 | 80 | 70 | 100 | 90 | 70 | 60 | 100 | 90 | 85 | 80 |
| CHICKWEED | 100 | 100 | 90 | 60 | 100 | 70 | 60 | 50 | 100 | 100 | 100 | 90 | 100 | 100 | 100 | 100 | 100 | 100 | 100 | 100 |
| DOWNY BROME | 100 | 100 | 100 | 80 | 90 | 90 | 80 | 40 | 90 | 60 | 30 | 0 | 50 | 30 | 0 | 0 | 70 | 50 | 30 | 0 |

| | CMPD 50 | | | | CMPD 51 | | | | CMPD 52 | | | | CMPD 53 | | | | CMPD 54 | | | | CMPD 55 | | | | CMPD 56 | | | |
|---|---|---|---|---|---|---|---|---|---|---|---|---|---|---|---|---|---|---|---|---|---|---|---|---|---|---|---|---|
| RATE = G/HA | 250 | 62 | 16 | 4 | 250 | 62 | 16 | 4 | 250 | 62 | 16 | 4 | 250 | 62 | 16 | 4 | 62 | 16 | 4 | 1 | 62 | 16 | 4 | 1 | 62 | 16 | 4 | 1 |
| POSTEMERGENCE | | | | | | | | | | | | | | | | | | | | | | | | | | | | |
| GIANT FOXTAIL | 90 | 70 | 50 | 30 | 90 | 60 | 30 | 0 | 80 | 70 | 30 | 0 | 70 | 50 | 30 | 0 | 90 | 60 | 30 | 0 | 50 | 0 | 0 | 0 | 70 | 70 | 50 | 20 |
| VELVETLEAF | 100 | 95 | 90 | 80 | 100 | 80 | 70 | 40 | 100 | 100 | 75 | 70 | 75 | 70 | 65 | 60 | 100 | 100 | 80 | 20 | 100 | 100 | 80 | 30 | 100 | 100 | 80 | 40 |
| SUGARBEET | 100 | 100 | 100 | 100 | 100 | 100 | 100 | 60 | 100 | 100 | 100 | 100 | 100 | 100 | 100 | 70 | 100 | 100 | 100 | 40 | 100 | 90 | 0 | 0 | 100 | 100 | 100 | 100 |
| CRABGRASS | 80 | 70 | 50 | 30 | 80 | 50 | 30 | 0 | 70 | 60 | 0 | 0 | 60 | 50 | 30 | 0 | 50 | 50 | 20 | 0 | 0 | 0 | 0 | 0 | 50 | 20 | 0 | 0 |
| TEAWEED | 85 | 80 | 60 | 50 | 80 | 60 | 40 | 30 | 90 | 70 | 0 | 0 | 60 | 50 | 40 | 30 | 100 | 70 | 20 | 0 | 80 | 30 | 20 | 0 | 60 | 60 | 20 | 0 |
| JIMSONWEED | 100 | 100 | 95 | 90 | 95 | 90 | 85 | 80 | 95 | 90 | 80 | 70 | 90 | 80 | 60 | 50 | 100 | 70 | 50 | 0 | 90 | 70 | 60 | 40 | 100 | 100 | 80 | 70 |
| RICE | 100 | 100 | 80 | 70 | 95 | 90 | 80 | 40 | 100 | 100 | 80 | 70 | 80 | 70 | 60 | 30 | 100 | 100 | 40 | 0 | 70 | 50 | 20 | 0 | 100 | 100 | 50 | 30 |
| COCKLEBUR | 90 | 70 | 50 | 30 | 100 | 60 | 30 | 0 | 90 | 80 | 60 | 0 | 0 | 0 | 0 | 0 | 50 | 50 | 30 | 0 | 90 | 70 | 30 | 0 | 100 | 80 | 30 | 0 |
| COTTON | 100 | 100 | 90 | 60 | 90 | 70 | 50 | 30 | 95 | 90 | 85 | 40 | 100 | 70 | 50 | 30 | 90 | 80 | 20 | 0 | 100 | 100 | 100 | 60 | 100 | 70 | 40 | 0 |
| SOYBEAN | 100 | 100 | 90 | 80 | 100 | 100 | 90 | 60 | 100 | 100 | 100 | 90 | 100 | 90 | 80 | 60 | 100 | 100 | 100 | 100 | 80 | 60 | 10 | 0 | 100 | 100 | 100 | 40 |
| BARNYARDGRASS | 90 | 80 | 70 | 60 | 100 | 90 | 80 | 70 | 80 | 70 | 50 | 30 | 90 | 80 | 70 | 60 | 100 | 90 | 80 | 70 | 80 | 30 | 0 | 0 | 80 | 80 | 70 | 40 |
| WILD OAT | 100 | 90 | 85 | 80 | 90 | 80 | 70 | 60 | 90 | 80 | 70 | 60 | 100 | 80 | 50 | 30 | 100 | 90 | 80 | 50 | 70 | 30 | 0 | 0 | 100 | 80 | 50 | 40 |
| MORNINGGLORY | 90 | 80 | 70 | 60 | 100 | 90 | 80 | 50 | 100 | 100 | 90 | 60 | 80 | 70 | 60 | 50 | 80 | 80 | 20 | 0 | 100 | 100 | 90 | 70 | 100 | 70 | 50 | 0 |
| WHEAT | 90 | 80 | 70 | 60 | 100 | 100 | 70 | 50 | 100 | 100 | 60 | 50 | 70 | 60 | 50 | 40 | 100 | 90 | 60 | 30 | 0 | 0 | 0 | 0 | 80 | 70 | 40 | 20 |
| SICKLEPOD | 85 | 60 | 30 | 0 | 70 | 50 | 30 | 0 | 80 | 60 | 20 | 0 | 70 | 50 | 40 | 0 | 50 | 40 | 20 | 0 | 80 | 20 | 0 | 0 | 60 | 40 | 0 | 0 |
| JOHNSONGRASS | 100 | 100 | 95 | 90 | 100 | 100 | 90 | 60 | 100 | 100 | 90 | 80 | 90 | 80 | 70 | 30 | 80 | 80 | 70 | 40 | 90 | 80 | 30 | 0 | 90 | 70 | 70 | 40 |
| NUTSEDGE | 100 | 50 | 30 | 0 | 90 | 80 | 30 | 0 | 100 | 90 | 40 | 30 | 90 | 40 | 30 | 0 | 60 | 50 | 0 | 0 | 100 | 40 | 20 | 0 | 100 | 30 | 0 | 0 |
| CORN | 70 | 60 | 50 | 40 | 90 | 60 | 0 | 0 | 70 | 60 | 50 | 0 | 60 | 30 | 0 | 0 | 100 | 100 | 30 | 20 | 100 | 100 | 20 | 0 | 100 | 100 | 50 | 30 |
| WILD BUCKWHEAT | 100 | 100 | 100 | 90 | 100 | 90 | 60 | 30 | 100 | 100 | 90 | 80 | 100 | 100 | 70 | 30 | 100 | 80 | 30 | 0 | 90 | 90 | 70 | 30 | 100 | 90 | 70 | 70 |
| BLACKGRASS | 100 | 100 | 70 | 50 | 100 | 100 | 50 | 0 | 90 | 70 | 60 | 50 | 70 | 60 | 50 | 30 | 100 | 90 | 50 | 40 | 30 | 0 | 0 | 0 | 80 | 60 | 40 | 0 |
| RAPE | 100 | 100 | 100 | 100 | 100 | 100 | 100 | 80 | 100 | 100 | 100 | 90 | 100 | 100 | 90 | 60 | 100 | 100 | 100 | 90 | 100 | 100 | 100 | 100 | 100 | 100 | 100 | 80 |
| BARLEY | 70 | 60 | 50 | 30 | 80 | 70 | 60 | 50 | 80 | 70 | 60 | 50 | 100 | 70 | 60 | 50 | 90 | 80 | 60 | 40 | 40 | 20 | 0 | 0 | 80 | 60 | 40 | 30 |
| GREEN FOXTAIL | 90 | 60 | 30 | 0 | 80 | 50 | 30 | 0 | 70 | 50 | 30 | 0 | 60 | 30 | 0 | 0 | 70 | 60 | 40 | 0 | 40 | 30 | 0 | 0 | 70 | 70 | 30 | 0 |
| CHEATGRASS | — | — | — | — | — | — | — | — | — | — | — | — | — | — | — | — | — | — | — | — | — | — | — | — | — | — | — | — |
| LAMBSQUARTERS | 90 | 80 | 70 | 50 | 100 | 90 | 70 | 50 | 100 | 90 | 60 | 50 | 100 | 85 | 80 | 50 | 100 | 80 | 80 | 70 | 100 | 100 | 80 | 80 | 100 | 100 | 90 | 70 |
| CHICKWEED | 100 | 100 | 100 | 100 | 100 | 100 | 90 | 70 | 100 | 100 | 100 | 100 | 100 | 100 | 90 | 60 | 100 | 100 | 100 | 80 | 100 | 100 | 70 | 70 | 100 | 90 | 80 | 40 |
| DOWNY BROME | 90 | 80 | 70 | 50 | 70 | 50 | 30 | 0 | 90 | 80 | 70 | 50 | 60 | 50 | 30 | 0 | 90 | 60 | 50 | 30 | 90 | 50 | 30 | 0 | 80 | 60 | 40 | 0 |

| | CMPD 57 | | | | CMPD 58 | | | | CMPD 59 | | | | CMPD 60 | | | | CMPD 61 | | | | CMPD 62 | | | | CMPD 63 | | | |
|---|---|---|---|---|---|---|---|---|---|---|---|---|---|---|---|---|---|---|---|---|---|---|---|---|---|---|---|---|
| RATE = G/HA | 62 | 16 | 4 | 1 | 62 | 16 | 4 | 1 | 62 | 16 | 4 | 1 | 62 | 16 | 4 | 1 | 62 | 16 | 4 | 1 | 62 | 16 | 4 | 1 | 62 | 16 | 4 | 1 |
| POSTEMERGENCE | | | | | | | | | | | | | | | | | | | | | | | | | | | | |
| GIANT FOXTAIL | 80 | 60 | 20 | 0 | 70 | 40 | 30 | 0 | 70 | 70 | 30 | 0 | 100 | 100 | 70 | 30 | 100 | 70 | — | 0 | 60 | 20 | 0 | 0 | 90 | 30 | 0 | 0 |
| VELVETLEAF | 100 | 90 | 50 | 30 | 100 | 90 | 60 | 0 | 100 | 90 | 50 | 20 | 100 | 100 | 100 | 50 | 100 | 100 | 80 | 0 | 100 | 40 | 20 | 0 | 100 | 70 | 50 | 40 |
| SUGARBEET | 100 | 100 | 100 | 40 | 100 | 100 | 100 | 40 | 100 | 100 | 100 | 80 | 100 | 100 | 90 | 90 | 100 | 90 | 80 | 60 | 100 | 80 | 80 | 70 | 100 | 100 | 100 | 80 |
| CRABGRASS | 50 | 20 | 0 | 0 | 50 | 40 | 0 | 0 | 50 | 50 | 20 | 0 | 90 | 30 | 0 | 0 | 100 | 50 | 0 | 0 | 60 | 30 | 0 | 0 | 90 | 60 | 30 | 0 |
| TEAWEED | 60 | 60 | 20 | 0 | 60 | 50 | 20 | 0 | 100 | 70 | 30 | — | 100 | 80 | 40 | 0 | 100 | 70 | 50 | 20 | 50 | 30 | 0 | 0 | 100 | 30 | 0 | 0 |
| JIMSONWEED | 100 | 80 | 50 | 30 | 100 | 80 | 80 | 40 | 100 | 80 | 80 | 30 | 100 | 90 | 85 | 70 | 100 | 100 | 90 | 40 | 100 | 100 | 90 | 0 | 100 | 90 | 90 | 80 |
| RICE | 90 | 90 | 50 | 0 | 90 | 90 | 80 | 20 | 90 | 90 | 90 | 30 | 100 | 100 | 90 | 30 | 100 | 100 | 70 | 40 | 100 | 100 | 40 | 20 | 100 | 100 | 90 | 30 |
| COCKLEBUR | 90 | 50 | 20 | 0 | 80 | 50 | 30 | 0 | 100 | 100 | 50 | 0 | 100 | 100 | 50 | 30 | 100 | 80 | 70 | 0 | 100 | 40 | 20 | 0 | 100 | 100 | 40 | 0 |
| COTTON | 100 | 100 | 20 | 0 | 90 | 90 | 50 | 40 | 80 | 60 | 40 | 0 | 100 | 100 | 90 | 30 | 100 | 100 | 90 | 90 | 90 | 30 | 20 | 0 | 100 | 80 | 30 | 0 |
| SOYBEAN | 100 | 100 | 50 | 20 | 100 | 100 | 100 | 40 | 100 | 100 | 100 | 40 | 100 | 90 | 90 | 80 | 100 | 90 | 90 | 70 | 100 | 100 | 100 | 60 | 100 | 100 | 90 | 80 |
| BARNYARDGRASS | 100 | 60 | 30 | 0 | 80 | 80 | 40 | 30 | 100 | 100 | 80 | 70 | 100 | 100 | 60 | 30 | 90 | 40 | 20 | 0 | 90 | 20 | 0 | 0 | 100 | 90 | 60 | 20 |
| WILD OAT | 100 | 80 | 40 | 30 | 90 | 80 | 50 | 50 | 100 | 80 | 80 | 40 | 100 | 90 | 70 | 70 | 100 | 90 | 70 | 50 | 100 | 70 | 60 | 40 | 100 | 90 | 70 | 30 |
| MORNINGGLORY | 100 | 80 | 20 | 0 | 90 | 40 | 20 | 0 | 100 | 90 | 40 | 0 | 100 | 100 | 60 | 60 | 100 | 100 | 100 | 80 | 100 | 100 | 80 | 60 | 100 | 90 | 90 | 80 |
| WHEAT | 80 | 40 | 20 | 0 | 100 | 70 | 50 | 40 | 90 | 70 | 50 | 40 | 100 | 70 | 40 | 10 | 90 | 70 | 40 | 0 | 100 | 80 | 70 | 30 | 100 | 90 | 60 | 40 |
| SICKLEPOD | 0 | 0 | 0 | 0 | 50 | 40 | 0 | 0 | 60 | 40 | 30 | 0 | 100 | 80 | 50 | 30 | 100 | 80 | 80 | 30 | 50 | 30 | 0 | 0 | 60 | 50 | 0 | 0 |
| JOHNSONGRASS | 90 | 70 | 40 | 0 | 100 | 100 | 100 | 40 | 90 | 90 | 80 | 60 | 100 | 100 | 80 | 30 | 100 | 90 | 40 | 30 | 100 | 100 | 30 | 0 | 100 | 100 | 90 | 40 |
| NUTSEDGE | 70 | 30 | 20 | 0 | 30 | 20 | 0 | 0 | 30 | 20 | 0 | 0 | 100 | 100 | 20 | 0 | 100 | 40 | 0 | 0 | 60 | 20 | 0 | 0 | 20 | 0 | 0 | 0 |
| CORN | 100 | 100 | 50 | 30 | 100 | 40 | 30 | 0 | 100 | 100 | 40 | 0 | 100 | 100 | 90 | 80 | 100 | 100 | 90 | 80 | 100 | 90 | 80 | 20 | 100 | 100 | 90 | 80 |

-continued

| | | | | | | | | | | | | | | | | | | | | | | | | | | | | |
|---|---|---|---|---|---|---|---|---|---|---|---|---|---|---|---|---|---|---|---|---|---|---|---|---|---|---|---|---|
| WILD BUCKWHEAT | 100 | 80 | 50 | 60 | 100 | 100 | 70 | 0 | 100 | 90 | 90 | 40 | 100 | 100 | 90 | 90 | 100 | 90 | 80 | 70 | 100 | 80 | 70 | 30 | 100 | 80 | 80 | 30 |
| BLACKGRASS | 70 | 40 | 30 | 0 | 80 | 50 | 40 | 0 | 80 | 50 | 40 | 40 | 90 | 70 | 40 | 40 | 90 | 70 | 30 | 0 | 100 | 90 | 50 | 30 | 90 | 80 | 70 | 40 |
| RAPE | 100 | 100 | 80 | 90 | 100 | 100 | 100 | 80 | 100 | 100 | 100 | 100 | 100 | 100 | 100 | 100 | 100 | 100 | 100 | 70 | 100 | 100 | 100 | 80 | 100 | 100 | 100 | 80 |
| BARLEY | 60 | 50 | 40 | 30 | 100 | 70 | 40 | 30 | 100 | 60 | 40 | 40 | 90 | 80 | 60 | 40 | 80 | 70 | 40 | 30 | 70 | 50 | 40 | 20 | 80 | 40 | 30 | 10 |
| GREEN FOXTAIL | 70 | 70 | 30 | 0 | 70 | 70 | 70 | 30 | 80 | 70 | 30 | 0 | 100 | 90 | 80 | 40 | 90 | 50 | 20 | 0 | 60 | 30 | 0 | 0 | 90 | 40 | 0 | 0 |
| CHEATGRASS | — | — | — | — | — | — | — | — | — | — | — | — | — | — | — | — | — | — | — | — | — | — | — | — | — | — | — | — |
| LAMBSQUARTERS | 100 | 70 | 70 | 70 | 70 | 70 | 30 | 0 | 100 | 80 | 80 | 70 | 90 | 90 | 80 | 80 | 90 | 90 | 90 | 90 | 90 | 50 | 50 | 40 | 90 | 90 | 90 | 50 |
| CHICKWEED | 100 | 100 | 90 | 50 | 100 | 100 | 80 | 50 | 100 | 100 | 100 | 70 | 100 | 100 | 100 | 80 | 100 | 100 | 90 | 80 | 100 | 100 | 80 | 50 | 100 | 100 | 80 | 70 |
| DOWNY BROME | 60 | 50 | 40 | 0 | 90 | 70 | 40 | 0 | 90 | 40 | 40 | 0 | 90 | 70 | 50 | 30 | 90 | 70 | 50 | 30 | 90 | 70 | 40 | 20 | 80 | 50 | 30 | 0 |

| | CMPD 64 | | | | CMPD 65 | | | | CMPD 66 | | | | CMPD 67 | | | | CMPD 68 | | | | CMPD 70 | | | | CMPD 71 | | | |
|---|---|---|---|---|---|---|---|---|---|---|---|---|---|---|---|---|---|---|---|---|---|---|---|---|---|---|---|---|
| RATE = G/HA | 62 | 16 | 4 | 1 | 250 | 62 | 16 | 4 | 62 | 16 | 4 | 1 | 250 | 62 | 16 | 4 | 250 | 62 | 16 | 4 | 62 | 16 | 4 | 1 | 250 | 62 | 16 | 4 |
| POSTEMERGENCE | | | | | | | | | | | | | | | | | | | | | | | | | | | | |
| GIANT FOXTAIL | 100 | 100 | 30 | 0 | 100 | 70 | 60 | 30 | 90 | 70 | 20 | 0 | 100 | 100 | 40 | 40 | 100 | 90 | 40 | 40 | 90 | 70 | 40 | 30 | 90 | 85 | 70 | 50 |
| VELVETLEAF | 100 | 100 | 80 | 70 | 100 | 100 | 100 | 90 | 100 | 100 | 90 | 60 | 100 | 100 | 100 | 70 | 100 | 100 | 90 | 70 | 90 | 80 | 50 | 30 | 90 | 90 | 50 | 30 |
| SUGARBEET | 100 | 100 | 90 | 60 | 100 | 100 | 100 | 100 | 100 | 100 | 90 | 70 | 100 | 100 | 100 | 100 | 100 | 100 | 100 | 80 | 100 | 100 | 90 | 80 | 100 | 100 | 90 | 80 |
| CRABGRASS | 90 | 80 | 30 | 0 | 30 | 20 | 0 | 0 | 30 | 0 | 0 | 0 | 70 | 70 | 40 | 0 | 90 | 50 | 30 | 0 | 50 | 30 | 0 | 0 | 90 | 90 | 30 | 0 |
| TEAWEED | 100 | 100 | 50 | 50 | 100 | 90 | 90 | 80 | 100 | 80 | 40 | 0 | 90 | 70 | 30 | 30 | 90 | 60 | 30 | 0 | 60 | 60 | 30 | 0 | 50 | 20 | 0 | 0 |
| JIMSONWEED | 80 | 80 | 80 | 30 | 100 | 100 | 100 | 90 | 100 | 90 | 90 | 80 | 100 | 100 | 95 | 85 | 100 | 100 | 90 | 80 | 100 | 100 | 70 | 50 | 95 | 90 | 90 | 50 |
| RICE | 100 | 100 | 90 | 40 | 100 | 100 | 90 | 50 | 100 | 100 | 30 | 20 | 100 | 100 | 90 | 60 | 100 | 100 | 70 | 40 | 100 | 90 | 90 | 80 | 100 | 100 | 80 | 60 |
| COCKLEBUR | 100 | 100 | 50 | 30 | 100 | 100 | 90 | 20 | 100 | 70 | 40 | 0 | 90 | 90 | 70 | 30 | 100 | 95 | 20 | 0 | 100 | 50 | 0 | 0 | 70 | 70 | 50 | 20 |
| COTTON | 100 | 90 | 90 | 30 | 90 | 90 | 40 | 30 | 95 | 70 | 70 | 30 | 80 | 80 | 80 | 40 | 90 | 40 | 40 | 0 | 80 | 30 | 0 | 0 | 70 | 40 | 20 | 0 |
| SOYBEAN | 100 | 100 | 100 | 70 | 100 | 100 | 100 | 90 | 100 | 100 | 100 | 40 | 100 | 100 | 100 | 100 | 100 | 100 | 80 | 80 | 100 | 100 | 80 | 60 | 100 | 100 | 90 | 60 |
| BARNYARDGRASS | 100 | 100 | 80 | 20 | 100 | 100 | 90 | 50 | 90 | 90 | 30 | 0 | 100 | 100 | 70 | 50 | 100 | 90 | 40 | 30 | 95 | 90 | 60 | 40 | 90 | 80 | 40 | 30 |
| WILD OAT | 100 | 100 | 80 | 30 | 100 | 100 | 100 | 90 | 100 | 100 | 90 | 60 | 100 | 100 | 90 | 70 | 100 | 100 | 100 | 80 | 100 | 80 | 60 | 40 | 100 | 100 | 95 | 80 |
| MORNINGGLORY | 100 | 90 | 80 | 50 | 100 | 100 | 40 | 20 | 100 | 90 | 80 | 20 | 90 | 90 | 90 | 0 | 100 | 100 | 70 | 30 | 90 | 30 | 0 | 0 | 20 | 0 | 0 | 0 |
| WHEAT | 100 | 100 | 90 | 90 | 100 | 100 | 90 | 60 | 90 | 80 | 80 | 60 | 90 | 90 | 80 | 40 | 90 | 80 | 70 | 30 | 90 | 80 | 40 | 0 | 90 | 90 | 70 | 50 |
| SICKLEPOD | 80 | 70 | 50 | 0 | 90 | 90 | 50 | 0 | 80 | 30 | 0 | 0 | 100 | 70 | 50 | 50 | 100 | 100 | 40 | 0 | 30 | 20 | 0 | 0 | 30 | 20 | 20 | 0 |
| JOHNSONGRASS | 90 | 90 | 90 | 20 | 100 | 100 | 90 | 80 | 90 | 90 | 40 | 30 | 100 | 100 | 90 | 60 | 100 | 90 | 80 | 50 | 90 | 90 | 70 | 30 | 100 | 100 | 80 | 70 |
| NUTSEDGE | 80 | 70 | 70 | 20 | 90 | 80 | 70 | 0 | 50 | 40 | 30 | 0 | 80 | 80 | 70 | 20 | 90 | 80 | 80 | 20 | 80 | 60 | 20 | 0 | 80 | 80 | 20 | 0 |
| CORN | 90 | 90 | 40 | 0 | 100 | 100 | 90 | 60 | 100 | 80 | 30 | 30 | 100 | 100 | 90 | 70 | 100 | 100 | 90 | 90 | 100 | 90 | — | 30 | 90 | 90 | 90 | 80 |
| WILD BUCKWHEAT | 100 | 100 | 70 | 40 | 100 | 100 | 100 | 90 | 100 | 100 | 80 | 70 | 100 | 100 | 100 | 100 | 100 | 100 | 100 | 100 | 70 | 70 | 40 | 40 | 100 | 100 | 90 | 70 |
| BLACKGRASS | 90 | 90 | 80 | 70 | 100 | 100 | 100 | 90 | 100 | 95 | 90 | 30 | 100 | 100 | 90 | 40 | 100 | 90 | 80 | 40 | 100 | 70 | 60 | 40 | 100 | 100 | 80 | 50 |
| RAPE | 100 | 100 | 90 | 80 | 100 | 100 | 100 | 100 | 100 | 100 | 100 | 80 | 100 | 100 | 100 | 100 | 100 | 100 | 100 | 100 | 100 | 100 | 100 | 100 | 100 | 100 | 100 | 90 |
| BARLEY | 100 | 90 | 90 | 80 | 100 | 100 | 95 | 90 | 95 | 95 | 90 | 60 | 95 | 90 | 80 | 80 | 90 | 80 | 50 | 30 | 70 | 40 | 30 | 0 | 100 | 90 | 70 | 60 |
| GREEN FOXTAIL | 100 | 100 | 40 | 20 | 90 | 80 | 50 | 30 | 90 | 40 | 0 | 0 | 100 | 100 | 20 | 20 | 100 | 80 | 20 | 20 | 90 | 30 | 30 | 0 | 90 | 50 | 50 | 40 |
| CHEATGRASS | — | — | — | — | — | — | — | — | — | — | — | — | — | — | — | — | — | — | — | — | — | — | — | — | — | — | — | — |
| LAMBSQUARTERS | 100 | 80 | 70 | 70 | 100 | 100 | 100 | 50 | 100 | 80 | 40 | 0 | 100 | 90 | 70 | 70 | 100 | 100 | 80 | 70 | 70 | 70 | 40 | 0 | 30 | 30 | 0 | 0 |
| CHICKWEED | 100 | 100 | 90 | 80 | 100 | 100 | 100 | 70 | 100 | 100 | 70 | 30 | 100 | 100 | 100 | 95 | 100 | 100 | 100 | 95 | 100 | 100 | 90 | 80 | 100 | 100 | 100 | 80 |
| DOWNY BROME | 100 | 100 | 100 | 80 | 100 | 100 | 90 | 70 | 100 | 100 | 80 | 70 | 90 | 90 | 80 | 40 | 100 | 90 | 70 | 40 | 100 | 60 | 40 | 0 | 100 | 90 | 80 | 30 |

| | CMPD 72 | | | | CMPD 74 | | | | CMPD 76 | | | | CMPD 77 | | | | CMPD 80 | | | | CMPD 81 | | | | CMPD 82 | | | |
|---|---|---|---|---|---|---|---|---|---|---|---|---|---|---|---|---|---|---|---|---|---|---|---|---|---|---|---|---|
| RATE = G/HA | 62 | 16 | 4 | 1 | 62 | 16 | 4 | 1 | 62 | 16 | 4 | 1 | 62 | 16 | 4 | 1 | 62 | 16 | 4 | 1 | 250 | 62 | 16 | 4 | 250 | 62 | 16 | 4 |
| POSTEMERGENCE | | | | | | | | | | | | | | | | | | | | | | | | | | | | |
| GIANT FOXTAIL | 90 | 80 | 50 | 30 | 100 | 60 | 30 | 0 | 60 | 30 | 0 | 0 | 50 | 30 | 0 | 0 | 100 | 80 | 50 | 30 | 100 | 80 | 60 | 30 | 100 | 70 | 40 | 0 |
| VELVETLEAF | 100 | 100 | 80 | 60 | 100 | 100 | 90 | 60 | 100 | 90 | 80 | 40 | 100 | 90 | 70 | 40 | 90 | 70 | 50 | 30 | 100 | 100 | 60 | 50 | 70 | 50 | 30 | 0 |
| SUGARBEET | 100 | 100 | 100 | 90 | 100 | 100 | 100 | 90 | 100 | 100 | 90 | 60 | 100 | 100 | 100 | 100 | 100 | 60 | 0 | 0 | 100 | 100 | 60 | 0 | 100 | 90 | 40 | 0 |
| CRABGRASS | 0 | 0 | 0 | 0 | 40 | 0 | 0 | 0 | 0 | 0 | 0 | 0 | 90 | 60 | 0 | 0 | 30 | 0 | 0 | 0 | 50 | 40 | 30 | 0 | 90 | 70 | 30 | 0 |
| TEAWEED | 70 | 50 | 40 | 30 | 90 | 70 | 50 | 30 | 70 | 30 | 0 | 0 | 90 | 60 | 20 | 0 | 80 | 70 | 30 | 0 | 90 | 60 | 30 | 0 | 50 | 30 | 0 | 0 |
| JIMSONWEED | 90 | 70 | 60 | 30 | 100 | 100 | 90 | 60 | 100 | 70 | 50 | 40 | 90 | 70 | 50 | 30 | 100 | 60 | 30 | 0 | 100 | 100 | 70 | 50 | 90 | 60 | 30 | 0 |
| RICE | 90 | 80 | 60 | 0 | 90 | 60 | 30 | 0 | 100 | 90 | 40 | 30 | 100 | 100 | 30 | 0 | 100 | 50 | 0 | 0 | 70 | 50 | 30 | 0 | 90 | 60 | 30 | 0 |
| COCKLEBUR | 30 | 0 | 0 | 0 | 70 | 50 | 0 | 0 | 0 | 0 | 0 | 0 | 40 | 30 | 0 | 0 | 80 | 30 | 0 | 0 | 90 | 80 | 50 | 30 | 50 | 30 | 0 | 0 |

-continued

| | | | | | | | | | | | | | | | | | | | | | | | | | | | | |
|---|---|---|---|---|---|---|---|---|---|---|---|---|---|---|---|---|---|---|---|---|---|---|---|---|---|---|---|---|
| COTTON | 60 | 0 | 0 | 0 | 100 | 40 | 0 | 0 | 40 | 30 | 0 | 0 | 60 | 30 | 0 | 0 | 90 | 30 | 0 | 0 | 90 | 70 | 40 | 0 | 20 | 0 | 0 | 0 |
| SOYBEAN | 100 | 100 | 90 | 50 | 100 | 90 | 80 | 30 | 100 | 90 | 70 | 30 | 100 | 100 | 80 | 70 | 100 | 80 | 40 | 0 | 100 | 90 | 60 | 30 | 90 | 70 | 30 | 0 |
| BARNYARDGRASS | 90 | 60 | 50 | 30 | 90 | 60 | 30 | 0 | 50 | 30 | 0 | 0 | 100 | 100 | 60 | 40 | 80 | 70 | 50 | 30 | 90 | 80 | 60 | 40 | 90 | 80 | 70 | 40 |
| WILD OAT | 80 | 70 | 30 | 0 | 80 | 70 | 30 | 0 | 60 | 50 | 40 | 0 | 80 | 50 | 30 | 0 | 80 | 50 | 30 | 0 | 100 | 60 | 30 | 0 | 100 | 60 | 30 | 0 |
| MORNINGGLORY | 80 | 70 | 50 | 0 | 90 | 40 | 30 | 0 | 80 | 50 | 0 | 0 | 90 | 60 | 0 | 0 | 70 | 30 | 0 | 0 | 90 | 60 | 30 | 0 | 100 | 50 | 0 | 0 |
| WHEAT | 70 | 40 | 0 | 0 | 70 | 40 | 30 | 0 | 70 | 50 | 30 | 0 | 80 | 70 | 30 | 0 | 30 | 0 | 0 | 0 | 80 | 40 | 0 | 0 | 70 | 30 | 0 | 0 |
| SICKLEPOD | 70 | 50 | 40 | 30 | 100 | 60 | 30 | 0 | 80 | 50 | 0 | 0 | 80 | 60 | 30 | 0 | 100 | 60 | 0 | 0 | 80 | 50 | 40 | 30 | 50 | 30 | 0 | 0 |
| JOHNSONGRASS | 90 | 70 | 60 | 30 | 90 | 60 | 30 | 0 | 70 | 50 | 30 | 0 | 100 | 90 | 50 | 30 | 90 | 70 | 50 | 0 | 90 | 80 | 60 | 30 | 90 | 80 | 70 | 30 |
| NUTSEDGE | 80 | 70 | 60 | 30 | 90 | 60 | 30 | 0 | 50 | 30 | 0 | 0 | 40 | 0 | 0 | 0 | 80 | 0 | 0 | 0 | 60 | 50 | 30 | 0 | 50 | 40 | 0 | 0 |
| CORN | 70 | 60 | 50 | 0 | 90 | 70 | 50 | 0 | 80 | 70 | 0 | 0 | 80 | 70 | 0 | 0 | 80 | 70 | 0 | 0 | 100 | 70 | 50 | 30 | 100 | 40 | 30 | 0 |
| WILD BUCKWHEAT | 100 | 100 | 100 | 80 | 100 | 90 | 80 | 70 | 100 | 90 | 80 | 40 | 100 | 90 | 70 | 60 | 100 | 100 | 70 | 30 | 100 | 100 | 70 | 30 | 100 | 100 | 50 | 0 |
| BLACKGRASS | 100 | 70 | 30 | 0 | 90 | 60 | 30 | 0 | 100 | 50 | 30 | 0 | 100 | 100 | 50 | 30 | 100 | 80 | 30 | 0 | 100 | 70 | 50 | 30 | 80 | 50 | 30 | 0 |
| RAPE | 100 | 100 | 100 | 100 | 100 | 100 | 100 | 90 | 100 | 100 | 100 | 100 | 100 | 100 | 100 | 100 | 100 | 100 | 100 | 60 | 100 | 100 | 100 | 100 | 100 | 100 | 60 | 40 |
| BARLEY | 60 | 40 | 20 | 0 | 90 | 40 | 0 | 0 | 50 | 30 | 0 | 0 | 60 | 30 | 0 | 0 | 70 | 50 | 30 | 0 | 80 | 70 | 60 | 50 | 70 | 60 | 50 | 40 |
| GREEN FOXTAIL | 80 | 40 | 30 | 0 | 70 | 60 | 0 | 0 | 60 | 30 | 0 | 0 | 50 | 30 | 0 | 0 | 70 | 60 | 30 | 0 | 90 | 80 | 70 | 30 | 70 | 50 | 0 | 0 |
| CHEATGRASS | — | — | — | — | — | — | — | — | — | — | — | — | — | — | — | — | — | — | — | — | — | — | — | — | — | — | — | — |
| LAMBSQUARTERS | 100 | 100 | 90 | 70 | 100 | 100 | 100 | 70 | 90 | 80 | 70 | 0 | 100 | 90 | 80 | 70 | 100 | 100 | 70 | 50 | 100 | 100 | 70 | 50 | 90 | 70 | 50 | 30 |
| CHICKWEED | 90 | 80 | 70 | 50 | 100 | 100 | 90 | 60 | 100 | 90 | 50 | 0 | 100 | 90 | 50 | 30 | 100 | 100 | 90 | 70 | 100 | 100 | 100 | 80 | 100 | 100 | 100 | 60 |
| DOWNY BROME | 70 | 40 | 20 | 0 | 100 | 60 | 30 | 0 | 100 | 60 | 30 | 0 | 70 | 50 | 30 | 0 | 40 | 0 | 0 | 0 | 90 | 50 | 30 | 0 | 90 | 30 | 0 | 0 |

| | CMPD 95 | | | | CMPD 96 | | | | CMPD 97 | | | |
|---|---|---|---|---|---|---|---|---|---|---|---|---|
| RATE = G/HA | 62 | 16 | 4 | 1 | 62 | 16 | 4 | 1 | 62 | 16 | 4 | 1 |
| POSTEMERGENCE | | | | | | | | | | | | |
| GIANT FOXTAIL | 30 | 20 | 0 | 0 | 10 | 0 | 0 | 0 | 50 | 30 | 10 | 0 |
| VELVETLEAF | 100 | 100 | 90 | 70 | 100 | 90 | 70 | 70 | 100 | 50 | 40 | 40 |
| SUGARBEET | 100 | 100 | 80 | 20 | 90 | 90 | 30 | 0 | 100 | 70 | 40 | — |
| CRABGRASS | 0 | 0 | 0 | 0 | 0 | 0 | 0 | 0 | 70 | 10 | 0 | 0 |
| TEAWEED | 80 | 70 | 70 | 20 | 70 | — | 60 | 20 | 80 | 30 | 30 | — |
| JIMSONWEED | 80 | 70 | 40 | 0 | 90 | 80 | 70 | 50 | 100 | 70 | 50 | 40 |
| RICE | 100 | 90 | 60 | 30 | 70 | 70 | 50 | 30 | 100 | 80 | 30 | 10 |
| COCKLEBUR | 90 | 50 | 10 | 0 | 30 | 30 | 20 | 0 | 30 | 20 | 10 | 0 |
| COTTON | — | — | — | — | — | — | — | — | — | — | — | — |
| SOYBEAN | 90 | 80 | 80 | 50 | 90 | 80 | 70 | 50 | 70 | 50 | 30 | 0 |
| BARNYARDGRASS | 100 | 90 | 80 | 30 | 70 | 40 | 30 | 0 | 100 | 90 | 40 | 20 |
| WILD OAT | 100 | 100 | 80 | 40 | 100 | 80 | 70 | 40 | 100 | 100 | 80 | 40 |
| MORNINGGLORY | 100 | 90 | 40 | 0 | 80 | 80 | 50 | 0 | 20 | 0 | 0 | 0 |
| WHEAT | 100 | 100 | 90 | 80 | 100 | 90 | 70 | 40 | 100 | 90 | 80 | 30 |
| SICKLEPOD | 30 | — | 0 | 0 | 10 | 0 | 0 | — | 20 | 0 | — | 0 |
| JOHNSONGRASS | 100 | 80 | 60 | 30 | 90 | 70 | 40 | 0 | 80 | 80 | 50 | 40 |
| NUTSEDGE | 60 | 30 | — | 20 | 0 | 0 | 0 | 0 | 60 | 40 | — | 10 |
| CORN | 20 | 20 | 10 | 0 | 10 | 0 | 0 | 0 | 0 | 0 | 0 | 0 |
| WILD BUCKWHEAT | 100 | 100 | 90 | 70 | 80 | 40 | 0 | 0 | 90 | 80 | 70 | 60 |
| BLACKGRASS | 100 | 100 | 90 | 70 | 100 | 100 | 60 | 40 | 100 | 100 | 80 | 30 |
| RAPE | 100 | 100 | 100 | 70 | 100 | 90 | 90 | 80 | 100 | 100 | 100 | 80 |
| BARLEY | 100 | 90 | 80 | 40 | 80 | 50 | 40 | 30 | 80 | 60 | 40 | 30 |
| GREEN FOXTAIL | 40 | 20 | 0 | 0 | 0 | 0 | 0 | 0 | 20 | 10 | 0 | 0 |
| CHEATGRASS | — | — | — | — | — | — | — | — | — | — | — | — |
| LAMBSQUARTERS | 100 | 100 | 100 | 80 | — | 80 | — | 30 | — | 100 | 40 | 40 |
| CHICKWEED | 100 | 100 | 90 | 60 | 100 | 100 | 20 | 0 | 100 | 90 | 40 | 0 |
| DOWNY BROME | 100 | 100 | 70 | 30 | 100 | 90 | 70 | 40 | 100 | 90 | 50 | 30 |

PREEMERGENCE

| RATE = G/HA | CMPD 1 250 | CMPD 1 62 | CMPD 1 16 | CMPD 1 4 | CMPD 2 250 | CMPD 2 62 | CMPD 2 16 | CMPD 2 4 | CMPD 3 250 | CMPD 3 62 | CMPD 3 16 | CMPD 3 4 | CMPD 4 250 | CMPD 4 62 | CMPD 4 16 | CMPD 4 4 |
|---|---|---|---|---|---|---|---|---|---|---|---|---|---|---|---|---|
| GIANT FOXTAIL | 100 | 40 | 20 | 0 | 100 | 100 | 70 | 50 | 100 | 100 | 70 | 40 | 100 | 80 | 50 | 0 |
| VELVETLEAF | 100 | 70 | 40 | 30 | 100 | 90 | 40 | 30 | 100 | 90 | 50 | — | 100 | 50 | 30 | 30 |
| SUGARBEET | 100 | 90 | 60 | 30 | 100 | 100 | 80 | 70 | 100 | 100 | 80 | 60 | 100 | 100 | 70 | 40 |
| CRABGRASS | 80 | 40 | 0 | 0 | 90 | 50 | 30 | 0 | 90 | 80 | 30 | 20 | 70 | 30 | 20 | 0 |
| TEAWEED | 90 | 70 | 40 | 0 | 100 | 90 | 70 | 30 | 100 | 90 | 70 | 30 | 90 | 80 | 30 | 0 |
| JIMSONWEED | 90 | 80 | 30 | 30 | 100 | 90 | 50 | 30 | 100 | 90 | 80 | 60 | 90 | 50 | 20 | 20 |
| RICE | 100 | 100 | 80 | 30 | 100 | 100 | 90 | 80 | 100 | 100 | 80 | 20 | 100 | 100 | 50 | 10 |
| COCKLEBUR | 80 | 40 | 20 | 0 | 100 | 80 | 20 | 0 | 100 | 90 | 20 | 0 | 90 | 30 | 0 | 0 |
| COTTON | 80 | 50 | 10 | 0 | 70 | 30 | 30 | 0 | 90 | 80 | 50 | 0 | 70 | 60 | 40 | 20 |
| SOYBEAN | 80 | 30 | 0 | 0 | 100 | 80 | 20 | 10 | 100 | 60 | 30 | 10 | 80 | 20 | 0 | 0 |
| BARNYARDGRASS | 100 | 100 | 50 | 20 | 100 | 100 | 90 | 40 | 100 | 100 | 50 | 30 | 100 | 60 | 20 | 0 |
| WILD OAT | 50 | 30 | 10 | 0 | 100 | 70 | 40 | 20 | 90 | 70 | 40 | 10 | 90 | 50 | 10 | 0 |
| MORNINGGLORY | 90 | 80 | 40 | 30 | 100 | 90 | 50 | 30 | 100 | 90 | 40 | 30 | 100 | 70 | 30 | 0 |
| WHEAT | 40 | 10 | 0 | 0 | 80 | 30 | 10 | 0 | 90 | 40 | 20 | 0 | 40 | 20 | 0 | 0 |
| SICKLEPOD | 90 | 40 | — | 0 | 100 | 70 | 50 | — | 100 | 100 | 50 | 20 | 80 | 50 | 0 | — |
| JOHNSONGRASS | 100 | 90 | 80 | 40 | 100 | 100 | 90 | 40 | 100 | 90 | 80 | 40 | 100 | 90 | 40 | 0 |
| NUTSEDGE | 80 | 60 | 30 | 0 | 100 | 60 | 40 | 0 | 100 | 40 | — | 0 | 100 | 90 | 30 | 0 |
| CORN | 100 | 50 | 30 | 10 | 100 | 90 | 10 | 0 | 100 | 100 | 30 | 10 | 100 | 20 | 10 | 0 |
| WILD BUCKWHEAT | 90 | 30 | — | 0 | 100 | 90 | 50 | 0 | 100 | 100 | 80 | 50 | 100 | 80 | 50 | 20 |
| BLACKGRASS | 80 | 70 | 40 | 10 | 90 | 90 | 70 | 40 | 100 | 80 | 70 | 30 | 90 | 70 | 40 | 20 |
| RAPE | 100 | 80 | 60 | 30 | 100 | 100 | 80 | 60 | 100 | 90 | 80 | 40 | 100 | 70 | 50 | 20 |
| BARLEY | 10 | 10 | 0 | 0 | 70 | 40 | 20 | 10 | 30 | 20 | 10 | 0 | 40 | 20 | 0 | 0 |
| GREEN FOXTAIL | 100 | 90 | 10 | 0 | 100 | 100 | 100 | 40 | 100 | 100 | 100 | 40 | 100 | 100 | 70 | 20 |
| CHEATGRASS | 90 | 60 | 50 | 30 | 100 | 80 | 70 | 50 | 100 | 90 | 70 | 40 | 90 | 90 | 40 | 20 |
| LAMBSQUARTERS | 100 | 70 | 50 | 0 | 100 | 100 | 60 | 40 | 100 | 100 | 60 | 30 | 100 | 100 | 40 | 0 |
| CHICKWEED | 90 | 80 | 70 | 20 | 100 | 100 | 80 | 60 | 100 | 90 | 90 | 40 | 100 | 50 | 10 | 0 |
| DOWNY BROME | — | — | — | — | — | — | — | — | — | — | — | — | — | — | — | — |

| RATE = G/HA | CMPD 5 62 | CMPD 5 16 | CMPD 5 4 | CMPD 5 1 | CMPD 6 62 | CMPD 6 16 | CMPD 6 4 | CMPD 6 1 | CMPD 7 250 | CMPD 7 62 | CMPD 8 250 | CMPD 8 62 | CMPD 8 16 | CMPD 9 250 | CMPD 9 62 | CMPD 9 16 |
|---|---|---|---|---|---|---|---|---|---|---|---|---|---|---|---|---|
| GIANT FOXTAIL | 100 | 70 | 30 | 0 | 90 | 40 | 40 | 0 | 20 | 0 | 90 | 70 | 0 | 100 | 90 | 60 |
| VELVETLEAF | 80 | 50 | 30 | 0 | 100 | 90 | 50 | 30 | 70 | 30 | 90 | 60 | 30 | 80 | 50 | 30 |
| SUGARBEET | 100 | 90 | 60 | 30 | 100 | 100 | 80 | 70 | 80 | 60 | 90 | 70 | 50 | 90 | 70 | 50 |
| CRABGRASS | 100 | 90 | 60 | 30 | 100 | 80 | 60 | 40 | 0 | 0 | 90 | 60 | 30 | 50 | 30 | 0 |
| TEAWEED | 90 | 70 | 50 | 30 | 90 | 80 | 40 | 30 | 30 | 20 | 80 | 50 | 30 | 80 | 50 | 30 |
| JIMSONWEED | 90 | 70 | 50 | 30 | 90 | 90 | 40 | 30 | 30 | 20 | 90 | 60 | 30 | 70 | 50 | 30 |
| RICE | 100 | 100 | 90 | 60 | 100 | 100 | 100 | 90 | 60 | 30 | 100 | 90 | 70 | 100 | 90 | 60 |
| COCKLEBUR | 90 | 80 | 70 | 50 | 100 | 90 | 70 | 30 | 0 | 0 | 70 | 30 | 0 | 70 | 30 | 0 |
| COTTON | 30 | 0 | 0 | 0 | 80 | 70 | 40 | 30 | 30 | 20 | 70 | 30 | 0 | 30 | 0 | 0 |
| SOYBEAN | 80 | 30 | 0 | 0 | 90 | 80 | 30 | 20 | 20 | 0 | 70 | 50 | 30 | 80 | 40 | 0 |
| BARNYARDGRASS | 90 | 60 | 0 | 0 | 100 | 90 | 80 | — | 20 | 0 | 90 | 60 | 30 | 60 | 30 | 0 |
| WILD OAT | 80 | 60 | 50 | 40 | 90 | 80 | 40 | 20 | 30 | — | 80 | 50 | 30 | 60 | 30 | 0 |
| MORNINGGLORY | 80 | 50 | 30 | 0 | 100 | 90 | 70 | 40 | 0 | 0 | 80 | 60 | 30 | 90 | 30 | 0 |
| WHEAT | 80 | 50 | 30 | 0 | 100 | 90 | 70 | 10 | 0 | 0 | 60 | 0 | 0 | 30 | 0 | 0 |
| SICKLEPOD | 100 | 100 | 60 | 30 | 100 | 100 | 70 | 40 | 40 | 0 | 90 | 80 | 70 | 90 | 30 | 0 |
| JOHNSONGRASS | 90 | 60 | 30 | 0 | 100 | 100 | 90 | 40 | 30 | — | 90 | 80 | 70 | 90 | 80 | 60 |
| NUTSEDGE | 70 | 50 | 0 | 0 | 70 | 60 | 30 | 0 | 20 | 0 | 60 | 30 | 0 | 70 | 30 | 0 |
| CORN | 90 | 30 | 0 | 0 | 100 | 100 | 30 | 20 | 10 | 0 | 90 | 60 | 0 | 100 | 80 | 0 |
| WILD BUCKWHEAT | 100 | 90 | 60 | 30 | 100 | 100 | 90 | 30 | 40 | 0 | 90 | 70 | 50 | 90 | 70 | 50 |
| BLACKGRASS | — | — | — | — | 100 | 80 | 40 | 20 | 100 | 30 | 90 | 70 | 50 | 80 | 50 | 30 |
| RAPE | 90 | 60 | 30 | 0 | 100 | 90 | 80 | 30 | 40 | 30 | 0 | 0 | 0 | 70 | 0 | 0 |
| BARLEY | 70 | 30 | 0 | 0 | 100 | 80 | 70 | 20 | 0 | 0 | 60 | 0 | 0 | 30 | 0 | 0 |
| GREEN FOXTAIL | 100 | 100 | 50 | 0 | 100 | 100 | 40 | 20 | 10 | 0 | 100 | 80 | 50 | 100 | 90 | 30 |
| CHEATGRASS | — | — | — | — | — | — | — | — | — | — | — | — | — | — | — | — |
| LAMBSQUARTERS | 100 | 90 | 80 | 50 | 100 | 100 | 100 | 50 | 40 | 30 | 90 | 70 | 50 | 90 | 60 | 30 |
| CHICKWEED | 100 | 100 | 100 | 70 | 100 | 90 | 90 | 40 | 100 | 40 | 90 | 70 | 30 | 90 | 70 | 50 |
| DOWNY BROME | 100 | 70 | 50 | 30 | 100 | 90 | 80 | 80 | 30 | 0 | 90 | 60 | 30 | 70 | 50 | 30 |

| RATE = G/HA | CMPD 10 250 | CMPD 10 62 | CMPD 10 16 | CMPD 11 250 | CMPD 11 62 | CMPD 11 16 | CMPD 12 250 | CMPD 12 62 | CMPD 12 16 | CMPD 13 250 | CMPD 13 62 | CMPD 13 16 | CMPD 13 4 |
|---|---|---|---|---|---|---|---|---|---|---|---|---|---|
| GIANT FOXTAIL | 100 | 80 | 50 | 100 | 100 | 80 | 100 | 100 | 50 | 100 | 90 | 60 | 30 |
| VELVETLEAF | 90 | 70 | 50 | 90 | 60 | 30 | 90 | 70 | 30 | 100 | 80 | 60 | 40 |
| SUGARBEET | 100 | 100 | 80 | 100 | 90 | 60 | 100 | 100 | 80 | 100 | 90 | 70 | 50 |
| CRABGRASS | 70 | 50 | 30 | 90 | 60 | 30 | 90 | 60 | 30 | 100 | 100 | 90 | 70 |
| TEAWEED | 90 | 70 | 50 | 70 | 30 | 0 | 90 | 70 | 50 | 90 | 80 | 70 | 60 |
| JIMSONWEED | 90 | 70 | 50 | 90 | 70 | 50 | 80 | 50 | 30 | 90 | 70 | 50 | 30 |
| RICE | 100 | 100 | 100 | 100 | 90 | 70 | 100 | 100 | 100 | 90 | 80 | 70 | 50 |
| COCKLEBUR | 70 | 50 | 30 | 70 | 30 | — | 80 | 60 | 30 | 80 | 70 | 60 | 30 |
| COTTON | 70 | 30 | 0 | 0 | 0 | 0 | 50 | 0 | 0 | 80 | 50 | 30 | 0 |
| SOYBEAN | 90 | 70 | 30 | 90 | 60 | 30 | 90 | 60 | 30 | 50 | 30 | 0 | 0 |
| BARNYARDGRASS | 100 | 60 | 30 | 90 | 60 | 30 | 70 | 50 | 30 | 30 | 0 | 0 | 0 |
| WILD OAT | 80 | 50 | 30 | 80 | 70 | 50 | 70 | 50 | 30 | 80 | 70 | 50 | 30 |
| MORNINGGLORY | 90 | 70 | — | 70 | 30 | 0 | 90 | 60 | 30 | 80 | 60 | 50 | 30 |
| WHEAT | 60 | 30 | 0 | 70 | 50 | 0 | 60 | 30 | 0 | 80 | 50 | 30 | 0 |
| SICKLEPOD | 90 | 80 | 50 | 70 | 60 | 50 | 70 | 30 | 0 | 100 | 100 | 60 | 30 |
| JOHNSONGRASS | 100 | 90 | 60 | 100 | 90 | 70 | 90 | 80 | 60 | 90 | 70 | 50 | 30 |
| NUTSEDGE | 70 | 50 | 30 | 80 | 50 | 30 | 60 | 30 | 0 | 100 | 100 | 50 | 0 |
| CORN | 70 | 0 | 0 | 90 | 80 | 0 | 90 | 30 | 0 | 70 | 50 | 30 | 0 |
| WILD BUCKWHEAT | 90 | 80 | 70 | 90 | 80 | 60 | 100 | 90 | 60 | 90 | 80 | 60 | 50 |

| RATE = G/HA | CMPD 15 250 | CMPD 15 62 | CMPD 15 16 | CMPD 20 62 | CMPD 20 16 | CMPD 20 4 | CMPD 20 1 | CMPD 22 250 | CMPD 22 62 | CMPD 22 16 | CMPD 22 4 | CMPD 23 62 | CMPD 23 16 | CMPD 23 4 | CMPD 23 1 |
|---|---|---|---|---|---|---|---|---|---|---|---|---|---|---|---|
| GIANT FOXTAIL | 100 | 90 | 40 | 100 | 50 | 30 | 20 | 90 | 80 | 60 | 20 | 50 | 40 | 40 | 0 |
| VELVETLEAF | 90 | 80 | 70 | 100 | 80 | 70 | 30 | 90 | 80 | 60 | 50 | 90 | 70 | 70 | 40 |
| SUGARBEET | 100 | 90 | 70 | 100 | 70 | 50 | 40 | 100 | 90 | 80 | 70 | 100 | 80 | 70 | 60 |
| CRABGRASS | 100 | 100 | 90 | 80 | 70 | 30 | 0 | 100 | 80 | 60 | 30 | 90 | 80 | 30 | 0 |
| TEAWEED | 95 | 90 | 85 | 100 | 90 | 60 | 30 | 90 | 80 | 50 | 30 | 90 | 40 | 20 | 10 |
| JIMSONWEED | 90 | 70 | 50 | 100 | 90 | 30 | 0 | 100 | 90 | 40 | 30 | 100 | 80 | 40 | 20 |
| RICE | 90 | 80 | 60 | 100 | 90 | 90 | 40 | 100 | 100 | 90 | 80 | 100 | 100 | 90 | 50 |
| COCKLEBUR | 90 | 80 | 70 | 90 | 70 | 30 | 20 | 80 | 50 | 30 | 0 | 40 | 30 | 20 | 0 |
| COTTON | 80 | 50 | 30 | 90 | 80 | 50 | 20 | 40 | 30 | 20 | 20 | 70 | 50 | 20 | 0 |
| SOYBEAN | 80 | 50 | 30 | 100 | 70 | 20 | 0 | 90 | 50 | 40 | 10 | 90 | 90 | 40 | 10 |
| BARNYARDGRASS | 100 | 70 | 30 | 100 | 100 | 40 | 20 | 100 | 100 | 50 | 40 | 100 | 60 | 40 | 0 |
| WILD OAT | 70 | 50 | 30 | 80 | 50 | 20 | 0 | 100 | 80 | 50 | 40 | 80 | 50 | 40 | 20 |
| MORNINGGLORY | 80 | 70 | 50 | 100 | 80 | 60 | 20 | 100 | 70 | 50 | 30 | 100 | 90 | 40 | 30 |
| WHEAT | 80 | 50 | 30 | 80 | 40 | 10 | 0 | 80 | 70 | 40 | 0 | 80 | 70 | 60 | 0 |
| SICKLEPOD | 100 | 100 | 50 | 100 | 60 | 30 | 0 | 100 | 100 | 40 | 30 | 100 | 100 | — | 0 |
| JOHNSONGRASS | 90 | 80 | 50 | 100 | 90 | 90 | 30 | 100 | 100 | 80 | 70 | 100 | 90 | 80 | 30 |
| NUTSEDGE | 90 | 70 | 50 | 90 | 60 | 20 | 0 | 100 | 40 | — | 20 | 30 | 10 | 0 | — |
| CORN | 100 | 90 | 30 | 100 | 40 | 30 | 20 | 100 | 90 | 30 | 10 | 100 | 90 | 30 | 0 |
| WILD BUCKWHEAT | 90 | 80 | 60 | 100 | 80 | 70 | 30 | 100 | 100 | 80 | — | 100 | 90 | 60 | 0 |

-continued

| | | | | | | | | | | | | | | | | | | | | | | | | | | | |
|---|---|---|---|---|---|---|---|---|---|---|---|---|---|---|---|---|---|---|---|---|---|---|---|---|---|---|---|
| BLACKGRASS | 100 | 90 | 60 | 100 | 70 | 50 | 90 | 70 | 50 | — | — | — | — | — | — | — | 90 | 90 | 70 | 20 | 90 | 90 | 60 | 40 | 90 | 40 | — | — |
| RAPE | 90 | 60 | 30 | 90 | 60 | 30 | 90 | 60 | 30 | 90 | 80 | 60 | 30 | 90 | 80 | 70 | 100 | 90 | 30 | 0 | 100 | 100 | 80 | 50 | 100 | 50 | 30 | 30 |
| BARLEY | 60 | 30 | 0 | 60 | 30 | 0 | 60 | 0 | 0 | 60 | 30 | 0 | 0 | 80 | 30 | 0 | 50 | 20 | 0 | 0 | 70 | 70 | 20 | 0 | 70 | 30 | 0 | 0 |
| GREEN FOXTAIL | 100 | 100 | 80 | 100 | 100 | 50 | 100 | 100 | 50 | 100 | 100 | 90 | 80 | 100 | 100 | 90 | 100 | 70 | 40 | 30 | 100 | 80 | 40 | 10 | 80 | 60 | 30 | 0 |
| CHEATGRASS | — | — | — | — | — | — | — | — | — | — | — | — | — | — | — | — | — | — | — | — | — | — | — | — | — | — | — | — |
| LAMBSQUARTERS | 100 | 90 | 80 | 100 | 90 | 80 | 100 | 80 | 50 | 100 | 90 | 80 | 70 | 100 | 100 | 90 | 100 | 90 | 90 | 80 | 100 | 90 | 40 | 40 | 100 | 90 | 70 | 60 |
| CHICKWEED | 100 | 100 | 90 | 100 | 90 | 70 | 100 | 100 | 70 | 100 | 100 | 100 | 70 | 100 | 100 | 90 | 100 | 100 | 80 | 80 | 100 | 100 | 100 | 80 | 100 | 100 | 100 | 80 |
| DOWNY BROME | 100 | 90 | 60 | 90 | 70 | 50 | 100 | 80 | 50 | 100 | 90 | 60 | 30 | 90 | 80 | 70 | 100 | 60 | 20 | 0 | 100 | 100 | 90 | 30 | 100 | 100 | 50 | 0 |

| | CMPD 27 | | | CMPD 28 | | | CMPD 29 | | | CMPD 31 | | | CMPD 32 | | CMPD 40 | | | CMPD 41 | | CMPD 42 | | | CMPD 44 | | | CMPD 45 | |
|---|---|---|---|---|---|---|---|---|---|---|---|---|---|---|---|---|---|---|---|---|---|---|---|---|---|---|---|
| RATE = G/HA | 250 | 62 | 16 | 250 | 62 | 16 | 250 | 62 | 16 | 250 | 62 | 16 | 250 | 62 | 250 | 62 | 16 | 250 | 62 | 250 | 62 | 16 | 250 | 62 | 16 | 250 | 62 |
| GIANT FOXTAIL | 50 | 0 | 0 | 90 | 70 | 30 | 95 | 90 | 80 | 70 | 60 | 50 | 70 | — | 100 | 100 | 100 | 100 | 90 | 100 | 100 | 90 | 100 | 100 | 90 | 100 | 90 |
| VELVETLEAF | 80 | 50 | 30 | 90 | 70 | 30 | 90 | 80 | 20 | 90 | 70 | 30 | 100 | 80 | 100 | 90 | 40 | 90 | 30 | 100 | 80 | 50 | 100 | 70 | 30 | 90 | 80 |
| SUGARBEET | 100 | 90 | 60 | 100 | 90 | 70 | 80 | 80 | 0 | 100 | 60 | 30 | 100 | 100 | 100 | 100 | 100 | 100 | 90 | 100 | 100 | 100 | 100 | 100 | 100 | 100 | 100 |
| CRABGRASS | 70 | 50 | 30 | 60 | 40 | 30 | 90 | 50 | 20 | 70 | 50 | 30 | 100 | 70 | 90 | 90 | 85 | 90 | 80 | 100 | 85 | 80 | 90 | 90 | 90 | 95 | 95 |
| TEAWEED | 90 | 60 | 30 | 60 | 50 | 30 | 90 | 30 | 0 | 80 | 30 | 0 | 100 | 80 | 100 | 100 | 90 | 100 | 90 | 100 | 95 | 80 | 100 | 100 | 40 | 100 | 90 |
| JIMSONWEED | 90 | 80 | 60 | 90 | 60 | 30 | 90 | 50 | 0 | 90 | 80 | 70 | 100 | 80 | 100 | 90 | 30 | 90 | 80 | 100 | 80 | 30 | 100 | 90 | 30 | 100 | 90 |
| RICE | 100 | 80 | 70 | 100 | 90 | 80 | 90 | 90 | 80 | 95 | 90 | 85 | 100 | 90 | 100 | 100 | 100 | 100 | 100 | 100 | 90 | 90 | 100 | 100 | 100 | 100 | 100 |
| COCKLEBUR | 90 | 60 | 0 | 60 | 30 | 0 | 90 | 90 | 40 | 60 | 50 | 30 | 90 | 40 | 90 | 80 | 70 | 90 | 60 | 90 | 80 | 30 | 90 | 80 | 60 | 100 | 90 |
| COTTON | 60 | 30 | 0 | 0 | 0 | 0 | 90 | 50 | 30 | 30 | 0 | 0 | 90 | 60 | 100 | 100 | 100 | 80 | 50 | 100 | 100 | 50 | 100 | 90 | 60 | 100 | 100 |
| SOYBEAN | 70 | 0 | 0 | 70 | 50 | 30 | 80 | 40 | 0 | 80 | 60 | 30 | 70 | 50 | 100 | 100 | 60 | 70 | 50 | 100 | 90 | 40 | 100 | 100 | 50 | 100 | 70 |
| BARNYARDGRASS | 50 | 40 | 30 | 40 | 30 | 20 | 90 | 90 | 80 | 50 | 40 | 30 | 80 | 40 | 100 | 100 | 80 | 100 | 80 | 100 | 100 | 40 | 100 | 100 | 80 | 100 | 100 |
| WILD OAT | 80 | 50 | 0 | 90 | 60 | 30 | 80 | 40 | 30 | 90 | 30 | 0 | 80 | 70 | 95 | 85 | 80 | 90 | 60 | 100 | 90 | 80 | 100 | 90 | 90 | 100 | 100 |
| MORNINGGLORY | 90 | 80 | 50 | 90 | 60 | 30 | 90 | 50 | 0 | 90 | 70 | 50 | 90 | 70 | 100 | 100 | 50 | 80 | 30 | 100 | 90 | 30 | 100 | 100 | 70 | 100 | 60 |
| WHEAT | 70 | 30 | 0 | 80 | 30 | 0 | 40 | 30 | 30 | 90 | 30 | 0 | 90 | 40 | 100 | 90 | 50 | 100 | 90 | 90 | 90 | 50 | 90 | 90 | 90 | 95 | 95 |
| SICKLEPOD | 80 | 50 | 30 | 90 | 30 | 0 | 100 | 40 | 40 | 100 | 60 | 30 | 100 | 90 | 100 | 100 | 90 | 90 | 40 | 100 | 90 | 90 | 100 | 95 | 50 | 100 | 100 |
| JOHNSONGRASS | 80 | 50 | 30 | 90 | 70 | 50 | 90 | 70 | 50 | 100 | 95 | 90 | 100 | 90 | 95 | 95 | 80 | 90 | 85 | 95 | 90 | 80 | 100 | 95 | 90 | 95 | 90 |
| NUTSEDGE | 80 | 40 | 0 | 70 | 50 | 30 | 0 | 0 | 0 | 70 | 50 | 30 | 50 | 30 | 100 | 90 | 70 | 90 | 50 | 80 | 50 | 30 | 90 | 70 | 20 | 70 | 30 |
| CORN | 70 | 0 | 0 | 100 | 80 | 30 | 90 | 60 | 30 | 80 | 0 | 0 | 70 | 40 | 100 | 100 | 60 | 90 | 80 | 100 | 100 | 30 | 100 | 100 | 50 | 100 | 100 |
| WILD BUCKWHEAT | 100 | 90 | 70 | 90 | 70 | 50 | 100 | 90 | 90 | 100 | 70 | 50 | 100 | 100 | 100 | 100 | 100 | 100 | 100 | 100 | 100 | 100 | 100 | 100 | 100 | 100 | 100 |
| BLACKGRASS | 70 | 50 | 30 | 80 | 70 | 50 | 80 | 70 | 60 | 80 | 50 | 0 | 90 | 80 | 100 | 90 | 90 | 90 | 80 | 100 | 90 | 80 | 90 | 80 | 70 | 100 | 100 |
| RAPE | 50 | 30 | 0 | 60 | 30 | 0 | 100 | 80 | 40 | 60 | 0 | 0 | 100 | 90 | 100 | 100 | 90 | 100 | 90 | 100 | 100 | 100 | 100 | 80 | 50 | 100 | 70 |
| BARLEY | 70 | 30 | 0 | 30 | 0 | 0 | 80 | 40 | 30 | 80 | 30 | 0 | 90 | 60 | 95 | 95 | 70 | 50 | 30 | 90 | 90 | 40 | 90 | 90 | 80 | 90 | 90 |
| GREEN FOXTAIL | 100 | 100 | 50 | 100 | 100 | 60 | 100 | 90 | 80 | 100 | 100 | 80 | 100 | 90 | 100 | 100 | 100 | 100 | 100 | 100 | 100 | 90 | 100 | 100 | 90 | 100 | 100 |
| CHEATGRASS | — | — | — | — | — | — | — | — | — | — | — | — | — | — | — | — | — | — | — | — | — | — | — | — | — | — | — |
| LAMBSQUARTERS | 90 | 80 | 50 | 90 | 80 | 50 | 80 | 60 | 80 | 70 | 50 | 30 | 100 | 100 | 90 | 90 | 90 | 90 | 90 | 90 | 90 | 90 | 90 | 40 | 30 | 90 | 70 |
| CHICKWEED | 100 | 100 | 100 | 100 | 90 | 80 | 100 | 100 | 80 | 90 | 70 | 50 | 100 | 100 | 100 | 100 | 100 | 100 | 80 | 100 | 100 | 90 | 100 | 100 | 80 | 80 | 80 |
| DOWNY BROME | 100 | 80 | 30 | 100 | 90 | 80 | 60 | 40 | 0 | 100 | 100 | 90 | 100 | 90 | 100 | 100 | 90 | 100 | 90 | 100 | 100 | 100 | 100 | 100 | 100 | 100 | 100 |

| | CMPD 45 | | CMPD 46 | | | CMPD 47 | | | | CMPD 48 | | | | CMPD 49 | | | |
|---|---|---|---|---|---|---|---|---|---|---|---|---|---|---|---|---|---|
| RATE = G/HA | 16 | 4 | 250 | 62 | 16 | 250 | 62 | 16 | 4 | 250 | 62 | 16 | 4 | 250 | 62 | 16 | 4 |
| GIANT FOXTAIL | 80 | 40 | 95 | 95 | 80 | 100 | 90 | 60 | 0 | 90 | 30 | 0 | 0 | 100 | 90 | 70 | 0 |
| VELVETLEAF | 40 | 0 | 100 | 90 | 60 | 100 | 90 | 60 | 30 | 90 | 70 | 50 | 30 | 90 | 85 | 80 | 70 |
| SUGARBEET | 100 | 70 | 100 | 80 | 70 | 90 | 85 | 80 | 60 | 90 | 70 | 50 | 30 | 90 | 80 | 70 | 50 |
| CRABGRASS | 90 | 90 | 90 | 85 | 70 | 90 | 80 | 70 | 50 | 90 | 70 | 50 | 30 | 90 | 80 | 70 | 60 |
| TEAWEED | 30 | 0 | 100 | 80 | 30 | 90 | 80 | 70 | 50 | 90 | 80 | 70 | 50 | 90 | 80 | 70 | 60 |
| JIMSONWEED | 30 | 0 | 100 | 70 | 30 | 90 | 70 | 30 | 0 | 90 | 70 | 50 | 30 | 90 | 80 | 70 | 60 |
| RICE | 100 | 100 | 100 | 100 | 80 | 90 | 80 | 70 | 30 | 90 | 80 | 70 | 60 | 90 | 80 | 70 | 0 |
| COCKLEBUR | 60 | 30 | 80 | 80 | 30 | 90 | 60 | 30 | 0 | 70 | 30 | 0 | 0 | 90 | 70 | 50 | 0 |
| COTTON | 50 | 20 | 100 | 90 | 30 | 90 | 60 | 30 | 0 | 70 | 50 | 30 | 0 | 80 | 50 | 30 | 0 |
| SOYBEAN | 60 | 30 | 100 | 60 | 40 | 80 | 50 | 30 | 0 | 30 | 0 | 0 | 0 | 70 | 50 | 30 | 0 |
| BARNYARDGRASS | 100 | 80 | 100 | 100 | 40 | 100 | 90 | 30 | 0 | 90 | 60 | 30 | 0 | 90 | 70 | 30 | 0 |
| WILD OAT | 90 | 80 | 90 | 40 | 20 | 70 | 50 | 30 | 0 | 50 | 0 | 0 | 0 | 70 | 50 | 30 | 0 |

-continued

| | | | | | | | | | | | | | | | | | |
|---|---|---|---|---|---|---|---|---|---|---|---|---|---|---|---|---|---|
| MORNINGGLORY | 40 | 20 | 100 | 80 | 50 | 90 | 80 | 70 | 50 | 90 | 60 | 30 | 0 | 90 | 70 | 50 | 30 |
| WHEAT | 95 | 90 | 90 | 30 | 0 | 70 | 60 | 50 | 40 | 40 | 0 | 0 | 0 | 60 | 50 | 0 | 0 |
| SICKLEPOD | 90 | 70 | 100 | 40 | 30 | 80 | 70 | 50 | 30 | 90 | 70 | 50 | 30 | 80 | 70 | 60 | 30 |
| JOHNSONGRASS | 85 | 80 | 90 | 90 | 80 | 90 | 80 | 60 | 0 | 90 | 70 | 50 | 30 | 90 | 80 | 60 | 50 |
| NUTSEDGE | 20 | 20 | 60 | 20 | 0 | 100 | 100 | 100 | 100 | 100 | 80 | 50 | 30 | 100 | 70 | 50 | 30 |
| CORN | 90 | 80 | 100 | 100 | 40 | 80 | 70 | 0 | 0 | 90 | 80 | 0 | 0 | 90 | 80 | 70 | 0 |
| WILD BUCKWHEAT | 100 | 70 | 100 | 100 | 90 | 100 | 100 | 90 | 70 | 100 | 100 | 90 | 80 | 95 | 90 | 85 | 80 |
| BLACKGRASS | 90 | 90 | 90 | 70 | 60 | 90 | 70 | 50 | 30 | 70 | 50 | 30 | 0 | 80 | 70 | 50 | 30 |
| RAPE | 50 | 40 | 60 | 40 | 0 | 90 | 70 | 50 | 0 | 90 | 80 | 70 | 60 | 100 | 100 | 90 | 50 |
| BARLEY | 90 | 90 | 95 | 80 | 40 | 40 | 30 | 0 | 0 | 60 | 30 | 0 | 0 | 70 | 30 | 0 | 0 |
| GREEN FOXTAIL | 70 | 40 | 100 | 100 | 90 | 100 | 90 | 70 | 30 | 90 | 30 | 0 | 0 | 100 | 100 | 50 | 30 |
| CHEATGRASS | — | — | — | — | — | — | — | — | — | — | — | — | — | — | — | — | — |
| LAMBSQUARTERS | 50 | 30 | 100 | 80 | 50 | 100 | 90 | 80 | 50 | 100 | 95 | 90 | 85 | 90 | 80 | 70 | 50 |
| CHICKWEED | 80 | 80 | 90 | 80 | 70 | 100 | 90 | 80 | 70 | 90 | 80 | 70 | 60 | 100 | 100 | 90 | 80 |
| DOWNY BROME | 100 | 100 | 100 | 100 | 95 | 80 | 50 | 30 | 0 | 60 | 30 | 0 | 0 | 90 | 60 | 30 | 0 |

| RATE = G/HA | CMPD 50 | | | | CMPD 51 | | | | CMPD 52 | | | CMPD 53 | | CMPD 54 | | | | CMPD 55 | | | | CMPD 56 | | | | CMPD 57 | |
|---|---|---|---|---|---|---|---|---|---|---|---|---|---|---|---|---|---|---|---|---|---|---|---|---|---|---|---|
| PREEMERGENCE | 250 | 62 | 16 | 4 | 62 | 16 | 4 | 1 | 250 | 62 | 16 | 250 | 62 | 250 | 62 | 16 | 4 | 250 | 62 | 16 | 4 | 250 | 62 | 16 | 4 | 250 | 62 |
| GIANT FOXTAIL | 100 | 80 | 0 | 0 | 90 | 80 | 30 | 0 | 100 | 90 | 80 | 100 | 90 | 100 | 90 | 80 | 30 | 100 | 70 | 40 | 20 | 95 | 90 | 80 | 20 | 90 | 90 |
| VELVETLEAF | 90 | 80 | 50 | 30 | 90 | 85 | 80 | 50 | 90 | 80 | 70 | 80 | 70 | 90 | 90 | 80 | 20 | 100 | 90 | 50 | 20 | 100 | 90 | 70 | 0 | 100 | 90 |
| SUGARBEET | 100 | 90 | 70 | 50 | 90 | 80 | 70 | 50 | 90 | 80 | 60 | 90 | 80 | 90 | 80 | 30 | 0 | 80 | 40 | 20 | 0 | 90 | 80 | 50 | 0 | 90 | 50 |
| CRABGRASS | 95 | 90 | 85 | 80 | 90 | 80 | 70 | 60 | 95 | 90 | 80 | 90 | 70 | 90 | 70 | 20 | 0 | 90 | 80 | 40 | 20 | 90 | 90 | 70 | 40 | 100 | 80 |
| TEAWEED | 90 | 70 | 50 | 30 | 90 | 70 | 50 | 30 | 90 | 80 | 70 | 80 | 60 | 90 | 90 | 0 | 0 | 80 | 80 | 40 | 20 | 90 | 90 | 50 | 0 | 90 | 90 |
| JIMSONWEED | 90 | 80 | 70 | 40 | 90 | 70 | 50 | 30 | 90 | 80 | 70 | 90 | 70 | 90 | 90 | 80 | 20 | 100 | 100 | 50 | 20 | 90 | 90 | 50 | 20 | 90 | 50 |
| RICE | 100 | 90 | 60 | 30 | 100 | 100 | 70 | 30 | 100 | 90 | 40 | 80 | 60 | 90 | 90 | 80 | 40 | 100 | 100 | 70 | 40 | 90 | 90 | 60 | 20 | 90 | 90 |
| COCKLEBUR | 90 | 60 | 30 | 0 | 70 | 50 | 30 | 0 | 90 | 60 | 30 | 0 | 0 | 90 | 80 | 50 | 30 | 40 | 20 | 0 | 0 | 90 | 60 | 30 | 0 | 90 | 80 |
| COTTON | 70 | 50 | 0 | 0 | 60 | 30 | 0 | 0 | 60 | 30 | 0 | 0 | 0 | 90 | 50 | 30 | 0 | 50 | 30 | 20 | 20 | 100 | 80 | 50 | 20 | 100 | 90 |
| SOYBEAN | 80 | 60 | 20 | 0 | 60 | 40 | 0 | 0 | 50 | 0 | 0 | 40 | 0 | 90 | 70 | 50 | 20 | 100 | 30 | 0 | 0 | 90 | 90 | 50 | 0 | 90 | 60 |
| BARNYARDGRASS | 100 | 100 | 30 | 0 | 100 | 70 | 0 | 0 | 100 | 80 | 50 | 90 | 60 | 95 | 95 | 80 | 70 | 100 | 100 | 40 | 30 | 95 | 90 | 20 | 0 | 100 | 70 |
| WILD OAT | 70 | 50 | 30 | 0 | 30 | 20 | 0 | 0 | 70 | 50 | 30 | 70 | 50 | 90 | 80 | 50 | 40 | 70 | 30 | 0 | 0 | 100 | 60 | 40 | 30 | 80 | 70 |
| MORNINGGLORY | 90 | 70 | 50 | 30 | 90 | 70 | 50 | 0 | 90 | 60 | 50 | 90 | 70 | 90 | 90 | 50 | 0 | 100 | 100 | 30 | 0 | 100 | 90 | 70 | 20 | 100 | 100 |
| WHEAT | 70 | 60 | 0 | 0 | 50 | 30 | 0 | 0 | 60 | 30 | 0 | 60 | 30 | 80 | 60 | 20 | 0 | 0 | 0 | 0 | 0 | 90 | 70 | 40 | 20 | 70 | 60 |
| SICKLEPOD | 90 | 80 | 70 | 50 | 90 | 80 | 70 | 60 | 70 | 60 | 50 | 70 | 50 | 100 | 40 | 40 | 0 | 100 | 50 | 20 | 0 | 90 | 80 | 40 | 0 | 50 | 40 |
| JOHNSONGRASS | 90 | 70 | 50 | 30 | 90 | 70 | 30 | 0 | 90 | 80 | 40 | 90 | 70 | 90 | 90 | 80 | 40 | 100 | 100 | — | — | 90 | 80 | 60 | 40 | 90 | 50 |
| NUTSEDGE | 30 | — | — | — | 100 | 100 | 100 | 100 | 100 | 100 | 90 | 100 | 100 | 100 | 90 | 20 | 0 | 100 | 30 | 0 | — | 20 | 0 | 0 | 0 | 90 | 90 |
| CORN | 90 | 60 | 20 | 0 | 70 | 0 | 0 | 0 | 70 | 0 | 0 | 90 | 70 | 90 | 80 | 60 | 30 | 60 | 30 | 20 | 0 | 100 | 90 | 80 | 20 | 100 | 90 |
| WILD BUCKWHEAT | 100 | 70 | 50 | 30 | 100 | 70 | 60 | 50 | 90 | 70 | 50 | 90 | 70 | 100 | 100 | 90 | 80 | 100 | 90 | 40 | 0 | 90 | 90 | 90 | 20 | 90 | 90 |
| BLACKGRASS | 80 | 70 | 50 | 30 | 70 | 30 | 0 | 0 | 80 | 50 | 30 | 90 | 70 | 80 | 80 | 70 | 50 | 80 | 70 | 30 | 0 | 80 | 70 | 30 | 30 | 80 | 70 |
| RAPE | 100 | 90 | 70 | 60 | 80 | 70 | 50 | 30 | 100 | 80 | 50 | 100 | 90 | 100 | 100 | 80 | 40 | 100 | 90 | 70 | 30 | 100 | 100 | 90 | 40 | 100 | 100 |
| BARLEY | 40 | 0 | 0 | 0 | 40 | 30 | 0 | 0 | 60 | 30 | 0 | 70 | 30 | 80 | 50 | 40 | 30 | 40 | 20 | 0 | 0 | 60 | 40 | 30 | 20 | 60 | 50 |
| GREEN FOXTAIL | 100 | 80 | 30 | 0 | 100 | 80 | 50 | 0 | 100 | 100 | 80 | 95 | 90 | 100 | 95 | 80 | 40 | 100 | 90 | 70 | 30 | 90 | 90 | 80 | 30 | 100 | 90 |
| CHEATGRASS | — | — | — | — | — | — | — | — | — | — | — | — | — | — | — | — | — | — | — | — | — | — | — | — | — | — | — |
| LAMBSQUARTERS | 100 | 90 | 70 | 50 | 100 | 90 | 70 | 50 | 90 | 70 | 50 | 100 | 100 | 100 | 90 | 80 | 0 | 100 | 90 | 80 | 80 | 90 | 90 | 90 | 80 | 100 | 90 |
| CHICKWEED | 100 | 90 | 70 | 50 | 100 | 90 | 60 | 30 | 100 | 90 | 70 | 90 | 80 | 100 | 90 | 80 | 80 | 100 | 100 | 80 | 60 | 100 | 90 | 80 | 70 | 100 | 90 |
| DOWNY BROME | 70 | 50 | 30 | 0 | 60 | 30 | 0 | 0 | 70 | 30 | 0 | 90 | 60 | 80 | 70 | 40 | 0 | 20 | 0 | 0 | 0 | 80 | 70 | 40 | 0 | 70 | 60 |

| RATE = G/HA | CMPD 57 | | CMPD 58 | | | | CMPD 59 | | | | CMPD 60 | | | | CMPD 61 | | | | CMPD 62 | | | | CMPD 63 | | | | CMPD 64 |
|---|---|---|---|---|---|---|---|---|---|---|---|---|---|---|---|---|---|---|---|---|---|---|---|---|---|---|---|
| PREEMERGENCE | 16 | 4 | 250 | 62 | 16 | 4 | 250 | 62 | 16 | 4 | 62 | 16 | 4 | 1 | 62 | 16 | 4 | 1 | 62 | 16 | 4 | 1 | 62 | 16 | 4 | 1 | 62 |
| GIANT FOXTAIL | 40 | 20 | 90 | 80 | 20 | 0 | 90 | 70 | 40 | 0 | 90 | 90 | 40 | 30 | 90 | 60 | 40 | 0 | 70 | 40 | 0 | 0 | 90 | 70 | 40 | 0 | 90 |
| VELVETLEAF | 50 | 0 | 80 | 50 | 0 | 0 | 90 | 80 | 30 | 0 | 100 | 90 | 80 | 30 | 100 | 70 | 40 | 20 | 100 | 90 | 80 | 20 | 90 | 90 | 40 | 20 | 100 |
| SUGARBEET | 30 | 0 | 90 | 80 | 30 | 0 | 90 | 90 | 30 | 0 | 100 | 60 | 30 | 0 | 100 | 40 | 20 | 0 | 60 | 40 | 0 | — | 80 | 80 | 50 | 0 | 100 |
| CRABGRASS | 40 | 70 | 80 | 50 | 30 | 30 | 90 | 70 | 70 | 70 | 90 | 80 | 40 | 0 | 90 | 90 | 50 | 20 | 90 | 70 | 60 | 20 | 100 | 80 | 40 | — | 90 |
| TEAWEED | 30 | 0 | 90 | 90 | 30 | 0 | 90 | 90 | 50 | 0 | — | — | — | — | — | — | — | — | — | — | — | — | — | — | — | — | — |
| JIMSONWEED | 40 | 20 | 90 | 50 | 50 | 20 | 90 | 70 | 20 | 0 | 100 | 40 | 20 | 0 | 100 | 100 | 80 | 30 | 80 | 30 | 10 | 0 | 100 | 90 | 40 | 0 | 100 |
| RICE | 80 | 20 | 90 | 60 | 20 | 0 | 100 | 90 | 80 | 30 | 100 | 90 | 30 | 0 | 100 | 80 | 10 | 0 | 100 | 70 | 10 | 0 | 100 | 100 | 10 | 0 | 100 |
| COCKLEBUR | 80 | 60 | 100 | 90 | 30 | 0 | 90 | 90 | 50 | 40 | 50 | 30 | 10 | 0 | 50 | 30 | — | 10 | 30 | — | 10 | 0 | 60 | — | 0 | 0 | 80 |
| COTTON | 80 | 30 | 100 | 50 | 30 | 20 | 100 | 80 | 50 | 20 | — | — | — | 10 | — | 30 | 10 | 10 | — | 20 | 10 | 0 | 100 | 100 | — | 50 | — |
| SOYBEAN | 10 | 0 | 90 | 20 | 0 | 0 | 90 | 50 | 20 | 0 | 90 | 30 | 20 | 0 | 90 | 60 | 10 | 0 | 100 | 60 | 30 | 10 | 90 | 90 | 30 | 20 | 100 |
| BARNYARDGRASS | 20 | 0 | 100 | 100 | 20 | 0 | 95 | 90 | 20 | 0 | 100 | 40 | 0 | 0 | 100 | 80 | 0 | 0 | 20 | 0 | 0 | 0 | 100 | 90 | 0 | 0 | 100 |
| WILD OAT | 40 | 40 | 60 | 40 | 30 | 0 | 60 | 40 | 30 | 30 | 70 | 50 | 20 | 0 | 50 | 0 | 0 | 0 | 60 | — | 0 | 0 | 60 | 10 | 0 | 0 | 90 |
| MORNINGGLORY | 70 | 20 | 100 | 100 | 50 | 0 | 100 | 100 | 100 | 50 | 90 | — | 30 | 0 | 100 | 70 | 60 | 30 | 100 | 70 | 40 | 30 | 90 | 90 | 90 | 40 | 90 |
| WHEAT | 20 | 0 | 40 | 20 | 0 | 0 | 80 | 50 | 30 | 0 | 50 | 10 | 0 | 0 | 40 | 10 | 0 | 0 | 40 | 20 | 10 | 0 | 30 | 10 | 0 | 0 | 90 |
| SICKLEPOD | 40 | 0 | 40 | 20 | 0 | 0 | 80 | 80 | 50 | 50 | — | — | — | — | — | — | — | — | — | — | — | — | — | — | — | — | — |
| JOHNSONGRASS | 40 | 0 | 80 | 80 | 50 | 0 | 90 | 80 | 50 | 50 | 100 | 20 | — | — | 100 | 90 | 40 | 0 | 90 | 70 | 50 | — | 100 | 90 | 80 | 10 | 100 |
| NUTSEDGE | 50 | 0 | 50 | 20 | 20 | 0 | 20 | 0 | 0 | 0 | 100 | 60 | 50 | 0 | 90 | 70 | 60 | 40 | 20 | — | 0 | 0 | 80 | 30 | — | — | 90 |
| CORN | 50 | 20 | 90 | 80 | 20 | 0 | 90 | 70 | 20 | 0 | 100 | 90 | 40 | 20 | 100 | 20 | 10 | — | 40 | 10 | — | 0 | 100 | 50 | 10 | — | 100 |
| WILD BUCKWHEAT | 90 | 80 | 90 | 90 | 90 | 30 | 90 | 90 | 90 | 80 | 100 | 90 | 40 | — | 100 | 100 | 100 | 50 | 100 | 90 | 90 | — | — | 100 | 100 | 90 | 100 |

-continued

| | | | | | | | | | | | | | | | | | | | | | | | | | | |
|---|---|---|---|---|---|---|---|---|---|---|---|---|---|---|---|---|---|---|---|---|---|---|---|---|---|---|
| BLACKGRASS | 50 | 40 | 80 | 70 | 50 | 40 | 70 | 70 | 60 | 40 | 90 | 70 | 50 | 50 | 90 | 60 | 40 | 40 | 80 | 60 | 30 | 0 | 90 | 40 | 20 | — | 100 |
| RAPE | 40 | 30 | 100 | 100 | 30 | 30 | 100 | 100 | 80 | 40 | — | — | — | — | — | — | — | — | — | — | — | — | — | — | — | — | — |
| BARLEY | 40 | 40 | 50 | 40 | 20 | 0 | 60 | 40 | 20 | 0 | 10 | 0 | 0 | 0 | 10 | 0 | 0 | 0 | 0 | 0 | 0 | 0 | 10 | 0 | 0 | 0 | 60 |
| GREEN FOXTAIL | 60 | 40 | 100 | 80 | 30 | 0 | 100 | 95 | 80 | 20 | 100 | 90 | 50 | 20 | 100 | 90 | 40 | 0 | 90 | 50 | 30 | 0 | 100 | 100 | 40 | 0 | 100 |
| CHEATGRASS | — | — | — | — | — | — | — | — | — | — | — | — | — | — | — | — | — | — | — | — | — | — | — | — | — | — | — |
| LAMBSQUARTERS | 90 | 0 | 80 | 80 | 50 | 30 | 90 | 90 | 90 | 50 | — | — | — | — | — | — | — | — | — | — | — | — | — | — | — | — | — |
| CHICKWEED | 50 | 30 | 100 | 90 | 50 | 50 | 90 | 90 | 80 | 30 | — | — | — | — | — | — | — | — | — | — | — | — | — | — | — | — | — |
| DOWNY BROME | 40 | 30 | 90 | 40 | 30 | 20 | 90 | 50 | 30 | 20 | 100 | — | — | 70 | 100 | 30 | 0 | 0 | 100 | 40 | 10 | 0 | 90 | 30 | — | 0 | 100 |

| RATE = G/HA | CMPD 64 | | | CMPD 65 | | | CMPD 66 | | | | CMPD 67 | | | CMPD 68 | | | CMPD 70 | | | | CMPD 71 | | | | CMPD 72 | | |
|---|---|---|---|---|---|---|---|---|---|---|---|---|---|---|---|---|---|---|---|---|---|---|---|---|---|---|---|
| PREEMERGENCE | 16 | 4 | 1 | 250 | 62 | 16 | 62 | 16 | 4 | 1 | 250 | 62 | 16 | 250 | 62 | 16 | 250 | 62 | 16 | 4 | 250 | 62 | 16 | 4 | 62 | 16 | 4 |
| GIANT FOXTAIL | 90 | 50 | 10 | 90 | 80 | 50 | 100 | 90 | 70 | 20 | 100 | 90 | 70 | 100 | 90 | 70 | 90 | 80 | 30 | 0 | 100 | 70 | 20 | 0 | 70 | 30 | 0 |
| VELVETLEAF | 80 | 50 | 10 | 100 | 100 | 100 | 100 | 100 | 80 | 20 | 100 | 100 | 50 | 100 | 70 | 50 | 80 | 20 | 0 | 0 | 50 | 20 | 0 | 0 | 90 | 80 | 60 |
| SUGARBEET | 80 | 70 | 40 | 100 | 100 | 100 | 100 | 100 | 80 | 30 | 100 | 100 | 80 | 100 | 90 | 90 | 40 | 30 | 0 | 0 | 90 | 80 | 30 | 0 | 70 | 60 | 50 |
| CRABGRASS | 80 | 70 | 20 | 100 | 80 | 80 | 100 | 80 | 70 | 0 | 100 | 90 | 70 | 90 | 90 | 70 | 90 | 40 | 20 | 20 | 90 | 40 | 20 | 0 | 90 | 80 | 70 |
| TEAWEED | — | — | — | 100 | 100 | 100 | 100 | 100 | 80 | 50 | 100 | 90 | 20 | 90 | 30 | 0 | 70 | 30 | 20 | 0 | 30 | 0 | 0 | 0 | 90 | 80 | 50 |
| JIMSONWEED | 50 | 20 | 0 | 100 | 100 | 100 | 100 | 100 | 100 | 100 | 100 | 100 | 80 | 100 | 90 | 90 | 100 | 50 | 50 | 50 | 90 | 80 | 30 | 30 | 90 | 80 | 60 |
| RICE | 100 | 60 | 0 | 100 | 100 | 100 | 100 | 100 | 100 | 20 | 100 | 100 | 70 | 100 | 90 | 90 | 100 | 80 | 30 | 0 | 100 | 80 | 30 | 0 | 100 | 90 | 80 |
| COCKLEBUR | 80 | 30 | — | 90 | 90 | 80 | 100 | 90 | 50 | 0 | 90 | 30 | 0 | 70 | 20 | 0 | 0 | 0 | 0 | 0 | 20 | 0 | 0 | 0 | 90 | 80 | 75 |
| COTTON | 30 | 20 | — | 100 | 100 | 70 | 100 | 80 | 50 | 0 | 100 | 50 | 0 | 90 | 30 | 0 | 20 | 0 | 0 | 0 | 90 | 0 | 0 | 0 | 0 | 0 | 0 |
| SOYBEAN | 30 | 20 | 0 | 100 | 100 | 80 | 100 | 80 | 50 | 20 | 100 | 80 | 60 | 100 | 70 | 50 | 50 | 20 | 0 | 0 | 70 | 30 | 0 | 0 | 40 | 20 | 0 |
| BARNYARDGRASS | 100 | 20 | 0 | 100 | 100 | 90 | 100 | 50 | 20 | 0 | 100 | 100 | 80 | 100 | 50 | 20 | 100 | 70 | 20 | 0 | 100 | 20 | 0 | 0 | 90 | 60 | 30 |
| WILD OAT | 80 | 40 | 20 | 100 | 90 | 90 | 90 | 90 | 40 | 20 | 80 | 80 | 70 | 80 | 70 | 40 | 40 | 20 | 0 | 0 | 70 | 50 | 40 | 30 | 60 | 30 | 0 |
| MORNINGGLORY | 90 | — | 70 | 100 | 100 | 100 | 100 | 100 | 20 | 0 | 100 | 70 | 30 | 100 | 70 | 30 | 100 | 100 | 70 | 50 | 30 | 0 | 0 | 0 | 90 | 70 | 30 |
| WHEAT | 10 | 0 | 0 | 90 | 90 | 80 | 90 | 90 | 80 | 20 | 90 | 80 | 40 | 80 | 50 | 20 | 40 | 20 | 0 | 0 | 90 | 20 | 0 | 0 | 50 | 30 | 0 |
| SICKLEPOD | — | — | — | 100 | 90 | 90 | 90 | 80 | 30 | 0 | 100 | 90 | 60 | 90 | 70 | 50 | 90 | 30 | 30 | 0 | 40 | 30 | 0 | 0 | 90 | 60 | 0 |
| JOHNSONGRASS | 100 | 50 | — | 100 | 90 | 80 | 100 | 90 | 70 | 20 | 100 | 90 | 70 | 100 | 80 | 50 | 90 | 70 | 20 | 0 | 90 | 70 | 50 | 0 | 90 | 50 | 0 |
| NUTSEDGE | 90 | 40 | 40 | 100 | 90 | 90 | 100 | 100 | 80 | 0 | 100 | 80 | 50 | 80 | 70 | 20 | 40 | 30 | 0 | 0 | 0 | 0 | 0 | 0 | 100 | 80 | 30 |
| CORN | 100 | 40 | 10 | 100 | 100 | 90 | 100 | 100 | 40 | 20 | 100 | 90 | 90 | 100 | 100 | 30 | 100 | 40 | 20 | 0 | 50 | 30 | 0 | 0 | 90 | 20 | 0 |
| WILD BUCKWHEAT | 100 | 100 | 90 | 100 | 100 | 90 | 100 | 100 | 90 | 50 | 100 | 100 | 90 | 100 | 100 | 80 | 70 | 70 | 0 | — | 80 | 80 | — | 0 | — | — | — |
| BLACKGRASS | 100 | 90 | 30 | 100 | 90 | 80 | 100 | 90 | 50 | 30 | 80 | 80 | 50 | 90 | 90 | 50 | 90 | 70 | 30 | 0 | 90 | 50 | 40 | 30 | 80 | 70 | 50 |
| RAPE | — | — | — | 100 | 100 | 100 | 100 | 100 | 100 | 80 | 100 | 100 | 90 | 100 | 100 | 100 | 70 | 30 | 0 | 0 | 80 | 70 | 0 | 0 | 90 | 70 | 50 |
| BARLEY | 10 | 0 | 0 | 90 | 90 | 80 | 90 | 90 | 40 | 20 | 80 | 50 | 30 | 60 | 40 | 20 | 60 | 50 | 20 | 0 | 70 | 20 | 0 | 0 | 40 | 20 | 0 |
| GREEN FOXTAIL | 100 | 60 | 20 | 90 | 80 | 50 | 100 | 90 | 60 | 0 | 100 | 95 | 90 | 100 | 95 | 50 | 90 | 80 | 30 | 0 | 90 | 70 | 30 | 0 | 100 | 90 | 60 |
| CHEATGRASS | — | — | — | — | — | — | — | — | — | — | — | — | — | — | — | — | — | — | — | — | — | — | — | — | — | — | — |
| LAMBSQUARTERS | — | — | — | 100 | 100 | 90 | 100 | 90 | 90 | 80 | 100 | 100 | 70 | 100 | 90 | 90 | 100 | 80 | 50 | 0 | 30 | 0 | 0 | 0 | 100 | 90 | 80 |
| CHICKWEED | — | — | — | 100 | 100 | 90 | 100 | 100 | 80 | 80 | 90 | 90 | 90 | 100 | 90 | 80 | 80 | 70 | 50 | 0 | 90 | 80 | 50 | 0 | 100 | 90 | 80 |
| DOWNY BROME | 100 | 60 | 0 | 90 | 90 | 70 | 100 | 90 | 80 | 40 | 90 | 80 | 40 | 90 | 70 | 20 | 80 | 20 | 0 | 0 | 90 | 50 | 30 | 0 | 30 | 20 | 0 |

| RATE = G/HA | CMPD 72 | CMPD 74 | | | | CMPD 76 | | | | CMPD 77 | | | | CMPD 80 | | | | CMPD 81 | | | | CMPD 82 | | | | CMPD 95 | |
|---|---|---|---|---|---|---|---|---|---|---|---|---|---|---|---|---|---|---|---|---|---|---|---|---|---|---|---|
| PREEMERGENCE | 1 | 250 | 62 | 16 | 4 | 62 | 16 | 4 | 1 | 62 | 16 | 4 | 1 | 62 | 16 | 4 | 1 | 250 | 62 | 16 | 4 | 250 | 62 | 16 | 4 | 250 | 62 |
| GIANT FOXTAIL | 0 | 100 | 90 | 60 | 30 | 50 | 20 | 0 | 0 | 70 | 30 | 0 | 0 | 100 | 60 | 50 | 40 | 100 | 100 | 70 | 50 | 90 | 60 | 30 | 0 | 40 | — |
| VELVETLEAF | 30 | 100 | 100 | 100 | 80 | 100 | 90 | 80 | 40 | 90 | 70 | 50 | 30 | 90 | 40 | 30 | 20 | 90 | 70 | 50 | 30 | 100 | 80 | 40 | 20 | 90 | 80 |
| SUGARBEET | 40 | 90 | 70 | 60 | 50 | 90 | 70 | 50 | 30 | 80 | 70 | 50 | 30 | 90 | 70 | 60 | 50 | 100 | 70 | 60 | 50 | 100 | 100 | 70 | 50 | 90 | 60 |
| CRABGRASS | 60 | 100 | 90 | 80 | 70 | 100 | 90 | 80 | 70 | 100 | 90 | 80 | 50 | 80 | 50 | 30 | 0 | 100 | 100 | 80 | 30 | 100 | 100 | 80 | 50 | 100 | 90 |
| TEAWEED | 0 | 95 | 90 | 80 | 70 | 80 | 70 | 30 | 0 | 100 | 90 | 50 | 0 | 90 | 60 | 30 | 0 | 90 | 80 | 50 | 30 | 90 | 80 | 50 | 30 | 90 | 90 |
| JIMSONWEED | 30 | 95 | 90 | 70 | 50 | 90 | 80 | 30 | 0 | 100 | 90 | 60 | 30 | 70 | 50 | 30 | 20 | 90 | 80 | 50 | 30 | 90 | 85 | 80 | 30 | 90 | 40 |
| RICE | 60 | 100 | 90 | 70 | 60 | 100 | 100 | 80 | 70 | 100 | 100 | 100 | 90 | 80 | 70 | 40 | 0 | 100 | 100 | 80 | 60 | 100 | 100 | 90 | 70 | 100 | 90 |
| COCKLEBUR | 50 | 90 | 80 | 50 | 30 | 30 | 0 | 0 | 0 | 80 | 70 | 30 | 0 | 80 | 60 | 50 | 30 | 90 | 80 | 70 | 50 | 90 | 80 | 70 | 30 | 90 | 80 |
| COTTON | 0 | 90 | 60 | 20 | 0 | 30 | 0 | 0 | 0 | 60 | 30 | 0 | 0 | 60 | 50 | 40 | 30 | 70 | 60 | 50 | 30 | 60 | 50 | 30 | 0 | 80 | 70 |
| SOYBEAN | 0 | 70 | 30 | 20 | 0 | 50 | 0 | 0 | 0 | 80 | 70 | 20 | 0 | 70 | 20 | 0 | 0 | 70 | 50 | 20 | 0 | 90 | 60 | 30 | 0 | 80 | 40 |
| BARNYARDGRASS | 0 | 100 | 90 | 60 | 30 | 90 | 60 | 30 | 0 | 100 | 100 | 60 | 0 | 100 | 50 | 30 | 0 | 100 | 90 | 60 | 30 | 100 | 100 | 80 | 60 | 70 | 60 |

-continued

| | | | | | | | | | | | | | | | | | | | | | | | | | | | |
|---|---|---|---|---|---|---|---|---|---|---|---|---|---|---|---|---|---|---|---|---|---|---|---|---|---|---|---|
| WILD OAT | 0 | 70 | 50 | 30 | 0 | 50 | 30 | 0 | 0 | 70 | 30 | 0 | 0 | 60 | 0 | 0 | 0 | 70 | 50 | 0 | 0 | 80 | 70 | 30 | 0 | 90 | 40 |
| MORNINGGLORY | 20 | 90 | 60 | 0 | 0 | 80 | 50 | 30 | 0 | 90 | 60 | 30 | 0 | 60 | 30 | 0 | 0 | 90 | 50 | 0 | 0 | 90 | 70 | 40 | 0 | 90 | 80 |
| WHEAT | 0 | 70 | 30 | 0 | 0 | 50 | 0 | 0 | 0 | 80 | 30 | 0 | 0 | 60 | 0 | 0 | 0 | 80 | 30 | 0 | 0 | 90 | 80 | 60 | 50 | 70 | 50 |
| SICKLEPOD | 0 | 90 | 80 | 50 | 30 | 90 | 70 | 30 | 0 | 90 | 80 | 30 | 0 | 70 | 30 | 0 | 0 | 90 | 60 | 30 | 0 | 95 | 90 | 60 | 30 | 100 | 40 |
| JOHNSONGRASS | 0 | 90 | 70 | 40 | 0 | 80 | 70 | 60 | 30 | 100 | 80 | 30 | 0 | 80 | 70 | 50 | 30 | 90 | 80 | 70 | 30 | 90 | 85 | 80 | 60 | 100 | 90 |
| NUTSEDGE | 0 | 100 | 50 | 30 | 0 | 90 | 50 | 0 | 0 | 70 | 60 | 50 | 30 | 100 | 30 | 0 | 0 | 100 | 100 | 100 | 90 | 100 | 90 | 60 | 30 | 90 | 70 |
| CORN | 0 | 90 | 80 | 0 | 0 | 50 | 0 | 0 | 0 | 80 | 0 | 0 | 0 | 60 | 0 | 0 | 0 | 90 | 70 | 30 | 20 | 80 | 70 | 60 | 30 | 90 | 30 |
| WILD BUCKWHEAT | — | — | — | — | — | — | — | — | — | — | — | — | — | 100 | 60 | 30 | 0 | 90 | 80 | 70 | 60 | 100 | 90 | 50 | 0 | 90 | 90 |
| BLACKGRASS | 30 | 90 | 80 | 70 | 60 | 80 | 60 | 30 | 0 | 95 | 70 | 50 | 30 | 80 | 50 | 30 | 0 | 90 | 80 | 30 | 0 | 100 | 70 | 60 | 50 | 90 | 80 |
| RAPE | 40 | 100 | 90 | 70 | 50 | 90 | 70 | 50 | 30 | 100 | 50 | 40 | 30 | 90 | 50 | 0 | 0 | 100 | 100 | 60 | 30 | 100 | 80 | 50 | 40 | 100 | 100 |
| BARLEY | 0 | 70 | 30 | 0 | 0 | 30 | 0 | 0 | 0 | 100 | 30 | 0 | 0 | 40 | 20 | 0 | 0 | 70 | 30 | 0 | 0 | 80 | 50 | 0 | 0 | 80 | 60 |
| GREEN FOXTAIL | 30 | 100 | 100 | 90 | 30 | 90 | 80 | 30 | 0 | 90 | 60 | 30 | 0 | 100 | 90 | 30 | 0 | 100 | 100 | 90 | 70 | 100 | 80 | 50 | 40 | 70 | 50 |
| CHEATGRASS | — | — | — | — | — | — | — | — | — | — | — | — | — | — | — | — | — | — | — | — | — | — | — | — | — | — | — |
| LAMBSQUARTERS | 50 | 100 | 100 | 90 | 80 | 90 | 70 | 50 | 30 | 100 | 100 | 70 | 50 | 100 | 100 | 100 | 100 | 100 | 100 | 100 | 100 | 100 | 100 | 90 | 80 | 100 | 100 |
| CHICKWEED | 70 | 100 | 90 | 80 | 60 | 95 | 90 | 70 | 50 | 95 | 90 | 80 | 70 | 100 | 100 | 80 | 50 | 100 | 90 | 80 | 60 | 100 | 90 | 80 | 70 | 100 | 100 |
| DOWNY BROME | 0 | 80 | 50 | 30 | 0 | 50 | 30 | 0 | 0 | 80 | 30 | 0 | 0 | 50 | 30 | 0 | 0 | 80 | 70 | 30 | 0 | 0 | 90 | 80 | 30 | 0 | 100 | 100 |

| RATE = G/HA | CMPD 95 | | CMPD 96 | | | | CMPD 97 | | | |
|---|---|---|---|---|---|---|---|---|---|---|
| PREEMERGENCE | 16 | 4 | 250 | 62 | 16 | 4 | 250 | 62 | 16 | 4 |
| GIANT FOXTAIL | 20 | 0 | 90 | 40 | 0 | 0 | 100 | 40 | 0 | 0 |
| VELVETLEAF | 40 | 30 | 90 | 80 | 50 | 0 | 90 | 40 | 30 | 30 |
| SUGARBEET | 50 | — | 80 | 40 | 40 | 30 | 90 | 70 | 40 | 20 |
| CRABGRASS | 70 | 0 | 90 | 80 | 70 | 40 | 90 | 50 | 40 | — |
| TEAWEED | 70 | 50 | 90 | 40 | 30 | 0 | 90 | 80 | 80 | 50 |
| JIMSONWEED | 40 | 30 | 90 | 70 | 30 | 0 | 90 | 40 | — | 20 |
| RICE | 80 | 20 | 100 | 70 | 30 | 10 | 100 | 90 | 80 | 10 |
| COCKLEBUR | 50 | — | 80 | 40 | 30 | 0 | 90 | 40 | 30 | 0 |
| COTTON | 30 | 0 | 90 | 40 | 30 | 0 | 90 | 70 | 50 | 30 |
| SOYBEAN | 10 | 0 | 90 | 40 | 10 | 0 | 80 | 30 | 10 | 0 |
| BARNYARDGRASS | 30 | 0 | 100 | 70 | 30 | 0 | 100 | 70 | 10 | 0 |
| WILD OAT | 0 | 0 | 90 | 40 | 20 | 0 | 90 | 70 | 30 | 10 |
| MORNINGGLORY | 40 | 30 | 90 | 70 | 50 | 30 | 90 | 70 | 40 | — |
| WHEAT | 20 | 0 | 80 | 50 | 10 | 0 | 80 | 60 | 10 | 0 |
| SICKLEPOD | 0 | 0 | 90 | 40 | — | — | 60 | — | — | — |
| JOHNSONGRASS | 40 | 0 | 100 | 60 | 40 | 20 | 100 | 90 | 40 | 30 |
| NUTSEDGE | 20 | 0 | 90 | 40 | 0 | 0 | 80 | — | 40 | 0 |
| CORN | 10 | 0 | 20 | 20 | 0 | — | 0 | 0 | 0 | 0 |
| WILD BUCKWHEAT | 40 | 30 | 90 | 40 | 30 | 0 | 90 | 80 | 50 | 30 |
| BLACKGRASS | 40 | 30 | 100 | 90 | 70 | 30 | 100 | 90 | 50 | 40 |
| RAPE | 90 | 40 | 90 | 70 | 60 | 50 | 90 | 90 | 70 | 50 |
| BARLEY | 50 | 10 | 70 | 60 | 20 | 10 | 70 | 50 | 30 | 10 |
| GREEN FOXTAIL | — | 20 | 100 | 100 | 50 | 0 | 100 | 100 | 40 | 0 |
| CHEATGRASS | — | — | — | — | — | — | — | — | — | — |
| LAMBSQUARTERS | 90 | 80 | 100 | 90 | 80 | 40 | 100 | 90 | 80 | 40 |
| CHICKWEED | 90 | 80 | 90 | 90 | 80 | 50 | 90 | 90 | 40 | 30 |
| DOWNY BROME | 80 | 40 | 100 | 90 | 60 | 20 | 90 | 80 | 30 | 0 |

TEST C

Seeds of annual bluegrass (*Poa annua*), spring and winter barley (*Hordeum vulgare*), birdseye speedwell (*Veronica persica*), blackgrass (*Alopecurus myosuroides*), black nightshade (*Solanum nigrum*), catchweed bedstraw (*Galium aparine*), cheatgrass (*Bromus secalinus*), downy brome (*Bromus tectorum*), field pennycress (*Thlaspi arvense*), field violet (*Viola arvensis*), green foxtail (*Setaria viridis*), Italian ryegrass (*Lolium multiflorum*), ivyleaf speedwell (*Veronica hederaefolis*), jointed goatgrass (*Aegilops cylindrica*), kochia (*Kochia scoparia*), lambsquarters (*Chenopodium album*), rape (*Brassica napus*), Russian thistle (*Salsola kali*), scentless chamomile (*Matricaria inodora*), sugarbeet (*Beta vulgaris*), spring and winter wheat (*Triticum aestivum*), wild buckwheat (*Polygonum convolvulus*), and wild oat (*Avena fatua*) were planted and treated preemergence with test chemicals dissolved in a non-phytotoxic solvent. At the same time, these crop and weed species were also treated with postemergence applications of test chemicals. Plants ranged in height from two to twenty-four cm for postemergence treatments. Blackgrass and wild oat were treated postemergence at two growth stages. Treated plants and controls were maintained in a greenhouse for approximately 21 days, after which all species were compared to controls and visually evaluated. The ratings, summarized in Table C, are based on a scale of 0 to 100 where 0 is no effect and 100 is complete control. A dash (-) response means no test.

TABLE C

| | CMPD 1 | | | | | CMPD 6 | | | | | CMPD 13 | | | |
|---|---|---|---|---|---|---|---|---|---|---|---|---|---|---|
| RATE G/HA | 125 | 64 | 32 | 16 | 8 | 64 | 32 | 16 | 8 | 4 | 32 | 16 | 8 | 4 |
| POSTEMERGENCE | | | | | | | | | | | | | | |
| SPRING WHEAT | 0 | 0 | 0 | 0 | 0 | 100 | 90 | 80 | 70 | 60 | 20 | 20 | 20 | 0 |
| SPRING BARLEY | 10 | 0 | 0 | 0 | 0 | 60 | 40 | 30 | 30 | 20 | 50 | 40 | 30 | 30 |
| WILD OAT STAGE 1 | 60 | 60 | 20 | 20 | 20 | 100 | 100 | 80 | 60 | 50 | 80 | 50 | 20 | 0 |
| DOWNY BROME | 20 | 10 | 10 | 0 | 0 | 90 | 70 | 70 | 60 | 40 | 90 | 90 | 40 | 20 |
| CHEATGRASS | 60 | 40 | 40 | 20 | 0 | 80 | 80 | 60 | 40 | 30 | 60 | 60 | 50 | 30 |
| BLACKGRASS STAGE 1 | 10 | 0 | 0 | 0 | 0 | 90 | 70 | 50 | 40 | 30 | 100 | 80 | 50 | 40 |
| BLUEGRASS | 20 | 0 | 0 | 0 | 0 | 80 | 80 | 80 | 40 | 30 | 40 | 20 | 10 | 0 |
| GREEN FOXTAIL | 80 | 70 | 70 | 50 | 50 | 90 | 80 | 70 | 40 | 20 | 90 | 90 | 90 | 70 |
| ITALIAN RYEGRASS | 100 | 100 | 90 | 70 | 40 | 100 | 100 | 100 | 100 | 80 | 80 | 40 | 40 | 20 |
| RAPE | 100 | 100 | 100 | 100 | 80 | 100 | 100 | 100 | 100 | 90 | 100 | 100 | 100 | 100 |
| WINTER WHEAT | 10 | 0 | 0 | 0 | 0 | 90 | 70 | 70 | 60 | 50 | 40 | 20 | 10 | 0 |
| WINTER BARLEY | 10 | 0 | 0 | 0 | 0 | 80 | 70 | 70 | 60 | 40 | 80 | 60 | 40 | 30 |
| JOINTED GOATGRASS | 0 | 0 | 0 | 0 | 0 | 100 | 80 | 70 | 50 | 40 | 70 | 60 | 40 | 20 |
| WILD OAT STAGE 2 | 70 | 30 | 0 | 0 | 0 | 90 | 90 | 80 | 80 | 60 | 90 | 90 | 50 | 20 |
| BLACKGRASS STAGE 2 | 50 | 50 | — | — | 10 | 80 | 60 | 40 | 30 | 20 | 40 | 10 | 10 | 0 |
| CATCHWEED BEDSTRAW | 100 | 70 | 60 | 40 | 30 | 100 | 100 | 90 | 40 | 20 | 60 | 30 | 20 | 10 |
| WILD BUCKWHEAT | 90 | 90 | 70 | 40 | 30 | 100 | 70 | 70 | 50 | 20 | 80 | 30 | 0 | 0 |
| KOCHIA | 100 | 90 | 90 | 70 | 20 | 100 | 70 | 70 | 50 | 20 | 100 | 100 | 80 | 60 |
| SCENTLESS CHAMOMILE | 100 | 90 | 70 | 70 | 50 | 100 | 100 | 100 | 40 | 20 | 100 | 100 | 100 | 70 |
| BLACK NIGHTSHADE | 50 | 50 | 30 | 20 | 10 | 70 | 30 | 10 | 0 | 0 | 70 | 20 | 20 | 20 |
| RUSSIAN THISTLE | — | — | 90 | 70 | 30 | — | — | — | — | — | — | — | — | — |
| BIRDSEYE SPEEDWELL | 100 | 100 | 100 | 70 | 40 | 100 | 80 | 60 | 40 | 20 | 0 | 0 | 0 | 0 |
| SUGARBEET | 100 | 100 | 90 | 80 | 60 | 100 | 100 | 100 | 80 | 80 | 100 | 100 | 100 | 100 |
| IVYLEAF SPEEDWELL | 100 | 40 | 20 | 0 | 0 | 60 | 40 | 20 | 10 | 0 | 20 | 0 | 0 | 0 |
| LAMBSQUARTERS | 100 | 80 | 70 | 60 | 30 | 100 | 70 | 60 | 50 | 30 | 70 | 50 | 50 | 40 |
| FIELD PENNYCRESS | 70 | 40 | 0 | 0 | 0 | 100 | 90 | 60 | 50 | 40 | 100 | 80 | 80 | 40 |
| FIELD VIOLET | 0 | 0 | 0 | 0 | 0 | 30 | 0 | 0 | 0 | 0 | 60 | 50 | 20 | 0 |
| PREEMERGENCE | | | | | | | | | | | | | | |
| SPRING WHEAT | 40 | 30 | 30 | 10 | 0 | 100 | 90 | 90 | 80 | 70 | 30 | 30 | 30 | 20 |
| SPRING BARLEY | 30 | 20 | 0 | 0 | 0 | 100 | 100 | 90 | 70 | 40 | 30 | 10 | 0 | 0 |
| WILD OAT | 20 | 0 | 0 | 0 | 0 | 90 | 80 | 60 | 50 | 30 | 50 | 20 | 0 | 0 |
| DOWNY BROME | 20 | 10 | 0 | 0 | 0 | 100 | 100 | 90 | 70 | 30 | 10 | 0 | 0 | 0 |
| CHEATGRASS | 70 | 70 | 40 | 30 | 20 | 100 | 100 | 90 | 70 | 50 | 40 | 40 | 10 | 0 |
| BLACKGRASS | 60 | 40 | 40 | 20 | 10 | 100 | 90 | 70 | 60 | 40 | 70 | 70 | 50 | 30 |
| BLUEGRASS | 50 | 40 | 40 | 20 | 20 | 90 | 90 | 80 | 80 | 60 | 70 | 50 | 20 | 0 |
| GREEN FOXTAIL | 90 | 70 | 40 | 30 | 10 | 100 | 100 | 70 | 60 | 30 | 100 | 80 | 50 | 40 |
| ITALIAN RYEGRASS | 80 | 70 | 30 | 10 | 0 | 90 | 90 | 80 | 60 | 30 | 70 | 50 | 20 | 10 |
| RAPE | 100 | 100 | 100 | 70 | 70 | 100 | 100 | 80 | 60 | 30 | 100 | 90 | 80 | 60 |
| WINTER WHEAT | 30 | 20 | 0 | 0 | 0 | 100 | 90 | 90 | 70 | 70 | 10 | 0 | 0 | 0 |
| WINTER BARLEY | 40 | 30 | 20 | 20 | 10 | 100 | 90 | 90 | 80 | 50 | 50 | 20 | 10 | 0 |
| JOINTED GOATGRASS | 30 | 0 | 0 | 0 | 0 | 70 | 70 | 60 | 50 | 30 | 40 | 40 | 20 | 0 |
| CATCHWEED BEDSTRAW | 40 | 10 | 0 | 0 | 0 | 90 | 70 | 70 | 60 | 50 | 50 | 50 | 40 | 30 |
| WILD BUCKWHEAT | 70 | 50 | 50 | 40 | 0 | 100 | 80 | 70 | 60 | 60 | 50 | 50 | 30 | 0 |
| KOCHIA | 50 | 20 | 10 | 0 | 0 | 90 | 70 | 20 | 10 | 0 | 70 | 70 | 30 | 0 |
| SCENTLESS CHAMOMILE | 80 | 80 | 70 | 60 | 40 | 100 | 100 | 90 | 70 | 30 | 100 | 90 | 90 | 70 |
| BLACK NIGHTSHADE | 50 | 20 | 10 | 0 | 0 | 30 | 20 | 0 | 0 | 0 | 60 | 10 | 0 | 0 |
| RUSSIAN THISTLE | — | — | — | — | — | — | — | — | — | — | — | — | — | — |
| BIRDSEYE SPEEDWELL | 70 | 60 | 40 | 30 | 20 | 90 | 70 | 70 | 50 | 40 | 20 | 0 | 0 | 0 |
| SUGARBEET | 80 | 60 | 40 | 20 | 0 | 100 | 100 | 100 | 80 | 70 | 90 | 90 | 80 | 60 |
| IVYLEAF SPEEDWELL | 100 | 100 | 90 | 70 | 50 | 100 | 100 | 100 | 100 | 70 | 20 | 20 | 0 | 0 |
| LAMBSQUARTERS | 90 | 90 | 60 | 50 | 40 | 90 | 90 | 70 | 40 | 20 | 90 | 90 | 80 | 60 |
| FIELD PENNYCRESS | 100 | 90 | 70 | 50 | 30 | 90 | 90 | 90 | 70 | 30 | 100 | 90 | 70 | 40 |
| FIELD VIOLET | 50 | 20 | 0 | 0 | 0 | 80 | 80 | 70 | 40 | 30 | 60 | 50 | 30 | 30 |

| | CMPD 20 | | | | | CMPD 22 | | | | | CMPD 23 | | | | |
|---|---|---|---|---|---|---|---|---|---|---|---|---|---|---|---|
| RATE G/HA | 32 | 16 | 8 | 4 | 2 | 64 | 32 | 16 | 8 | 4 | 32 | 16 | 8 | 4 | 2 |
| POSTEMERGENCE | | | | | | | | | | | | | | | |
| SPRING WHEAT | 70 | 60 | 50 | 40 | 30 | 100 | 90 | 40 | 40 | 30 | 50 | 20 | 0 | 0 | 0 |
| SPRING BARLEY | 80 | 60 | 50 | 20 | 20 | 90 | 70 | 60 | 50 | 30 | 30 | 10 | 10 | 0 | 0 |

TABLE C-continued

| | | | | | | | | | | | | | | | |
|---|---|---|---|---|---|---|---|---|---|---|---|---|---|---|---|
| WILD OAT STAGE 1 | 100 | 100 | 90 | 90 | 90 | 100 | 100 | 100 | 100 | 60 | 100 | 90 | 80 | 60 | 60 |
| DOWNY BROME | 70 | 40 | 40 | 20 | 0 | 100 | 90 | 90 | 70 | 40 | 50 | 30 | 30 | 10 | 0 |
| CHEATGRASS | 50 | 50 | 50 | 40 | 20 | 100 | 70 | 70 | 30 | 20 | 80 | 70 | 50 | 30 | 20 |
| BLACKGRASS STAGE 1 | 90 | 90 | 80 | 40 | 30 | 70 | 70 | 60 | 50 | 30 | 20 | 20 | 20 | 0 | 0 |
| BLUEGRASS | 60 | 60 | 30 | 20 | 0 | 90 | 80 | 60 | 50 | 40 | 10 | 10 | 0 | 0 | 0 |
| GREEN FOXTAIL | 40 | 40 | 40 | 40 | 30 | 80 | 70 | 40 | 40 | 30 | 70 | 70 | 70 | 30 | 20 |
| ITALIAN RYEGRASS | 100 | 90 | 90 | 70 | 30 | 100 | 100 | 100 | 90 | 70 | 100 | 90 | 70 | 60 | 20 |
| RAPE | 100 | 100 | 100 | 100 | 100 | 100 | 100 | 100 | 100 | 90 | 100 | 100 | 100 | 90 | 90 |
| WINTER WHEAT | 70 | 60 | 60 | 30 | 20 | 90 | 60 | 50 | 40 | 40 | 40 | 40 | 20 | 10 | 10 |
| WINTER BARLEY | 70 | 60 | 60 | 50 | 40 | 90 | 90 | 70 | 50 | 30 | 40 | 10 | 10 | 0 | 0 |
| JOINTED GOATGRASS | 80 | 80 | 70 | 40 | 30 | 90 | 90 | 80 | 60 | 40 | 50 | 40 | 20 | 10 | 0 |
| WILD OAT STAGE 2 | 100 | 100 | 90 | 90 | 90 | 100 | 100 | 100 | 90 | 70 | 100 | 100 | 50 | 20 | 0 |
| BLACKGRASS STAGE 2 | 80 | 70 | 70 | 50 | 30 | 90 | 50 | 50 | 40 | 20 | 60 | 60 | 50 | 20 | 20 |
| CATCHWEED BEDSTRAW | 80 | 80 | 50 | 40 | 10 | 90 | 60 | 50 | 20 | 0 | 70 | 30 | 10 | 0 | 0 |
| WILD BUCKWHEAT | 100 | 100 | 100 | 100 | 60 | 70 | 40 | 30 | 30 | 20 | 0 | 10 | 0 | 0 | 0 |
| KOCHIA | 90 | 70 | 60 | 40 | 20 | 40 | 30 | 10 | 0 | 0 | 60 | 60 | 50 | 40 | 20 |
| SCENTLESS CHAMOMILE | 90 | 80 | 70 | 30 | 10 | 100 | 60 | 50 | 50 | 30 | 100 | 90 | 80 | 70 | 50 |
| BLACK NIGHTSHADE | 0 | 0 | 0 | 0 | 0 | 40 | 20 | 10 | 0 | 0 | 10 | 0 | 0 | 0 | 0 |
| RUSSIAN THISTLE | — | — | — | — | — | — | — | — | — | — | — | — | — | — | — |
| BIRDSEYE SPEEDWELL | 10 | 0 | 0 | 0 | 0 | 0 | 0 | 0 | 0 | 0 | 20 | 10 | 0 | 0 | 0 |
| SUGARBEET | 100 | 100 | 100 | 90 | 90 | 100 | 100 | 100 | 80 | 60 | 100 | 100 | 90 | 80 | 60 |
| IVYLEAF SPEEDWELL | 40 | 10 | 0 | 0 | 0 | 0 | 0 | 0 | 0 | 0 | 20 | 20 | 0 | 0 | 0 |
| LAMBSQUARTERS | 90 | 90 | 80 | 80 | 70 | 20 | 10 | 0 | 0 | 0 | 70 | 70 | 60 | 50 | 30 |
| FIELD PENNYCRESS | 90 | 90 | 90 | 90 | 70 | 100 | 90 | 80 | 80 | 40 | 100 | 100 | 90 | 80 | 60 |
| FIELD VIOLET | 20 | 0 | 0 | 0 | 0 | 0 | 0 | 0 | 0 | 0 | 0 | 0 | 0 | 0 | 0 |
| PREEMERGENCE | | | | | | | | | | | | | | | |
| SPRING WHEAT | 70 | 40 | 30 | 20 | 10 | 90 | 80 | 70 | 70 | 50 | 90 | 80 | 60 | 50 | 40 |
| SPRING BARLEY | 80 | 70 | 50 | 30 | 0 | 50 | 40 | 40 | 20 | 10 | 70 | 40 | 20 | 0 | 0 |
| WILD OAT | 70 | 40 | 10 | 0 | 0 | 30 | 30 | 30 | 20 | 10 | 30 | 10 | 0 | 0 | 0 |
| DOWNY BROME | 30 | 30 | 10 | 0 | 0 | 90 | 60 | 40 | 20 | 20 | 80 | 50 | 10 | 0 | 0 |
| CHEATGRASS | 80 | 70 | 60 | 30 | 20 | 100 | 80 | 70 | 30 | 20 | 90 | 90 | 40 | 20 | 0 |
| BLACKGRASS | 60 | 60 | 60 | 40 | 20 | 80 | 70 | 70 | 60 | 30 | 70 | 40 | 20 | 0 | 0 |
| BLUEGRASS | 80 | 80 | 40 | 40 | 30 | 90 | 80 | 80 | 70 | 50 | 70 | 70 | 50 | 30 | 20 |
| GREEN FOXTAIL | 100 | 80 | 80 | 40 | 20 | 70 | 70 | 50 | 40 | 20 | 80 | 40 | 10 | 0 | 0 |
| ITALIAN RYEGRASS | 90 | 70 | 30 | 30 | 0 | 80 | 60 | 30 | 20 | 0 | 90 | 70 | 50 | 20 | 10 |
| RAPE | 100 | 100 | 70 | 40 | 30 | 90 | 90 | 80 | 50 | 30 | 90 | 70 | 40 | 10 | 0 |
| WINTER WHEAT | 80 | 70 | 50 | 40 | 20 | 90 | 70 | 60 | 40 | 30 | 70 | 60 | 40 | 30 | 10 |
| WINTER BARLEY | 80 | 60 | 50 | 30 | 20 | 60 | 60 | 50 | 50 | 30 | 80 | 80 | 50 | 30 | 10 |
| JOINTED GOATGRASS | 20 | 10 | 0 | 0 | 0 | 30 | 30 | 10 | 0 | 0 | 30 | 20 | 0 | 0 | 0 |
| CATCHWEED BEDSTRAW | 40 | 20 | 20 | 20 | 0 | 90 | 70 | 60 | 40 | 30 | 70 | 60 | 50 | 50 | 30 |
| WILD BUCKWHEAT | 70 | 60 | 20 | 0 | 0 | 90 | 70 | 70 | 60 | 40 | 40 | 20 | 0 | 0 | 0 |
| KOCHIA | 30 | 20 | 10 | 10 | 0 | 30 | 20 | 0 | 0 | 0 | 20 | 10 | 0 | 0 | 0 |
| SCENTLESS CHAMOMILE | 100 | 100 | 100 | 90 | 80 | 90 | 90 | 80 | 60 | 40 | 90 | 90 | 80 | 40 | 30 |
| BLACK NIGHTSHADE | 10 | 0 | 0 | 0 | 0 | 50 | 50 | 40 | 30 | 0 | 30 | 10 | 0 | 0 | 0 |
| RUSSIAN THISTLE | — | — | — | — | — | — | — | — | — | — | — | — | — | — | — |
| BIRDSEYE SPEEDWELL | 40 | 20 | 0 | 0 | 0 | 40 | 0 | 0 | 0 | 0 | 40 | 40 | 40 | 10 | 0 |
| SUGARBEET | 100 | 80 | 70 | 70 | 50 | 100 | 90 | 90 | 70 | 60 | 100 | 90 | 70 | 70 | 70 |
| IVYLEAF SPEEDWELL | 0 | 0 | 0 | 0 | 0 | 100 | 60 | 40 | 0 | 0 | 10 | 10 | 0 | 0 | 0 |
| LAMBSQUARTERS | 90 | 90 | 80 | 80 | 50 | 80 | 80 | 80 | 60 | 20 | 80 | 80 | 40 | 30 | 10 |
| FIELD PENNYCRESS | 100 | 100 | 90 | 70 | 50 | 90 | 90 | 60 | 30 | 0 | 50 | 20 | 0 | 0 | 0 |
| FIELD VIOLET | 30 | 30 | 20 | 0 | 0 | 40 | 30 | 0 | 0 | 0 | 70 | 30 | 20 | 0 | 0 |

| | CMPD 27 | | | | | CMPD 28 | | | | | | CMPD 29 | | | |
|---|---|---|---|---|---|---|---|---|---|---|---|---|---|---|---|
| RATE G/HA | 125 | 64 | 32 | 16 | 8 | 125 | 64 | 32 | 16 | 8 | 4 | 125 | 64 | 32 | 16 | 8 |
| POSTEMERGENCE | | | | | | | | | | | | | | | | |
| SPRING WHEAT | 30 | 10 | 0 | 0 | 0 | 50 | 40 | 20 | 10 | 0 | 0 | 100 | 70 | 70 | 30 | 10 |
| SPRING BARLEY | 10 | 0 | 0 | 0 | 0 | 70 | 60 | 30 | 10 | 0 | 0 | 100 | 100 | 80 | 70 | 50 |
| WILD OAT STAGE 1 | 100 | 90 | 80 | 10 | 0 | 100 | 100 | 90 | 90 | 90 | 20 | 100 | 100 | 100 | 100 | 90 |
| DOWNY BROME | 10 | 0 | 0 | 0 | 0 | 90 | 60 | 50 | 20 | 0 | 0 | 100 | 100 | 90 | 70 | 40 |
| CHEATGRASS | 60 | 40 | 10 | 0 | 0 | 100 | 90 | 80 | 40 | 10 | 0 | 80 | 80 | 80 | 50 | 20 |
| BLACKGRASS STAGE 1 | 80 | 60 | 30 | 30 | 0 | 80 | 70 | 30 | 20 | 10 | 0 | 90 | 90 | 60 | 50 | 20 |
| BLUEGRASS | 0 | 0 | 0 | 0 | 0 | 80 | 70 | 40 | 20 | 0 | 0 | 100 | 100 | 80 | 60 | 10 |
| GREEN FOXTAIL | 40 | 40 | 20 | 0 | 0 | 100 | 90 | 80 | 60 | 50 | 10 | 100 | 100 | 90 | 70 | 20 |
| ITALIAN RYEGRASS | 20 | 0 | 0 | 0 | 0 | 100 | 90 | 70 | 50 | 10 | 0 | 100 | 100 | 90 | 90 | 30 |
| RAPE | 90 | 40 | 10 | 0 | 0 | 80 | 60 | 0 | 0 | 0 | 0 | 100 | 100 | 90 | 90 | 70 |
| WINTER WHEAT | 30 | 10 | 0 | 0 | 0 | 40 | 40 | 20 | 20 | 0 | 0 | 90 | 90 | 80 | 60 | 30 |
| WINTER BARLEY | 30 | 10 | 0 | 0 | 0 | 90 | 70 | 30 | 10 | 0 | 0 | 100 | 100 | 90 | 60 | 20 |
| JOINTED GOATGRASS | 20 | 0 | 0 | 0 | 0 | 90 | 80 | 80 | 30 | 10 | 0 | 100 | 100 | 90 | 80 | 40 |
| WILD OAT STAGE 2 | 100 | 100 | 70 | 50 | 30 | 90 | 90 | 80 | 80 | 70 | 20 | 100 | 100 | 100 | 100 | 70 |
| BLACKGRASS STAGE 2 | 70 | 60 | 20 | 10 | 0 | 80 | 60 | 40 | 10 | 0 | 0 | 90 | 70 | 60 | 20 | 0 |
| CATCHWEED BEDSTRAW | 80 | 40 | 10 | 10 | 0 | 90 | 50 | 50 | 20 | 0 | 0 | 40 | 40 | 40 | 10 | 0 |
| WILD BUCKWHEAT | 0 | 0 | 0 | 0 | 0 | 0 | 0 | 0 | 0 | 0 | 0 | 50 | 50 | 20 | 0 | 0 |
| KOCHIA | 30 | 10 | 0 | 0 | 0 | 70 | 60 | 20 | 0 | 0 | 0 | 60 | 60 | | 40 | 10 |
| SCENTLESS CHAMOMILE | 100 | 70 | 50 | 40 | 0 | 70 | 60 | 50 | 50 | 40 | 20 | 70 | 30 | 30 | 20 | 0 |
| BLACK NIGHTSHADE | 60 | 50 | 0 | 0 | 0 | 50 | 50 | 40 | 40 | 20 | 0 | 50 | 40 | 40 | 40 | 10 |
| RUSSIAN THISTLE | 100 | 100 | 70 | 40 | 20 | 100 | 100 | 90 | 90 | 70 | 50 | 100 | 100 | 100 | 80 | 60 |
| BIRDSEYE SPEEDWELL | 0 | 0 | 0 | 0 | 0 | 30 | 20 | 10 | 0 | 0 | 0 | 20 | 0 | 0 | 0 | 0 |
| SUGARBEET | 90 | 70 | 60 | 30 | 20 | 100 | 100 | 90 | 90 | 70 | 20 | 100 | 100 | 90 | 80 | 50 |
| IVYLEAF SPEEDWELL | 0 | 0 | 0 | 0 | 0 | 50 | 10 | 0 | 0 | 0 | 0 | 10 | 0 | 0 | 0 | 0 |
| LAMBSQUARTERS | 40 | 30 | 0 | 0 | 0 | 30 | 10 | 0 | 0 | 0 | 0 | 30 | 10 | 10 | 0 | 0 |
| FIELD PENNYCRESS | 70 | 70 | 60 | 40 | 30 | 70 | 70 | 60 | 50 | 30 | 20 | 90 | 70 | 60 | 60 | 50 |
| FIELD VIOLET | 0 | 0 | 0 | 0 | 0 | 10 | 0 | 0 | 0 | 0 | 0 | 20 | 0 | 0 | 0 | 0 |

TABLE C-continued

| | | | | | | | | | | | | | | | | |
|---|---|---|---|---|---|---|---|---|---|---|---|---|---|---|---|---|
| PREEMERGENCE | | | | | | | | | | | | | | | | |
| SPRING WHEAT | 60 | 50 | 30 | 10 | 0 | 0 | 0 | 0 | 0 | 0 | 0 | 30 | 20 | 20 | 10 | 0 |
| SPRING BARLEY | 10 | 0 | 0 | 0 | 0 | 20 | 10 | 0 | 0 | 0 | 0 | 80 | 40 | 20 | 10 | 0 |
| WILD OAT | 60 | 20 | 0 | 0 | 0 | 40 | 30 | 0 | 0 | 0 | 0 | 50 | 20 | 0 | 0 | 0 |
| DOWNY BROME | 40 | 20 | 20 | 0 | 0 | 0 | 0 | 0 | 0 | 0 | 0 | 40 | 40 | 20 | 0 | 0 |
| CHEATGRASS | 20 | 0 | 0 | 0 | 0 | 40 | 10 | 0 | 0 | 0 | 0 | 70 | 60 | 40 | 30 | 10 |
| BLACKGRASS | 50 | 30 | 10 | 0 | 0 | 50 | 20 | 10 | 0 | 0 | 0 | 70 | 70 | 40 | 30 | 10 |
| BLUEGRASS | 50 | 30 | 0 | 0 | 0 | 20 | 20 | 10 | 10 | 0 | 0 | 80 | 80 | 60 | 20 | 0 |
| GREEN FOXTAIL | 100 | 50 | 10 | 0 | 0 | 100 | 30 | 10 | 0 | 0 | 0 | 100 | 90 | 90 | 30 | 10 |
| ITALIAN RYEGRASS | 60 | 30 | 10 | 0 | 0 | 40 | 40 | 20 | 10 | 0 | 0 | 80 | 40 | 20 | 10 | 0 |
| RAPE | 80 | 30 | 10 | 0 | 0 | 30 | 30 | 10 | 0 | 0 | 0 | 100 | 100 | 80 | 30 | 0 |
| WINTER WHEAT | 60 | 50 | 20 | 0 | 0 | 0 | 0 | 0 | 0 | 0 | 0 | 30 | 30 | 10 | 0 | 0 |
| WINTER BARLEY | 70 | 40 | 10 | 0 | 0 | 70 | 50 | 20 | 10 | 0 | 0 | 60 | 30 | 20 | 10 | 0 |
| JOINTED GOATGRASS | 20 | 10 | 0 | 0 | 0 | 20 | 10 | 0 | 0 | 0 | 0 | 30 | 10 | 0 | 0 | 0 |
| CATCHWEED BEDSTRAW | 40 | 10 | 0 | 0 | 0 | 50 | 40 | 10 | 0 | 0 | 0 | 60 | 50 | 20 | 0 | 0 |
| WILD BUCKWHEAT | 20 | 0 | 0 | 0 | 0 | 70 | 60 | 40 | 0 | 0 | 0 | 80 | 80 | 70 | 30 | 0 |
| KOCHIA | 10 | 10 | 0 | 0 | 0 | 50 | 20 | 10 | 0 | 0 | 0 | 20 | 20 | 10 | 0 | 0 |
| SCENTLESS CHAMOMILE | 90 | 90 | 80 | 60 | 40 | 100 | 90 | 80 | 80 | 40 | 30 | 90 | 90 | 90 | 70 | 60 |
| BLACK NIGHTSHADE | 60 | 40 | 40 | 30 | 10 | 30 | 30 | 20 | 10 | 0 | 0 | 30 | 30 | 30 | 10 | 0 |
| RUSSIAN THISTLE | 100 | 100 | 90 | 80 | 60 | 100 | 100 | 90 | 90 | 70 | 40 | 100 | 70 | 20 | 0 | 0 |
| BIRDSEYE SPEEDWELL | 60 | 60 | 40 | 30 | 10 | 70 | 60 | 20 | 10 | 10 | 0 | 80 | 70 | 50 | 30 | 20 |
| SUGARBEET | 90 | 70 | 70 | 60 | 60 | 70 | 60 | 60 | 50 | 50 | 30 | 100 | 100 | 90 | 70 | 60 |
| IVYLEAF SPEEDWELL | 30 | 10 | 0 | 0 | 0 | 40 | 20 | 0 | 0 | 0 | 0 | 30 | 20 | 0 | 0 | 0 |
| LAMBSQUARTERS | 70 | 70 | 70 | 50 | 30 | 50 | 30 | 20 | 0 | 0 | 0 | 80 | 30 | 10 | 0 | 0 |
| FIELD PENNYCRESS | 70 | 70 | 30 | 10 | 0 | 90 | 70 | 60 | 60 | 40 | 30 | 100 | 80 | 80 | 60 | 50 |
| FIELD VIOLET | 70 | 30 | 10 | 0 | 0 | 40 | 10 | 0 | 0 | 0 | 0 | 40 | 40 | 30 | 10 | 0 |

| | CMPD 54 | | | | | | CMPD 55 | | | | | CMPD 56 | | | | | |
|---|---|---|---|---|---|---|---|---|---|---|---|---|---|---|---|---|---|
| RATE G/HA | 32 | 16 | 8 | 4 | 2 | 1 | 125 | 64 | 32 | 16 | 8 | 32 | 16 | 8 | 4 | 2 | 1 |
| POSTEMERGENCE | | | | | | | | | | | | | | | | | |
| SPRING WHEAT | 70 | 50 | 30 | 10 | 0 | 0 | 0 | 0 | 0 | 0 | 0 | 60 | 10 | 10 | 0 | 0 | 0 |
| SPRING BARLEY | 70 | 60 | 50 | 40 | 20 | 10 | 10 | 10 | 0 | 0 | 0 | 60 | 40 | 20 | 10 | 0 | 0 |
| WILD OAT STAGE 1 | 100 | 100 | 100 | 70 | 70 | 0 | 40 | 40 | 20 | 0 | 0 | 100 | 100 | 70 | 70 | 40 | 10 |
| DOWNY BROME | 60 | 30 | 30 | 10 | 0 | 0 | 0 | 0 | 0 | 0 | 0 | 10 | 0 | 0 | 0 | 0 | 0 |
| CHEATGRASS | 70 | 70 | 50 | 30 | 20 | 0 | 10 | 10 | 0 | 0 | 0 | 60 | 60 | 50 | 20 | 0 | 0 |
| BLACKGRASS STAGE 1 | 80 | 60 | 30 | 10 | 0 | 0 | 10 | 0 | 0 | 0 | 0 | 60 | 50 | 10 | 0 | 0 | 0 |
| BLUEGRASS | 50 | 10 | 0 | 0 | 0 | 0 | 10 | 10 | 10 | 0 | 0 | 10 | 0 | 0 | 0 | 0 | 0 |
| GREEN FOXTAIL | 100 | 90 | 70 | 60 | 30 | 0 | 60 | 50 | 40 | 20 | 10 | 70 | 50 | 30 | 10 | 0 | 0 |
| ITALIAN RYEGRASS | 70 | 40 | 10 | 0 | 0 | 0 | 10 | 0 | 0 | 0 | 0 | 30 | 10 | 0 | 0 | 0 | 0 |
| RAPE | 100 | 100 | 100 | 100 | 100 | 90 | 100 | 100 | 90 | 80 | 60 | 100 | 100 | 70 | 70 | 70 | 40 |
| WINTER WHEAT | 70 | 50 | 30 | 10 | 0 | 0 | 0 | 0 | 0 | 0 | 0 | 80 | 50 | 40 | 20 | 0 | 0 |
| WINTER BARLEY | 60 | 50 | 50 | 40 | 40 | 20 | 0 | 0 | 0 | 0 | 0 | 80 | 70 | 50 | 20 | 10 | 0 |
| JOINTED GOATGRASS | 40 | 40 | 20 | 20 | 0 | 0 | 0 | 0 | 0 | 0 | 0 | 70 | 30 | 10 | 0 | 0 | 0 |
| WILD OAT STAGE 2 | 100 | 90 | 90 | 90 | 70 | 20 | — | 30 | 20 | 0 | 0 | 100 | 100 | 100 | 70 | 30 | 10 |
| BLACKGRASS STAGE 2 | 60 | 60 | 50 | 40 | 10 | 0 | 50 | 30 | 20 | 10 | 0 | 20 | 20 | 0 | 0 | 0 | 0 |
| CATCHWEED BEDSTRAW | 50 | 30 | 20 | 10 | 0 | 0 | 70 | 50 | 40 | 10 | 0 | 60 | 40 | 30 | 10 | 0 | 0 |
| WILD BUCKWHEAT | 100 | 80 | 80 | 70 | — | 30 | — | — | — | — | — | 60 | — | — | — | — | 20 |
| KOCHIA | 100 | 80 | 70 | 60 | 50 | 40 | 90 | 90 | 70 | 60 | 20 | 60 | 50 | 50 | 30 | 0 | 0 |
| SCENTLESS CHAMOMILE | 100 | 60 | 50 | 30 | 0 | 0 | 60 | 60 | 40 | 30 | 10 | 80 | 70 | 40 | 20 | 0 | 0 |
| BLACK NIGHTSHADE | 20 | 20 | 10 | 10 | 0 | 0 | 70 | 50 | 30 | 30 | 20 | 10 | 0 | 0 | 0 | 0 | 0 |
| RUSSIAN THISTLE | — | — | — | — | — | — | — | — | — | — | — | — | — | — | — | — | — |
| BIRDSEYE SPEEDWELL | 30 | 10 | 0 | 0 | 0 | 0 | 10 | 10 | 10 | 0 | 0 | 20 | 0 | 0 | 0 | 0 | 0 |
| SUGARBEET | 100 | 100 | 90 | 40 | 20 | 0 | 70 | 30 | 30 | 10 | 10 | 90 | 70 | 70 | 40 | 20 | 10 |
| IVYLEAF SPEEDWELL | 30 | 20 | 0 | 0 | 0 | 0 | 30 | 20 | 10 | 0 | 0 | 80 | 60 | 50 | 30 | 10 | 0 |
| LAMBSQUARTERS | 90 | 90 | 70 | 70 | 50 | 30 | 70 | 40 | 30 | 20 | 20 | 90 | 70 | 70 | 70 | 20 | 0 |
| FIELD PENNYCRESS | 100 | 100 | 70 | 60 | 40 | 20 | 100 | 100 | 100 | 80 | 80 | 100 | 100 | 80 | 70 | 50 | 0 |
| FIELD VIOLET | 10 | 0 | 0 | 0 | 0 | 0 | 10 | 0 | 0 | 0 | 0 | 20 | 20 | 0 | 0 | 0 | 0 |
| PREEMERGENCE | | | | | | | | | | | | | | | | | |
| SPRING WHEAT | 10 | 0 | 0 | 0 | 0 | 0 | 20 | 10 | 0 | 0 | 0 | 0 | 0 | 0 | 0 | 0 | 0 |
| SPRING BARLEY | 10 | 0 | 0 | 0 | 0 | 0 | 20 | 0 | 0 | 0 | 0 | 40 | 10 | 0 | 0 | 0 | 0 |
| WILD OAT | 70 | 20 | 0 | 0 | 0 | 0 | 30 | 20 | 10 | 0 | 0 | 0 | 0 | 0 | 0 | 0 | 0 |
| DOWNY BROME | 20 | 20 | 0 | 0 | 0 | 0 | 10 | 10 | 10 | 0 | 0 | 70 | 50 | 10 | 0 | 0 | 0 |
| CHEATGRASS | 70 | 30 | 0 | 0 | 0 | 0 | 10 | 10 | 10 | 0 | 0 | 20 | 10 | 0 | 0 | 0 | 0 |
| BLACKGRASS | 70 | 10 | 0 | 0 | 0 | 0 | 20 | 10 | 10 | 0 | 0 | 0 | 0 | 0 | 0 | 0 | 0 |
| BLUEGRASS | 20 | 20 | 10 | 0 | 0 | 0 | 0 | 0 | 0 | 0 | 0 | 20 | 0 | 0 | 0 | 0 | 0 |
| GREEN FOXTAIL | 100 | 80 | 20 | 0 | 0 | 0 | 80 | 70 | 30 | 30 | 10 | 40 | 10 | 0 | 0 | 0 | 0 |
| ITALIAN RYEGRASS | 30 | 10 | 0 | 0 | 0 | 0 | 60 | 30 | 20 | 10 | 10 | 10 | 0 | 0 | 0 | 0 | 0 |
| RAPE | 100 | 100 | 80 | 60 | 20 | 0 | 100 | 80 | 70 | 30 | 20 | 20 | 0 | 0 | 0 | 0 | 0 |
| WINTER WHEAT | 30 | 10 | 0 | 0 | 0 | 0 | 30 | 10 | 0 | 0 | 0 | 10 | 0 | 0 | 0 | 0 | 0 |
| WINTER BARLEY | 20 | 10 | 0 | 0 | 0 | 0 | 30 | 10 | 0 | 0 | 0 | 20 | 10 | 0 | 0 | 0 | 0 |
| JOINTED GOATGRASS | 20 | 10 | 10 | 0 | 0 | 0 | 10 | 10 | 10 | 10 | 0 | 20 | 20 | 10 | 0 | 0 | 0 |
| CATCHWEED BEDSTRAW | 30 | 10 | 10 | 0 | 0 | 0 | 70 | 40 | 30 | 30 | 10 | 40 | 10 | 0 | 0 | 0 | 0 |
| WILD BUCKWHEAT | 60 | 20 | 10 | 0 | 0 | 0 | 30 | 20 | 10 | 10 | 0 | 20 | 10 | 0 | 0 | 0 | 0 |
| KOCHIA | 100 | 30 | 0 | 0 | 0 | 0 | 100 | 70 | 70 | 30 | 30 | 70 | 70 | 40 | 20 | 0 | 0 |
| SCENTLESS CHAMOMILE | 90 | 90 | 80 | 70 | 60 | 30 | 100 | 80 | 80 | 70 | 70 | 100 | 90 | 90 | 80 | 70 | 50 |
| BLACK NIGHTSHADE | 40 | 20 | 20 | 10 | 0 | 0 | 60 | 50 | 50 | 20 | 20 | 10 | 0 | 0 | 0 | 0 | 0 |
| RUSSIAN THISTLE | — | — | — | — | — | — | — | — | — | — | — | — | — | — | — | — | — |
| BIRDSEYE SPEEDWELL | 80 | 70 | 60 | 40 | 20 | 0 | 80 | 80 | 60 | 50 | 20 | 90 | 90 | 60 | 30 | 20 | 10 |
| SUGARBEET | 80 | 80 | 50 | 30 | 20 | 0 | 20 | 10 | 10 | 0 | 0 | 60 | 60 | 50 | 50 | 40 | 30 |
| IVYLEAF SPEEDWELL | 20 | 10 | 10 | 0 | 0 | 0 | 0 | — | 0 | 0 | 0 | 90 | 60 | 30 | 20 | 20 | 10 |
| LAMBSQUARTERS | 30 | 30 | 0 | 0 | 0 | 0 | 70 | 70 | 50 | 40 | 20 | 100 | 90 | 80 | 30 | 20 | 0 |

TABLE C-continued

| | | | | | | | | | | | | | | | | | | |
|---|---|---|---|---|---|---|---|---|---|---|---|---|---|---|---|---|---|---|
| FIELD PENNYCRESS | 80 | 80 | 70 | — | 20 | 0 | 20 | — | 20 | 20 | 20 | 100 | 100 | 90 | 70 | 50 | | 10 |
| FIELD VIOLET | 30 | 30 | 10 | 0 | 0 | 0 | — | — | 0 | — | 0 | 90 | 90 | 90 | 80 | 30 | | 10 |
| | CMPD 57 | | | | | | CMPD 64 | | | | | | CMPD 67 | | | | | |
| RATE G/HA | 32 | 16 | 8 | 4 | 2 | 1 | 64 | 32 | 16 | 8 | 4 | 2 | 32 | 16 | 8 | 4 | 2 | 1 |
| POSTEMERGENCE | | | | | | | | | | | | | | | | | | |
| SPRING WHEAT | 30 | 20 | 0 | 0 | 0 | 0 | 100 | 100 | 100 | 90 | 90 | 70 | 30 | 10 | 10 | 0 | 0 | 0 |
| SPRING BARLEY | 20 | 0 | 0 | 0 | 0 | 0 | 100 | 100 | 100 | 100 | 100 | 70 | 50 | 30 | 10 | 10 | 0 | 0 |
| WILD OAT STAGE 1 | 80 | 50 | 40 | 10 | 0 | 0 | 90 | 80 | 80 | 80 | 80 | 70 | 80 | 80 | 70 | 60 | 40 | 30 |
| DOWNY BROME | 0 | 0 | 0 | 0 | 0 | 0 | 100 | 80 | 80 | 70 | 60 | 50 | 60 | 30 | 20 | 10 | 0 | 0 |
| CHEATGRASS | 20 | 20 | 0 | 0 | 0 | 0 | 80 | 80 | 70 | 60 | 50 | 40 | 70 | 40 | 30 | 20 | 10 | 0 |
| BLACKGRASS STAGE 1 | 10 | 0 | 0 | 0 | 0 | 0 | 100 | 100 | 80 | 80 | 70 | 50 | 40 | 30 | 20 | 10 | 0 | 0 |
| BLUEGRASS | 20 | 10 | 0 | 0 | 0 | 0 | 100 | 90 | 90 | 50 | 30 | 0 | 30 | 20 | 0 | 0 | 0 | 0 |
| GREEN FOXTAIL | 20 | 10 | 0 | 0 | 0 | 0 | 100 | 100 | 90 | 80 | 60 | 50 | 100 | 90 | 80 | 60 | 50 | 30 |
| ITALIAN RYEGRASS | 40 | 10 | 0 | 0 | 0 | 0 | 90 | 80 | 70 | 20 | 10 | 0 | 70 | 50 | 20 | 0 | 0 | 0 |
| RAPE | 100 | 90 | 90 | 70 | 50 | 10 | 100 | 100 | 100 | 100 | 70 | 20 | 100 | 100 | 100 | 90 | 70 | 20 |
| WINTER WHEAT | 60 | 50 | 20 | 0 | 0 | 0 | 100 | 100 | 100 | 90 | 80 | 70 | 60 | 40 | 10 | 0 | 0 | 0 |
| WINTER BARLEY | 40 | 20 | 10 | 0 | 0 | 0 | 100 | 100 | 100 | 100 | 100 | 60 | 60 | 30 | 20 | 10 | 10 | 0 |
| JOINTED GOATGRASS | 0 | 0 | 0 | 0 | 0 | 0 | 100 | 100 | 100 | 100 | 70 | 50 | 50 | 30 | 20 | 10 | 0 | 0 |
| WILD OAT STAGE 2 | 100 | 80 | 50 | 20 | 0 | 0 | 100 | 100 | 100 | 100 | 80 | 30 | 90 | 90 | 90 | 60 | 40 | 30 |
| BLACKGRASS STAGE 2 | 10 | 0 | 0 | 0 | 0 | 0 | 100 | 90 | 70 | 70 | 60 | 30 | 40 | 20 | 10 | 0 | 0 | 0 |
| CATCHWEED BEDSTRAW | 20 | 10 | 0 | 0 | 0 | 0 | 80 | 50 | 40 | 30 | 30 | 0 | 70 | 50 | 10 | 10 | 0 | 0 |
| WILD BUCKWHEAT | 70 | 30 | 0 | 0 | 0 | 0 | 70 | 60 | 60 | 50 | 50 | 40 | 70 | 60 | 50 | 20 | 20 | 0 |
| KOCHIA | 30 | 20 | 20 | 10 | 0 | 0 | 50 | 50 | 50 | 30 | 30 | 30 | 60 | 60 | 30 | 10 | 10 | 10 |
| SCENTLESS CHAMOMILE | 30 | 30 | 20 | 0 | 0 | 0 | 100 | 100 | 90 | 80 | 60 | 50 | 100 | 80 | 50 | 50 | 30 | 0 |
| BLACK NIGHTSHADE | 30 | 20 | 10 | 10 | 10 | 0 | 20 | 20 | 20 | 20 | 20 | 0 | 10 | 10 | 0 | 0 | 0 | 0 |
| RUSSIAN THISTLE | — | — | — | — | — | — | 50 | 0 | 0 | 0 | 0 | 0 | 100 | 70 | 50 | 30 | 10 | 0 |
| BIRDSEYE SPEEDWELL | 0 | 0 | 0 | 0 | 0 | 0 | 0 | 0 | 0 | 0 | 0 | 0 | 0 | 0 | 0 | 0 | 0 | 0 |
| SUGARBEET | 60 | 30 | 30 | 0 | 0 | 0 | 90 | 80 | 70 | 60 | 50 | 30 | 100 | 90 | 90 | 60 | 40 | 30 |
| IVYLEAF SPEEDWELL | 0 | 0 | 0 | 0 | 0 | 0 | 90 | 80 | — | — | 60 | — | — | — | — | 20 | 0 | 0 |
| LAMBSQUARTERS | 40 | 40 | 30 | 30 | 10 | 0 | 80 | 70 | 60 | 60 | 50 | 40 | 80 | 70 | 60 | 50 | 30 | 30 |
| FIELD PENNYCRESS | 90 | 70 | 60 | 50 | 20 | 0 | 100 | 90 | 90 | 70 | 60 | 40 | 90 | 70 | 70 | 50 | 50 | 20 |
| FIELD VIOLET | 0 | 0 | 0 | 0 | 0 | 0 | 60 | 50 | 50 | 10 | 10 | 0 | 80 | 70 | 40 | 30 | 30 | 0 |
| PREEMERGENCE | | | | | | | | | | | | | | | | | | |
| SPRING WHEAT | 20 | 10 | 0 | 0 | 0 | 0 | 100 | 90 | 40 | 40 | 10 | 0 | 10 | 10 | 0 | 0 | 0 | 0 |
| SPRING BARLEY | 10 | 0 | 0 | 0 | 0 | 0 | 80 | 70 | 40 | 30 | 10 | 0 | 30 | 30 | 0 | 0 | 0 | 0 |
| WILD OAT | 10 | 0 | 0 | 0 | 0 | 0 | 70 | 50 | 20 | 10 | 0 | 0 | 50 | 30 | 10 | 0 | 0 | 0 |
| DOWNY BROME | 20 | 0 | 0 | 0 | 0 | 0 | 90 | 90 | 70 | 30 | 20 | 0 | 10 | 10 | 10 | 10 | 0 | 0 |
| CHEATGRASS | 0 | 0 | 0 | 0 | 0 | 0 | 90 | 80 | 70 | 50 | 30 | 10 | 40 | 20 | 10 | 0 | 0 | 0 |
| BLACKGRASS | 30 | 10 | 10 | 0 | 0 | 0 | 90 | 90 | 80 | 60 | 40 | 20 | 10 | 10 | 0 | 0 | 0 | 0 |
| BLUEGRASS | 10 | 0 | 0 | 0 | 0 | 0 | 90 | 90 | 80 | 80 | 20 | 0 | 20 | 10 | 10 | 0 | 0 | 0 |
| GREEN FOXTAIL | 30 | 0 | 0 | 0 | 0 | 0 | 100 | 90 | 90 | 40 | 40 | 0 | 40 | 10 | 0 | 0 | 0 | 0 |
| ITALIAN RYEGRASS | 10 | 0 | 0 | 0 | 0 | 0 | 30 | 30 | 10 | 10 | 0 | 0 | 40 | 30 | 20 | 0 | 0 | 0 |
| RAPE | 100 | 70 | 30 | 0 | 0 | 0 | 100 | 60 | 50 | 40 | 20 | 0 | 90 | 70 | 50 | 30 | 20 | 10 |
| WINTER WHEAT | 40 | 20 | 0 | 0 | 0 | 0 | 80 | 60 | 10 | 10 | 0 | 0 | 10 | 10 | 0 | 0 | 0 | 0 |
| WINTER BARLEY | 30 | 10 | 0 | 0 | 0 | 0 | 90 | 70 | 30 | 0 | 0 | 0 | 20 | 10 | 10 | 0 | 0 | 0 |
| JOINTED GOATGRASS | 20 | 0 | 0 | 0 | 0 | 0 | 90 | 70 | 10 | 0 | 0 | 0 | 10 | 0 | 0 | 0 | 0 | 0 |
| CATCHWEED BEDSTRAW | 40 | 40 | 20 | 10 | 0 | 0 | 70 | 50 | 50 | 0 | 0 | 0 | 40 | 30 | 10 | 0 | 0 | 0 |
| WILD BUCKWHEAT | 40 | 10 | 0 | 0 | 0 | 0 | 50 | 30 | 30 | 0 | 0 | 0 | 30 | 30 | 10 | 0 | 0 | 0 |
| KOCHIA | 40 | 30 | 0 | 0 | 0 | 0 | 30 | 30 | 30 | 10 | 10 | 10 | 90 | 70 | 40 | 40 | 30 | 10 |
| SCENTLESS CHAMOMILE | 90 | 80 | 80 | 70 | 30 | 20 | 90 | 80 | 70 | 50 | 50 | 10 | 90 | 80 | 60 | 20 | 0 | 0 |
| BLACK NIGHTSHADE | 70 | 50 | 50 | 40 | 20 | 0 | 20 | 20 | 20 | 10 | 10 | 10 | 60 | 30 | 20 | 0 | 0 | 0 |
| RUSSIAN THISTLE | — | — | — | — | — | — | 10 | 0 | 0 | 0 | 0 | 0 | 10 | 10 | 0 | 0 | 0 | 0 |
| BIRDSEYE SPEEDWELL | 80 | 80 | 50 | 30 | 20 | 0 | 50 | 0 | 0 | 0 | 0 | 0 | 30 | 10 | 0 | 0 | 0 | 0 |
| SUGARBEET | 60 | 60 | 40 | 30 | 20 | 0 | 100 | 90 | 70 | 60 | 50 | 40 | 100 | 100 | 90 | 60 | 40 | 30 |
| IVYLEAF SPEEDWELL | 60 | 60 | 40 | 30 | 30 | 20 | 70 | 70 | 70 | 50 | 10 | 10 | 0 | 0 | 0 | 0 | 0 | 0 |
| LAMBSQUARTERS | 80 | 80 | 40 | 40 | 20 | 0 | 90 | 60 | 50 | 20 | 20 | 10 | 80 | 50 | 20 | 10 | 0 | 0 |
| FIELD PENNYCRESS | 100 | 90 | 90 | 90 | 80 | 70 | 100 | 90 | 80 | 30 | 10 | 0 | 100 | 70 | 60 | 60 | 30 | 20 |
| FIELD VIOLET | 100 | 70 | 70 | 40 | 40 | 30 | 100 | 30 | — | 20 | 10 | 0 | 50 | 20 | 10 | 0 | 0 | 0 |

TEST D

Seeds of annual bluegrass (*Poa annua*), barley (*Hordeum vulgare*), blackgrass (*Alopecurus myosuroides*), chickweed (*Stellaria media*), green foxtail (*Setaria viridis*), ladysthumb smartweed (*Polygonum persicaria*), lambsquarters (*Chenopodium album*), redroot pigweed (*Amaranthus retroflexus*), sugarbeet (*Beta vulgaris*), wild buckwheat (*Polygonum convolvulus*), wild mustard (*Brassica* spp.), and wild oat (*Avena fatua*) were planted and treated preemergence with test chemicals dissolved in a non-phytotoxic solvent. At the same time, these crop and weed species were also treated with postemergence applications of test chemicals. Plants ranged in height from two to twenty cm for postemergence treatments. Treated plants and controls were maintained in a greenhouse for approximately 24 days, after which all species were compared to controls and visually evaluated. The ratings, summarized in Table D, are based on a scale of 0 to 100 where 0 is no effect and 100 is complete control.

TABLE D

| | CMPD 55 | | | | CMPD 59 | | |
|---|---|---|---|---|---|---|---|
| RATE GM/HA | 64 | 32 | 16 | 8 | 64 | 32 | 16 |
| POSTEMERGENCE | | | | | | | |
| BARLEY | 30 | 0 | 0 | 0 | 70 | 50 | 30 |

TABLE D-continued

| | CMPD 55 | | | | CMPD 59 | | |
|---|---|---|---|---|---|---|---|
| CHICKWEED | 80 | 40 | 20 | 0 | 100 | 100 | 100 |
| LAMBSQUARTERS | 100 | 100 | 30 | 30 | 100 | 100 | 75 |
| REDROOT PIGWEED | 100 | 100 | 100 | 80 | 100 | 100 | 100 |
| LADYSTHUMB SMARTWEED | 90 | 70 | 70 | 70 | 90 | 80 | 80 |
| WILD BUCKWHEAT | 100 | 80 | 80 | 30 | 100 | 100 | 90 |
| MUSTARD | 100 | 100 | 100 | 80 | 100 | 100 | 100 |
| BLUEGRASS | 100 | 0 | 0 | 0 | 100 | 20 | 20 |
| BLACKGRASS | 40 | 20 | 0 | 0 | 90 | 70 | 0 |
| GREEN FOXTAIL | 70 | 70 | 70 | 0 | 100 | 80 | 30 |
| WILD OAT | 20 | 20 | 20 | 0 | 90 | 70 | 40 |
| SUGARBEET | 80 | 70 | 40 | 30 | 100 | 90 | 70 |

| RATE GM/HA | 64 | 32 | 64 | 32 |
|---|---|---|---|---|
| PREEMERGENCE | | | | |
| BARLEY | 30 | 20 | 30 | 30 |
| CHICKWEED | 80 | 30 | 100 | 0 |
| LAMBSQUARTERS | 70 | 70 | 100 | 100 |
| REDROOT PIGWEED | 100 | 70 | 100 | 100 |
| LADYSTHUMB SMARTWEED | 50 | 50 | 100 | 0 |
| WILD BUCKWHEAT | 30 | 30 | 100 | 20 |
| MUSTARD | 100 | 100 | 100 | 100 |
| BLUEGRASS | 0 | 0 | 30 | 0 |
| BLACKGRASS | 50 | 50 | 50 | 20 |
| GREEN FOXTAIL | 70 | 30 | 90 | 90 |
| WILD OAT | 30 | 20 | 50 | 30 |
| SUGARBEET | 30 | 30 | 80 | 60 |

TEST E

Seeds of barnyardgrass (*Echinochloa crus-galli*), bermudagrass (*cynodon dactylon*), broadleaf signalgrass (*Brachiaria platyphylla*), cocklebur (*Xanthium pensylvanicum*), cotton (*Gossypium hirsutum*), fall panicum (*Panicum dichotomiflorm*), goosegrass (*Eleusine indica*), groundcherry (*Physalis heterophylla*), ivyleaf morningglory (*Ipomoea hederacea*), johnsongrass (*Sorghum halepense*), ladysthumb smartweed (*Polygonum persicaria*), lambsquarters (*Chenopodium album*), large crabgrass (*Digitaria sanguinalis*), prickly sida (*Sida spinosa*), purslane (*Portulaca oleracea*), redroot pigweed (*Amaranthus retroflexus*), sicklepod (*Cassia obtusifolia*), and velvetlead (*Abutilon theophrasti*) and purple nutsedge (*Cyperus rotundus*) tubers were planted and treated preemergence with test chemicals dissolved in a non-phytotoxic solvent. At the same time, these crop and weed species were also treated with postemergence applications of test chemicals. Plants ranged in height from five to twelve cm for postemergence treatments. Treated plants and controls were maintained in a greenhouse for approximately 21 days, after which all species were compared to controls and visually evaluated. The ratings, summarized in Table E, are based on a scale of 0 to 100 where 0 is no effect and 100 is complete control. A dash (-) response means no test.

TABLE E

| | CMPD 1 | | | | | CMPD 6 | | | | |
|---|---|---|---|---|---|---|---|---|---|---|
| RATE GM/HA | 64 | 32 | 16 | 8 | 4 | 16 | 8 | 4 | 2 | 1 |
| POSTEMERGENCE | | | | | | | | | | |
| COTTON | 30 | 0 | 0 | 0 | 0 | 90 | 60 | 15 | 10 | 0 |
| REDROOT PIGWEED | 100 | 100 | 100 | 80 | 70 | 100 | 100 | 100 | 100 | 100 |
| LAMBSQUARTERS | 100 | 95 | 100 | 50 | 0 | 100 | 100 | 100 | 90 | 20 |
| VELVETLEAF | 100 | 95 | 90 | 60 | 50 | 95 | 90 | 70 | 60 | 30 |
| PRICKLY SIDA | 80 | 20 | 20 | 0 | 0 | 60 | 50 | 40 | 10 | 0 |
| SICKLEPOD | 50 | 0 | 0 | 0 | 0 | 100 | 95 | 95 | 40 | 30 |
| COCKLEBUR | 98 | 80 | 90 | 60 | 60 | 100 | 100 | 95 | 60 | 60 |
| PURSLANE | 100 | 90 | 60 | 60 | 50 | 100 | 100 | 95 | 95 | 90 |
| IVYLEAF MORNINGGLORY | 95 | 30 | 0 | 0 | 0 | 100 | 100 | 95 | 90 | 80 |
| GOOSEGRASS | 0 | 0 | 0 | 0 | 0 | 20 | 0 | 0 | 0 | 0 |
| BERMUDAGRASS | 0 | 0 | 0 | 0 | 0 | 50 | 50 | 30 | 10 | 0 |
| BARNYARDGRASS | 100 | 50 | 30 | 30 | 30 | 98 | 95 | 90 | 70 | 40 |
| JOHNSONGRASS | 50 | 30 | 20 | 0 | 0 | 100 | 100 | 90 | 90 | 60 |
| FALL PANICUM | 0 | 0 | 0 | 0 | 0 | 70 | 60 | 40 | 30 | 0 |
| LARGE CRABGRASS | 0 | 0 | 0 | 0 | 0 | 60 | 20 | 10 | 0 | 0 |
| SIGNALGRASS | 20 | 0 | 0 | 0 | 0 | 100 | 98 | 90 | 80 | 60 |
| PURPLE NUTSEDGE | 100 | 70 | 20 | 20 | 0 | 0 | 0 | 0 | 0 | 0 |
| LADYSTHUMB SMARTWEED | 100 | 70 | 50 | 0 | 0 | 100 | 100 | 100 | 100 | 50 |
| GROUNDCHERRY | 100 | 20 | 0 | 0 | 0 | 60 | 60 | 30 | 20 | 10 |

| | CMPD 22 | | | | | CMPD 23 | | | | |
|---|---|---|---|---|---|---|---|---|---|---|
| RATE GM/HA | 16 | 8 | 4 | 2 | 1 | 16 | 8 | 4 | 2 | 1 |
| POSTEMERGENCE | | | | | | | | | | |
| COTTON | 20 | 10 | 0 | 0 | 0 | 40 | 40 | 10 | 0 | 0 |
| REDROOT PIGWEED | 100 | 90 | 70 | 60 | 50 | 100 | 100 | 100 | 95 | 90 |
| LAMBSQUARTERS | 60 | 20 | 0 | 0 | 0 | 100 | 95 | 95 | 70 | 0 |
| VELVETLEAF | 95 | 60 | 30 | 10 | 0 | 95 | 90 | 80 | 60 | 40 |
| PRICKLY SIDA | 10 | 10 | 0 | 0 | 0 | 60 | 50 | 30 | 20 | 0 |
| SICKLEPOD | 60 | 40 | 0 | 0 | 0 | 90 | 90 | 30 | 0 | 0 |

TABLE E-continued

| | | | | | | | | | | |
|---|---|---|---|---|---|---|---|---|---|---|
| COCKLEBUR | 100 | 95 | 70 | 0 | 0 | 100 | 100 | 100 | 90 | 40 |
| PURSLANE | 0 | 0 | 0 | 0 | 0 | 100 | 100 | 98 | 95 | — |
| IVYLEAF MORNINGGLORY | 40 | 40 | 20 | 10 | 10 | 98 | 98 | 98 | 95 | 50 |
| GOOSEGRASS | 0 | 0 | 0 | 0 | 0 | 0 | 0 | 0 | 0 | 0 |
| BERMUDAGRASS | 20 | 20 | 0 | 0 | 0 | 20 | 20 | 0 | 0 | 0 |
| BARNYARDGRASS | 70 | 30 | 20 | 0 | 0 | 95 | 95 | 80 | 50 | 40 |
| JOHNSONGRASS | 60 | 30 | 20 | 10 | 0 | 90 | 80 | 60 | 30 | 30 |
| FALL PANICUM | 60 | 0 | 0 | 0 | 0 | 50 | 0 | 0 | 0 | 0 |
| LARGE CRABGRASS | 0 | 0 | 0 | 0 | 0 | 20 | 0 | 0 | 0 | 0 |
| SIGNALGRASS | 60 | 20 | 20 | 0 | 0 | 60 | 40 | 20 | 20 | 10 |
| PURPLE NUTSEDGE | 30 | 0 | 0 | 0 | 0 | 0 | 0 | 0 | 0 | 0 |
| LADYSTHUMB SMARTWEED | 100 | 95 | 80 | 20 | 20 | 100 | 98 | 80 | 50 | 50 |
| GROUNDCHERRY | 30 | 0 | 0 | 0 | 0 | 60 | 30 | 0 | 0 | 0 |

What is claimed is:

1. A compound of the formula

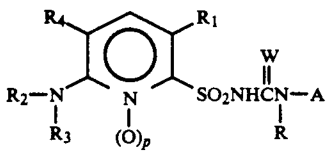

I wherein

W is O or S;

R is H or $CH_3$;

$R_1$ is H, F, Cl, Br, I, Cn, $C_1$-$C_2$ alkyl, $C_1$-$C_2$ haloalkyl, $OCH_3$, $OCH_2CH_3$, $OCH_2CF_3$, $OCF_2H$, $SCH_3$, $SCF_2F$, $C_1$-$C_3$ alkylsulfonyl or $SO_2CF_2H$;

$R_2$ is H, $C_1$-$C_{14}$ alkyl, $C_1$-$C_2$ haloalkyl, CN, OH, $C_1$-$C_2$ alkoxy, $NH_2$, $NHCH_3$, $N(CH_3)_2$, $C_1$-$C_2$ alkyl substituted by CN, $C_1$-$C_2$ alkoxy or $C_1$-$C_2$ alkylthio, $C_3$-$C_4$ cycloalkyl, $C_3$-$C_4$ alkenyl, $C_3$-$C_4$ alkynyl or $C(O)R_5$;

$R_3$ is H, $C_1$-$C_4$ alkyl or $C_1$-$C_2$ haloalkyl; or $R_2$ and $R_3$ may be taken together as $-(CH_2)_n-$ or $-CH_2CH_2OCH_2CH_2-$ or

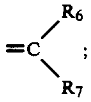

;

$R_4$ is H, F, Cl or $CH_3$;

$R_5$ is H, $C_1$-$C_3$ alkyl, $C_1$-$C_2$ alkoxy, $NH_2$, $NHCH_3$ or $N(CH_3)_2$;

$R_6$ is H, $C_1$-$C_2$ alkyl or phenyl;

$R_7$ is H or $CH_3$;

n is 2, 3, 4 or 5;

p is 0 or 1;

A is

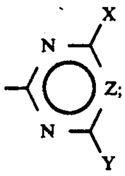

A-1

X is H, $C_1$-$C_4$ alkyl, $C_1$-$C_4$ alkoxy, $C_1$-$C_4$ haloalkoxy, $C_1$-$C_4$ haloalkyl, $C_1$-$C_4$ haloalkylthio, $C_1$-$C_4$ alkylthio, halogen, $C_2$-$C_5$ alkoxyalkyl, $C_2$-$C_5$ alkoxyalkoxy, amino, $C_1$-$C_3$ alkylamino or di($C_1$-$C_3$ alkyl) amino;

Y is H, $C_1$-$C_4$ alkyl, $C_1$-$C_4$ haloalkoxy, $C_1$-$C_4$ haloalkylthio, $C_1$-$C_4$ alkylthio, $C_2$-$C_5$ alkoxyalkyl, $C_2$-$C_5$ alkoxylalkoxy, amino, $C_1$-$C_3$ alkylamino, di($C_1$-$C_3$ alkyl)amino, $C_3$-$C_4$ alkenyloxy, $C_3$-$C_4$ alkynyloxy, $C_2$-$C_5$ alkylthioalkyl, $C_2$-$C_5$ alkylsulfinylalkyl, $C_2$-$C_5$ alkylsulfonylalkyl, $C_1$-$C_4$ haloalkyl, $C_2$-$C_4$ alkynyl, $C_3$-$C_5$ cycloalkyl, azido, cyano,

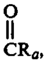, 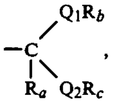, 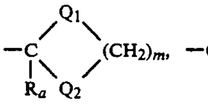, 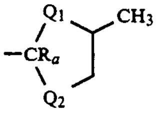

or $N(OCH_3)CH_3$;

m is 2 or 3;

$Q_1$ and $Q_2$ are independently O or S;

$R_a$ is H or $C_1$-$C_3$ alkyl;

$R_b$ and $R_c$ are independently $C_1$-$C_3$ alkyl; and

Z is CH, $CCH_3$, $CC_2H_5$, CCl or CBr;

and their agriculturally suitable salts; provided that 1) when X is halogen, then Z is CH and Y is $OCH_3$, $OC_2H_5$, $NH_2$, $NHCH_3$, $N(CH_3)_2$, $OCF_2H$, $OCF_2Br$ or $N(OCH_3)CH_3$;

2) when X and/or Y is $C_1$ haloalkoxy, then Z is CH;

3) when W is S, then R is H, Z is CH and Y is $CH_3$, $OCH_3$, $OC_2H_5$, $CH_2OCH_3$, $C_2H_5$, $CF_3$, $SCH_3$, $OCH_2CH{=}CH_2$, $OCH_2C{\equiv}CH$, $OCH_2CH_2OCH_3$, $CH(OCH_3)_2$ or

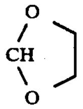

;

and 4) when the total number of carbon atoms of X and Y is greater than four, then the combined number of carbons of $R_2$ and $R_3$ is less than or equal to six.

2. The compounds of claim 1 wherein $R_2$ is $C_1$-$C_2$ haloalkyl, OH, $C_1$-$C_2$ alkoxy, $NH_2$, $NHCH_3$, $N(CH_3)_2$, $C_1$-$C_2$ alkyl substituted by $C_1$-$C_2$ alkylthio, $C_3$-$C_4$ cycloalkyl or $C(O)R_5$;

$R_3$ is H, $C_1$-$C_4$ alkyl or $C_1$-$C_2$ haloalkyl; or $R_2$ and $R_3$ are taken together as $-(CH_2)_n-$ or

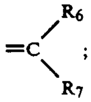

;

and n is 2 or 3.

3. The compounds of claim 3 wherein:

W is O;

X is $C_1$–$C_2$ alkyl, $C_1$–$C_2$ alkoxy, F, Cl, Br, I, $OCF_2H$, $CH_2F$, $CF_3$, $OCH_2CH_2F$, $OCH_2CHF_2$, $OCH_2CF_3$, $CH_2Cl$ or $CH_2Br$;

Y is H, $C_1$–$C_2$ alkyl, $C_1$–$C_2$ alkoxy, $CH_2OCH_3$, $CH_2OCH_2CH_3$, $NHCH_3$, $N(OCH_3)CH_3$, $N(CH_3)_2$, $CF_3$, $SCH_3$, $OCH_2CH{=}CH_2$, $OCH_2C{\equiv}CH$, $OCH_2CH_2OCH_3$, $CH_2SCH_3$, $C(O)R_a$,

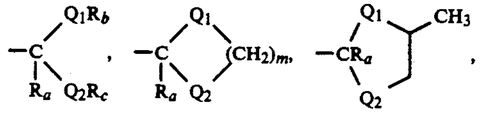

$OCF_2H$, $SCF_2H$, $OCF_2Br$, cyclcopropyl, $C{\equiv}CH$ or $C{\equiv}CCH_3$; and Z is CH.

4. The compounds of claim 3 wherein $R_2$ is $NH_2$, $NHCH_3$, $N(CH_3)_2$, $CF_3$, OH, $OCH_3$, $CH_2SCH_3$, cyclopropyl or $C(O)R_5$ $R_3$ is H, $CH_3$ or $CH_2CH_3$; or $R_2$ and $R_3$ are taken together as $-(CH_2)_n-$ or

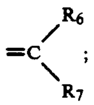

;

$R_5$ is H, $CH_3$, $OCH_3$, $NH_2$, $NHCH_3$ or $N(CH_3)_2$; and $R_6$ is H or $C_1$–$C_2$ alkyl.

5. The compounds of claim 4 wherein

A is A-1;

X is $CH_3$, $OCH_3$, $OCH_2CH_3$, Cl, $OCF_2H$ or $OCH_2CF_3$; and

Y is $CH_3$, $OCH_3$, $CH_2CH_3$, $CH_2OCH_3$, $NHCH_3$ or $CH(OCH_3)_2$.

6. The compounds of claim 5 wherein

R is H;

$R_1$ is H; and p is O.

7. The compounds of claim 1 wherein $R_2$ is $C_1$–$C_4$ alkyl, CN, $C_1$–$C_2$ alkyl substituted by CN or $C_1$–$C_2$ alkoxy, $C_3$–$C_4$ alkenyl or $C_3$–$C_4$ alkynyl;

$R_3$ is H, $C_1$–$C_4$ alkyl or $C_1$–$C_2$ haloalkyl; or $R_2$ and $R_3$ are taken together as $-(CH_2)_n-$ or $-CH_2CH_2OCH_2CH_2-$; and n is 4 or 5.

8. The compounds of claim 7 wherein

W is O;

X is $C_1$–$C_2$ alkyl, $C_1$–$C_2$ alkoxy, F, Cl, Br, I, $OCF_2H$, $CH_2F$, $CF_3$, $OCH_2CH_2F$, $OCH_2CHF_2$, $OCH_2CF_3$, $CH_2Cl$ or $CH_2Br$;

Y is H, $C_1$–$C_2$ alkyl, $C_1$–$C_2$ alkoxy, $CH_2OCH_3$, $CH_2OCH_2CH_3$, $NHCH_3$, $N(OCH_3)CH_3$, $N(CH_3)_2$, $CF_3$, $SCH_3$, $OCH_2CH{=}CH_2$, $OCH_2C{\equiv}CH$, $OCH_2CH_2OCH_3$, $CH_2SCH_3$, $C(O)R_a$,

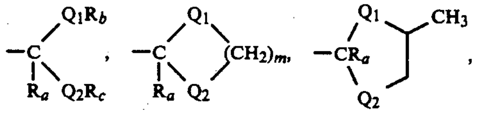

$OCF_2H$, $SCF_2H$, $OCF_2Br$, cyclopropyl, $C{\equiv}CH$ or $C{\equiv}CCH_3$; and Z is CH.

9. The compounds of claim 8 wherein $R_2$ is H, $C_1$–$C_4$ alkyl, CN, $CH_2CN$, $CH_2OCH_3$, allyl or propargyl; and $R_3$ is H, $CH_3$ or $CH_2CH_3$.

10. The compounds of claim 9 wherein

X is $CH_3$, $OCH_3$, $OCH_2CH_3$, Cl, $OCF_2H$ or $OCH_2CF_3$; and

Y is $CH_3$, $OCH_3$, $CH_2CH_3$, $CH_2OCH_3$, $NHCH_3$ or $CH(OCH_3)_2$.

11. The compounds of claim 10 wherein

R is H;

$R_1$ is H; and p is O.

12. The compounds of claim 1 which is N-[[(4,6-dimethoxy-2-pyrimidinyl)-amino]carbonyl]-6-(dimethylamino)-2-pyridinesulfonamide.

13. An agriculturally suitable composition for controlling the growth of undesired vegetation comprising an effective amount of a compound as in any of claims 1-12 and at least one of the following: surfactant, solid diluent or liquid diluent.

14. A method for controlling the growth of undesired vegetation which comprises applying to the locus to be protected an effective amount of a compound as in any of claims 1-12.

* * * * *

UNITED STATES PATENT AND TRADEMARK OFFICE
CERTIFICATE OF CORRECTION

PATENT NO. : 5,032,166

DATED : JULY 16, 1991

INVENTOR(S) : ERIC D. TAYLOR

It is certified that error appears in the above-identified patent and that said Letters Patent is hereby corrected as shown below:

On the title page, change "Eric D. Taylor" to --Eric G. Gaylor--.

Column 2, line 53, change " $C_1C_4$ " to -- $C_1$-$C_4$ --.

Column 2, line 62, change " R " to -- $R_4$ --.

Column 3, line 33, change " haloalky l " to -- haloalkyl --.

Column 4, line 18, change " alkylm " to -- alkyl --.

Column 5, line 33, change " P is O " to -- p is 0 --.

Column 6, line 6, change " O " to -- 0 --.

Column 6, line 62, change " $CH_{20}CH_3$ " to -- $CH_2OCH_3$ --.

Column 6, line 67, change " O " to -- 0 --.

Column 7, line 38, change " O " to -- 0 --.

Column 7, line 47, change " traizin " to -- triazin --.

Column 7, line 49, change " comPrises " to -- comprises --.

Column 7, line 64, change " O " to -- 0 --.

UNITED STATES PATENT AND TRADEMARK OFFICE
CERTIFICATE OF CORRECTION

PATENT NO. : 5,032,166
DATED : JULY 16, 1991
INVENTOR(S) : ERIC D. TAYLOR

It is certified that error appears in the above-identified patent and that said Letters Patent is hereby corrected as shown below:

Column 8, line 54, change " patent " to -- Patent --.

Column 8, line 59, change " paten " to -- Patent --.

Column 8, line 67, change " 4-7 " to -- 3-7 --.

Column 9, line 22, add -- (d) --.

Column 9, line 27, change "$SO_2NH_{2(d)}$" to -- $SO_2NH_2$ --

Column 9, line 40, change " (1964) " to -- (1964)) --.

Column 9, line 56, change " butyIsulfonamide " to -- butylsulfonamide --.

Column 10, line 2, insert -- Equation 4 --.

Column 10, line 35, change " dihalopyride " to -- dihalopyridine --.

Column 10, line 36, change " Wiley-Interscience " to-- Wiley-Interscience, --.

Column 10, line 60, insert -- Equation 5 --.

Column 11, line 15, change " hydroxylpyridine " to -- hydroxypyridine --.

UNITED STATES PATENT AND TRADEMARK OFFICE

CERTIFICATE OF CORRECTION

PATENT NO. : 5,032,166

DATED : JULY 16, 1991

INVENTOR(S) : Eric D. Taylor

It is certified that error appears in the above-identified patent and that said Letters Patent is hereby corrected as shown below:

Column 11, line 24, insert -- Equation 6 -.

Column 11, line 60, insert -- Equation 7 --.

Column 12, line 30, change " patent " to -- Patent --.

Column 12, line 31, change " patent " to -- Patent --.

Column 13, line 12, change " br32 " to -- br = --.

Column 13, line 49, change " bulylamine " to -- butylamine --.

Column 14, line 16, change " aminosulfonly] " to -- aminosulfonyl --.

Column 223, line 27, change " Cn, " to -- CN, --.

Column 223, line 29, change " $SCF_2F$," to -- $SCF_2H$, --.

Column 223, line 30, change " $C_1$-$C_{14}$ " to -- $C_1$-$C_4$ --.

Column 223, line 66, after "$C_1$-$C_4$ alkyl," insert -- $C_1$-$C_4$ alkoxy --.

Column 223, line 68, change " alkoxylalkoxy " to -- alkoxyalkoxy --.

Column 224, line 67, change " 3 " to -- 2 --.

Column 225, line 21, after " $C(O)R_5$ " insert -- ; --.

Column 225, line 43, change " O " to -- 0 --.

UNITED STATES PATENT AND TRADEMARK OFFICE
CERTIFICATE OF CORRECTION

PATENT NO. : 5,032,166

DATED : JULY 16, 1991

INVENTOR(S) : Eric D. Taylor

It is certified that error appears in the above-identified patent and that said Letters Patent is hereby corrected as shown below:

Column 226, line 35, change " O " to -- 0 --.

Column 226, line 36, change " compounds " to -- compound --.

Signed and Sealed this

Twenty-sixth Day of January, 1993

*Attest:*

STEPHEN G. KUNIN

*Attesting Officer*

*Acting Commissioner of Patents and Trademarks*